US011639380B2

(12) United States Patent
Cady et al.

(10) Patent No.: US 11,639,380 B2
(45) Date of Patent: *May 2, 2023

(54) ACUTE TREATMENT AND RAPID TREATMENT OF HEADACHE USING ANTI-CGRP ANTIBODIES

(71) Applicant: H. LUNDBECK A/S, Valby (DK)

(72) Inventors: Roger K. Cady, Bothell, WA (US); Jeffrey T. L. Smith, Dublin (IE); Joseph Hirman, Bothell, WA (US); Barbara Schaeffler, Bothell, WA (US); Lahar Mehta, Valby (DK)

(73) Assignee: H. LUNDBECK A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/736,925

(22) Filed: Jan. 8, 2020

(65) Prior Publication Data

US 2020/0216524 A1 Jul. 9, 2020

Related U.S. Application Data

(60) Provisional application No. 62/789,828, filed on Jan. 8, 2019, provisional application No. 62/872,989, filed on Jul. 11, 2019, provisional application No. 62/842,162, filed on May 2, 2019.

(51) Int. Cl.
| | |
|---|---|
| *C07K 16/18* | (2006.01) |
| *A61K 9/00* | (2006.01) |
| *A61K 39/395* | (2006.01) |
| *A61K 31/4172* | (2006.01) |
| *A61K 47/26* | (2006.01) |
| *A61K 38/00* | (2006.01) |
| *A61P 25/06* | (2006.01) |
| *A61K 45/06* | (2006.01) |
| *A61K 39/00* | (2006.01) |

(52) U.S. Cl.
CPC ............ *C07K 16/18* (2013.01); *A61K 9/0019* (2013.01); *A61K 31/4172* (2013.01); *A61K 39/3955* (2013.01); *A61K 45/06* (2013.01); *A61K 47/26* (2013.01); *A61P 25/06* (2018.01); *A61K 38/00* (2013.01); *A61K 2039/505* (2013.01); *A61K 2039/545* (2013.01); *C07K 2317/24* (2013.01)

(58) Field of Classification Search
CPC .. C07K 16/18; A61K 9/0019; A61K 39/3955; A61K 38/00
See application file for complete search history.

(56) References Cited

U.S. PATENT DOCUMENTS

| | | |
|---|---|---|
| 5,116,964 A | 5/1992 | Capon et al. |
| 5,266,561 A | 11/1993 | Cooper et al. |
| 5,364,841 A | 11/1994 | Cooper et al. |
| 5,585,089 A | 12/1996 | Queen et al. |
| 5,624,821 A | 4/1997 | Winter et al. |
| 5,648,260 A | 7/1997 | Winter et al. |
| 5,942,227 A | 8/1999 | Cooper et al. |
| 6,180,370 B1 | 1/2001 | Queen et al. |
| 6,313,097 B1 | 11/2001 | Eberlein et al. |
| 6,509,014 B1 | 1/2003 | De Lacharriere et al. |
| 6,521,609 B1 | 2/2003 | Doods et al. |
| 6,737,056 B1 | 5/2004 | Presta |
| 6,956,107 B2 | 10/2005 | Fung et al. |
| 7,279,471 B2 | 10/2007 | Mueller et al. |
| 7,479,488 B2 | 1/2009 | Mueller et al. |
| 7,696,209 B2 | 4/2010 | Mueller et al. |
| 7,700,735 B2 | 4/2010 | Young et al. |
| 7,879,991 B2 | 2/2011 | Vater et al. |
| 7,927,863 B2 | 4/2011 | Cregg et al. |
| 7,935,340 B2 | 5/2011 | Garcia-Martinez et al. |
| 8,007,794 B2 | 8/2011 | Zeller et al. |
| 8,293,239 B2 | 10/2012 | Poulsen et al. |
| 8,298,536 B2 | 10/2012 | Poulsen et al. |
| 8,586,045 B2 | 11/2013 | Zeller et al. |
| 8,597,649 B2 | 12/2013 | Zeller et al. |
| 8,623,366 B2 | 1/2014 | Pios et al. |
| 8,734,802 B1 | 5/2014 | Zeller et al. |
| 9,073,991 B2 | 7/2015 | Allan et al. |
| 9,708,393 B2 | 7/2017 | Russo et al. |
| 9,745,373 B2 | 8/2017 | Kovacevich et al. |
| 9,855,332 B2 | 1/2018 | Russo et al. |
| 10,066,009 B2 | 9/2018 | Kovacevich et al. |
| 10,179,809 B2 | 1/2019 | Kovacevich et al. |
| 10,189,895 B2 | 1/2019 | Kovacevich et al. |
| 10,208,112 B2 | 2/2019 | Kovacevich et al. |
| 10,214,582 B2 | 2/2019 | Kovacevich et al. |

(Continued)

FOREIGN PATENT DOCUMENTS

| | | |
|---|---|---|
| AU | 2006313434 | 5/2007 |
| CA | 2611433 | 12/2006 |

(Continued)

OTHER PUBLICATIONS

Warne, European J. Pharm. Biompharm., 2011, 78:208-12.*

(Continued)

*Primary Examiner* — Olga N Chernyshev
(74) *Attorney, Agent, or Firm* — Robin L. Teskin; Baker, Donelson, Bearman, Caldwell & Berkowitz PC

(57) ABSTRACT

Methods for rapid treatment of chronic migraine are provided. Exemplary methods provide relief from migraine within 24 hours of administration. Also provided are methods for acute treatment of migraine. Exemplary methods comprise administration of an anti-CGRP antagonist antibody to a patient in need thereof.

11 Claims, 63 Drawing Sheets

Specification includes a Sequence Listing.

(56) References Cited

U.S. PATENT DOCUMENTS

| | | |
|---|---|---|
| 10,266,587 B2 | 4/2019 | Russo et al. |
| 10,533,048 B2 | 1/2020 | Kovacevich et al. |
| 2001/0036647 A1 | 11/2001 | Choudary et al. |
| 2002/0162125 A1 | 10/2002 | Salmon et al. |
| 2002/0164707 A1 | 11/2002 | Adamou et al. |
| 2003/0027213 A1 | 2/2003 | Zhu et al. |
| 2003/0181462 A1 | 9/2003 | Doods et al. |
| 2003/0194404 A1 | 10/2003 | Greenfeder et al. |
| 2004/0110170 A1 | 6/2004 | Pisegna et al. |
| 2004/0132824 A1 | 7/2004 | Gil et al. |
| 2005/0234054 A1 | 10/2005 | Mueller et al. |
| 2006/0183700 A1 | 8/2006 | Vater et al. |
| 2006/0270045 A1 | 11/2006 | Cregg et al. |
| 2009/0023644 A1 | 1/2009 | Southard et al. |
| 2009/0028784 A1 | 1/2009 | Garcia-Martinez et al. |
| 2009/0220489 A1 | 9/2009 | Zeller et al. |
| 2010/0152171 A1 | 6/2010 | Rudolf et al. |
| 2011/0054150 A1 | 3/2011 | Poulsen et al. |
| 2011/0257371 A1 | 10/2011 | Poulsen et al. |
| 2011/0305711 A1 | 12/2011 | Allan et al. |
| 2012/0000192 A1 | 1/2012 | Zeller et al. |
| 2012/0114741 A1 | 5/2012 | Aung-Din |
| 2012/0225075 A1 | 9/2012 | Pios et al. |
| 2012/0294797 A1 | 11/2012 | Kovacevich et al. |
| 2012/0294802 A1 | 11/2012 | Russo et al. |
| 2012/0294822 A1 | 11/2012 | Russo et al. |
| 2013/0216535 A1 | 8/2013 | Zeller et al. |
| 2013/0295087 A1 | 11/2013 | Poulsen et al. |
| 2013/0295088 A1 | 11/2013 | Poulsen et al. |
| 2015/0266948 A1 | 9/2015 | Bigal et al. |
| 2017/0088612 A1 | 3/2017 | Bigal |
| 2018/0142029 A1 | 5/2018 | Boone et al. |
| 2018/0161434 A1 | 6/2018 | Russo et al. |
| 2019/0211085 A1 | 7/2019 | Kovacevich et al. |
| 2019/0240331 A1 | 8/2019 | Russo et al. |
| 2019/0367590 A1 | 12/2019 | Russo et al. |
| 2020/0010537 A1 | 1/2020 | Baker et al. |
| 2020/0216524 A1 | 7/2020 | Cady et al. |
| 2020/0216525 A1 | 7/2020 | Cady et al. |

FOREIGN PATENT DOCUMENTS

| | | |
|---|---|---|
| CA | 2626120 | 12/2012 |
| CN | 101309704 | 11/2008 |
| CN | 101979650 | 2/2011 |
| CN | 103421114 | 12/2013 |
| EA | 015526 | 10/2008 |
| EP | 0212432 | 3/1987 |
| EP | 1031350 | 8/2000 |
| EP | 1770091 | 4/2007 |
| EP | 1556020 | 2/2009 |
| EP | 1957106 | 10/2013 |
| JP | HEI6-87890 | 3/1994 |
| JP | 08-268874 | 10/1996 |
| JP | 2005523418 | 8/2005 |
| JP | 2007517911 | 7/2007 |
| JP | 2009-515942 | 4/2009 |
| JP | 2011046710 | 3/2011 |
| JP | 2011513386 | 4/2011 |
| JP | 2011513387 | 4/2011 |
| JP | 5123197 | 1/2013 |
| KR | 10-1250049 | 4/2013 |
| RU | 2329062 | 7/2008 |
| WO | WO 1996/0004928 | 2/1996 |
| WO | WO 97/09046 | 3/1997 |
| WO | WO 98/09630 | 3/1998 |
| WO | WO 98/11128 | 3/1998 |
| WO | WO 98/56779 | 12/1998 |
| WO | WO 00/18764 | 4/2000 |
| WO | WO 2001/022972 | 4/2001 |
| WO | WO 2003/045424 | 6/2003 |
| WO | WO 2003/093472 | 11/2003 |
| WO | WO 03/104236 | 12/2003 |
| WO | WO 2004/003019 | 1/2004 |
| WO | WO 2004/014351 | 2/2004 |
| WO | WO 2004/050683 | 6/2004 |
| WO | WO 2004058184 | 7/2004 |
| WO | WO 2004/082602 | 9/2004 |
| WO | WO 2004/082605 | 9/2004 |
| WO | WO 2004/082678 | 9/2004 |
| WO | WO 2004/083187 | 9/2004 |
| WO | WO 2004/087649 | 10/2004 |
| WO | WO 2004/091514 | 10/2004 |
| WO | WO 2004/092166 | 10/2004 |
| WO | WO 2004/092168 | 10/2004 |
| WO | WO 2004096122 | 11/2004 |
| WO | WO 2004097421 | 11/2004 |
| WO | WO 2005/009962 | 2/2005 |
| WO | WO 2005/040395 | 5/2005 |
| WO | WO 2005041757 | 5/2005 |
| WO | WO 2005070444 | 8/2005 |
| WO | WO 2005/100360 | 10/2005 |
| WO | WO 2006/077212 | 7/2006 |
| WO | WO 2007/025212 | 3/2007 |
| WO | WO 2007/048026 | 4/2007 |
| WO | WO 2007/054800 | 5/2007 |
| WO | WO 2007/054809 | 5/2007 |
| WO | WO 2007/061676 | 5/2007 |
| WO | WO 2007/076336 | 7/2007 |
| WO | WO 2007/141285 | 12/2007 |
| WO | WO 2008/011190 | 1/2008 |
| WO | WO 2009/109908 | 9/2009 |
| WO | WO 2009/109911 | 9/2009 |
| WO | WO 2010075238 | 7/2010 |
| WO | WO 2011/024113 | 3/2011 |
| WO | WO 2011/156324 | 12/2011 |
| WO | 2015143409 | 9/2015 |
| WO | 2016171742 | 10/2016 |
| WO | 2016205037 | 12/2016 |

OTHER PUBLICATIONS

"Cluster Headache," Wolff's Headache 1974, p. 348.
"Highlights of Prescribing Information" BLA STN 103000/5215—FDA Approved Labeling Text, Botox Package Insert, Oct. 2010, 25 pages.
"Teva to Acquire Labrys Biologies, Inc.: Novel Migraine Prophylaxis Treatment Adds Significant New Dimension to Teva's Growing Pain Care Franchise""Business Wire Jun. 3, 2014." 4 pages.
"TMJ Disorders," National Institute of Dental and Craniofacial Research, NIH Publication No. 15-3487, Apr. 2015. 20 pages.
Abdiche YN, et al. "Probing the binding mechanism and affinity of tanezumab, a recombinant humanized anti-NGF monoclonal antibody, using a repertoire of biosensors," Protein Sci. Aug. 2008;17(8):1326-35.
Adwanikar H, et al. Spinal CGRP1 receptors contribute to supraspinally organized pain behavior and pain-related sensitization of amygdala neurons. Pain. Nov. 2007;132(1-2):53-66. Epub Mar. 1, 2007.
Akerman S, et al. "Nitric oxide synthase inhibitors can antagonize neurogenic and calcitonin gene-related peptide induced dilation of dural meningeal vessels," Br J Pharmacol. Sep. 2002;137(1):62-8.
Akerman, S., et al. "Pearls and pitfalls in experimental in vivo models of migraine: dural trigeminovascular nociception," Cephalalgia. Jun. 2013;33(8):577-92.
Alder Biopharmaceuticals Inc., "Alder Presents Positive ALD403 Clinical Data at European Headache and Migraine Trust International Congress," Press Release, Sep. 15, 2016.
Alder Biopharmaceuticals Inc., "Alder Presents Positive Clinical Data for ALD403 at the 17th Congress of the International Headache Society" Press Release, May 15, 2015. (3 pages).
Alder Biopharmaceuticals Inc., "Alder Reports Phase 2b Trial of ALD403 Meets Primary and Secondary Endpoints Demonstrating Migraine Prevention in Patients with Chronic Migraine," Press Release, Mar. 28, 2016. (4 pages).
Alder Biopharmaceuticals Inc., "Alder Reports Positive Top-Line 24-Week Data Demonstrating Persistent Migraine Prevention in Phase 2b Study of ALD403 in Patients with Chronic Migraine" Press Release, Jul. 25, 2016. (3 pages).
Alder Biopharmaceuticals Inc., "Data From Proof-of-Concept Clinical Trial of ALD403, a Monoclonal Antibody Against CGRP for the

(56) References Cited

OTHER PUBLICATIONS

Prevention of Migraine, to be Presented at 56th Annual Scientific Meeting of the American Headache Society," Press Release, Jun. 26, 2014. 2 pages.
Almagro JC et al. "Chapter 13 Antibody Engineering: Humanization, Affinity Maturation, and Selection Techniques." Therapeutic Monoclonal Antibodies: From Bench to Clinic (Zhiqiang An (Editor)) Oct. 2009: 311-34.
Amara SG, et al. "Expression in brain of a messenger RNA encoding a novel neuropeptide homologous to calcitonin gene-related peptide." Science. Sep. 1, 19853;229(4718):1094-7.
Ambalavanar R., et al. "Deep tissue inflammation upregulates neuropeptides and evokes nociceptive behaviors which are modulated by a neuropeptide antagonist." Pain. Jan. 2006;120(1-2):53-68. Epub Dec. 13, 2005.
Amrutkar DV. "Calcitonin gene-related peptide (CGRP) uptake and release in rat dura mater, trigeminal ganglion and trigeminal nucleus caudalis," PhD thesis, Faculty of Health and Medical Sciences University of Copenhagen, Academic advisor: Inger Jansen-Olesen and Jes Olesen, Submitted: Feb. 20, 2013.
An Z. "Therapeutic Monoclonal Antibodies: From Bench to Clinic." Wiley & Sons, Inc., 2009 Chapter 31, 711-62.
Andersen DC, et al. "Production technologies for monoclonal antibodies and their fragments," Curr Opin Biotechnol. Oct. 2004;15(5):456-62.
Andrew DP, et al. "Monoclonal antibodies distinguishing alpha and beta forms of calcitonin gene-related peptide." J Immunol Methods. Nov. 6, 1990;134(1):87-94.
Antibody Structure and Function, Chapter 4 of Elgert's Immunology: Understanding the Immune System, pp. 58-78. Wiley 1998.
Aoki KR. "Review of a proposed mechanism for the antinociceptive action of botulinum toxin type A," Neurotoxicology. Oct. 2005;26(5):785-93.
Aoki-Nagase T, et al. "Attenuation of antigen-induced airway hyperresponsiveness in CGRP-deficient mice," Am J Physiol Lung Cell Mol Physiol. Nov. 2002;283(5):L963-70.
Armour KL, et al. "Recombinant human IgG molecules lacking Fcgamma receptor I binding and monocyte triggering activities," Eur J Immunol. Aug. 1999;29(8):2613-24.
Arulmani U, et al. "Calcitonin gene-related peptide and its role in migraine pathophysiology." Eur J Pharmacol. Oct. 1, 2004;500(1-3):315-30.
Arulmani U, et al. "Experimental migraine models and their relevance in migraine therapy," Cephalalgia. Jun. 2006;26(6):642-59.
Arulmozhi DK, et al., "Migraine: current concepts and emerging therapies." Vascul Pharmacol. Sep. 2005;43(3):176-87.
Asghar, MS, et al. "Evidence for a vascular factor in migraine," Ann Neurol. Apr. 2011;69(4):635-45.
Ashina M, "Vascular changes have a primary role in migraine," Cephalalgia. Apr. 2012;32(5):428-30.
Ashina M, et al. "Evidence for increased plasma levels of calcitonin gene-related peptide in migraine outside of attacks." Pain. May 2000;86(1-2):133-8.
Ashina M, et al. "Pearls and pitfalls in human pharmacological models of migraine: 30 years' experience," Cephalalgia. Jun. 2013;33(8):540-53.
Ashina M, et al. "Plasma levels of calcitonin gene-related peptide in chronic tension-type headache," Neurology. Nov. 14, 2000;55(9):1335-40.
Ashina M. "Calcitonin gene-related peptide in tension-type headache," ScientificWorldJournal. Jun. 7, 2002;2:1527-31.
Aziz Q., "Visceral hypersensitivity: fact or fiction." Gastroenterology. Aug. 2006;131(2):661-4.
Bagdy, G, et al. "Headache-type adverse effects of NO donors: vasodilation and beyond," Br J Pharmacol. May 2010;160(1):20-35.
Balint RF, et al. "Antibody engineering by parsimonious mutagenesis." Gene. Dec. 27, 1993;137(1):109-18.
Barker JN, et al. "Progress in psoriasis. Psoriasis: from gene to clinic. London, UK, Dec. 5-7, 1996," Mol Med Today. May 1997;3(5):193-4.

Batra SK, et al. "Pharmacokinetics and biodistribution of genetically engineered antibodies," Curr Opin Biotechnol. Dec. 2002;13(6):603-8.
Baxter LT, et al. "Biodistribution of monoclonal antibodies: scale-up from mouse to human using a physiologically based pharmacokinetic model," Cancer Res. Oct. 15, 1995;55(20):4611-22.
Bell RD, et al. "Breaching the blood-brain barrier for drug delivery," Neuron. Jan. 8, 2014;81(1):1-3.
Benarroch EE. "CGRP: sensory neuropeptide with multiple neurologic implications," Neurology. Jul. 19, 2011;77(3):281-7.
Benemei S, et al. "CGRP receptors in the control of pain and inflammation," Curr Opin Pharmacol. Feb. 2009;9(1):9-14.
Benemei S, et al. "Migraine," Handb Exp Pharmacol. 2009;(194):75-89.
Benemei S, et al. "Pain pharmacology in migraine: focus on CGRP and CGRP receptors," Neurol Sci. May 2007;28 Suppl 2:S89-93.
Benincosa LJ, et al. "Pharmacokinetics and Pharmacodynamics of a Humanized Monoclonal Antibody to Factor IX in Cynomolgus Monkeys," J Pharmacol Exp Ther. Feb. 2000;292(2):810-6.
Bennett AD, et al. "Alleviation of mechanical and thermal allodynia by CGRP(8-37) in a rodent model of chronic central pain." Pain. May 2000;86(1-2):163-75.
Benschop U.S. Appl. No. 60/753,044, filed Dec. 22, 2005. File History. 48 pages.
Biacore 3000 Instrument Handbook, Mar. 1999. 201 pages.
Bigal and Krymchantowski, "Emerging drugs for migraine prophylaxis and treatment," Med. Gen. Med. 2006;8(2):31.
Bigal M. "Clinical Trials Update—2012: Year in Review—A Comment" Headache. Jun. 2013;53(6):1003-4.
Bigal ME, et al. "Emerging drugs for migraine prophylaxis and treatment," MedGenMed. May 4, 2006;8(2):31.
Bigal ME, et al. "Ergotamine and dihydroergotamine: a review," Curr Pain Headache Rep. Feb. 2003;7(1):55-62.
Bigal ME, et al. "Headache prevention outcome and body mass index," Cephalalgia. Apr. 2006;26(4):445-50.
Bigal ME, et al. "Migraine in the Triptan Era: Lessons From Epidemiology, Pathophysiology, and Clinical Science," Headache. Feb. 2009;49 Suppl 1:S21-33.
Bigal ME, et al. "Migraine in the triptan era: progresses achieved, lessons learned and future developments," Arq Neuropsiquiatr. Jun. 2009;67(2B):559-69.
Bigal ME, et al. "Modifiable risk factors for migraine progression," Headache. Oct. 2006;46(9):1334-43.
Bigal ME, et al. "Monoclonal Antibodies for Migraine: Preventing Calcitonin Gene-Related Peptide Activity," CNS Drugs. May 2014;28(5):389-99.
Bigal ME, et al. "New developments in migraine prophylaxis," Expert Opin Pharmacother. Apr. 2003;4(4):433-43.
Bigal ME, et al. "New migraine preventive options: an update with pathophysiological considerations," Rev Hosp Clin Fac Med Sao Paulo. Nov.-Dec. 2002;57(6):293-8.
Bigal ME, et al. "Obesity and migraine: a population study," Neurology. Feb. 28, 2006;66(4):545-50.
Bigal ME, et al. "Obesity is a risk factor for transformed migraine but not chronic tension-type headache," Neurology. Jul. 25, 2006;67(2):252-7.
Bigal ME, et al. "Prophylactic migraine therapy: emerging treatment options," Curr Pain Headache Rep. Jun. 2004;8(3):178-84.
Bigal ME, et al. "Safety and tolerability of LBR-101, a humanized monoclonal antibody that blocks the binding of CGRP to its receptor: Results of the Phase 1 program," Cephalalgia. Dec. 23, 2013;34(7):483-492.
Bigal ME, et al. "Safety, tolerability, and efficacy of TEV-48125 for preventive treatment of high-frequency episodic migraine: a multicentre, randomised, double-blind, placebo-controlled, phase 2b study," Lancet Neurol. Nov. 2015;14(11):1081-90.
Bigal ME, et al. "The preventive treatment of migraine," Neurologist. Jul. 2006;12(4):204-13.
Bigal ME, et al. "The triptans," Expert Rev Neurother. May 2009;9(5):649-59.
Bigal, ME "Glutamate Receptor Antagonists," Headache Currents, 1:20-21. Jul. 2004.

(56) References Cited

OTHER PUBLICATIONS

Birder L, et al. "Neural control of the lower urinary tract: peripheral and spinal mechanisms," Neurourol Urodyn. 2010;29(1):128-39.
Boeckh M, et al. "Phase 1 Evaluation of the Respiratory Syncytial Virus-Specific Monoclonal Antibody Palivizumab in Recipients of Hematopoietic Stem Cell Transplants," J Infect Dis. Aug. 1, 2001;184(3):350-4.
Bolay H, et al. "Intrinsic brain activity triggers trigeminal meningeal afferents in a migrane model," Nat Med. Feb. 2002;8(2):136-42.
Brain SD, et al. "CGRP receptors: a headache to study, but will antagonists prove therapeutic in migraine?" Trends Pharmacol Sci. Feb. 2002;23(2):51-3.
Brain SD, et al. "Vascular actions of calcitonin gene-related peptide and adrenomedullin." Physiol Rev. Jul. 2004;84(3):903-34.
Brekke OH, et al. "Therapeutic Antibodies For Human Diseases at the Dawn of The Twenty-First Century," Nat Rev Drug Discov. Jan. 2003;2(1):52-62.
Brorson K, et al. "Mutational analysis of avidity and fine specificity of anti-levan antibodies." J Immunol. Dec. 15, 1999;163(12):6694-701.
Brüggemann M, et al. "The Immunogenicity of Chimeric Antibodies," J Exp Med. Dec. 1, 1989;170(6):2153-7.
Brummell DA, et al. "Probing the combining site of an anti-carbohydrate antibody by saturation-mutagenesis: role of the heavy-chain CDR3 residues." Biochemistry. Feb. 2, 1993;32(4):1180-7.
Buckley TL, et al. "The partial inhibition of inflammatory responses induced by capsaicin using the Fab fragment of a selective calcitonin gene-related peptide antiserum in rabbit skin." Neuroscience. Jun. 1992;48(4):963-8.
Burks EA, "In vitro scanning saturation mutagenesis of an antibody binding pocket." Proc Natl Acad Sci U S A. Jan. 21, 1997;94(2):412-7.
Buzzi MG, et al. "The antimigraine drug, sumatriptan (GR43175), selectively blocks neurogenic plasma extravasation from blood vessels in dura mater," Br J Pharmacol. Jan. 1990;99(1):202-6.
Carter PJ. "Potent antibody therapeutics by design," Nat Rev Immunol. May 2006;6(5):343-57.
Casset F, et al. "A peptide mimetic of an anti-CD4 monoclonal antibody by rational design." Biochem Biophys Res Commun. Jul. 18, 2003;307(1):198-205.
Castaño A, et al. "Headache in symptomatic intracranial hypertension secondary to leptospirosis: a case report," Cephalalgia. Apr. 2005;25(4):309-11.
Cernuda-Morollón E, et al. "CGRP and VIP levels as predictors of efficacy of Onabotulinumtoxin type A in chronic migraine," Headache. Jun. 2014;54(6):987-95.
Chancellor MB, et al. "Neurophysiology of stress urinary incontinence," Rev Urol. 2004;6 Suppl 3:S19-28.
Charbit, A et al. "Dopamine: what's new in migraine?" Curr Opin Neurol. Jun. 2010;23(3):275-81.
Charles A, "Migraine is not primarily a vascular disorder," Cephalalgia. Apr. 2012;32(5):431-2.
Chauhan M, et al. "Studies on the effects of the N-terminal domain antibodies of calcitonin receptor-like receptor and receptor activity-modifying protein 1 on calcitonin gene-related peptide-induced vasorelaxation in rat uterine artery," Biol Reprod. Jun. 2004;70(6):1658-63.
Chen JT, et al. "Menopausal flushes and calcitonin-gene-related peptide," Lancet. Jul. 3, 1993;342(8862):49.
Chen Y, et al. "Selection and analysis of an optimized anti-VEGF antibody: crystal structure of an affinity-matured Fab in complex with antigen." J Mol Biol. Nov. 5, 1999;293(4):865-81.
Cheung B et al. "Adrenomedullin: Its Role in the Cardiovascular System," Semin Vasc Med. May 2004;4(2):129-34.
Chowdhury PS, et al. "Tailor-made antibody therapeutics," Methods. May 2005;36(1):11-24.
Chuang YC, et al. "Intraprostatic botulinum toxin a injection inhibits cyclooxygenase-2 expression and suppresses prostatic pain on capsaicin induced prostatitis model in rat," J Urol. Aug. 2008;180(2):742-8.
Chuang YC, et al. "Urodynamic and immunohistochemical evaluation of intravesical botulinum toxin A delivery using liposomes," J Urol. Aug. 2009;182(2):786-92.
Cianchetti C. "The role of the neurovascular scalp structures in migraine," Cephalalgia. Jul. 2012;32(10):778-84.
Colcher D, et al. "Pharmacokinetics and biodistribution of genetically-engineered antibodies," Q J Nucl Med. Dec. 1998;42(4):225-41.
Colman PM. "Effects of amino acid sequence changes on antibody-antigen interactions." Res Immunol. Jan. 1994;145(1):33-6.
Conner AC, et al. "Interaction of calcitonin-gene-related peptide with its receptors." Biochem Soc Trans. Aug. 2002;30(4):451-5.
Conner AC, et al. "Ligand binding and activation of the CGRP receptor," Biochem Soc Trans. Aug. 2007;35(Pt 4):729-32.
Connor K M et al: "Randomized, controlled trial of telcagepant for the acute treatment of migraine.", Neurology Sep. 22, 2009, vol. 73, No. 12, Sep. 22, 2009 (Sep. 22, 2009), pp. 970-977, XP002732737, ISSN: 1526-632X.
Correia IR. "Stability of IgG isotypes in serum," MAbs. May-Jun. 2010;2(3):221-32.
Cottrell GS, et al. "Localization of calcitonin receptor-like receptor (CLR) and receptor activity-modifying protein 1 (RAMP1) in human gastrointestinal tract," Peptides. Jun. 2012;35(2):202-11.
Covell DG, et al. "Pharmacokinetics of monoclonal immunoglobulin G1, F(ab')2, and Fab' in mice." Cancer Res. Aug. 1986;46(8):3969-78.
Cutrer F. "Pathophysiology of Migraine," Semin Neurol. Apr. 2006;26(2):171-80.
Cutrer F. "Pathophysiology of Migraine," Semin Neurol. Apr. 2010;30(2):120-30.
Dakhama A, et al. "Calcitonin gene-related peptide: role in airway homeostasis," Curr Opin Pharmacol. Jun. 2004;4(3):215-20.
Davies J, et al. "Affinity improvement of single antibody VH domains: residues in all three hypervariable regions affect antigen binding." Immunotechnology. Sep. 1996;2(3):169-79.
Davis CD et al. "The Tortuous Road to an Ideal CGRP Function Blocker for the Treatment of Migraine," Curr Top Med Chem. 2008;8(16):1468-79.
Davletov B, et al. "Beyond Botox: advantages and limitations of individual botulinum neurotoxins," Trends Neurosci. Aug. 2005;28(8):446-52.
De Pascalis R, et al. "Grafting of "abbreviated" complementarity-determining regions containing specificity-determining residues essential for ligand contact to engineer a less immunogenic humanized monoclonal antibody." J Immunol. Sep. 15, 2002;169(6):3076-84.
Delafoy L, et al. "Interactive involvement of brain derived neurotrophic factor, nerve growth factor, and calcitonin gene related peptide in colonic hypersensitivity in the rat." Gut. Jul. 2006;55(7):940-5. Epub Jan. 9, 2006.
Denekas T, et al. "Inhibition of stimulated meningeal blood flow by a calcitonin gene-related peptide binding mirror-image RNA oligonucleotide," Br J Pharmacol. Jun. 2006;148(4):536-43.
Deng R et al. "Projecting human pharmacokinetics of therapeutic antibodies from nonclinical data," MAbs. Jan.-Feb. 2011;3(1):61-6.
Derosa G, et al. "Optimizing combination treatment in the management of type 2 diabetes," Vase Health Risk Manag. 2007;3(5):665-71.
Diamond S, et al. "Patterns of diagnosis and acute and preventive treatment for migraine in the United States: results from the American Migraine Prevalence and Prevention study," Headache. Mar. 2007;47(3):355-63.
Diener HC, et al. "Utility of topiramate for the treatment of patients with chronic migraine in the presence or absence of acute medication overuse," Cephalalgia. Oct. 2009;29(10):1021-7.
Dockray et al., "Immunoneutralization studies with calcitonin gene-related peptide," Ann. NY Acad Sci. 1992;657:258-67.
Dodick D, et al. "Cluster Headache: Diagnosis, Management and Treatment," Wolff's Headache 2001, p. 283.
Dodick DW, et al. "Safety and efficacy of ALD403, an antibody to calcitonin gene-related peptide, for the prevention of frequent

(56) References Cited

OTHER PUBLICATIONS episodic migraine: a randomised, double-blind, placebo-controlled, exploratory phase 2 trial," Lancet Neurol. Nov. 2014;13(11):1100-7.
Doggrell S. "Migraine and beyond: cardiovascular therapeutic potential for CGRP modulators," Expert Opin Investig Drugs. Jun. 2001;10(6):1131-8.
Dolgin E. "Antibody drugs set to revive flagging migraine target," Nat Rev Drug Discov. Apr. 2013;12(4):249-50.
Doods H, et al. "Pharmacological profile of BIBN4096BS, the first selective small molecule CGRP antagonist." Br J Pharmacol. Feb. 2000;129(3):420-3.
Doods, H et al. "CGRP antagonists: unravelling the role of CGRP in migraine," Trends Pharmacol Sci. Nov. 2007;28(11):580-7.
Dooley JS, et al. "Antibiotics in the treatment of biliary infection," Gut. Sep. 1984;25(9):988-98.
Drake AW, et al. "Characterizing high-affinity antigen/antibody complexes by kinetic- and equilibrium-based methods," Anal Biochem. May 1, 2004;328(1):35-43.
Dressler and Saberi, "Botulinum toxin: mechanisms of action," Eur. Neurol, 2005;53:3-9.
Dressler D, et al. "Botulinum toxin: mechanisms of action," Arq Neuropsiquiatr. Mar. 2005;63(1):180-5.
Dufner P, et al. "Harnessing phage and ribosome display for antibody optimisation." Trends Biotechnol. Nov. 2006;24(11):523-9. Epub Sep. 26, 2006.
Durham P. "CGRP-receptor antagonists—a fresh approach to migraine therapy?" N Engl J Med. Mar. 11, 2004;350(11):1073-5.
Durham Paul L et al: "Calcitonin Gene-Related Peptide (CGRP) Receptor Antagonists in the Treatment of Migraine", CNS Drugs, vol. 24, No. 7, 2010, pp. 539-548.
Durham PL et al. "New insights into the molecular actions of serotonergic antimigraine drugs," Pharmacol Ther. Apr.-May 2002;94(1-2):77-92.
Durham PL, et al. "Regulation of calcitonin gene-related peptide secretion from trigeminal nerve cells by botulinum toxin type A: implications for migraine therapy," Headache. Jan. 2004;44(1):35-42; discussion 42-3.
Durham PL. "Calcitonin Gene-Related Peptide (CGRP) and Migraine," Headache. Jun. 2006;46 Suppl 1:S3-8.
Durham PL. "Inhibition of calcitonin gene-related peptide function: a promising strategy for treating migraine," Headache. Sep. 2008;48(8):1269-75.
Edvinsson L et al. "Blockade of CGRP receptors in the intracranial vasculature: a new target in the treatment of headache," Cephalalgia. Aug. 2004;24(8):611-22.
Edvinsson L et al. "CGRP Receptor Antagonism and Migraine," Neurotherapeutics. Apr. 2010;7(2):164-75.
Edvinsson L et al. "Extracerebral manifestations in migraine. A peptidergic involvement?" J Intern Med. Oct. 1990;228(4):299-304.
Edvinsson L et al. "Neurobiology in primary headaches," Brain Res Brain Res Rev. Jun. 2005;48(3):438-56.
Edvinsson L et al. "Perivascular neuropeptides (NPY, VIP, CGRP and SP) in human brain vessels after subarachnoid haemorrhage," Acta Neurol Scand. Nov. 1994;90(5):324-30.
Edvinsson L et al. "The blood-brain barrier in migraine treatment," Cephalalgia. Dec. 2008;28(12):1245-58.
Edvinsson L et al: "New drugs in migraine treatment and prophylaxis: telcagepant and topiramate", The Lancet, The Lancet Publishing Group, GB, vol. 376, No. 9741, Aug. 21, 2010 (Aug. 21, 2010), pp. 645-655.
Edvinsson L, et al. "Calcitonin gene-related peptide and cerebral blood vessels: distribution and vasomotor effects," J Cereb Blood Flow Metab. Dec. 1987;7(6):720-8.
Edvinsson L, et al. "Inhibitory effect of BIBN4096BS, CGRP(8-37), a CGRP antibody and an RNA-Spiegelmeron CGRP induced vasodilatation in the perfused and non-perfused rat middle cerebral artery." Br J Pharmacol. Mar. 2007;150(5):633-40. Epub Jan. 22, 2007.
Edvinsson L, et al. "Innervation of the human middle meningeal artery: immunohistochemistry, ultrastructure, and role of endothelium for vasomotility," Peptides. 1998;19(7):1213-25.
Edvinsson L, et al. "Neuropeptides in migraine and cluster headache," Cephalalgia. Oct. 1994;14(5):320-7.
Edvinsson L. "Aspects on the Pathophysiology of Migraine and Cluster Headache," Pharmacol Toxicol. Aug. 2001;89(2):65-73.
Edvinsson L. "Calcitonin Gene-Related Peptide (CGRP) and the Pathophysiology of Headache Therapeutic Implications," CNS Drugs. 2001;15(10):745-53.
Edvinsson L. "CGRP blockers in migraine therapy: where do they act?" Br J Pharmacol. Dec. 2008;155(7):967-9.
Edvinsson L. "CGRP-receptor antagonism in migraine treatment," Lancet. Dec. 20, 2008;372(9656):2089-90.
Edvinsson L. "Clinical Data on the CGRP Antagonist BIBN4096BS for Treatment of Migraine Attacks," CNS Drug Rev. 2005 Spring;11(1):69-76.
Edvinsson L. "Innervation and effects of dilatory neuropeptides on cerebral vessels. New aspects," Blood Vessels. 1991;28(1-3):35-45.
Edvinsson L. "Neuronal Signal Substances as Biomarkers of Migraine," Headache. Jul.-Aug. 2006;46(7):1088-94.
Edvinsson L. "New therapeutic target in primary headaches— blocking the CGRP receptor," Expert Opin Ther Targets. Jun. 2003;7(3):377-83.
Edvinsson L. "Novel migraine therapy with calcitonin gene-regulated peptide receptor antagonists," Expert Opin Ther Targets. Sep. 2007;11(9):1179-88.
Edvinsson L: "CGRP blockers in migraine therapy: where do they act?", British Journal of Pharmacology, vol. 155, No. 7, Dec. 2008 (Dec. 2008), pp. 967-969.
Edvinsson Lars: "CGRP-receptor antagonism in migraine treatment.", Lancet Dec. 20, 2008, vol. 372, No. 9656, Dec. 20, 2008 (Dec. 20, 2008), pp. 2089-2090.
Eftekhari S et al. "Differentiation of Nerve Fibers Storing CGRP and CGRP Receptors in the Peripheral Trigeminovascular System," J Pain. Nov. 2013;14(11):1289-303.
Elshourbagy NA, et al. "Molecular cloning and characterization of the porcine calcitonin gene-related peptide receptor." Endocrinology. Apr. 1998;139(4):1678-83.
Emerick GT. "Migraines in the Presence of Glaucoma, Recent advances in diagnosis and management," Glaucoma Today, Sep./Oct. 2008, 21-23.
Escott et al., "Effect of a calcitonin gene-related peptide antagonist (CGRP8-37) on skin vasodilatation and oedema induced by stimulation of the rat saphenous nerve," Br. J. Pharmacol. 1993;110:772-6.
Escott KJ, et al. "Trigeminal ganglion stimulation increases facial skin blood flow in the rat: a major role for calcitonin gene-related peptide." Brain Res. Jan. 9, 1995;669(1):93-9.
Esfandyari T. "The Role Of Calcitonin Gene-Related Peptide (CGRP) In Colonic Inflammation, and Secretion in the Rat Distal Colon," Thesis, University of Calagary, Department of Neuroscience and Gastrointestinal Sciences. 1999. 145 pages.
Evans BN, et al. "CGRP-RCP, a novel protein required for signal transduction at calcitonin gene-related peptide and adrenomedullin receptors," J Biol Chem. Oct. 6, 2000;275(40):31438-43.
Evans RW, et al. "Target doses and titration schedules for migraine preventive medications," Headache. Jan. 2006;46(1):160-4.
Evans RW. "Exploding head syndrome followed by sleep paralysis: a rare migraine aura," Headache. Apr. 2006;46(4):682-3.
Everitt DE et al. "The Pharmacokinetics, Antigenicity, and Fusion-Inhibition Activity of RSHZ19, a Humanized Monoclonal Antibody to Respiratory Syncytial Virus, in Healthy Volunteers," J Infect Dis. Sep. 1996;174(3):463-9.
Faraci FM, et al. "Vascular responses of dura mater," Am J Physiol. Jul. 1989;257(1 Pt 2):H157-61.
Farinelli, I et al. "Future drugs for migraine," Intern Emerg Med. Oct. 2009;4(5):367-73.
Feuerstein G et al. "Clinical perspectives of calcitonin gene related peptide pharmacology," Can J Physiol Pharmacol. Jul. 1995;73(7):1070-4.

(56) References Cited

OTHER PUBLICATIONS

File History U.S. Appl. No. 60/736,623, filed Nov. 14, 2005, Zeller, et al. Antagonist Antibodies Directed Against Calcitonin Gene-Related Peptide and Methods Using Same. 110 pages.
Fischer MJ et al. "The Nonpeptide Calcitonin Gene-Related Peptide Receptor Antagonist BIBN4096BS Lowers the Activity of Neurons with Meningeal Input in the Rat Spinal Trigeminal Nucleus," J Neurosci. Jun. 22, 2005;25(25):5877-83.
Fischer MJ. "Calcitonin gene-related peptide receptor antagonists for migraine," Expert Opin Investig Drugs. Jul. 2010;19(7):815-23.
Forssman B, et al. "Atenolol for migraine prophylaxis," Headache. Jul. 1983;23(4):188-90.
Forster ER, et al. "The role of calcitonin gene-related peptide in gastric mucosal protection in the rat," Exp Physiol. Jul. 1991;76(4):623-6.
Friend PJ, et al. "Phase I study of an engineered aglycosylated humanized CD3 antibody in renal transplant rejection," Transplantation. Dec. 15, 1999;68(11):1632-7.
Frobert Y, et al. "A sensitive sandwich enzyme immunoassay for calcitonin gene-related peptide (CGRP): characterization and application." Peptides. 1999;20(2):275-84.
Galitsky BA, et al. "Predicting amino acid sequences of the antibody human VH chains from its first several residues," Proc Natl Acad Sci USA. Apr. 28, 1998;95(9):5193-8.
Gallai V, et al. "Vasoactive peptide levels in the plasma of young migraine patients with and without aura assessed both interictally and ictally." Cephalalgia. Oct. 1995;15(5):384-90.
Gangula PR, et al. "Increased blood pressure in alpha-calcitonin gene-related peptide/calcitonin gene knockout mice," Hypertension. Jan. 2000;35(1 Pt 2):470-5.
Gearing D, et al. "A fully caninised anti-NGF monoclonal antibody for pain relief in dogs," BMC Vet Res. Nov. 9, 2013;9:226.
Geppetti P et al. "Antidromic vasodilatation and the migraine mechanism," J Headache Pain. Mar. 2012;13(2):103-11.
Geppetti P et al. "CGRP and migraine: neurogenic inflammation revisited," J Headache Pain. Apr. 2005;6(2):61-70.
Geppetti P et al. "Novel therapeutic targets," Neurol Sci. May 2006;27 Suppl 2:S111-4.
Giamberardino MA, et al. "Emerging drugs for migraine treatment," Expert Opin Emerg Drugs. Mar. 2015;20(1):137-47.
Gillies S et al. "Improving the efficacy of antibody-interleukin 2 fusion proteins by reducing their interaction with Fc receptors," Cancer Res. May 1, 1999 ;59(9):2159-66.
Giniatullin R et al. "Molecular Mechanisms of Sensitization of Pain-transducing P2X3 Receptors by the Migraine Mediators CGRP and NGF," Mol Neurobiol. Feb. 2008;37(1):83-90.
Glennie MJ, et al. "Clinical trials of antibody therapy," Immunol Today. Aug. 2000;21(8):403-10.
Glover V, et al. "Can the vascular and neurogenic theories of migraine finally be reconciled?" Trends Pharmacol Sci. Jan. 1989;10(1):1-3.
Goadsby PJ et al. "Release of vasoactive peptides in the extracerebral circulation of humans and the cat during activation of the trigeminovascular system," Ann Neurol. Feb. 1988;23(2):193-6.
Goadsby PJ, et al. "Migraine—current understanding and treatment." N Engl J Med. Jan. 24, 2002;346(4):257-70.
Goadsby PJ, et al. "Vasoactive peptide release in the extracerebral circulation of humans during migraine headache." Ann Neurol. Aug. 1990;28(2):183-7.
Goadsby PJ. "Advances in the understanding of headache," Br Med Bull. Oct. 5, 2005;73-74:83-92. Print 2005.
Goadsby PJ. "Calcitonin gene-related peptide antagonists as treatments of migraine and other primary headaches," Drugs. 2005;65(18):2557-67.
Goadsby PJ. "Can we develop neurally acting drugs for the treatment of migraine?" Nat Rev Drug Discov. Sep. 2005;4(9):741-50.
Goadsby PJ. "Headache: a good year for research," Lancet Neurol. Jan. 2006;5(1):5-6.
Goadsby PJ. "Migraine Pathophysiology," Headache. Apr. 2005;45 Suppl 1:S14-24.
Goadsby PJ. "New targets in the acute treatment of headache," Curr Opin Neurol. Jun. 2005;18(3):283-8.
Goadsby PJ. "The vascular theory of migraine—a great story wrecked by the facts," Brain. Jan. 2009;132(Pt 1):6-7.
Goadsby, PJ, et al. "Randomized, double-blind, placebo-controlled trial of ALD403, an anti-CGRP antibody in the prevention of frequent episodic migraine." 56th Annual Scientific Meeting of the American Headache Society, Jun. 2014. 4 pages.
Gómez-Foix AM, et al., "Anti-insulin effects of amylin and calcitonin-gene-related peptide on hepatic glycogen metabolism," Biochem J. Jun. 15, 1991;276 ( Pt 3):607-10.
Green LL, et al. "Antigen-specific human monoclonal antibodies from mice engineered with human Ig heavy and light chain YACs," Nat Genet. May 1994;7(1):13-21.
Grunenberger F. "[Calcitonin gene-related peptide (CGRP): a vasodilator neuropeptide with many potential applications]" Pathol Biol (Paris). Dec. 1993;41(10):936-42.
Gupta S et al. "Evidence for CGRP re-uptake in rat dura mater encephali," Br J Pharmacol. Dec. 2010;161(8):1885-98.
Gupta S et al. "Intravital microscopy on a closed cranial window in mice: a model to study trigeminovascular mechanisms involved in migraine," Cephalalgia. Nov. 2006;26(11):1294-303.
Gupta S et al. "Potential role of female sex hormones in the pathophysiology of migraine," Pharmacol Ther. Feb. 2007;113(2):321-40.
Gupta S et al. "The relevance of preclinical research models for the development of antimigraine drugs: focus on 5-HT(1B/1D) and CGRP receptors," Pharmacol Ther. Oct. 2010; 128(1):170-90.
Hakala JM, et al. "Modelling constrained calcitonin gene-related peptide analogues." Protein Eng. Feb. 1996;9(2):143-8.
Halimi S, et al. "Combination treatment in the management of type 2 diabetes: focus on vildagliptin and metformin as a single tablet," Vasc Health Risk Manag. 2008;4(3):481-92.
Hanes J et al. "Picomolar affinity antibodies from a fully synthetic naive library selected and evolved by ribosome display," Nat Biotechnol. Dec. 2000;18(12):1287-92.
Hansen JM, et al. "Calcitonin gene-related peptide triggers migraine-like attacks in patients with migraine with aura," Cephalalgia. Oct. 2010;30(10):1179-86.
Hargreaves R. "New Migraine and Pain Research," Headache. Apr. 2007;47 Suppl 1:S26-43.
Hatcher JP, et al. "Biologies: the next-generation therapeutics for analgesia?" Expert Rev Neurother. Nov. 2011;11(11):1653-8.
Hay D et al. "A comparison of the actions of BIBN4096BS and CGRP(8-37) on CGRP and adrenomedullin receptors expressed on SK-N-MC, L6, col. 29 and Rat 2 cells," Br J Pharmacol. Sep. 2002;137(1):80-6.
Hay D et al. "International Union of Pharmacology. LXIX. Status of the Calcitonin Gene-Related Peptide Subtype 2 Receptor," Pharmacol Rev. Jun. 2008;60(2):143-5.
Hay D et al. "The pharmacology of CGRP-responsive receptors in cultured and transfected cells," Peptides. Nov. 2004;25(11):2019-26.
Hay D et al. "The Preclinical Pharmacology of BIBN4096BS, a CGRP Antagonist," Cardiovasc Drug Rev. 2005 Spring;23(1):31-42.
Hay D. "What Makes a CGRP2 Receptor?" Clin Exp Pharmacol Physiol. Oct. 2007;34(10):963-71.
Hay DL, et al. "CL/RAMP2 and CL/RAMP3 produce pharmacologically distinct adrenomedullin receptors: a comparison of effects of adrenomedullin22-52, CGRP8-37 and BIBN4096BS," Br J Pharmacol. Oct. 2003;140(3):477-86. Epub Aug. 26, 2003.
Hershey JC, et al. "Investigation of the species selectivity of a nonpeptide CGRP receptor antagonist using a novel pharmacodynamic assay," Regul Pept. Apr. 15, 2005;127(1-3):71-7.
Hill RG et al. "Neuropeptide and Kinin Antagonists," Handb Exp Pharmacol. 2007;(177):181-216.
Hillmen P, et al. "Effect of eculizumab on hemolysis and transfusion requirements in patients with paroxysmal nocturnal hemoglobinuria," N Engl J Med. Feb. 5, 2004;350(6):552-9.
Hinton PR, et al. "Engineered human IgG antibodies with longer serum half-lives in primates," J Biol Chem. Feb. 20, 2004;279(8):6213-6.

(56) References Cited

OTHER PUBLICATIONS

Hirsch S et al. "The CGRP receptor antagonist BIBN4096BS peripherally alleviates inflammatory pain in rats," Pain. May 2013;154(5):700-7.
Ho TW et al. "CGRP and its receptors provide new insights into migraine pathophysiology," Nat Rev Neurol. Oct. 2010;6(10):573-82.
Ho TW, et al. "Impact of recent prior opioid use on rizatriptan efficacy. A post hoc pooled analysis," Headache. Mar. 2009;49(3):395-403.
Ho TW, et al. "Randomized controlled trial of the CGRP receptor antagonist telcagepant for migraine prevention," Neurology. Sep. 9, 2014;83(11):958-66.
Ho TW, et al. "Efficacy and tolerability of MK-0974 (telcagepant), a new oral antagonist of calcitonin gene-related peptide receptor, compared with zolmitriptan for acute migraine: a randomised, placebo-controlled, parallel-treatment trial," Lancet. Dec. 20, 2008;372(9656):2115-23.
Hoff AO et al. "Increased bone mass is an unexpected phenotype associated with deletion of the calcitonin gene," J Clin Invest. Dec. 2002;110(12):1849-57.
Hoffmann J, et al. "New Agents for Acute Treatment of Migraine: CGRP Receptor Antagonists, iNOS Inhibitors," Curr Treat Options Neurol. Feb. 2012;14(1):50-9.
Holland J et al. "Calcitonin Gene-Related Peptide Reduces Brain Injury in a Rat Model of Focal Cerebral Ischemia," Stroke. Oct. 1994;25(10):2055-8; discussion 2058-9.
Holliger P, et al. "Engineered antibody fragments and the rise of single domains," Nat Biotechnol. Sep. 2005;23(9):1126-36.
Holm P, et al. "Functional mapping and single chain construction of the anti-cytokeratin 8 monoclonal antibody TS1." Mol Immunol. Feb. 2007;44(6):1075-84. Epub Sep. 20, 2006.
Holman JJ, et al. "Human alpha- and beta-CGRP and rat alpha-CGRP are coronary vasodilators in the rat." Peptides. Mar.-Apr. 1986;7(2):231-5.
Holt LJ, et al. "Domain antibodies: proteins for therapy." Trends Biotechnol. Nov. 2003;21(11):484-90.
Holzer P et al. "Afferent Nerve-Mediated Protection Against Deep Mucosal Damage in the Rat Stomach," Gastroenterology. Apr. 1990;98(4):838-48.
Holzer P et al. "Sensory neurons mediate protective vasodilatation in rat gastric mucosa," Am J Physiol. Mar. 1991;260(3 Pt 1):G363-70.
Holzer P et al. "Stimulation of Afferent Nerve Endings by Intragastric Capsaicin Protects Against Ethanol-Induced Damage of Gastric Mucosa," Neuroscience. Dec. 1988;27(3):981-7.
Holzer P. "Implications of tachykinins and calcitonin gene-related peptide in inflammatory bowel disease," Digestion. Jul.-Aug. 1998;59(4):269-83.
Holzer P. "Capsaicin: Cellular Targets, Mechanisms of Action, and Selectivity for Thin Sensory Neurons," Pharmacol Rev. Jun. 1991;43(2):143-201.
Hong KW, et al. "Effect of omega-conotoxin GVIA and omega-agatoxin IVA on the capsaicin-sensitive calcitonin gene-related peptide release and autoregulatory vasodilation in rat pial arteries," J Cereb Blood Flow Metab. Jan. 1999;19(1):53-60.
Hong KW, et al. "Pharmacological coupling and functional role for CGRP receptors in the vasodilation of rat pial arterioles," Am J Physiol. Jan. 1996;270(1 Pt2):H317-23.
Hong KW, et al. "Pharmacological evidence that calcitonin gene-related peptide is implicated in cerebral autoregulation," Am J Physiol. Jan. 1994;266(1 Pt 2):H11-6.
Hoogenboom HR, et al. "Multi-subunit proteins on the surface of filamentous phage: methodologies for displaying antibody (Fab) heavy and light chains," Nucleic Acids Res. Aug. 11, 1991;19(15):4133-7.
Hoogenboom HR. "Selecting and screening recombinant antibody libraries," Nat Biotechnol. Sep. 2005;23(9):1105-16.

Hopkins, CR. "ACS Chemical Neuroscience Molecule Spotlight on Telcagepant (MK-0974)," ACS Chem Neurosci. Jul. 20, 2011;2(7):334-5.
Hu H, et al. "Acute migraine treatment with rizatriptan in real world settings—focusing on treatment strategy, effectiveness, and behavior," Headache. Feb. 2009;49 Suppl 1:S34-42.
Hubbard JA, et al. "Identification of the epitopes of calcitonin gene-related peptide (CGRP) for two anti CGRP monoclonal antibodies by 2D NMR," Protein Sci. Sep. 1997;6(9):1945-52.
Hudson PJ, et al. "Engineered antibodies," Nat Med. Jan. 2003;9(1):129-34.
Hughes SR et al. "A calcitonin gene-related peptide (CGRP) antagonist (CGRP8-37) inhibits microvascular responses induced by CGRP and capsaicin in skin," Br J Pharmacol. Nov. 1991;104(3):738-42.
Hurley D. "CGRP Drug Improves Wellness on Headache-Free Days, Study Finds," Neurology Today, p. 31, Jul. 2016.
Hwang WY, et al. "Immunogenicity of engineered antibodies," Methods. May 2005;36(1):3-10.
Ibrahimi K, et al. "Development of an experimental model to study trigeminal nerve-mediated vasodilation on the human forehead," Cephalalgia. Jan. 3, 2014;34(7):514-522.
Idusogie EE, at al. "Mapping of the C1q Binding Site on Rituxan, a Chimeric Antibody with a Human IgG1 Fc," J Immunol. Apr. 15, 2000;164(8):4178-84.
Iovino M, et al. "Safety, tolerability and pharmacokinetics of BIBN 4096 BS, the first selective small molecule calcitonin gene-related peptide receptor antagonist, following single intravenous administration in healthy volunteers," Cephalalgia. Aug. 2004;24(8):645-56.
Janeway CA et al. "Immuno Biology: The Immune System in Health and Disease." Current Biology Ltd./Garland Publishing Inc. 1994 Glossary p. G:2.
Jang YJ, et al. "The structural basis for DNA binding by an anti-DNA autoantibody." Mol Immunol. Dec. 1998;35(18):1207-17.
Jansen-Olesen I, et al. "In-depth characterization of CGRP receptors in human intracranial arteries," Eur J Pharmacol. Nov. 28, 2003;481(2-3):207-16.
Jones PT, et al. "Replacing the complementarity-determining regions in a human antibody with those from a mouse," Nature. May 29-Jun. 4, 1986;321(6069):522-5.
Juaneda C, et al. "The molecular pharmacology of CGRP and related peptide receptor subtypes," Trends Pharmacol Sci. Nov. 2000;21(11):432-8.
Juhasz G, et al. "NO-induced migraine attack: strong increase in plasma calcitonin gene-related peptide (CGRP) concentration and negative correlation with platelet serotonin release." Pain. Dec. 2003;106(3):461-70.
Juhl L, et al. "Effect of two novel CGRP-binding compounds in a closed cranial window rat model," Eur J Pharmacol. Jul. 12, 2007;567(1-2):117-24.
Julia V, et al. "Tachykininergic mediation of viscerosensitive responses to acute inflammation in rats: role of CGRP." Am J Physiol. Jan. 1997;272(1 Pt 1):G141-6.
Jung ST, et al. "Bypassing glycosylation: engineering aglycosylated full-length IgG antibodies for human therapy," Curr Opin Biotechnol. Dec. 2011;22(6):858-67.
Kaiser EA, et al. "CGRP and migraine: could PACAP play a role too?" Neuropeptides. Dec. 2013;47(6):451-61.
Kapoor K, et al. "Effects of BIBN4096BS on cardiac output distribution and on CGRP-induced carotid haemodynamic responses in the pig," Eur J Pharmacol. Aug. 15, 2003;475(1-3):69-77.
Kapoor K, et al. "Effects of the CGRP receptor antagonist BIBN4096BS on capsaicin-induced carotid haemodynamic changes in anaesthetised pigs," Br J Pharmacol. Sep. 2003;140(2):329-38.
Kapoor, K. "Novel Potential Antimigraine Compounds: Carotid and Systemic Haemodynamic Effects in a Porcine Model of Migraine," Thesis, Erasmus University, Rotterdam. With summary in Dutch. 2003. 157 pages.
Karasek C., et al. "Characterization of the intrinsic binding features of three anti-CGRP therapeutic antibodies effective in preventing migraine: a comparative pre-clinical case study of ALD403, LY-2951742,

(56) References Cited

OTHER PUBLICATIONS

TEV-48125." 5th European Headache and Migraine Trust International Congress, Sep. 2016. 4 pages.
Kato K, et al. "CGRP antagonists enhance gastric acid secretion in 2-h pylorus-ligated rats," Peptides. 1995;16(7):1257-62.
Kawamura M, et al. "Antinociceptive effect of intrathecally administered antiserum against calcitonin gene-related peptide on thermal and mechanical noxious stimuli in experimental hyperalgesic rats." Brain Res. Sep. 11, 1989;497(1):199-203.
Kaymakcalan Z, et al. "Comparisons of affinities, avidities, and complement activation of adalimumab, infliximab, and etanercept in binding to soluble andmembrane tumor necrosis factor," Clin Immunol. May 2009;131(2):308-16.
Keates AC, et al. "CGRP upregulation in dorsal root ganglia and ileal mucosa during Clostridium difficile toxin A-induced enteritis," Am J Physiol. Jan. 1998;274(1 Pt 1):G196-202.
Kennel SJ, et al. "Direct Binding of Radioiodinated Monoclonal Antibody to Tumor Cells: Significance of Antibody Purity and Affinity for Drug Targeting or Tumor Imaging," Hybridoma. 1983;2(3):297-310.
Kim SJ, et al. "Antibody Engineering for the Development of Therapeutic Antibodies," Mol Cells. Aug. 31, 2005;20(1):17-29.
Kipriyanov S, et al. "Generation and Production of Engineered Antibodies," Mol Biotechnol. Jan. 2004;26(1):39-60.
Kipriyanov S. "Generation of Antibody Molecules Through Antibody Engineering" from Methods in Molecular Biology, vol. 207: Recombinant Antibodies for Cancer Therapy Methods and Protocols, 2003 pp. 3-25.
Knotkova H, et al. "Imaging intracranial plasma extravasation in a migraine patient: a case report," Pain Med. May-Jun. 2007;8(4):383-7.
Kobayashi D, et al. "Calcitonin Gene-Related Peptide Mediated Neurogenic Vasorelaxation in the Isolated Canine Lingual Artery," Jpn J Pharmacol. Apr. 1995;67(4):329-39.
Kobayashi H, et al. "Tryptophan H33 plays an important role in pyrimidine (6-4) pyrimidone photoproduct binding by a high-affinity antibody." Protein Eng. Oct. 1999;12(10):879-84.
Krymchantowski AV, et al. "New and emerging prophylactic agents for migraine," CNS Drugs. 2002;16(9):611-34.
Krymchantowski AV, et al. "Rizatriptan in migraine," Expert Rev Neurother. Sep. 2005;5(5):597-603.
Krymchantowski AV, et al. "Rizatriptan vs. rizatriptan plus trimebutine for the acute treatment of migraine: a double-blind, randomized, cross-over, placebo-controlled study," Cephalalgia. Jul. 2006;26(7):871-4.
Krymchantowski AV, et al. "Topiramate plus nortriptyline in the preventive treatment of migraine: a controlled study for nonresponders," J Headache Pain. Jan. 2012;13(1):53-9.
Kumar S, et al. "Molecular cloning and expression of the Fabs of human autoantibodies in *Escherichia coli*. Determination of the heavy or light chain contribution to the anti-DNA/-cardiolipin activity of the Fab." J Biol Chem. Nov. 10, 2000;275(45):35129-36.
Kunkel RS, et al. "Surgical treatment of chronic migrainous neuralgia," Cleve Clin Q. 1974 Winter;41(4):189-92.
Kuraishi Y, et al. "Antinociception induced in rats by intrathecal administration of antiserum against calcitonin gene-related peptide." Neurosci Lett. Oct. 17, 1988;92(3):325-9.
Kurosawa M, et al. "Increase of meningeal blood flow after electrical stimulation of rat dura mater encephali: mediation by calcitonin gene-related peptide," Br J Pharmacol. Apr. 1995;114(7):1397-402.
Kuus-Reichel K, et al. "Will Immunogenicity Limit the Use, Efficacy, and Future Development of Therapeutic Monoclonal Antibodies?" Clin Diagn Lab Immunol. Jul. 1994;1(4):365-72.
Lambrecht N, et al. "Role of calcitonin gene-related peptide and nitric oxide in the gastroprotective effect of capsaicin in the rat," Gastroenterology. May 1993;104(5):1371-80.
Lance J. "Migraine Pain Originates from Blood Vessels," Headache Pathogenesis: Monoamines, Neuropeptides, Purines, and Nitric Oxide, edited by J. Olesen and L. Edvinsson, Lippincott-Raven Publishers, Philedelphia, 1997. Chapter 1, pp. 3-9.
Lassen LH, et al. "CGRP may play a causative role in migraine." Cephalalgia. Feb. 2002;22(1):54-61.
Lassen LH, et al. "Involvement of calcitonin gene-related peptide in migraine: regional cerebral blood flow and blood flow velocity in migraine patients," J Headache Pain. Jun. 2008;9(3):151-7.
Lazzeria M, et al. "The Challenge of the Overactive Bladder: From Laboratory to New Drugs," European Association of Urology, vol. 5, Issue 6, Dec. 2007, pp. 250-258.
Lee CV, et al. "High-affinity human antibodies from phage-displayed synthetic Fab libraries with a single framework scaffold," J Mol Biol. Jul. 23, 2004;340(5):1073-93.
Leighton B, et al. "Pancreatic amylin and calcitonin gene-related peptide cause resistance to insulin in skeletal muscle in vitro," Nature. Oct. 13, 1988;335(6191):632-5.
Levêque D, et al. "Pharmacokinetics of therapeutic monoclonal antibodies used in oncology," Anticancer Res. May-Jun. 2005;25(3c):2327-43.
Levy D, et al. "A critical view on the role of migraine triggers in the genesis of migraine pain," Headache. Jun. 2009;49(6):953-7.
Levy D, et al. "Calcitonin gene-related peptide does not excite or sensitize meningeal nociceptors: implications for the pathophysiology of migraine," Ann Neurol. Nov. 2005;58(5):698-705.
Levy D, et al. "Migraine pain and nociceptor activation—where do we stand?" Headache. May 2010;50(5):909-16.
Levy D, et al. "The vascular theory of migraine: leave it or love it?" Ann Neurol. Apr. 2011;69(4):600-1.
Li DS, et al. "Role of calcitonin gene-related peptide in gastric hyperemic response to intragastric capsaicin," Am J Physiol. Oct. 1991;261(4 Pt 1):G657-61.
Lin HC, et al. "Immunoneutralization of Calcitonin Gene-Related Peptide (CGRP) During Inhibition of Intestinal Transit by Fat," Gastroenterology vol. 114, No. 4, 1998. 1 page. Abstract No. G3253.
Lin YS, et al. "Preclinical pharmacokinetics, interspecies scaling, and tissue distribution of a humanized monoclonal antibody against vascular endothelial growth factor," J Pharmacol Exp Ther. Jan. 1999;288(1):371-8.
Link AS, et al. "Treatment of migraine attacks based on the interaction with the trigemino-cerebrovascular system," J Headache Pain. Feb. 2008;9(1):5-12.
Lipton RB, et al. "CGRP antagonists in the acute treatment of migraine," Lancet Neurol. Jun. 2004;3(6):332.
Lipton RB, et al. "Headache: triumphs in translational research," Lancet Neurol. Jan. 2005;4(1):11-2.
Lipton RB, et al. "Moving forward—essential questions for the next 10 years," Headache. Feb. 2009;49 Suppl 1:S43-6.
Little M, et al. "Of mice and men: hybridoma and recombinant antibodies." Immunol Today. Aug. 2000;21(8):364-70.
Lonberg N, et al. "Antigen-specific human antibodies from mice comprising four distinct genetic modifications," Nature. Apr. 28, 1994;368(6474):856-9.
Lonberg N, et al. "Human antibodies from transgenic animals," Nat Biotechnol. Sep. 2005;23(9):1117-25.
Longoni M, et al. "Inflammation and excitotoxicity: role in migraine pathogenesis," Neurol Sci. May 2006;27 Suppl 2:S107-10.
Louis SM, et al. "Antibodies to calcitonin-gene related peptide reduce inflammation induced by topical mustard oil but not that due to carrageenin in the rat." Neurosci Lett. Jul. 31, 1989;102(2-3):257-60.
Louis SM, et al. "Immunization with calcitonin gene-related peptide reduces the inflammatory response to adjuvant arthritis in the rat," Neuroscience. 1990;39(3):727-31.
Louis SM, et al. "The role of substance P and calcitonin gene-related peptide in neurogenic plasma extravasation and vasodilatation in the rat." Neuroscience. 1989;32(3):581-6.
MacCallum RM, et al. "Antibody-antigen interactions: contact analysis and binding site topography." J Mol Biol. Oct. 11, 1996;262(5):732-45.
MacGregor EA. "Migraine in pregnancy and lactation: a clinical review," J Fam Plann Reprod Health Care. Apr. 2007;33(2):83-93.
Majima, M, et al. "Roles of calcitonin gene-related peptide in enhancement of angiogenesis," Inflammation and Regeneration vol. 31 No. 2 Mar. 2011, 146-150.

(56) References Cited

OTHER PUBLICATIONS

Mallee JJ, et al. "Receptor activity-modifying protein 1 determines the species selectivity of non-peptide CGRP receptor antagonists." J Biol Chem. Apr. 19, 2002;277(16):14294-8.
Marcelo E. Bigal et al: "Calcitonin Gene-Related Peptide (CGRP) and Migraine Current Understanding and State of Development", Headache, vol. 53, No. 8, Sep. 12, 2013 (Sep. 12, 2013), pp. 1230-1244.
Mareska M, et al. "Lambert-Eaton myasthenic syndrome," Semin Neurol. Jun. 2004;24(2):149-53.
Marquez de Prado B and Russo AF, "CGRP receptor antagonists: A new frontier of anti-migraine medications," Drug Discov Today Ther Strateg. 2006 Winter;3(4):593-597.
Marshall I, et al. "Human and rat alpha-CGRP but not calcitonin cause mesenteric vasodilatation in rats." Eur J Pharmacol. Apr. 16, 1986;123(2):217-22.
Martínez-Sáenz A, et al. "Role of calcitonin gene-related peptide in inhibitory neurotransmission to the pig bladder neck," J Urol. Aug. 2011;186(2):728-35.
Maynard JA, et al. "Protection against anthrax toxin by recombinant antibody fragments correlates with antigen affinity," Nat Biotechnol. Jun. 2002;20(6):597-601.
McCafferty J, et al. "Phage antibodies: filamentous phage displaying antibody variable domains," Nature. Dec. 6, 1990;348(6301):552-4.
McCulloch J, et al. "Calcitonin gene-related peptide: functional role in cerebrovascular regulation," Proc Natl Acad Sci U S A. Aug. 1986;83(15):5731-5.
McLatchie LM, et al. "RAMPs regulate the transport and ligand specificity of the calcitonin-receptor-like receptor," Nature. May 28, 1998;393(6683):333-9.
Mehrotra S, et al. "Current and prospective pharmacological targets in relation to antimigraine action," Naunyn Schmiedebergs Arch Pharmacol. Oct. 2008;378(4):371-94.
Mense S. "Pathophysiology of low back pain and the transition to the chronic state—experimental data and new concepts." Schmerz. Dec. 2001;15(6):413-7.
Messlinger K, et al. "Neuropeptide effects in the trigeminal system: pathophysiology and clinical relevance in migraine," Keio J Med. 2011;60(3):82-9.
Messlinger K. "Migraine: where and how does the pain originate?" Exp Brain Res. Jun. 2009;196(1):179-93.
Messlinger, et al. "Inhibition of neurogenic blood flow increases in the rat cranial dura matter by a CGRP-binding Spiegelmer," Cephalalgia, No. F022 2004.
Middlemiss DN. "Direct evidence for an interaction of beta-adrenergic blockers with the 5-HT receptor," Nature. May 19, 1977;267(5608):289-90.
Middlemiss DN. "Stereoselective blockade at [3H]5-HT binding sites and at the 5-HT autoreceptor by propranolol," Eur J Pharmacol. Jun. 1, 1984;101(3-4):289-93.
Mirick GR, et al. "A review of human anti-globulin antibody (HAGA, HAMA, HACA, HAHA) responses to monoclonal antibodies. Not four letter words," Q J Nucl Med Mol Imaging. Dec. 2004;48(4):251-7.
Molina JM, et al. "Induction of insulin resistance in vivo by amylin and calcitonin gene-related peptide," Diabetes. Feb. 1990;39(2):260-5.
Moore CK, et al. "Urological Applications of Botulinum Toxin," Female Urology: A Practical Clinical Guide. 2007 Chapter 14:213-217.
Moore EL, et al. "Targeting a family B GPCR/RAMP receptor complex: CGRP receptor antagonists and migraine," Br J Pharmacol. May 2012;166(1):66-78.
Morara S, et al. "Monoclonal antibodies reveal expression of the CGRP receptor in Purkinje cells, interneurons and astrocytes of rat cerebellar cortex," Neuroreport. Nov. 16, 1998;9(16):3755-9.
Morell A, et al. "Metabolic properties of IgG subclasses in man." J Clin Invest. Apr. 1970;49(4):673-80.

Morrison SL, et al. "Chimeric human antibody molecules: mouse antigen-binding domains with human constant region domains," Proc Natl Acad Sci U S A. Nov. 1984;81(21):6851-5.
Moskowitz MA, "Neurogenic inflammation in the pathophysiology and treatment of migraine," Neurology. Jun. 1993;43(6 Suppl 3):S16-20.
Moskowitz MA, et al. "CGRP: blood flow and more?" Cephalalgia. Aug. 1996;16(5):287.
Moskowitz MA. "Pathophysiology of headache—past and present," Headache. Apr. 2007;47 Suppl 1:S58-63.
Mould DR, et al. "A population pharmacokinetic-pharmacodynamic analysis of single doses of clenoliximab in patients with rheumatoid arthritis," Clin Pharmacol Ther. Sep. 1999;66(3):246-57.
Mountain A, et al. "Engineering antibodies for therapy," Biotechnol Genet Eng Rev. 1992;10:1-142.
Muff R, et al. "Calcitonin, calcitonin gene-related peptide, adrenomedullin and amylin: homologous peptides, separate receptors and overlapping biological actions," Eur J Endocrinol. Jul. 1995;133(1):17-20.
Mulderry PK, et al. "Differential expression of alpha-CGRP and beta-CGRP by primary sensory neurons and enteric autonomic neurons of the rat." Neuroscience. Apr. 1988;25(1):195-205.
Mullins MW, et al. "Characterization of a calcitonin gene-related peptide (CGRP) receptor on mouse bone marrow cells." Regul Pept. Nov. 19, 1993;49(1):65-72.
Nakamura-Craig M, et al. "Effect of neurokinin A, substance P and calcitonin gene related peptide in peripheral hyperalgesia in the rat paw." Neurosci Lett. Mar. 11, 1991;124(1):49-51.
Naot D, et al. "The role of peptides and receptors of the calcitonin family in the regulation of bone metabolism," Bone. Nov. 2008;43(5):813-8.
Negro A, et al. "CGRP receptor antagonists: an expanding drug class for acute migraine?" Expert Opin Investig Drugs. Jun. 2012;21(6):807-18.
Newman R, et al. "Modification of the Fc region of a primatized IgG antibody to human CD4 retains its ability to modulate CD4 receptors but does not deplete CD4(+) T cells in chimpanzees," Clin Immunol. Feb. 2001;98(2):164-74.
Ng-Mak DS, et al. "Migraine treatment with rizatriptan and almotriptan: a crossover study," Headache. May 2009;49(5):655-62.
Nippon Rinsho, "Recent Development of Calcitonin Gene-related Peptide (CGRP) receptor antagonist," 2005, vol. 63, Suppl.10, pp. 263-266 [Original With English Translation].
Nishimoto N, et al. "Anti-interleukin-6 receptor antibody therapy in rheumatic diseases," Endocr Metab Immune Disord Drug Targets. Dec. 2006;6(4):373-81.
Oates PJ, et al. "Studies on the mechanism of ethanol-induced gastric damage in rats," Gastroenterology. Jan. 1988;94(1):10-21.
Ober RJ, et al. "Visualizing the site and dynamics of IgG salvage by the MHC class I-related receptor, FcRn," J Immunol. Feb. 15, 2004;172(4):2021-9.
O'Connell JP, et al. "On the role of the C-terminus of alpha-calcitonin-gene-related peptide (alpha CGRP). The structure of des-phenylalaninamide37-alpha CGRP and its interaction with the CGRP receptor," Biochem J. Apr. 1, 1993;291 ( Pt 1):205-10.
Oh-hashi Y, et al. "Elevated sympathetic nervous activity in mice deficient in alphaCGRP," Circ Res. Nov. 23, 2001;89(11):983-90.
Olesen J, et al. "Calcitonin gene-related peptide receptor antagonist BIBN 4096 BS for the acute treatment of migraine." N Engl J Med. Mar. 11, 2004;350(11):1104-10.
Olesen J, et al. "Chapter 16: Calcitonin Gene-Related Peptide and Other Peptides." The Headaches Third Edition. Lippincott Williams & Wilkins 2006 159-164.
Olesen J, et al. "Chapter 31: CGRP Involvement in Mirgaines." The Headaches Third Edition. Lippincott Williams & Wilkins 2006 289-99.
Olesen J, et al. "Emerging migraine treatments and drug targets," Trends Pharmacol Sci. Jun. 2011;32(6):352-9.
Olesen J, et al. "Finding new drug targets for the treatment of migraine attacks," Cephalalgia. Sep. 2009;29(9):909-20.
Olesen J, et al. "Migraine: a research field matured for the basic neurosciences," Trends Neurosci. Jan. 1991;14(1):3-5.

(56) References Cited

OTHER PUBLICATIONS

Olesen J, et al. "Origin of pain in migraine: evidence for peripheral sensitisation," Lancet Neurol. Jul. 2009;8(7):679-90.
Olesen J. "Migraine: A neural pathway for photophobia in migraine," Nat Rev Neurol. May 2010;6(5):241-2.
Ondo WG, et al. "Botulinum toxin A for chronic daily headache: a randomized, placebo-controlled, parallel design study," Cephalalgia. Jan. 2004;24(1):60-5.
O'Sullivan J, et al. "Migraine development, treatments, research advances, and anesthesia implications," AANA J. Feb. 2006;74(1):61-9.
Ottosson A, et al. "Release of histamine from dural mast cells by substance P and calcitonin gene-related peptide," Cephalalgia. May 1997;17(3):166-74.
Pabst MA, et al. "Ablation of capsaicin sensitive afferent nerves impairs defence but not rapid repair of rat gastric mucosa," Gut. Jul. 1993;34(7):897-903.
Panconesi A, et al. "Migraine pain: reflections against vasodilatation," J Headache Pain. Oct. 2009;10(5):317-25.
Panka DJ, et al. "Defining the structural correlates responsible for loss of arsonate affinity in an IDCR antibody isolated from an autoimmune mouse," Mol Immunol. Aug. 1993;30(11):1013-20.
Paone DV, et al. "Calcitonin gene-related peptide receptor antagonists for the treatment of migraine: a patent review," Expert Opin Ther Pat. Dec. 2009;19(12):1675-713.
Papadopoulos N, et al. "Binding and neutralization of vascular endothelial growth factor (VEGF) and related ligands by VEGF Trap, ranibizumab and bevacizumab." Angiogenesis. Jun. 2012;15(2):171-85.
Papp K, et al. "The treatment of moderate to severe psoriasis with a new anti-CD11a monoclonal antibody," J Am Acad Dermatol. Nov. 2001;45(5):665-74.
Pavlou AK, et al. "Recombinant protein therapeutics-success rates, market trends and values to 2010," Nat Biotechnol. Dec. 2004;22(12):1513-9.
Peroutka SJ, et al. "Neurogenic inflammation and migraine: implications for the therapeutics," Mol Interv. Oct. 2005;5(5):304-11.
Peskar BM, et al. "A monoclonal antibody to calcitonin gene-related peptide abolishes capsaicin-induced gastroprotection." EurJ Pharmacol. Nov. 30, 1993;250(1):201-3.
Petersen KA, et al. "BIBN4096BS antagonizes human alpha-calcitonin gene related peptide-induced headache and extracerebral artery dilatation." Clin Pharmacol Ther. Mar. 2005;77(3):202-13.
Petersen KA, et al. "Effect of hypotension and carbon dioxide changes in an improved genuine closed cranial window rat model," Cephalalgia. Jan. 2005;25(1):23-9.
Petersen KA, et al. "Inhibitory effect of BIBN4096BS on cephalic vasodilatation induced by CGRP ortranscranial electrical stimulation in the rat." Br J Pharmacol. Nov. 2004;143(6):697-704.
Petersen KA, et al. "Presence and function of the calcitonin gene-related peptide receptor on rat pial arteries investigated in vitro and in vivo," Cephalalgia. Jun. 2005;25(6):424-32.
Petersen KA, et al. "The effect of nonpeptide CGRP-antagonist, BIBN4096BS on human-alphaCGRP induced headache and hemodynamics in healthy volunteers," Cephalalgia, vol. 23, extract from Abstracts of the XI Congress of the International Headache Society, p. 725, 2003.
Petkova SB, et al. "Enhanced half-life of genetically engineered human IgG1 antibodies in a humanized FcRn mouse model: potential application in humorally mediated autoimmune disease," Int Immunol. Dec. 2006;18(12):1759-69.
Pietrobon D, et al. "Pathophysiology of migraine," Annu Rev Physiol. 2013;75:365-91.
Plessas IN, et al. "Migraine-like episodic pain behavior in a dog: can dogs suffer from migraines?" J Vet Intern Med. Sep.-Oct. 2013;27(5):1034-40.
Plourde V, et al. "CGRP antagonists and capsaicin on celiac ganglia partly prevent postoperative gastric ileus." Peptides. Nov.-Dec. 1993;14(6):1225-9.

Poyner DR, et al. "International Union of Pharmacology. XXXII. The mammalian calcitonin gene-related peptides, adrenomedullin, amylin, and calcitonin receptors," Pharmacol Rev. Jun. 2002;54(2):233-46.
Presta L. "Antibody engineering for therapeutics," Curr Opin Struct Biol. Aug. 2003;13(4):519-25.
Presta LG, et al. "Engineering therapeutic antibodies for improved function," Biochem Soc Trans. Aug. 2002;30(4):487-90.
Prewett M, et al. "The biologic effects of C225, a chimeric monoclonal antibody to the EGFR, on human prostate carcinoma." J Immunother Emphasis Tumor Immunol. Nov. 1996;19(6):419-27.
Qing-Hui Niu, et al. "Expression of mast cell and calcition gene related peptides in the mucosa of irritable bowel syndrome," World Chinese Journal of Digestology, Jan. 18, 2009 p. 213-217; ISSN 1099-3079.
Raddant AC, et al. "Calcitonin gene-related peptide in migraine: intersection of peripheral inflammation and central modulation," Expert Rev Mol Med. Nov. 29, 2011;13:e36.
Ramadan NM, et al. "New and future migraine therapy," Pharmacol Ther. Oct. 2006;112(1):199-212.
Ramadan NM. "Acute treatments: future developments," Curr Med Res Opin. 2001;17 Suppl 1:s81-6.
Ramos ML, et al. "AMG 334 CGRP antibody for migraine: time to celebrate?" Lancet Neurol. Apr. 2016;15(4):347-9.
Rapoport AM, Bigal ME, et al. "Naratriptan in the preventive treatment of refractory chronic migraine." In Olsen J, Silberstein SD, Tfelt-Hansen P, eds. Preventive Pharmacotherapy of Headache Disorders. Copenhagen: Oxford University Press, 2004, Chapter 31.
Rapoport AM, et al. "Intranasal medications for the treatment of migraine and cluster headache," CNS Drugs. 2004;18(10):671-85.
Rapoport AM, et al. "Levetiracetam in the preventive treatmentof transformed migraine: A prospective, open-label, pilot study," Curr Ther Res Clin Exp. May 2005;66(3):212-21.
Rapoport AM, et al. "Migraine preventive therapy: current and emerging treatment options," Neurol Sci. May 2005;26 Suppl 2:s111-20.
Rapoport AM, et al. "Preventive migraine therapy: what is new," Neurol Sci. Oct. 2004;25 Suppl 3:S177-85.
Raybould HE, et al. "Selective ablation of spinal afferent neurons containing CGRP attenuates gastric hyperemic response to acid," Peptides. Mar.-Apr. 1992;13(2):249-54.
Reasbeck PG, et al. "Calcitonin gene-related peptide: enteric and cardiovascular effects in the dog," Gastroenterology. Oct. 1988;95(4):966-71.
Recober A, et al. "Calcitonin gene-related peptide: A molecular link between obesity and migraine?" Drug News Perspect. Mar. 2010;23(2):112-7.
Recober A, et al. "Calcitonin gene-related peptide: an update on the biology," Curr Opin Neurol. Jun. 2009;22(3):241-6.
Recober A, et al. "Olcegepant, a non-peptide CGRP1 antagonist for migraine treatment," IDrugs. Aug. 2007;10(8):566-74.
Recober A, et al., "Role of calcitonin gene-related peptide in light-aversive behavior: implications for migraine," J Neurosci. Jul. 8, 2009;29(27):8798-804.
Reddy MP, et al. "Elimination of Fc receptor-dependent effector functions of a modified IgG4 monoclonal antibody to human CD4," J Immunol. Feb. 15, 2000;164(4):1925-33.
Reff ME, et al. "A review of modifications to recombinant antibodies: attempt to increase efficacy in oncology applications," Crit Rev Oncol Hematol. Oct. 2001;40(1):25-35.
Reff ME, et al. "Depletion of B cells in vivo by a chimeric mouse human monoclonal antibody to CD20," Blood. Jan. 15, 1994;83(2):435-45.
Reichert JM, et al. "Monoclonal antibody successes in the clinic," Nat Biotechnol. Sep. 2005;23(9):1073-8.
Reinshagen M, et al. "Calcitonin gene-related peptide mediates the protective effect of sensory nerves in a model of colonic injury." J Pharmacol Exp Ther. Aug. 1998;286(2):657-61.
Reuter U, et al. "Experimental models of migraine," Funct Neurol. 2000;15 Suppl 3:9-18.
Reuter U. "Anti-CGRP antibodies: a new approach to migraine prevention," Lancet Neurol. Sep. 2014;13(9):857-9.

(56) References Cited

OTHER PUBLICATIONS

Rolston RK, et al., "Intravenous calcitonin gene-related peptide stimulates net water secretion in rat colon in vivo," Dig Dis Sci. Apr. 1989;34(4):612-6.

Roon KI, et al. "No acute antimigraine efficacy of CP-122,288, a highly potent inhibitor of neurogenic inflammation: results of two randomized, double-blind, placebo-controlled clinical trials," Ann Neurol. Feb. 2000;47(2):238-41.

Roopenian DC, et al. "FcRn: the neonatal Fc receptor comes of age," Nat Rev Immunol. Sep. 2007;7(9):715-25.

Roque AC, et al. "Antibodies and genetically engineered related molecules: production and purification," Biotechnol Prog. May-Jun. 2004;20(3):639-54.

Roskos LK, et al. "The Clinical Pharmacology of Therapeutic Monoclonal Antibodies," Drug Development Research 2004 61:108-120.

Rother RP, et al. "Discovery and development of the complement inhibitor eculizumab for the treatment of paroxysmal nocturnal hemoglobinuria," Nat Biotechnol. Nov. 2007;25(11):1256-64.

Rovero P, et al. "CGRP antagonist activity of short C-terminal fragments of human alpha CGRP, CGRP(23-37) and CGRP(19-37)." Peptides. Sep.-Oct. 1992;13(5):1025-7.

Rudikoff S, et al. "Single amino acid substitution altering antigen-binding specificity." Proc Natl Acad Sci U S A. Mar. 1982;79(6):1979-83.

Ruiz-Gayo M, et al. "Vasodilatory effects of cholecystokinin: new role for an old peptide?" Regul Pept. Dec. 10, 2006;137(3):179-84.

Russo AF, et al., "A Potential Preclinical Migraine Model: CGRP-Sensitized Mice," Mol Cell Pharmacol. 2009;1(5):264-270.

Russo AF. "Calcitonin gene-related peptide (CGRP): a new target for migraine," Annu Rev Pharmacol Toxicol. 2015;55:533-52.

Russo. "CGRP Meeting Abstract Book," The 4th International Meeting on CGRP, Copenhagen, Sep. 2001, 71 pages.

Russo. "CGRP Meeting Abstract Book," Joint International Symposium on Calictonin Gene-Related Peptide, Amylin and Calcitonin; 4th Symposium on Adrenomedullin and Proadrenomedullin N-20 Peptide, Zurich, Switzerland, Mar. 2004. 38 pages.

Ryan AM, et al. "Preclinical safety evaluation of rhuMAbVEGF, an antiangiogenic humanized monoclonal antibody," Toxicol Pathol. Jan.-Feb. 1999;27(1):78-86.

Ryan S. "Medicines for migraine," Arch Dis Child Educ Pract Ed. Apr. 2007;92(2):ep50-5.

Saleh MN, et al. "Phase I trial of the chimeric anti-GD2 monoclonal antibody ch14.18 in patients with malignant melanoma." Hum Antibodies Hybridomas. Jan. 1992;3(1):19-24.

Salonen R, et al. "Triptans: do they differ?" Curr Pain Headache Rep. Apr. 2002;6(2):133-9.

Salvatore CA, et al. "Pharmacological characterization of MK-0974 [N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide], a potent and orally active calcitonin gene-related peptide receptor antagonist for the treatment of migraine," J Pharmacol Exp Ther. Feb. 2008;324(2):416-21.

Sams-Nielsen A, et al. "Pharmacological evidence for CGRP uptake into perivascular capsaicin sensitive nerve terminals," Br J Pharmacol. Mar. 2001;132(5):1145-53.

Saphire EO, et al. "Crystal structure of a neutralizing human IGG against HIV-1: a template for vaccine design," Science. Aug. 10, 2001;293(5532):1155-9.

Schaible HG, et al. "Mechanisms of pain in arthritis." Ann N Y Acad Sci. Jun. 2002;966:343-54.

Schelstraete C, et al. "CGRP antagonists: hope for a new era in acute migraine treatment," Acta Neurol Belg. Dec. 2009;109(4):252-61.

Schier R, et al. "Isolation of high-affinity monomeric human anti-c-erbB-2 single chain Fv using affinity-driven selection," J Mol Biol. Jan. 12, 1996;255(1):28-43.

Schier R, et al. "Isolation of picomolar affinity anti-c-erbB-2 single-chain Fv by molecular evolution of the complementarity determining regions in the center of the antibody binding site," J Mol Biol. Nov. 8, 1996;263(4):551-67.

Schifter S. "Circulating concentrations of calcitonin gene-related peptide (CGRP) in normal man determined with a new, highly sensitive radioimmunoassay," Peptides. Mar.-Apr. 1991;12(2):365-9.

Schindler M, et al. "Binding properties of the novel, non-peptide CGRP receptor antagonist radioligand, [(3)H]BIBN4096BS," Eur J Pharmacol. May 10, 2002;442(3):187-93.

Schoenen J, et al. "Almotriptan and its combination with aceclofenac for migraine attacks: a study of efficacy and the influence of auto-evaluated brush allodynia," Cephalalgia. Oct. 2008;28(10):1095-105.

Schreiber CP. "The pathophysiology of migraine," Dis Mon. Oct. 2006;52(10):385-401.

Schwenger N, et al. "Interaction of calcitonin gene-related peptide, nitric oxide and histamine release in neurogenic blood flow and afferent activation in the rat cranial dura mater," Cephalalgia. Jun. 2007;27(6):481-91.

Schytz HW, et al. "What have we learnt from triggering migraine?" Curr Opin Neurol. Jun. 2010;23(3):259-65.

Seike M, et al. "Increased synthesis of calcitonin gene-related peptide stimulates keratinocyte proliferation in murine UVB-irradiated skin," J Dermatol Sci. Feb. 2002;28(2):135-43.

Selenko N, et al. "CD20 antibody (C2B8)-induced apoptosis of lymphoma cells promotes phagocytosis by dendritic cells and cross-priming of CD8+ cytotoxic T cells," Leukemia. Oct. 2001;15(10):1619-26.

Seong J, et al. "Radiation-induced alteration of pain-related signals in an animal model with bone invasion from cancer." Ann N Y Acad Sci. Dec. 2004;1030:179-86.

Seybold VS. "The role of peptides in central sensitization," Handb Exp Pharmacol. 2009;(194):451-91.

Shaw NE, et al. "The effect of monoclonal antibodies to calcitonin gene-related peptide (CGRP) on CGRP-induced vasodilatation in pig coronary artery rings," Br J Pharmacol. May 1992;106(1):196-8.

Sheets MD, et al. "Efficient construction of a large nonimmune phage antibody library: the production of high-affinity human single-chain antibodies to protein antigens," Proc Natl Acad Sci U S A. May 26, 1998;95(11):6157-62.

Sheftell FD, et al. "Naratriptan in the preventive treatment of refractory transformed migraine: a prospective pilot study," Headache. Nov.-Dec. 2005;45(10):1400-6.

Shen YT, et al. "Functional role of alpha-calcitonin gene-related peptide in the regulation of the cardiovascular system," J Pharmacol Exp Ther. Aug. 2001;298(2):551-8.

Shevel E. "The extracranial vascular theory of migraine—a great story confirmed by the facts," Headache. Mar. 2011;51(3):409-17.

Shields RL, et al. "High resolution mapping of the binding site on human IgG1 for Fc gamma RI, Fc gamma RII, Fc gamma RIII, and FcRn and design of IgG1 variants with improved binding to the Fc gamma R," J Biol Chem. Mar. 2, 2001;276(9):6591-604.

Shulkes A, et al. "Production of calcitonin gene related peptide, calcitonin and PTH-related protein by a prostatic adenocarcinoma," Clin Endocrinol (Oxf). May 1991;34(5):387-93.

Silberstein S, et al. "Botulinum toxin type A as a migraine preventive treatment. For the Botox Migraine Clinical Research Group," Headache. Jun. 2000;40(6):445-50.

Silberstein SD, "Practice parameter: evidence-based guidelines for migraine headache (an evidence-based review): report of the Quality Standards Subcommittee of the American Academy of Neurology," Neurology. Sep. 26, 2000;55(6):754-62.

Silberstein SD. "Emerging target-based paradigms to prevent and treat migraine," Clin Pharmacol Ther. Jan. 2013;93(1):78-85.

Silverman AJ, et al. "Mast cells migrate from blood to brain," J Neurosci. Jan. 1, 2000;20(1):401-8.

Simmons LC, et al. "Expression of full-length immunoglobulins in *Escherichia coli*: rapid and efficient production of aglycosylated antibodies," J Immunol Methods. May 1, 2002;263(1-2):133-47.

Sixt ML, et al. "Calcitonin gene-related peptide receptor antagonist olcegepant acts in the spinal trigeminal nucleus," Brain. Nov. 2009;132(Pt 11):3134-41.

(56) References Cited

OTHER PUBLICATIONS

Skofitsch G, et al. "Comparative immunohistochemical distribution of amylin-like and calcitonin gene related peptide like immunoreactivity in the rat central nervous system," Can J Physiol Pharmacol. Jul. 1995;73(7):945-56.
Smillie SJ, et al. "Calcitonin gene-related peptide (CGRP) and its role in hypertension," Neuropeptides. Apr. 2011;45(2):93-104.
Smith KA, et al. "Demystified . . . recombinant antibodies," J Clin Pathol. Sep. 2004;57(9):912-7.
Smith TW, et al. "Reversal of advanced digoxin intoxication with Fab fragments of digoxin-specific antibodies." N Engl J Med. Apr. 8, 1976;294(15):797-800.
Smith-Gill SJ, et al. "Contributions of immunoglobulin heavy and light chains to antibody specificity for lysozyme and two haptens." J Immunol. Dec. 15, 1987;139(12):4135-44.
Solomon S. "Major therapeutic advances in the past 25 years," Headache. Apr. 2007;47 Suppl 1:S20-2.
Song MK, et al. "Light chain of natural antibody plays a dominant role in protein antigen binding." Biochem Biophys Res Commun. Feb. 16, 2000;268(2):390-4.
Spetz AC, et al. "Momentary increase in plasma calcitonin gene-related peptide is involved in hot flashes in men treated with castration for carcinoma of the prostate," J Urol. Nov. 2001;166(5):1720-3.
Sprenger T, et al. "Migraine pathogenesis and state of pharmacological treatment options," BMC Med. Nov. 16, 2009;7:71.
Stensrud P, et al. "Comparative trial of Tenormin (atenolol) and Inderal (propranolol) in migraine," Headache. Jul. 1980;20(4):204-7.
Storer RJ, et al. "Calcitonin gene-related peptide (CGRP) modulates nociceptive trigeminovascular transmission in the cat," Br J Pharmacol. Aug. 2004;142(7):1171-81.
Stovner LJ, et al. "New drugs for migraine," J Headache Pain. Dec. 2009;10(6):395-406.
Strassman AM, et al. "On the origin of headaches," Endeavour. 1997;21(3):97-100.
Strassman AM, et al. "Response properties of dural nociceptors in relation to headache," J Neurophysiol. Mar. 2006;95(3):1298-306.
Subramanian KN, et al. "Safety, tolerance and pharmacokinetics of a humanized monoclonal antibody to respiratory syncytial virus in premature infants and infants with bronchopulmonary dysplasia," MEDI-493 Study Group, Pediatr Infect Dis J. Feb. 1998;17(2):110-5.
Tam SH, et al. "Abciximab (ReoPro, chimeric 7E3 Fab) demonstrates equivalent affinity and functional blockade of glycoprotein IIb/IIIa and alpha(v)beta3 integrins," Circulation. Sep. 15, 1998;98(11):1085-91.
Tamura M, et al. "Structural correlates of an anticarcinoma antibody: identification of specificity-determining residues (SDRs) and development of a minimally immunogenic antibody variant by retention of SDRs only." J Immunol. Feb. 1, 2000;164(3):1432-41.
Tan et al., "Demonstration of the neurotransmitter role of calcitonin gene-related peptides (CGRP) by immunoblockade with anti-CGRP monoclonal antibodies," Br J Pharmacol. Mar. 1994;111(3):703-10.
Tan KK, et al. "Calcitonin gene-related peptide as an endogenous vasodilator: immunoblockade studies in vivo with an anti-calcitonin gene-related peptide monoclonal antibody and its Fab' fragment." Clin Sci (Lond). Dec. 1995;89(6):565-73.
Tanaka H, et al. "Inhibition of calcitonin gene-related peptide (CGRP) has the potential to extend first-phase insulin secretion," Exp Clin Endocrinol Diabetes. May 2013;121(5):280-5.
Taylor AW, et al. "Suppression of nitric oxide generated by inflammatory macrophages by calcitonin gene-related peptide in aqueous humor," Invest Ophthalmol Vis Sci. Jul. 1998;39(8):1372-8.
Tedstone, et al. "The effect of islet amyloid polypeptide (amylin) and calcitonin gene-related peptide on glucose removal in the anaesthetized rat and on insulin secretion from rat pancreatic islets in vitro," Biosci Rep. Aug. 1990;10(4):339-45.
Tepper SJ, Bigal ME, et al. "Botulinum toxin type A in the treatment of refractory headache." In Olsen J, Silberstein SD, Tfelt-Hansen P, eds. Preventive Pharmacotherapy of Headache Disorders. Copenhagen: Oxford University Press, 2004, Chapter 20.
Tepper SJ, et al. "Botulinum neurotoxin type A in the preventive treatment of refractory headache: a review of 100 consecutive cases," Headache. Sep. 2004;44(8):794-800.
Tepper SJ, et al. "Clinical and preclinical rationale for CGRP-receptor antagonists in the treatment of migraine," Headache. Sep. 2008;48(8):1259-68.
Tepper SJ, et al. "Mechanisms of action of the 5-HT1B/1D receptor agonists," Arch Neurol. Jul. 2002;59(7):1084-8.
Teva Pharmaceutical Industries Ltd., Press Release, "Teva to Acquire Labrys Biologies, Inc.", Jun. 3, 2014. 4 pages.
Tfelt-Hansen P, et al. "Effervescent metoclopramide and aspirin (Migravess) versus effervescent aspirin or placebo for migraine attacks: a double-blind study," Cephalalgia. Jun. 1984;4(2):107-11.
Tfelt-Hansen P, et al. "Possible site of action of CGRP antagonists in migraine," Cephalalgia. Apr. 2011;31(6):748-50.
Tfelt-Hansen PC. "Verisimilitude (or "truthlikeness") as an alternative to pro and cons: migraine and cluster headache mechanisms," J Headache Pain. Oct. 2010;11(5):379-89.
Theoharides TC, et al. "The role of mast cells in migraine pathophysiology," Brain Res Brain Res Rev. Jul. 2005;49(1):65-76.
Thomas TC, et al. "Inhibition of complement activity by humanized anti-C5 antibody and single-chain Fv," Mol Immunol. Dec. 1996;33(17-18):1389-401.
Tjen-A-Looi S, et al. "CGRP and somatostatin modulate chronic hypoxic pulmonary hypertension," Am J Physiol. Sep. 1992;263(3 Pt 2):H681-90.
Toda M, et al. "Neuronal system-dependent facilitation of tumor angiogenesis and tumor growth by calcitonin gene-related peptide," Proc Natl Acad Sci U S A. Sep. 9, 2008;105(36):13550-5.
Todd J. Schwedt et al: "14th International Headache Congress: Basic Science Highlights", Headache, vol. 50, No. 3, Mar. 1, 2010 (Mar. 1, 2010), pp. 520-526.
Tokuda Y, et al. "Dose escalation and pharmacokinetic study of a humanized anti-HER2 monoclonal antibody in patients with HER2/neu-overexpressing metastatic breast cancer," Br J Cancer. Dec. 1999;81(8):1419-25.
Tsujikawa K, et al. "Hypertension and dysregulated proinflammatory cytokine production in receptor activity-modifying protein 1-deficient mice," Proc Natl Acad Sci U S A. Oct. 16, 2007;104(42):16702-7.
Turner LC, et al. "A neural shift theory of migraine," Neuroepidemiology. 1993;12(4):249-50.
Tvedskov JF, et al. "No increase of calcitonin gene-related peptide in jugular blood during migraine." Ann Neurol. Oct. 2005;58(4):561-8.
Tzabazis AZ, et al. "Antihyperalgesic effect of a recombinant herpes virus encoding antisense for calcitonin gene-related peptide." Anesthesiology. Jun. 2007;106(6):1196-203.
Uhr M, et al. "Penetration of endogenous steroid hormones corticosterone, cortisol, aldosterone and progesterone into the brain is enhanced in mice deficient for both mdr1a and mdr1b P-glycoproteins," J Neuroendocrinol. Sep. 2002;14(9):753-9.
Unger J. "Migraine headaches: a historical prospective, a glimpse into the future, and migraine epidemiology," Dis Mon. Oct. 2006;52(10):367-84.
Vajdos FF, et al. "Comprehensive functional maps of the antigen-binding site of an anti-ErbB2 antibody obtained with shotgun scanning mutagenesis." J Mol Biol. Jul. 5, 2002;320(2):415-28.
Van der Schueren BJ, et al. "Calcitonin gene-related peptide8-37 antagonizes capsaicin-induced vasodilation in the skin: evaluation of a human in vivo pharmacodynamic model," J Pharmacol Exp Ther. Apr. 2008;325(1):248-55.
Van Rossum D, et al. "Neuroanatomical localization, pharmacological characterization and functions of CGRP, related peptides and their receptors," Neurosci Biobehav Rev. Sep. 1997;21(5):649-78.
Vater A, et al. "Short bioactive Spiegelmers to migraine-associated calcitonin gene-related peptide rapidly identified by a novel approach: tailored-SELEX." Nucleic Acids Res. Nov. 1, 2003;31(21):e130.
Vaughan TJ, et al. "Human antibodies with sub-nanomolar affinities isolated from a large non-immunized phage display library," Nat Biotechnol. Mar. 1996;14(3):309-14.

(56) References Cited

OTHER PUBLICATIONS

Villalón CM, et al. "The role of CGRP in the pathophysiology of migraine and efficacy of CGRP receptor antagonists as acute antimigraine drugs," Pharmacol Ther. Dec. 2009;124(3):309-23.
Vincent A, et al. "Molecular targets for autoimmune and genetic disorders of neuromuscular transmission," EurJ Biochem. Dec. 2000;267(23):6717-28.
Vogler B, et al. "Role of melatonin in the pathophysiology of migraine: implications for treatment," CNS Drugs. 2006;20(5):343-50.
Volcy M, et al. "Botulinum toxin A for the treatment of greater occipital neuralgia and trigeminal neuralgia: a case report with pathophysiological considerations," Cephalalgia. Mar. 2006;26(3):336-40.
Von Mehren M, et al. "Monoclonal antibody therapy for cancer," Annu Rev Med. 2003;54:343-69.
Wachter C, et al. "Visceral vasodilatation and somatic vasoconstriction evoked by acid challenge of the rat gastric mucosa: diversity of mechanisms," J Physiol. Jul. 15, 1995;486 ( Pt 2):505-16.
Wacnik PW, et al. "Tumor-induced mechanical hyperalgesia involves CGRP receptors and altered innervation and vascularization of DsRed2 fluorescent hindpaw tumors." Pain. May 2005;115(1-2):95-106.
Waeber C, et al. "Migraine as an inflammatory disorder." Neurology. May 24, 2005;64(10 Suppl 2):S9-15.
Walker CS, et al. "Mice lacking the neuropeptide alpha-calcitonin gene-related peptide are protected against diet-induced obesity," Endocrinology. Sep. 2010;151(9):4257-69.
Walker CS, et al. "Regulation of signal transduction by calcitonin gene-related peptide receptors," Trends Pharmacol Sci. Oct. 2010;31(10):476-83.
Ward ES, et al. "Binding activities of a repertoire of single immunoglobulin variable domains secreted from *Escherichia coli*." Nature. Oct. 12, 1989;341(6242):544-6.
Weir AN, et al. "Formatting antibody fragments to mediate specific therapeutic functions," Biochem Soc Trans. Aug. 2002;30(4):512-6.
Welch KM, et al. "Mismatch in how oestrogen modulates molecular and neuronal function may explain menstrual migraine," Neurol Sci. May 2006;27 Suppl 2:S190-2.
Werther WA, et al. "Humanization of an anti-lymphocyte function-associated antigen (LFA)-1 monoclonal antibody and reengineering of the humanized antibody for binding to rhesus LFA-1," J Immunol. Dec. 1, 1996;157(11):4986-95.
Wick EC, et al. "Transient receptor potential vanilloid 1, calcitonin gene-related peptide, and substance P mediate nociception in acute pancreatitis." Am J Physiol Gastrointest Liver Physiol. May 2006;290(5):G959-69. Epub Jan. 6, 2006.
Willats WG. "Phage display: practicalities and prospects," Plant Mol Biol. Dec. 2002;50(6):837-54.
Williamson DJ, et al. "Intravital microscope studies on the effects of neurokinin agonists and calcitonin gene-related peptide on dural vessel diameter in the anaesthetized rat," Cephalalgia. Jun. 1997;17(4):518-24.
Williamson DJ, et al. "Neurogenic inflammation in the context of migraine," Microsc Res Tech. May 1, 2001;53(3):167-78.
Williamson DJ, et al. "Sumatriptan inhibits neurogenic vasodilation of dural blood vessels in the anaesthetized rat—intravital microscope studies," Cephalalgia. Jun. 1997;17(4):525-31.
Williamson DJ, et al. "The anti-migraine 5-HT(1B/1D) agonist rizatriptan inhibits neurogenic dural vasodilation in anaesthetized guinea-pigs," Br J Pharmacol. Aug. 2001;133(7):1029-34.
Williamson DJ, et al. "The novel anti-migraine agent rizatriptan inhibits neurogenic dural vasodilation and extravasation," Eur J Pharmacol. Jun. 5, 1997;328(1):61-4.
Wimalawansa SJ, et al. "Comparative study of distribution and biochemical characterization of brain calcitonin gene-related peptide receptors in five different species," Neuroscience. May 1993;54(2):513-9.
Wimalawansa SJ, et al. "Validation, role in perioperative assessment, and clinical applications of an immunoradiometric assay for human calcitonin," Peptides. 1995;16(2):307-12.
Wimalawansa SJ. "Amylin, calcitonin gene-related peptide, calcitonin, and adrenomedullin: a peptide superfamily," Crit Rev Neurobiol. 1997;11(2-3):167-239.
Wimalawansa SJ. "Calcitonin gene-related peptide and its receptors: molecular genetics, physiology, pathophysiology, and therapeutic potentials," Endocr Rev. Oct. 1996;17(5):533-85.
Wimalawansa SJ. "Effects of in vivo stimulation on molecular forms of circulatory calcitonin and calcitonin gene-related peptide in man," Mol Cell Endocrinol. May 28, 1990;71(1):13-9.
Winkler K, et al. "Changing the antigen binding specificity by single point mutations of an anti-p24 (HIV-1) antibody." J Immunol. Oct. 15, 2000;165(8):4505-14.
Winter G, et al. "Making antibodies by phage display technology," Annu Rev Immunol. 1994;12:433-55.
Wong G, et al. "Safety and tolerability of LBR-101, a humanized monoclonal antibody that blocks the binding of CGRP to its receptor," Labrys Biologies Poster, 1 page, 2013 International Headache Congress.
Wong HC, et al. "Monoclonal antibody to rat alpha-CGRP: production, characterization, and in vivo immunoneutralization activity." Hybridoma. Feb. 1993;12(1):93-106.
Wong HC, et al. "Preparation of a monoclonal antibody to rat alpha-CGRP for in vivo immunoneutralization of peptides." Ann N Y Acad Sci. Jun. 30, 1992;657:525-7.
Wu D, et al. "Development and potential of non-peptide antagonists for calcitonin-gene-related peptide (CGRP) receptors: evidence for CGRP receptor heterogeneity," Biochem Soc Trans. Aug. 2002;30(4):468-73.
Wu H, et al. "Humanization of a murine monoclonal antibody by simultaneous optimization of framework and CDR residues." J Mol Biol. Nov. 19, 1999;294(1):151-62.
Wu H, et al. "Humanized antibodies and their applications," Methods. May 2005;36(1):1-2.
Wyon Y, et al. "Postmenopausal women with vasomotor symptoms have increased urinary excretion of calcitonin gene-related peptide," Maturitas. Nov. 16, 1998;30(3):289-94.
Xu, F.T. Study on the Mechanism of SP and CGRP in the Chronic Pain and Knee Joint. Master Thesis. Guangxi Medical University. May 2005. (In Chinese with English abstract).
Yallampalli C, et al. "Calcitonin gene-related peptide in pregnancy and its emerging receptor heterogeneity," Trends Endocrinol Metab. Aug. 2002;13(6):263-9.
Yoshikawa R, et al. "Suppression of ovalbumin-induced allergic diarrhea by diminished intestinal peristalsis in RAMP1-deficient mice," Biochem Biophys Res Commun. Jul. 8, 2011;410(3):389-93.
Yu LC, et al. "Roles of calcitonin gene-related peptide and its receptors in pain-related behavioral responses in the central nervous system," Neurosci Biobehav Rev. Sep. 2009;33(8):1185-91.
Zeller J, et al. "CGRP function-blocking antibodies inhibit neurogenic vasodilatation without affecting heart rate or arterial blood pressure in the rat." Br J Pharmacol. Dec. 2008;155(7):1093-103. doi: 10.1038/bjp.2008.334. Epub Sep. 8, 2008.
Zhang L, et al. "Arthritic calcitonin/alpha calcitonin gene-related peptide knockout mice have reduced nociceptive hypersensitivity," Pain. Jan. 2001;89(2-3):265-73.
Zhang M, et al. "Rheumatoid factor specificity of a VH3-encoded antibody is dependent on the heavy chain CDR3 region and is independent of protein A binding." J Immunol. Sep. 1, 1998;161(5):2284-9.
Zhuang X, et al. "Brain mast cell degranulation regulates blood-brain barrier," J Neurobiol. Dec. 1996;31(4):393-403.
Zittel et al., "Role of spinal afferents and calcitonin gene-related peptide in the postoperative gastric ileus in anesthetized rats," Ann Surg. Jan. 1994;219(1):79-87.
Zittel TT, et al. "Calcitonin gene-related peptide and spinal afferents partly mediate postoperative colonic ileus in the rat," Surgery. May 1998;123(5):518-27.

(56) References Cited

OTHER PUBLICATIONS

Zuckier LS, et al. "Chimeric human-mouse IgG antibodies with shuffled constant region exons demonstrate that multiple domains contribute to in vivo half-life," Cancer Res. Sep. 1, 1998;58(17):3905-8.
Misura, et al. "The Eptinezumab: CGRP Complex Structure and Characterization of the Ligand Binding Interface," poster Presented at the American Headache Society (AHS) 61st Annual Scientific Meeting Jul. 11-14, 2019.
Rita Costa A, Elisa Rodrigues M, Henriques M, Azeredo J, Oliveira R. Guidelines to cell engineering for monoclonal antibody production. Eur J Pharm Biopharm. 2010;74(2):127-138. doi:10.1016/j.ejpb.2009.10.002.
Potgieter TI, Cukan M, Drummond JE, et al. Production of monoclonal antibodies by glycoengineered Pichia pastoris. J Biotechnol. 2009;139(4):318-325. doi:10.1016/j.jbiotec.2008.12.015.
Trill JJ, Shatzman AR, Ganguly S. Production of monoclonal antibodies in COS and CHO cells. Curr Opin Biotechnol. 1995;6(5):553-560. doi:10.1016/0958-1669(95)80092-1.
Scuteri et al. "New trends in migraine pharmacology: targeting calcitonin gene-related peptide (CGRP) with monoclonal antibodies." Frontiers in pharmacology. Apr. 9, 2019;10:363.
Kopruszinski et al. "Prevention of stress-or nitric oxide donor-induced medication overuse headache by a calcitonin gene-related peptide antibody in rodents." Cephalalgia. May 2017;37(6):560-70.
Iranian Office Action dated Apr. 15, 2022, for Pat. Appl. No. 140050140003002468, filed Jun. 15, 2021 entitled "Treatment of Medication Overuse Headache Using AntiCGRP or Anit-CGRP-R Antibodies".
Iranian Office Action dated Feb. 7, 2022, for Pat. Appl. No. 140050140003002305, filed Jun. 9, 2021 entitled "Acute Treatment and Rapid Treatment of Headache Using Anti-CGRP Antibodies."
Carlsen, Louise Ninett, et al. "Complete detoxification is the most effective treatment of medication-overuse headache: a randomized controlled open-label trial." Cephalalgia 38.2 (2018): 225-236.
Cevoli, Sabina, et al. "Family history for chronic headache and drug overuse as a risk factor for headache chronification." Headache: The Journal of Head and Face Pain 49.3 (2009): 412-418.
Chen, Zhiye, et al. "Altered functional connectivity architecture of the brain in medication overuse headache using resting state fMRI." The Journal of Headache and Pain 18.1 (2017): 1-9.
Ferrari, Anna, et al. "Need for analgesics/drugs of abuse: a comparison between headache patients and addicts by the Leeds Dependence Questionnaire (LDQ)." Cephalalgia 26.2 (2006): 187-193.
Ferraro, Stefania et al. "In medication-overuse headache, fMRI shows long-lasting dysfunction in midbrain areas." Headache vol. 52,10 (2012): 1520-34. doi:10.1111/j.1526-4610.2012.02276.x.
Find, Ninette Louise et al. "Medication overuse headache in Europe and Latin America: general demographic and clinical characteristics, referral pathways and national distribution of painkillers in a descriptive, multinational, multicenter study." The journal of headache and pain 17.1 (2016): 1-12.
Fuh, Jong-Ling et al. "Does medication overuse headache represent a behavior of dependence?." Pain vol. 119,1-3 (2005): 49-55. doi:10.1016/j.pain.2005.09.034.
Fumal, Arnaud, et al. "Orbitofrontal cortex involvement in chronic analgesic-overuse headache evolving from episodic migraine." Brain 129.2 (2006): 543-550.
"Headache Classification Committee of the International Headache Society (IHS) The International Classification of Headache Disorders, 3rd edition." Cephalalgia : an international journal of headache vol. 38,1 (2018): 1-211. doi:10.1177/0333102417738202.
Grande, Ragnhild Berling, et al. "The Severity of Dependence Scale detects people with medication overuse: the Akershus study of chronic headache." Journal of Neurology, Neurosurgery & Psychiatry 80.7 (2009): 784-789.
Lai, Tzu-Hsien, et al. "Gray matter changes related to medication overuse in patients with chronic migraine." Cephalalgia 36.14 (2016): 1324-1333.
Lundqvist, C., et al. "An adapted Severity of Dependence Scale is valid for the detection of medication overuse: the Akershus study of chronic headache." European Journal of Neurology 18.3 (2011): 512-518.
Newman-Norlund, Roger D., et al. "Cortical and subcortical changes following sphenopalatine ganglion blocks in chronic migraine with medication overuse headache: a preliminary longitudinal study." Women's midlife health 6.1 (2020): 1-8.
Riederer, Franz, et al. "Decrease of gray matter volume in the midbrain is associated with treatment response in medication-overuse headache: possible influence of orbitofrontal cortex." Journal of Neuroscience 33.39 (2013): 15343-15349.
Riederer, Franz, et al. "Grey matter changes associated with medication-overuse headache: correlations with disease related disability and anxiety." The world journal of biological psychiatry 13.7 (2012): 517-525.
Torta, D. M., et al. "Nucleus accumbens functional connectivity discriminates medication-overuse headache." NeuroImage: Clinical 11 (2016): 686-693.
Lundqvist, Christofer, et al. "The severity of dependence score correlates with medication overuse in persons with secondary chronic headaches. The Akershus study of chronic headache." Pain® 148.3 (2010): 487-491.
Winner et al. "Effects of Intravenous Eptinezumab vs Placebo on Headache Pain and Most Bothersome Symptom When Initiated During a Migraine Attack: A Randomized Clinical Trial." JAMA. Jun. 15, 2021;325(23):2348-56.
Goadsby et al. Pathophysiology of Migraine: A Disorder of Sensory Processing. Physiological reviews. Apr;97(2):553-622, 1997.
Messlinger et al. "The Big CGRP Flood-sources, Sinks and Signalling Sites in the Trigeminovascular System." The Journal of Headache and Pain. Dec. 2018;19(1):1-7.
Kumar et al. "Protective role of α-calcitonin gene-related peptide in cardiovascular diseases." Frontiers in physiology. Jul. 2, 2019;10:821.
Van Dongen et al. "Migraine biomarkers in cerebrospinal fluid: A systematic review and meta-analysis." Cephalalgia. Jan. 2017;37(1):49-63.
Christensen et al. "Migraine induction with calcitonin gene-related peptide in patients from erenumab trials." The Journal of Headache and Pain. Dec. 2018;19(1):1-9.
Covasala et al. "Calcitonin gene-related peptide receptors in rat trigeminal ganglion do not control spinal trigeminal activity." Journal of neurophysiology. Jul. 15, 2012;108(2):431-40.
Storer et al. "Calcitonin gene-related peptide (CGRP) modulates nociceptive trigeminovascular transmission in the cat." British journal of pharmacology. Aug. 2004;142(7):1171-81.
Burstein et al. "The neurobiology of photophobia." Journal of neuro-ophthalmology: the official journal of the North American Neuro-Ophthalmology Society. Mar. 2019;39(1):94.
Wang et al. "Monoclonal antibody exposure in rat and cynomolgus monkey cerebrospinal fluid following systemic administration." Fluids and Barriers of the CNS. Dec. 2018;15(1):1-0.
Kelman L. "Pain characteristics of the acute migraine attack." Headache: The Journal of Head and Face Pain. Jun. 2006;46(6):942-53.
[No Author Attributed] Clinical Trial No. LY2951742, started Mar. 2015, "A Study of LY2951742 in Participants With Episodic Cluster Headache," from ClinicalTrials.gov [database online], Retrieved from the Internet: <https://clinicaltrials.gov/ct2/show/study/NCT02397473?term=LY2951742&rank=9>, retrieved Sep. 3, 2016. 6 pages.
[No Author Attributed] [machine translated from website] "Dysfunction of the temporomandibular joint," as published on the Colgate-Palmolive Company website [online], Retrieved from the Internet: <http://www.colgate.ru/ru/ru/oc/oral-health/conditions/temporomandibular-disorder> 2017; 7 pages.
Androulakis, X Michelle et al. "Central Executive and Default Mode Network Intranet work Functional Connectivity Patterns in Chronic Migraine." Journal of neurological disorders vol. 6,5 (2018): 393. doi:10.4172/2329-6895.1000393.

(56) References Cited

OTHER PUBLICATIONS

Alstadhaug, Karl B et al. "Preventing and treating medication overuse headache." Pain reports vol. 2,4 e612. Jul. 26, 2017, doi:10.1097/PR9.0000000000000612.

* cited by examiner

Figure 1A - Heavy Chain Protein Sequence

| Sequence Name | FR1 | CDR1 | FR2 | CDR2 |
|---|---|---|---|---|
| Ab1 | QSLEESGGRLVTPGTPLTLTCTVSGLDLS | SYYMQ | WVRQAPGKGLEWIG | VIGINDNTYYASWAKG |
| Ab2 | EVQLVESGGGLVQPGGSLRLSCAVSGLDLS | SYYMQ | WVRQAPGKGLEWVG | VIGINDNTYYASWAKG |
| Ab3 | EVQLVESGGGLVQPGGSLRLSCAVSGLDLS | SYYMQ | WVRQAPGKGLEWVG | VIGINDNTYYASWAKG |
| Ab4 | QSLEESGGRLVTPGTPLTLTCTVSGIDLS | GYYMN | WVRQAPGKGLEWIG | VIGINGATYYASWAKG |
| Ab5 | EVQLVESGGGLVQPGGSLRLSCAVSGIDLS | GYYMN | WVRQAPGKGLEWVG | VIGINGATYYASWAKG |
| Ab6 | EVQLVESGGGLVQPGGSLRLSCAVSGIDLS | GYYMN | WVRQAPGKGLEWVG | VIGINGATYYASWAKG |
| Ab7 | QEQLKESGGRLVTPGTSLTLTCTVSGIDLS | NHYMQ | WVRQAPGKGLEWIG | VVGINGRTYYASWAKG |
| Ab8 | EVQLVESGGGLVQPGGSLRLSCAVSGIDLS | SYYMQ | WVRQAPGKGLEWVG | VVGINGRTYYASWAKG |
| Ab9 | QSLEESGGRLVTPGTPLTLTCTVSGIGLS | SYYMQ | WVRQSPGRGLEWIG | VIGSDGKTYYATWAKG |
| Ab10 | EVQLVESGGGLVQPGGSLRLSCAVSGIGLS | SYYMQ | WVRQAPGKGLEWVG | VIGSDGKTYYATWAKG |
| Ab11 | QSLEESGGRLVTPGGSLTLTCTVSGIDVT | NYYMQ | WVRQAPGKGLEWIG | VIGVNGKRYYASWAKG |
| Ab12 | EVQLVESGGGLVQPGGSLRLSCAVSGIDVT | NYYMQ | WVRQAPGKGLEWVG | VIGVNGKRYYASWAKG |
| Ab13 | QSVEESGGGLVQPEGSLTLTCTASGFDFS | SNAMW | WVRQAPGKGLEWIG | CIYNGDGSTYYASWVNG |
| Ab14 | EVQLVESGGGLVQPGGSLRLSCAVSGIGLS | SYYMQ | WVRQAPGKGLEWVG | VIGSDGKTYYATWAKG |

Figure 1B - Heavy Chain Protein Sequence

| Sequence Name | FR3 | CDR3 | FR4 |
|---|---|---|---|
| Ab1 | RFTISRASSTTVDLKMTSLTTEDTATYFCAR | GDI | WGPGTLVTVSS |
| Ab2 | RFTISRDNSKTTVYLQMNSLRAEDTAVYFCAR | GDI | WGQGTLVTVSS |
| Ab3 | RFTISRDNSKTTVYLQMNSLRAEDTAVYFCAR | GDI | WGQGTLVTVSS |
| Ab4 | RFTISKTSSTTVDLKMTSLTTEDTATYFCAR | GDI | WGPGTLVTVSS |
| Ab5 | RFTISRDNSKTTVYLQMNSLRAEDTAVYFCAR | GDI | WGQGTLVTVSS |
| Ab6 | RFTISRDNSKTTVYLQMNSLRAEDTAVYFCAR | GDI | WGQGTLVTVSS |
| Ab7 | RFTISRTSSTTVDLKMTRLTTEDTATYFCAR | GDI | WGPGTLVTVSS |
| Ab8 | RFTISRDNSKTTVYLQMNSLRAEDTAVYFCAR | GDI | WGQGTLVTVSS |
| Ab9 | RFTISRDNSKTTVDLRMASLTTEDTATYFCTR | GDI | WGPGTLVTVSS |
| Ab10 | RFTISRDNSKTTVYLQMNSLRAEDTAVYFCTR | GDI | WGQGTLVTVSS |
| Ab11 | RFTISKTSSTTVDLKMTSLTTEDTATYFCAR | GDI | WGPGTLVTVSS |
| Ab12 | RFTISRDNSKTTVYLQMNSLRAEDTAVYFCAR | GDI | WGQGTLVTVSS |
| Ab13 | RFSISKTSSTTVTLQLNSLFVADTATYYCAR | DLDL | WGFGTLVTVSS |
| Ab14 | RFTISRDNSKTTVYLQMNSLRAEDTAVYFCTR | GDI | WGQGTLVTVSS |

Figure 1C - Heavy Chain Protein Sequence

| Sequence Name | Constant Region |
|---|---|
| Ab1 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab2 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab3 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab4 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab5 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab6 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab7 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab8 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab9 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab10 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab11 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab12 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab13 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab14 | ASTKGPSVFPLAPSSKSTSGGTAALGCLVKDYFPEPVTVSWNSGALTSGVHTFPAVLQSSGLYSLSSVVTVPSSSLGTQTYICNV |

Figure 1D - Heavy Chain Protein Sequence

| Sequence Name | Constant Region |
|---|---|
| Ab1 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab2 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab3 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab4 | NHKPSNTKVDKRVDARVEPKSCDKTHTCPPCPAPELLGGPSVFLFPPKPKDTLMISRTPEVTCVVVDVSHEDPEVKFNWYVDGVEVHNA |
| Ab5 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab6 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab7 | NHKPSNTKVDKRVDARVEPKSCDKTHTCPPCPAPELLGGPSVFLFPPKPKDTLMISRTPEVTCVVVDVSHEDPEVKFNWYVDGVEVHNA |
| Ab8 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab9 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab10 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab11 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab12 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab13 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab14 | NHKPSNTKVDKRVDARVEPKSCDKTHTCPPCPAPELLGGPSVFLFPPKPKDTLMISRTPEVTCVVVDVSHEDPEVKFNWYVDGVEVHNA |

Figure 1E - Heavy Chain Protein Sequence Constant Region

| Sequence Name | Sequence | |
|---|---|---|
| Ab1 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 1) |
| Ab2 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 41) |
| Ab3 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 81) |
| Ab4 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 121) |
| Ab5 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 161) |
| Ab6 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 201) |
| Ab7 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 241) |
| Ab8 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 281) |
| Ab9 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 321) |
| Ab10 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 361) |
| Ab11 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 401) |
| Ab12 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 441) |
| Ab13 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 481) |
| Ab14 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 521) |

Figure 1F - Heavy Chain Protein Sequence Constant Region

| Sequence Name | Sequence | |
|---|---|---|
| Ab1 | YPSDIAVEWESNGQPENNYKTTPPVLDSDGSFFLYSKLTVDKSRWQQGNVFSCSVMHEALHNHYTQKSLSLSPGK | (SEQ ID NO: 1) |
| Ab2 | YPSDIAVEWESNGQPENNYKTTPPVLDSDGSFFLYSKLTVDKSRWQQGNVFSCSVMHEALHNHYTQKSLSLSPGK | (SEQ ID NO: 41) |
| Ab3 | YPSDIAVEWESNGQPENNYKTTPPVLDSDGSFFLYSKLTVDKSRWQQGNVFSCSVMHEALHNHYTQKSLSLSPGK | (SEQ ID NO: 81) |
| Ab4 | YPSDIAVEWESNGQPENNYKTTPPVLDSDGSFFLYSKLTVDKSRWQQGNVFSCSVMHEALHNHYTQKSLSLSPGK | (SEQ ID NO: 121) |
| Ab5 | YPSDIAVEWESNGQPENNYKTTPPVLDSDGSFFLYSKLTVDKSRWQQGNVFSCSVMHEALHNHYTQKSLSLSPGK | (SEQ ID NO: 161) |
| Ab6 | YPSDIAVEWESNGQPENNYKTTPPVLDSDGSFFLYSKLTVDKSRWQQGNVFSCSVMHEALHNHYTQKSLSLSPGK | (SEQ ID NO: 201) |
| Ab7 | YPSDIAVEWESNGQPENNYKTTPPVLDSDGSFFLYSKLTVDKSRWQQGNVFSCSVMHEALHNHYTQKSLSLSPGK | (SEQ ID NO: 241) |
| Ab8 | YPSDIAVEWESNGQPENNYKTTPPVLDSDGSFFLYSKLTVDKSRWQQGNVFSCSVMHEALHNHYTQKSLSLSPGK | (SEQ ID NO: 281) |
| Ab9 | YPSDIAVEWESNGQPENNYKTTPPVLDSDGSFFLYSKLTVDKSRWQQGNVFSCSVMHEALHNHYTQKSLSLSPGK | (SEQ ID NO: 321) |
| Ab10 | YPSDIAVEWESNGQPENNYKTTPPVLDSDGSFFLYSKLTVDKSRWQQGNVFSCSVMHEALHNHYTQKSLSLSPGK | (SEQ ID NO: 361) |
| Ab11 | YPSDIAVEWESNGQPENNYKTTPPVLDSDGSFFLYSKLTVDKSRWQQGNVFSCSVMHEALHNHYTQKSLSLSPGK | (SEQ ID NO: 401) |
| Ab12 | YPSDIAVEWESNGQPENNYKTTPPVLDSDGSFFLYSKLTVDKSRWQQGNVFSCSVMHEALHNHYTQKSLSLSPGK | (SEQ ID NO: 441) |
| Ab13 | YPSDIAVEWESNGQPENNYKTTPPVLDSDGSFFLYSKLTVDKSRWQQGNVFSCSVMHEALHNHYTQKSLSLSPGK | (SEQ ID NO: 481) |
| Ab14 | YPSDIAVEWESNGQPENNYKTTPPVLDSDGSFFLYSKLTVDKSRWQQGNVFSCSVMHEALHNHYTQKSLSLSPGK | (SEQ ID NO: 521) |

Figure 2A - Light Chain Protein Sequence

| Sequence Name | FR1 | CDR1 | FR2 | CDR2 |
|---|---|---|---|---|
| Ab1 | QVLTQTASPVSAAVGSTVTINC | QASQSVYDNNYLA | WYQQKPGQPPKQLIY | STSTLAS |
| Ab2 | QVLTQSPSSLSASVGDRVTINC | QASQSVYDNNYLA | WYQQKPGKVPKQLIY | STSTLAS |
| Ab3 | QVLTQSPSSLSASVGDRVTINC | QASQSVYDNNYLA | WYQQKPGKVPKQLIY | STSTLAS |
| Ab4 | QVLTQTPSPVSAAVGSTVTINC | QASQSVYHNTYLA | WYQQKPGQPPKQLIY | DASTLAS |
| Ab5 | QVLTQSPSSLSASVGDRVTINC | QASQSVYHNTYLA | WYQQKPGKVPKQLIY | STSTLAS |
| Ab6 | QVLTQSPSSLSASVGDRVTINC | QASQSVYHNTYLA | WYQQKPGKVPKQLIY | DASTLAS |
| Ab7 | QVLTQTASPVSAAVGSTVTINC | QASQSVYNYNYLA | WYQQKPGQPPKQLIY | STSTLAS |
| Ab8 | QVLTQSPSSLSASVGDRVTINC | QASQNVYNNNYLA | WYQQKPGKVPKQLIY | STSTLAS |
| Ab9 | QVLTQTPSPVSAAVGSTVTINC | QASQNVYNNNYLA | WYQQKPGQPPKQLIY | STSTLAS |
| Ab10 | QVLTQSPSSLSASVGDRVTINC | RASQSVYYNNYLA | WYQQKPGKVPKQLIY | STSTLAS |
| Ab11 | QVLTQTASPVSPAVGSTVTINC | RASQSVYYNNYLA | WYQQKPGQPPKQLIY | STSTLAS |
| Ab12 | QVLTQSPSSLSASVGDRVTINC | QASESLYNNNALA | WYQQKPGKVPKQLIY | STSTLAS |
| Ab13 | AIVMTQTPSSKSVPVGDTVTINC | QASESLYNNNALA | WFQQKPGQPPKRLIY | DASKLAS |
| Ab14 | QVLTQSPSSLSASVGDRVTINC | QASQNVYNNNYLA | WYQQKPGKVPKQLIY | STSTLAS |

Figure 2B - Light Chain Protein Sequence

| Sequence Name | FR3 | CDR3 | FR4 |
|---|---|---|---|
| Ab1 | GVSSRFKGSGSGSGTQFTLTITSDLECADAATYYC | LGSYDCSSGDCFV | FGGGTEVVVKR |
| Ab2 | GVPSRFSGSGSGTDFTLTISSLQPEDVATYYC | LGSYDCSSGDCFV | FGGGTKVEIKR |
| Ab3 | GVPSRFSGSGSGTDFTLTISSLQPEDVATYYC | LGSYDCSSGDCFV | FGGGTKVEIKR |
| Ab4 | GVPSRFSGSGSGTQFTLTISGVQCNDAAAYYC | LGSYDCTNGDCFV | FGGGTKVEIKR |
| Ab5 | GVPSRFSGSGSGTDFTLTISSLQPEDVATYYC | LGSYDCTNGDCFV | FGGGTKVEIKR |
| Ab6 | GVPSRFSGSGSGTDFTLTISSLQPEDVATYYC | LGSYDCTNGDCFV | FGGGTKVEIKR |
| Ab7 | GVSSRFKGSGSGSGTQFTLTISDVQCDDAATYYC | LGSYDCSTGDCFV | FGGGTEVVVKR |
| Ab8 | GVPSRFSGSGSGTDFTLTISSLQPEDVATYYC | LGSYDCSTGDCFV | FGGGTKVEIKR |
| Ab9 | GVSSRFRGSGSGSGTQFTLTISDVQCDDAATYYC | LGSYDCSRGDCFV | FGGGTEVVVKR |
| Ab10 | GVPSRFSGSGSGTDFTLTISSLQPEDVATYYC | LGSYDCSRGDCFV | FGGGTKVEIKR |
| Ab11 | GVSSRFKGSGSGSGTDFTLTISDVQCDDAATYYC | LGSYDCSNGDCFV | FGGGTEVVVKR |
| Ab12 | GVPSRFSGSGSGTDFTLTISSLQPEDVATYYC | LGSYDCSNGDCFV | FGGSTKVEIKR |
| Ab13 | GVPSRFSGGGSGTQFTLTISGVQCDDAATYYC | GGYRSDSVDGVA | FAGGTEVVVKR |
| Ab14 | GVPSRFSGSGSGTDFTLTISSLQPEDVATYYC | LGSYDCSRGDCFV | FGGGTKVEIKR |

Figure 2C - Light Chain Protein Sequence

| Sequence Name | Constant Region | |
|---|---|---|
| Ab1 | TVAAPSVFIFPPSDEQLKSGTASVVCLLNNFYPREAKVQWKVDNALQSGNSQESVTEQDSKDSTYSLSSTLTLSKADYEKHKVYA | |
| Ab2 | TVAAPSVFIFPPSDEQLKSGTASVVCLLNNFYPREAKVQWKVDNALQSGNSQESVTEQDSKDSTYSLSSTLTLSKADYEKHKVYA | |
| Ab3 | TVAAPSVFIFPPSDEQLKSGTASVVCLLNNFYPREAKVQWKVDNALQSGNSQESVTEQDSKDSTYSLSSTLTLSKADYEKHKVYA | |
| Ab4 | TVAAPSVFIFPPSDEQLKSGTASVVCLLNNFYPREAKVQWKVDNALQSGNSQESVTEQDSKDSTYSLSSTLTLSKADYEKHKVYA | |
| Ab5 | TVAAPSVFIFPPSDEQLKSGTASVVCLLNNFYPREAKVQWKVDNALQSGNSQESVTEQDSKDSTYSLSSTLTLSKADYEKHKVYA | |
| Ab6 | TVAAPSVFIFPPSDEQLKSGTASVVCLLNNFYPREAKVQWKVDNALQSGNSQESVTEQDSKDSTYSLSSTLTLSKADYEKHKVYA | |
| Ab7 | TVAAPSVFIFPPSDEQLKSGTASVVCLLNNFYPREAKVQWKVDNALQSGNSQESVTEQDSKDSTYSLSSTLTLSKADYEKHKVYA | |
| Ab8 | TVAAPSVFIFPPSDEQLKSGTASVVCLLNNFYPREAKVQWKVDNALQSGNSQESVTEQDSKDSTYSLSSTLTLSKADYEKHKVYA | |
| Ab9 | TVAAPSVFIFPPSDEQLKSGTASVVCLLNNFYPREAKVQWKVDNALQSGNSQESVTEQDSKDSTYSLSSTLTLSKADYEKHKVYA | |
| Ab10 | TVAAPSVFIFPPSDEQLKSGTASVVCLLNNFYPREAKVQWKVDNALQSGNSQESVTEQDSKDSTYSLSSTLTLSKADYEKHKVYA | |
| Ab11 | TVAAPSVFIFPPSDEQLKSGTASVVCLLNNFYPREAKVQWKVDNALQSGNSQESVTEQDSKDSTYSLSSTLTLSKADYEKHKVYA | |
| Ab12 | TVAAPSVFIFPPSDEQLKSGTASVVCLLNNFYPREAKVQWKVDNALQSGNSQESVTEQDSKDSTYSLSSTLTLSKADYEKHKVYA | |
| Ab13 | TVAAPSVFIFPPSDEQLKSGTASVVCLLNNFYPREAKVQWKVDNALQSGNSQESVTEQDSKDSTYSLSSTLTLSKADYEKHKVYA | |
| Ab14 | TVAAPSVFIFPPSDEQLKSGTASVVCLLNNFYPREAKVQWKVDNALQSGNSQESVTEQDSKDSTYSLSSTLTLSKADYEKHKVYA | |

Figure 2D - Light Chain Protein Sequence

| Sequence Name | Constant Region | |
|---|---|---|
| Ab1 | CEVTHQGLSSPVTKSFNRGEC | (SEQ ID NO: 21) |
| Ab2 | CEVTHQGLSSPVTKSFNRGEC | (SEQ ID NO: 61) |
| Ab3 | CEVTHQGLSSPVTKSFNRGEC | (SEQ ID NO: 101) |
| Ab4 | CEVTHQGLSSPVTKSFNRGEC | (SEQ ID NO: 141) |
| Ab5 | CEVTHQGLSSPVTKSFNRGEC | (SEQ ID NO: 181) |
| Ab6 | CEVTHQGLSSPVTKSFNRGEC | (SEQ ID NO: 221) |
| Ab7 | CEVTHQGLSSPVTKSFNRGEC | (SEQ ID NO: 261) |
| Ab8 | CEVTHQGLSSPVTKSFNRGEC | (SEQ ID NO: 301) |
| Ab9 | CEVTHQGLSSPVTKSFNRGEC | (SEQ ID NO: 341) |
| Ab10 | CEVTHQGLSSPVTKSFNRGEC | (SEQ ID NO: 381) |
| Ab11 | CEVTHQGLSSPVTKSFNRGEC | (SEQ ID NO: 421) |
| Ab12 | CEVTHQGLSSPVTKSFNRGEC | (SEQ ID NO: 461) |
| Ab13 | CEVTHQGLSSPVTKSFNRGEC | (SEQ ID NO: 501) |
| Ab14 | CEVTHQGLSSPVTKSFNRGEC | (SEQ ID NO: 541) |

Figure 3A - Heavy Chain DNA Sequence

| Sequence Name | FR1 |
|---|---|
| Ab1 | CAGTCGCTGGAGGAGTCCGGGGGAGTCGCCTGGTCACGCCTGGGACACCCCTGGACACTCACCTGCACAGTCTCTGGACTCGACCTCAGT |
| Ab2 | GAGGTGCAGCTTGTGGAGTCTGGGGGAGGCTTGGTCCAGCCTGGGGGGTCCCTGAGACTCTCCTGTGCAGTCTCTGGACTCGACCTCAGT |
| Ab3 | GAGGTGCAGCTTGTGGAGTCTGGGGGAGGCTTGGTCCAGCCTGGGGGGTCCCTGAGACTCTCCTGTGCAGTCTCTGGACTCGACCTCAGT |
| Ab4 | CAGTCGCTGGAGGAGTCCGGGGGAGTCGCCTGGTCACGCCTGGGACACCCCTGGACACTCACCTGTTCCGTCTGTGCATCGACCTCAGT |
| Ab5 | GAGGTGCAGCTTGTGGAGTCTGGGGGAGGCTTGGTCCAGCCTGGGGGGTCCCTGAGACTCTCCTGTGCAGTCTCTGGAATCGACCTCAGT |
| Ab6 | GAGGTGCAGCTTGTGGAGTCTGGGGGAGGCTTGGTCCAGCCTGGGGGGTCCCTGAGACTCTCCTGTGCAGTCTCTGGAATCGACCTCAGT |
| Ab7 | CAGGAGCAGCTGAAGGAGTCCGGGGGTCGGGGTCGCCCTGGTCACGCCTGGGACATCCCTGAGACTCTCCTGACACTCGACCTCAGT |
| Ab8 | GAGGTGCAGCTTGTGGAGTCTGGGGGAGGCTTGGTCCAGCCTGGGGGGTCCCTGAGACTCTCCTGTGCAGTCTCTGGAATCGACCTCAGT |
| Ab9 | CAGTCGCTGGAGGAGTCCGGGGGAGTCGCCTGGTCACGCCTGGGACACCCCTGGACACTCACCTGCACAGTCTCTGGAATCGGCCTCAGT |
| Ab10 | GAGGTGCAGCTTGTGGAGTCTGGGGGAGGCTTGGTCCAGCCTGGGGGGTCCCTGAGACTCTCCTGTGCAGTCTCTGGAATCGACGTCACT |
| Ab11 | CAGTCGCTGGAGGAGTCCGGGGGAGTCGCCTGGTCACGCCTGGGACACCCCTGGACACTCACCTGCACAGTCTCTGGAATCGACGTCACT |
| Ab12 | GAGGTGCAGCTTGTGGAGTCTGGGGGAGGCTTGGTCCAGCCTGGGGGGTCCCTGAGACTCTCCTGTGCAGTCTCTGGAATCGACGTCACT |
| Ab13 | CAGTCGGTGGAGGAGTCCGGGGGAGTCCGGGGAGGCCTGGGCTCGCCCTGAGGCCTGGGAGCCTGAGACTCTCACCTGACACTCGAATCGACTTCAGT |
| Ab14 | GAGGTGCAGCTTGTGTGGAGTCTGGGAGTCGGGAGTCGCCTGGAGCCTGAGCCTGAGACTCTCCTGTGCAGTCTCTGGAATCGGCCTCAGT |

Figure 3B - Heavy Chain DNA Sequence

| Sequence Name | CDR1 | FR2 |
|---|---|---|
| Ab1 | AGCTACTACATGCAA | TGGGTCCGCCAGGCTCCAGGGAAGGGGCTGGAATGGATCGGA |
| Ab2 | AGCTACTACATGCAA | TGGGTCCGTCAGGCTCCAGGGAAGGGGCTGGAGTGGGTCGGA |
| Ab3 | AGCTACTACATGCAA | TGGGTCCGTCAGGCTCCAGGGAAGGGGCTGGAGTGGGTCGGA |
| Ab4 | GGCTACTACATGAAC | TGGGTCCGCCAGGCTCCAGGGAAGGGGCTGGAATGGATCGGA |
| Ab5 | GGCTACTACATGAAC | TGGGTCCGTCAGGCTCCAGGGAAGGGGCTGGAGTGGGTCGGA |
| Ab6 | GGCTACTACATGAAC | TGGGTCCGTCAGGCTCCAGGGAAGGGGCTGGAGTGGGTCGGA |
| Ab7 | AACCACTACATGCAA | TGGGTCCGCCAGGCTCCAGGGAAGGGGCTGGAGTGGATCGGA |
| Ab8 | AACCACTACATGCAA | TGGGTCCGTCAGGCTCCAGGGAAGGGGCTGGAGTGGGTCGGA |
| Ab9 | AGCTACTACATGCAG | TGGGTCCGCCAGTCTCCAGGGAAGGGGCTGGAATGGATCGGA |
| Ab10 | AGCTACTACATGCAA | TGGGTCCGTCAGGCTCCAGGGAAGGGGCTGGAGTGGGTCGGA |
| Ab11 | AACTACTATATGCAA | TGGGTCCGCCAGGCTCCAGGGAAGGGGCTGGAATGGATCGGA |
| Ab12 | AACTACTACATGCAA | TGGGTCCGTCAGGCTCCAGGGAAGGGGCTGGAATGGGTCGGA |
| Ab13 | AGCAATGCAATGTGG | TGGGTCCGCCAGGCTCCAGGGAAGGGGCTGGAGTGGATCGGA |
| Ab14 | AGCTACTACATGCAA | TGGGTCCGTCAGGCTCCAGGGAAGGGGCTGGAGTGGGTCGGA |

Figure 3C - Heavy Chain DNA Sequence

| Sequence Name | CDR2 |
|---|---|
| Ab1 | GTCATTGGTATTAATGATAACACATACTACGCGAGCTGGGCGAAAGGC |
| Ab2 | GTCATTGGTATCAATGATAACACATACTACGCGAGCTGGGCGAAAGGC |
| Ab3 | GTCATTGGTATCAATGATAACACATACTACGCGAGCTGGGCGAAAGGC |
| Ab4 | GTCATTGGTATTAATGGTGCCACATACTACGCGAGCTGGGCGAAAGGC |
| Ab5 | GTCATTGGTATTAATGGTGCCACATACTACGCGAGCTGGGCGAAAGGC |
| Ab6 | GTCATTGGTATTAATGGTGCCACATACTACGCGAGCTGGGCGAAAGGC |
| Ab7 | GTCGTTGGTATTAATGGTCGCACATACTACGCGAGCTGGGCGAAAGGC |
| Ab8 | GTCGTTGGTATCAATGGTCGCACATACTACGCGAGCTGGGCGAAAGGC |
| Ab9 | GTCATTGGTAGTGATGGTAAGACATACTACGCGAGCTGGGCGAAAGGC |
| Ab10 | GTCATTGGTAGTGATGGTAAGACATACTACGCGAGCTGGGCGAAAGGC |
| Ab11 | GTCATTGGTGTGAATGGTAAGAGATACTACGCGAGCTGGGCGAAAGGC |
| Ab12 | GTCATTGGTGTGAATGGTAAGAGATACTACGCGAGCTGGGCGAAAGGC |
| Ab13 | TGCATTTACAATGGTGATGGCAGCACATACTACGCGAGCTGGGTGAATGGC |
| Ab14 | GTCATTGGTAGTGATGGTAAGACATACTACGCGAGCTGGGCGAAAGGC |

Figure 3D - Heavy Chain DNA Sequence

| Sequence Name | FR3 |
|---|---|
| Ab1 | CGATTCACCATCTCCAGAGCCTCGTCGACCGTGGATCTGAAAATGACCAGTCTGAGAATGAACAGCCTGAGAGCTGAGGACACGGCCACCTATTTCTGTGCCAGA |
| Ab2 | CGATTCACCATCTCCAGAGACACAATTCCAAGACCACGGTGTATCTTCAAATGAACAGCCTGAGAGCTGAGGACACGGCCACTGCTGTGTGTATTTCTGTGCTAGA |
| Ab3 | CGATTCACCATCTCCAGAGACACAATTCCAAGACCACGGTGTATCTTCAAATGAACAGCCTGAGAGCTGAGGACACGGCCACTGCTGTGTGTATTTCTGTGCTAGA |
| Ab4 | CGATTCACCATCTCCAAAACCTCGTCGACCAATTCCAAGACCACGGTGGATCTGAAAATGACCAGTCTGAGAGCTGAGGACACGGCCACTGCTGTGTGTATTTCTGTGCCAGA |
| Ab5 | CGATTCACCATCTCCAGAGACACAATTCCAAGACCACGGTGTGATCTGTATCTTCAAATGAACAGCCTGAGAACCGAGGACACGGCCACTGCTGTGTGTATTTCTGTGCCAGA |
| Ab6 | CGATTCACCATCTCCAGAGACACAATTCCAAGACCACGGTGTGATCTGTATCTTCAAATGAACAGCCTGAGAACCGAGGACACGGCCACTGCTGTGTGTATTTCTGTGCTAGA |
| Ab7 | CGATTCACCATCTCCAGAGACAACCTCGTCGACCAATTCCAAGACCACGGTGGATCTGTATCTTCAAATGACCAGTCTGAGAATGACCAGGCTGAGGACACGGCCACCTATTTCTGTGCCAGA |
| Ab8 | CGATTCACCATCTCCAGAGACAACCTCGTCGACCAATTCCAAGACCACGGTGGATCTGTATCTTCAAATGGCCAGTCTGAGAATGACCAGGCTGAGGACACGGCCACCTATTTCTGTGCCAGA |
| Ab9 | CGATTCACCATCTCCAAGAGACCTCGTCGACCAATTCCAAGACCACGGTGGATCTGTATCTTGAAAATGACCAGTCTGAGAATGGCCAAATGACCAGGCTGAGGACACGGCCACCTATTTCTGTACCAGA |
| Ab10 | CGATTCACCATCTCCAGAGACAACCTCGTCGACCAATTCCAAGACCACGGTGGATCTGTATCTGAAAATGACCAGTCTGAAATGACCAGCTGAGGACACTGTGACAGCCTGTGTGTATTTCTGTGCCAGA |
| Ab11 | CGATTCACCATCTCCAAAACCTCGTCGACCAATTCCAAGACCACGGTGGATCTGAAATGACCAGTCTGAAAATGGCCAAATGACCAGCTGAGGACACGGCCACTGCTGTGTGTATTTCTGTGCCAGA |
| Ab12 | CGATTCACCATCTCCAGAGACAACCTCGTGTATCTTCCAAGACCACGGTGTACCTGTATCTTTCAAATGACCAGTCTGAAATGACCAGCTGAGGACACGGCCACTGCTGTGTGTATTTCTGTGCCAGA |
| Ab13 | CGATTCTCCATCTCCAAAACCTCGTCCAAGACCACGGTATCTCGCAACTGAATAGTCTGACACAGCCTGCGGACAGTCGCGGACACGGCCACGTATTATTGTGCGAGA |
| Ab14 | CGATTCACCATCTCCAGAGACAACCTCGTCGACCAATTCCAAGACCACGGTGTATCTTCAAATGAACAGCCTGAGAGCTGAGGACACGGCCACTGCTGTGTATTTCTGTACCAGA |

Figure 3E - Heavy Chain DNA Sequence

| Sequence Name | CDR3 | FR4 | Constant Region |
|---|---|---|---|
| Ab1 | GGGGACATC | TGGGGCCAAGGGACCACCCTCGTCACCGTCTCGAGC | GCCTCCACCAAGGGCCCATCGGTCTTCCCCCTGGCACCCTCCTCC |
| Ab2 | GGGGACATC | TGGGGCCAAGGGACCACCCTCGTCACCGTCTCGAGC | GCCTCCACCAAGGGCCCATCGGTCTTCCCCCTGGCACCCTCCTCC |
| Ab3 | GGGGACATC | TGGGGCCAAGGGACCACCCTCGTCACCGTCTCGAGC | GCCTCCACCAAGGGCCCATCGGTCTTCCCCCTGGCACCCTCCTCC |
| Ab4 | GGGGACATC | TGGGGCCAAGGGACCACCCTCGTCACCGTCTCGAGC | GCCTCCACCAAGGGCCCATCGGTCTTCCCCCTGGCACCCTCCTCC |
| Ab5 | GGGGACATC | TGGGGCCAAGGGACCACCCTCGTCACCGTCTCGAGC | GCCTCCACCAAGGGCCCATCGGTCTTCCCCCTGGCACCCTCCTCC |
| Ab6 | GGGGACATC | TGGGGCCAAGGGACCACCCTCGTCACCGTCTCGAGC | GCCTCCACCAAGGGCCCATCGGTCTTCCCCCTGGCACCCTCCTCC |
| Ab7 | GGGGACATC | TGGGGCCAAGGGACCACCCTCGTCACCGTCTCGAGC | GCCTCCACCAAGGGCCCATCGGTCTTCCCCCTGGCACCCTCCTCC |
| Ab8 | GGGGACATC | TGGGGCCAAGGGACCACCCTCGTCACCGTCTCGAGC | GCCTCCACCAAGGGCCCATCGGTCTTCCCCCTGGCACCCTCCTCC |
| Ab9 | GGGGACATC | TGGGGCCAAGGGACCCCCCTCGTCACCGTCTCGAGC | GCCTCCACCAAGGGCCCATCGGTCTTCCCCCTGGCACCCTCCTCC |
| Ab10 | GGGGACATC | TGGGGCCAAGGGACCACCCTCGTCACCGTCTCGAGC | GCCTCCACCAAGGGCCCATCGGTCTTCCCCCTGGCACCCTCCTCC |
| Ab11 | GGCGACATC | TGGGGCCAAGGGACCCCCCTCGTCACCGTCTCGAGC | GCCTCCACCAAGGGCCCATCGGTCTTCCCCCTGGCACCCTCCTCC |
| Ab12 | GGGGACATC | TGGGGCCAAGGGACCACCCTCGTCACCGTCTCGAGC | GCCTCCACCAAGGGCCCATCGGTCTTCCCCCTGGCACCCTCCTCC |
| Ab13 | GATCTTGACTTG | TGGGGCCCAAGGGCACCCTCGTCACCGTCTCGAGC | GCCTCCACCAAGGGCCCATCGGTCTTCCCCCTGGCACCCTCCTCC |
| Ab14 | GGGGACATC | TGGGGCCAAGGGACCACCCTCGTCACCGTCTCGAGC | GCCTCCACCAAGGGCCCATCGGTCTTCCCCCTGGCACCCTCCTCC |

Figure 3F - Heavy Chain DNA Sequence

| Sequence Name | Constant Region |
|---|---|
| Ab1 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab2 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab3 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab4 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab5 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab6 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab7 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab8 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab9 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab10 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab11 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab12 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab13 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab14 | AAGAGCACCTCTGGGGGCACAGCGGCCCTGGGCTGCCTGGTCAAGGACTACTTCCCCGAACCGGTGACGGTGTCGTGGAACTCAGGCGCC |

Figure 3G - Heavy Chain DNA Sequence

| Sequence Name | Constant Region |
|---|---|
| Ab1 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab2 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab3 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab4 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab5 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab6 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab7 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab8 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab9 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab10 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab11 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab12 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab13 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab14 | CTGACCAGCGGCGTGCACACCTTCCCGGCTGTCCTACAGTCCTCAGGACTCTACTCCCTCAGCAGCGTGGTGACCGTGCCCTCCAGCAGC |

Figure 3H - Heavy Chain DNA Sequence

| Sequence Name | Constant Region |
|---|---|
| Ab1 | TTGGGCACCCAGACCTACATCTGCAACGTGAATCACAAGCCCAGCAACACCAAGGTGGACAAGAGAGTTGAGCCCAAATCTTGTGACAAA |
| Ab2 | TTGGGCACCCAGACCTACATCTGCAACGTGAATCACAAGCCCAGCAACACCAAGGTGGACAAGAGAGTTGAGCCCAAATCTTGTGACAAA |
| Ab3 | TTGGGCACCCAGACCTACATCTGCAACGTGAATCACAAGCCCAGCAACACCAAGGTGGACAAGAGAGTTGAGCCCAAATCTTGTGACAAA |
| Ab4 | TTGGGCACCCAGACCTACATCTGCAACGTGAATCACAAGCCCAGCAACACCAAGGTGGACAAGAGAGTTGAGCCCAAATCTTGTGACAAA |
| Ab5 | TTGGGCACCCAGACCTACATCTGCAACGTGAATCACAAGCCCAGCAACACCAAGGTGGACAAGAGAGTTGAGCCCAAATCTTGTGACAAA |
| Ab6 | TTGGGCACCCAGACCTACATCTGCAACGTGAATCACAAGCCCAGCAACACCAAGGTGGACAAGAGAGTTGAGCCCAAATCTTGTGACAAA |
| Ab7 | TTGGGCACCCAGACCTACATCTGCAACGTGAATCACAAGCCCAGCAACACCAAGGTGGACAAGAGAGTTGAGCCCAAATCTTGTGACAAA |
| Ab8 | TTGGGCACCCAGACCTACATCTGCAACGTGAATCACAAGCCCAGCAACACCAAGGTGGACAAGAGAGTTGAGCCCAAATCTTGTGACAAA |
| Ab9 | TTGGGCACCCAGACCTACATCTGCAACGTGAATCACAAGCCCAGCAACACCAAGGTGGACAAGAGAGTTGAGCCCAAATCTTGTGACAAA |
| Ab10 | TTGGGCACCCAGACCTACATCTGCAACGTGAATCACAAGCCCAGCAACACCAAGGTGGACAAGAGAGTTGAGCCCAAATCTTGTGACAAA |
| Ab11 | TTGGGCACCCAGACCTACATCTGCAACGTGAATCACAAGCCCAGCAACACCAAGGTGGACAAGAGAGTTGAGCCCAAATCTTGTGACAAA |
| Ab12 | TTGGGCACCCAGACCTACATCTGCAACGTGAATCACAAGCCCAGCAACACCAAGGTGGACAAGAGAGTTGAGCCCAAATCTTGTGACAAA |
| Ab13 | TTGGGCACCCAGACCTACATCTGCAACGTGAATCACAAGCCCAGCAACACCAAGGTGGACAAGAGAGTTGAGCCCAAATCTTGTGACAAA |
| Ab14 | TTGGGCACCCAGACCTACATCTGCAACGTGAATCACAAGCCCAGCAACACCAAGGTGGACAAGAGAGTTGAGCCCAAATCTTGTGACAAA |

Figure 3I - Heavy Chain DNA Sequence

| Sequence Name | Constant Region |
|---|---|
| Ab1 | ACTCACACACATGCCCACCGTGCCCAGCACCTGAACTCCTGGGGGGACCGTCAGTCTTCCTCTTCCCCCCAAAACCCAAGGACACCCTCATG |
| Ab2 | ACTCACACACATGCCCACCGTGCCCAGCACCTGAACTCCTGGGGGGACCGTCAGTCTTCCTCTTCCCCCCAAAACCCAAGGACACCCTCATG |
| Ab3 | ACTCACACACATGCCCACCGTGCCCAGCACCTGAACTCCTGGGGGGACCGTCAGTCTTCCTCTTCCCCCCAAAACCCAAGGACACCCTCATG |
| Ab4 | ACTCACACACATGCCCACCGTGCCCAGCACCTGAACTCCTGGGGGGACCGTCAGTCTTCCTCTTCCCCCCAAAACCCAAGGACACCCTCATG |
| Ab5 | ACTCACACACATGCCCACCGTGCCCAGCACCTGAACTCCTGGGGGGACCGTCAGTCTTCCTCTTCCCCCCAAAACCCAAGGACACCCTCATG |
| Ab6 | ACTCACACACATGCCCACCGTGCCCAGCACCTGAACTCCTGGGGGGACCGTCAGTCTTCCTCTTCCCCCCAAAACCCAAGGACACCCTCATG |
| Ab7 | ACTCACACACATGCCCACCGTGCCCAGCACCTGAACTCCTGGGGGGACCGTCAGTCTTCCTCTTCCCCCCAAAACCCAAGGACACCCTCATG |
| Ab8 | ACTCACACACATGCCCACCGTGCCCAGCACCTGAACTCCTGGGGGGACCGTCAGTCTTCCTCTTCCCCCCAAAACCCAAGGACACCCTCATG |
| Ab9 | ACTCACACACATGCCCACCGTGCCCAGCACCTGAACTCCTGGGGGGACCGTCAGTCTTCCTCTTCCCCCCAAAACCCAAGGACACCCTCATG |
| Ab10 | ACTCACACACATGCCCACCGTGCCCAGCACCTGAACTCCTGGGGGGACCGTCAGTCTTCCTCTTCCCCCCAAAACCCAAGGACACCCTCATG |
| Ab11 | ACTCACACACATGCCCACCGTGCCCAGCACCTGAACTCCTGGGGGGACCGTCAGTCTTCCTCTTCCCCCCAAAACCCAAGGACACCCTCATG |
| Ab12 | ACTCACACACATGCCCACCGTGCCCAGCACCTGAACTCCTGGGGGGACCGTCAGTCTTCCTCTTCCCCCCAAAACCCAAGGACACCCTCATG |
| Ab13 | ACTCACACACATGCCCACCGTGCCCAGCACCTGAACTCCTGGGGGGACCGTCAGTCTTCCTCTTCCCCCCAAAACCCAAGGACACCCTCATG |
| Ab14 | ACTCACACACATGCCCACCGTGCCCAGCACCTGAACTCCTGGGGGGACCGTCAGTCTTCCTCTTCCCCCCAAAACCCAAGGACACCCTCATG |

Figure 3J - Heavy Chain DNA Sequence

| Sequence Name | Constant Region |
|---|---|
| Ab1 | ATCTCCCGGACCCCTGAGGTCACATGCGTGGTGGTGGACGTGAGCCACGAAGACCCTGAGGTCAAGTTCAACTGGTACGTGGACGGCGTG |
| Ab2 | ATCTCCCGGACCCCTGAGGTCACATGCGTGGTGGTGGACGTGAGCCACGAAGACCCTGAGGTCAAGTTCAACTGGTACGTGGACGGCGTG |
| Ab3 | ATCTCCCGGACCCCTGAGGTCACATGCGTGGTGGTGGACGTGAGCCACGAAGACCCTGAGGTCAAGTTCAACTGGTACGTGGACGGCGTG |
| Ab4 | ATCTCCCGGACCCCTGAGGTCACATGCGTGGTGGTGGACGTGAGCCACGAAGACCCTGAGGTCAAGTTCAACTGGTACGTGGACGGCGTG |
| Ab5 | ATCTCCCGGACCCCTGAGGTCACATGCGTGGTGGTGGACGTGAGCCACGAAGACCCTGAGGTCAAGTTCAACTGGTACGTGGACGGCGTG |
| Ab6 | ATCTCCCGGACCCCTGAGGTCACATGCGTGGTGGTGGACGTGAGCCACGAAGACCCTGAGGTCAAGTTCAACTGGTACGTGGACGGCGTG |
| Ab7 | ATCTCCCGGACCCCTGAGGTCACATGCGTGGTGGTGGACGTGAGCCACGAAGACCCTGAGGTCAAGTTCAACTGGTACGTGGACGGCGTG |
| Ab8 | ATCTCCCGGACCCCTGAGGTCACATGCGTGGTGGTGGACGTGAGCCACGAAGACCCTGAGGTCAAGTTCAACTGGTACGTGGACGGCGTG |
| Ab9 | ATCTCCCGGACCCCTGAGGTCACATGCGTGGTGGTGGACGTGAGCCACGAAGACCCTGAGGTCAAGTTCAACTGGTACGTGGACGGCGTG |
| Ab10 | ATCTCCCGGACCCCTGAGGTCACATGCGTGGTGGTGGACGTGAGCCACGAAGACCCTGAGGTCAAGTTCAACTGGTACGTGGACGGCGTG |
| Ab11 | ATCTCCCGGACCCCTGAGGTCACATGCGTGGTGGTGGACGTGAGCCACGAAGACCCTGAGGTCAAGTTCAACTGGTACGTGGACGGCGTG |
| Ab12 | ATCTCCCGGACCCCTGAGGTCACATGCGTGGTGGTGGACGTGAGCCACGAAGACCCTGAGGTCAAGTTCAACTGGTACGTGGACGGCGTG |
| Ab13 | ATCTCCCGGACCCCTGAGGTCACATGCGTGGTGGTGGACGTGAGCCACGAAGACCCTGAGGTCAAGTTCAACTGGTACGTGGACGGCGTG |
| Ab14 | ATCTCCCGGACCCCTGAGGTCACATGCGTGGTGGTGGACGTGAGCCACGAAGACCCTGAGGTCAAGTTCAACTGGTACGTGGACGGCGTG |

Figure 3K - Heavy Chain DNA Sequence

| Sequence Name | Constant Region |
|---|---|
| Ab1 | GAGGTGCATAATGCCAAGACAAAAGCCGGGGAGGAGCAGTACGCCAGCACGTACCGTGTGGTCAGCGTCCTCACCGTCCTGCACCAGGAC |
| Ab2 | GAGGTGCATAATGCCAAGACAAAAGCCGGGGAGGAGCAGTACGCCAGCACGTACCGTGTGGTCAGCGTCCTCACCGTCCTGCACCAGGAC |
| Ab3 | GAGGTGCATAATGCCAAGACAAAAGCCGGGGAGGAGCAGTACGCCAGCACGTACCGTGTGGTCAGCGTCCTCACCGTCCTGCACCAGGAC |
| Ab4 | GAGGTGCATAATGCCAAGACAAAAGCCGGGGAGGAGCAGTACGCCAGCACGTACCGTGTGGTCAGCGTCCTCACCGTCCTGCACCAGGAC |
| Ab5 | GAGGTGCATAATGCCAAGACAAAAGCCGGGGAGGAGCAGTACGCCAGCACGTACCGTGTGGTCAGCGTCCTCACCGTCCTGCACCAGGAC |
| Ab6 | GAGGTGCATAATGCCAAGACAAAAGCCGGGGAGGAGCAGTACGCCAGCACGTACCGTGTGGTCAGCGTCCTCACCGTCCTGCACCAGGAC |
| Ab7 | GAGGTGCATAATGCCAAGACAAAAGCCGGGGAGGAGCAGTACGCCAGCACGTACCGTGTGGTCAGCGTCCTCACCGTCCTGCACCAGGAC |
| Ab8 | GAGGTGCATAATGCCAAGACAAAAGCCGGGGAGGAGCAGTACGCCAGCACGTACCGTGTGGTCAGCGTCCTCACCGTCCTGCACCAGGAC |
| Ab9 | GAGGTGCATAATGCCAAGACAAAAGCCGGGGAGGAGCAGTACGCCAGCACGTACCGTGTGGTCAGCGTCCTCACCGTCCTGCACCAGGAC |
| Ab10 | GAGGTGCATAATGCCAAGACAAAAGCCGGGGAGGAGCAGTACGCCAGCACGTACCGTGTGGTCAGCGTCCTCACCGTCCTGCACCAGGAC |
| Ab11 | GAGGTGCATAATGCCAAGACAAAAGCCGGGGAGGAGCAGTACGCCAGCACGTACCGTGTGGTCAGCGTCCTCACCGTCCTGCACCAGGAC |
| Ab12 | GAGGTGCATAATGCCAAGACAAAAGCCGGGGAGGAGCAGTACGCCAGCACGTACCGTGTGGTCAGCGTCCTCACCGTCCTGCACCAGGAC |
| Ab13 | GAGGTGCATAATGCCAAGACAAAAGCCGGGGAGGAGCAGTACGCCAGCACGTACCGTGTGGTCAGCGTCCTCACCGTCCTGCACCAGGAC |
| Ab14 | GAGGTGCATAATGCCAAGACAAAAGCCGGGGAGGAGCAGTACGCCAGCACGTACCGTGTGGTCAGCGTCCTCACCGTCCTGCACCAGGAC |

Figure 3L - Heavy Chain DNA Sequence

| Sequence Name | Constant Region |
|---|---|
| Ab1 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab2 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab3 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab4 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab5 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab6 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab7 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab8 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab9 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab10 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab11 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab12 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab13 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab14 | TGGCTGAATGGCAAGGAGTACAAGTGCAAGGTCTCCAACAAAGCCCTCCCAGCCCCCATCGAGAAAACCATCTCCAAAGCCAAAGGGCAG |

Figure 3M – Heavy Chain DNA Sequence

Constant Region

| Sequence Name | |
|---|---|
| Ab1 | CCCCGAGAACCACAGGTGTACACCCTGCCCCCATCCCGGGAGGAGATGACCAAGAACCAGGTCAGCCTGACCTGCCTGGTCAAAGGCTTC |
| Ab2 | CCCCGAGAACCACAGGTGTACACCCTGCCCCCATCCCGGGAGGAGATGACCAAGAACCAGGTCAGCCTGACCTGCCTGGTCAAAGGCTTC |
| Ab3 | CCCCGAGAACCACAGGTGTACACCCTGCCCCCATCCCGGGAGGAGATGACCAAGAACCAGGTCAGCCTGACCTGCCTGGTCAAAGGCTTC |
| Ab4 | CCCCGAGAACCACAGGTGTACACCCTGCCCCCATCCCGGGAGGAGATGACCAAGAACCAGGTCAGCCTGACCTGCCTGGTCAAAGGCTTC |
| Ab5 | CCCCGAGAACCACAGGTGTACACCCTGCCCCCATCCCGGGAGGAGATGACCAAGAACCAGGTCAGCCTGACCTGCCTGGTCAAAGGCTTC |
| Ab6 | CCCCGAGAACCACAGGTGTACACCCTGCCCCCATCCCGGGAGGAGATGACCAAGAACCAGGTCAGCCTGACCTGCCTGGTCAAAGGCTTC |
| Ab7 | CCCCGAGAACCACAGGTGTACACCCTGCCCCCATCCCGGGAGGAGATGACCAAGAACCAGGTCAGCCTGACCTGCCTGGTCAAAGGCTTC |
| Ab8 | CCCCGAGAACCACAGGTGTACACCCTGCCCCCATCCCGGGAGGAGATGACCAAGAACCAGGTCAGCCTGACCTGCCTGGTCAAAGGCTTC |
| Ab9 | CCCCGAGAACCACAGGTGTACACCCTGCCCCCATCCCGGGAGGAGATGACCAAGAACCAGGTCAGCCTGACCTGCCTGGTCAAAGGCTTC |
| Ab10 | CCCCGAGAACCACAGGTGTACACCCTGCCCCCATCCCGGGAGGAGATGACCAAGAACCAGGTCAGCCTGACCTGCCTGGTCAAAGGCTTC |
| Ab11 | CCCCGAGAACCACAGGTGTACACCCTGCCCCCATCCCGGGAGGAGATGACCAAGAACCAGGTCAGCCTGACCTGCCTGGTCAAAGGCTTC |
| Ab12 | CCCCGAGAACCACAGGTGTACACCCTGCCCCCATCCCGGGAGGAGATGACCAAGAACCAGGTCAGCCTGACCTGCCTGGTCAAAGGCTTC |
| Ab13 | CCCCGAGAACCACAGGTGTACACCCTGCCCCCATCCCGGGAGGAGATGACCAAGAACCAGGTCAGCCTGACCTGCCTGGTCAAAGGCTTC |
| Ab14 | CCCCGAGAACCACAGGTGTACACCCTGCCCCCATCCCGGGAGGAGATGACCAAGAACCAGGTCAGCCTGACCTGCCTGGTCAAAGGCTTC |

Figure 3N – Heavy Chain DNA Sequence

Constant Region

| Sequence Name | |
|---|---|
| Ab1 | TATCCCAGCGACATCGCCGTGGAGTGGGAGAGCAATGGGCAGCCGGAGAACAACTACAAGACCACGCCTCCCGTGCTGGACTCCGACGGC |
| Ab2 | TATCCCAGCGACATCGCCGTGGAGTGGGAGAGCAATGGGCAGCCGGAGAACAACTACAAGACCACGCCTCCCGTGCTGGACTCCGACGGC |
| Ab3 | TATCCCAGCGACATCGCCGTGGAGTGGGAGAGCAATGGGCAGCCGGAGAACAACTACAAGACCACGCCTCCCGTGCTGGACTCCGACGGC |
| Ab4 | TATCCCAGCGACATCGCCGTGGAGTGGGAGAGCAATGGGCAGCCGGAGAACAACTACAAGACCACGCCTCCCGTGCTGGACTCCGACGGC |
| Ab5 | TATCCCAGCGACATCGCCGTGGAGTGGGAGAGCAATGGGCAGCCGGAGAACAACTACAAGACCACGCCTCCCGTGCTGGACTCCGACGGC |
| Ab6 | TATCCCAGCGACATCGCCGTGGAGTGGGAGAGCAATGGGCAGCCGGAGAACAACTACAAGACCACGCCTCCCGTGCTGGACTCCGACGGC |
| Ab7 | TATCCCAGCGACATCGCCGTGGAGTGGGAGAGCAATGGGCAGCCGGAGAACAACTACAAGACCACGCCTCCCGTGCTGGACTCCGACGGC |
| Ab8 | TATCCCAGCGACATCGCCGTGGAGTGGGAGAGCAATGGGCAGCCGGAGAACAACTACAAGACCACGCCTCCCGTGCTGGACTCCGACGGC |
| Ab9 | TATCCCAGCGACATCGCCGTGGAGTGGGAGAGCAATGGGCAGCCGGAGAACAACTACAAGACCACGCCTCCCGTGCTGGACTCCGACGGC |
| Ab10 | TATCCCAGCGACATCGCCGTGGAGTGGGAGAGCAATGGGCAGCCGGAGAACAACTACAAGACCACGCCTCCCGTGCTGGACTCCGACGGC |
| Ab11 | TATCCCAGCGACATCGCCGTGGAGTGGGAGAGCAATGGGCAGCCGGAGAACAACTACAAGACCACGCCTCCCGTGCTGGACTCCGACGGC |
| Ab12 | TATCCCAGCGACATCGCCGTGGAGTGGGAGAGCAATGGGCAGCCGGAGAACAACTACAAGACCACGCCTCCCGTGCTGGACTCCGACGGC |
| Ab13 | TATCCCAGCGACATCGCCGTGGAGTGGGAGAGCAATGGGCAGCCGGAGAACAACTACAAGACCACGCCTCCCGTGCTGGACTCCGACGGC |
| Ab14 | TATCCCAGCGACATCGCCGTGGAGTGGGAGAGCAATGGGCAGCCGGAGAACAACTACAAGACCACGCCTCCCGTGCTGGACTCCGACGGC |

Figure 3O – Heavy Chain DNA Sequence

| Sequence Name | Constant Region | |
|---|---|---|
| Ab1 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 11) |
| Ab2 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 51) |
| Ab3 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 91) |
| Ab4 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 131) |
| Ab5 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 171) |
| Ab6 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 211) |
| Ab7 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 251) |
| Ab8 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 291) |
| Ab9 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 331) |
| Ab10 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 371) |
| Ab11 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 411) |
| Ab12 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 451) |
| Ab13 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 491) |
| Ab14 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 531) |

Figure 3P – Heavy Chain DNA Sequence

| Sequence Name | Constant Region | |
|---|---|---|
| Ab1 | CACAACCACTACACGCAGAAGAGCCTCTCCCTGTCTCCGGGTAAATGA | (SEQ ID NO: 11) |
| Ab2 | CACAACCACTACACGCAGAAGAGCCTCTCCCTGTCTCCGGGTAAATGA | (SEQ ID NO: 51) |
| Ab3 | CACAACCACTACACGCAGAAGAGCCTCTCCCTGTCTCCGGGTAAATGA | (SEQ ID NO: 91) |
| Ab4 | CACAACCACTACACGCAGAAGAGCCTCTCCCTGTCTCCGGGTAAATGA | (SEQ ID NO: 131) |
| Ab5 | CACAACCACTACACGCAGAAGAGCCTCTCCCTGTCTCCGGGTAAATGA | (SEQ ID NO: 171) |
| Ab6 | CACAACCACTACACGCAGAAGAGCCTCTCCCTGTCTCCGGGTAAATGA | (SEQ ID NO: 211) |
| Ab7 | CACAACCACTACACGCAGAAGAGCCTCTCCCTGTCTCCGGGTAAATGA | (SEQ ID NO: 251) |
| Ab8 | CACAACCACTACACGCAGAAGAGCCTCTCCCTGTCTCCGGGTAAATGA | (SEQ ID NO: 291) |
| Ab9 | CACAACCACTACACGCAGAAGAGCCTCTCCCTGTCTCCGGGTAAATGA | (SEQ ID NO: 331) |
| Ab10 | CACAACCACTACACGCAGAAGAGCCTCTCCCTGTCTCCGGGTAAATGA | (SEQ ID NO: 371) |
| Ab11 | CACAACCACTACACGCAGAAGAGCCTCTCCCTGTCTCCGGGTAAATGA | (SEQ ID NO: 411) |
| Ab12 | CACAACCACTACACGCAGAAGAGCCTCTCCCTGTCTCCGGGTAAATGA | (SEQ ID NO: 451) |
| Ab13 | CACAACCACTACACGCAGAAGAGCCTCTCCCTGTCTCCGGGTAAATGA | (SEQ ID NO: 491) |
| Ab14 | CACAACCACTACACGCAGAAGAGCCTCTCCCTGTCTCCGGGTAAATGA | (SEQ ID NO: 531) |

Figure 4A - Light Chain DNA Sequence

| Sequence Name | FR1 |
|---|---|
| Ab1 | CAAGTGCTGACCCAGTCTGCATCCCCGTGTCTGCAGCTGTGGGAAGCACAGTCACCATCAATTGC |
| Ab2 | CAAGTGCTGACCCAGTCTCCATCCTCCCTGTCTGCATCTGTAGGAGACAGAGTCACCATCAATTGC |
| Ab3 | CAAGTGCTGACCCAGTCTCCATCCTCCCTGTCTGCATCTGTAGGAGACAGAGTCACCATCAATTGC |
| Ab4 | CAAGTGCTGACCCAGTCTCCATCCCCGTGTCTGCATCTGTAGGAGACACAGAGTCACCATCAATTGC |
| Ab5 | CAAGTGCTGACCCAGTCTCCATCCTCCCTGTCTGCATCTGTAGGAGACAGAGTCACCATCAATTGC |
| Ab6 | CAAGTGCTGACCCAGTCTCCATCCTCCCTGTCTGCATCTGTAGGAGACAGAGTCACCATCAATTGC |
| Ab7 | CAAGTGCTGACCCAGTCTCCATCCTCCCGTGTCTGCAGCTGTGGGAAGCACAGTCACCATCAATTGC |
| Ab8 | CAAGTGCTGACCCAGTCTCCATCCTCCATCCTGTCTCTGCATCTGTAGGAGACAGAGTCACCATCAATTGC |
| Ab9 | CAAGTGCTGACCCAGTCTCCATCCCCGTGTCTGCATCTGTAGGAGACACAGAGTCACCATCAATTGC |
| Ab10 | CAAGTGCTGACCCAGTCTCCATCCTCCATCCTGTCTCTGCATCTGTAGGAGACAGAGTCACCATCAATTGC |
| Ab11 | CAGGTGCTGACCCAGTCTGACCCAGTCTGCATCCCCGTGTCTGCATCTGTGGGAAGCACAGTCACCATCAATTGC |
| Ab12 | CAAGTGCTGACCCAGTCTCCATCCTCCATCTGTCTGCATCTGTAGGAGACAGAGTCACCATCAATTGC |
| Ab13 | GCCATCGTGATGACCCAGACTCCAGTCTCCATCTTCCAAGTCTGTGCCTGTGGGAGACACAGTCACCATCAATTGC |
| Ab14 | CAAGTGCTGATGACCCAGTCTCCATCCTCCCTGTCTGCATCTGTAGGAGACAGAGTCACCATCAATTGC |

Figure 4B - Light Chain DNA Sequence

| Sequence Name | CDR1 | FR2 |
|---|---|---|
| Ab1 | CAGGCCAGTCAGAGTGTTTATGATAACAACTACCTAGCC | TGGTATCAGCAGAAACCAGGGCAGCCTCCCAAGCAACTGATCTAT |
| Ab2 | CAGGCCAGTCAGAGTCAGAGAGTGTTTATGATAACAACTACCTACCAGCC | TGGTATCAGCAGAAACCAGGGAAAGTTCCTAAGCAACTGATCTAT |
| Ab3 | CAGGCCAGTCAGAGTGTTTATGATAACAACTACCTAGCC | TGGTATCAGCAGAAACCAGGGAAAGTTCCTAAGCAACTGATCTAT |
| Ab4 | CAGGCCAGTCAGAGTGTTTATCATAACACCTACCTGGCC | TGGTATCAGCAGAAACCAGGGCAGCCTCCCAAACAACTGATCTAT |
| Ab5 | CAGGCCAGTCAGAGTGTTTATCATAACACCTACCTGGCC | TGGTATCAGCAGAAACCAGGGAAAGTTCCTAAGCAACTGATCTAT |
| Ab6 | CAGGCCAGTCAGAGTGTTTATCATAACACCTACCTGGCC | TGGTATCAGCAGAAACCAGGGCAGCCTCCCAAGCAACTGATCTAT |
| Ab7 | CAGGCCAGTCAGAGTGTTTATAATTACAACTACCTTGCC | TGGTATCAGCAGAAACCAGGGCAGCCTCCCAAGCAACTGATCTAT |
| Ab8 | CAGGCCAGTCAGAGTGTTTACAATTACAACTACCTTGCC | TGGTATCAGCAGAAACCAGGGCAGCCTCCCAAGCAACTGATCTAT |
| Ab9 | CAGGCCAGTCAGAATGTTTATACAATAACAACTACCTAGCC | TGGTATCAGCAGAAACCAGGGCAGCCTCCCAAGCAACTGATCTAT |
| Ab10 | CAGGCCAGTCAGAATGTTTATTATTAACAATAACAACTACCTAGCC | TGGTATCAGCAGAAACCAGGGCAGCCTCCCAAGCAACTGATCTAT |
| Ab11 | CGGGCCAGTCAGAGTGTTTTATTATTACTATAACAACTACCTAGCC | TGGTATCAGCAGAAACCAGGGCAGCCTCCCAAGCAACTGATCTAT |
| Ab12 | CGGGCCAGTCAGAGTGTTTACTATAATAACAACTACCTAGCC | TGGTATCAGCAGAAACCAGGGCAGCCTCCCAAGCAACTGATCTAT |
| Ab13 | CAGGCCAGTGAGTCAGAGTCTTTTATAATAACAACGCCTTGGCC | TGGTTTCAGCAGAAACCAGGGCAGCCTCCCAAGCAACTGATCTAT |
| Ab14 | CAGGCCAGTCAGAATGTTTACAATAACAACTACCTAGCC | TGGTATCAGCAGAAACCAGGGCAGCCTCCTAAGCAACTGATCTAT |

Figure 4C - Light Chain DNA Sequence

| Sequence Name | CDR2 | FR3 |
|---|---|---|
| Ab1 | TCTACATCCACTCTGGCATCT | GGGGTCTCATCGCGGTTCAAAGGCAGTGGATCTGGGACACAGTTCACTCTCACCA |
| Ab2 | TCTTACATCCACTCTGGCATCT | GGGGTCCCCATCTCGTTTCAGTGGCAGTGGATCTGGGACACAGATTTCACTCTCACCA |
| Ab3 | TCTACATCCACTCTGGCATCT | GGGGTCCCCATCTCGTTTCAGTGGCAGTGGATCTGGGACACAGATTCACTCTCACCA |
| Ab4 | GATGCATCCACTCTGGCGTCT | GGGGTCCCCATCGCGGTTCAGTGGCAGTGGATCTGGGACACAGTTCACTCTCACCA |
| Ab5 | GATGCATCCACTCTGGCATCT | GGGGTCCCCATCCGTTTCAGTGGCAGTGGATCTGGGACACAGTTCACTCTCACCA |
| Ab6 | GATGCATCCACTCTGGCATCT | GGGGTCCCCATCCGTTTCAGTGGCAGTGGATCTGGGACACAGTTCACTCTCACCA |
| Ab7 | TCTACATCCACTCTGGCATCT | GGGGTCTCATCGCGATTCAAAGGCAGTGGATCTGGGACACAGTTCACTCTCACCA |
| Ab8 | TCTACATCCACTCTGGCATCT | GGGGTCCCCATCTCGTTTCAGTGGCAGTGGATCTGGGACACAGTTCACTCTCACCA |
| Ab9 | TCTACGTCCACTCTGGCATCT | GGGGTCCCCATCTCATCGCGATTCAGAGGCAGTGGATCGGGACACAGTTCACTCTCACCA |
| Ab10 | TCTACATCCACTCTGGCATCT | GGGGTCCCCATCGCGATTCGTTTCAGTGGCAGTGGATCTGGGACACAGATTCACTCTCACCA |
| Ab11 | TCTTACATCCACTCTGGCATCT | GGGGTCTCATCGCGGGTTCAAAGGCAGTGGATCTGGGACACAGTTCACTCTCACCA |
| Ab12 | TCTACATCCACTCTGGCATCT | GGGGTCCCCATCTCGTTTCAGTGGCAGTGGATCTGGGACACAGTTCACTCTCACCA |
| Ab13 | GATGCATCCAAACTGGCATCT | GGGGTCCCCATCGCGGTGGTTTCAGTGGCGGTGGATCTGGGACACAGTTCACTCTCACCA |
| Ab14 | TCTACATCCACTCTGGCATCT | GGGGTCCCCATCTCGTTTCAGTGGCAGTGGATCTGGGACACAGATTCACTCTCACCA |

Figure 4D - Light Chain DNA Sequence

| Sequence Name | FR3 | CDR3 |
|---|---|---|
| Ab1 | TCAGGCGACCTGGAGTGTGCCGATGCTGCCACTTACTACTGT | CTAGGCAGTTATGATTGTAGTAGTGGTGATTGTTTTGTT |
| Ab2 | TCAGCAGCCTGCAGCCTGAAGATGTTGCAACTTATTACTGT | CTAGGCAGTTATGATTGATTGTAGTAGTGGTGATTGATTGTTTTGTT |
| Ab3 | TCAGCAGCCTGCAGCCTGAAGATGTTGCAACTTATTACTGT | CTAGGCAGTTATGATTGATTGTAGTAGTGGTGATTGATTGTTTTGTT |
| Ab4 | TCAGCGGCGTGCAGTGTAACGATGCTGCCGCTTACTACTGT | CTGGGCAGTTATGATTGATTGTAGTAATGGTGATTGTTTTGTT |
| Ab5 | TCAGCAGCCTGCAGTGTGAAGATGTTGCAACTTATTACTGT | CTGGGCAGTTATGATTGATTGTACTAATGGTGATTGTTTTGTT |
| Ab6 | TCAGCAGCCTGCAGTGTGAAGATGTTGCAACTTATTACTGT | CTGGGCAGTTATGATTGATTGTACTAATGGTGATTGTTTTGTT |
| Ab7 | TCAGCGACGTGCAGTGTGACGATGCTGCCACTTACTACTGT | CTGGGCAGTTATGACTAGTAGTGACTAGTGGTGATTGTTTTGTT |
| Ab8 | TCAGCAGCCTGCAGTGTGAAGATGTTGCAACTTATTACTGT | CTGGGCAGTTATGATTGATTGATTGTAGTAGTGGTGATTGTTTTGTT |
| Ab9 | TCAGCAGCCTGCAGTGTGACGATGCTGCCACTTACTACTGT | CTAGGCAGTTATGATTGATTGTAGTAGTCGTGGTGATTGTTTTGTT |
| Ab10 | TCAGCAGCCTGCAGTGTGACGATGCTGCCACTTATTACTGT | CTAGGCAGTTATGATTGATTGTAGTAGTAATGGTGATTGTTTTGTT |
| Ab11 | TCAGCAGCCTGCAGTGTGAAGATGTTGCAACTTATTACTGT | CTAGGCAGTTATGATTGATTGTAGTAGTCGTGATTGTTTTGTT |
| Ab12 | TCAGCAGCCTGCAGCCTGAAGATGTTGCAACTTATTACTGT | CTGGGCAGTTATGATTGATTGTAGTAGTGGTGATTGTTTTGTT |
| Ab13 | TCAGTGGCTGCAGTGTGACGATGCTGCCACTTACTACTGT | GGAGGCTACAGAAGTGATAGTGTTGATGGTGTTGCT |
| Ab14 | TCAGCAGCCTGCAGCCTGAAGATGTTGCAACTTATTACTGT | CTGGGCAGTTATGATTGTAGTCGTGGTGATTGTTTTGTT |

Figure 4E - Light Chain DNA Sequence

| Sequence Name | FR4 | Constant Region |
|---|---|---|
| Ab1 | TTCGGCGGAGGGACCGAGGTGGTGCAAACGT | ACGGTGGCTGCACCATCTGTCTTCATCTTCCCGCCATCTGATGAGCAGTTG |
| Ab2 | TTCGGCGGAGGGACCAAGGTGGAAATCAAACGT | ACGGTGGCTGCACCATCTGTCTTCATCTTCCCGCCATCTGATGAGCAGTTG |
| Ab3 | TTCGGCGGAGGGACCAAGGTGGAAATCAAACGT | ACGGTGGCTGCACCATCTGTCTTCATCTTCCCGCCATCTGATGAGCAGTTG |
| Ab4 | TTCGGCGGAGGGACCAAGGTGGTGGTCAAACGT | ACGGTGGCTGCACCATCTGTCTTCATCTTCCCGCCATCTGATGAGCAGTTG |
| Ab5 | TTCGGCGGAGGGACCAAGGTGGAAATCAAACGT | ACGGTGGCTGCACCATCTGTCTTCATCTTCCCGCCATCTGATGAGCAGTTG |
| Ab6 | TTCGGCGGAGGGACCGAGGTGGTGGTCAAACGT | ACGGTGGCTGCACCATCTGTCTTCATCTTCCCGCCATCTGATGAGCAGTTG |
| Ab7 | TTCGGCGGAGGGACCAAGGTGGAAATCAAACGT | ACGGTGGCTGCACCATCTGTCTTCATCTTCCCGCCATCTGATGAGCAGTTG |
| Ab8 | TTCGGCCGAGGGACCAAGGTGGAAATCAAACGT | ACGGTGGCTGCACCATCTGTCTTCATCTTCCCGCCATCTGATGAGCAGTTG |
| Ab9 | TTCGGCGGAGGGACCGAGGTGGTGGTCAAACGT | ACGGTGGCTGCACCATCTGTCTTCATCTTCCCGCCATCTGATGAGCAGTTG |
| Ab10 | TTCGGCGGAGGGACCAAGGTGGAAATCAAACGT | ACGGTGGCTGCACCATCTGTCTTCATCTTCCCGCCATCTGATGAGCAGTTG |
| Ab11 | TTCGGCGGAGGGACCGAGGTGGTGGTCAAACGT | ACGGTGGCTGCACCATCTGTCTTCATCTTCCCGCCATCTGATGAGCAGTTG |
| Ab12 | TTCGGCGGAGGGACCAAGGTGGAAATCAAACGT | ACGGTGGCTGCACCATCTGTCTTCATCTTCCCGCCATCTGATGAGCAGTTG |
| Ab13 | TTCGGCCGAGGGACCGAGGTGGTGGTCAAACGT | ACGGTGGCTGCACCATCTGTCTTCATCTTCCCGCCATCTGATGAGCAGTTG |
| Ab14 | TTCGGCGGAGGGACCAAGGTGGAAATCAAACGT | ACGGTGGCTGCACCATCTGTCTTCATCTTCCCGCCATCTGATGAGCAGTTG |

Figure 4F - Light Chain DNA Sequence

| Sequence Name | Constant Region |
|---|---|
| Ab1 | AAATCTGGAACTGCCTCTGTTGTGTGCCTGCTGAATAACTTCTATCCCAGAGAGGCCAAAGTACAGTGGAAGGTGGATAACGCCC |
| Ab2 | AAATCTGGAACTGCCTCTGTTGTGTGCCTGCTGAATAACTTCTATCCCAGAGAGGCCAAAGTACAGTGGAAGGTGGATAACGCCC |
| Ab3 | AAATCTGGAACTGCCTCTGTTGTGTGCCTGCTGAATAACTTCTATCCCAGAGAGGCCAAAGTACAGTGGAAGGTGGATAACGCCC |
| Ab4 | AAATCTGGAACTGCCTCTGTTGTGTGCCTGCTGAATAACTTCTATCCCAGAGAGGCCAAAGTACAGTGGAAGGTGGATAACGCCC |
| Ab5 | AAATCTGGAACTGCCTCTGTCTGTTGTGCGCCTGCTGAATAACTTCTATCCCAGAGAGGCCAAAGTACAGTGGAAGGTGGATAACGCCC |
| Ab6 | AAATCTGGAACTGCCTCTGTTGTGTGCCTGCTGAATAACTTCTATCCCAGAGAGGCCAAAGTACAGTGGAAGGTGGATAACGCCC |
| Ab7 | AAATCTGGAACTGCCTCTGTTGTGTGCCTGCTGAATAACTTCTATCCCAGAGAGGCCAAAGTACAGTGGAAGGTGGATAACGCCC |
| Ab8 | AAATCTGGAACTGCCTCTGTTGTGTGCCTGCTGAATAACTTCTATCCCAGAGAGGCCAAAGTACAGTGGAAGGTGGATAACGCCC |
| Ab9 | AAATCTGGAACTGCCTCTGTTGTGTGCCTGCTGAATAACTTCTATCCCAGAGAGGCCAAAGTACAGTGGAAGGTGGATAACGCCC |
| Ab10 | AAATCTGGAACTGCCTCTGTTGTGTGCCTGCTGAATAACTTCTATCCCAGAGAGGCCAAAGTACAGTGGAAGGTGGATAACGCCC |
| Ab11 | AAATCTGGAACTGCCTCTGTTGTGTGCCTGCTGAATAACTTCTATCCCAGAGAGGCCAAAGTACAGTGGAAGGTGGATAACGCCC |
| Ab12 | AAATCTGGAACTGCCTCTGTTGTGTGCCTGCTGAATAACTTCTATCCCAGAGAGGCCAAAGTACAGTGGAAGGTGGATAACGCCC |
| Ab13 | AAATCTGGAACTGCCTCTGTTGTGTGCCTGCTGAATAACTTCTATCCCAGAGAGGCCAAAGTACAGTGGAAGGTGGATAACGCCC |
| Ab14 | AAATCTGGAACTGCCTCTGTTGTGTGCCTGCTGAATAACTTCTATCCCAGAGAGGCCAAAGTACAGTGGAAGGTGGATAACGCCC |

Figure 4G - Light Chain DNA Sequence

| Sequence Name | Constant Region |
|---|---|
| Ab1 | TCCAATCGGGTAACTCCCAGGAGAGTGTCACAGAGCAGGACAGCAGCACCTACAGCCTCAGCAGCAGCACCCTGACGCTGAG |
| Ab2 | TCCAATCGGGTAACTCCCAGGAGAGTGTCACAGAGCAGGACAGCAGCACCTACAGCCTCAGCAGCAGCACCCTGACGCTGAG |
| Ab3 | TCCAATCGGGTAACTCCCAGGAGAGTGTCACAGAGCAGGACAGCAGCACCTACAGCCTCAGCAGCAGCACCCTGACGCTGAG |
| Ab4 | TCCAATCGGGTAACTCCCAGGAGAGTGTCACAGAGCAGGACAGCAGCACCTACAGCCTCAGCAGCAGCACCCTGACGCTGAG |
| Ab5 | TCCAATCGGGTAACTCCCAGGAGAGTGTCACAGAGCAGGACAGCAGCACCTACAGCCTCAGCAGCAGCACCCTGACGCTGAG |
| Ab6 | TCCAATCGGGTAACTCCCAGGAGAGTGTCACAGAGCAGGACAGCAGCACCTACAGCCTCAGCAGCAGCACCCTGACGCTGAG |
| Ab7 | TCCAATCGGGTAACTCCCAGGAGAGTGTCACAGAGCAGGACAGCAGCACCTACAGCCTCAGCAGCAGCACCCTGACGCTGAG |
| Ab8 | TCCAATCGGGTAACTCCCAGGAGAGTGTCACAGAGCAGGACAGCAGCACCTACAGCCTCAGCAGCAGCACCCTGACGCTGAG |
| Ab9 | TCCAATCGGGTAACTCCCAGGAGAGTGTCACAGAGCAGGACAGCAGCACCTACAGCCTCAGCAGCAGCACCCTGACGCTGAG |
| Ab10 | TCCAATCGGGTAACTCCCAGGAGAGTGTCACAGAGCAGGACAGCAGCACCTACAGCCTCAGCAGCAGCACCCTGACGCTGAG |
| Ab11 | TCCAATCGGGTAACTCCCAGGAGAGTGTCACAGAGCAGGACAGCAGCACCTACAGCCTCAGCAGCAGCACCCTGACGCTGAG |
| Ab12 | TCCAATCGGGTAACTCCCAGGAGAGTGTCACAGAGCAGGACAGCAGCACCTACAGCCTCAGCAGCAGCACCCTGACGCTGAG |
| Ab13 | TCCAATCGGGTAACTCCCAGGAGAGTGTCACAGAGCAGGACAGCAGCACCTACAGCCTCAGCAGCAGCACCCTGACGCTGAG |
| Ab14 | TCCAATCGGGTAACTCCCAGGAGAGTGTCACAGAGCAGGACAGCAGCACCTACAGCCTCAGCAGCAGCACCCTGACGCTGAG |

Figure 4H - Light Chain DNA Sequence

| Sequence Name | Constant Region |
|---|---|
| Ab1 | CAAAGCAGACTACGAGAAACACAAAGTCTACGCCTGCGAAGTCACCCATCAGGGCCTGAGCTCGCCCGTCACAAAGAGCTTCAAC |
| Ab2 | CAAAGCAGACTACGAGAAACACAAAGTCTACGCCTGCGAAGTCACCCATCAGGGCCTGAGCTCGCCCGTCACAAAGAGCTTCAAC |
| Ab3 | CAAAGCAGACTACGAGAAACACAAAGTCTACGCCTGCGAAGTCACCCATCAGGGCCTGAGCTCGCCCGTCACAAAGAGCTTCAAC |
| Ab4 | CAAAGCAGACTACGAGAAACACAAAGTCTACGCCTGCGAAGTCACCCATCAGGGCCTGAGCTCGCCCGTCACAAAGAGCTTCAAC |
| Ab5 | CAAAGCAGACTACGAGAAACACAAAGTCTACGCCTGCGAAGTCACCCATCAGGGCCTGAGCTCGCCCGTCACAAAGAGCTTCAAC |
| Ab6 | CAAAGCAGACTACGAGAAACACAAAGTCTACGCCTGCGAAGTCACCCATCAGGGCCTGAGCTCGCCCGTCACAAAGAGCTTCAAC |
| Ab7 | CAAAGCAGACTACGAGAAACACAAAGTCTACGCCTGCGAAGTCACCCATCAGGGCCTGAGCTCGCCCGTCACAAAGAGCTTCAAC |
| Ab8 | CAAAGCAGACTACGAGAAACACAAAGTCTACGCCTGCGAAGTCACCCATCAGGGCCTGAGCTCGCCCGTCACAAAGAGCTTCAAC |
| Ab9 | CAAAGCAGACTACGAGAAACACAAAGTCTACGCCTGCGAAGTCACCCATCAGGGCCTGAGCTCGCCCGTCACAAAGAGCTTCAAC |
| Ab10 | CAAAGCAGACTACGAGAAACACAAAGTCTACGCCTGCGAAGTCACCCATCAGGGCCTGAGCTCGCCCGTCACAAAGAGCTTCAAC |
| Ab11 | CAAAGCAGACTACGAGAAACACAAAGTCTACGCCTGCGAAGTCACCCATCAGGGCCTGAGCTCGCCCGTCACAAAGAGCTTCAAC |
| Ab12 | CAAAGCAGACTACGAGAAACACAAAGTCTACGCCTGCGAAGTCACCCATCAGGGCCTGAGCTCGCCCGTCACAAAGAGCTTCAAC |
| Ab13 | CAAAGCAGACTACGAGAAACACAAAGTCTACGCCTGCGAAGTCACCCATCAGGGCCTGAGCTCGCCCGTCACAAAGAGCTTCAAC |
| Ab14 | CAAAGCAGACTACGAGAAACACAAAGTCTACGCCTGCGAAGTCACCCATCAGGGCCTGAGCTCGCCCGTCACAAAGAGCTTCAAC |

Figure 4I - Light Chain DNA Sequence

| Sequence Name | |
|---|---|
| Ab1 | AGGGGAGAGAGTGTTAG (SEQ ID NO: 31) |
| Ab2 | AGGGGAGAGAGTGTTAG (SEQ ID NO: 71) |
| Ab3 | AGGGGAGAGAGTGTTAG (SEQ ID NO: 111) |
| Ab4 | AGGGGAGAGAGTGTTAG (SEQ ID NO: 151) |
| Ab5 | AGGGGAGAGAGTGTTAG (SEQ ID NO: 191) |
| Ab6 | AGGGGAGAGAGTGTTAG (SEQ ID NO: 231) |
| Ab7 | AGGGGAGAGAGTGTTAG (SEQ ID NO: 271) |
| Ab8 | AGGGGAGAGAGTGTTAG (SEQ ID NO: 311) |
| Ab9 | AGGGGAGAGAGTGTTAG (SEQ ID NO: 351) |
| Ab10 | AGGGGAGAGAGTGTTAG (SEQ ID NO: 391) |
| Ab11 | AGGGGAGAGAGTGTTAG (SEQ ID NO: 431) |
| Ab12 | AGGGGAGAGAGTGTTAG (SEQ ID NO: 471) |
| Ab13 | AGGGGAGAGAGTGTTAG (SEQ ID NO: 511) |
| Ab14 | AGGGGAGAGAGTGTTAG (SEQ ID NO: 551) |

Figure 5
Heavy Chain Protein Sequence Features

| Antibody | Variable Region Coordinates | SEQ ID NO: | CDR1 Coordinates | SEQ ID NO: | CDR2 Coordinates | SEQ ID NO: | CDR3 Coordinates | SEQ ID NO: |
|---|---|---|---|---|---|---|---|---|
| Ab1 | 1-109 | 2 | 30-34 | 4 | 49-64 | 6 | 96-98 | 8 |
| Ab2 | 1-111 | 42 | 31-35 | 44 | 50-65 | 46 | 98-100 | 48 |
| Ab3 | 1-111 | 82 | 31-35 | 84 | 50-65 | 86 | 98-100 | 88 |
| Ab4 | 1-109 | 122 | 30-34 | 124 | 49-64 | 126 | 96-98 | 128 |
| Ab5 | 1-111 | 162 | 31-35 | 164 | 50-65 | 166 | 98-100 | 168 |
| Ab6 | 1-111 | 202 | 31-35 | 204 | 50-65 | 206 | 98-100 | 208 |
| Ab7 | 1-110 | 242 | 31-35 | 244 | 50-65 | 246 | 97-99 | 248 |
| Ab8 | 1-111 | 282 | 31-35 | 284 | 50-65 | 286 | 98-100 | 288 |
| Ab9 | 1-109 | 322 | 30-34 | 324 | 49-64 | 326 | 96-98 | 328 |
| Ab10 | 1-111 | 362 | 31-35 | 364 | 50-65 | 366 | 98-100 | 368 |
| Ab11 | 1-109 | 402 | 30-34 | 404 | 49-64 | 406 | 96-98 | 408 |
| Ab12 | 1-111 | 442 | 31-35 | 444 | 50-65 | 446 | 98-100 | 448 |
| Ab13 | 1-111 | 482 | 30-34 | 484 | 49-65 | 486 | 97-100 | 488 |
| Ab14 | 1-111 | 522 | 31-35 | 524 | 50-65 | 526 | 98-100 | 528 |

Figure 6
Heavy Chain Protein Sequence Features

| Antibody | FR1 Coordinates | SEQ ID NO: | FR2 Coordinates | SEQ ID NO: | FR3 Coordinates | SEQ ID NO: | FR4 Coordinates | SEQ ID NO: | Constant Region Coordinates | SEQ ID NO: |
|---|---|---|---|---|---|---|---|---|---|---|
| Ab1 | 1-29 | 3 | 35-48 | 5 | 65-95 | 7 | 99-109 | 9 | 110-439 | 10 |
| Ab2 | 1-30 | 43 | 36-49 | 45 | 66-97 | 47 | 101-111 | 49 | 112-441 | 50 |
| Ab3 | 1-30 | 83 | 36-49 | 85 | 66-97 | 87 | 101-111 | 89 | 112-441 | 90 |
| Ab4 | 1-29 | 123 | 35-48 | 125 | 65-95 | 127 | 99-109 | 129 | 110-439 | 130 |
| Ab5 | 1-30 | 163 | 36-49 | 165 | 66-97 | 167 | 101-111 | 169 | 112-441 | 170 |
| Ab6 | 1-30 | 203 | 36-49 | 205 | 66-97 | 207 | 101-111 | 209 | 112-441 | 210 |
| Ab7 | 1-30 | 243 | 36-49 | 245 | 66-96 | 247 | 100-110 | 249 | 111-440 | 250 |
| Ab8 | 1-30 | 283 | 36-49 | 285 | 66-97 | 287 | 101-111 | 289 | 112-441 | 290 |
| Ab9 | 1-29 | 323 | 35-48 | 325 | 65-95 | 327 | 99-109 | 329 | 110-439 | 330 |
| Ab10 | 1-30 | 363 | 36-49 | 365 | 66-97 | 367 | 101-111 | 369 | 112-441 | 370 |
| Ab11 | 1-29 | 403 | 35-48 | 405 | 65-95 | 407 | 99-109 | 409 | 110-439 | 410 |
| Ab12 | 1-30 | 443 | 36-49 | 445 | 66-97 | 447 | 101-111 | 449 | 112-441 | 450 |
| Ab13 | 1-29 | 483 | 35-48 | 485 | 66-96 | 487 | 101-111 | 489 | 112-441 | 490 |
| Ab14 | 1-30 | 523 | 36-49 | 525 | 66-97 | 527 | 101-111 | 529 | 112-441 | 530 |

Figure 7
Light Chain Protein Sequence Features

| Antibody | Variable Region Coordinates | SEQ ID NO: | CDR1 Coordinates | SEQ ID NO: | CDR2 Coordinates | SEQ ID NO: | CDR3 Coordinates | SEQ ID NO: |
|---|---|---|---|---|---|---|---|---|
| Ab1 | 1-113 | 22 | 23-35 | 24 | 51-57 | 26 | 90-102 | 28 |
| Ab2 | 1-113 | 62 | 23-35 | 64 | 51-57 | 66 | 90-102 | 68 |
| Ab3 | 1-113 | 102 | 23-35 | 104 | 51-57 | 106 | 90-102 | 108 |
| Ab4 | 1-113 | 142 | 23-35 | 144 | 51-57 | 146 | 90-102 | 148 |
| Ab5 | 1-113 | 182 | 23-35 | 184 | 51-57 | 186 | 90-102 | 188 |
| Ab6 | 1-113 | 222 | 23-35 | 224 | 51-57 | 226 | 90-102 | 228 |
| Ab7 | 1-113 | 262 | 23-35 | 264 | 51-57 | 266 | 90-102 | 268 |
| Ab8 | 1-113 | 302 | 23-35 | 304 | 51-57 | 306 | 90-102 | 308 |
| Ab9 | 1-113 | 342 | 23-35 | 344 | 51-57 | 346 | 90-102 | 348 |
| Ab10 | 1-113 | 382 | 23-35 | 384 | 51-57 | 386 | 90-102 | 388 |
| Ab11 | 1-113 | 422 | 23-35 | 424 | 51-57 | 426 | 90-102 | 428 |
| Ab12 | 1-113 | 462 | 23-35 | 464 | 51-57 | 466 | 90-102 | 468 |
| Ab13 | 1-113 | 502 | 24-36 | 504 | 52-58 | 506 | 91-102 | 508 |
| Ab14 | 1-113 | 542 | 23-35 | 544 | 51-57 | 546 | 90-102 | 548 |

Figure 8
Light Chain Protein Sequence Features

| Antibody | FR1 Coordinates | SEQ ID NO: | FR2 Coordinates | SEQ ID NO: | FR3 Coordinates | SEQ ID NO: | FR4 Coordinates | SEQ ID NO: | Constant Region Coordinates | SEQ ID NO: |
|---|---|---|---|---|---|---|---|---|---|---|
| Ab1 | 1-22 | 23 | 36-50 | 25 | 58-89 | 27 | 103-113 | 29 | 114-219 | 30 |
| Ab2 | 1-22 | 63 | 36-50 | 65 | 58-89 | 67 | 103-113 | 69 | 114-219 | 70 |
| Ab3 | 1-22 | 103 | 36-50 | 105 | 58-89 | 107 | 103-113 | 109 | 114-219 | 110 |
| Ab4 | 1-22 | 143 | 36-50 | 145 | 58-89 | 147 | 103-113 | 149 | 114-219 | 150 |
| Ab5 | 1-22 | 183 | 36-50 | 185 | 58-89 | 187 | 103-113 | 189 | 114-219 | 190 |
| Ab6 | 1-22 | 223 | 36-50 | 225 | 58-89 | 227 | 103-113 | 229 | 114-219 | 230 |
| Ab7 | 1-22 | 263 | 36-50 | 265 | 58-89 | 267 | 103-113 | 269 | 114-219 | 270 |
| Ab8 | 1-22 | 303 | 36-50 | 305 | 58-89 | 307 | 103-113 | 309 | 114-219 | 310 |
| Ab9 | 1-22 | 343 | 36-50 | 345 | 58-89 | 347 | 103-113 | 349 | 114-219 | 350 |
| Ab10 | 1-22 | 383 | 36-50 | 385 | 58-89 | 387 | 103-113 | 389 | 114-219 | 390 |
| Ab11 | 1-22 | 423 | 36-50 | 425 | 58-89 | 427 | 103-113 | 429 | 114-219 | 430 |
| Ab12 | 1-22 | 463 | 36-50 | 465 | 58-89 | 467 | 103-113 | 469 | 114-219 | 470 |
| Ab13 | 1-23 | 503 | 37-51 | 505 | 59-90 | 507 | 103-113 | 509 | 114-219 | 510 |
| Ab14 | 1-22 | 543 | 36-50 | 545 | 58-89 | 547 | 103-113 | 549 | 114-219 | 550 |

Figure 9
Heavy Chain DNA Sequence Features

| Antibody | Variable Region Coordinates | SEQ ID NO: | CDR1 Coordinates | SEQ ID NO: | CDR2 Coordinates | SEQ ID NO: | CDR3 Coordinates | SEQ ID NO: |
|---|---|---|---|---|---|---|---|---|
| Ab1 | 1-327 | 12 | 88-102 | 14 | 145-192 | 16 | 286-294 | 18 |
| Ab2 | 1-333 | 52 | 91-105 | 54 | 148-195 | 56 | 292-300 | 58 |
| Ab3 | 1-333 | 92 | 91-105 | 94 | 148-195 | 96 | 292-300 | 98 |
| Ab4 | 1-327 | 132 | 88-102 | 134 | 145-192 | 136 | 286-294 | 138 |
| Ab5 | 1-333 | 172 | 91-105 | 174 | 148-195 | 176 | 292-300 | 178 |
| Ab6 | 1-333 | 212 | 91-105 | 214 | 148-195 | 216 | 292-300 | 218 |
| Ab7 | 1-330 | 252 | 91-105 | 254 | 148-195 | 256 | 289-297 | 258 |
| Ab8 | 1-333 | 292 | 91-105 | 294 | 148-195 | 296 | 292-300 | 298 |
| Ab9 | 1-327 | 332 | 88-102 | 334 | 145-192 | 336 | 286-294 | 338 |
| Ab10 | 1-333 | 372 | 91-105 | 374 | 148-195 | 376 | 292-300 | 378 |
| Ab11 | 1-327 | 412 | 88-102 | 414 | 145-192 | 416 | 286-294 | 418 |
| Ab12 | 1-333 | 452 | 91-105 | 454 | 148-195 | 456 | 292-300 | 458 |
| Ab13 | 1-333 | 492 | 88-102 | 494 | 145-195 | 496 | 289-300 | 498 |
| Ab14 | 1-333 | 532 | 91-105 | 534 | 148-195 | 536 | 292-300 | 538 |

Figure 10
Heavy Chain DNA Sequence Features

| Antibody | FR1 Coordinates | SEQ ID NO: | FR2 Coordinates | SEQ ID NO: | FR3 Coordinates | SEQ ID NO: | FR4 Coordinates | SEQ ID NO: | Constant Region Coordinates | SEQ ID NO: |
|---|---|---|---|---|---|---|---|---|---|---|
| Ab1 | 1-87 | 13 | 103-144 | 15 | 193-285 | 17 | 295-327 | 19 | 328-1320 | 20 |
| Ab2 | 1-90 | 53 | 106-147 | 55 | 196-291 | 57 | 301-333 | 59 | 334-1326 | 60 |
| Ab3 | 1-90 | 93 | 106-147 | 95 | 196-291 | 97 | 301-333 | 99 | 334-1326 | 100 |
| Ab4 | 1-87 | 133 | 103-144 | 135 | 193-285 | 137 | 295-327 | 139 | 328-1320 | 140 |
| Ab5 | 1-90 | 173 | 106-147 | 175 | 196-291 | 177 | 301-333 | 179 | 334-1326 | 180 |
| Ab6 | 1-90 | 213 | 106-147 | 215 | 196-291 | 217 | 301-333 | 219 | 334-1326 | 220 |
| Ab7 | 1-90 | 253 | 106-147 | 255 | 196-288 | 257 | 298-330 | 259 | 331-1323 | 260 |
| Ab8 | 1-90 | 293 | 106-147 | 295 | 196-291 | 297 | 301-333 | 299 | 334-1326 | 300 |
| Ab9 | 1-87 | 333 | 103-144 | 335 | 193-285 | 337 | 295-327 | 339 | 328-1320 | 340 |
| Ab10 | 1-90 | 373 | 106-147 | 375 | 196-291 | 377 | 301-333 | 379 | 334-1326 | 380 |
| Ab11 | 1-87 | 413 | 103-144 | 415 | 193-285 | 417 | 295-327 | 419 | 328-1320 | 420 |
| Ab12 | 1-90 | 453 | 106-147 | 455 | 196-291 | 457 | 301-333 | 459 | 334-1326 | 460 |
| Ab13 | 1-87 | 493 | 103-144 | 495 | 196-288 | 497 | 301-333 | 499 | 334-1326 | 500 |
| Ab14 | 1-90 | 533 | 106-147 | 535 | 196-291 | 537 | 301-333 | 539 | 334-1326 | 540 |

Figure 11
Light Chain DNA Sequence Features

| Antibody | Variable Region Coordinates | SEQ ID NO: | CDR1 Coordinates | SEQ ID NO: | CDR2 Coordinates | SEQ ID NO: | CDR3 Coordinates | SEQ ID NO: |
|---|---|---|---|---|---|---|---|---|
| Ab1 | 1-339 | 32 | 67-105 | 34 | 151-171 | 36 | 268-306 | 38 |
| Ab2 | 1-339 | 72 | 67-105 | 74 | 151-171 | 76 | 268-306 | 78 |
| Ab3 | 1-339 | 112 | 67-105 | 114 | 151-171 | 116 | 268-306 | 118 |
| Ab4 | 1-339 | 152 | 67-105 | 154 | 151-171 | 156 | 268-306 | 158 |
| Ab5 | 1-339 | 192 | 67-105 | 194 | 151-171 | 196 | 268-306 | 198 |
| Ab6 | 1-339 | 232 | 67-105 | 234 | 151-171 | 236 | 268-306 | 238 |
| Ab7 | 1-339 | 272 | 67-105 | 274 | 151-171 | 276 | 268-306 | 278 |
| Ab8 | 1-339 | 312 | 67-105 | 314 | 151-171 | 316 | 268-306 | 318 |
| Ab9 | 1-339 | 352 | 67-105 | 354 | 151-171 | 356 | 268-306 | 358 |
| Ab10 | 1-339 | 392 | 67-105 | 394 | 151-171 | 396 | 268-306 | 398 |
| Ab11 | 1-339 | 432 | 67-105 | 434 | 151-171 | 436 | 268-306 | 438 |
| Ab12 | 1-339 | 472 | 67-105 | 474 | 151-171 | 476 | 268-306 | 478 |
| Ab13 | 1-339 | 512 | 70-108 | 514 | 154-174 | 516 | 271-306 | 518 |
| Ab14 | 1-339 | 552 | 67-105 | 554 | 151-171 | 556 | 268-306 | 558 |

Figure 12.
Light Chain DNA Sequence Features

| Antibody | FR1 Coordinates | SEQ ID NO: | FR2 Coordinates | SEQ ID NO: | FR3 Coordinates | SEQ ID NO: | FR4 Coordinates | SEQ ID NO: | Constant Region Coordinates | SEQ ID NO: |
|---|---|---|---|---|---|---|---|---|---|---|
| Ab1 | 1-66 | 33 | 106-150 | 35 | 172-267 | 37 | 307-339 | 39 | 340-660 | 40 |
| Ab2 | 1-66 | 73 | 106-150 | 75 | 172-267 | 77 | 307-339 | 79 | 340-660 | 80 |
| Ab3 | 1-66 | 113 | 106-150 | 115 | 172-267 | 117 | 307-339 | 119 | 340-660 | 120 |
| Ab4 | 1-66 | 153 | 106-150 | 155 | 172-267 | 157 | 307-339 | 159 | 340-660 | 160 |
| Ab5 | 1-66 | 193 | 106-150 | 195 | 172-267 | 197 | 307-339 | 199 | 340-660 | 200 |
| Ab6 | 1-66 | 233 | 106-150 | 235 | 172-267 | 237 | 307-339 | 239 | 340-660 | 240 |
| Ab7 | 1-66 | 273 | 106-150 | 275 | 172-267 | 277 | 307-339 | 279 | 340-660 | 280 |
| Ab8 | 1-66 | 313 | 106-150 | 315 | 172-267 | 317 | 307-339 | 319 | 340-660 | 320 |
| Ab9 | 1-66 | 353 | 106-150 | 355 | 172-267 | 357 | 307-339 | 359 | 340-660 | 360 |
| Ab10 | 1-66 | 393 | 106-150 | 395 | 172-267 | 397 | 307-339 | 399 | 340-660 | 400 |
| Ab11 | 1-66 | 433 | 106-150 | 435 | 172-267 | 437 | 307-339 | 439 | 340-660 | 440 |
| Ab12 | 1-66 | 473 | 106-150 | 475 | 172-267 | 477 | 307-339 | 479 | 340-660 | 480 |
| Ab13 | 1-69 | 513 | 109-153 | 515 | 175-270 | 517 | 307-339 | 519 | 340-660 | 520 |
| Ab14 | 1-66 | 553 | 106-150 | 555 | 172-267 | 557 | 307-339 | 559 | 340-660 | 560 |

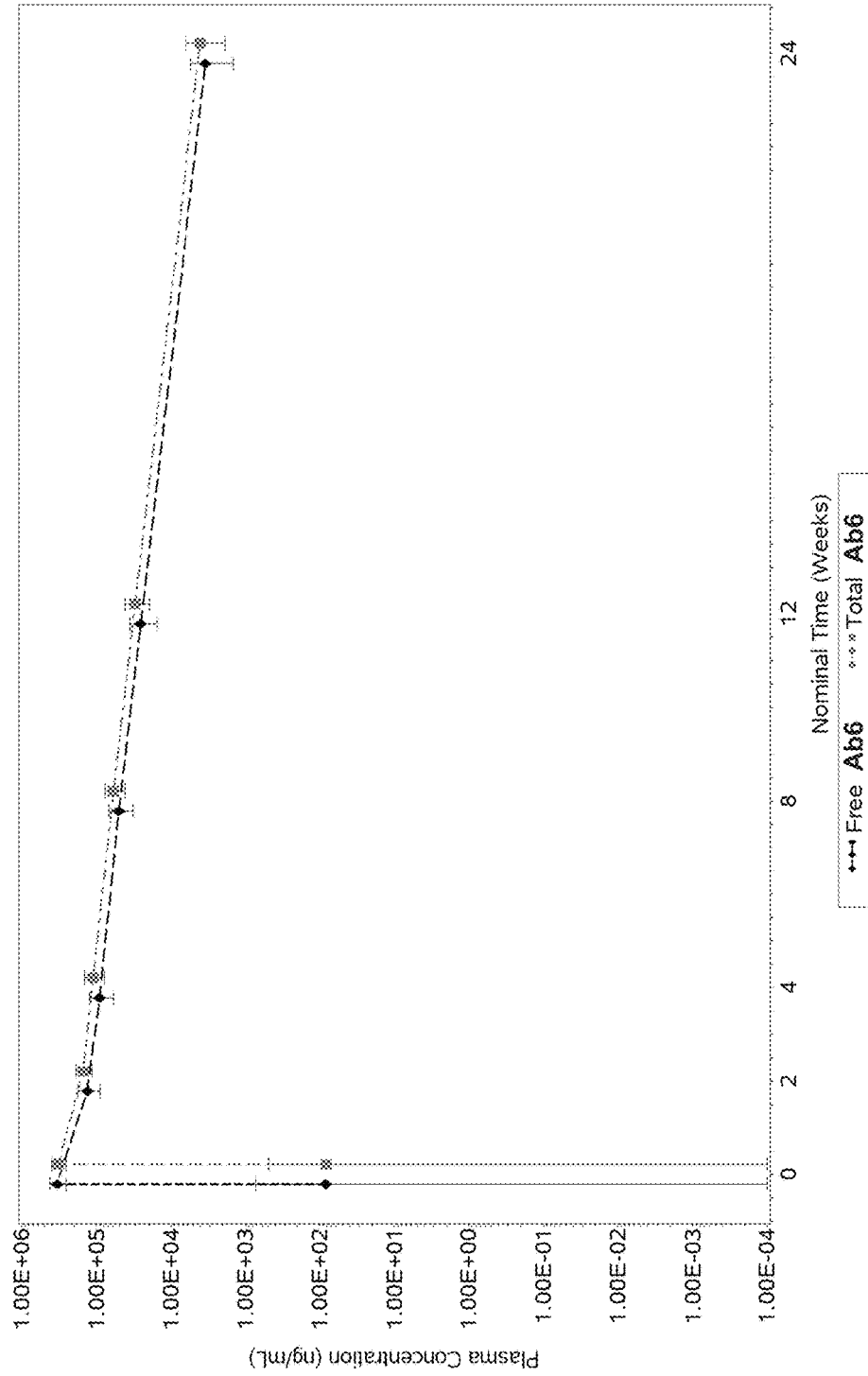
FIG. 20. PK Profile

FIG. 21. PK Parameters

Plasma Free Ab6*

| | $C_{max}$ (μg/mL) | $AUC_{0-\infty}$ (mg*hr/mL) | Half-Life (Days) | Vz (L) | CL (mL/hr) |
|---|---|---|---|---|---|
| N | 81 | 78 | 78 | 78 | 78 |
| Mean | 336 | 219 | 31 | 5.2 | 5.0 |
| SD | 80 | 64 | 8 | 2.1 | 1.5 |

* - Following 1000 mg Ab6 IV single-dose

FIG. 34. Mean (±SD) Change from Baseline In Study Endpoints

| Endpoint | Weeks 1-4 | | Weeks 5-8 | | Weeks 9-12 | |
|---|---|---|---|---|---|---|
| | Placebo i.v. (n=82) | Ab6 1000mg i.v. (n=81) | Placebo i.v. (n=82) | Ab6 1000mg i.v. (n=81) | Placebo i.v. (n=82) | Ab6 1000mg i.v. (n=81) |
| Migraine Days | -3.9 (3.5) | -5.6 (3.3)[1] | -4.6 (3.6) | -5.6 (3.0)[2] | -4.6 (3.5) | -5.6 (4.0)[3] |
| Migraine Episodes | -3.0 (2.7) | -3.7 (2.4) | -3.7 (2.9) | -3.8 (2.2) | -3.7 (2.8) | -3.9 (2.6) |
| Migraine Hours | -33.7 (41.8) | -58.0 (49.1) | -36.1 (45.9) | -54.4 (48.3) | -37.1 (40.0) | -54.6 (60.5) |
| Average Migraine Severity[4] | -0.16 (0.58) | -0.31 (0.58) | -0.10 (0.54) | -0.16 (0.50) | -0.08 (0.54) | -0.11 (0.43) |
| Headache Frequency | -4.0 (3.8) | -5.6 (3.4) | -5.0 (3.7) | -5.3 (3.5) | -5.1 (3.7) | -5.9 (3.8) |
| HIT-6 score | -5.8 (7.8) | -10.2 (9.8) | -8.1 (8.9) | -9.9 (9.7) | -7.7 (9.0) | -10.1 (10.6) |
| MSQ RFP | 19.9 (23.8) | 29.3 (24.3) | 25.2 (24.8) | 28.8 (24.7) | 22.2 (23.1) | 28.5 (24.5) |
| MSQ RFR | 16.3 (23.2) | 21.1 (23.9) | 20.2 (22.1) | 20.9 (23.3) | 18.0 (20.5) | 21.4 (23.1) |
| MSQ EF | 19.4 (27.6) | 25.1 (28.3) | 21.2 (25.1) | 23.8 (25.8) | 21.1 (25.1) | 23.1 (26.8) |

[1] p<0.001; [2] p=0.03; [3] p=0.06; [4] Severity measured on a 4 point scale with 1 = mild and 4 = severe FIG. 36. Chronic migraine ≥ 50% responder rates FIG. 37. Chronic migraine ≥ 75% responder rates FIG. 38. Chronic migraine 100% responder rates

|  | Placebo | 100 mg | 300 mg |
|---|---|---|---|
| Subjects, n | 366 | 356 | 350 |
| Mean age, years (SD) | 39.6 (11.3) | 41.0 (11.7) | 41.0 (10.4) |
| Mean BMI, kg/m² (SD) | 27.0 (5.6) | 26.4 (5.0) | 26.3 (5.0) |
| Female, % | 89 | 86 | 90 |
| Mean years from migraine diagnosis | 17.0 | 18.3 | 19.0 |
| Mean duration of chronic migraine, years (SD) | 11.6 (10.9) | 11.6 (11.7) | 12.4 (11.2) |
| ≥1 prophylactic medication, n (%)* | 163 (44.5) | 161 (45.2) | 155 (44.3) |
| Mean migraine days/month (SD) | 16.2 (4.6) | 16.1 (4.6) | 16.1 (4.8) |
| Mean headache days/month (SD) | 20.6 (3.0) | 20.4 (3.1) | 20.4 (3.2) |

FIG. 39

FIG. 40. Difference from placebo in change from baseline in mean migraine days (MMD) over months 1-3 by baseline subgroup FIG. 41. Difference from placebo in change from baseline in mean migraine days (MMD) over months 1-3 by baseline subgroup

|  | Month 1 | | | Month 6 | | |
| --- | --- | --- | --- | --- | --- | --- |
|  | Ab6 100 mg | Ab6 400 mg | Placebo | Ab6 100 mg | Ab6 400 mg | Placebo |
| Baseline use | | | | | | |
| 1–9 days/month, n | 37 | 49 | 49 | 37 | 49 | 49 |
| ≥10 days/month, n | 264 | 265 | 260 | 264 | 265 | 260 |
| ≥1 day/month, mean (SD) | 18.3 (9.05) | 18.4 (9.61) | 17.9 (8.60) | 18.3 (9.05) | 18.4 (9.61) | 17.9 (8.60) |
| Post-baseline use, mean (SD) | | | | | | |
| ≥1 day/month | 10.7 (9.39) | 10.2 (9.87) | 13.8 (9.52) | 10.8 (11.18) | 8.6 (9.97) | 11.5 (10.16) |
| Change from baseline, mean (SD) | | | | | | |
| ≥1 day/month | -7.8 (8.08) | -8.3 (7.64) | -4.5 (7.46) | -8.1 (9.90) | -9.6 (9.92) | -7.0 (9.39) |
| 1–9 days/month | -1.5 (4.44) | -2.3 (4.34) | -1.0 (5.29) | -0.8 (6.63) | -2.6 (4.57) | -1.3 (4.83) |
| ≥10 days/month | -8.7 (8.08) | -9.4 (7.62) | -5.1 (7.63) | -8.9 (9.88) | -11.1 (10.10) | -7.9 (9.64) |
| Percent change from baseline, mean (SD) | | | | | | |
| ≥1 day/month | -42.6 (39.98) | -47.0 (40.90) | -22.4 (52.02) | -40.7 (60.66) | -52.9 (48.97) | -34.7 (58.48) |
| 1–9 days/month | -31.8 (67.95) | -47.3 (65.38) | -9.5 (100.52) | 1.4 (132.84) | -45.0 (73.05) | -11.2 (108.44) |
| ≥10 days/month | -44.1 (34.24) | -47.0 (34.73) | -24.8 (36.17) | -45.3 (44.91) | -54.5 (42.52) | -38.5 (44.63) |

FIG. 45.

FIG. 49. Summary of Acute Medication Days by Subgroups of Episodic Migraine Patients with Baseline Acute Medication Use

|  | Month 1 | | | Month 6 | | |
|---|---|---|---|---|---|---|
|  | Ab6 100 mg | Ab6 400 mg | Placebo | Ab6 100 mg | Ab6 400 mg | Placebo |
| Baseline use |  |  |  |  |  |  |
| 1-9 days/month, n | 117 | 111 | 108 | 117 | 111 | 108 |
| ≥10 days/month, n | 42 | 41 | 44 | 42 | 41 | 44 |
| ≥1 day/month, mean (SD) | 7.5 (4.97) | 7.5 (4.58) | 7.8 (4.98) | 7.5 (4.97) | 7.5 (4.58) | 7.8 (4.98) |
| Post-baseline use, mean (SD) |  |  |  |  |  |  |
| ≥1 day/month | 4.3 (3.99) | 4.2 (4.45) | 5.7 (5.04) | 4.2 (5.87) | 3.5 (3.92) | 5.1 (5.19) |
| Change from baseline, mean (SD) |  |  |  |  |  |  |
| ≥1 day/month | -3.3 (4.14) | -3.2 (4.20) | -2.2 (4.68) | -2.8 (4.92) | -4.1 (4.60) | -2.3 (4.69) |
| 1-9 days/month | -2.0 (2.91) | -2.2 (3.57) | -1.3 (3.10) | -2.4 (3.11) | -2.7 (3.83) | -1.6 (3.52) |
| ≥10 days/month | -6.6 (5.11) | -5.8 (4.66) | -4.3 (6.82) | -4.0 (8.60) | -7.4 (4.60) | -4.1 (6.60) |
| Percent change from baseline, mean (SD) |  |  |  |  |  |  |
| ≥1 day/month | -36.9 (63.96) | -39.4 (77.71) | -22.4 (60.27) | -45.4 (62.28) | -50.9 (59.88) | -22.5 (95.61) |
| 1-9 days/month | -33.9 (72.22) | -37.0 (88.45) | -19.7 (64.62) | -50.1 (59.65) | -48.2 (68.26) | -18.2 (107.55) |
| ≥10 days/month | -45.1 (30.26) | -45.9 (34.95) | -29.1 (47.94) | -29.2 (69.14) | -57.2 (32.59) | -33.9 (52.53) |

SEQUENCE LISTING

<160> NUMBER OF SEQ ID NOS: 567

<210> SEQ ID NO 1
<211> LENGTH: 439
<212> TYPE: PRT
<213> ORGANISM: Artificial
<220> FEATURE:
<223> OTHER INFORMATION: Engineered antibody sequence

<400> SEQUENCE: 1

```
Gln Ser Leu Glu Glu Ser Gly Gly Arg Leu Val Thr Pro Gly Thr Pro
1               5                   10                  15

Leu Thr Leu Thr Cys Thr Val Ser Gly Leu Asp Leu Ser Ser Tyr Tyr
            20                  25                  30

Met Gln Trp Val Arg Gln Ala Pro Gly Lys Gly Leu Glu Trp Ile Gly
        35                  40                  45

Val Ile Gly Ile Asn Asp Asn Thr Tyr Tyr Ala Ser Trp Ala Lys Gly
    50                  55                  60

Arg Phe Thr Ile Ser Arg Ala Ser Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Asp Ile Trp Gly Pro Gly Thr Leu Val Thr Val Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Arg Val Glu
        195                 200                 205

Pro Lys Ser Cys Asp Lys Thr His Thr Cys Pro Pro Cys Pro Ala Pro
    210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Ala Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Ser Arg Glu Glu Met Thr Lys
            340                 345                 350

Asn Gln Val Ser Leu Thr Cys Leu Val Lys Gly Phe Tyr Pro Ser Asp
```

```
                    355                 360                 365
Ile Ala Val Glu Trp Glu Ser Asn Gly Gln Pro Glu Asn Asn Tyr Lys
            370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
                420                 425                 430

Leu Ser Leu Ser Pro Gly Lys
        435

<210> SEQ ID NO 2
<211> LENGTH: 109
<212> TYPE: PRT
<213> ORGANISM: Artificial
<220> FEATURE:
<223> OTHER INFORMATION: Engineered antibody sequence

<400> SEQUENCE: 2

Gln Ser Leu Glu Glu Ser Gly Gly Arg Leu Val Thr Pro Gly Thr Pro
1               5                   10                  15

Leu Thr Leu Thr Cys Thr Val Ser Gly Leu Asp Leu Ser Ser Tyr Tyr
                20                  25                  30

Met Gln Trp Val Arg Gln Ala Pro Gly Lys Gly Leu Glu Trp Ile Gly
            35                  40                  45

Val Ile Gly Ile Asn Asp Asn Thr Tyr Tyr Ala Ser Trp Ala Lys Gly
        50                  55                  60

Arg Phe Thr Ile Ser Arg Ala Ser Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Asp Ile Trp Gly Pro Gly Thr Leu Val Thr Val Ser Ser
            100                 105

<210> SEQ ID NO 3
<211> LENGTH: 29
<212> TYPE: PRT
<213> ORGANISM: Artificial
<220> FEATURE:
<223> OTHER INFORMATION: Engineered antibody sequence

<400> SEQUENCE: 3

Gln Ser Leu Glu Glu Ser Gly Gly Arg Leu Val Thr Pro Gly Thr Pro
1               5                   10                  15

Leu Thr Leu Thr Cys Thr Val Ser Gly Leu Asp Leu Ser
                20                  25

<210> SEQ ID NO 4
<211> LENGTH: 5
<212> TYPE: PRT
<213> ORGANISM: Artificial
<220> FEATURE:
<223> OTHER INFORMATION: Engineered antibody sequence

<400> SEQUENCE: 4

Ser Tyr Tyr Met Gln
1               5

<210> SEQ ID NO 5
```

```
<211> LENGTH: 14
<212> TYPE: PRT
<213> ORGANISM: Artificial
<220> FEATURE:
<223> OTHER INFORMATION: Engineered antibody sequence

<400> SEQUENCE: 5

Trp Val Arg Gln Ala Pro Gly Lys Gly Leu Glu Trp Ile Gly
1               5                   10

<210> SEQ ID NO 6
<211> LENGTH: 16
<212> TYPE: PRT
<213> ORGANISM: Artificial
<220> FEATURE:
<223> OTHER INFORMATION: Engineered antibody sequence

<400> SEQUENCE: 6

Val Ile Gly Ile Asn Asp Asn Thr Tyr Tyr Ala Ser Trp Ala Lys Gly
1               5                   10                  15

<210> SEQ ID NO 7
<211> LENGTH: 31
<212> TYPE: PRT
<213> ORGANISM: Artificial
<220> FEATURE:
<223> OTHER INFORMATION: Engineered antibody sequence

<400> SEQUENCE: 7

Arg Phe Thr Ile Ser Arg Ala Ser Ser Thr Thr Val Asp Leu Lys Met
1               5                   10                  15

Thr Ser Leu Thr Thr Glu Asp Thr Ala Thr Tyr Phe Cys Ala Arg
            20                  25                  30

<210> SEQ ID NO 8
<211> LENGTH: 3
<212> TYPE: PRT
<213> ORGANISM: Artificial
<220> FEATURE:
<223> OTHER INFORMATION: Engineered antibody sequence

<400> SEQUENCE: 8

Gly Asp Ile
1

<210> SEQ ID NO 9
<211> LENGTH: 11
<212> TYPE: PRT
<213> ORGANISM: Artificial
<220> FEATURE:
<223> OTHER INFORMATION: Engineered antibody sequence

<400> SEQUENCE: 9

Trp Gly Pro Gly Thr Leu Val Thr Val Ser Ser
1               5                   10

<210> SEQ ID NO 10
<211> LENGTH: 330
<212> TYPE: PRT
<213> ORGANISM: Artificial
<220> FEATURE:
<223> OTHER INFORMATION: Engineered antibody sequence

<400> SEQUENCE: 10

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

<210> SEQ ID NO 11
<211> LENGTH: 1320
<212> TYPE: DNA
<213> ORGANISM: Artificial
<220> FEATURE:
<223> OTHER INFORMATION: Engineered antibody sequence

<400> SEQUENCE: 11

```
cagtcgctgg aggagtccgg gggtcgcctg gtcacgcctg ggacacccct gacactcacc      60
tgcacagtct ctggactcga cctcagtagc tactacatgc aatgggtccg ccaggctcca     120 gggaagggc tggaatggat cggagtcatt ggtattaatg ataacacata ctacgcgagc     180
tgggcgaaag gccgattcac catctccaga gcctcgtcga ccacggtgga tctgaaaatg     240
accagtctga caaccgagga cacggccacc tatttctgtg ccagagggga catctggggc     300
```

```
ccaggcaccc tcgtcaccgt ctcgagcgcc tccaccaagg gcccatcggt cttccccctg      360
gcaccctcct ccaagagcac ctctgggggc acagcggccc tgggctgcct ggtcaaggac      420
tacttccccg aaccggtgac ggtgtcgtgg aactcaggcg ccctgaccag cggcgtgcac      480
accttcccgg ctgtcctaca gtcctcagga ctctactccc tcagcagcgt ggtgaccgtg      540
ccctccagca gcttgggcac ccagacctac atctgcaacg tgaatcacaa gcccagcaac      600
accaaggtgg acaagagagt tgagcccaaa tcttgtgaca aaactcacac atgcccaccg      660
tgcccagcac ctgaactcct ggggggaccg tcagtcttcc tcttccccc aaaacccaag       720 gacaccctca tgatctcccg acccctgag gtcacatgcg tggtggtgga cgtgagccac       780
gaagaccctg aggtcaagtt caactggtac gtggacggcg tggaggtgca taatgccaag      840
acaaagccgc gggaggagca gtacgccagc acgtaccgtg tggtcagcgt cctcaccgtc      900
ctgcaccagg actggctgaa tgcaaggag tacaagtgca aggtctccaa caaagccctc       960
ccagccccca tcgagaaaac catctccaaa gccaaagggc agccccgaga accacaggtg     1020
tacaccctgc cccatcccg ggaggagatg accaagaacc aggtcagcct gacctgcctg      1080
gtcaaaggct tctatcccag cgacatcgcc gtggagtggg agagcaatgg gcagccggag     1140
aacaactaca agaccacgcc tcccgtgctg gactccgacg gctccttctt cctctacagc     1200
aagctcaccg tggacaagag caggtggcag caggggaacg tcttctcatg ctccgtgatg     1260
catgaggctc tgcacaacca ctacacgcag aagagcctct ccctgtctcc gggtaaatga    1320

<210> SEQ ID NO 12
<211> LENGTH: 327
<212> TYPE: DNA
<213> ORGANISM: Artificial
<220> FEATURE:
<223> OTHER INFORMATION: Engineered antibody sequence

<400> SEQUENCE: 12
cagtcgctgg aggagtccgg gggtcgcctg gtcacgcctg gacacccct gacactcacc        60 tgcacagtct ctggactcga cctcagtagc tactacatgc aatgggtccg ccaggctcca      120
gggaaggggc tggaatggat cggagtcatt ggtattaatg ataacacata ctacgcgagc      180
tgggcgaaag gccgattcac catctccaga gcctcgtcga ccacggtgga tctgaaaatg      240
accagtctga aaccgaggac acggccacc tatttctgtg ccagagggga catctggggc       300
ccaggcaccc tcgtcaccgt ctcgagc                                          327

<210> SEQ ID NO 13
<211> LENGTH: 87
<212> TYPE: DNA
<213> ORGANISM: Artificial
<220> FEATURE:
<223> OTHER INFORMATION: Engineered antibody sequence

<400> SEQUENCE: 13
cagtcgctgg aggagtccgg gggtcgcctg gtcacgcctg gacacccct gacactcacc        60 tgcacagtct ctggactcga cctcagt                                           87

<210> SEQ ID NO 14
<211> LENGTH: 15
<212> TYPE: DNA
<213> ORGANISM: Artificial
<220> FEATURE:
<223> OTHER INFORMATION: Engineered antibody sequence
```

```
<400> SEQUENCE: 14
agctactaca tgcaa                                                        15

<210> SEQ ID NO 15
<211> LENGTH: 42
<212> TYPE: DNA
<213> ORGANISM: Artificial
<220> FEATURE:
<223> OTHER INFORMATION: Engineered antibody sequence

<400> SEQUENCE: 15
tgggtccgcc aggctccagg gaagggctg gaatggatcg ga                           42

<210> SEQ ID NO 16
<211> LENGTH: 48
<212> TYPE: DNA
<213> ORGANISM: Artificial
<220> FEATURE:
<223> OTHER INFORMATION: Engineered antibody sequence

<400> SEQUENCE: 16
gtcattggta ttaatgataa cacatactac gcgagctggg cgaaaggc                    48

<210> SEQ ID NO 17
<211> LENGTH: 93
<212> TYPE: DNA
<213> ORGANISM: Artificial
<220> FEATURE:
<223> OTHER INFORMATION: Engineered antibody sequence

<400> SEQUENCE: 17
cgattcacca tctccagagc ctcgtcgacc acggtggatc tgaaaatgac cagtctgaca       60
accgaggaca cggccaccta tttctgtgcc aga                                    93

<210> SEQ ID NO 18
<211> LENGTH: 9
<212> TYPE: DNA
<213> ORGANISM: Artificial
<220> FEATURE:
<223> OTHER INFORMATION: Engineered antibody sequence

<400> SEQUENCE: 18 ggggacatc                                                                9

<210> SEQ ID NO 19
<211> LENGTH: 33
<212> TYPE: DNA
<213> ORGANISM: Artificial
<220> FEATURE:
<223> OTHER INFORMATION: Engineered antibody sequence

<400> SEQUENCE: 19
tggggcccag gcaccctcgt caccgtctcg agc                                    33

<210> SEQ ID NO 20
<211> LENGTH: 993
<212> TYPE: DNA
<213> ORGANISM: Artificial
<220> FEATURE:
<223> OTHER INFORMATION: Engineered antibody sequence

<400> SEQUENCE: 20
gcctccacca agggcccatc ggtcttcccc ctggcaccct cctccaagag cacctctggg       60
ggcacagcgg ccctgggctg cctggtcaag gactacttcc ccgaaccggt gacggtgtcg      120
```

```
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagag agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacgcc    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa tga                                 993
```

```
<210> SEQ ID NO 21
<211> LENGTH: 219
<212> TYPE: PRT
<213> ORGANISM: Artificial
<220> FEATURE:
<223> OTHER INFORMATION: Engineered antibody sequence

<400> SEQUENCE: 21
```

```
Gln Val Leu Thr Gln Thr Ala Ser Pro Val Ser Ala Ala Val Gly Ser
1               5                   10                  15

Thr Val Thr Ile Asn Cys Gln Ala Ser Gln Ser Val Tyr Asp Asn Asn
            20                  25                  30

Tyr Leu Ala Trp Tyr Gln Gln Lys Pro Gly Gln Pro Pro Lys Gln Leu
        35                  40                  45

Ile Tyr Ser Thr Ser Thr Leu Ala Ser Gly Val Ser Ser Arg Phe Lys
    50                  55                  60

Gly Ser Gly Ser Gly Thr Gln Phe Thr Leu Thr Ile Ser Asp Leu Glu
65                  70                  75                  80

Cys Ala Asp Ala Ala Thr Tyr Tyr Cys Leu Gly Ser Tyr Asp Cys Ser
                85                  90                  95

Ser Gly Asp Cys Phe Val Phe Gly Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

```
Pro Val Thr Lys Ser Phe Asn Arg Gly Glu Cys
    210                 215
```

<210> SEQ ID NO 22
<211> LENGTH: 113
<212> TYPE: PRT
<213> ORGANISM: Artificial
<220> FEATURE:
<223> OTHER INFORMATION: Engineered antibody sequence

<400> SEQUENCE: 22

```
Gln Val Leu Thr Gln Thr Ala Ser Pro Val Ser Ala Ala Val Gly Ser
1               5                   10                  15

Thr Val Thr Ile Asn Cys Gln Ala Ser Gln Ser Val Tyr Asp Asn Asn
            20                  25                  30

Tyr Leu Ala Trp Tyr Gln Gln Lys Pro Gly Gln Pro Lys Gln Leu
        35                  40                  45

Ile Tyr Ser Thr Ser Thr Leu Ala Ser Gly Val Ser Ser Arg Phe Lys
    50                  55                  60

Gly Ser Gly Ser Gly Thr Gln Phe Thr Leu Thr Ile Ser Asp Leu Glu
65                  70                  75                  80

Cys Ala Asp Ala Ala Thr Tyr Tyr Cys Leu Gly Ser Tyr Asp Cys Ser
                85                  90                  95

Ser Gly Asp Cys Phe Val Phe Gly Gly Gly Thr Glu Val Val Val Lys
            100                 105                 110

Arg
```

<210> SEQ ID NO 23
<211> LENGTH: 22
<212> TYPE: PRT
<213> ORGANISM: Artificial
<220> FEATURE:
<223> OTHER INFORMATION: Engineered antibody sequence

<400> SEQUENCE: 23

```
Gln Val Leu Thr Gln Thr Ala Ser Pro Val Ser Ala Ala Val Gly Ser
1               5                   10                  15

Thr Val Thr Ile Asn Cys
            20
```

<210> SEQ ID NO 24
<211> LENGTH: 13
<212> TYPE: PRT
<213> ORGANISM: Artificial
<220> FEATURE:
<223> OTHER INFORMATION: Engineered antibody sequence

<400> SEQUENCE: 24

```
Gln Ala Ser Gln Ser Val Tyr Asp Asn Asn Tyr Leu Ala
1               5                   10
```

<210> SEQ ID NO 25
<211> LENGTH: 15
<212> TYPE: PRT
<213> ORGANISM: Artificial
<220> FEATURE:
<223> OTHER INFORMATION: Engineered antibody sequence

<400> SEQUENCE: 25

```
Trp Tyr Gln Gln Lys Pro Gly Gln Pro Pro Lys Gln Leu Ile Tyr
1               5                   10                  15
```

```
<210> SEQ ID NO 26
<211> LENGTH: 7
<212> TYPE: PRT
<213> ORGANISM: Artificial
<220> FEATURE:
<223> OTHER INFORMATION: Engineered antibody sequence

<400> SEQUENCE: 26

Ser Thr Ser Thr Leu Ala Ser
1               5

<210> SEQ ID NO 27
<211> LENGTH: 32
<212> TYPE: PRT
<213> ORGANISM: Artificial
<220> FEATURE:
<223> OTHER INFORMATION: Engineered antibody sequence

<400> SEQUENCE: 27

Gly Val Ser Ser Arg Phe Lys Gly Ser Gly Ser Gly Thr Gln Phe Thr
1               5                   10                  15

Leu Thr Ile Ser Asp Leu Glu Cys Ala Asp Ala Ala Thr Tyr Tyr Cys
            20                  25                  30

<210> SEQ ID NO 28
<211> LENGTH: 13
<212> TYPE: PRT
<213> ORGANISM: Artificial
<220> FEATURE:
<223> OTHER INFORMATION: Engineered antibody sequence

<400> SEQUENCE: 28

Leu Gly Ser Tyr Asp Cys Ser Ser Gly Asp Cys Phe Val
1               5                   10

<210> SEQ ID NO 29
<211> LENGTH: 11
<212> TYPE: PRT
<213> ORGANISM: Artificial
<220> FEATURE:
<223> OTHER INFORMATION: Engineered antibody sequence

<400> SEQUENCE: 29

Phe Gly Gly Gly Thr Glu Val Val Val Lys Arg
1               5                   10

<210> SEQ ID NO 30
<211> LENGTH: 106
<212> TYPE: PRT
<213> ORGANISM: Artificial
<220> FEATURE:
<223> OTHER INFORMATION: Engineered antibody sequence

<400> SEQUENCE: 30

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80
```

His Lys Val Tyr Ala Cys Glu Val Thr His Gln Gly Leu Ser Ser Pro
            85                  90                  95

Val Thr Lys Ser Phe Asn Arg Gly Glu Cys
            100                 105

<210> SEQ ID NO 31
<211> LENGTH: 660
<212> TYPE: DNA
<213> ORGANISM: Artificial
<220> FEATURE:
<223> OTHER INFORMATION: Engineered antibody sequence

<400> SEQUENCE: 31
caagtgctga cccagactgc atccccgtg tctgcagctg tgggaagcac agtcaccatc       60
aattgccagg ccagtcagag tgtttatgat aacaactacc tagcctggta tcagcagaaa    120
ccagggcagc tcccaagca actgatctat tctacatcca ctctggcatc tggggtctca    180
tcgcggttca aaggcagtgg atctgggaca cagttcactc tcaccatcag cgacctggag    240
tgtgccgatg ctgccactta ctactgtcta ggcagttatg attgtagtag tggtgattgt    300
tttgttttcg gcggagggac cgaggtggtg gtcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacagggg agagtgttag    660

<210> SEQ ID NO 32
<211> LENGTH: 339
<212> TYPE: DNA
<213> ORGANISM: Artificial
<220> FEATURE:
<223> OTHER INFORMATION: Engineered antibody sequence

<400> SEQUENCE: 32
caagtgctga cccagactgc atccccgtg tctgcagctg tgggaagcac agtcaccatc       60
aattgccagg ccagtcagag tgtttatgat aacaactacc tagcctggta tcagcagaaa    120
ccagggcagc tcccaagca actgatctat tctacatcca ctctggcatc tggggtctca    180
tcgcggttca aaggcagtgg atctgggaca cagttcactc tcaccatcag cgacctggag    240
tgtgccgatg ctgccactta ctactgtcta ggcagttatg attgtagtag tggtgattgt    300
tttgttttcg gcggagggac cgaggtggtg gtcaaacgt                            339

<210> SEQ ID NO 33
<211> LENGTH: 66
<212> TYPE: DNA
<213> ORGANISM: Artificial
<220> FEATURE:
<223> OTHER INFORMATION: Engineered antibody sequence

<400> SEQUENCE: 33
caagtgctga cccagactgc atccccgtg tctgcagctg tgggaagcac agtcaccatc       60
aattgc                                                                66

<210> SEQ ID NO 34
<211> LENGTH: 39
<212> TYPE: DNA

```
<213> ORGANISM: Artificial
<220> FEATURE:
<223> OTHER INFORMATION: Engineered antibody sequence

<400> SEQUENCE: 34
caggccagtc agagtgttta tgataacaac tacctagcc                      39

<210> SEQ ID NO 35
<211> LENGTH: 45
<212> TYPE: DNA
<213> ORGANISM: Artificial
<220> FEATURE:
<223> OTHER INFORMATION: Engineered antibody sequence

<400> SEQUENCE: 35
tggtatcagc agaaaccagg gcagcctccc aagcaactga tctat               45

<210> SEQ ID NO 36
<211> LENGTH: 21
<212> TYPE: DNA
<213> ORGANISM: Artificial
<220> FEATURE:
<223> OTHER INFORMATION: Engineered antibody sequence

<400> SEQUENCE: 36
tctacatcca ctctggcatc t                                         21

<210> SEQ ID NO 37
<211> LENGTH: 96
<212> TYPE: DNA
<213> ORGANISM: Artificial
<220> FEATURE:
<223> OTHER INFORMATION: Engineered antibody sequence

<400> SEQUENCE: 37
ggggtctcat cgcggttcaa aggcagtgga tctgggacac agttcactct caccatcagc   60
gacctggagt gtgccgatgc tgccacttac tactgt                         96

<210> SEQ ID NO 38
<211> LENGTH: 39
<212> TYPE: DNA
<213> ORGANISM: Artificial
<220> FEATURE:
<223> OTHER INFORMATION: Engineered antibody sequence

<400> SEQUENCE: 38
ctaggcagtt atgattgtag tagtggtgat tgttttgtt                      39

<210> SEQ ID NO 39
<211> LENGTH: 33
<212> TYPE: DNA
<213> ORGANISM: Artificial
<220> FEATURE:
<223> OTHER INFORMATION: Engineered antibody sequence

<400> SEQUENCE: 39
ttcggcggag ggaccgaggt ggtggtcaaa cgt                            33

<210> SEQ ID NO 40
<211> LENGTH: 321
<212> TYPE: DNA
<213> ORGANISM: Artificial
<220> FEATURE:
<223> OTHER INFORMATION: Engineered antibody sequence

<400> SEQUENCE: 40
```

```
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata cgccctcca atcgggtaac tcccaggaga gtgtcacaga gcaggacagc    180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                              321
```

```
<210> SEQ ID NO 41
<211> LENGTH: 441
<212> TYPE: PRT
<213> ORGANISM: Artificial
<220> FEATURE:
<223> OTHER INFORMATION: Engineered antibody sequence

<400> SEQUENCE: 41
```

```
Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ile Asn Asp Asn Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
            85                  90                  95

Arg Gly Asp Ile Trp Gly Gln Gly Thr Leu Val Thr Val Ser Ser Ala
        100                 105                 110

Ser Thr Lys Gly Pro Ser Val Phe Pro Leu Ala Pro Ser Ser Lys Ser
    115                 120                 125

Thr Ser Gly Gly Thr Ala Ala Leu Gly Cys Leu Val Lys Asp Tyr Phe
130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
            165                 170                 175

Ser Ser Val Val Thr Val Pro Ser Ser Ser Leu Gly Thr Gln Thr Tyr
        180                 185                 190

Ile Cys Asn Val Asn His Lys Pro Ser Asn Thr Lys Val Asp Lys Arg
    195                 200                 205

Val Glu Pro Lys Ser Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Lys Phe Asn Trp Tyr
        260                 265                 270

Val Asp Gly Val Glu Val His Asn Ala Lys Thr Lys Pro Arg Glu Glu
    275                 280                 285

Gln Tyr Ala Ser Thr Tyr Arg Val Val Ser Val Leu Thr Val Leu His
290                 295                 300
```

```
Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
            325                 330                 335

Pro Arg Glu Pro Gln Val Tyr Thr Leu Pro Pro Ser Arg Glu Glu Met
        340                 345                 350

Thr Lys Asn Gln Val Ser Leu Thr Cys Leu Val Lys Gly Phe Tyr Pro
    355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
            435                 440

<210> SEQ ID NO 42
<211> LENGTH: 111
<212> TYPE: PRT
<213> ORGANISM: Artificial
<220> FEATURE:
<223> OTHER INFORMATION: Engineered antibody sequence

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ile Asn Asp Asn Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110

<210> SEQ ID NO 43
<211> LENGTH: 30
<212> TYPE: PRT
<213> ORGANISM: Artificial
<220> FEATURE:
<223> OTHER INFORMATION: Engineered antibody sequence

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser
            20                  25                  30

<210> SEQ ID NO 44
<211> LENGTH: 5
<212> TYPE: PRT
```

<213> ORGANISM: Artificial
<220> FEATURE:
<223> OTHER INFORMATION: Engineered antibody sequence

<400> SEQUENCE: 44

Ser Tyr Tyr Met Gln
1               5

<210> SEQ ID NO 45
<211> LENGTH: 14
<212> TYPE: PRT
<213> ORGANISM: Artificial
<220> FEATURE:
<223> OTHER INFORMATION: Engineered antibody sequence

<400> SEQUENCE: 45

Trp Val Arg Gln Ala Pro Gly Lys Gly Leu Glu Trp Val Gly
1               5                   10

<210> SEQ ID NO 46
<211> LENGTH: 16
<212> TYPE: PRT
<213> ORGANISM: Artificial
<220> FEATURE:
<223> OTHER INFORMATION: Engineered antibody sequence

<400> SEQUENCE: 46

Val Ile Gly Ile Asn Asp Asn Thr Tyr Tyr Ala Ser Trp Ala Lys Gly
1               5                   10                  15

<210> SEQ ID NO 47
<211> LENGTH: 32
<212> TYPE: PRT
<213> ORGANISM: Artificial
<220> FEATURE:
<223> OTHER INFORMATION: Engineered antibody sequence

<400> SEQUENCE: 47

Arg Phe Thr Ile Ser Arg Asp Asn Ser Lys Thr Thr Val Tyr Leu Gln
1               5                   10                  15

Met Asn Ser Leu Arg Ala Glu Asp Thr Ala Val Tyr Phe Cys Ala Arg
            20                  25                  30

<210> SEQ ID NO 48
<211> LENGTH: 3
<212> TYPE: PRT
<213> ORGANISM: Artificial
<220> FEATURE:
<223> OTHER INFORMATION: Engineered antibody sequence

<400> SEQUENCE: 48

Gly Asp Ile
1

<210> SEQ ID NO 49
<211> LENGTH: 11
<212> TYPE: PRT
<213> ORGANISM: Artificial
<220> FEATURE:
<223> OTHER INFORMATION: Engineered antibody sequence

<400> SEQUENCE: 49

Trp Gly Gln Gly Thr Leu Val Thr Val Ser Ser
1               5                   10

<210> SEQ ID NO 50

<211> LENGTH: 330
<212> TYPE: PRT
<213> ORGANISM: Artificial
<220> FEATURE:
<223> OTHER INFORMATION: Engineered antibody sequence

<400> SEQUENCE: 50

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 51
<211> LENGTH: 1326
<212> TYPE: DNA
<213> ORGANISM: Artificial
<220> FEATURE:
<223> OTHER INFORMATION: Engineered antibody sequence

<400> SEQUENCE: 51

```
gaggtgcagc ttgtggagtc tgggggaggc ttggtccagc ctgggggtc cctgagactc      60
tcctgtgcag tctctggact cgacctcagt agctactaca tgcaatgggt ccgtcaggct    120
ccagggaagg ggctggagtg ggtcggagtc attggtatca atgataacac atactacgcg    180
agctgggcga aaggccgatt caccatctcc agagacaatt ccaagaccac ggtgtatctt    240
caaatgaaca gcctgagagc tgaggacact gctgtgtatt tctgtgctag aggggacatc    300
tggggccaag ggaccctcgt caccgtctcg agcgcctcca caagggccc atcggtcttc     360
cccctggcac cctcctccaa gagcacctct ggggcacag cggccctggg ctgcctggtc     420
aaggactact cccccgaacc ggtgacggtg tcgtggaact caggcgccct gaccagcggc    480
gtgcacacct tcccggctgt cctacagtcc tcaggactct actccctcag cagcgtggtg    540
accgtgccct ccagcagctt gggcacccag acctacatct gcaacgtgaa tcacaagccc    600
agcaacacca aggtggacaa gagagttgag cccaaatctt gtgacaaaac tcacacatgc    660
ccaccgtgcc cagcacctga actcctgggg ggaccgtcag tcttcctctt ccccccaaaa    720
cccaaggaca cctcatgat ctcccggacc cctgaggtca catgcgtggt ggtggacgtg     780
agccacgaag accctgaggt caagttcaac tggtacgtgg acggcgtgga ggtgcataat    840
gccaagacaa agccgcggga ggagcagtac gccagcacgt accgtgtggt cagcgtcctc    900
accgtcctgc accaggactg gctgaatggc aaggagtaca agtgcaaggt ctccaacaaa    960
gccctcccag cccccatcga gaaaaccatc tccaaagcca agggcagcc ccgagaacca    1020
caggtgtaca ccctgccccc atcccgggag gagatgacca gaaccaggt cagcctgacc    1080
tgcctggtca aaggcttcta tcccagcgac atcgccgtgg agtgggagag caatgggcag   1140
ccggagaaca actacaagac cacgcctccc gtgctggact ccgacggctc cttcttcctc   1200
tacagcaagc tcaccgtgga caagagcagg tggcagcagg ggaacgtctt ctcatgctcc   1260
gtgatgcatg aggctctgca caaccactac acgcagaaga gcctctcct gtctccgggt   1320
aaatga                                                                1326
```

<210> SEQ ID NO 52
<211> LENGTH: 333
<212> TYPE: DNA
<213> ORGANISM: Artificial
<220> FEATURE:
<223> OTHER INFORMATION: Engineered antibody sequence

<400> SEQUENCE: 52

```
gaggtgcagc ttgtggagtc tgggggaggc ttggtccagc ctgggggtc cctgagactc      60
tcctgtgcag tctctggact cgacctcagt agctactaca tgcaatgggt ccgtcaggct    120
ccagggaagg ggctggagtg ggtcggagtc attggtatca atgataacac atactacgcg    180
agctgggcga aaggccgatt caccatctcc agagacaatt ccaagaccac ggtgtatctt    240
caaatgaaca gcctgagagc tgaggacact gctgtgtatt tctgtgctag aggggacatc    300
tggggccaag ggaccctcgt caccgtctcg agc                                  333
```

<210> SEQ ID NO 53
<211> LENGTH: 90
<212> TYPE: DNA
<213> ORGANISM: Artificial
<220> FEATURE:
<223> OTHER INFORMATION: Engineered antibody sequence

<400> SEQUENCE: 53

```
gaggtgcagc ttgtggagtc tggggggaggc ttggtccagc ctgggggtc cctgagactc    60 tcctgtgcag tctctggact cgacctcagt                                     90
```

<210> SEQ ID NO 54
<211> LENGTH: 15
<212> TYPE: DNA
<213> ORGANISM: Artificial
<220> FEATURE:
<223> OTHER INFORMATION: Engineered antibody sequence

<400> SEQUENCE: 54

```
agctactaca tgcaa                                                     15
```

<210> SEQ ID NO 55
<211> LENGTH: 42
<212> TYPE: DNA
<213> ORGANISM: Artificial
<220> FEATURE:
<223> OTHER INFORMATION: Engineered antibody sequence

<400> SEQUENCE: 55

```
tgggtccgtc aggctccagg gaaggggctg gagtgggtcg ga                       42
```

<210> SEQ ID NO 56
<211> LENGTH: 48
<212> TYPE: DNA
<213> ORGANISM: Artificial
<220> FEATURE:
<223> OTHER INFORMATION: Engineered antibody sequence

<400> SEQUENCE: 56

```
gtcattggta tcaatgataa cacatactac gcgagctggg cgaaaggc                 48
```

<210> SEQ ID NO 57
<211> LENGTH: 96
<212> TYPE: DNA
<213> ORGANISM: Artificial
<220> FEATURE:
<223> OTHER INFORMATION: Engineered antibody sequence

<400> SEQUENCE: 57

```
cgattcacca tctccagaga caattccaag accacggtgt atcttcaaat gaacagcctg    60
agagctgagg acactgctgt gtatttctgt gctaga                              96
```

<210> SEQ ID NO 58
<211> LENGTH: 9
<212> TYPE: DNA
<213> ORGANISM: Artificial
<220> FEATURE:
<223> OTHER INFORMATION: Engineered antibody sequence

<400> SEQUENCE: 58

```
ggggacatc                                                            9
```

<210> SEQ ID NO 59
<211> LENGTH: 33
<212> TYPE: DNA
<213> ORGANISM: Artificial
<220> FEATURE:
<223> OTHER INFORMATION: Engineered antibody sequence

<400> SEQUENCE: 59

```
tggggccaag ggaccctcgt caccgtctcg agc                                 33
```

<210> SEQ ID NO 60
<211> LENGTH: 993
<212> TYPE: DNA
<213> ORGANISM: Artificial
<220> FEATURE:
<223> OTHER INFORMATION: Engineered antibody sequence

<400> SEQUENCE: 60

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacgcc     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggaggag      720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa tga                                  993
```

<210> SEQ ID NO 61
<211> LENGTH: 219
<212> TYPE: PRT
<213> ORGANISM: Artificial
<220> FEATURE:
<223> OTHER INFORMATION: Engineered antibody sequence

<400> SEQUENCE: 61

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asp Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Ser Gly Asp Cys Phe Val Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe 130                 135                 140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 62
<211> LENGTH: 113
<212> TYPE: PRT
<213> ORGANISM: Artificial
<220> FEATURE:
<223> OTHER INFORMATION: Engineered antibody sequence

<400> SEQUENCE: 62

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asp Asn Asn
                20                  25                  30

Tyr Leu Ala Trp Tyr Gln Gln Lys Pro Gly Lys Val Pro Lys Gln Leu
            35                  40                  45

Ile Tyr Ser Thr Ser Thr Leu Ala Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Ser Gly Asp Cys Phe Val Phe Gly Gly Gly Thr Lys Val Glu Ile Lys
                100                 105                 110

Arg

<210> SEQ ID NO 63
<211> LENGTH: 22
<212> TYPE: PRT
<213> ORGANISM: Artificial
<220> FEATURE:
<223> OTHER INFORMATION: Engineered antibody sequence

<400> SEQUENCE: 63

Gln Val Leu Thr Gln Ser Pro Ser Ser Leu Ser Ala Ser Val Gly Asp
1               5                   10                  15

Arg Val Thr Ile Asn Cys
                20

<210> SEQ ID NO 64
<211> LENGTH: 13
<212> TYPE: PRT
<213> ORGANISM: Artificial
<220> FEATURE:
<223> OTHER INFORMATION: Engineered antibody sequence

<400> SEQUENCE: 64

Gln Ala Ser Gln Ser Val Tyr Asp Asn Asn Tyr Leu Ala
1               5                   10

```
<210> SEQ ID NO 65
<211> LENGTH: 15
<212> TYPE: PRT
<213> ORGANISM: Artificial
<220> FEATURE:
<223> OTHER INFORMATION: Engineered antibody sequence

<400> SEQUENCE: 65

Trp Tyr Gln Gln Lys Pro Gly Lys Val Pro Lys Gln Leu Ile Tyr
1               5                   10                  15

<210> SEQ ID NO 66
<211> LENGTH: 7
<212> TYPE: PRT
<213> ORGANISM: Artificial
<220> FEATURE:
<223> OTHER INFORMATION: Engineered antibody sequence

<400> SEQUENCE: 66

Ser Thr Ser Thr Leu Ala Ser
1               5

<210> SEQ ID NO 67
<211> LENGTH: 32
<212> TYPE: PRT
<213> ORGANISM: Artificial
<220> FEATURE:
<223> OTHER INFORMATION: Engineered antibody sequence

<400> SEQUENCE: 67

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 68
<211> LENGTH: 13
<212> TYPE: PRT
<213> ORGANISM: Artificial
<220> FEATURE:
<223> OTHER INFORMATION: Engineered antibody sequence

<400> SEQUENCE: 68

Leu Gly Ser Tyr Asp Cys Ser Ser Gly Asp Cys Phe Val
1               5                   10

<210> SEQ ID NO 69
<211> LENGTH: 11
<212> TYPE: PRT
<213> ORGANISM: Artificial
<220> FEATURE:
<223> OTHER INFORMATION: Engineered antibody sequence

<400> SEQUENCE: 69

Phe Gly Gly Gly Thr Lys Val Glu Ile Lys Arg
1               5                   10

<210> SEQ ID NO 70
<211> LENGTH: 106
<212> TYPE: PRT
<213> ORGANISM: Artificial
<220> FEATURE:
<223> OTHER INFORMATION: Engineered antibody sequence

<400> SEQUENCE: 70

Thr Val Ala Ala Pro Ser Val Phe Ile Phe Pro Pro Ser Asp Glu Gln
```

```
                1               5                  10                 15
             Leu Lys Ser Gly Thr Ala Ser Val Val Cys Leu Leu Asn Asn Phe Tyr
                             20                 25                 30

Pro Arg Glu Ala Lys Val Gln Trp Lys Val Asp Asn Ala Leu Gln Ser
                             35                 40                 45

Gly Asn Ser Gln Glu Ser Val Thr Glu Gln Asp Ser Lys Asp Ser Thr
                 50                 55                 60

Tyr Ser Leu Ser Ser Thr Leu Thr Leu Ser Lys Ala Asp Tyr Glu Lys
             65                 70                 75                 80

His Lys Val Tyr Ala Cys Glu Val Thr His Gln Gly Leu Ser Ser Pro
                             85                 90                 95

Val Thr Lys Ser Phe Asn Arg Gly Glu Cys
                             100                105
```

<210> SEQ ID NO 71
<211> LENGTH: 660
<212> TYPE: DNA
<213> ORGANISM: Artificial
<220> FEATURE:
<223> OTHER INFORMATION: Engineered antibody sequence

<400> SEQUENCE: 71

| caagtgctga cccagtctcc atcctccctg tctgcatctg taggagacag agtcaccatc | 60 |
| aattgccagg ccagtcagag tgtttatgat aacaactacc tagcctggta tcagcagaaa | 120 |
| ccagggaaag ttcctaagca actgatctat tctacatcca ctctggcatc tggggtccca | 180 |
| tctcgtttca gtggcagtgg atctgggaca gatttcactc tcaccatcag cagcctgcag | 240 |
| cctgaagatg ttgcaactta ttactgtcta ggcagttatg attgtagtag tggtgattgt | 300 |
| tttgttttcg gcggaggaac caaggtggaa atcaaacgta cggtggctgc accatctgtc | 360 |
| ttcatcttcc cgccatctga tgagcagttg aaatctggaa ctgcctctgt tgtgtgcctg | 420 |
| ctgaataact tctatcccag agaggccaaa gtacagtgga aggtggataa cgccctccaa | 480 |
| tcgggtaact cccaggagag tgtcacagag caggacagca aggacagcac ctacagcctc | 540 |
| agcagcaccc tgacgctgag caaagcagac tacgagaaac acaaagtcta cgcctgcgaa | 600 |
| gtcacccatc agggcctgag ctcgcccgtc acaaagagct tcaacagggg agagtgttag | 660 |

<210> SEQ ID NO 72
<211> LENGTH: 339
<212> TYPE: DNA
<213> ORGANISM: Artificial
<220> FEATURE:
<223> OTHER INFORMATION: Engineered antibody sequence

<400> SEQUENCE: 72

| caagtgctga cccagtctcc atcctccctg tctgcatctg taggagacag agtcaccatc | 60 |
| aattgccagg ccagtcagag tgtttatgat aacaactacc tagcctggta tcagcagaaa | 120 |
| ccagggaaag ttcctaagca actgatctat tctacatcca ctctggcatc tggggtccca | 180 |
| tctcgtttca gtggcagtgg atctgggaca gatttcactc tcaccatcag cagcctgcag | 240 |
| cctgaagatg ttgcaactta ttactgtcta ggcagttatg attgtagtag tggtgattgt | 300 |
| tttgttttcg gcggaggaac caaggtggaa atcaaacgt | 339 |

<210> SEQ ID NO 73
<211> LENGTH: 66
<212> TYPE: DNA
<213> ORGANISM: Artificial

```
<220> FEATURE:
<223> OTHER INFORMATION: Engineered antibody sequence

<400> SEQUENCE: 73
caagtgctga cccagtctcc atcctccctg tctgcatctg taggagacag agtcaccatc    60
aattgc                                                              66

<210> SEQ ID NO 74
<211> LENGTH: 39
<212> TYPE: DNA
<213> ORGANISM: Artificial
<220> FEATURE:
<223> OTHER INFORMATION: Engineered antibody sequence

<400> SEQUENCE: 74
caggccagtc agagtgttta tgataacaac tacctagcc                           39

<210> SEQ ID NO 75
<211> LENGTH: 45
<212> TYPE: DNA
<213> ORGANISM: Artificial
<220> FEATURE:
<223> OTHER INFORMATION: Engineered antibody sequence

<400> SEQUENCE: 75
tggtatcagc agaaaccagg gaaagttcct aagcaactga tctat                    45

<210> SEQ ID NO 76
<211> LENGTH: 21
<212> TYPE: DNA
<213> ORGANISM: Artificial
<220> FEATURE:
<223> OTHER INFORMATION: Engineered antibody sequence

<400> SEQUENCE: 76
tctacatcca ctctggcatc t                                              21

<210> SEQ ID NO 77
<211> LENGTH: 96
<212> TYPE: DNA
<213> ORGANISM: Artificial
<220> FEATURE:
<223> OTHER INFORMATION: Engineered antibody sequence

<400> SEQUENCE: 77
ggggtcccat ctcgtttcag tggcagtgga tctgggacag atttcactct caccatcagc    60
agcctgcagc ctgaagatgt tgcaacttat tactgt                              96

<210> SEQ ID NO 78
<211> LENGTH: 39
<212> TYPE: DNA
<213> ORGANISM: Artificial
<220> FEATURE:
<223> OTHER INFORMATION: Engineered antibody sequence

<400> SEQUENCE: 78
ctaggcagtt atgattgtag tagtggtgat tgttttgtt                           39

<210> SEQ ID NO 79
<211> LENGTH: 33
<212> TYPE: DNA
<213> ORGANISM: Artificial
<220> FEATURE:
<223> OTHER INFORMATION: Engineered antibody sequence
```

<400> SEQUENCE: 79
ttcggcggag gaaccaaggt ggaaatcaaa cgt                                    33

<210> SEQ ID NO 80
<211> LENGTH: 321
<212> TYPE: DNA
<213> ORGANISM: Artificial
<220> FEATURE:
<223> OTHER INFORMATION: Engineered antibody sequence

<400> SEQUENCE: 80
acggtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgtta g                                               321

<210> SEQ ID NO 81
<211> LENGTH: 441
<212> TYPE: PRT
<213> ORGANISM: Artificial
<220> FEATURE:
<223> OTHER INFORMATION: Engineered antibody sequence

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ile Asn Asp Asn Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Ala Arg
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys

-continued

```
             225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
            275                 280                 285

Gln Tyr Ala Ser Thr Tyr Arg Val Val Ser Val Leu Thr Val Leu His
        290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 82
<211> LENGTH: 111
<212> TYPE: PRT
<213> ORGANISM: Artificial
<220> FEATURE:
<223> OTHER INFORMATION: Engineered antibody sequence

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ile Asn Asp Asn Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110

<210> SEQ ID NO 83
<211> LENGTH: 30
<212> TYPE: PRT
<213> ORGANISM: Artificial
<220> FEATURE:
<223> OTHER INFORMATION: Engineered antibody sequence
```

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser
            20                  25                  30

<210> SEQ ID NO 84
<211> LENGTH: 5
<212> TYPE: PRT
<213> ORGANISM: Artificial
<220> FEATURE:
<223> OTHER INFORMATION: Engineered antibody sequence

<400> SEQUENCE: 84

Ser Tyr Tyr Met Gln
1               5

<210> SEQ ID NO 85
<211> LENGTH: 14
<212> TYPE: PRT
<213> ORGANISM: Artificial
<220> FEATURE:
<223> OTHER INFORMATION: Engineered antibody sequence

<400> SEQUENCE: 85

Trp Val Arg Gln Ala Pro Gly Lys Gly Leu Glu Trp Val Gly
1               5                   10

<210> SEQ ID NO 86
<211> LENGTH: 16
<212> TYPE: PRT
<213> ORGANISM: Artificial
<220> FEATURE:
<223> OTHER INFORMATION: Engineered antibody sequence

<400> SEQUENCE: 86

Val Ile Gly Ile Asn Asp Asn Thr Tyr Tyr Ala Ser Trp Ala Lys Gly
1               5                   10                  15

<210> SEQ ID NO 87
<211> LENGTH: 32
<212> TYPE: PRT
<213> ORGANISM: Artificial
<220> FEATURE:
<223> OTHER INFORMATION: Engineered antibody sequence

<400> SEQUENCE: 87

Arg Phe Thr Ile Ser Arg Asp Asn Ser Lys Thr Thr Val Tyr Leu Gln
1               5                   10                  15

Met Asn Ser Leu Arg Ala Glu Asp Thr Ala Val Tyr Phe Cys Ala Arg
            20                  25                  30

<210> SEQ ID NO 88
<211> LENGTH: 3
<212> TYPE: PRT
<213> ORGANISM: Artificial
<220> FEATURE:
<223> OTHER INFORMATION: Engineered antibody sequence

<400> SEQUENCE: 88

Gly Asp Ile
1

<210> SEQ ID NO 89

```
<211> LENGTH: 11
<212> TYPE: PRT
<213> ORGANISM: Artificial
<220> FEATURE:
<223> OTHER INFORMATION: Engineered antibody sequence

<400> SEQUENCE: 89

Trp Gly Gln Gly Thr Leu Val Thr Val Ser Ser
1               5                   10

<210> SEQ ID NO 90
<211> LENGTH: 330
<212> TYPE: PRT
<213> ORGANISM: Artificial
<220> FEATURE:
<223> OTHER INFORMATION: Engineered antibody sequence

<400> SEQUENCE: 90

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

Gln Lys Ser Leu Ser Leu Ser Pro Gly Lys
  305         310         315         320
                325             330

<210> SEQ ID NO 91
<211> LENGTH: 1326
<212> TYPE: DNA
<213> ORGANISM: Artificial
<220> FEATURE:
<223> OTHER INFORMATION: Engineered antibody sequence

<400> SEQUENCE: 91

| | | | |
|---|---|---|---|
| gaggtgcagc ttgtggagtc tgggggaggc ttggtccagc ctgggggtc cctgagactc | | | 60 |
| tcctgtgcag tctctggact cgacctcagt agctactaca tgcaatgggt ccgtcaggct | | | 120 |
| ccagggaagg gctggagtg gtcggagtc attggtatca atgataacac atactacgcg | | | 180 |
| agctgggcga aaggccgatt caccatctcc agagacaatt ccaagaccac ggtgtatctt | | | 240 |
| caaatgaaca gcctgagagc tgaggacact gctgtgtatt tctgtgctag aggggacatc | | | 300 |
| tggggccaag ggaccctcgt caccgtctcg agcgcctcca caagggccc atcggtcttc | | | 360 |
| cccctggcac cctcctccaa gagcacctct ggggcacag cggccctggg ctgcctggtc | | | 420 |
| aaggactact ccccgaacc ggtgacggtg tcgtggaact caggcgccct gaccagcggc | | | 480 |
| gtgcacacct tcccggctgt cctacagtcc tcaggactct actccctcag cagcgtggtg | | | 540 |
| accgtgccct ccagcagctt gggcacccag acctacatct gcaacgtgaa tcacaagccc | | | 600 |
| agcaacacca aggtggacgc gagagttgag cccaaatctt gtgacaaaac tcacacatgc | | | 660 |
| ccaccgtgcc cagcacctga actcctgggg ggaccgtcag tcttcctctt ccccccaaaa | | | 720 |
| cccaaggaca ccctcatgat ctcccggacc cctgaggtca catgcgtggt ggtggacgtg | | | 780 |
| agccacgaag accctgaggt caagttcaac tggtacgtgg acggcgtgga ggtgcataat | | | 840 |
| gccaagacaa agccgcggga ggagcagtac gccagcacgt accgtgtggt cagcgtcctc | | | 900 |
| accgtcctgc accaggactg gctgaatggc aaggagtaca agtgcaaggt ctccaacaaa | | | 960 |
| gccctcccag cccccatcga gaaaaccatc tccaaagcca agggcagcc ccgagaacca | | | 1020 |
| caggtgtaca ccctgccccc atcccgggag gagatgacca agaaccaggt cagcctgacc | | | 1080 |
| tgcctggtca aaggcttcta tcccagcgac atcgccgtgg agtgggagag caatgggcag | | | 1140 |
| ccggagaaca actacaagac cacgcctccc gtgctggact ccgacggctc cttcttcctc | | | 1200 |
| tacagcaagc tcaccgtgga caagagcagg tggcagcagg ggaacgtctt ctcatgctcc | | | 1260 |
| gtgatgcatg aggctctgca caaccactac acgcagaaga gcctctccct gtctccgggt | | | 1320 |
| aaatga | | | 1326 |

<210> SEQ ID NO 92
<211> LENGTH: 333
<212> TYPE: DNA
<213> ORGANISM: Artificial
<220> FEATURE:
<223> OTHER INFORMATION: Engineered antibody sequence

<400> SEQUENCE: 92

| | | | |
|---|---|---|---|
| gaggtgcagc ttgtggagtc tgggggaggc ttggtccagc ctgggggtc cctgagactc | | | 60 |
| tcctgtgcag tctctggact cgacctcagt agctactaca tgcaatgggt ccgtcaggct | | | 120 |
| ccagggaagg gctggagtg gtcggagtc attggtatca atgataacac atactacgcg | | | 180 |
| agctgggcga aaggccgatt caccatctcc agagacaatt ccaagaccac ggtgtatctt | | | 240 |

```
caaatgaaca gcctgagagc tgaggacact gctgtgtatt tctgtgctag agggacatc      300 tggggccaag ggaccctcgt caccgtctcg agc                                 333
```

<210> SEQ ID NO 93
<211> LENGTH: 90
<212> TYPE: DNA
<213> ORGANISM: Artificial
<220> FEATURE:
<223> OTHER INFORMATION: Engineered antibody sequence

<400> SEQUENCE: 93

```
gaggtgcagc ttgtggagtc tgggggaggc ttggtccagc ctgggggtc cctgagactc      60 tcctgtgcag tctctggact cgacctcagt                                      90
```

<210> SEQ ID NO 94
<211> LENGTH: 15
<212> TYPE: DNA
<213> ORGANISM: Artificial
<220> FEATURE:
<223> OTHER INFORMATION: Engineered antibody sequence

<400> SEQUENCE: 94

```
agctactaca tgcaa                                                      15
```

<210> SEQ ID NO 95
<211> LENGTH: 42
<212> TYPE: DNA
<213> ORGANISM: Artificial
<220> FEATURE:
<223> OTHER INFORMATION: Engineered antibody sequence

<400> SEQUENCE: 95

```
tgggtccgtc aggctccagg gaaggggctg gagtgggtcg ga                        42
```

<210> SEQ ID NO 96
<211> LENGTH: 48
<212> TYPE: DNA
<213> ORGANISM: Artificial
<220> FEATURE:
<223> OTHER INFORMATION: Engineered antibody sequence

<400> SEQUENCE: 96

```
gtcattggta tcaatgataa cacatactac gcgagctggg cgaaaggc                  48
```

<210> SEQ ID NO 97
<211> LENGTH: 96
<212> TYPE: DNA
<213> ORGANISM: Artificial
<220> FEATURE:
<223> OTHER INFORMATION: Engineered antibody sequence

<400> SEQUENCE: 97

```
cgattcacca tctccagaga caattccaag accacggtgt atcttcaaat gaacagcctg      60
agagctgagg acactgctgt gtatttctgt gctaga                               96
```

<210> SEQ ID NO 98
<211> LENGTH: 9
<212> TYPE: DNA
<213> ORGANISM: Artificial
<220> FEATURE:
<223> OTHER INFORMATION: Engineered antibody sequence

<400> SEQUENCE: 98

```
ggggacatc                                                             9
```

<210> SEQ ID NO 99
<211> LENGTH: 33
<212> TYPE: DNA
<213> ORGANISM: Artificial
<220> FEATURE:
<223> OTHER INFORMATION: Engineered antibody sequence

<400> SEQUENCE: 99
tggggccaag ggaccctcgt caccgtctcg agc                                33

<210> SEQ ID NO 100
<211> LENGTH: 993
<212> TYPE: DNA
<213> ORGANISM: Artificial
<220> FEATURE:
<223> OTHER INFORMATION: Engineered antibody sequence

<400> SEQUENCE: 100
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacgcgag agttgagccc   300
aaatcttgtg acaaaactca cacatgccca ccgtgcccag cacctgaact cctggggggga   360
ccgtcagtct tcctcttccc cccaaaaccc aaggacaccc tcatgatctc ccggaccccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacgcc   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa tga                                993

<210> SEQ ID NO 101
<211> LENGTH: 219
<212> TYPE: PRT
<213> ORGANISM: Artificial
<220> FEATURE:
<223> OTHER INFORMATION: Engineered antibody sequence

<400> SEQUENCE: 101

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asp Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

```
Gly Ser Gly Ser Gly Thr Asp Phe Thr Leu Thr Ile Ser Ser Leu Gln
 65                  70                  75                  80

Pro Glu Asp Val Ala Thr Tyr Tyr Cys Leu Gly Ser Tyr Asp Cys Ser
                 85                  90                  95

Ser Gly Asp Cys Phe Val Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 102
<211> LENGTH: 113
<212> TYPE: PRT
<213> ORGANISM: Artificial
<220> FEATURE:
<223> OTHER INFORMATION: Engineered antibody sequence

<400> SEQUENCE: 102

```
Gln Val Leu Thr Gln Ser Pro Ser Ser Leu Ser Ala Ser Val Gly Asp
 1               5                  10                  15

Arg Val Thr Ile Asn Cys Gln Ala Ser Gln Ser Val Tyr Asp Asn Asn
             20                  25                  30

Tyr Leu Ala Trp Tyr Gln Gln Lys Pro Gly Lys Val Pro Lys Gln Leu
         35                  40                  45

Ile Tyr Ser Thr Ser Thr Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Val Ala Thr Tyr Tyr Cys Leu Gly Ser Tyr Asp Cys Ser
                 85                  90                  95

Ser Gly Asp Cys Phe Val Phe Gly Gly Gly Thr Lys Val Glu Ile Lys
            100                 105                 110

Arg
```

<210> SEQ ID NO 103
<211> LENGTH: 22
<212> TYPE: PRT
<213> ORGANISM: Artificial
<220> FEATURE:
<223> OTHER INFORMATION: Engineered antibody sequence

<400> SEQUENCE: 103

```
Gln Val Leu Thr Gln Ser Pro Ser Ser Leu Ser Ala Ser Val Gly Asp
 1               5                  10                  15

Arg Val Thr Ile Asn Cys
             20
```

<210> SEQ ID NO 104
<211> LENGTH: 13
<212> TYPE: PRT
<213> ORGANISM: Artificial
<220> FEATURE:
<223> OTHER INFORMATION: Engineered antibody sequence

<400> SEQUENCE: 104

Gln Ala Ser Gln Ser Val Tyr Asp Asn Asn Tyr Leu Ala
1               5                   10

<210> SEQ ID NO 105
<211> LENGTH: 15
<212> TYPE: PRT
<213> ORGANISM: Artificial
<220> FEATURE:
<223> OTHER INFORMATION: Engineered antibody sequence

<400> SEQUENCE: 105

Trp Tyr Gln Gln Lys Pro Gly Lys Val Pro Lys Gln Leu Ile Tyr
1               5                   10                  15

<210> SEQ ID NO 106
<211> LENGTH: 7
<212> TYPE: PRT
<213> ORGANISM: Artificial
<220> FEATURE:
<223> OTHER INFORMATION: Engineered antibody sequence

<400> SEQUENCE: 106

Ser Thr Ser Thr Leu Ala Ser
1               5

<210> SEQ ID NO 107
<211> LENGTH: 32
<212> TYPE: PRT
<213> ORGANISM: Artificial
<220> FEATURE:
<223> OTHER INFORMATION: Engineered antibody sequence

<400> SEQUENCE: 107

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 108
<211> LENGTH: 13
<212> TYPE: PRT
<213> ORGANISM: Artificial
<220> FEATURE:
<223> OTHER INFORMATION: Engineered antibody sequence

<400> SEQUENCE: 108

Leu Gly Ser Tyr Asp Cys Ser Ser Gly Asp Cys Phe Val
1               5                   10

<210> SEQ ID NO 109
<211> LENGTH: 11
<212> TYPE: PRT
<213> ORGANISM: Artificial
<220> FEATURE:
<223> OTHER INFORMATION: Engineered antibody sequence

<400> SEQUENCE: 109

Phe Gly Gly Gly Thr Lys Val Glu Ile Lys Arg

```
<210> SEQ ID NO 110
<211> LENGTH: 106
<212> TYPE: PRT
<213> ORGANISM: Artificial
<220> FEATURE:
<223> OTHER INFORMATION: Engineered antibody sequence

<400> SEQUENCE: 110

Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105

<210> SEQ ID NO 111
<211> LENGTH: 660
<212> TYPE: DNA
<213> ORGANISM: Artificial
<220> FEATURE:
<223> OTHER INFORMATION: Engineered antibody sequence

<400> SEQUENCE: 111
caagtgctga cccagtctcc atcctccctg tctgcatctg taggagacag agtcaccatc     60
aattgccagg ccagtcagag tgtttatgat aacaactacc tagcctggta tcagcagaaa    120
ccagggaaag ttcctaagca actgatctat tctacatcca ctctggcatc tggggtccca    180
tctcgtttca gtggcagtgg atctgggaca gatttcactc tcaccatcag cagcctgcag    240
cctgaagatg ttgcaactta ttactgtcta ggcagttatg attgtagtag tggtgattgt    300
tttgttttcg gcggaggaac caaggtggaa atcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660

<210> SEQ ID NO 112
<211> LENGTH: 339
<212> TYPE: DNA
<213> ORGANISM: Artificial
<220> FEATURE:
<223> OTHER INFORMATION: Engineered antibody sequence

<400> SEQUENCE: 112
caagtgctga cccagtctcc atcctccctg tctgcatctg taggagacag agtcaccatc     60
aattgccagg ccagtcagag tgtttatgat aacaactacc tagcctggta tcagcagaaa    120
```

```
ccagggaaag ttcctaagca actgatctat tctacatcca ctctggcatc tggggtccca    180
tctcgtttca gtggcagtgg atctgggaca gatttcactc tcaccatcag cagcctgcag    240
cctgaagatg ttgcaactta ttactgtcta ggcagttatg attgtagtag tggtgattgt    300
tttgttttcg gcggaggaac caaggtggaa atcaaacgt                           339
```

<210> SEQ ID NO 113
<211> LENGTH: 66
<212> TYPE: DNA
<213> ORGANISM: Artificial
<220> FEATURE:
<223> OTHER INFORMATION: Engineered antibody sequence

<400> SEQUENCE: 113

```
caagtgctga cccagtctcc atcctccctg tctgcatctg taggagacag agtcaccatc    60
aattgc                                                               66
```

<210> SEQ ID NO 114
<211> LENGTH: 39
<212> TYPE: DNA
<213> ORGANISM: Artificial
<220> FEATURE:
<223> OTHER INFORMATION: Engineered antibody sequence

<400> SEQUENCE: 114

```
caggccagtc agagtgttta tgataacaac tacctagcc                           39
```

<210> SEQ ID NO 115
<211> LENGTH: 45
<212> TYPE: DNA
<213> ORGANISM: Artificial
<220> FEATURE:
<223> OTHER INFORMATION: Engineered antibody sequence

<400> SEQUENCE: 115

```
tggtatcagc agaaaccagg gaaagttcct aagcaactga tctat                    45
```

<210> SEQ ID NO 116
<211> LENGTH: 21
<212> TYPE: DNA
<213> ORGANISM: Artificial
<220> FEATURE:
<223> OTHER INFORMATION: Engineered antibody sequence

<400> SEQUENCE: 116

```
tctacatcca ctctggcatc t                                              21
```

<210> SEQ ID NO 117
<211> LENGTH: 96
<212> TYPE: DNA
<213> ORGANISM: Artificial
<220> FEATURE:
<223> OTHER INFORMATION: Engineered antibody sequence

<400> SEQUENCE: 117

```
ggggtcccat ctcgtttcag tggcagtgga tctgggacag atttcactct caccatcagc    60
agcctgcagc ctgaagatgt tgcaacttat tactgt                              96
```

<210> SEQ ID NO 118
<211> LENGTH: 39
<212> TYPE: DNA
<213> ORGANISM: Artificial
<220> FEATURE:
<223> OTHER INFORMATION: Engineered antibody sequence

<400> SEQUENCE: 118
ctaggcagtt atgattgtag tagtggtgat tgttttgtt                                    39

<210> SEQ ID NO 119
<211> LENGTH: 33
<212> TYPE: DNA
<213> ORGANISM: Artificial
<220> FEATURE:
<223> OTHER INFORMATION: Engineered antibody sequence

<400> SEQUENCE: 119
ttcggcggag gaaccaaggt ggaaatcaaa cgt                                           33

<210> SEQ ID NO 120
<211> LENGTH: 321
<212> TYPE: DNA
<213> ORGANISM: Artificial
<220> FEATURE:
<223> OTHER INFORMATION: Engineered antibody sequence

<400> SEQUENCE: 120
acggtggctg caccatctgt cttcatcttc ccgccatctg atgagcagtt gaaatctgga            60
actgcctctg ttgtgtgcct gctgaataac ttctatccca gagaggccaa agtacagtgg           120
aaggtggata acgccctcca atcgggtaac tcccaggaga gtgtcacaga gcaggacagc           180
aaggacagca cctacagcct cagcagcacc ctgacgctga gcaaagcaga ctacgagaaa           240
cacaaagtct acgcctgcga agtcacccat cagggcctga gctcgcccgt cacaaagagc           300
ttcaacaggg gagagtgtta g                                                     321

<210> SEQ ID NO 121
<211> LENGTH: 439
<212> TYPE: PRT
<213> ORGANISM: Artificial
<220> FEATURE:
<223> OTHER INFORMATION: Engineered antibody sequence

<400> SEQUENCE: 121

Gln Ser Leu Glu Glu Ser Gly Gly Arg Leu Val Thr Pro Gly Thr Pro
1               5                   10                  15

Leu Thr Leu Thr Cys Ser Val Ser Gly Ile Asp Leu Ser Gly Tyr Tyr
            20                  25                  30

Met Asn Trp Val Arg Gln Ala Pro Gly Lys Gly Leu Glu Trp Ile Gly
        35                  40                  45

Val Ile Gly Ile Asn Gly Ala Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Asp Ile Trp Gly Pro Gly Thr Leu Val Thr Val Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

```
Thr Phe Pro Ala Val Leu Gln Ser Ser Gly Leu Tyr Ser Leu Ser Ser
                165                 170                 175

Val Val Thr Val Pro Ser Ser Leu Gly Thr Gln Thr Tyr Ile Cys
            180                 185                 190

Asn Val Asn His Lys Pro Ser Asn Thr Lys Val Asp Lys Arg Val Glu
            195                 200                 205

Pro Lys Ser Cys Asp Lys Thr His Thr Cys Pro Pro Cys Pro Ala Pro
            210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
            245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
            275                 280                 285

Ala Ser Thr Tyr Arg Val Val Ser Val Leu Thr Val Leu His Gln Asp
            290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
            325                 330                 335

Glu Pro Gln Val Tyr Thr Leu Pro Pro Ser Arg Glu Glu Met Thr Lys
            340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
            370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
            405                 410                 415

Cys Ser Val Met His Glu Ala Leu His Asn His Tyr Thr Gln Lys Ser
            420                 425                 430

Leu Ser Leu Ser Pro Gly Lys
            435

<210> SEQ ID NO 122
<211> LENGTH: 109
<212> TYPE: PRT
<213> ORGANISM: Artificial
<220> FEATURE:
<223> OTHER INFORMATION: Engineered antibody sequence

<400> SEQUENCE: 122

Gln Ser Leu Glu Glu Ser Gly Gly Arg Leu Val Thr Pro Gly Thr Pro
1               5                   10                  15

Leu Thr Leu Thr Cys Ser Val Ser Gly Ile Asp Leu Ser Gly Tyr Tyr
            20                  25                  30

Met Asn Trp Val Arg Gln Ala Pro Gly Lys Gly Leu Glu Trp Ile Gly
            35                  40                  45

Val Ile Gly Ile Asn Gly Ala Thr Tyr Tyr Ala Ser Trp Ala Lys Gly
            50                  55                  60

Arg Phe Thr Ile Ser Lys Thr Ser Thr Thr Val Asp Leu Lys Met
65                  70                  75                  80
```

```
Thr Ser Leu Thr Thr Glu Asp Thr Ala Thr Tyr Phe Cys Ala Arg Gly
                85                  90                  95
Asp Ile Trp Gly Pro Gly Thr Leu Val Thr Val Ser Ser
            100                 105
```

<210> SEQ ID NO 123
<211> LENGTH: 29
<212> TYPE: PRT
<213> ORGANISM: Artificial
<220> FEATURE:
<223> OTHER INFORMATION: Engineered antibody sequence

<400> SEQUENCE: 123

```
Gln Ser Leu Glu Glu Ser Gly Gly Arg Leu Val Thr Pro Gly Thr Pro
1               5                   10                  15
Leu Thr Leu Thr Cys Ser Val Ser Gly Ile Asp Leu Ser
            20                  25
```

<210> SEQ ID NO 124
<211> LENGTH: 5
<212> TYPE: PRT
<213> ORGANISM: Artificial
<220> FEATURE:
<223> OTHER INFORMATION: Engineered antibody sequence

<400> SEQUENCE: 124

```
Gly Tyr Tyr Met Asn
1               5
```

<210> SEQ ID NO 125
<211> LENGTH: 14
<212> TYPE: PRT
<213> ORGANISM: Artificial
<220> FEATURE:
<223> OTHER INFORMATION: Engineered antibody sequence

<400> SEQUENCE: 125

```
Trp Val Arg Gln Ala Pro Gly Lys Gly Leu Glu Trp Ile Gly
1               5                   10
```

<210> SEQ ID NO 126
<211> LENGTH: 16
<212> TYPE: PRT
<213> ORGANISM: Artificial
<220> FEATURE:
<223> OTHER INFORMATION: Engineered antibody sequence

<400> SEQUENCE: 126

```
Val Ile Gly Ile Asn Gly Ala Thr Tyr Tyr Ala Ser Trp Ala Lys Gly
1               5                   10                  15
```

<210> SEQ ID NO 127
<211> LENGTH: 31
<212> TYPE: PRT
<213> ORGANISM: Artificial
<220> FEATURE:
<223> OTHER INFORMATION: Engineered antibody sequence

<400> SEQUENCE: 127

```
Arg Phe Thr Ile Ser Lys Thr Ser Ser Thr Thr Val Asp Leu Lys Met
1               5                   10                  15
Thr Ser Leu Thr Thr Glu Asp Thr Ala Thr Tyr Phe Cys Ala Arg
            20                  25                  30
```

<210> SEQ ID NO 128

```
<211> LENGTH: 3
<212> TYPE: PRT
<213> ORGANISM: Artificial
<220> FEATURE:
<223> OTHER INFORMATION: Engineered antibody sequence

<400> SEQUENCE: 128

Gly Asp Ile
1

<210> SEQ ID NO 129
<211> LENGTH: 11
<212> TYPE: PRT
<213> ORGANISM: Artificial
<220> FEATURE:
<223> OTHER INFORMATION: Engineered antibody sequence

<400> SEQUENCE: 129

Trp Gly Pro Gly Thr Leu Val Thr Val Ser Ser
1               5                   10

<210> SEQ ID NO 130
<211> LENGTH: 330
<212> TYPE: PRT
<213> ORGANISM: Artificial
<220> FEATURE:
<223> OTHER INFORMATION: Engineered antibody sequence

<400> SEQUENCE: 130

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 131
<211> LENGTH: 1320
<212> TYPE: DNA
<213> ORGANISM: Artificial
<220> FEATURE:
<223> OTHER INFORMATION: Engineered antibody sequence

<400> SEQUENCE: 131

| | |
|---|---|
| cagtcgctgg aggagtccgg gggtcgcctg gtcacgcctg gacacccct gacactcacc | 60 |
| tgttccgtct ctggcatcga cctcagtggc tactacatga actgggtccg ccaggctcca | 120 |
| gggaaggggc tggaatggat cggagtcatt ggtattaatg gtgccacata ctacgcgagc | 180 |
| tgggcgaaag gccgattcac catctccaaa acctcgtcga ccacggtgga tctgaaaatg | 240 |
| accagtctga aaccgaggga cacggccacc tatttctgtg ccagagggga catctggggc | 300 |
| ccgggcaccc tcgtcaccgt ctcgagcgcc tccaccaagg gcccatcggt cttccccctg | 360 |
| gcaccctcct ccaagagcac ctctgggggc acagcggccc tgggctgcct ggtcaaggac | 420 |
| tacttccccg aaccggtgac ggtgtcgtgg aactcaggcg ccctgaccag cggcgtgcac | 480 |
| accttcccgg ctgtcctaca gtcctcagga ctctactccc tcagcagcgt ggtgaccgtg | 540 |
| ccctccagca gcttgggcac ccagacctac atctgcaacg tgaatcacaa gcccagcaac | 600 |
| accaaggtgg acaagagagt tgagcccaaa tcttgtgaca aaactcacac atgcccaccg | 660 |
| tgcccagcac ctgaactcct ggggggaccg tcagtcttcc tcttcccccc aaaacccaag | 720 |
| gacaccctca tgatctcccg gacccctgag gtcacatgcg tggtggtgga cgtgagccac | 780 |
| gaagaccctg aggtcaagtt caactggtac gtggacggcg tggaggtgca taatgccaag | 840 |
| acaaagccgc gggaggagca gtacgccagc acgtaccgtg tggtcagcgt cctcaccgtc | 900 |
| ctgcaccagg actggctgaa tggcaaggag tacaagtgca aggtctccaa caaagccctc | 960 |
| ccagccccca tcgagaaaac catctccaaa gccaaagggc agccccgaga accacaggtg | 1020 |
| tacaccctgc ccccatcccg ggaggagatg accaagaacc aggtcagcct gacctgcctg | 1080 |
| gtcaaaggct tctatcccag cgacatcgcc gtggagtggg agagcaatgg gcagccggag | 1140 |
| aacaactaca agaccacgcc tcccgtgctg gactccgacg gctccttctt cctctacagc | 1200 |
| aagctcaccg tggacaagag caggtggcag caggggaacg tcttctcatg ctccgtgatg | 1260 |
| catgaggctc tgcacaacca ctacacgcag aagagcctct ccctgtctcc gggtaaatga | 1320 |

<210> SEQ ID NO 132
<211> LENGTH: 327
<212> TYPE: DNA
<213> ORGANISM: Artificial
<220> FEATURE:
<223> OTHER INFORMATION: Engineered antibody sequence

<400> SEQUENCE: 132

```
cagtcgctgg aggagtccgg gggtcgcctg gtcacgcctg ggacacccct gacactcacc      60
tgttccgtct ctggcatcga cctcagtggc tactacatga actgggtccg ccaggctcca     120
gggaaggggc tggaatggat cggagtcatt ggtattaatg gtgccacata ctacgcgagc     180
tgggcgaaag gccgattcac catctccaaa acctcgtcga ccacggtgga tctgaaaatg     240
accagtctga caaccgagga cacggccacc tatttctgtg ccagagggga catctggggc     300
ccgggcaccc tcgtcaccgt ctcgagc                                         327
```

<210> SEQ ID NO 133
<211> LENGTH: 87
<212> TYPE: DNA
<213> ORGANISM: Artificial
<220> FEATURE:
<223> OTHER INFORMATION: Engineered antibody sequence

<400> SEQUENCE: 133

```
cagtcgctgg aggagtccgg gggtcgcctg gtcacgcctg ggacacccct gacactcacc      60
tgttccgtct ctggcatcga cctcagt                                          87
```

<210> SEQ ID NO 134
<211> LENGTH: 15
<212> TYPE: DNA
<213> ORGANISM: Artificial
<220> FEATURE:
<223> OTHER INFORMATION: Engineered antibody sequence

<400> SEQUENCE: 134

```
ggctactaca tgaac                                                       15
```

<210> SEQ ID NO 135
<211> LENGTH: 42
<212> TYPE: DNA
<213> ORGANISM: Artificial
<220> FEATURE:
<223> OTHER INFORMATION: Engineered antibody sequence

<400> SEQUENCE: 135

```
tgggtccgcc aggctccagg gaaggggctg gaatggatcg ga                         42
```

<210> SEQ ID NO 136
<211> LENGTH: 48
<212> TYPE: DNA
<213> ORGANISM: Artificial
<220> FEATURE:
<223> OTHER INFORMATION: Engineered antibody sequence

<400> SEQUENCE: 136

```
gtcattggta ttaatggtgc cacatactac gcgagctggg cgaaaggc                   48
```

<210> SEQ ID NO 137
<211> LENGTH: 93
<212> TYPE: DNA
<213> ORGANISM: Artificial
<220> FEATURE:
<223> OTHER INFORMATION: Engineered antibody sequence

<400> SEQUENCE: 137

```
cgattcacca tctccaaaac ctcgtcgacc acggtggatc tgaaaatgac cagtctgaca      60
accgaggaca cggccaccta tttctgtgcc aga                                   93
```

<210> SEQ ID NO 138
<211> LENGTH: 9
<212> TYPE: DNA
<213> ORGANISM: Artificial
<220> FEATURE:
<223> OTHER INFORMATION: Engineered antibody sequence

<400> SEQUENCE: 138 ggggacatc                                                                9

<210> SEQ ID NO 139
<211> LENGTH: 33
<212> TYPE: DNA
<213> ORGANISM: Artificial
<220> FEATURE:
<223> OTHER INFORMATION: Engineered antibody sequence

<400> SEQUENCE: 139
tggggcccgg gcaccctcgt caccgtctcg agc                                     33

<210> SEQ ID NO 140
<211> LENGTH: 993
<212> TYPE: DNA
<213> ORGANISM: Artificial
<220> FEATURE:
<223> OTHER INFORMATION: Engineered antibody sequence

<400> SEQUENCE: 140
gcctccacca agggcccatc ggtcttcccc ctggcaccct cctccaagag cacctctggg        60
ggcacagcgg ccctgggctg cctggtcaag gactacttcc ccgaaccggt gacggtgtcg       120
tggaactcag gcgccctgac cagcggcgtg cacaccttcc cggctgtcct acagtcctca       180
ggactctact ccctcagcag cgtggtgacc gtgccctcca gcagcttggg cacccagacc       240
tacatctgca acgtgaatca caagcccagc aacaccaagg tggacaagag agttgagccc       300
aaatcttgtg acaaaactca cacatgccca ccgtgcccag cacctgaact cctgggggga       360
ccgtcagtct tcctcttccc cccaaaaccc aaggacaccc tcatgatctc ccggacccct       420
gaggtcacat gcgtggtggt ggacgtgagc cacgaagacc ctgaggtcaa gttcaactgg       480
tacgtggacg gcgtggaggt gcataatgcc aagacaaagc cgcgggagga gcagtacgcc       540
agcacgtacc gtgtggtcag cgtcctcacc gtcctgcacc aggactggct gaatggcaag       600
gagtacaagt gcaaggtctc caacaaagcc ctcccagccc catcgagaa aaccatctcc       660
aaagccaaag ggcagccccg agaaccacag gtgtacaccc tgcccccatc ccgggaggag       720
atgaccaaga accaggtcag cctgacctgc ctggtcaaag gcttctatcc cagcgacatc       780
gccgtggagt gggagagcaa tgggcagccg gagaacaact acaagaccac gcctcccgtg       840
ctggactccg acggctcctt cttcctctac agcaagctca ccgtggacaa gagcaggtgg       900
cagcagggga acgtcttctc atgctccgtg atgcatgagg ctctgcacaa ccactacacg       960
cagaagagcc tctccctgtc tccgggtaaa tga                                    993

<210> SEQ ID NO 141
<211> LENGTH: 219
<212> TYPE: PRT
<213> ORGANISM: Artificial
<220> FEATURE:
<223> OTHER INFORMATION: Engineered antibody sequence

<400> SEQUENCE: 141

Gln Val Leu Thr Gln Thr Pro Ser Pro Val Ser Ala Ala Val Gly Ser

```
1               5                   10                  15
Thr Val Thr Ile Asn Cys Gln Ala Ser Gln Ser Val Tyr His Asn Thr
                20                  25                  30
Tyr Leu Ala Trp Tyr Gln Gln Lys Pro Gly Gln Pro Pro Lys Gln Leu
                35                  40                  45
Ile Tyr Asp Ala Ser Thr Leu Ala Ser Gly Val Pro Ser Arg Phe Ser
        50                  55                  60
Gly Ser Gly Ser Gly Thr Gln Phe Thr Leu Thr Ile Ser Gly Val Gln
65                  70                  75                  80
Cys Asn Asp Ala Ala Ala Tyr Tyr Cys Leu Gly Ser Tyr Asp Cys Thr
                85                  90                  95
Asn Gly Asp Cys Phe Val Phe Gly Gly Gly Thr Glu Val Val Val Lys
                100                 105                 110
Arg Thr Val Ala Ala Pro Ser Val Phe Ile Phe Pro Pro Ser Asp Glu
                115                 120                 125
Gln Leu Lys Ser Gly Thr Ala Ser Val Val Cys Leu Leu Asn Asn Phe
            130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
            195                 200                 205
Pro Val Thr Lys Ser Phe Asn Arg Gly Glu Cys
            210                 215

<210> SEQ ID NO 142
<211> LENGTH: 113
<212> TYPE: PRT
<213> ORGANISM: Artificial
<220> FEATURE:
<223> OTHER INFORMATION: Engineered antibody sequence

<400> SEQUENCE: 142

Gln Val Leu Thr Gln Thr Pro Ser Pro Val Ser Ala Ala Val Gly Ser
1               5                   10                  15
Thr Val Thr Ile Asn Cys Gln Ala Ser Gln Ser Val Tyr His Asn Thr
                20                  25                  30
Tyr Leu Ala Trp Tyr Gln Gln Lys Pro Gly Gln Pro Pro Lys Gln Leu
                35                  40                  45
Ile Tyr Asp Ala Ser Thr Leu Ala Ser Gly Val Pro Ser Arg Phe Ser
        50                  55                  60
Gly Ser Gly Ser Gly Thr Gln Phe Thr Leu Thr Ile Ser Gly Val Gln
65                  70                  75                  80
Cys Asn Asp Ala Ala Ala Tyr Tyr Cys Leu Gly Ser Tyr Asp Cys Thr
                85                  90                  95
Asn Gly Asp Cys Phe Val Phe Gly Gly Gly Thr Glu Val Val Val Lys
                100                 105                 110
Arg

<210> SEQ ID NO 143
<211> LENGTH: 22
<212> TYPE: PRT
<213> ORGANISM: Artificial
```

```
<220> FEATURE:
<223> OTHER INFORMATION: Engineered antibody sequence

<400> SEQUENCE: 143

Gln Val Leu Thr Gln Thr Pro Ser Pro Val Ser Ala Ala Val Gly Ser
1               5                   10                  15

Thr Val Thr Ile Asn Cys
            20

<210> SEQ ID NO 144
<211> LENGTH: 13
<212> TYPE: PRT
<213> ORGANISM: Artificial
<220> FEATURE:
<223> OTHER INFORMATION: Engineered antibody sequence

<400> SEQUENCE: 144

Gln Ala Ser Gln Ser Val Tyr His Asn Thr Tyr Leu Ala
1               5                   10

<210> SEQ ID NO 145
<211> LENGTH: 15
<212> TYPE: PRT
<213> ORGANISM: Artificial
<220> FEATURE:
<223> OTHER INFORMATION: Engineered antibody sequence

<400> SEQUENCE: 145

Trp Tyr Gln Gln Lys Pro Gly Gln Pro Pro Lys Gln Leu Ile Tyr
1               5                   10                  15

<210> SEQ ID NO 146
<211> LENGTH: 7
<212> TYPE: PRT
<213> ORGANISM: Artificial
<220> FEATURE:
<223> OTHER INFORMATION: Engineered antibody sequence

<400> SEQUENCE: 146

Asp Ala Ser Thr Leu Ala Ser
1               5

<210> SEQ ID NO 147
<211> LENGTH: 32
<212> TYPE: PRT
<213> ORGANISM: Artificial
<220> FEATURE:
<223> OTHER INFORMATION: Engineered antibody sequence

<400> SEQUENCE: 147

Gly Val Pro Ser Arg Phe Ser Gly Ser Gly Ser Gly Thr Gln Phe Thr
1               5                   10                  15

Leu Thr Ile Ser Gly Val Gln Cys Asn Asp Ala Ala Ala Tyr Tyr Cys
            20                  25                  30

<210> SEQ ID NO 148
<211> LENGTH: 13
<212> TYPE: PRT
<213> ORGANISM: Artificial
<220> FEATURE:
<223> OTHER INFORMATION: Engineered antibody sequence

<400> SEQUENCE: 148

Leu Gly Ser Tyr Asp Cys Thr Asn Gly Asp Cys Phe Val
1               5                   10
```

<210> SEQ ID NO 149
<211> LENGTH: 11
<212> TYPE: PRT
<213> ORGANISM: Artificial
<220> FEATURE:
<223> OTHER INFORMATION: Engineered antibody sequence

<400> SEQUENCE: 149

Phe Gly Gly Gly Thr Glu Val Val Val Lys Arg
1               5                   10

<210> SEQ ID NO 150
<211> LENGTH: 106
<212> TYPE: PRT
<213> ORGANISM: Artificial
<220> FEATURE:
<223> OTHER INFORMATION: Engineered antibody sequence

<400> SEQUENCE: 150

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 151
<211> LENGTH: 660
<212> TYPE: DNA
<213> ORGANISM: Artificial
<220> FEATURE:
<223> OTHER INFORMATION: Engineered antibody sequence

<400> SEQUENCE: 151
caagtgctga cccagactcc atccccgtg tctgcagctg tgggaagcac agtcaccatc    60
aattgccagg ccagtcagag tgtttatcat aacacctacc tggcctggta tcagcagaaa   120
ccagggcagc ctcccaaaca actgatctat gatgcatcca ctctggcgtc tggggtccca   180
tcgcggttca gcggcagtgg atctgggaca cagttcactc tcaccatcag cggcgtgcag   240
tgtaacgatg ctgccgctta ctactgtctg gcagttatg attgtactaa tggtgattgt   300
tttgttttcg gcggagggac cgaggtggtg gtcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

<210> SEQ ID NO 152
<211> LENGTH: 339

```
<212> TYPE: DNA
<213> ORGANISM: Artificial
<220> FEATURE:
<223> OTHER INFORMATION: Engineered antibody sequence

<400> SEQUENCE: 152
caagtgctga cccagactcc atcccccgtg tctgcagctg tgggaagcac agtcaccatc      60
aattgccagg ccagtcagag tgtttatcat aacacctacc tggcctggta tcagcagaaa     120
ccagggcagc ctcccaaaca actgatctat gatgcatcca ctctggcgtc tggggtccca     180
tcgcggttca gcggcagtgg atctgggaca cagttcactc tcaccatcag cggcgtgcag     240
tgtaacgatg ctgccgctta ctactgtctg ggcagttatg attgtactaa tggtgattgt     300
tttgttttcg gcggagggac cgaggtggtg gtcaaacgt                             339

<210> SEQ ID NO 153
<211> LENGTH: 66
<212> TYPE: DNA
<213> ORGANISM: Artificial
<220> FEATURE:
<223> OTHER INFORMATION: Engineered antibody sequence

<400> SEQUENCE: 153
caagtgctga cccagactcc atcccccgtg tctgcagctg tgggaagcac agtcaccatc      60
aattgc                                                                 66

<210> SEQ ID NO 154
<211> LENGTH: 39
<212> TYPE: DNA
<213> ORGANISM: Artificial
<220> FEATURE:
<223> OTHER INFORMATION: Engineered antibody sequence

<400> SEQUENCE: 154
caggccagtc agagtgttta tcataacacc tacctggcc                             39

<210> SEQ ID NO 155
<211> LENGTH: 45
<212> TYPE: DNA
<213> ORGANISM: Artificial
<220> FEATURE:
<223> OTHER INFORMATION: Engineered antibody sequence

<400> SEQUENCE: 155
tggtatcagc agaaaccagg gcagcctccc aaacaactga tctat                      45

<210> SEQ ID NO 156
<211> LENGTH: 21
<212> TYPE: DNA
<213> ORGANISM: Artificial
<220> FEATURE:
<223> OTHER INFORMATION: Engineered antibody sequence

<400> SEQUENCE: 156
gatgcatcca ctctggcgtc t                                                21

<210> SEQ ID NO 157
<211> LENGTH: 96
<212> TYPE: DNA
<213> ORGANISM: Artificial
<220> FEATURE:
<223> OTHER INFORMATION: Engineered antibody sequence

<400> SEQUENCE: 157
```

```
ggggtcccat cgcggttcag cggcagtgga tctgggacac agttcactct caccatcagc    60
ggcgtgcagt gtaacgatgc tgccgcttac tactgt                              96
```

<210> SEQ ID NO 158
<211> LENGTH: 39
<212> TYPE: DNA
<213> ORGANISM: Artificial
<220> FEATURE:
<223> OTHER INFORMATION: Engineered antibody sequence

<400> SEQUENCE: 158

```
ctgggcagtt atgattgtac taatggtgat tgttttgtt                           39
```

<210> SEQ ID NO 159
<211> LENGTH: 33
<212> TYPE: DNA
<213> ORGANISM: Artificial
<220> FEATURE:
<223> OTHER INFORMATION: Engineered antibody sequence

<400> SEQUENCE: 159

```
ttcggcggag ggaccgaggt ggtggtcaaa cgt                                 33
```

<210> SEQ ID NO 160
<211> LENGTH: 321
<212> TYPE: DNA
<213> ORGANISM: Artificial
<220> FEATURE:
<223> OTHER INFORMATION: Engineered antibody sequence

<400> SEQUENCE: 160

```
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321
```

<210> SEQ ID NO 161
<211> LENGTH: 441
<212> TYPE: PRT
<213> ORGANISM: Artificial
<220> FEATURE:
<223> OTHER INFORMATION: Engineered antibody sequence

<400> SEQUENCE: 161

```
Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

Tyr Met Asn Trp Val Arg Gln Ala Pro Gly Lys Gly Leu Glu Trp Val
        35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser Ala
```

```
              100                 105                 110
Ser Thr Lys Gly Pro Ser Val Phe Pro Leu Ala Pro Ser Ser Lys Ser
            115                 120                 125

Thr Ser Gly Gly Thr Ala Ala Leu Gly Cys Leu Val Lys Asp Tyr Phe
        130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Arg
        195                 200                 205

Val Glu Pro Lys Ser Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 162
<211> LENGTH: 111
<212> TYPE: PRT
<213> ORGANISM: Artificial
<220> FEATURE:
<223> OTHER INFORMATION: Engineered antibody sequence

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
```

```
                  20                  25                  30

Tyr Met Asn Trp Val Arg Gln Ala Pro Gly Lys Gly Leu Glu Trp Val
              35                  40                  45

Gly Val Ile Gly Ile Asn Gly Ala Thr Tyr Tyr Ala Ser Trp Ala Lys
          50                  55                  60

Gly Arg Phe Thr Ile Ser Arg Asp Asn Ser Lys Thr Thr Val Tyr Leu
 65                  70                  75                  80

Gln Met Asn Ser Leu Arg Ala Glu Asp Thr Ala Val Tyr Phe Cys Ala
                  85                  90                  95

Arg Gly Asp Ile Trp Gly Gln Gly Thr Leu Val Thr Val Ser Ser
              100                 105                 110

<210> SEQ ID NO 163
<211> LENGTH: 30
<212> TYPE: PRT
<213> ORGANISM: Artificial
<220> FEATURE:
<223> OTHER INFORMATION: Engineered antibody sequence

<400> SEQUENCE: 163

Glu Val Gln Leu Val Glu Ser Gly Gly Gly Leu Val Gln Pro Gly Gly
 1               5                  10                  15

Ser Leu Arg Leu Ser Cys Ala Val Ser Gly Ile Asp Leu Ser
              20                  25                  30

<210> SEQ ID NO 164
<211> LENGTH: 5
<212> TYPE: PRT
<213> ORGANISM: Artificial
<220> FEATURE:
<223> OTHER INFORMATION: Engineered antibody sequence

<400> SEQUENCE: 164

Gly Tyr Tyr Met Asn
 1               5

<210> SEQ ID NO 165
<211> LENGTH: 14
<212> TYPE: PRT
<213> ORGANISM: Artificial
<220> FEATURE:
<223> OTHER INFORMATION: Engineered antibody sequence

<400> SEQUENCE: 165

Trp Val Arg Gln Ala Pro Gly Lys Gly Leu Glu Trp Val Gly
 1               5                  10

<210> SEQ ID NO 166
<211> LENGTH: 16
<212> TYPE: PRT
<213> ORGANISM: Artificial
<220> FEATURE:
<223> OTHER INFORMATION: Engineered antibody sequence

<400> SEQUENCE: 166

Val Ile Gly Ile Asn Gly Ala Thr Tyr Tyr Ala Ser Trp Ala Lys Gly
 1               5                  10                  15

<210> SEQ ID NO 167
<211> LENGTH: 32
<212> TYPE: PRT
<213> ORGANISM: Artificial
<220> FEATURE:
<223> OTHER INFORMATION: Engineered antibody sequence
```

<400> SEQUENCE: 167

```
Arg Phe Thr Ile Ser Arg Asp Asn Ser Lys Thr Thr Val Tyr Leu Gln
1               5                   10                  15

Met Asn Ser Leu Arg Ala Glu Asp Thr Ala Val Tyr Phe Cys Ala Arg
            20                  25                  30
```

<210> SEQ ID NO 168
<211> LENGTH: 3
<212> TYPE: PRT
<213> ORGANISM: Artificial
<220> FEATURE:
<223> OTHER INFORMATION: Engineered antibody sequence

<400> SEQUENCE: 168

```
Gly Asp Ile
1
```

<210> SEQ ID NO 169
<211> LENGTH: 11
<212> TYPE: PRT
<213> ORGANISM: Artificial
<220> FEATURE:
<223> OTHER INFORMATION: Engineered antibody sequence

<400> SEQUENCE: 169

```
Trp Gly Gln Gly Thr Leu Val Thr Val Ser Ser
1               5                   10
```

<210> SEQ ID NO 170
<211> LENGTH: 330
<212> TYPE: PRT
<213> ORGANISM: Artificial
<220> FEATURE:
<223> OTHER INFORMATION: Engineered antibody sequence

<400> SEQUENCE: 170

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
```

|     |     |     |     | 180 |     |     |     | 185 |     |     |     | 190 |     |     |
| --- | --- | --- | --- | --- | --- | --- | --- | --- | --- | --- | --- | --- | --- | --- |
| His | Gln | Asp | Trp | Leu | Asn | Gly | Lys | Glu | Tyr | Lys | Cys | Lys | Val | Ser | Asn |
|     |     |     |     | 195 |     |     |     | 200 |     |     |     | 205 |     |     |
| Lys | Ala | Leu | Pro | Ala | Pro | Ile | Glu | Lys | Thr | Ile | Ser | Lys | Ala | Lys | Gly |
|     |     |     |     | 210 |     |     |     | 215 |     |     |     | 220 |     |     |
| Gln | Pro | Arg | Glu | Pro | Gln | Val | Tyr | Thr | Leu | Pro | Pro | Ser | Arg | Glu | Glu |
| 225 |     |     |     |     |     | 230 |     |     |     |     |     | 235 |     |     | 240 |
| Met | Thr | Lys | Asn | Gln | Val | Ser | Leu | Thr | Cys | Leu | Val | Lys | Gly | Phe | Tyr |
|     |     |     |     | 245 |     |     |     | 250 |     |     |     | 255 |     |     |
| Pro | Ser | Asp | Ile | Ala | Val | Glu | Trp | Glu | Ser | Asn | Gly | Gln | Pro | Glu | Asn |
|     |     |     |     | 260 |     |     |     | 265 |     |     |     | 270 |     |     |
| Asn | Tyr | Lys | Thr | Thr | Pro | Pro | Val | Leu | Asp | Ser | Asp | Gly | Ser | Phe | Phe |
|     |     |     |     | 275 |     |     |     | 280 |     |     |     | 285 |     |     |
| Leu | Tyr | Ser | Lys | Leu | Thr | Val | Asp | Lys | Ser | Arg | Trp | Gln | Gln | Gly | Asn |
|     |     |     |     | 290 |     |     |     | 295 |     |     |     | 300 |     |     |
| Val | Phe | Ser | Cys | Ser | Val | Met | His | Glu | Ala | Leu | His | Asn | His | Tyr | Thr |
| 305 |     |     |     |     |     | 310 |     |     |     |     |     | 315 |     |     | 320 |
| Gln | Lys | Ser | Leu | Ser | Leu | Ser | Pro | Gly | Lys |
|     |     |     |     | 325 |     |     |     | 330 |     |

<210> SEQ ID NO 171
<211> LENGTH: 1326
<212> TYPE: DNA
<213> ORGANISM: Artificial
<220> FEATURE:
<223> OTHER INFORMATION: Engineered antibody sequence

<400> SEQUENCE: 171

```
gaggtgcagc ttgtggagtc tgggggaggc ttggtccagc ctggggggtc cctgagactc      60
tcctgtgcag tctctggaat cgacctcagt ggctactaca tgaactgggt ccgtcaggct     120
ccagggaagg ggctggagtg ggtcggagtc attggtatta atggtgccac atactacgcg     180
agctgggcga aaggccgatt caccatctcc agagacaatt ccaagaccac ggtgtatctt     240
caaatgaaca gcctgagagc tgaggacact gctgtgtatt tctgtgctag agggacatc     300
tggggccaag gaccctcgt caccgtctcg agcgcctcca ccaagggccc atcggtcttc     360
cccctggcac cctcctccaa gagcacctct gggggcacag cggccctggg ctgcctggtc     420
aaggactact tccccgaacc ggtgacggtg tcgtggaact caggcgccct gaccagcggc     480
gtgcacacct tcccggctgt cctacagtcc tcaggactct actccctcag cagcgtggtg     540
accgtgccct ccagcagctt gggcacccag acctacatct gcaacgtgaa tcacaagccc     600
agcaacacca aggtggacaa gagagttgag cccaaatctt gtgacaaaac tcacacatgc     660
ccaccgtgcc cagcacctga actcctgggg gaccgtcag tcttcctctt ccccccaaaa     720
cccaaggaca ccctcatgat ctcccggacc cctgaggtca catgcgtggt ggtggacgtg     780
agccacgaag accctgaggt caagttcaac tggtacgtgg acggcgtgga ggtgcataat     840
gccaagacaa agccgcggga ggagcagtac gccagcacgt accgtgtggt cagcgtcctc     900
accgtcctgc accaggactg gctgaatggc aaggagtaca agtgcaaggt ctccaacaaa     960
gccctcccag cccccatcga gaaaaccatc tccaaagcca agggcagccc cgagaaccca    1020
caggtgtaca ccctgccccc atcccgggag gagatgacca agaaccaggt cagcctgacc    1080
tgcctggtca aaggcttcta tcccagcgac atcgccgtgg agtgggagag caatgggcag    1140
ccggagaaca actacaagac cacgcctccc gtgctggact ccgacggctc cttcttcctc    1200
```

```
tacagcaagc tcaccgtgga caagagcagg tggcagcagg ggaacgtctt ctcatgctcc   1260
gtgatgcatg aggctctgca caaccactac acgcagaaga gcctctccct gtctccgggt   1320
aaatga                                                              1326

<210> SEQ ID NO 172
<211> LENGTH: 333
<212> TYPE: DNA
<213> ORGANISM: Artificial
<220> FEATURE:
<223> OTHER INFORMATION: Engineered antibody sequence

<400> SEQUENCE: 172
gaggtgcagc ttgtggagtc tgggggaggc ttggtccagc ctggggggtc cctgagactc     60
tcctgtgcag tctctggaat cgacctcagt ggctactaca tgaactgggt ccgtcaggct    120
ccagggaagg ggctggagtg ggtcggagtc attggtatta atggtgccac atactacgcg    180
agctgggcga aaggccgatt caccatctcc agagacaatt ccaagaccac ggtgtatctt    240
caaatgaaca gcctgagagc tgaggacact gctgtgtatt tctgtgctag aggggacatc    300
tggggccaag ggaccctcgt caccgtctcg agc                                 333

<210> SEQ ID NO 173
<211> LENGTH: 90
<212> TYPE: DNA
<213> ORGANISM: Artificial
<220> FEATURE:
<223> OTHER INFORMATION: Engineered antibody sequence

<400> SEQUENCE: 173
gaggtgcagc ttgtggagtc tgggggaggc ttggtccagc ctggggggtc cctgagactc     60
tcctgtgcag tctctggaat cgacctcagt                                      90

<210> SEQ ID NO 174
<211> LENGTH: 15
<212> TYPE: DNA
<213> ORGANISM: Artificial
<220> FEATURE:
<223> OTHER INFORMATION: Engineered antibody sequence

<400> SEQUENCE: 174
ggctactaca tgaac                                                      15

<210> SEQ ID NO 175
<211> LENGTH: 42
<212> TYPE: DNA
<213> ORGANISM: Artificial
<220> FEATURE:
<223> OTHER INFORMATION: Engineered antibody sequence

<400> SEQUENCE: 175
tgggtccgtc aggctccagg gaaggggctg gagtgggtcg ga                        42

<210> SEQ ID NO 176
<211> LENGTH: 48
<212> TYPE: DNA
<213> ORGANISM: Artificial
<220> FEATURE:
<223> OTHER INFORMATION: Engineered antibody sequence

<400> SEQUENCE: 176
gtcattggta ttaatggtgc cacatactac gcgagctggg cgaaaggc                  48
```

<210> SEQ ID NO 177
<211> LENGTH: 96
<212> TYPE: DNA
<213> ORGANISM: Artificial
<220> FEATURE:
<223> OTHER INFORMATION: Engineered antibody sequence

<400> SEQUENCE: 177

```
cgattcacca tctccagaga caattccaag accacggtgt atcttcaaat gaacagcctg    60
agagctgagg acactgctgt gtatttctgt gctaga                              96
```

<210> SEQ ID NO 178
<211> LENGTH: 9
<212> TYPE: DNA
<213> ORGANISM: Artificial
<220> FEATURE:
<223> OTHER INFORMATION: Engineered antibody sequence

<400> SEQUENCE: 178

```
ggggacatc                                                             9
```

<210> SEQ ID NO 179
<211> LENGTH: 33
<212> TYPE: DNA
<213> ORGANISM: Artificial
<220> FEATURE:
<223> OTHER INFORMATION: Engineered antibody sequence

<400> SEQUENCE: 179

```
tggggccaag ggaccctcgt caccgtctcg agc                                 33
```

<210> SEQ ID NO 180
<211> LENGTH: 993
<212> TYPE: DNA
<213> ORGANISM: Artificial
<220> FEATURE:
<223> OTHER INFORMATION: Engineered antibody sequence

<400> SEQUENCE: 180

```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctgggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacgcc   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag gcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
```
cagaagagcc tctccctgtc tccgggtaaa tga                                    993

```
<210> SEQ ID NO 181
<211> LENGTH: 219
<212> TYPE: PRT
<213> ORGANISM: Artificial
<220> FEATURE:
<223> OTHER INFORMATION: Engineered antibody sequence

<400> SEQUENCE: 181
```

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 182
<211> LENGTH: 113
<212> TYPE: PRT
<213> ORGANISM: Artificial
<220> FEATURE:
<223> OTHER INFORMATION: Engineered antibody sequence

<400> SEQUENCE: 182
```

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

```
Pro Glu Asp Val Ala Thr Tyr Tyr Cys Leu Gly Ser Tyr Asp Cys Thr
            85                  90                  95

Asn Gly Asp Cys Phe Val Phe Gly Gly Gly Thr Lys Val Glu Ile Lys
            100                 105                 110

Arg

<210> SEQ ID NO 183
<211> LENGTH: 22
<212> TYPE: PRT
<213> ORGANISM: Artificial
<220> FEATURE:
<223> OTHER INFORMATION: Engineered antibody sequence

<400> SEQUENCE: 183

Gln Val Leu Thr Gln Ser Pro Ser Ser Leu Ser Ala Ser Val Gly Asp
1               5                   10                  15

Arg Val Thr Ile Asn Cys
            20

<210> SEQ ID NO 184
<211> LENGTH: 13
<212> TYPE: PRT
<213> ORGANISM: Artificial
<220> FEATURE:
<223> OTHER INFORMATION: Engineered antibody sequence

<400> SEQUENCE: 184

Gln Ala Ser Gln Ser Val Tyr His Asn Thr Tyr Leu Ala
1               5                   10

<210> SEQ ID NO 185
<211> LENGTH: 15
<212> TYPE: PRT
<213> ORGANISM: Artificial
<220> FEATURE:
<223> OTHER INFORMATION: Engineered antibody sequence

<400> SEQUENCE: 185

Trp Tyr Gln Gln Lys Pro Gly Lys Val Pro Lys Gln Leu Ile Tyr
1               5                   10                  15

<210> SEQ ID NO 186
<211> LENGTH: 7
<212> TYPE: PRT
<213> ORGANISM: Artificial
<220> FEATURE:
<223> OTHER INFORMATION: Engineered antibody sequence

<400> SEQUENCE: 186

Asp Ala Ser Thr Leu Ala Ser
1               5

<210> SEQ ID NO 187
<211> LENGTH: 32
<212> TYPE: PRT
<213> ORGANISM: Artificial
<220> FEATURE:
<223> OTHER INFORMATION: Engineered antibody sequence

<400> SEQUENCE: 187

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30
```

<210> SEQ ID NO 188
<211> LENGTH: 13
<212> TYPE: PRT
<213> ORGANISM: Artificial
<220> FEATURE:
<223> OTHER INFORMATION: Engineered antibody sequence

<400> SEQUENCE: 188

Leu Gly Ser Tyr Asp Cys Thr Asn Gly Asp Cys Phe Val
1               5                   10

<210> SEQ ID NO 189
<211> LENGTH: 11
<212> TYPE: PRT
<213> ORGANISM: Artificial
<220> FEATURE:
<223> OTHER INFORMATION: Engineered antibody sequence

<400> SEQUENCE: 189

Phe Gly Gly Gly Thr Lys Val Glu Ile Lys Arg
1               5                   10

<210> SEQ ID NO 190
<211> LENGTH: 106
<212> TYPE: PRT
<213> ORGANISM: Artificial
<220> FEATURE:
<223> OTHER INFORMATION: Engineered antibody sequence

<400> SEQUENCE: 190

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 191
<211> LENGTH: 660
<212> TYPE: DNA
<213> ORGANISM: Artificial
<220> FEATURE:
<223> OTHER INFORMATION: Engineered antibody sequence

<400> SEQUENCE: 191
caagtgctga cccagtctcc atcctccctg tctgcatctg taggagacag agtcaccatc      60
aattgccagg ccagtcagag tgtttatcat aacacctacc tggcctggta tcagcagaaa     120
ccagggaaag ttcctaagca actgatctat gatgcatcca ctctggcatc tggggtccca     180
tctcgtttca gtggcagtgg atctgggaca gatttcactc tcaccatcag cagcctgcag     240
cctgaagatg ttgcaactta ttactgtctg ggcagttatg attgtactaa tggtgattgt     300
tttgttttcg gcggaggaac caaggtggaa atcaaacgta cggtggctgc accatctgtc     360

```
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660
```

<210> SEQ ID NO 192
<211> LENGTH: 339
<212> TYPE: DNA
<213> ORGANISM: Artificial
<220> FEATURE:
<223> OTHER INFORMATION: Engineered antibody sequence

<400> SEQUENCE: 192

```
caagtgctga cccagtctcc atcctccctg tctgcatctg taggagacag agtcaccatc     60
aattgccagg ccagtcagag tgtttatcat aacacctacc tggcctggta tcagcagaaa    120
ccagggaaag ttcctaagca actgatctat gatgcatcca ctctggcatc tggggtccca    180
tctcgtttca gtggcagtgg atctgggaca gatttcactc tcaccatcag cagcctgcag    240
cctgaagatg ttgcaactta ttactgtctg ggcagttatg attgtactaa tggtgattgt    300
tttgttttcg gcggaggaac caaggtggaa atcaaacgt                           339
```

<210> SEQ ID NO 193
<211> LENGTH: 66
<212> TYPE: DNA
<213> ORGANISM: Artificial
<220> FEATURE:
<223> OTHER INFORMATION: Engineered antibody sequence

<400> SEQUENCE: 193

```
caagtgctga cccagtctcc atcctccctg tctgcatctg taggagacag agtcaccatc     60
aattgc                                                                66
```

<210> SEQ ID NO 194
<211> LENGTH: 39
<212> TYPE: DNA
<213> ORGANISM: Artificial
<220> FEATURE:
<223> OTHER INFORMATION: Engineered antibody sequence

<400> SEQUENCE: 194

```
caggccagtc agagtgttta tcataacacc tacctggcc                            39
```

<210> SEQ ID NO 195
<211> LENGTH: 45
<212> TYPE: DNA
<213> ORGANISM: Artificial
<220> FEATURE:
<223> OTHER INFORMATION: Engineered antibody sequence

<400> SEQUENCE: 195

```
tggtatcagc agaaaccagg gaaagttcct aagcaactga tctat                     45
```

<210> SEQ ID NO 196
<211> LENGTH: 21
<212> TYPE: DNA
<213> ORGANISM: Artificial
<220> FEATURE:
<223> OTHER INFORMATION: Engineered antibody sequence

<400> SEQUENCE: 196
gatgcatcca ctctggcatc t                                             21

<210> SEQ ID NO 197
<211> LENGTH: 96
<212> TYPE: DNA
<213> ORGANISM: Artificial
<220> FEATURE:
<223> OTHER INFORMATION: Engineered antibody sequence

<400> SEQUENCE: 197
ggggtcccat ctcgtttcag tggcagtgga tctgggacag atttcactct caccatcagc    60
agcctgcagc ctgaagatgt tgcaacttat tactgt                              96

<210> SEQ ID NO 198
<211> LENGTH: 39
<212> TYPE: DNA
<213> ORGANISM: Artificial
<220> FEATURE:
<223> OTHER INFORMATION: Engineered antibody sequence

<400> SEQUENCE: 198
ctgggcagtt atgattgtac taatggtgat tgttttgtt                           39

<210> SEQ ID NO 199
<211> LENGTH: 33
<212> TYPE: DNA
<213> ORGANISM: Artificial
<220> FEATURE:
<223> OTHER INFORMATION: Engineered antibody sequence

<400> SEQUENCE: 199
ttcggcggag gaaccaaggt ggaaatcaaa cgt                                 33

<210> SEQ ID NO 200
<211> LENGTH: 321
<212> TYPE: DNA
<213> ORGANISM: Artificial
<220> FEATURE:
<223> OTHER INFORMATION: Engineered antibody sequence

<400> SEQUENCE: 200
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321

<210> SEQ ID NO 201
<211> LENGTH: 441
<212> TYPE: PRT
<213> ORGANISM: Artificial
<220> FEATURE:
<223> OTHER INFORMATION: Engineered antibody sequence

<400> SEQUENCE: 201

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

```
Tyr Met Asn Trp Val Arg Gln Ala Pro Gly Lys Gly Leu Glu Trp Val
         35                  40                  45
Gly Val Ile Gly Ile Asn Gly Ala Thr Tyr Tyr Ala Ser Trp Ala Lys
 50                  55                  60
Gly Arg Phe Thr Ile Ser Arg Asp Asn Ser Lys Thr Thr Val Tyr Leu
 65                  70                  75                  80
Gln Met Asn Ser Leu Arg Ala Glu Asp Thr Ala Val Tyr Phe Cys Ala
             85                  90                  95
Arg Gly Asp Ile Trp Gly Gln Gly Thr Leu Val Thr Val Ser Ser Ala
             100                 105                 110
Ser Thr Lys Gly Pro Ser Val Phe Pro Leu Ala Pro Ser Ser Lys Ser
             115                 120                 125
Thr Ser Gly Gly Thr Ala Ala Leu Gly Cys Leu Val Lys Asp Tyr Phe
130                 135                 140
Pro Glu Pro Val Thr Val Ser Trp Asn Ser Gly Ala Leu Thr Ser Gly
145                 150                 155                 160
Val His Thr Phe Pro Ala Val Leu Gln Ser Ser Gly Leu Tyr Ser Leu
             165                 170                 175
Ser Ser Val Val Thr Val Pro Ser Ser Ser Leu Gly Thr Gln Thr Tyr
             180                 185                 190
Ile Cys Asn Val Asn His Lys Pro Ser Asn Thr Lys Val Asp Ala Arg
             195                 200                 205
Val Glu Pro Lys Ser Cys Asp Lys Thr His Thr Cys Pro Pro Cys Pro
             210                 215                 220
Ala Pro Glu Leu Leu Gly Gly Pro Ser Val Phe Leu Phe Pro Pro Lys
225                 230                 235                 240
Pro Lys Asp Thr Leu Met Ile Ser Arg Thr Pro Glu Val Thr Cys Val
             245                 250                 255
Val Val Asp Val Ser His Glu Asp Pro Glu Val Lys Phe Asn Trp Tyr
             260                 265                 270
Val Asp Gly Val Glu Val His Asn Ala Lys Thr Lys Pro Arg Glu Glu
             275                 280                 285
Gln Tyr Ala Ser Thr Tyr Arg Val Val Ser Val Leu Thr Val Leu His
290                 295                 300
Gln Asp Trp Leu Asn Gly Lys Glu Tyr Lys Cys Lys Val Ser Asn Lys
305                 310                 315                 320
Ala Leu Pro Ala Pro Ile Glu Lys Thr Ile Ser Lys Ala Lys Gly Gln
             325                 330                 335
Pro Arg Glu Pro Gln Val Tyr Thr Leu Pro Pro Ser Arg Glu Glu Met
             340                 345                 350
Thr Lys Asn Gln Val Ser Leu Thr Cys Leu Val Lys Gly Phe Tyr Pro
             355                 360                 365
Ser Asp Ile Ala Val Glu Trp Glu Ser Asn Gly Gln Pro Glu Asn Asn
370                 375                 380
Tyr Lys Thr Thr Pro Pro Val Leu Asp Ser Asp Gly Ser Phe Phe Leu
385                 390                 395                 400
Tyr Ser Lys Leu Thr Val Asp Lys Ser Arg Trp Gln Gln Gly Asn Val
             405                 410                 415
Phe Ser Cys Ser Val Met His Glu Ala Leu His Asn His Tyr Thr Gln
             420                 425                 430
Lys Ser Leu Ser Leu Ser Pro Gly Lys
             435                 440
```

-continued

```
<210> SEQ ID NO 202
<211> LENGTH: 111
<212> TYPE: PRT
<213> ORGANISM: Artificial
<220> FEATURE:
<223> OTHER INFORMATION: Engineered antibody sequence

<400> SEQUENCE: 202
```

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

Tyr Met Asn Trp Val Arg Gln Ala Pro Gly Lys Gly Leu Glu Trp Val
        35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110

```
<210> SEQ ID NO 203
<211> LENGTH: 30
<212> TYPE: PRT
<213> ORGANISM: Artificial
<220> FEATURE:
<223> OTHER INFORMATION: Engineered antibody sequence

<400> SEQUENCE: 203
```

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser
            20                  25                  30

```
<210> SEQ ID NO 204
<211> LENGTH: 5
<212> TYPE: PRT
<213> ORGANISM: Artificial
<220> FEATURE:
<223> OTHER INFORMATION: Engineered antibody sequence

<400> SEQUENCE: 204
```

Gly Tyr Tyr Met Asn
1               5

```
<210> SEQ ID NO 205
<211> LENGTH: 14
<212> TYPE: PRT
<213> ORGANISM: Artificial
<220> FEATURE:
<223> OTHER INFORMATION: Engineered antibody sequence

<400> SEQUENCE: 205
```

Trp Val Arg Gln Ala Pro Gly Lys Gly Leu Glu Trp Val Gly
1               5                   10

```
<210> SEQ ID NO 206
<211> LENGTH: 16
<212> TYPE: PRT
<213> ORGANISM: Artificial
<220> FEATURE:
<223> OTHER INFORMATION: Engineered antibody sequence
```

<400> SEQUENCE: 206

Val Ile Gly Ile Asn Gly Ala Thr Tyr Tyr Ala Ser Trp Ala Lys Gly
1               5                   10                  15

<210> SEQ ID NO 207
<211> LENGTH: 32
<212> TYPE: PRT
<213> ORGANISM: Artificial
<220> FEATURE:
<223> OTHER INFORMATION: Engineered antibody sequence

<400> SEQUENCE: 207

Arg Phe Thr Ile Ser Arg Asp Asn Ser Lys Thr Thr Val Tyr Leu Gln
1               5                   10                  15

Met Asn Ser Leu Arg Ala Glu Asp Thr Ala Val Tyr Phe Cys Ala Arg
                20                  25                  30

<210> SEQ ID NO 208
<211> LENGTH: 3
<212> TYPE: PRT
<213> ORGANISM: Artificial
<220> FEATURE:
<223> OTHER INFORMATION: Engineered antibody sequence

<400> SEQUENCE: 208

Gly Asp Ile
1

<210> SEQ ID NO 209
<211> LENGTH: 11
<212> TYPE: PRT
<213> ORGANISM: Artificial
<220> FEATURE:
<223> OTHER INFORMATION: Engineered antibody sequence

<400> SEQUENCE: 209

Trp Gly Gln Gly Thr Leu Val Thr Val Ser Ser
1               5                   10

<210> SEQ ID NO 210
<211> LENGTH: 330
<212> TYPE: PRT
<213> ORGANISM: Artificial
<220> FEATURE:
<223> OTHER INFORMATION: Engineered antibody sequence

<400> SEQUENCE: 210

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
            100                 105                 110

```
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Ala Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 211
<211> LENGTH: 1326
<212> TYPE: DNA
<213> ORGANISM: Artificial
<220> FEATURE:
<223> OTHER INFORMATION: Engineered antibody sequence

<400> SEQUENCE: 211
gaggtgcagc ttgtggagtc tggggggaggc ttggtccagc ctggggggtc cctgagactc      60
tcctgtgcag tctctggaat cgacctcagt ggctactaca tgaactgggt ccgtcaggct     120
ccagggaagg gctggagtg gtcggagtc attggtatta atggtgccac atactacgcg      180
agctgggcga aaggccgatt caccatctcc agagacaatt ccaagaccac ggtgtatctt     240
caaatgaaca gcctgagagc tgaggacact gctgtgtatt tctgtgctag aggggacatc     300
tggggccaag ggaccctcgt caccgtctcg agcgcctcca ccaagggccc atcggtcttc     360
cccctggcac cctcctccaa gagcacctct gggggcacag cggccctggg ctgcctggtc     420
aaggactact tccccgaacc ggtgacggtg tcgtggaact caggcgccct gaccagcggc     480
gtgcacacct tcccggctgt cctacagtcc tcaggactct actccctcag cagcgtggtg     540
accgtgccct ccagcagctt gggcacccag acctacatct gcaacgtgaa tcacaagccc     600
agcaacacca aggtggacgc gagagttgag cccaaatctt gtgacaaaac tcacacatgc     660
ccaccgtgcc cagcacctga actcctgggg ggaccgtcag tcttcctctt ccccccaaaa     720
cccaaggaca ccctcatgat ctcccggacc cctgaggtca catgcgtggt ggtggacgtg     780
agccacgaag accctgaggt caagttcaac tggtacgtgg acggcgtgga ggtgcataat     840
```

```
gccaagacaa agccgcggga ggagcagtac gccagcacgt accgtgtggt cagcgtcctc    900
accgtcctgc accaggactg gctgaatggc aaggagtaca agtgcaaggt ctccaacaaa    960
gccctcccag cccccatcga gaaaaccatc tccaaagcca agggcagcc ccgagaacca   1020 caggtgtaca ccctgccccc atcccgggag gagatgacca gaaccaggt cagcctgacc   1080 tgcctggtca aaggcttcta tcccagcgac atcgccgtgg agtgggagag caatgggcag   1140
ccggagaaca actacaagac cacgcctccc gtgctggact ccgacggctc cttcttcctc   1200
tacagcaagc tcaccgtgga caagagcagg tggcagcagg ggaacgtctt ctcatgctcc   1260
gtgatgcatg aggctctgca caaccactac acgcagaaga gcctctccct gtctccgggt   1320
aaatga                                                              1326

<210> SEQ ID NO 212
<211> LENGTH: 333
<212> TYPE: DNA
<213> ORGANISM: Artificial
<220> FEATURE:
<223> OTHER INFORMATION: Engineered antibody sequence

<400> SEQUENCE: 212
gaggtgcagc ttgtggagtc tgggggaggc ttggtccagc ctggggggtc cctgagactc     60
tcctgtgcag tctctggaat cgacctcagt ggctactaca tgaactgggt ccgtcaggct    120
ccagggaagg ggctggagtg ggtcggagtc attggtatta atggtgccac atactacgcg    180
agctgggcga aaggccgatt caccatctcc agagacaatt ccaagaccac ggtgtatctt    240
caaatgaaca gcctgagagc tgaggacact gctgtgtatt tctgtgctag aggggacatc    300
tggggccaag ggaccctcgt caccgtctcg agc                                 333

<210> SEQ ID NO 213
<211> LENGTH: 90
<212> TYPE: DNA
<213> ORGANISM: Artificial
<220> FEATURE:
<223> OTHER INFORMATION: Engineered antibody sequence

<400> SEQUENCE: 213
gaggtgcagc ttgtggagtc tgggggaggc ttggtccagc ctggggggtc cctgagactc     60
tcctgtgcag tctctggaat cgacctcagt                                     90

<210> SEQ ID NO 214
<211> LENGTH: 15
<212> TYPE: DNA
<213> ORGANISM: Artificial
<220> FEATURE:
<223> OTHER INFORMATION: Engineered antibody sequence

<400> SEQUENCE: 214
ggctactaca tgaac                                                     15

<210> SEQ ID NO 215
<211> LENGTH: 42
<212> TYPE: DNA
<213> ORGANISM: Artificial
<220> FEATURE:
<223> OTHER INFORMATION: Engineered antibody sequence

<400> SEQUENCE: 215
tgggtccgtc aggctccagg gaaggggctg gagtgggtcg ga                       42
```

<210> SEQ ID NO 216
<211> LENGTH: 48
<212> TYPE: DNA
<213> ORGANISM: Artificial
<220> FEATURE:
<223> OTHER INFORMATION: Engineered antibody sequence

<400> SEQUENCE: 216
gtcattggta ttaatggtgc cacatactac gcgagctggg cgaaaggc        48

<210> SEQ ID NO 217
<211> LENGTH: 96
<212> TYPE: DNA
<213> ORGANISM: Artificial
<220> FEATURE:
<223> OTHER INFORMATION: Engineered antibody sequence

<400> SEQUENCE: 217
cgattcacca tctccagaga caattccaag accacggtgt atcttcaaat gaacagcctg        60
agagctgagg acactgctgt gtatttctgt gctaga                                  96

<210> SEQ ID NO 218
<211> LENGTH: 9
<212> TYPE: DNA
<213> ORGANISM: Artificial
<220> FEATURE:
<223> OTHER INFORMATION: Engineered antibody sequence

<400> SEQUENCE: 218 ggggacatc                                                                 9

<210> SEQ ID NO 219
<211> LENGTH: 33
<212> TYPE: DNA
<213> ORGANISM: Artificial
<220> FEATURE:
<223> OTHER INFORMATION: Engineered antibody sequence

<400> SEQUENCE: 219
tggggccaag ggaccctcgt caccgtctcg agc                                     33

<210> SEQ ID NO 220
<211> LENGTH: 993
<212> TYPE: DNA
<213> ORGANISM: Artificial
<220> FEATURE:
<223> OTHER INFORMATION: Engineered antibody sequence

<400> SEQUENCE: 220
gcctccacca agggcccatc ggtcttcccc ctggcaccct cctccaagag cacctctggg        60
ggcacagcgg ccctgggctg cctggtcaag gactacttcc ccgaaccggt gacggtgtcg       120
tggaactcag gcgccctgac cagcggcgtg cacaccttcc cggctgtcct acagtcctca       180
ggactctact ccctcagcag cgtggtgacc gtgccctcca gcagcttggg cacccagacc       240
tacatctgca acgtgaatca caagcccagc aacaccaagg tggacgcgag agttgagccc       300
aaatcttgtg acaaaactca cacatgccca ccgtgcccag cacctgaact cctgggggga       360
ccgtcagtct tcctcttccc cccaaaaccc aaggacaccc tcatgatctc ccggacccct       420
gaggtcacat gcgtggtggt ggacgtgagc cacgaagacc ctgaggtcaa gttcaactgg       480
tacgtggacg gcgtggaggt gcataatgcc aagacaaagc cgcgggagga gcagtacgcc       540
agcacgtacc gtgtggtcag cgtcctcacc gtcctgcacc aggactggct gaatggcaag       600

```
gagtacaagt gcaaggtctc caacaaagcc ctcccagccc ccatcgagaa aaccatctcc    660
aaagccaaag ggcagccccg agaaccacag gtgtacaccc tgcccccatc ccggaggag     720 atgaccaaga accaggtcag cctgacctgc ctggtcaaag gcttctatcc agcgacatc    780 gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa tga                                 993
```

```
<210> SEQ ID NO 221
<211> LENGTH: 219
<212> TYPE: PRT
<213> ORGANISM: Artificial
<220> FEATURE:
<223> OTHER INFORMATION: Engineered antibody sequence

<400> SEQUENCE: 221
```

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 222
<211> LENGTH: 113
<212> TYPE: PRT
<213> ORGANISM: Artificial
<220> FEATURE:
<223> OTHER INFORMATION: Engineered antibody sequence

<400> SEQUENCE: 222
```

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
                100                 105                 110

Arg

<210> SEQ ID NO 223
<211> LENGTH: 22
<212> TYPE: PRT
<213> ORGANISM: Artificial
<220> FEATURE:
<223> OTHER INFORMATION: Engineered antibody sequence

<400> SEQUENCE: 223

Gln Val Leu Thr Gln Ser Pro Ser Ser Leu Ser Ala Ser Val Gly Asp
1               5                   10                  15

Arg Val Thr Ile Asn Cys
            20

<210> SEQ ID NO 224
<211> LENGTH: 13
<212> TYPE: PRT
<213> ORGANISM: Artificial
<220> FEATURE:
<223> OTHER INFORMATION: Engineered antibody sequence

<400> SEQUENCE: 224

Gln Ala Ser Gln Ser Val Tyr His Asn Thr Tyr Leu Ala
1               5                   10

<210> SEQ ID NO 225
<211> LENGTH: 15
<212> TYPE: PRT
<213> ORGANISM: Artificial
<220> FEATURE:
<223> OTHER INFORMATION: Engineered antibody sequence

<400> SEQUENCE: 225

Trp Tyr Gln Gln Lys Pro Gly Lys Val Pro Lys Gln Leu Ile Tyr
1               5                   10                  15

<210> SEQ ID NO 226
<211> LENGTH: 7
<212> TYPE: PRT
<213> ORGANISM: Artificial
<220> FEATURE:
<223> OTHER INFORMATION: Engineered antibody sequence

<400> SEQUENCE: 226

Asp Ala Ser Thr Leu Ala Ser
1               5

<210> SEQ ID NO 227
<211> LENGTH: 32

```
<212> TYPE: PRT
<213> ORGANISM: Artificial
<220> FEATURE:
<223> OTHER INFORMATION: Engineered antibody sequence

<400> SEQUENCE: 227

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 228
<211> LENGTH: 13
<212> TYPE: PRT
<213> ORGANISM: Artificial
<220> FEATURE:
<223> OTHER INFORMATION: Engineered antibody sequence

<400> SEQUENCE: 228

Leu Gly Ser Tyr Asp Cys Thr Asn Gly Asp Cys Phe Val
1               5                   10

<210> SEQ ID NO 229
<211> LENGTH: 11
<212> TYPE: PRT
<213> ORGANISM: Artificial
<220> FEATURE:
<223> OTHER INFORMATION: Engineered antibody sequence

<400> SEQUENCE: 229

Phe Gly Gly Gly Thr Lys Val Glu Ile Lys Arg
1               5                   10

<210> SEQ ID NO 230
<211> LENGTH: 106
<212> TYPE: PRT
<213> ORGANISM: Artificial
<220> FEATURE:
<223> OTHER INFORMATION: Engineered antibody sequence

<400> SEQUENCE: 230

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 231
<211> LENGTH: 660
<212> TYPE: DNA
<213> ORGANISM: Artificial
<220> FEATURE:
<223> OTHER INFORMATION: Engineered antibody sequence

<400> SEQUENCE: 231
```

```
caagtgctga cccagtctcc atcctccctg tctgcatctg taggagacag agtcaccatc    60
aattgccagg ccagtcagag tgtttatcat aacacctacc tggcctggta tcagcagaaa   120
ccagggaaag ttcctaagca actgatctat gatgcatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtactaa tggtgattgt   300
tttgttttcg gcggaggaac caaggtggaa atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660
```

<210> SEQ ID NO 232
<211> LENGTH: 339
<212> TYPE: DNA
<213> ORGANISM: Artificial
<220> FEATURE:
<223> OTHER INFORMATION: Engineered antibody sequence

<400> SEQUENCE: 232

```
caagtgctga cccagtctcc atcctccctg tctgcatctg taggagacag agtcaccatc    60
aattgccagg ccagtcagag tgtttatcat aacacctacc tggcctggta tcagcagaaa   120
ccagggaaag ttcctaagca actgatctat gatgcatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtactaa tggtgattgt   300
tttgttttcg gcggaggaac caaggtggaa atcaaacgt                          339
```

<210> SEQ ID NO 233
<211> LENGTH: 66
<212> TYPE: DNA
<213> ORGANISM: Artificial
<220> FEATURE:
<223> OTHER INFORMATION: Engineered antibody sequence

<400> SEQUENCE: 233

```
caagtgctga cccagtctcc atcctccctg tctgcatctg taggagacag agtcaccatc    60
aattgc                                                               66
```

<210> SEQ ID NO 234
<211> LENGTH: 39
<212> TYPE: DNA
<213> ORGANISM: Artificial
<220> FEATURE:
<223> OTHER INFORMATION: Engineered antibody sequence

<400> SEQUENCE: 234

```
caggccagtc agagtgttta tcataacacc tacctggcc                           39
```

<210> SEQ ID NO 235
<211> LENGTH: 45
<212> TYPE: DNA
<213> ORGANISM: Artificial
<220> FEATURE:
<223> OTHER INFORMATION: Engineered antibody sequence

<400> SEQUENCE: 235
tggtatcagc agaaaccagg gaaagttcct aagcaactga tctat        45

<210> SEQ ID NO 236
<211> LENGTH: 21
<212> TYPE: DNA
<213> ORGANISM: Artificial
<220> FEATURE:
<223> OTHER INFORMATION: Engineered antibody sequence

<400> SEQUENCE: 236
gatgcatcca ctctggcatc t        21

<210> SEQ ID NO 237
<211> LENGTH: 96
<212> TYPE: DNA
<213> ORGANISM: Artificial
<220> FEATURE:
<223> OTHER INFORMATION: Engineered antibody sequence

<400> SEQUENCE: 237
ggggtcccat ctcgtttcag tggcagtgga tctgggacag atttcactct caccatcagc        60
agcctgcagc ctgaagatgt tgcaacttat tactgt        96

<210> SEQ ID NO 238
<211> LENGTH: 39
<212> TYPE: DNA
<213> ORGANISM: Artificial
<220> FEATURE:
<223> OTHER INFORMATION: Engineered antibody sequence

<400> SEQUENCE: 238
ctgggcagtt atgattgtac taatggtgat tgttttgtt        39

<210> SEQ ID NO 239
<211> LENGTH: 33
<212> TYPE: DNA
<213> ORGANISM: Artificial
<220> FEATURE:
<223> OTHER INFORMATION: Engineered antibody sequence

<400> SEQUENCE: 239
ttcggcggag gaaccaaggt ggaaatcaaa cgt        33

<210> SEQ ID NO 240
<211> LENGTH: 321
<212> TYPE: DNA
<213> ORGANISM: Artificial
<220> FEATURE:
<223> OTHER INFORMATION: Engineered antibody sequence

<400> SEQUENCE: 240
acggtggctg caccatctgt cttcatcttc ccgccatctg atgagcagtt gaaatctgga        60
actgcctctg ttgtgtgcct gctgaataac ttctatccca gagaggccaa agtacagtgg        120
aaggtggata acgccctcca atcgggtaac tcccaggaga gtgtcacaga gcaggacagc        180
aaggacagca cctacagcct cagcagcacc ctgacgctga gcaaagcaga ctacgagaaa        240
cacaaagtct acgcctgcga agtcacccat cagggcctga gctcgcccgt cacaaagagc        300
ttcaacaggg gagagtgtta g        321

<210> SEQ ID NO 241
<211> LENGTH: 440

```
<212> TYPE: PRT
<213> ORGANISM: Artificial
<220> FEATURE:
<223> OTHER INFORMATION: Engineered antibody sequence

<400> SEQUENCE: 241
```

| | | | | | | | | | | | | | | |
|---|---|---|---|---|---|---|---|---|---|---|---|---|---|---|
| Gln | Glu | Gln | Leu | Lys | Glu | Ser | Gly | Gly | Arg | Leu | Val | Thr | Pro | Gly | Thr |
| 1 | | | | 5 | | | | | 10 | | | | | 15 | |
| Ser | Leu | Thr | Leu | Thr | Cys | Thr | Val | Ser | Gly | Ile | Asp | Leu | Ser | Asn | His |
| | | | 20 | | | | | 25 | | | | | 30 | | |
| Tyr | Met | Gln | Trp | Val | Arg | Gln | Ala | Pro | Gly | Lys | Gly | Leu | Glu | Trp | Ile |
| | | | 35 | | | | | 40 | | | | | 45 | | |
| Gly | Val | Val | Gly | Ile | Asn | Gly | Arg | Thr | Tyr | Tyr | Ala | Ser | Trp | Ala | Lys |
| | 50 | | | | | 55 | | | | | 60 | | | | |
| Gly | Arg | Phe | Thr | Ile | Ser | Arg | Thr | Ser | Ser | Thr | Thr | Val | Asp | Leu | Lys |
| 65 | | | | | 70 | | | | | 75 | | | | | 80 |
| Met | Thr | Arg | Leu | Thr | Thr | Glu | Asp | Thr | Ala | Thr | Tyr | Phe | Cys | Ala | Arg |
| | | | | 85 | | | | | 90 | | | | | 95 | |
| Gly | Asp | Ile | Trp | Gly | Pro | Gly | Thr | Leu | Val | Thr | Val | Ser | Ser | Ala | Ser |
| | | | 100 | | | | | 105 | | | | | 110 | | |
| Thr | Lys | Gly | Pro | Ser | Val | Phe | Pro | Leu | Ala | Pro | Ser | Ser | Lys | Ser | Thr |
| | | | 115 | | | | | 120 | | | | | 125 | | |
| Ser | Gly | Gly | Thr | Ala | Ala | Leu | Gly | Cys | Leu | Val | Lys | Asp | Tyr | Phe | Pro |
| | 130 | | | | | 135 | | | | | 140 | | | | |
| Glu | Pro | Val | Thr | Val | Ser | Trp | Asn | Ser | Gly | Ala | Leu | Thr | Ser | Gly | Val |
| 145 | | | | | 150 | | | | | 155 | | | | | 160 |
| His | Thr | Phe | Pro | Ala | Val | Leu | Gln | Ser | Ser | Gly | Leu | Tyr | Ser | Leu | Ser |
| | | | | 165 | | | | | 170 | | | | | 175 | |
| Ser | Val | Val | Thr | Val | Pro | Ser | Ser | Ser | Leu | Gly | Thr | Gln | Thr | Tyr | Ile |
| | | | 180 | | | | | 185 | | | | | 190 | | |
| Cys | Asn | Val | Asn | His | Lys | Pro | Ser | Asn | Thr | Lys | Val | Asp | Lys | Arg | Val |
| | | | 195 | | | | | 200 | | | | | 205 | | |
| Glu | Pro | Lys | Ser | Cys | Asp | Lys | Thr | His | Thr | Cys | Pro | Pro | Cys | Pro | Ala |
| | 210 | | | | | 215 | | | | | 220 | | | | |
| Pro | Glu | Leu | Leu | Gly | Gly | Pro | Ser | Val | Phe | Leu | Phe | Pro | Pro | Lys | Pro |
| 225 | | | | | 230 | | | | | 235 | | | | | 240 |
| Lys | Asp | Thr | Leu | Met | Ile | Ser | Arg | Thr | Pro | Glu | Val | Thr | Cys | Val | Val |
| | | | | 245 | | | | | 250 | | | | | 255 | |
| Val | Asp | Val | Ser | His | Glu | Asp | Pro | Glu | Val | Lys | Phe | Asn | Trp | Tyr | Val |
| | | | 260 | | | | | 265 | | | | | 270 | | |
| Asp | Gly | Val | Glu | Val | His | Asn | Ala | Lys | Thr | Lys | Pro | Arg | Glu | Glu | Gln |
| | | | 275 | | | | | 280 | | | | | 285 | | |
| Tyr | Ala | Ser | Thr | Tyr | Arg | Val | Val | Ser | Val | Leu | Thr | Val | Leu | His | Gln |
| | 290 | | | | | 295 | | | | | 300 | | | | |
| Asp | Trp | Leu | Asn | Gly | Lys | Glu | Tyr | Lys | Cys | Lys | Val | Ser | Asn | Lys | Ala |
| 305 | | | | | 310 | | | | | 315 | | | | | 320 |
| Leu | Pro | Ala | Pro | Ile | Glu | Lys | Thr | Ile | Ser | Lys | Ala | Lys | Gly | Gln | Pro |
| | | | | 325 | | | | | 330 | | | | | 335 | |
| Arg | Glu | Pro | Gln | Val | Tyr | Thr | Leu | Pro | Pro | Ser | Arg | Glu | Glu | Met | Thr |
| | | | 340 | | | | | 345 | | | | | 350 | | |
| Lys | Asn | Gln | Val | Ser | Leu | Thr | Cys | Leu | Val | Lys | Gly | Phe | Tyr | Pro | Ser |
| | | | 355 | | | | | 360 | | | | | 365 | | |
| Asp | Ile | Ala | Val | Glu | Trp | Glu | Ser | Asn | Gly | Gln | Pro | Glu | Asn | Asn | Tyr |
| | 370 | | | | | 375 | | | | | 380 | | | | |

```
Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
                420                 425                 430

Ser Leu Ser Leu Ser Pro Gly Lys
            435                 440

<210> SEQ ID NO 242
<211> LENGTH: 110
<212> TYPE: PRT
<213> ORGANISM: Artificial
<220> FEATURE:
<223> OTHER INFORMATION: Engineered antibody sequence

<400> SEQUENCE: 242

Gln Glu Gln Leu Lys Glu Ser Gly Gly Arg Leu Val Thr Pro Gly Thr
1               5                   10                  15

Ser Leu Thr Leu Thr Cys Thr Val Ser Gly Ile Asp Leu Ser Asn His
                20                  25                  30

Tyr Met Gln Trp Val Arg Gln Ala Pro Gly Lys Gly Leu Glu Trp Ile
            35                  40                  45

Gly Val Val Gly Ile Asn Gly Arg Thr Tyr Tyr Ala Ser Trp Ala Lys
        50                  55                  60

Gly Arg Phe Thr Ile Ser Arg Thr Ser Thr Thr Val Asp Leu Lys
65                  70                  75                  80

Met Thr Arg Leu Thr Thr Glu Asp Thr Ala Thr Tyr Phe Cys Ala Arg
                85                  90                  95

Gly Asp Ile Trp Gly Pro Gly Thr Leu Val Thr Val Ser Ser
            100                 105                 110

<210> SEQ ID NO 243
<211> LENGTH: 30
<212> TYPE: PRT
<213> ORGANISM: Artificial
<220> FEATURE:
<223> OTHER INFORMATION: Engineered antibody sequence

<400> SEQUENCE: 243

Gln Glu Gln Leu Lys Glu Ser Gly Gly Arg Leu Val Thr Pro Gly Thr
1               5                   10                  15

Ser Leu Thr Leu Thr Cys Thr Val Ser Gly Ile Asp Leu Ser
                20                  25                  30

<210> SEQ ID NO 244
<211> LENGTH: 5
<212> TYPE: PRT
<213> ORGANISM: Artificial
<220> FEATURE:
<223> OTHER INFORMATION: Engineered antibody sequence

<400> SEQUENCE: 244

Asn His Tyr Met Gln
1               5

<210> SEQ ID NO 245
<211> LENGTH: 14
<212> TYPE: PRT
<213> ORGANISM: Artificial
<220> FEATURE:
<223> OTHER INFORMATION: Engineered antibody sequence
```

```
<400> SEQUENCE: 245

Trp Val Arg Gln Ala Pro Gly Lys Gly Leu Glu Trp Ile Gly
1               5                   10

<210> SEQ ID NO 246
<211> LENGTH: 16
<212> TYPE: PRT
<213> ORGANISM: Artificial
<220> FEATURE:
<223> OTHER INFORMATION: Engineered antibody sequence

<400> SEQUENCE: 246

Val Val Gly Ile Asn Gly Arg Thr Tyr Tyr Ala Ser Trp Ala Lys Gly
1               5                   10                  15

<210> SEQ ID NO 247
<211> LENGTH: 31
<212> TYPE: PRT
<213> ORGANISM: Artificial
<220> FEATURE:
<223> OTHER INFORMATION: Engineered antibody sequence

<400> SEQUENCE: 247

Arg Phe Thr Ile Ser Arg Thr Ser Ser Thr Thr Val Asp Leu Lys Met
1               5                   10                  15
Thr Arg Leu Thr Thr Glu Asp Thr Ala Thr Tyr Phe Cys Ala Arg
            20                  25                  30

<210> SEQ ID NO 248
<211> LENGTH: 3
<212> TYPE: PRT
<213> ORGANISM: Artificial
<220> FEATURE:
<223> OTHER INFORMATION: Engineered antibody sequence

<400> SEQUENCE: 248

Gly Asp Ile
1

<210> SEQ ID NO 249
<211> LENGTH: 11
<212> TYPE: PRT
<213> ORGANISM: Artificial
<220> FEATURE:
<223> OTHER INFORMATION: Engineered antibody sequence

<400> SEQUENCE: 249

Trp Gly Pro Gly Thr Leu Val Thr Val Ser Ser
1               5                   10

<210> SEQ ID NO 250
<211> LENGTH: 330
<212> TYPE: PRT
<213> ORGANISM: Artificial
<220> FEATURE:
<223> OTHER INFORMATION: Engineered antibody sequence

<400> SEQUENCE: 250

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 251
<211> LENGTH: 1323
<212> TYPE: DNA
<213> ORGANISM: Artificial
<220> FEATURE:
<223> OTHER INFORMATION: Engineered antibody sequence

<400> SEQUENCE: 251
caggagcagc tgaaggagtc cggggggtcgc ctggtcacgc ctgggacatc cctgacactc      60
acctgcaccg tctctggaat cgacctcagt aaccactaca tgcaatgggt ccgccaggct     120
ccagggaagg ggctggagtg gatcggagtc gttggtatta atggtcgcac atactacgcg     180
agctgggcga aaggccgatt caccatctcc agaacctcgt cgaccacggt ggatctgaaa     240
atgaccaggc tgacaaccga ggacacggcc acctatttct gtgccagagg ggacatctgg     300
ggcccaggca ccctggtcac cgtctcgagc gcctccacca agggcccatc ggtcttcccc     360
ctggcaccct cctccaagag cacctctggg ggcacagcgg ccctgggctg cctggtcaag     420

```
gactacttcc ccgaaccggt gacggtgtcg tggaactcag gcgccctgac cagcggcgtg    480
cacaccttcc cggctgtcct acagtcctca ggactctact ccctcagcag cgtggtgacc    540
gtgccctcca gcagcttggg cacccagacc tacatctgca acgtgaatca caagcccagc    600
aacaccaagg tggacaagag agttgagccc aaatcttgtg acaaaactca cacatgccca    660
ccgtgcccag cacctgaact cctgggggga ccgtcagtct tcctcttccc cccaaaaccc    720
aaggacaccc tcatgatctc ccggacccct gaggtcacat gcgtggtggt ggacgtgagc    780
cacgaagacc ctgaggtcaa gttcaactgg tacgtggacg gcgtggaggt gcataatgcc    840
aagacaaagc cgcgggagga gcagtacgcc agcacgtacc gtgtggtcag cgtcctcacc    900
gtcctgcacc aggactggct gaatggcaag gagtacaagt gcaaggtctc caacaaagcc    960
ctcccagccc ccatcgagaa aaccatctcc aaagccaaag gcagccccg agaaccacag    1020
gtgtacaccc tgcccccatc ccgggaggag atgaccaaga accaggtcag cctgacctgc    1080
ctggtcaaag gcttctatcc cagcgacatc gccgtggagt gggagagcaa tgggcagccg    1140
gagaacaact acaagaccac gcctcccgtg ctggactccg acggctcctt cttcctctac    1200
agcaagctca ccgtggacaa gagcaggtgg cagcagggga acgtcttctc atgctccgtg    1260
atgcatgagg ctctgcacaa ccactacacg cagaagagcc tctccctgtc tccgggtaaa    1320
tga                                                                  1323

<210> SEQ ID NO 252
<211> LENGTH: 330
<212> TYPE: DNA
<213> ORGANISM: Artificial
<220> FEATURE:
<223> OTHER INFORMATION: Engineered antibody sequence

<400> SEQUENCE: 252
caggagcagc tgaaggagtc cggggtcgc ctggtcacgc ctgggacatc cctgacactc    60
acctgcaccg tctctggaat cgacctcagt aaccactaca tgcaatgggt ccgccaggct    120
ccagggaagg gctggagtg atcggagtc gttggtatta atggtcgcac atactacgcg     180
agctgggcga aaggccgatt caccatctcc agaacctcgt cgaccacggt ggatctgaaa    240
atgaccaggc tgacaaccga ggacacggcc acctatttct gtgccagagg ggacatctgg    300
ggcccaggca ccctggtcac cgtctcgagc                                     330

<210> SEQ ID NO 253
<211> LENGTH: 90
<212> TYPE: DNA
<213> ORGANISM: Artificial
<220> FEATURE:
<223> OTHER INFORMATION: Engineered antibody sequence

<400> SEQUENCE: 253
caggagcagc tgaaggagtc cggggtcgc ctggtcacgc ctgggacatc cctgacactc    60
acctgcaccg tctctggaat cgacctcagt                                    90

<210> SEQ ID NO 254
<211> LENGTH: 15
<212> TYPE: DNA
<213> ORGANISM: Artificial
<220> FEATURE:
<223> OTHER INFORMATION: Engineered antibody sequence

<400> SEQUENCE: 254
aaccactaca tgcaa                                                     15
```

<210> SEQ ID NO 255
<211> LENGTH: 42
<212> TYPE: DNA
<213> ORGANISM: Artificial
<220> FEATURE:
<223> OTHER INFORMATION: Engineered antibody sequence

<400> SEQUENCE: 255
tgggtccgcc aggctccagg gaaggggctg gagtggatcg ga                42

<210> SEQ ID NO 256
<211> LENGTH: 48
<212> TYPE: DNA
<213> ORGANISM: Artificial
<220> FEATURE:
<223> OTHER INFORMATION: Engineered antibody sequence

<400> SEQUENCE: 256
gtcgttggta ttaatggtcg cacatactac gcgagctggg cgaaaggc         48

<210> SEQ ID NO 257
<211> LENGTH: 93
<212> TYPE: DNA
<213> ORGANISM: Artificial
<220> FEATURE:
<223> OTHER INFORMATION: Engineered antibody sequence

<400> SEQUENCE: 257
cgattcacca tctccagaac ctcgtcgacc acggtggatc tgaaaatgac caggctgaca    60
accgaggaca cggccaccta tttctgtgcc aga                                 93

<210> SEQ ID NO 258
<211> LENGTH: 9
<212> TYPE: DNA
<213> ORGANISM: Artificial
<220> FEATURE:
<223> OTHER INFORMATION: Engineered antibody sequence

<400> SEQUENCE: 258 ggggacatc                                                       9

<210> SEQ ID NO 259
<211> LENGTH: 33
<212> TYPE: DNA
<213> ORGANISM: Artificial
<220> FEATURE:
<223> OTHER INFORMATION: Engineered antibody sequence

<400> SEQUENCE: 259
tggggcccag gcaccctggt caccgtctcg agc                            33

<210> SEQ ID NO 260
<211> LENGTH: 993
<212> TYPE: DNA
<213> ORGANISM: Artificial
<220> FEATURE:
<223> OTHER INFORMATION: Engineered antibody sequence

<400> SEQUENCE: 260
gcctccacca agggcccatc ggtcttcccc ctggcaccct cctccaagag cacctctggg    60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180

```
ggactctact ccctcagcag cgtggtgacc gtgccctcca gcagcttggg cacccagacc    240
tacatctgca acgtgaatca caagcccagc aacaccaagg tggacaagag agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcggaggga gcagtacgcc    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa tga                                 993
```

<210> SEQ ID NO 261
<211> LENGTH: 219
<212> TYPE: PRT
<213> ORGANISM: Artificial
<220> FEATURE:
<223> OTHER INFORMATION: Engineered antibody sequence

<400> SEQUENCE: 261

Gln Val Leu Thr Gln Thr Ala Ser Pro Val Ser Ala Ala Val Gly Ser
1               5                   10                  15

Thr Val Thr Ile Asn Cys Gln Ala Ser Gln Ser Val Tyr Asn Tyr Asn
            20                  25                  30

Tyr Leu Ala Trp Tyr Gln Gln Lys Pro Gly Gln Pro Pro Lys Gln Leu
        35                  40                  45

Ile Tyr Ser Thr Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Ser Tyr Asp Cys Ser
                85                  90                  95

Thr Gly Asp Cys Phe Val Phe Gly Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 262
<211> LENGTH: 113
<212> TYPE: PRT
<213> ORGANISM: Artificial
<220> FEATURE:
<223> OTHER INFORMATION: Engineered antibody sequence

<400> SEQUENCE: 262

Gln Val Leu Thr Gln Thr Ala Ser Pro Val Ser Ala Ala Val Gly Ser
1               5                   10                  15

Thr Val Thr Ile Asn Cys Gln Ala Ser Gln Ser Val Tyr Asn Tyr Asn
            20                  25                  30

Tyr Leu Ala Trp Tyr Gln Gln Lys Pro Gly Gln Pro Pro Lys Gln Leu
        35                  40                  45

Ile Tyr Ser Thr Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Ser Tyr Asp Cys Ser
                85                  90                  95

Thr Gly Asp Cys Phe Val Phe Gly Gly Thr Glu Val Val Val Lys
            100                 105                 110

Arg

<210> SEQ ID NO 263
<211> LENGTH: 22
<212> TYPE: PRT
<213> ORGANISM: Artificial
<220> FEATURE:
<223> OTHER INFORMATION: Engineered antibody sequence

<400> SEQUENCE: 263

Gln Val Leu Thr Gln Thr Ala Ser Pro Val Ser Ala Ala Val Gly Ser
1               5                   10                  15

Thr Val Thr Ile Asn Cys
            20

<210> SEQ ID NO 264
<211> LENGTH: 13
<212> TYPE: PRT
<213> ORGANISM: Artificial
<220> FEATURE:
<223> OTHER INFORMATION: Engineered antibody sequence

<400> SEQUENCE: 264

Gln Ala Ser Gln Ser Val Tyr Asn Tyr Asn Tyr Leu Ala
1               5                   10

<210> SEQ ID NO 265
<211> LENGTH: 15
<212> TYPE: PRT
<213> ORGANISM: Artificial
<220> FEATURE:
<223> OTHER INFORMATION: Engineered antibody sequence

<400> SEQUENCE: 265

Trp Tyr Gln Gln Lys Pro Gly Gln Pro Pro Lys Gln Leu Ile Tyr
1               5                   10                  15

<210> SEQ ID NO 266
<211> LENGTH: 7

<212> TYPE: PRT
<213> ORGANISM: Artificial
<220> FEATURE:
<223> OTHER INFORMATION: Engineered antibody sequence

<400> SEQUENCE: 266

Ser Thr Ser Thr Leu Ala Ser
1               5

<210> SEQ ID NO 267
<211> LENGTH: 32
<212> TYPE: PRT
<213> ORGANISM: Artificial
<220> FEATURE:
<223> OTHER INFORMATION: Engineered antibody sequence

<400> SEQUENCE: 267

Gly Val Ser Ser Arg Phe Lys Gly Ser Gly Ser Gly Thr Gln Phe Thr
1               5                   10                  15

Leu Thr Ile Ser Asp Val Gln Cys Asp Asp Ala Ala Thr Tyr Tyr Cys
            20                  25                  30

<210> SEQ ID NO 268
<211> LENGTH: 13
<212> TYPE: PRT
<213> ORGANISM: Artificial
<220> FEATURE:
<223> OTHER INFORMATION: Engineered antibody sequence

<400> SEQUENCE: 268

Leu Gly Ser Tyr Asp Cys Ser Thr Gly Asp Cys Phe Val
1               5                   10

<210> SEQ ID NO 269
<211> LENGTH: 11
<212> TYPE: PRT
<213> ORGANISM: Artificial
<220> FEATURE:
<223> OTHER INFORMATION: Engineered antibody sequence

<400> SEQUENCE: 269

Phe Gly Gly Gly Thr Glu Val Val Val Lys Arg
1               5                   10

<210> SEQ ID NO 270
<211> LENGTH: 106
<212> TYPE: PRT
<213> ORGANISM: Artificial
<220> FEATURE:
<223> OTHER INFORMATION: Engineered antibody sequence

<400> SEQUENCE: 270

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 271
<211> LENGTH: 660
<212> TYPE: DNA
<213> ORGANISM: Artificial
<220> FEATURE:
<223> OTHER INFORMATION: Engineered antibody sequence

<400> SEQUENCE: 271
caagtgctga cccagactgc atccccgtg tctgcagctg tgggaagcac agtcaccatc      60
aattgccagg ccagtcagag tgtttataat tacaactacc ttgcctggta tcagcagaaa    120
ccagggcagc ctcccaagca actgatctat tctacatcca ctctggcatc tggggtctca    180
tcgcgattca aaggcagtgg atctgggaca cagttcactc tcaccatcag cgacgtgcag    240
tgtgacgatg ctgccactta ctactgtcta ggcagttatg actgtagtac tggtgattgt    300
tttgttttcg gcggagggac cgaggtggtg gtcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660

<210> SEQ ID NO 272
<211> LENGTH: 339
<212> TYPE: DNA
<213> ORGANISM: Artificial
<220> FEATURE:
<223> OTHER INFORMATION: Engineered antibody sequence

<400> SEQUENCE: 272
caagtgctga cccagactgc atccccgtg tctgcagctg tgggaagcac agtcaccatc      60
aattgccagg ccagtcagag tgtttataat tacaactacc ttgcctggta tcagcagaaa    120
ccagggcagc ctcccaagca actgatctat tctacatcca ctctggcatc tggggtctca    180
tcgcgattca aaggcagtgg atctgggaca cagttcactc tcaccatcag cgacgtgcag    240
tgtgacgatg ctgccactta ctactgtcta ggcagttatg actgtagtac tggtgattgt    300
tttgttttcg gcggagggac cgaggtggtg gtcaaacgt                            339

<210> SEQ ID NO 273
<211> LENGTH: 66
<212> TYPE: DNA
<213> ORGANISM: Artificial
<220> FEATURE:
<223> OTHER INFORMATION: Engineered antibody sequence

<400> SEQUENCE: 273
caagtgctga cccagactgc atccccgtg tctgcagctg tgggaagcac agtcaccatc      60
aattgc                                                                66

<210> SEQ ID NO 274
<211> LENGTH: 39
<212> TYPE: DNA
<213> ORGANISM: Artificial
<220> FEATURE:
<223> OTHER INFORMATION: Engineered antibody sequence

<400> SEQUENCE: 274
caggccagtc agagtgttta taattacaac taccttgcc        39

<210> SEQ ID NO 275
<211> LENGTH: 45
<212> TYPE: DNA
<213> ORGANISM: Artificial
<220> FEATURE:
<223> OTHER INFORMATION: Engineered antibody sequence

<400> SEQUENCE: 275
tggtatcagc agaaaccagg gcagcctccc aagcaactga tctat        45

<210> SEQ ID NO 276
<211> LENGTH: 21
<212> TYPE: DNA
<213> ORGANISM: Artificial
<220> FEATURE:
<223> OTHER INFORMATION: Engineered antibody sequence

<400> SEQUENCE: 276
tctacatcca ctctggcatc t        21

<210> SEQ ID NO 277
<211> LENGTH: 96
<212> TYPE: DNA
<213> ORGANISM: Artificial
<220> FEATURE:
<223> OTHER INFORMATION: Engineered antibody sequence

<400> SEQUENCE: 277
ggggtctcat cgcgattcaa aggcagtgga tctgggacac agttcactct caccatcagc        60
gacgtgcagt gtgacgatgc tgccacttac tactgt        96

<210> SEQ ID NO 278
<211> LENGTH: 39
<212> TYPE: DNA
<213> ORGANISM: Artificial
<220> FEATURE:
<223> OTHER INFORMATION: Engineered antibody sequence

<400> SEQUENCE: 278
ctaggcagtt atgactgtag tactggtgat tgttttgtt        39

<210> SEQ ID NO 279
<211> LENGTH: 33
<212> TYPE: DNA
<213> ORGANISM: Artificial
<220> FEATURE:
<223> OTHER INFORMATION: Engineered antibody sequence

<400> SEQUENCE: 279
ttcggcggag ggaccgaggt ggtggtcaaa cgt        33

<210> SEQ ID NO 280
<211> LENGTH: 321
<212> TYPE: DNA
<213> ORGANISM: Artificial
<220> FEATURE:
<223> OTHER INFORMATION: Engineered antibody sequence

<400> SEQUENCE: 280
acggtggctg caccatctgt cttcatcttc ccgccatctg atgagcagtt gaaatctgga        60

```
actgcctctg ttgtgtgcct gctgaataac ttctatccca gagaggccaa agtacagtgg      120
aaggtggata cgccctcca atcgggtaac tcccaggaga gtgtcacaga gcaggacagc       180
aaggacagca cctacagcct cagcagcacc ctgacgctga gcaaagcaga ctacgagaaa      240
cacaaagtct acgcctgcga agtcacccat cagggcctga gctcgcccgt cacaaagagc      300
ttcaacaggg gagagtgtta g                                                321
```

<210> SEQ ID NO 281
<211> LENGTH: 441
<212> TYPE: PRT
<213> ORGANISM: Artificial
<220> FEATURE:
<223> OTHER INFORMATION: Engineered antibody sequence

<400> SEQUENCE: 281

```
Glu Val Gln Leu Val Glu Ser Gly Gly Gly Leu Val Gln Pro Gly Gly
  1               5                  10                  15

Ser Leu Arg Leu Ser Cys Ala Val Ser Gly Ile Asp Leu Ser Asn His
             20                  25                  30

Tyr Met Gln Trp Val Arg Gln Ala Pro Gly Lys Gly Leu Glu Trp Val
         35                  40                  45

Gly Val Val Gly Ile Asn Gly Arg Thr Tyr Tyr Ala Ser Trp Ala Lys
     50                  55                  60

Gly Arg Phe Thr Ile Ser Arg Asp Asn Ser Lys Thr Thr Val Tyr Leu
 65                  70                  75                  80

Gln Met Asn Ser Leu Arg Ala Glu Asp Thr Ala Val Tyr Phe Cys Ala
                 85                  90                  95

Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Arg
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320
```

```
Ala Leu Pro Ala Pro Ile Glu Lys Thr Ile Ser Lys Ala Lys Gly Gln
            325                 330                 335

Pro Arg Glu Pro Gln Val Tyr Thr Leu Pro Pro Ser Arg Glu Glu Met
        340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 282
<211> LENGTH: 111
<212> TYPE: PRT
<213> ORGANISM: Artificial
<220> FEATURE:
<223> OTHER INFORMATION: Engineered antibody sequence

<400> SEQUENCE: 282

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Asn His
            20                  25                  30

Tyr Met Gln Trp Val Arg Gln Ala Pro Gly Lys Gly Leu Glu Trp Val
        35                  40                  45

Gly Val Val Gly Ile Asn Gly Arg Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110

<210> SEQ ID NO 283
<211> LENGTH: 30
<212> TYPE: PRT
<213> ORGANISM: Artificial
<220> FEATURE:
<223> OTHER INFORMATION: Engineered antibody sequence

<400> SEQUENCE: 283

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser
            20                  25                  30

<210> SEQ ID NO 284
<211> LENGTH: 5
<212> TYPE: PRT
<213> ORGANISM: Artificial
<220> FEATURE:
<223> OTHER INFORMATION: Engineered antibody sequence
```

<400> SEQUENCE: 284

Asn His Tyr Met Gln
1               5

<210> SEQ ID NO 285
<211> LENGTH: 14
<212> TYPE: PRT
<213> ORGANISM: Artificial
<220> FEATURE:
<223> OTHER INFORMATION: Engineered antibody sequence

<400> SEQUENCE: 285

Trp Val Arg Gln Ala Pro Gly Lys Gly Leu Glu Trp Val Gly
1               5                   10

<210> SEQ ID NO 286
<211> LENGTH: 16
<212> TYPE: PRT
<213> ORGANISM: Artificial
<220> FEATURE:
<223> OTHER INFORMATION: Engineered antibody sequence

<400> SEQUENCE: 286

Val Val Gly Ile Asn Gly Arg Thr Tyr Tyr Ala Ser Trp Ala Lys Gly
1               5                   10                  15

<210> SEQ ID NO 287
<211> LENGTH: 32
<212> TYPE: PRT
<213> ORGANISM: Artificial
<220> FEATURE:
<223> OTHER INFORMATION: Engineered antibody sequence

<400> SEQUENCE: 287

Arg Phe Thr Ile Ser Arg Asp Asn Ser Lys Thr Thr Val Tyr Leu Gln
1               5                   10                  15

Met Asn Ser Leu Arg Ala Glu Asp Thr Ala Val Tyr Phe Cys Ala Arg
            20                  25                  30

<210> SEQ ID NO 288
<211> LENGTH: 3
<212> TYPE: PRT
<213> ORGANISM: Artificial
<220> FEATURE:
<223> OTHER INFORMATION: Engineered antibody sequence

<400> SEQUENCE: 288

Gly Asp Ile
1

<210> SEQ ID NO 289
<211> LENGTH: 11
<212> TYPE: PRT
<213> ORGANISM: Artificial
<220> FEATURE:
<223> OTHER INFORMATION: Engineered antibody sequence

<400> SEQUENCE: 289

Trp Gly Gln Gly Thr Leu Val Thr Val Ser Ser
1               5                   10

<210> SEQ ID NO 290
<211> LENGTH: 330
<212> TYPE: PRT
<213> ORGANISM: Artificial
<220> FEATURE:
<223> OTHER INFORMATION: Engineered antibody sequence

<400> SEQUENCE: 290

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 291
<211> LENGTH: 1326
<212> TYPE: DNA
<213> ORGANISM: Artificial
<220> FEATURE:
<223> OTHER INFORMATION: Engineered antibody sequence

<400> SEQUENCE: 291
gaggtgcagc ttgtggagtc tgggggaggc ttggtccagc ctggggggtc cctgagactc    60

| | |
|---|---|
| tcctgtgcag tctctggaat cgacctcagt aaccactaca tgcaatgggt ccgtcaggct | 120 |
| ccagggaagg ggctggagtg ggtcggagtc gttggtatca atggtcgcac atactacgcg | 180 |
| agctgggcga aaggccgatt caccatctcc agagacaatt ccaagaccac ggtgtatctt | 240 |
| caaatgaaca gcctgagagc tgaggacact gctgtgtatt tctgtgctag aggggacatc | 300 |
| tggggccaag ggaccctcgt caccgtctcg agcgcctcca ccaagggccc atcggtcttc | 360 |
| cccctggcac cctcctccaa gagcacctct ggggcacag cggccctggg ctgcctggtc | 420 |
| aaggactact tccccgaacc ggtgacggtg tcgtggaact caggcgccct gaccagcggc | 480 |
| gtgcacacct tcccggctgt cctacagtcc tcaggactct actccctcag cagcgtggtg | 540 |
| accgtgccct ccagcagctt gggcacccag acctacatct gcaacgtgaa tcacaagccc | 600 |
| agcaacacca aggtggacaa gagagttgag cccaaatctt gtgacaaaac tcacacatgc | 660 |
| ccaccgtgcc cagcacctga actcctgggg gaccgtcag tcttcctctt ccccccaaaa | 720 |
| cccaaggaca ccctcatgat ctcccggacc cctgaggtca catgcgtggt ggtggacgtg | 780 |
| agccacgaag accctgaggt caagttcaac tggtacgtgg acggcgtgga ggtgcataat | 840 |
| gccaagacaa agccgcggga ggagcagtac gccagcacgt accgtgtggt cagcgtcctc | 900 |
| accgtcctgc accaggactg gctgaatggc aaggagtaca agtgcaaggt ctccaacaaa | 960 |
| gccctcccag cccccatcga gaaaaccatc tccaaagcca aagggcagcc ccgagaacca | 1020 |
| caggtgtaca ccctgccccc atcccgggag gagatgacca agaaccaggt cagcctgacc | 1080 |
| tgcctggtca aaggcttcta tcccagcgac atcgccgtgg agtgggagag caatgggcag | 1140 |
| ccggagaaca actacaagac cacgcctccc gtgctggact ccgacggctc cttcttcctc | 1200 |
| tacagcaagc tcaccgtgga caagagcagg tggcagcagg ggaacgtctt ctcatgctcc | 1260 |
| gtgatgcatg aggctctgca caaccactac acgcagaaga gcctctccct gtctccgggt | 1320 |
| aaatga | 1326 |

<210> SEQ ID NO 292
<211> LENGTH: 333
<212> TYPE: DNA
<213> ORGANISM: Artificial
<220> FEATURE:
<223> OTHER INFORMATION: Engineered antibody sequence

<400> SEQUENCE: 292

| | |
|---|---|
| gaggtgcagc ttgtggagtc tgggggaggc ttggtccagc ctgggggtc cctgagactc | 60 |
| tcctgtgcag tctctggaat cgacctcagt aaccactaca tgcaatgggt ccgtcaggct | 120 |
| ccagggaagg ggctggagtg ggtcggagtc gttggtatca atggtcgcac atactacgcg | 180 |
| agctgggcga aaggccgatt caccatctcc agagacaatt ccaagaccac ggtgtatctt | 240 |
| caaatgaaca gcctgagagc tgaggacact gctgtgtatt tctgtgctag aggggacatc | 300 |
| tggggccaag ggaccctcgt caccgtctcg agc | 333 |

<210> SEQ ID NO 293
<211> LENGTH: 90
<212> TYPE: DNA
<213> ORGANISM: Artificial
<220> FEATURE:
<223> OTHER INFORMATION: Engineered antibody sequence

<400> SEQUENCE: 293

| | |
|---|---|
| gaggtgcagc ttgtggagtc tgggggaggc ttggtccagc ctgggggtc cctgagactc | 60 |

```
tcctgtgcag tctctggaat cgacctcagt                                          90
```

<210> SEQ ID NO 294
<211> LENGTH: 15
<212> TYPE: DNA
<213> ORGANISM: Artificial
<220> FEATURE:
<223> OTHER INFORMATION: Engineered antibody sequence

<400> SEQUENCE: 294

```
aaccactaca tgcaa                                                          15
```

<210> SEQ ID NO 295
<211> LENGTH: 42
<212> TYPE: DNA
<213> ORGANISM: Artificial
<220> FEATURE:
<223> OTHER INFORMATION: Engineered antibody sequence

<400> SEQUENCE: 295

```
tgggtccgtc aggctccagg gaagggctg gagtgggtcg ga                             42
```

<210> SEQ ID NO 296
<211> LENGTH: 48
<212> TYPE: DNA
<213> ORGANISM: Artificial
<220> FEATURE:
<223> OTHER INFORMATION: Engineered antibody sequence

<400> SEQUENCE: 296

```
gtcgttggta tcaatggtcg cacatactac gcgagctggg cgaaaggc                      48
```

<210> SEQ ID NO 297
<211> LENGTH: 96
<212> TYPE: DNA
<213> ORGANISM: Artificial
<220> FEATURE:
<223> OTHER INFORMATION: Engineered antibody sequence

<400> SEQUENCE: 297

```
cgattcacca tctccagaga caattccaag accacggtgt atcttcaaat gaacagcctg         60
agagctgagg acactgctgt gtatttctgt gctaga                                   96
```

<210> SEQ ID NO 298
<211> LENGTH: 9
<212> TYPE: DNA
<213> ORGANISM: Artificial
<220> FEATURE:
<223> OTHER INFORMATION: Engineered antibody sequence

<400> SEQUENCE: 298

```
ggggacatc                                                                  9
```

<210> SEQ ID NO 299
<211> LENGTH: 33
<212> TYPE: DNA
<213> ORGANISM: Artificial
<220> FEATURE:
<223> OTHER INFORMATION: Engineered antibody sequence

<400> SEQUENCE: 299

```
tggggccaag ggaccctcgt caccgtctcg agc                                      33
```

<210> SEQ ID NO 300
<211> LENGTH: 993

<212> TYPE: DNA
<213> ORGANISM: Artificial
<220> FEATURE:
<223> OTHER INFORMATION: Engineered antibody sequence

<400> SEQUENCE: 300

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacgcc     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa tga                                  993
```

<210> SEQ ID NO 301
<211> LENGTH: 219
<212> TYPE: PRT
<213> ORGANISM: Artificial
<220> FEATURE:
<223> OTHER INFORMATION: Engineered antibody sequence

<400> SEQUENCE: 301

```
Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asn Tyr Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Thr Gly Asp Cys Phe Val Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
```

```
                 145                 150                 155                 160
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 302
<211> LENGTH: 113
<212> TYPE: PRT
<213> ORGANISM: Artificial
<220> FEATURE:
<223> OTHER INFORMATION: Engineered antibody sequence

<400> SEQUENCE: 302

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asn Tyr Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Thr Gly Asp Cys Phe Val Phe Gly Gly Thr Lys Val Glu Ile Lys
            100                 105                 110

Arg

<210> SEQ ID NO 303
<211> LENGTH: 22
<212> TYPE: PRT
<213> ORGANISM: Artificial
<220> FEATURE:
<223> OTHER INFORMATION: Engineered antibody sequence

<400> SEQUENCE: 303

Gln Val Leu Thr Gln Ser Pro Ser Ser Leu Ser Ala Ser Val Gly Asp
1               5                   10                  15

Arg Val Thr Ile Asn Cys
            20

<210> SEQ ID NO 304
<211> LENGTH: 13
<212> TYPE: PRT
<213> ORGANISM: Artificial
<220> FEATURE:
<223> OTHER INFORMATION: Engineered antibody sequence

<400> SEQUENCE: 304

Gln Ala Ser Gln Ser Val Tyr Asn Tyr Asn Tyr Leu Ala
1               5                   10

<210> SEQ ID NO 305
<211> LENGTH: 15
```

```
<212> TYPE: PRT
<213> ORGANISM: Artificial
<220> FEATURE:
<223> OTHER INFORMATION: Engineered antibody sequence

<400> SEQUENCE: 305

Trp Tyr Gln Gln Lys Pro Gly Lys Val Pro Lys Gln Leu Ile Tyr
1               5                   10                  15

<210> SEQ ID NO 306
<211> LENGTH: 7
<212> TYPE: PRT
<213> ORGANISM: Artificial
<220> FEATURE:
<223> OTHER INFORMATION: Engineered antibody sequence

<400> SEQUENCE: 306

Ser Thr Ser Thr Leu Ala Ser
1               5

<210> SEQ ID NO 307
<211> LENGTH: 32
<212> TYPE: PRT
<213> ORGANISM: Artificial
<220> FEATURE:
<223> OTHER INFORMATION: Engineered antibody sequence

<400> SEQUENCE: 307

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 308
<211> LENGTH: 13
<212> TYPE: PRT
<213> ORGANISM: Artificial
<220> FEATURE:
<223> OTHER INFORMATION: Engineered antibody sequence

<400> SEQUENCE: 308

Leu Gly Ser Tyr Asp Cys Ser Thr Gly Asp Cys Phe Val
1               5                   10

<210> SEQ ID NO 309
<211> LENGTH: 11
<212> TYPE: PRT
<213> ORGANISM: Artificial
<220> FEATURE:
<223> OTHER INFORMATION: Engineered antibody sequence

<400> SEQUENCE: 309

Phe Gly Gly Gly Thr Lys Val Glu Ile Lys Arg
1               5                   10

<210> SEQ ID NO 310
<211> LENGTH: 106
<212> TYPE: PRT
<213> ORGANISM: Artificial
<220> FEATURE:
<223> OTHER INFORMATION: Engineered antibody sequence

<400> SEQUENCE: 310

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
```

```
                    20                  25                  30
Pro Arg Glu Ala Lys Val Gln Trp Lys Val Asp Asn Ala Leu Gln Ser
                35                  40                  45

Gly Asn Ser Gln Glu Ser Val Thr Glu Gln Asp Ser Lys Asp Ser Thr
            50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 311
<211> LENGTH: 660
<212> TYPE: DNA
<213> ORGANISM: Artificial
<220> FEATURE:
<223> OTHER INFORMATION: Engineered antibody sequence

<400> SEQUENCE: 311
caagtgctga cccagtctcc atcctccctg tctgcatctg taggagacag agtcaccatc      60
aattgccagg ccagtcagag tgtttacaat tacaactacc ttgcctggta tcagcagaaa     120
ccagggaaag ttcctaagca actgatctat tctacatcca ctctggcatc tggggtccca     180
tctcgtttca gtggcagtgg atctgggaca gatttcactc tcaccatcag cagcctgcag     240
cctgaagatg ttgcaactta ttactgtctg ggcagttatg attgtagtac tggtgattgt     300
tttgttttcg gcggaggaac caaggtggaa atcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 312
<211> LENGTH: 339
<212> TYPE: DNA
<213> ORGANISM: Artificial
<220> FEATURE:
<223> OTHER INFORMATION: Engineered antibody sequence

<400> SEQUENCE: 312
caagtgctga cccagtctcc atcctccctg tctgcatctg taggagacag agtcaccatc      60
aattgccagg ccagtcagag tgtttacaat tacaactacc ttgcctggta tcagcagaaa     120
ccagggaaag ttcctaagca actgatctat tctacatcca ctctggcatc tggggtccca     180
tctcgtttca gtggcagtgg atctgggaca gatttcactc tcaccatcag cagcctgcag     240
cctgaagatg ttgcaactta ttactgtctg ggcagttatg attgtagtac tggtgattgt     300
tttgttttcg gcggaggaac caaggtggaa atcaaacgt                            339

<210> SEQ ID NO 313
<211> LENGTH: 66
<212> TYPE: DNA
<213> ORGANISM: Artificial
<220> FEATURE:
<223> OTHER INFORMATION: Engineered antibody sequence
```

```
<400> SEQUENCE: 313
caagtgctga cccagtctcc atcctccctg tctgcatctg taggagacag agtcaccatc       60
aattgc                                                                 66

<210> SEQ ID NO 314
<211> LENGTH: 39
<212> TYPE: DNA
<213> ORGANISM: Artificial
<220> FEATURE:
<223> OTHER INFORMATION: Engineered antibody sequence

<400> SEQUENCE: 314
caggccagtc agagtgttta caattacaac taccttgcc                             39

<210> SEQ ID NO 315
<211> LENGTH: 45
<212> TYPE: DNA
<213> ORGANISM: Artificial
<220> FEATURE:
<223> OTHER INFORMATION: Engineered antibody sequence

<400> SEQUENCE: 315
tggtatcagc agaaaccagg gaaagttcct aagcaactga tctat                      45

<210> SEQ ID NO 316
<211> LENGTH: 21
<212> TYPE: DNA
<213> ORGANISM: Artificial
<220> FEATURE:
<223> OTHER INFORMATION: Engineered antibody sequence

<400> SEQUENCE: 316
tctacatcca ctctggcatc t                                                21

<210> SEQ ID NO 317
<211> LENGTH: 96
<212> TYPE: DNA
<213> ORGANISM: Artificial
<220> FEATURE:
<223> OTHER INFORMATION: Engineered antibody sequence

<400> SEQUENCE: 317
ggggtcccat ctcgtttcag tggcagtgga tctgggacag atttcactct caccatcagc       60
agcctgcagc ctgaagatgt tgcaacttat tactgt                                96

<210> SEQ ID NO 318
<211> LENGTH: 39
<212> TYPE: DNA
<213> ORGANISM: Artificial
<220> FEATURE:
<223> OTHER INFORMATION: Engineered antibody sequence

<400> SEQUENCE: 318
ctgggcagtt atgattgtag tactggtgat tgttttgtt                             39

<210> SEQ ID NO 319
<211> LENGTH: 33
<212> TYPE: DNA
<213> ORGANISM: Artificial
<220> FEATURE:
<223> OTHER INFORMATION: Engineered antibody sequence

<400> SEQUENCE: 319
ttcggcggag gaaccaaggt ggaaatcaaa cgt                                   33
```

<210> SEQ ID NO 320
<211> LENGTH: 321
<212> TYPE: DNA
<213> ORGANISM: Artificial
<220> FEATURE:
<223> OTHER INFORMATION: Engineered antibody sequence

<400> SEQUENCE: 320

```
acggtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgtta g                                               321
```

<210> SEQ ID NO 321
<211> LENGTH: 439
<212> TYPE: PRT
<213> ORGANISM: Artificial
<220> FEATURE:
<223> OTHER INFORMATION: Engineered antibody sequence

<400> SEQUENCE: 321

```
Gln Ser Leu Glu Glu Ser Gly Gly Arg Leu Val Thr Pro Gly Thr Pro
1               5                   10                  15
Leu Thr Leu Thr Cys Thr Val Ser Gly Ile Gly Leu Ser Ser Tyr Tyr
            20                  25                  30
Met Gln Trp Val Arg Gln Ser Pro Gly Arg Gly Leu Glu Trp Ile Gly
        35                  40                  45
Val Ile Gly Ser Asp Gly Lys Thr Tyr Tyr Ala Thr Trp Ala Lys Gly
    50                  55                  60
Arg Phe Thr Ile Ser Lys Thr Ser Ser Thr Thr Val Asp Leu Arg Met
65                  70                  75                  80
Ala Ser Leu Thr Thr Glu Asp Thr Ala Thr Tyr Phe Cys Thr Arg Gly
                85                  90                  95
Asp Ile Trp Gly Pro Gly Thr Leu Val Thr Val Ser Ser Ala Ser Thr
            100                 105                 110
Lys Gly Pro Ser Val Phe Pro Leu Ala Pro Ser Ser Lys Ser Thr Ser
        115                 120                 125
Gly Gly Thr Ala Ala Leu Gly Cys Leu Val Lys Asp Tyr Phe Pro Glu
    130                 135                 140
Pro Val Thr Val Ser Trp Asn Ser Gly Ala Leu Thr Ser Gly Val His
145                 150                 155                 160
Thr Phe Pro Ala Val Leu Gln Ser Ser Gly Leu Tyr Ser Leu Ser Ser
                165                 170                 175
Val Val Thr Val Pro Ser Ser Ser Leu Gly Thr Gln Thr Tyr Ile Cys
            180                 185                 190
Asn Val Asn His Lys Pro Ser Asn Thr Lys Val Asp Lys Arg Val Glu
        195                 200                 205
Pro Lys Ser Cys Asp Lys Thr His Thr Cys Pro Pro Cys Pro Ala Pro
    210                 215                 220
Glu Leu Leu Gly Gly Pro Ser Val Phe Leu Phe Pro Pro Lys Pro Lys
225                 230                 235                 240
Asp Thr Leu Met Ile Ser Arg Thr Pro Glu Val Thr Cys Val Val Val
```

-continued

```
                245                 250                 255
Asp Val Ser His Glu Asp Pro Glu Val Lys Phe Asn Trp Tyr Val Asp
            260                 265                 270
Gly Val Glu Val His Asn Ala Lys Thr Lys Pro Arg Glu Glu Gln Tyr
        275                 280                 285
Ala Ser Thr Tyr Arg Val Val Ser Val Leu Thr Val Leu His Gln Asp
    290                 295                 300
Trp Leu Asn Gly Lys Glu Tyr Lys Cys Lys Val Ser Asn Lys Ala Leu
305                 310                 315                 320
Pro Ala Pro Ile Glu Lys Thr Ile Ser Lys Ala Lys Gly Gln Pro Arg
                325                 330                 335
Glu Pro Gln Val Tyr Thr Leu Pro Pro Ser Arg Glu Glu Met Thr Lys
            340                 345                 350
Asn Gln Val Ser Leu Thr Cys Leu Val Lys Gly Phe Tyr Pro Ser Asp
        355                 360                 365
Ile Ala Val Glu Trp Glu Ser Asn Gly Gln Pro Glu Asn Asn Tyr Lys
    370                 375                 380
Thr Thr Pro Pro Val Leu Asp Ser Asp Gly Ser Phe Phe Leu Tyr Ser
385                 390                 395                 400
Lys Leu Thr Val Asp Lys Ser Arg Trp Gln Gln Gly Asn Val Phe Ser
                405                 410                 415
Cys Ser Val Met His Glu Ala Leu His Asn His Tyr Thr Gln Lys Ser
            420                 425                 430
Leu Ser Leu Ser Pro Gly Lys
            435

<210> SEQ ID NO 322
<211> LENGTH: 109
<212> TYPE: PRT
<213> ORGANISM: Artificial
<220> FEATURE:
<223> OTHER INFORMATION: Engineered antibody sequence

<400> SEQUENCE: 322

Gln Ser Leu Glu Glu Ser Gly Gly Arg Leu Val Thr Pro Gly Thr Pro
1               5                   10                  15
Leu Thr Leu Thr Cys Thr Val Ser Gly Ile Gly Leu Ser Ser Tyr Tyr
            20                  25                  30
Met Gln Trp Val Arg Gln Ser Pro Gly Arg Gly Leu Glu Trp Ile Gly
        35                  40                  45
Val Ile Gly Ser Asp Gly Lys Thr Tyr Tyr Ala Thr Trp Ala Lys Gly
    50                  55                  60
Arg Phe Thr Ile Ser Lys Thr Ser Ser Thr Val Asp Leu Arg Met
65                  70                  75                  80
Ala Ser Leu Thr Thr Glu Asp Thr Ala Thr Tyr Phe Cys Thr Arg Gly
                85                  90                  95
Asp Ile Trp Gly Pro Gly Thr Leu Val Thr Val Ser Ser
            100                 105

<210> SEQ ID NO 323
<211> LENGTH: 29
<212> TYPE: PRT
<213> ORGANISM: Artificial
<220> FEATURE:
<223> OTHER INFORMATION: Engineered antibody sequence

<400> SEQUENCE: 323
```

Gln Ser Leu Glu Glu Ser Gly Gly Arg Leu Val Thr Pro Gly Thr Pro
1               5                   10                  15

Leu Thr Leu Thr Cys Thr Val Ser Gly Ile Gly Leu Ser
            20                  25

<210> SEQ ID NO 324
<211> LENGTH: 5
<212> TYPE: PRT
<213> ORGANISM: Artificial
<220> FEATURE:
<223> OTHER INFORMATION: Engineered antibody sequence

<400> SEQUENCE: 324

Ser Tyr Tyr Met Gln
1               5

<210> SEQ ID NO 325
<211> LENGTH: 14
<212> TYPE: PRT
<213> ORGANISM: Artificial
<220> FEATURE:
<223> OTHER INFORMATION: Engineered antibody sequence

<400> SEQUENCE: 325

Trp Val Arg Gln Ser Pro Gly Arg Gly Leu Glu Trp Ile Gly
1               5                   10

<210> SEQ ID NO 326
<211> LENGTH: 16
<212> TYPE: PRT
<213> ORGANISM: Artificial
<220> FEATURE:
<223> OTHER INFORMATION: Engineered antibody sequence

<400> SEQUENCE: 326

Val Ile Gly Ser Asp Gly Lys Thr Tyr Tyr Ala Thr Trp Ala Lys Gly
1               5                   10                  15

<210> SEQ ID NO 327
<211> LENGTH: 31
<212> TYPE: PRT
<213> ORGANISM: Artificial
<220> FEATURE:
<223> OTHER INFORMATION: Engineered antibody sequence

<400> SEQUENCE: 327

Arg Phe Thr Ile Ser Lys Thr Ser Ser Thr Thr Val Asp Leu Arg Met
1               5                   10                  15

Ala Ser Leu Thr Thr Glu Asp Thr Ala Thr Tyr Phe Cys Thr Arg
            20                  25                  30

<210> SEQ ID NO 328
<211> LENGTH: 3
<212> TYPE: PRT
<213> ORGANISM: Artificial
<220> FEATURE:
<223> OTHER INFORMATION: Engineered antibody sequence

<400> SEQUENCE: 328

Gly Asp Ile
1

<210> SEQ ID NO 329
<211> LENGTH: 11
<212> TYPE: PRT
<213> ORGANISM: Artificial

```
<220> FEATURE:
<223> OTHER INFORMATION: Engineered antibody sequence

<400> SEQUENCE: 329

Trp Gly Pro Gly Thr Leu Val Thr Val Ser Ser
1               5                   10

<210> SEQ ID NO 330
<211> LENGTH: 330
<212> TYPE: PRT
<213> ORGANISM: Artificial
<220> FEATURE:
<223> OTHER INFORMATION: Engineered antibody sequence

<400> SEQUENCE: 330

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

<210> SEQ ID NO 331
<211> LENGTH: 1320
<212> TYPE: DNA
<213> ORGANISM: Artificial
<220> FEATURE:
<223> OTHER INFORMATION: Engineered antibody sequence

<400> SEQUENCE: 331

```
cagtcgctgg aggagtccgg gggtcgcctg gtcacgcctg ggacacccct gacactcacc      60
tgcacagtct ctggaatcgg cctcagtagc tactacatgc agtgggtccg ccagtctcca     120
gggagggggc tggaatggat cggagtcatt ggtagtgatg gtaagacata ctacgcgacc     180
tgggcgaaag gccgattcac catctccaag acctcgtcga ccacggtgga tctgagaatg     240
gccagtctga caaccgagga cacggccacc tatttctgta ccagagggga catctggggc     300
ccggggaccc tcgtcaccgt ctcgagcgcc tccaccaagg gcccatcggt cttccccctg     360
gcaccctcct ccaagagcac ctctgggggc acagcggccc tgggctgcct ggtcaaggac     420
tacttccccg aaccggtgac ggtgtcgtgg aactcaggcg ccctgaccag cggcgtgcac     480
accttcccgg ctgtcctaca gtcctcagga ctctactccc tcagcagcgt ggtgaccgtg     540
ccctccagca gcttgggcac ccagacctac atctgcaacg tgaatcacaa gcccagcaac     600
accaaggtgg acaagagagt tgagcccaaa tcttgtgaca aaactcacac atgcccaccg     660
tgcccagcac ctgaactcct ggggggaccg tcagtcttcc tcttccccc aaaacccaag     720
gacaccctca tgatctcccg gacccctgag gtcacatgcg tggtggtgga cgtgagccac     780
gaagaccctg aggtcaagtt caactggtac gtggacggcg tggaggtgca taatgccaag     840
acaaagccgc gggaggagca gtacgccagc acgtaccgtg tggtcagcgt cctcaccgtc     900
ctgcaccagg actggctgaa tgcaaggag tacaagtgca aggtctccaa caaagccctc     960
ccagccccca tcgagaaaac catctccaaa gccaaagggc agccccgaga accacaggtg    1020
tacaccctgc cccatcccg ggaggagatg accaagaacc aggtcagcct gacctgcctg    1080
gtcaaaggct tctatcccag cgacatcgcc gtggagtggg agagcaatgg gcagccggag    1140
aacaactaca agaccacgcc tcccgtgctg gactccgacg gctccttctt cctctacagc    1200
aagctcaccg tggacaagag caggtggcag caggggaacg tcttctcatg ctccgtgatg    1260
catgaggctc tgcacaacca ctacacgcag aagagcctct ccctgtctcc gggtaaatga    1320
```

<210> SEQ ID NO 332
<211> LENGTH: 327
<212> TYPE: DNA
<213> ORGANISM: Artificial
<220> FEATURE:
<223> OTHER INFORMATION: Engineered antibody sequence

<400> SEQUENCE: 332

```
cagtcgctgg aggagtccgg gggtcgcctg gtcacgcctg ggacacccct gacactcacc      60
tgcacagtct ctggaatcgg cctcagtagc tactacatgc agtgggtccg ccagtctcca     120
gggagggggc tggaatggat cggagtcatt ggtagtgatg gtaagacata ctacgcgacc     180
tgggcgaaag gccgattcac catctccaag acctcgtcga ccacggtgga tctgagaatg     240
gccagtctga caaccgagga cacggccacc tatttctgta ccagagggga catctggggc     300
ccggggaccc tcgtcaccgt ctcgagc                                         327
```

```
<210> SEQ ID NO 333
<211> LENGTH: 87
<212> TYPE: DNA
<213> ORGANISM: Artificial
<220> FEATURE:
<223> OTHER INFORMATION: Engineered antibody sequence

<400> SEQUENCE: 333
cagtcgctgg aggagtccgg gggtcgcctg gtcacgcctg ggacacccct gacactcacc      60
tgcacagtct ctggaatcgg cctcagt                                         87

<210> SEQ ID NO 334
<211> LENGTH: 15
<212> TYPE: DNA
<213> ORGANISM: Artificial
<220> FEATURE:
<223> OTHER INFORMATION: Engineered antibody sequence

<400> SEQUENCE: 334
agctactaca tgcag                                                      15

<210> SEQ ID NO 335
<211> LENGTH: 42
<212> TYPE: DNA
<213> ORGANISM: Artificial
<220> FEATURE:
<223> OTHER INFORMATION: Engineered antibody sequence

<400> SEQUENCE: 335
tgggtccgcc agtctccagg gaggggggctg gaatggatcg ga                       42

<210> SEQ ID NO 336
<211> LENGTH: 48
<212> TYPE: DNA
<213> ORGANISM: Artificial
<220> FEATURE:
<223> OTHER INFORMATION: Engineered antibody sequence

<400> SEQUENCE: 336
gtcattggta gtgatggtaa gacatactac gcgacctggg cgaaaggc                  48

<210> SEQ ID NO 337
<211> LENGTH: 93
<212> TYPE: DNA
<213> ORGANISM: Artificial
<220> FEATURE:
<223> OTHER INFORMATION: Engineered antibody sequence

<400> SEQUENCE: 337
cgattcacca tctccaagac ctcgtcgacc acggtggatc tgagaatggc cagtctgaca      60
accgaggaca cggccaccta tttctgtacc aga                                  93

<210> SEQ ID NO 338
<211> LENGTH: 9
<212> TYPE: DNA
<213> ORGANISM: Artificial
<220> FEATURE:
<223> OTHER INFORMATION: Engineered antibody sequence

<400> SEQUENCE: 338 ggggacatc                                                             9

<210> SEQ ID NO 339
<211> LENGTH: 33
<212> TYPE: DNA
```

<213> ORGANISM: Artificial
<220> FEATURE:
<223> OTHER INFORMATION: Engineered antibody sequence

<400> SEQUENCE: 339

```
tggggcccgg ggaccctcgt caccgtctcg agc                                33
```

<210> SEQ ID NO 340
<211> LENGTH: 993
<212> TYPE: DNA
<213> ORGANISM: Artificial
<220> FEATURE:
<223> OTHER INFORMATION: Engineered antibody sequence

<400> SEQUENCE: 340

```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctggggggga  360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacgcc   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag gcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa tga                                993
```

<210> SEQ ID NO 341
<211> LENGTH: 219
<212> TYPE: PRT
<213> ORGANISM: Artificial
<220> FEATURE:
<223> OTHER INFORMATION: Engineered antibody sequence

<400> SEQUENCE: 341

```
Gln Val Leu Thr Gln Thr Pro Ser Pro Val Ser Ala Ala Val Gly Ser
1               5                   10                  15

Thr Val Thr Ile Asn Cys Gln Ala Ser Gln Asn Val Tyr Asn Asn Asn
            20                  25                  30

Tyr Leu Ala Trp Tyr Gln Gln Lys Pro Gly Gln Pro Pro Lys Gln Leu
        35                  40                  45

Ile Tyr Ser Thr Ser Thr Leu Ala Ser Gly Val Ser Ser Arg Phe Arg
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Ser Tyr Asp Cys Ser
                85                  90                  95
```

-continued

Arg Gly Asp Cys Phe Val Phe Gly Gly Thr Glu Val Val Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 342
<211> LENGTH: 113
<212> TYPE: PRT
<213> ORGANISM: Artificial
<220> FEATURE:
<223> OTHER INFORMATION: Engineered antibody sequence

<400> SEQUENCE: 342

Gln Val Leu Thr Gln Thr Pro Ser Pro Val Ser Ala Ala Val Gly Ser
1               5                   10                  15

Thr Val Thr Ile Asn Cys Gln Ala Ser Gln Asn Val Tyr Asn Asn Asn
            20                  25                  30

Tyr Leu Ala Trp Tyr Gln Lys Pro Gly Gln Pro Pro Lys Gln Leu
        35                  40                  45

Ile Tyr Ser Thr Ser Thr Leu Ala Ser Gly Val Ser Ser Arg Phe Arg
50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Ser Tyr Asp Cys Ser
                85                  90                  95

Arg Gly Asp Cys Phe Val Phe Gly Gly Thr Glu Val Val Lys
            100                 105                 110

Arg

<210> SEQ ID NO 343
<211> LENGTH: 22
<212> TYPE: PRT
<213> ORGANISM: Artificial
<220> FEATURE:
<223> OTHER INFORMATION: Engineered antibody sequence

<400> SEQUENCE: 343

Gln Val Leu Thr Gln Thr Pro Ser Pro Val Ser Ala Ala Val Gly Ser
1               5                   10                  15

Thr Val Thr Ile Asn Cys
            20

<210> SEQ ID NO 344
<211> LENGTH: 13
<212> TYPE: PRT
<213> ORGANISM: Artificial

<220> FEATURE:
<223> OTHER INFORMATION: Engineered antibody sequence

<400> SEQUENCE: 344

Gln Ala Ser Gln Asn Val Tyr Asn Asn Tyr Leu Ala
1               5                   10

<210> SEQ ID NO 345
<211> LENGTH: 15
<212> TYPE: PRT
<213> ORGANISM: Artificial
<220> FEATURE:
<223> OTHER INFORMATION: Engineered antibody sequence

<400> SEQUENCE: 345

Trp Tyr Gln Gln Lys Pro Gly Gln Pro Pro Lys Gln Leu Ile Tyr
1               5                   10                  15

<210> SEQ ID NO 346
<211> LENGTH: 7
<212> TYPE: PRT
<213> ORGANISM: Artificial
<220> FEATURE:
<223> OTHER INFORMATION: Engineered antibody sequence

<400> SEQUENCE: 346

Ser Thr Ser Thr Leu Ala Ser
1               5

<210> SEQ ID NO 347
<211> LENGTH: 32
<212> TYPE: PRT
<213> ORGANISM: Artificial
<220> FEATURE:
<223> OTHER INFORMATION: Engineered antibody sequence

<400> SEQUENCE: 347

Gly Val Ser Ser Arg Phe Arg Gly Ser Gly Ser Gly Thr Gln Phe Thr
1               5                   10                  15

Leu Thr Ile Ser Asp Val Gln Cys Asp Asp Ala Ala Thr Tyr Tyr Cys
            20                  25                  30

<210> SEQ ID NO 348
<211> LENGTH: 13
<212> TYPE: PRT
<213> ORGANISM: Artificial
<220> FEATURE:
<223> OTHER INFORMATION: Engineered antibody sequence

<400> SEQUENCE: 348

Leu Gly Ser Tyr Asp Cys Ser Arg Gly Asp Cys Phe Val
1               5                   10

<210> SEQ ID NO 349
<211> LENGTH: 11
<212> TYPE: PRT
<213> ORGANISM: Artificial
<220> FEATURE:
<223> OTHER INFORMATION: Engineered antibody sequence

<400> SEQUENCE: 349

Phe Gly Gly Gly Thr Glu Val Val Val Lys Arg
1               5                   10

<210> SEQ ID NO 350
<211> LENGTH: 106

```
<212> TYPE: PRT
<213> ORGANISM: Artificial
<220> FEATURE:
<223> OTHER INFORMATION: Engineered antibody sequence

<400> SEQUENCE: 350

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 351
<211> LENGTH: 660
<212> TYPE: DNA
<213> ORGANISM: Artificial
<220> FEATURE:
<223> OTHER INFORMATION: Engineered antibody sequence

<400> SEQUENCE: 351
caagtgctga cccagactcc atcccccgtg tctgcagctg tgggaagcac agtcaccatc    60
aattgccagg ccagtcagaa tgtttataat aacaactacc tagcctggta tcagcagaaa   120
ccagggcagc ctcccaagca actgatctat tctacgtcca ctctggcatc tggggtctca   180
tcgcgattca gaggcagtgg atctgggaca cagttcactc tcaccatcag cgacgtgcag   240
tgtgacgatg ctgccactta ctactgtcta ggcagttatg attgtagtcg tggtgattgt   300
tttgttttcg gcggagggac cgaggtggtg gtcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

<210> SEQ ID NO 352
<211> LENGTH: 339
<212> TYPE: DNA
<213> ORGANISM: Artificial
<220> FEATURE:
<223> OTHER INFORMATION: Engineered antibody sequence

<400> SEQUENCE: 352
caagtgctga cccagactcc atcccccgtg tctgcagctg tgggaagcac agtcaccatc    60
aattgccagg ccagtcagaa tgtttataat aacaactacc tagcctggta tcagcagaaa   120
ccagggcagc ctcccaagca actgatctat tctacgtcca ctctggcatc tggggtctca   180
tcgcgattca gaggcagtgg atctgggaca cagttcactc tcaccatcag cgacgtgcag   240
tgtgacgatg ctgccactta ctactgtcta ggcagttatg attgtagtcg tggtgattgt   300
```

```
tttgttttcg gcggagggac cgaggtggtg gtcaaacgt                    339

<210> SEQ ID NO 353
<211> LENGTH: 66
<212> TYPE: DNA
<213> ORGANISM: Artificial
<220> FEATURE:
<223> OTHER INFORMATION: Engineered antibody sequence

<400> SEQUENCE: 353
caagtgctga cccagactcc atcccccgtg tctgcagctg tgggaagcac agtcaccatc    60
aattgc                                                               66

<210> SEQ ID NO 354
<211> LENGTH: 39
<212> TYPE: DNA
<213> ORGANISM: Artificial
<220> FEATURE:
<223> OTHER INFORMATION: Engineered antibody sequence

<400> SEQUENCE: 354
caggccagtc agaatgttta taataacaac tacctagcc                           39

<210> SEQ ID NO 355
<211> LENGTH: 45
<212> TYPE: DNA
<213> ORGANISM: Artificial
<220> FEATURE:
<223> OTHER INFORMATION: Engineered antibody sequence

<400> SEQUENCE: 355
tggtatcagc agaaaccagg gcagcctccc aagcaactga tctat                    45

<210> SEQ ID NO 356
<211> LENGTH: 21
<212> TYPE: DNA
<213> ORGANISM: Artificial
<220> FEATURE:
<223> OTHER INFORMATION: Engineered antibody sequence

<400> SEQUENCE: 356
tctacgtcca ctctggcatc t                                              21

<210> SEQ ID NO 357
<211> LENGTH: 96
<212> TYPE: DNA
<213> ORGANISM: Artificial
<220> FEATURE:
<223> OTHER INFORMATION: Engineered antibody sequence

<400> SEQUENCE: 357
ggggtctcat cgcgattcag aggcagtgga tctgggacac agttcactct caccatcagc    60
gacgtgcagt gtgacgatgc tgccacttac tactgt                              96

<210> SEQ ID NO 358
<211> LENGTH: 39
<212> TYPE: DNA
<213> ORGANISM: Artificial
<220> FEATURE:
<223> OTHER INFORMATION: Engineered antibody sequence

<400> SEQUENCE: 358
ctaggcagtt atgattgtag tcgtggtgat tgttttgtt                           39
```

<210> SEQ ID NO 359
<211> LENGTH: 33
<212> TYPE: DNA
<213> ORGANISM: Artificial
<220> FEATURE:
<223> OTHER INFORMATION: Engineered antibody sequence

<400> SEQUENCE: 359
ttcggcggag ggaccgaggt ggtggtcaaa cgt                          33

<210> SEQ ID NO 360
<211> LENGTH: 321
<212> TYPE: DNA
<213> ORGANISM: Artificial
<220> FEATURE:
<223> OTHER INFORMATION: Engineered antibody sequence

<400> SEQUENCE: 360
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgcccteca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                            321

<210> SEQ ID NO 361
<211> LENGTH: 441
<212> TYPE: PRT
<213> ORGANISM: Artificial
<220> FEATURE:
<223> OTHER INFORMATION: Engineered antibody sequence

<400> SEQUENCE: 361

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Gly Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ser Asp Gly Lys Thr Tyr Tyr Ala Thr Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Thr
                85                  90                  95

Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

```
Ile Cys Asn Val Asn His Lys Pro Ser Asn Thr Lys Val Asp Lys Arg
        195                 200                 205

Val Glu Pro Lys Ser Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
        290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
        370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
            435                 440

<210> SEQ ID NO 362
<211> LENGTH: 111
<212> TYPE: PRT
<213> ORGANISM: Artificial
<220> FEATURE:
<223> OTHER INFORMATION: Engineered antibody sequence

<400> SEQUENCE: 362

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Gly Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ser Asp Gly Lys Thr Tyr Tyr Ala Thr Trp Ala Lys
50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Thr
                85                  90                  95

Arg Gly Asp Ile Trp Gly Gln Gly Thr Leu Val Thr Val Ser Ser
            100                 105                 110
```

<210> SEQ ID NO 363
<211> LENGTH: 30
<212> TYPE: PRT
<213> ORGANISM: Artificial
<220> FEATURE:
<223> OTHER INFORMATION: Engineered antibody sequence

<400> SEQUENCE: 363

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Gly Leu Ser
            20                  25                  30

<210> SEQ ID NO 364
<211> LENGTH: 5
<212> TYPE: PRT
<213> ORGANISM: Artificial
<220> FEATURE:
<223> OTHER INFORMATION: Engineered antibody sequence

<400> SEQUENCE: 364

Ser Tyr Tyr Met Gln
1               5

<210> SEQ ID NO 365
<211> LENGTH: 14
<212> TYPE: PRT
<213> ORGANISM: Artificial
<220> FEATURE:
<223> OTHER INFORMATION: Engineered antibody sequence

<400> SEQUENCE: 365

Trp Val Arg Gln Ala Pro Gly Lys Gly Leu Glu Trp Val Gly
1               5                   10

<210> SEQ ID NO 366
<211> LENGTH: 16
<212> TYPE: PRT
<213> ORGANISM: Artificial
<220> FEATURE:
<223> OTHER INFORMATION: Engineered antibody sequence

<400> SEQUENCE: 366

Val Ile Gly Ser Asp Gly Lys Thr Tyr Tyr Ala Thr Trp Ala Lys Gly
1               5                   10                  15

<210> SEQ ID NO 367
<211> LENGTH: 32
<212> TYPE: PRT
<213> ORGANISM: Artificial
<220> FEATURE:
<223> OTHER INFORMATION: Engineered antibody sequence

<400> SEQUENCE: 367

Arg Phe Thr Ile Ser Arg Asp Asn Ser Lys Thr Thr Val Tyr Leu Gln
1               5                   10                  15

Met Asn Ser Leu Arg Ala Glu Asp Thr Ala Val Tyr Phe Cys Thr Arg
            20                  25                  30

<210> SEQ ID NO 368
<211> LENGTH: 3
<212> TYPE: PRT
<213> ORGANISM: Artificial
<220> FEATURE:
<223> OTHER INFORMATION: Engineered antibody sequence -continued

<400> SEQUENCE: 368

Gly Asp Ile
1

<210> SEQ ID NO 369
<211> LENGTH: 11
<212> TYPE: PRT
<213> ORGANISM: Artificial
<220> FEATURE:
<223> OTHER INFORMATION: Engineered antibody sequence

<400> SEQUENCE: 369

Trp Gly Gln Gly Thr Leu Val Thr Val Ser Ser
1               5                   10

<210> SEQ ID NO 370
<211> LENGTH: 330
<212> TYPE: PRT
<213> ORGANISM: Artificial
<220> FEATURE:
<223> OTHER INFORMATION: Engineered antibody sequence

<400> SEQUENCE: 370

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 371
<211> LENGTH: 1326
<212> TYPE: DNA
<213> ORGANISM: Artificial
<220> FEATURE:
<223> OTHER INFORMATION: Engineered antibody sequence

<400> SEQUENCE: 371

| | | | | | |
|---|---|---|---|---|---|
| gaggtgcagc | ttgtggagtc | tgggggaggc | ttggtccagc | ctggggggtc | cctgagactc | 60 |
| tcctgtgcag | tctctggaat | cggcctcagt | agctactaca | tgcaatgggt | ccgtcaggct | 120 |
| ccagggaagg | ggctggagtg | gtcggagtc | attggtagtg | atggtaagac | atactacgcg | 180 |
| acctgggcga | aaggccgatt | caccatctcc | agagacaatt | ccaagaccac | ggtgtatctt | 240 |
| caaatgaaca | gcctgagagc | tgaggacact | gctgtgtatt | tctgtaccag | aggggacatc | 300 |
| tggggccaag | ggaccctcgt | caccgtctcg | agcgcctcca | ccaagggccc | atcggtcttc | 360 |
| cccctggcac | cctcctccaa | gagcacctct | gggggcacag | cggccctggg | ctgcctggtc | 420 |
| aaggactact | tccccgaacc | ggtgacggtg | tcgtggaact | caggcgccct | gaccagcggc | 480 |
| gtgcacacct | tcccggctgt | cctacagtcc | tcaggactct | actccctcag | cagcgtggtg | 540 |
| accgtgccct | ccagcagctt | gggcacccag | acctacatct | gcaacgtgaa | tcacaagccc | 600 |
| agcaacacca | aggtggacaa | gagagttgag | cccaaatctt | gtgacaaaac | tcacacatgc | 660 |
| ccaccgtgcc | cagcacctga | actcctgggg | ggaccgtcag | tcttcctctt | ccccccaaaa | 720 |
| cccaaggaca | ccctcatgat | ctcccggacc | cctgaggtca | catgcgtggt | ggtggacgtg | 780 |
| agccacgaag | accctgaggt | caagttcaac | tggtacgtgg | acggcgtgga | ggtgcataat | 840 |
| gccaagacaa | agccgcggga | ggagcagtac | gccagcacgt | accgtgtggt | cagcgtcctc | 900 |
| accgtcctgc | accaggactg | gctgaatggc | aaggagtaca | agtgcaaggt | ctccaacaaa | 960 |
| gccctcccag | cccccatcga | gaaaaccatc | tccaaagcca | aagggcagcc | ccgagaacca | 1020 |
| caggtgtaca | ccctgccccc | atcccgggag | gagatgacca | agaaccaggt | cagcctgacc | 1080 |
| tgcctggtca | aaggcttcta | tcccagcgac | atcgccgtgg | agtgggagag | caatgggcag | 1140 |
| ccggagaaca | actacaagac | cacgcctccc | gtgctggact | ccgacggctc | cttcttcctc | 1200 |
| tacagcaagc | tcaccgtgga | caagagcagg | tggcagcagg | ggaacgtctt | ctcatgctcc | 1260 |
| gtgatgcatg | aggctctgca | caaccactac | acgcagaaga | gcctctccct | gtctccgggt | 1320 |
| aaatga | | | | | | 1326 |

<210> SEQ ID NO 372
<211> LENGTH: 333
<212> TYPE: DNA
<213> ORGANISM: Artificial
<220> FEATURE:
<223> OTHER INFORMATION: Engineered antibody sequence

<400> SEQUENCE: 372

```
gaggtgcagc ttgtggagtc tgggggaggc ttggtccagc ctgggggtc cctgagactc      60 tcctgtgcag tctctggaat cggcctcagt agctactaca tgcaatgggt ccgtcaggct    120
ccagggaagg ggctggagtg ggtcggagtc attggtagtg atggtaagac atactacgcg    180
acctgggcga aaggccgatt caccatctcc agagacaatt ccaagaccac ggtgtatctt    240
caaatgaaca gcctgagagc tgaggacact gctgtgtatt tctgtaccag aggggacatc    300
tggggccaag gaccctcgt caccgtctcg agc                                   333

<210> SEQ ID NO 373
<211> LENGTH: 90
<212> TYPE: DNA
<213> ORGANISM: Artificial
<220> FEATURE:
<223> OTHER INFORMATION: Engineered antibody sequence

<400> SEQUENCE: 373
gaggtgcagc ttgtggagtc tgggggaggc ttggtccagc ctgggggtc cctgagactc      60 tcctgtgcag tctctggaat cggcctcagt                                       90

<210> SEQ ID NO 374
<211> LENGTH: 15
<212> TYPE: DNA
<213> ORGANISM: Artificial
<220> FEATURE:
<223> OTHER INFORMATION: Engineered antibody sequence

<400> SEQUENCE: 374
agctactaca tgcaa                                                       15

<210> SEQ ID NO 375
<211> LENGTH: 42
<212> TYPE: DNA
<213> ORGANISM: Artificial
<220> FEATURE:
<223> OTHER INFORMATION: Engineered antibody sequence

<400> SEQUENCE: 375
tgggtccgtc aggctccagg gaaggggctg gagtgggtcg ga                         42

<210> SEQ ID NO 376
<211> LENGTH: 48
<212> TYPE: DNA
<213> ORGANISM: Artificial
<220> FEATURE:
<223> OTHER INFORMATION: Engineered antibody sequence

<400> SEQUENCE: 376
gtcattggta gtgatggtaa gacatactac gcgacctggg cgaaaggc                   48

<210> SEQ ID NO 377
<211> LENGTH: 96
<212> TYPE: DNA
<213> ORGANISM: Artificial
<220> FEATURE:
<223> OTHER INFORMATION: Engineered antibody sequence

<400> SEQUENCE: 377
cgattcacca tctccagaga caattccaag accacggtgt atcttcaaat gaacagcctg      60
agagctgagg acactgctgt gtatttctgt accaga                                96

<210> SEQ ID NO 378
<211> LENGTH: 9
```

```
<212> TYPE: DNA
<213> ORGANISM: Artificial
<220> FEATURE:
<223> OTHER INFORMATION: Engineered antibody sequence

<400> SEQUENCE: 378 ggggacatc                                                               9

<210> SEQ ID NO 379
<211> LENGTH: 33
<212> TYPE: DNA
<213> ORGANISM: Artificial
<220> FEATURE:
<223> OTHER INFORMATION: Engineered antibody sequence

<400> SEQUENCE: 379
tggggccaag ggaccctcgt caccgtctcg agc                                   33

<210> SEQ ID NO 380
<211> LENGTH: 993
<212> TYPE: DNA
<213> ORGANISM: Artificial
<220> FEATURE:
<223> OTHER INFORMATION: Engineered antibody sequence

<400> SEQUENCE: 380
gcctccacca agggcccatc ggtcttcccc ctggcaccct cctccaagag cacctctggg        60
ggcacagcgg ccctgggctg cctggtcaag gactacttcc ccgaaccggt gacggtgtcg       120
tggaactcag gcgccctgac cagcggcgtg cacaccttcc cggctgtcct acagtcctca       180
ggactctact ccctcagcag cgtggtgacc gtgccctcca gcagcttggg cacccagacc       240
tacatctgca acgtgaatca caagcccagc aacaccaagg tggacaagag agttgagccc       300
aaatcttgtg acaaaactca cacatgccca ccgtgcccag cacctgaact cctggggggga      360 ccgtcagtct tcctcttccc cccaaaaccc aaggacaccc tcatgatctc ccggacccct       420
gaggtcacat gcgtggtggt ggacgtgagc cacgaagacc ctgaggtcaa gttcaactgg       480
tacgtggacg gcgtggaggt gcataatgcc aagacaaagc cgcgggagga gcagtacgcc       540
agcacgtacc gtgtggtcag cgtcctcacc gtcctgcacc aggactggct gaatggcaag       600
gagtacaagt gcaaggtctc caacaaagcc ctcccagccc ccatcgagaa aaccatctcc       660
aaagccaaag ggcagccccg agaaccacag gtgtacaccc tgcccccatc ccgggaggag       720
atgaccaaga accaggtcag cctgacctgc ctggtcaaag gcttctatcc cagcgacatc       780
gccgtggagt gggagagcaa tgggcagccg gagaacaact acaagaccac gcctcccgtg       840
ctggactccg acggctcctt cttcctctac agcaagctca ccgtggacaa gagcaggtgg       900
cagcagggga acgtcttctc atgctccgtg atgcatgagg ctctgcacaa ccactacacg       960
cagaagagcc tctccctgtc tccgggtaaa tga                                    993

<210> SEQ ID NO 381
<211> LENGTH: 219
<212> TYPE: PRT
<213> ORGANISM: Artificial
<220> FEATURE:
<223> OTHER INFORMATION: Engineered antibody sequence

<400> SEQUENCE: 381

Gln Val Leu Thr Gln Ser Pro Ser Ser Leu Ser Ala Ser Val Gly Asp
1               5                   10                  15

Arg Val Thr Ile Asn Cys Gln Ala Ser Gln Asn Val Tyr Asn Asn Asn
```

```
                    20                  25                  30

Tyr Leu Ala Trp Tyr Gln Gln Lys Pro Gly Lys Val Pro Lys Gln Leu
            35                  40                  45

Ile Tyr Ser Thr Ser Thr Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Arg Gly Asp Cys Phe Val Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 382
<211> LENGTH: 113
<212> TYPE: PRT
<213> ORGANISM: Artificial
<220> FEATURE:
<223> OTHER INFORMATION: Engineered antibody sequence

<400> SEQUENCE: 382

Gln Val Leu Thr Gln Ser Pro Ser Ser Leu Ser Ala Ser Val Gly Asp
1               5                   10                  15

Arg Val Thr Ile Asn Cys Gln Ala Ser Gln Asn Val Tyr Asn Asn Asn
            20                  25                  30

Tyr Leu Ala Trp Tyr Gln Gln Lys Pro Gly Lys Val Pro Lys Gln Leu
            35                  40                  45

Ile Tyr Ser Thr Ser Thr Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Arg Gly Asp Cys Phe Val Phe Gly Gly Gly Thr Lys Val Glu Ile Lys
                100                 105                 110

Arg

<210> SEQ ID NO 383
<211> LENGTH: 22
<212> TYPE: PRT
<213> ORGANISM: Artificial
<220> FEATURE:
<223> OTHER INFORMATION: Engineered antibody sequence
```

<400> SEQUENCE: 383

Gln Val Leu Thr Gln Ser Pro Ser Ser Leu Ser Ala Ser Val Gly Asp
1               5                   10                  15

Arg Val Thr Ile Asn Cys
            20

<210> SEQ ID NO 384
<211> LENGTH: 13
<212> TYPE: PRT
<213> ORGANISM: Artificial
<220> FEATURE:
<223> OTHER INFORMATION: Engineered antibody sequence

<400> SEQUENCE: 384

Gln Ala Ser Gln Asn Val Tyr Asn Asn Asn Tyr Leu Ala
1               5                   10

<210> SEQ ID NO 385
<211> LENGTH: 15
<212> TYPE: PRT
<213> ORGANISM: Artificial
<220> FEATURE:
<223> OTHER INFORMATION: Engineered antibody sequence

<400> SEQUENCE: 385

Trp Tyr Gln Gln Lys Pro Gly Lys Val Pro Lys Gln Leu Ile Tyr
1               5                   10                  15

<210> SEQ ID NO 386
<211> LENGTH: 7
<212> TYPE: PRT
<213> ORGANISM: Artificial
<220> FEATURE:
<223> OTHER INFORMATION: Engineered antibody sequence

<400> SEQUENCE: 386

Ser Thr Ser Thr Leu Ala Ser
1               5

<210> SEQ ID NO 387
<211> LENGTH: 32
<212> TYPE: PRT
<213> ORGANISM: Artificial
<220> FEATURE:
<223> OTHER INFORMATION: Engineered antibody sequence

<400> SEQUENCE: 387

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 388
<211> LENGTH: 13
<212> TYPE: PRT
<213> ORGANISM: Artificial
<220> FEATURE:
<223> OTHER INFORMATION: Engineered antibody sequence

<400> SEQUENCE: 388

Leu Gly Ser Tyr Asp Cys Ser Arg Gly Asp Cys Phe Val
1               5                   10

<210> SEQ ID NO 389
<211> LENGTH: 11

```
<212> TYPE: PRT
<213> ORGANISM: Artificial
<220> FEATURE:
<223> OTHER INFORMATION: Engineered antibody sequence

<400> SEQUENCE: 389

Phe Gly Gly Gly Thr Lys Val Glu Ile Lys Arg
1               5                   10

<210> SEQ ID NO 390
<211> LENGTH: 106
<212> TYPE: PRT
<213> ORGANISM: Artificial
<220> FEATURE:
<223> OTHER INFORMATION: Engineered antibody sequence

<400> SEQUENCE: 390

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 391
<211> LENGTH: 660
<212> TYPE: DNA
<213> ORGANISM: Artificial
<220> FEATURE:
<223> OTHER INFORMATION: Engineered antibody sequence

<400> SEQUENCE: 391
caagtgctga cccagtctcc atcctccctg tctgcatctg taggagacag agtcaccatc    60
aattgccagg ccagtcagaa tgtttacaat aacaactacc tagcctggta tcagcagaaa   120
ccagggaaag ttcctaagca actgatctat tctacatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtagtcg tggtgattgt   300
tttgttttcg gcggaggaac caaggtggaa atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

<210> SEQ ID NO 392
<211> LENGTH: 339
<212> TYPE: DNA
<213> ORGANISM: Artificial
<220> FEATURE:
```

<223> OTHER INFORMATION: Engineered antibody sequence

<400> SEQUENCE: 392

```
caagtgctga cccagtctcc atcctccctg tctgcatctg taggagacag agtcaccatc      60
aattgccagg ccagtcagaa tgtttacaat aacaactacc tagcctggta tcagcagaaa     120
ccagggaaag ttcctaagca actgatctat tctacatcca ctctggcatc tggggtccca     180
tctcgtttca gtggcagtgg atctgggaca gatttcactc tcaccatcag cagcctgcag     240
cctgaagatg ttgcaactta ttactgtctg ggcagttatg attgtagtcg tggtgattgt     300
tttgttttcg gcggaggaac caaggtggaa atcaaacgt                            339
```

<210> SEQ ID NO 393
<211> LENGTH: 66
<212> TYPE: DNA
<213> ORGANISM: Artificial
<220> FEATURE:
<223> OTHER INFORMATION: Engineered antibody sequence

<400> SEQUENCE: 393

```
caagtgctga cccagtctcc atcctccctg tctgcatctg taggagacag agtcaccatc      60
aattgc                                                                 66
```

<210> SEQ ID NO 394
<211> LENGTH: 39
<212> TYPE: DNA
<213> ORGANISM: Artificial
<220> FEATURE:
<223> OTHER INFORMATION: Engineered antibody sequence

<400> SEQUENCE: 394

```
caggccagtc agaatgttta caataacaac tacctagcc                             39
```

<210> SEQ ID NO 395
<211> LENGTH: 45
<212> TYPE: DNA
<213> ORGANISM: Artificial
<220> FEATURE:
<223> OTHER INFORMATION: Engineered antibody sequence

<400> SEQUENCE: 395

```
tggtatcagc agaaaccagg gaaagttcct aagcaactga tctat                      45
```

<210> SEQ ID NO 396
<211> LENGTH: 21
<212> TYPE: DNA
<213> ORGANISM: Artificial
<220> FEATURE:
<223> OTHER INFORMATION: Engineered antibody sequence

<400> SEQUENCE: 396

```
tctacatcca ctctggcatc t                                                21
```

<210> SEQ ID NO 397
<211> LENGTH: 96
<212> TYPE: DNA
<213> ORGANISM: Artificial
<220> FEATURE:
<223> OTHER INFORMATION: Engineered antibody sequence

<400> SEQUENCE: 397

```
ggggtcccat ctcgtttcag tggcagtgga tctgggacag atttcactct caccatcagc      60
agcctgcagc ctgaagatgt tgcaacttat tactgt                                96
```

<210> SEQ ID NO 398
<211> LENGTH: 39
<212> TYPE: DNA
<213> ORGANISM: Artificial
<220> FEATURE:
<223> OTHER INFORMATION: Engineered antibody sequence

<400> SEQUENCE: 398
ctgggcagtt atgattgtag tcgtggtgat tgttttgtt                             39

<210> SEQ ID NO 399
<211> LENGTH: 33
<212> TYPE: DNA
<213> ORGANISM: Artificial
<220> FEATURE:
<223> OTHER INFORMATION: Engineered antibody sequence

<400> SEQUENCE: 399
ttcggcggag gaaccaaggt ggaaatcaaa cgt                                   33

<210> SEQ ID NO 400
<211> LENGTH: 321
<212> TYPE: DNA
<213> ORGANISM: Artificial
<220> FEATURE:
<223> OTHER INFORMATION: Engineered antibody sequence

<400> SEQUENCE: 400
acggtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat caggggctga gctcgcccgt cacaaagagc     300
ttcaacaggg gagagtgtta g                                              321

<210> SEQ ID NO 401
<211> LENGTH: 439
<212> TYPE: PRT
<213> ORGANISM: Artificial
<220> FEATURE:
<223> OTHER INFORMATION: Engineered antibody sequence

<400> SEQUENCE: 401

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Val Thr Asn Tyr Tyr
            20                  25                  30

Met Gln Trp Val Arg Gln Ala Pro Gly Lys Gly Leu Glu Trp Ile Gly
        35                  40                  45

Val Ile Gly Val Asn Gly Lys Arg Tyr Tyr Ala Ser Trp Ala Lys Gly
    50                  55                  60

Arg Phe Thr Ile Ser Lys Thr Ser Ser Thr Val Asp Leu Lys Met
65                  70                  75                  80

Thr Ser Leu Thr Thr Glu Asp Thr Ala Thr Tyr Phe Cys Ala Arg Gly
                85                  90                  95

Asp Ile Trp Gly Pro Gly Thr Leu Val Thr Val Ser Ser Ala Ser Thr
            100                 105                 110

Lys Gly Pro Ser Val Phe Pro Leu Ala Pro Ser Ser Lys Ser Thr Ser

```
                115                 120                 125
Gly Gly Thr Ala Ala Leu Gly Cys Leu Val Lys Asp Tyr Phe Pro Glu
            130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Leu Gly Thr Gln Thr Tyr Ile Cys
            180                 185                 190

Asn Val Asn His Lys Pro Ser Asn Thr Lys Val Asp Lys Arg Val Glu
                195                 200                 205

Pro Lys Ser Cys Asp Lys Thr His Thr Cys Pro Pro Cys Pro Ala Pro
210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
                260                 265                 270

Gly Val Glu Val His Asn Ala Lys Thr Lys Pro Arg Glu Glu Gln Tyr
            275                 280                 285

Ala Ser Thr Tyr Arg Val Val Ser Val Leu Thr Val Leu His Gln Asp
            290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Ser Arg Glu Glu Met Thr Lys
                340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
            370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
                420                 425                 430

Leu Ser Leu Ser Pro Gly Lys
            435

<210> SEQ ID NO 402
<211> LENGTH: 109
<212> TYPE: PRT
<213> ORGANISM: Artificial
<220> FEATURE:
<223> OTHER INFORMATION: Engineered antibody sequence

<400> SEQUENCE: 402

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Val Thr Asn Tyr Tyr
            20                  25                  30

Met Gln Trp Val Arg Gln Ala Pro Gly Lys Gly Leu Glu Trp Ile Gly
```

```
                35                  40                  45
Val Ile Gly Val Asn Gly Lys Arg Tyr Tyr Ala Ser Trp Ala Lys Gly
     50                  55                  60

Arg Phe Thr Ile Ser Lys Thr Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Asp Ile Trp Gly Pro Gly Thr Leu Val Thr Val Ser Ser
            100                 105

<210> SEQ ID NO 403
<211> LENGTH: 29
<212> TYPE: PRT
<213> ORGANISM: Artificial
<220> FEATURE:
<223> OTHER INFORMATION: Engineered antibody sequence

<400> SEQUENCE: 403

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Val Thr
            20                  25

<210> SEQ ID NO 404
<211> LENGTH: 5
<212> TYPE: PRT
<213> ORGANISM: Artificial
<220> FEATURE:
<223> OTHER INFORMATION: Engineered antibody sequence

<400> SEQUENCE: 404

Asn Tyr Tyr Met Gln
1               5

<210> SEQ ID NO 405
<211> LENGTH: 14
<212> TYPE: PRT
<213> ORGANISM: Artificial
<220> FEATURE:
<223> OTHER INFORMATION: Engineered antibody sequence

<400> SEQUENCE: 405

Trp Val Arg Gln Ala Pro Gly Lys Gly Leu Glu Trp Ile Gly
1               5                   10

<210> SEQ ID NO 406
<211> LENGTH: 16
<212> TYPE: PRT
<213> ORGANISM: Artificial
<220> FEATURE:
<223> OTHER INFORMATION: Engineered antibody sequence

<400> SEQUENCE: 406

Val Ile Gly Val Asn Gly Lys Arg Tyr Tyr Ala Ser Trp Ala Lys Gly
1               5                   10                  15

<210> SEQ ID NO 407
<211> LENGTH: 31
<212> TYPE: PRT
<213> ORGANISM: Artificial
<220> FEATURE:
<223> OTHER INFORMATION: Engineered antibody sequence

<400> SEQUENCE: 407
```

Arg Phe Thr Ile Ser Lys Thr Ser Ser Thr Thr Val Asp Leu Lys Met
1               5                   10                  15

Thr Ser Leu Thr Thr Glu Asp Thr Ala Thr Tyr Phe Cys Ala Arg
            20                  25                  30

<210> SEQ ID NO 408
<211> LENGTH: 3
<212> TYPE: PRT
<213> ORGANISM: Artificial
<220> FEATURE:
<223> OTHER INFORMATION: Engineered antibody sequence

<400> SEQUENCE: 408

Gly Asp Ile
1

<210> SEQ ID NO 409
<211> LENGTH: 11
<212> TYPE: PRT
<213> ORGANISM: Artificial
<220> FEATURE:
<223> OTHER INFORMATION: Engineered antibody sequence

<400> SEQUENCE: 409

Trp Gly Pro Gly Thr Leu Val Thr Val Ser Ser
1               5                   10

<210> SEQ ID NO 410
<211> LENGTH: 330
<212> TYPE: PRT
<213> ORGANISM: Artificial
<220> FEATURE:
<223> OTHER INFORMATION: Engineered antibody sequence

<400> SEQUENCE: 410

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn

|     |     |     | 195 |     |     |     | 200 |     |     |     | 205 |     |     |
| --- | --- | --- | --- | --- | --- | --- | --- | --- | --- | --- | --- | --- | --- |
| Lys | Ala | Leu | Pro | Ala | Pro | Ile | Glu | Lys | Thr | Ile | Ser | Lys | Ala | Lys | Gly |
|     | 210 |     |     |     | 215 |     |     |     | 220 |     |     |     |     |

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 411
<211> LENGTH: 1320
<212> TYPE: DNA
<213> ORGANISM: Artificial
<220> FEATURE:
<223> OTHER INFORMATION: Engineered antibody sequence

<400> SEQUENCE: 411

```
cagtcgctgg aggagtccgg gggtcgcctg gtcacgcctg gaggatccct gacactcacc      60
tgcacagtct ctggaatcga cgtcactaac tactatatgc aatgggtccg ccaggctcca     120
gggaaggggc tggaatggat cggagtcatt ggtgtgaatg gtaagagata ctacgcgagc     180
tgggcgaaag gccgattcac catctccaaa acctcgtcga ccacggtgga tctgaaaatg     240
accagtctga aaccgaggac acggccacct atttctgtgt ccagaggcga catctggggc     300
ccggggaccc tcgtcaccgt ctcgagcgcc tccaccaagg gcccatcggt cttccccctg     360
gcaccctcct ccaagagcac ctctgggggc acagcggccc tgggctgcct ggtcaaggac     420
tacttccccg aaccggtgac ggtgtcgtgg aactcaggcg ccctgaccag cggcgtgcac     480
accttccggg ctgtcctaca gtcctcagga ctctactccc tcagcagcgt ggtgaccgtg     540
ccctccagca gcttgggcac ccagacctac atctgcaacg tgaatcacaa gcccagcaac     600
accaaggtgg acaagagagt tgagcccaaa tcttgtgaca aaactcacac atgcccaccg     660
tgcccagcac ctgaactcct ggggggaccg tcagtcttcc tcttcccccc aaaacccaag     720
gacaccctca tgatctcccg gacccctgag gtcacatgcg tggtggtgga cgtgagccac     780
gaagaccctg aggtcaagtt caactggtac gtggacggcg tggaggtgca taatgccaag     840
acaaagccgc gggaggagca gtacgccagc acgtaccgtg tggtcagcgt cctcaccgtc     900
ctgcaccagg actggctgaa tggcaaggag tacaagtgca aggtctccaa caaagccctc     960
ccagccccca tcgagaaaac catctccaaa gccaaagggc agccccgaga accacaggtg    1020
tacaccctgc cccatcccg ggaggagatg accaagaacc aggtcagcct gacctgcctg     1080
gtcaaaggct tctatcccag cgacatcgcc gtggagtggg agagcaatgg gcagccggag    1140
aacaactaca agaccacgcc tcccgtgctg gactccgacg gctccttctt cctctacagc    1200
aagctcaccg tggacaagag caggtggcag caggggaacg tcttctcatg ctccgtgatg    1260
catgaggctc tgcacaacca ctacacgcag aagagcctct ccctgtctcc gggtaaatga    1320
```

```
<210> SEQ ID NO 412
<211> LENGTH: 327
<212> TYPE: DNA
<213> ORGANISM: Artificial
<220> FEATURE:
<223> OTHER INFORMATION: Engineered antibody sequence

<400> SEQUENCE: 412
cagtcgctgg aggagtccgg gggtcgcctg gtcacgcctg gaggatccct gacactcacc      60
tgcacagtct ctggaatcga cgtcactaac tactatatgc aatgggtccg ccaggctcca     120
gggaaggggc tggaatggat cggagtcatt ggtgtgaatg gtaagagata ctacgcgagc     180
tgggcgaaag gccgattcac catctccaaa acctcgtcga ccacggtgga tctgaaaatg     240
accagtctga caaccgagga cacggccacc tatttctgtg ccagaggcga catctggggc     300
ccggggaccc tcgtcaccgt ctcgagc                                         327

<210> SEQ ID NO 413
<211> LENGTH: 87
<212> TYPE: DNA
<213> ORGANISM: Artificial
<220> FEATURE:
<223> OTHER INFORMATION: Engineered antibody sequence

<400> SEQUENCE: 413
cagtcgctgg aggagtccgg gggtcgcctg gtcacgcctg gaggatccct gacactcacc      60
tgcacagtct ctggaatcga cgtcact                                          87

<210> SEQ ID NO 414
<211> LENGTH: 15
<212> TYPE: DNA
<213> ORGANISM: Artificial
<220> FEATURE:
<223> OTHER INFORMATION: Engineered antibody sequence

<400> SEQUENCE: 414
aactactata tgcaa                                                       15

<210> SEQ ID NO 415
<211> LENGTH: 42
<212> TYPE: DNA
<213> ORGANISM: Artificial
<220> FEATURE:
<223> OTHER INFORMATION: Engineered antibody sequence

<400> SEQUENCE: 415
tgggtccgcc aggctccagg gaaggggctg gaatggatcg ga                         42

<210> SEQ ID NO 416
<211> LENGTH: 48
<212> TYPE: DNA
<213> ORGANISM: Artificial
<220> FEATURE:
<223> OTHER INFORMATION: Engineered antibody sequence

<400> SEQUENCE: 416
gtcattggtg tgaatggtaa gagatactac gcgagctggg cgaaaggc                   48

<210> SEQ ID NO 417
<211> LENGTH: 93
<212> TYPE: DNA
<213> ORGANISM: Artificial
<220> FEATURE:
```

<223> OTHER INFORMATION: Engineered antibody sequence

<400> SEQUENCE: 417

| cgattcacca tctccaaaac ctcgtcgacc acggtggatc tgaaaatgac cagtctgaca | 60 |
| accgaggaca cggccaccta tttctgtgcc aga | 93 |

<210> SEQ ID NO 418
<211> LENGTH: 9
<212> TYPE: DNA
<213> ORGANISM: Artificial
<220> FEATURE:
<223> OTHER INFORMATION: Engineered antibody sequence

<400> SEQUENCE: 418

| ggcgacatc | 9 |

<210> SEQ ID NO 419
<211> LENGTH: 33
<212> TYPE: DNA
<213> ORGANISM: Artificial
<220> FEATURE:
<223> OTHER INFORMATION: Engineered antibody sequence

<400> SEQUENCE: 419

| tggggcccgg ggaccctcgt caccgtctcg agc | 33 |

<210> SEQ ID NO 420
<211> LENGTH: 993
<212> TYPE: DNA
<213> ORGANISM: Artificial
<220> FEATURE:
<223> OTHER INFORMATION: Engineered antibody sequence

<400> SEQUENCE: 420

| gcctccacca agggcccatc ggtcttcccc ctggcaccct cctccaagag cacctctggg | 60 |
| ggcacagcgg ccctgggctg cctggtcaag gactacttcc ccgaaccggt gacggtgtcg | 120 |
| tggaactcag gcgccctgac cagcggcgtg cacaccttcc cggctgtcct acagtcctca | 180 |
| ggactctact ccctcagcag cgtggtgacc gtgccctcca gcagcttggg cacccagacc | 240 |
| tacatctgca acgtgaatca caagcccagc aacaccaagg tggacaagag agttgagccc | 300 |
| aaatcttgtg acaaaactca cacatgccca ccgtgcccag cacctgaact cctgggggga | 360 |
| ccgtcagtct tcctcttccc cccaaaaccc aaggacaccc tcatgatctc ccggacccct | 420 |
| gaggtcacat gcgtggtggt ggacgtgagc cacgaagacc ctgaggtcaa gttcaactgg | 480 |
| tacgtggacg gcgtggaggt gcataatgcc aagacaaagc cgcgggagga gcagtacgcc | 540 |
| agcacgtacc gtgtggtcag cgtcctcacc gtcctgcacc aggactggct gaatggcaag | 600 |
| gagtacaagt gcaaggtctc caacaaagcc ctcccagccc catcgagaa aaccatctcc | 660 |
| aaagccaaag gcagccccg agaaccacag gtgtacaccc tgcccccatc ccgggaggag | 720 |
| atgaccaaga accaggtcag cctgacctgc ctggtcaaag gcttctatcc cagcgacatc | 780 |
| gccgtggagt gggagagcaa tgggcagccg gagaacaact acaagaccac gcctcccgtg | 840 |
| ctggactccg acggctcctt cttcctctac agcaagctca ccgtggacaa gagcaggtgg | 900 |
| cagcagggga acgtcttctc atgctccgtg atgcatgagg ctctgcacaa ccactacacg | 960 |
| cagaagagcc tctccctgtc tccgggtaaa tga | 993 |

<210> SEQ ID NO 421
<211> LENGTH: 219

```
<212> TYPE: PRT
<213> ORGANISM: Artificial
<220> FEATURE:
<223> OTHER INFORMATION: Engineered antibody sequence

<400> SEQUENCE: 421
```

| | | | | | | | | | | | | | | | |
|---|---|---|---|---|---|---|---|---|---|---|---|---|---|---|---|
| Gln | Val | Leu | Thr | Gln | Thr | Ala | Ser | Pro | Val | Ser | Pro | Ala | Val | Gly | Ser |
| 1 | | | | 5 | | | | | 10 | | | | | 15 | |
| Thr | Val | Thr | Ile | Asn | Cys | Arg | Ala | Ser | Gln | Ser | Val | Tyr | Tyr | Asn | Asn |
| | | | 20 | | | | | 25 | | | | | 30 | | |
| Tyr | Leu | Ala | Trp | Tyr | Gln | Gln | Lys | Pro | Gly | Gln | Pro | Pro | Lys | Gln | Leu |
| | | 35 | | | | | 40 | | | | | 45 | | | |
| Ile | Tyr | Ser | Thr | Ser | Thr | Leu | Ala | Ser | Gly | Val | Ser | Ser | Arg | Phe | Lys |
| 50 | | | | | 55 | | | | | 60 | | | | | |
| Gly | Ser | Gly | Ser | Gly | Thr | Gln | Phe | Thr | Leu | Thr | Ile | Ser | Asp | Val | Gln |
| 65 | | | | | 70 | | | | | 75 | | | | | 80 |
| Cys | Asp | Asp | Ala | Ala | Thr | Tyr | Tyr | Cys | Leu | Gly | Ser | Tyr | Asp | Cys | Ser |
| | | | | 85 | | | | | 90 | | | | | 95 | |
| Asn | Gly | Asp | Cys | Phe | Val | Phe | Gly | Gly | Thr | Glu | Val | Val | Val | Lys |
| | | | 100 | | | | | 105 | | | | | 110 | | |
| Arg | Thr | Val | Ala | Ala | Pro | Ser | Val | Phe | Ile | Phe | Pro | Pro | Ser | Asp | Glu |
| | | 115 | | | | | 120 | | | | | 125 | | | |
| Gln | Leu | Lys | Ser | Gly | Thr | Ala | Ser | Val | Val | Cys | Leu | Leu | Asn | Asn | Phe |
| 130 | | | | | 135 | | | | | 140 | | | | | |
| Tyr | Pro | Arg | Glu | Ala | Lys | Val | Gln | Trp | Lys | Val | Asp | Asn | Ala | Leu | Gln |
| 145 | | | | 150 | | | | | 155 | | | | | 160 | |
| Ser | Gly | Asn | Ser | Gln | Glu | Ser | Val | Thr | Glu | Gln | Asp | Ser | Lys | Asp | Ser |
| | | | | 165 | | | | | 170 | | | | | 175 | |
| Thr | Tyr | Ser | Leu | Ser | Ser | Thr | Leu | Thr | Leu | Ser | Lys | Ala | Asp | Tyr | Glu |
| | | | 180 | | | | | 185 | | | | | 190 | | |
| Lys | His | Lys | Val | Tyr | Ala | Cys | Glu | Val | Thr | His | Gln | Gly | Leu | Ser | Ser |
| | | 195 | | | | | 200 | | | | | 205 | | | |
| Pro | Val | Thr | Lys | Ser | Phe | Asn | Arg | Gly | Glu | Cys |
| | 210 | | | | | 215 | | | | |

```
<210> SEQ ID NO 422
<211> LENGTH: 113
<212> TYPE: PRT
<213> ORGANISM: Artificial
<220> FEATURE:
<223> OTHER INFORMATION: Engineered antibody sequence

<400> SEQUENCE: 422
```

| | | | | | | | | | | | | | | | |
|---|---|---|---|---|---|---|---|---|---|---|---|---|---|---|---|
| Gln | Val | Leu | Thr | Gln | Thr | Ala | Ser | Pro | Val | Ser | Pro | Ala | Val | Gly | Ser |
| 1 | | | | 5 | | | | | 10 | | | | | 15 | |
| Thr | Val | Thr | Ile | Asn | Cys | Arg | Ala | Ser | Gln | Ser | Val | Tyr | Tyr | Asn | Asn |
| | | | 20 | | | | | 25 | | | | | 30 | | |
| Tyr | Leu | Ala | Trp | Tyr | Gln | Gln | Lys | Pro | Gly | Gln | Pro | Pro | Lys | Gln | Leu |
| | | 35 | | | | | 40 | | | | | 45 | | | |
| Ile | Tyr | Ser | Thr | Ser | Thr | Leu | Ala | Ser | Gly | Val | Ser | Ser | Arg | Phe | Lys |
| 50 | | | | | 55 | | | | | 60 | | | | | |
| Gly | Ser | Gly | Ser | Gly | Thr | Gln | Phe | Thr | Leu | Thr | Ile | Ser | Asp | Val | Gln |
| 65 | | | | | 70 | | | | | 75 | | | | | 80 |
| Cys | Asp | Asp | Ala | Ala | Thr | Tyr | Tyr | Cys | Leu | Gly | Ser | Tyr | Asp | Cys | Ser |
| | | | | 85 | | | | | 90 | | | | | 95 | |
| Asn | Gly | Asp | Cys | Phe | Val | Phe | Gly | Gly | Thr | Glu | Val | Val | Val | Lys |
| | | | 100 | | | | | 105 | | | | | 110 | | |

Arg

<210> SEQ ID NO 423
<211> LENGTH: 22
<212> TYPE: PRT
<213> ORGANISM: Artificial
<220> FEATURE:
<223> OTHER INFORMATION: Engineered antibody sequence

<400> SEQUENCE: 423

Gln Val Leu Thr Gln Thr Ala Ser Pro Val Ser Pro Ala Val Gly Ser
1               5                   10                  15

Thr Val Thr Ile Asn Cys
            20

<210> SEQ ID NO 424
<211> LENGTH: 13
<212> TYPE: PRT
<213> ORGANISM: Artificial
<220> FEATURE:
<223> OTHER INFORMATION: Engineered antibody sequence

<400> SEQUENCE: 424

Arg Ala Ser Gln Ser Val Tyr Tyr Asn Asn Tyr Leu Ala
1               5                   10

<210> SEQ ID NO 425
<211> LENGTH: 15
<212> TYPE: PRT
<213> ORGANISM: Artificial
<220> FEATURE:
<223> OTHER INFORMATION: Engineered antibody sequence

<400> SEQUENCE: 425

Trp Tyr Gln Gln Lys Pro Gly Gln Pro Pro Lys Gln Leu Ile Tyr
1               5                   10                  15

<210> SEQ ID NO 426
<211> LENGTH: 7
<212> TYPE: PRT
<213> ORGANISM: Artificial
<220> FEATURE:
<223> OTHER INFORMATION: Engineered antibody sequence

<400> SEQUENCE: 426

Ser Thr Ser Thr Leu Ala Ser
1               5

<210> SEQ ID NO 427
<211> LENGTH: 32
<212> TYPE: PRT
<213> ORGANISM: Artificial
<220> FEATURE:
<223> OTHER INFORMATION: Engineered antibody sequence

<400> SEQUENCE: 427

Gly Val Ser Ser Arg Phe Lys Gly Ser Gly Ser Gly Thr Gln Phe Thr
1               5                   10                  15

Leu Thr Ile Ser Asp Val Gln Cys Asp Asp Ala Ala Thr Tyr Tyr Cys
            20                  25                  30

<210> SEQ ID NO 428
<211> LENGTH: 13
<212> TYPE: PRT
<213> ORGANISM: Artificial

<220> FEATURE:
<223> OTHER INFORMATION: Engineered antibody sequence

<400> SEQUENCE: 428

Leu Gly Ser Tyr Asp Cys Ser Asn Gly Asp Cys Phe Val
1               5                   10

<210> SEQ ID NO 429
<211> LENGTH: 11
<212> TYPE: PRT
<213> ORGANISM: Artificial
<220> FEATURE:
<223> OTHER INFORMATION: Engineered antibody sequence

<400> SEQUENCE: 429

Phe Gly Gly Gly Thr Glu Val Val Val Lys Arg
1               5                   10

<210> SEQ ID NO 430
<211> LENGTH: 106
<212> TYPE: PRT
<213> ORGANISM: Artificial
<220> FEATURE:
<223> OTHER INFORMATION: Engineered antibody sequence

<400> SEQUENCE: 430

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 431
<211> LENGTH: 660
<212> TYPE: DNA
<213> ORGANISM: Artificial
<220> FEATURE:
<223> OTHER INFORMATION: Engineered antibody sequence

<400> SEQUENCE: 431
caggtgctga cccagactgc atcccccgtg tctccagctg tgggaagcac agtcaccatc    60
aattgccggg ccagtcagag tgtttattat aacaactacc tagcctggta tcagcagaaa   120
ccagggcagc ctcccaagca actgatctat tctacatcca ctctggcatc tggggtctca   180
tcgcggttca aaggcagtgg atctgggaca cagttcactc tcaccatcag cgacgtgcag   240
tgtgacgatg ctgccactta ctactgtcta ggcagttatg attgtagtaa tggtgattgt   300
tttgttttcg gcggagggac cgaggtggtg gtcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660

<210> SEQ ID NO 432
<211> LENGTH: 339
<212> TYPE: DNA
<213> ORGANISM: Artificial
<220> FEATURE:
<223> OTHER INFORMATION: Engineered antibody sequence

<400> SEQUENCE: 432
caggtgctga cccagactgc atcccccgtg tctccagctg tgggaagcac agtcaccatc     60
aattgccggg ccagtcagag tgtttattat aacaactacc tagcctggta tcagcagaaa    120
ccagggcagc ctcccaagca actgatctat tctacatcca ctctggcatc tggggtctca    180
tcgcggttca aaggcagtgg atctgggaca cagttcactc tcaccatcag cgacgtgcag    240
tgtgacgatg ctgccactta ctactgtcta ggcagttatg attgtagtaa tggtgattgt    300
tttgttttcg gcggagggac cgaggtggtg gtcaaacgt                           339

<210> SEQ ID NO 433
<211> LENGTH: 66
<212> TYPE: DNA
<213> ORGANISM: Artificial
<220> FEATURE:
<223> OTHER INFORMATION: Engineered antibody sequence

<400> SEQUENCE: 433
caggtgctga cccagactgc atcccccgtg tctccagctg tgggaagcac agtcaccatc     60
aattgc                                                                66

<210> SEQ ID NO 434
<211> LENGTH: 39
<212> TYPE: DNA
<213> ORGANISM: Artificial
<220> FEATURE:
<223> OTHER INFORMATION: Engineered antibody sequence

<400> SEQUENCE: 434
cgggccagtc agagtgttta ttataacaac tacctagcc                            39

<210> SEQ ID NO 435
<211> LENGTH: 45
<212> TYPE: DNA
<213> ORGANISM: Artificial
<220> FEATURE:
<223> OTHER INFORMATION: Engineered antibody sequence

<400> SEQUENCE: 435
tggtatcagc agaaaccagg gcagcctccc aagcaactga tctat                     45

<210> SEQ ID NO 436
<211> LENGTH: 21
<212> TYPE: DNA
<213> ORGANISM: Artificial
<220> FEATURE:
<223> OTHER INFORMATION: Engineered antibody sequence

<400> SEQUENCE: 436
tctacatcca ctctggcatc t                                               21

<210> SEQ ID NO 437

```
<211> LENGTH: 96
<212> TYPE: DNA
<213> ORGANISM: Artificial
<220> FEATURE:
<223> OTHER INFORMATION: Engineered antibody sequence

<400> SEQUENCE: 437
ggggtctcat cgcggttcaa aggcagtgga tctgggacac agttcactct caccatcagc      60
gacgtgcagt gtgacgatgc tgccacttac tactgt                                96

<210> SEQ ID NO 438
<211> LENGTH: 39
<212> TYPE: DNA
<213> ORGANISM: Artificial
<220> FEATURE:
<223> OTHER INFORMATION: Engineered antibody sequence

<400> SEQUENCE: 438
ctaggcagtt atgattgtag taatggtgat tgttttgtt                             39

<210> SEQ ID NO 439
<211> LENGTH: 33
<212> TYPE: DNA
<213> ORGANISM: Artificial
<220> FEATURE:
<223> OTHER INFORMATION: Engineered antibody sequence

<400> SEQUENCE: 439
ttcggcggag ggaccgaggt ggtggtcaaa cgt                                   33

<210> SEQ ID NO 440
<211> LENGTH: 321
<212> TYPE: DNA
<213> ORGANISM: Artificial
<220> FEATURE:
<223> OTHER INFORMATION: Engineered antibody sequence

<400> SEQUENCE: 440
acggtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgtta g                                              321

<210> SEQ ID NO 441
<211> LENGTH: 441
<212> TYPE: PRT
<213> ORGANISM: Artificial
<220> FEATURE:
<223> OTHER INFORMATION: Engineered antibody sequence

<400> SEQUENCE: 441

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Val Thr Asn Tyr
            20                  25                  30

Tyr Met Gln Trp Val Arg Gln Ala Pro Gly Lys Gly Leu Glu Trp Val
        35                  40                  45

Gly Val Ile Gly Val Asn Gly Lys Arg Tyr Tyr Ala Ser Trp Ala Lys
    50                  55                  60
```

```
Gly Arg Phe Thr Ile Ser Arg Asp Asn Ser Lys Thr Val Tyr Leu
65                  70                  75                  80

Gln Met Asn Ser Leu Arg Ala Glu Asp Thr Ala Val Tyr Phe Cys Ala
            85                  90                  95

Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
            115                 120                 125

Thr Ser Gly Gly Thr Ala Ala Leu Gly Cys Leu Val Lys Asp Tyr Phe
            130             135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Arg
            195                 200                 205

Val Glu Pro Lys Ser Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
            275                 280                 285

Gln Tyr Ala Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
            325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
            370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
            435                 440

<210> SEQ ID NO 442
<211> LENGTH: 111
<212> TYPE: PRT
<213> ORGANISM: Artificial
<220> FEATURE:
```

<223> OTHER INFORMATION: Engineered antibody sequence

<400> SEQUENCE: 442

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Val Thr Asn Tyr
            20                  25                  30

Tyr Met Gln Trp Val Arg Gln Ala Pro Gly Lys Gly Leu Glu Trp Val
        35                  40                  45

Gly Val Ile Gly Val Asn Gly Lys Arg Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110

<210> SEQ ID NO 443
<211> LENGTH: 30
<212> TYPE: PRT
<213> ORGANISM: Artificial
<220> FEATURE:
<223> OTHER INFORMATION: Engineered antibody sequence

<400> SEQUENCE: 443

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Val Thr
            20                  25                  30

<210> SEQ ID NO 444
<211> LENGTH: 5
<212> TYPE: PRT
<213> ORGANISM: Artificial
<220> FEATURE:
<223> OTHER INFORMATION: Engineered antibody sequence

<400> SEQUENCE: 444

Asn Tyr Tyr Met Gln
1               5

<210> SEQ ID NO 445
<211> LENGTH: 14
<212> TYPE: PRT
<213> ORGANISM: Artificial
<220> FEATURE:
<223> OTHER INFORMATION: Engineered antibody sequence

<400> SEQUENCE: 445

Trp Val Arg Gln Ala Pro Gly Lys Gly Leu Glu Trp Val Gly
1               5                   10

<210> SEQ ID NO 446
<211> LENGTH: 16
<212> TYPE: PRT
<213> ORGANISM: Artificial
<220> FEATURE:
<223> OTHER INFORMATION: Engineered antibody sequence

<400> SEQUENCE: 446

Val Ile Gly Val Asn Gly Lys Arg Tyr Tyr Ala Ser Trp Ala Lys Gly
1               5                   10                  15

<210> SEQ ID NO 447
<211> LENGTH: 32
<212> TYPE: PRT
<213> ORGANISM: Artificial
<220> FEATURE:
<223> OTHER INFORMATION: Engineered antibody sequence

<400> SEQUENCE: 447

Arg Phe Thr Ile Ser Arg Asp Asn Ser Lys Thr Thr Val Tyr Leu Gln
1               5                   10                  15

Met Asn Ser Leu Arg Ala Glu Asp Thr Ala Val Tyr Phe Cys Ala Arg
            20                  25                  30

<210> SEQ ID NO 448
<211> LENGTH: 3
<212> TYPE: PRT
<213> ORGANISM: Artificial
<220> FEATURE:
<223> OTHER INFORMATION: Engineered antibody sequence

<400> SEQUENCE: 448

Gly Asp Ile
1

<210> SEQ ID NO 449
<211> LENGTH: 11
<212> TYPE: PRT
<213> ORGANISM: Artificial
<220> FEATURE:
<223> OTHER INFORMATION: Engineered antibody sequence

<400> SEQUENCE: 449

Trp Gly Gln Gly Thr Leu Val Thr Val Ser Ser
1               5                   10

<210> SEQ ID NO 450
<211> LENGTH: 330
<212> TYPE: PRT
<213> ORGANISM: Artificial
<220> FEATURE:
<223> OTHER INFORMATION: Engineered antibody sequence

<400> SEQUENCE: 450

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Ala Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 451
<211> LENGTH: 1326
<212> TYPE: DNA
<213> ORGANISM: Artificial
<220> FEATURE:
<223> OTHER INFORMATION: Engineered antibody sequence

<400> SEQUENCE: 451
gaggtgcagc ttgtggagtc tgggggaggc ttggtccagc ctgggggtc cctgagactc      60 tcctgtgcag tctctggaat cgacgtcact aactactaca tgcaatgggt ccgtcaggct     120
ccagggaagg gctgagtgg gtcggagtc attggtgtga atggtaagag atactacgcg     180
agctgggcga aaggccgatt caccatctcc agagacaatt ccaagaccac ggtgtatctt     240
caaatgaaca gcctgagagc tgaggacact gctgtgtatt tctgtgccag aggggacatc     300
tggggccaag gaccctcgt caccgtctcg agcgcctcca ccaagggccc atcggtcttc     360
cccctggcac cctcctccaa gagcacctct ggggcacag cggccctggg ctgcctggtc     420
aaggactact ccccgaacc ggtgacggtg tcgtggaact caggcgccct gaccagcggc     480
gtgcacacct tcccggctgt cctacagtcc tcaggactct actccctcag cagcgtggtg     540
accgtgccct ccagcagctt gggcacccag acctacatct gcaacgtgaa tcacaagccc     600
agcaacacca aggtggacaa gagagttgag cccaaatctt gtgacaaaac tcacacatgc     660
ccaccgtgcc cagcacctga actcctgggg ggaccgtcag tcttcctctt ccccccaaaa     720
cccaaggaca cctcatgat ctcccggacc cctgaggtca catgcgtggt ggtggacgtg     780
agccacgaag accctgaggt caagttcaac tggtacgtgg acggcgtgga ggtgcataat     840
gccaagacaa agccgcggga ggagcagtac gccagcacgt accgtgtggt cagcgtcctc     900
accgtcctgc accaggactg gctgaatggc aaggagtaca gtgcaaggt ctccaacaaa     960

-continued

```
gccctcccag cccccatcga gaaaaccatc tccaaagcca aagggcagcc ccgagaacca    1020
caggtgtaca ccctgccccc atcccgggag gagatgacca agaaccaggt cagcctgacc    1080
tgcctggtca aaggcttcta tcccagcgac atcgccgtgg agtgggagag caatgggcag    1140
ccggagaaca actacaagac cacgcctccc gtgctggact ccgacggctc cttcttcctc    1200
tacagcaagc tcaccgtgga caagagcagg tggcagcagg ggaacgtctt ctcatgctcc    1260
gtgatgcatg aggctctgca caaccactac acgcagaaga gcctctccct gtctccgggt    1320
aaatga                                                              1326
```

<210> SEQ ID NO 452
<211> LENGTH: 333
<212> TYPE: DNA
<213> ORGANISM: Artificial
<220> FEATURE:
<223> OTHER INFORMATION: Engineered antibody sequence

<400> SEQUENCE: 452

```
gaggtgcagc ttgtggagtc tgggggaggc ttggtccagc ctggggggtc cctgagactc     60
tcctgtgcag tctctggaat cgacgtcact aactactaca tgcaatgggt ccgtcaggct    120
ccagggaagg ggctggagtg ggtcggagtc attggtgtga atggtaagag atactacgcg    180
agctgggcga aaggccgatt caccatctcc agagacaatt ccaagaccac ggtgtatctt    240
caaatgaaca gcctgagagc tgaggacact gctgtgtatt tctgtgccag aggggacatc    300
tggggccaag ggaccctcgt caccgtctcg agc                                 333
```

<210> SEQ ID NO 453
<211> LENGTH: 90
<212> TYPE: DNA
<213> ORGANISM: Artificial
<220> FEATURE:
<223> OTHER INFORMATION: Engineered antibody sequence

<400> SEQUENCE: 453

```
gaggtgcagc ttgtggagtc tgggggaggc ttggtccagc ctggggggtc cctgagactc     60
tcctgtgcag tctctggaat cgacgtcact                                     90
```

<210> SEQ ID NO 454
<211> LENGTH: 15
<212> TYPE: DNA
<213> ORGANISM: Artificial
<220> FEATURE:
<223> OTHER INFORMATION: Engineered antibody sequence

<400> SEQUENCE: 454

```
aactactaca tgcaa                                                     15
```

<210> SEQ ID NO 455
<211> LENGTH: 42
<212> TYPE: DNA
<213> ORGANISM: Artificial
<220> FEATURE:
<223> OTHER INFORMATION: Engineered antibody sequence

<400> SEQUENCE: 455

```
tgggtccgtc aggctccagg gaaggggctg gagtgggtcg ga                       42
```

<210> SEQ ID NO 456
<211> LENGTH: 48
<212> TYPE: DNA
<213> ORGANISM: Artificial

<220> FEATURE:
<223> OTHER INFORMATION: Engineered antibody sequence

<400> SEQUENCE: 456
gtcattggtg tgaatggtaa gagatactac gcgagctggg cgaaaggc        48

<210> SEQ ID NO 457
<211> LENGTH: 96
<212> TYPE: DNA
<213> ORGANISM: Artificial
<220> FEATURE:
<223> OTHER INFORMATION: Engineered antibody sequence

<400> SEQUENCE: 457
cgattcacca tctccagaga caattccaag accacggtgt atcttcaaat gaacagcctg    60
agagctgagg acactgctgt gtatttctgt gccaga                              96

<210> SEQ ID NO 458
<211> LENGTH: 9
<212> TYPE: DNA
<213> ORGANISM: Artificial
<220> FEATURE:
<223> OTHER INFORMATION: Engineered antibody sequence

<400> SEQUENCE: 458 ggggacatc        9

<210> SEQ ID NO 459
<211> LENGTH: 33
<212> TYPE: DNA
<213> ORGANISM: Artificial
<220> FEATURE:
<223> OTHER INFORMATION: Engineered antibody sequence

<400> SEQUENCE: 459
tggggccaag ggaccctcgt caccgtctcg agc        33

<210> SEQ ID NO 460
<211> LENGTH: 993
<212> TYPE: DNA
<213> ORGANISM: Artificial
<220> FEATURE:
<223> OTHER INFORMATION: Engineered antibody sequence

<400> SEQUENCE: 460
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctggggggga   360 ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacgcc   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720

```
atgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctac agcaagctca ccgtggacaa gagcaggtgg      900
cagcagggga acgtcttctc atgctccgtg atgcatgagg ctctgcacaa ccactacacg      960
cagaagagcc tctccctgtc tccgggtaaa tga                                   993
```

<210> SEQ ID NO 461
<211> LENGTH: 219
<212> TYPE: PRT
<213> ORGANISM: Artificial
<220> FEATURE:
<223> OTHER INFORMATION: Engineered antibody sequence

<400> SEQUENCE: 461

```
Gln Val Leu Thr Gln Ser Pro Ser Ser Leu Ser Ala Ser Val Gly Asp
1               5                   10                  15

Arg Val Thr Ile Asn Cys Arg Ala Ser Gln Ser Val Tyr Tyr Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Asn Gly Asp Cys Phe Val Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 462
<211> LENGTH: 113
<212> TYPE: PRT
<213> ORGANISM: Artificial
<220> FEATURE:
<223> OTHER INFORMATION: Engineered antibody sequence

<400> SEQUENCE: 462

```
Gln Val Leu Thr Gln Ser Pro Ser Ser Leu Ser Ala Ser Val Gly Asp
1               5                   10                  15

Arg Val Thr Ile Asn Cys Arg Ala Ser Gln Ser Val Tyr Tyr Asn Asn
            20                  25                  30

Tyr Leu Ala Trp Tyr Gln Gln Lys Pro Gly Lys Val Pro Lys Gln Leu
```

```
                35                  40                  45
Ile Tyr Ser Thr Ser Thr Leu Ala Ser Gly Val Pro Ser Arg Phe Ser
             50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                 85                  90                  95

Asn Gly Asp Cys Phe Val Phe Gly Gly Gly Thr Lys Val Glu Ile Lys
            100                 105                 110

Arg

<210> SEQ ID NO 463
<211> LENGTH: 22
<212> TYPE: PRT
<213> ORGANISM: Artificial
<220> FEATURE:
<223> OTHER INFORMATION: Engineered antibody sequence

<400> SEQUENCE: 463

Gln Val Leu Thr Gln Ser Pro Ser Ser Leu Ser Ala Ser Val Gly Asp
1               5                   10                  15

Arg Val Thr Ile Asn Cys
            20

<210> SEQ ID NO 464
<211> LENGTH: 13
<212> TYPE: PRT
<213> ORGANISM: Artificial
<220> FEATURE:
<223> OTHER INFORMATION: Engineered antibody sequence

<400> SEQUENCE: 464

Arg Ala Ser Gln Ser Val Tyr Tyr Asn Asn Tyr Leu Ala
1               5                   10

<210> SEQ ID NO 465
<211> LENGTH: 15
<212> TYPE: PRT
<213> ORGANISM: Artificial
<220> FEATURE:
<223> OTHER INFORMATION: Engineered antibody sequence

<400> SEQUENCE: 465

Trp Tyr Gln Gln Lys Pro Gly Lys Val Pro Lys Gln Leu Ile Tyr
1               5                   10                  15

<210> SEQ ID NO 466
<211> LENGTH: 7
<212> TYPE: PRT
<213> ORGANISM: Artificial
<220> FEATURE:
<223> OTHER INFORMATION: Engineered antibody sequence

<400> SEQUENCE: 466

Ser Thr Ser Thr Leu Ala Ser
1               5

<210> SEQ ID NO 467
<211> LENGTH: 32
<212> TYPE: PRT
<213> ORGANISM: Artificial
<220> FEATURE:
<223> OTHER INFORMATION: Engineered antibody sequence
```

```
<400> SEQUENCE: 467

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 468
<211> LENGTH: 13
<212> TYPE: PRT
<213> ORGANISM: Artificial
<220> FEATURE:
<223> OTHER INFORMATION: Engineered antibody sequence

<400> SEQUENCE: 468

Leu Gly Ser Tyr Asp Cys Ser Asn Gly Asp Cys Phe Val
1               5                   10

<210> SEQ ID NO 469
<211> LENGTH: 11
<212> TYPE: PRT
<213> ORGANISM: Artificial
<220> FEATURE:
<223> OTHER INFORMATION: Engineered antibody sequence

<400> SEQUENCE: 469

Phe Gly Gly Gly Thr Lys Val Glu Ile Lys Arg
1               5                   10

<210> SEQ ID NO 470
<211> LENGTH: 106
<212> TYPE: PRT
<213> ORGANISM: Artificial
<220> FEATURE:
<223> OTHER INFORMATION: Engineered antibody sequence

<400> SEQUENCE: 470

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 471
<211> LENGTH: 660
<212> TYPE: DNA
<213> ORGANISM: Artificial
<220> FEATURE:
<223> OTHER INFORMATION: Engineered antibody sequence

<400> SEQUENCE: 471
caagtgctga cccagtctcc atcctccctg tctgcatctg taggagacag agtcaccatc      60
aattgccggg ccagtcagag tgtttactat aacaactacc tagcctggta tcagcagaaa     120
```

```
ccagggaaag ttcctaagca actgatctat tctacatcca ctctggcatc tggggtccca    180
tctcgtttca gtggcagtgg atctgggaca gatttcactc tcaccatcag cagcctgcag    240
cctgaagatg ttgcaactta ttactgtctg ggcagttatg attgtagtaa tggtgattgt    300
tttgttttcg gcggaggaac caaggtggaa atcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660
```

<210> SEQ ID NO 472
<211> LENGTH: 339
<212> TYPE: DNA
<213> ORGANISM: Artificial
<220> FEATURE:
<223> OTHER INFORMATION: Engineered antibody sequence

<400> SEQUENCE: 472

```
caagtgctga cccagtctcc atcctccctg tctgcatctg taggagacag agtcaccatc     60
aattgccggg ccagtcagag tgtttactat aacaactacc tagcctggta tcagcagaaa    120
ccagggaaag ttcctaagca actgatctat tctacatcca ctctggcatc tggggtccca    180
tctcgtttca gtggcagtgg atctgggaca gatttcactc tcaccatcag cagcctgcag    240
cctgaagatg ttgcaactta ttactgtctg ggcagttatg attgtagtaa tggtgattgt    300
tttgttttcg gcggaggaac caaggtggaa atcaaacgt                          339
```

<210> SEQ ID NO 473
<211> LENGTH: 66
<212> TYPE: DNA
<213> ORGANISM: Artificial
<220> FEATURE:
<223> OTHER INFORMATION: Engineered antibody sequence

<400> SEQUENCE: 473

```
caagtgctga cccagtctcc atcctccctg tctgcatctg taggagacag agtcaccatc     60
aattgc                                                               66
```

<210> SEQ ID NO 474
<211> LENGTH: 39
<212> TYPE: DNA
<213> ORGANISM: Artificial
<220> FEATURE:
<223> OTHER INFORMATION: Engineered antibody sequence

<400> SEQUENCE: 474

```
cgggccagtc agagtgttta ctataacaac tacctagcc                           39
```

<210> SEQ ID NO 475
<211> LENGTH: 45
<212> TYPE: DNA
<213> ORGANISM: Artificial
<220> FEATURE:
<223> OTHER INFORMATION: Engineered antibody sequence

<400> SEQUENCE: 475

```
tggtatcagc agaaaccagg gaaagttcct aagcaactga tctat                    45
```

-continued

<210> SEQ ID NO 476
<211> LENGTH: 21
<212> TYPE: DNA
<213> ORGANISM: Artificial
<220> FEATURE:
<223> OTHER INFORMATION: Engineered antibody sequence

<400> SEQUENCE: 476
tctacatcca ctctggcatc t                                              21

<210> SEQ ID NO 477
<211> LENGTH: 96
<212> TYPE: DNA
<213> ORGANISM: Artificial
<220> FEATURE:
<223> OTHER INFORMATION: Engineered antibody sequence

<400> SEQUENCE: 477
ggggtcccat ctcgtttcag tggcagtgga tctgggacag atttcactct caccatcagc    60
agcctgcagc ctgaagatgt tgcaacttat tactgt                              96

<210> SEQ ID NO 478
<211> LENGTH: 39
<212> TYPE: DNA
<213> ORGANISM: Artificial
<220> FEATURE:
<223> OTHER INFORMATION: Engineered antibody sequence

<400> SEQUENCE: 478
ctgggcagtt atgattgtag taatggtgat tgttttgtt                           39

<210> SEQ ID NO 479
<211> LENGTH: 33
<212> TYPE: DNA
<213> ORGANISM: Artificial
<220> FEATURE:
<223> OTHER INFORMATION: Engineered antibody sequence

<400> SEQUENCE: 479
ttcggcggag gaaccaaggt ggaaatcaaa cgt                                 33

<210> SEQ ID NO 480
<211> LENGTH: 321
<212> TYPE: DNA
<213> ORGANISM: Artificial
<220> FEATURE:
<223> OTHER INFORMATION: Engineered antibody sequence

<400> SEQUENCE: 480
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321

<210> SEQ ID NO 481
<211> LENGTH: 441
<212> TYPE: PRT
<213> ORGANISM: Artificial
<220> FEATURE:
<223> OTHER INFORMATION: Engineered antibody sequence

```
<400> SEQUENCE: 481

Gln Ser Val Glu Glu Ser Gly Gly Leu Val Gln Pro Gly Gly Ser
1               5                   10                  15

Leu Thr Leu Thr Cys Thr Ala Ser Gly Phe Asp Phe Ser Ser Asn Ala
            20                  25                  30

Met Trp Trp Val Arg Gln Ala Pro Gly Lys Gly Leu Glu Trp Ile Gly
        35                  40                  45

Cys Ile Tyr Asn Gly Asp Gly Ser Thr Tyr Tyr Ala Ser Trp Val Asn
    50                  55                  60

Gly Arg Phe Ser Ile Ser Lys Thr Ser Ser Thr Thr Val Thr Leu Gln
65              70                  75                  80

Leu Asn Ser Leu Thr Val Ala Asp Thr Ala Thr Tyr Tyr Cys Ala Arg
                85                  90                  95

Asp Leu Asp Leu Trp Gly Pro Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Arg
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415
```

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 482
<211> LENGTH: 111
<212> TYPE: PRT
<213> ORGANISM: Artificial
<220> FEATURE:
<223> OTHER INFORMATION: Engineered antibody sequence

<400> SEQUENCE: 482

Gln Ser Val Glu Glu Ser Gly Gly Gly Leu Val Gln Pro Glu Gly Ser
1               5                   10                  15

Leu Thr Leu Thr Cys Thr Ala Ser Gly Phe Asp Phe Ser Asn Ala
            20                  25                  30

Met Trp Trp Val Arg Gln Ala Pro Gly Lys Gly Leu Glu Trp Ile Gly
        35                  40                  45

Cys Ile Tyr Asn Gly Asp Gly Ser Thr Tyr Tyr Ala Ser Trp Val Asn
    50                  55                  60

Gly Arg Phe Ser Ile Ser Lys Thr Ser Ser Thr Val Thr Leu Gln
65                  70                  75                  80

Leu Asn Ser Leu Thr Val Ala Asp Thr Ala Tyr Tyr Cys Ala Arg
                85                  90                  95

Asp Leu Asp Leu Trp Gly Pro Gly Thr Leu Val Thr Val Ser Ser
            100                 105                 110

<210> SEQ ID NO 483
<211> LENGTH: 29
<212> TYPE: PRT
<213> ORGANISM: Artificial
<220> FEATURE:
<223> OTHER INFORMATION: Engineered antibody sequence

<400> SEQUENCE: 483

Gln Ser Val Glu Glu Ser Gly Gly Gly Leu Val Gln Pro Glu Gly Ser
1               5                   10                  15

Leu Thr Leu Thr Cys Thr Ala Ser Gly Phe Asp Phe Ser
            20                  25

<210> SEQ ID NO 484
<211> LENGTH: 5
<212> TYPE: PRT
<213> ORGANISM: Artificial
<220> FEATURE:
<223> OTHER INFORMATION: Engineered antibody sequence

<400> SEQUENCE: 484

Ser Asn Ala Met Trp
1               5

<210> SEQ ID NO 485
<211> LENGTH: 14
<212> TYPE: PRT
<213> ORGANISM: Artificial
<220> FEATURE:
<223> OTHER INFORMATION: Engineered antibody sequence

<400> SEQUENCE: 485

Trp Val Arg Gln Ala Pro Gly Lys Gly Leu Glu Trp Ile Gly
1               5                   10

<210> SEQ ID NO 486
<211> LENGTH: 17
<212> TYPE: PRT
<213> ORGANISM: Artificial
<220> FEATURE:
<223> OTHER INFORMATION: Engineered antibody sequence

<400> SEQUENCE: 486

Cys Ile Tyr Asn Gly Asp Gly Ser Thr Tyr Tyr Ala Ser Trp Val Asn
1               5                   10                  15

Gly

<210> SEQ ID NO 487
<211> LENGTH: 31
<212> TYPE: PRT
<213> ORGANISM: Artificial
<220> FEATURE:
<223> OTHER INFORMATION: Engineered antibody sequence

<400> SEQUENCE: 487

Arg Phe Ser Ile Ser Lys Thr Ser Ser Thr Thr Val Thr Leu Gln Leu
1               5                   10                  15

Asn Ser Leu Thr Val Ala Asp Thr Ala Thr Tyr Tyr Cys Ala Arg
            20                  25                  30

<210> SEQ ID NO 488
<211> LENGTH: 4
<212> TYPE: PRT
<213> ORGANISM: Artificial
<220> FEATURE:
<223> OTHER INFORMATION: Engineered antibody sequence

<400> SEQUENCE: 488

Asp Leu Asp Leu
1

<210> SEQ ID NO 489
<211> LENGTH: 11
<212> TYPE: PRT
<213> ORGANISM: Artificial
<220> FEATURE:
<223> OTHER INFORMATION: Engineered antibody sequence

<400> SEQUENCE: 489

Trp Gly Pro Gly Thr Leu Val Thr Val Ser Ser
1               5                   10

<210> SEQ ID NO 490
<211> LENGTH: 330
<212> TYPE: PRT
<213> ORGANISM: Artificial
<220> FEATURE:
<223> OTHER INFORMATION: Engineered antibody sequence

<400> SEQUENCE: 490

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 491
<211> LENGTH: 1326
<212> TYPE: DNA
<213> ORGANISM: Artificial
<220> FEATURE:
<223> OTHER INFORMATION: Engineered antibody sequence

<400> SEQUENCE: 491
cagtcggtgg aggagtccgg gggaggcctg gtccagcctg agggatccct gacactcacc      60
tgcacagcct ctggattcga cttcagtagc aatgcaatgt ggtgggtccg ccaggctcca     120
gggaaggggc tggagtggat cggatgcatt tacaatggta tggcagcac atactacgcg      180 agctgggtga atggccgatt ctccatctcc aaaacctcgt cgaccacggt gactctgcaa     240
ctgaatagtc tgacagtcgc ggacacggcc acgtattatt gtgcgagaga tcttgacttg     300
tggggcccgg gcaccctcgt caccgtctcg agcgcctcca ccaagggccc atcggtcttc     360
cccctggcac cctcctccaa gagcacctct ggggggcacag cggccctggg ctgcctggtc    420
aaggactact ccccgaacc ggtgacggtg tcgtggaact caggcgccct gaccagcggc      480
gtgcacacct tcccggctgt cctacagtcc tcaggactct actccctcag cagcgtggtg    540

```
accgtgccct ccagcagctt gggcacccag acctacatct gcaacgtgaa tcacaagccc      600
agcaacacca aggtggacaa gagagttgag cccaaatctt gtgacaaaac tcacacatgc      660
ccaccgtgcc cagcacctga actcctgggg ggaccgtcag tcttcctctt ccccccaaaa      720
cccaaggaca ccctcatgat ctcccggacc cctgaggtca catgcgtggt ggtggacgtg      780
agccacgaag accctgaggt caagttcaac tggtacgtgg acggcgtgga ggtgcataat      840
gccaagacaa agccgcggga ggagcagtac gccagcacgt accgtgtggt cagcgtcctc      900
accgtcctgc accaggactg gctgaatggc aaggagtaca gtgcaaggt ctccaacaaa       960 gcctcccag cccccatcga gaaaaccatc tccaaagcca agggcagcc ccgagaacca       1020 caggtgtaca ccctgccccc atcccgggag gagatgacca gaaccaggt cagcctgacc       1080 tgcctggtca aaggcttcta tcccagcgac atcgccgtgg agtgggagag caatgggcag     1140
ccggagaaca actacaagac cacgcctccc gtgctggact ccgacggctc cttcttcctc     1200
tacagcaagc tcaccgtgga caagagcagg tggcagcagg ggaacgtctt ctcatgctcc     1260
gtgatgcatg aggctctgca caaccactac acgcagaaga gcctctccct gtctccgggt     1320
aaatga                                                                1326

<210> SEQ ID NO 492
<211> LENGTH: 333
<212> TYPE: DNA
<213> ORGANISM: Artificial
<220> FEATURE:
<223> OTHER INFORMATION: Engineered antibody sequence

<400> SEQUENCE: 492
cagtcggtgg aggagtccgg gggaggcctg gtccagcctg agggatccct gacactcacc       60
tgcacagcct ctggattcga cttcagtagc aatgcaatgt ggtgggtccg ccaggctcca      120
gggaaggggc tggagtggat cggatgcatt tacaatggtg atggcagcac atactacgcg      180
agctgggtga atggccgatt ctccatctcc aaaacctcgt cgaccacggt gactctgcaa      240
ctgaatagtc tgacagtcgc ggacacggcc acgtattatt gtgcgagaga tcttgacttg      300
tggggcccgg gcaccctcgt caccgtctcg agc                                    333

<210> SEQ ID NO 493
<211> LENGTH: 87
<212> TYPE: DNA
<213> ORGANISM: Artificial
<220> FEATURE:
<223> OTHER INFORMATION: Engineered antibody sequence

<400> SEQUENCE: 493
cagtcggtgg aggagtccgg gggaggcctg gtccagcctg agggatccct gacactcacc       60
tgcacagcct ctggattcga cttcagt                                            87

<210> SEQ ID NO 494
<211> LENGTH: 15
<212> TYPE: DNA
<213> ORGANISM: Artificial
<220> FEATURE:
<223> OTHER INFORMATION: Engineered antibody sequence

<400> SEQUENCE: 494
agcaatgcaa tgtgg                                                         15

<210> SEQ ID NO 495
```

```
<211> LENGTH: 42
<212> TYPE: DNA
<213> ORGANISM: Artificial
<220> FEATURE:
<223> OTHER INFORMATION: Engineered antibody sequence

<400> SEQUENCE: 495
tgggtccgcc aggctccagg gaagggctg gagtggatcg ga                    42

<210> SEQ ID NO 496
<211> LENGTH: 51
<212> TYPE: DNA
<213> ORGANISM: Artificial
<220> FEATURE:
<223> OTHER INFORMATION: Engineered antibody sequence

<400> SEQUENCE: 496
tgcatttaca atggtgatgg cagcacatac tacgcgagct gggtgaatgg c          51

<210> SEQ ID NO 497
<211> LENGTH: 93
<212> TYPE: DNA
<213> ORGANISM: Artificial
<220> FEATURE:
<223> OTHER INFORMATION: Engineered antibody sequence

<400> SEQUENCE: 497
cgattctcca tctccaaaac ctcgtcgacc acggtgactc tgcaactgaa tagtctgaca    60
gtcgcggaca cggccacgta ttattgtgcg aga                                 93

<210> SEQ ID NO 498
<211> LENGTH: 12
<212> TYPE: DNA
<213> ORGANISM: Artificial
<220> FEATURE:
<223> OTHER INFORMATION: Engineered antibody sequence

<400> SEQUENCE: 498
gatcttgact tg                                                    12

<210> SEQ ID NO 499
<211> LENGTH: 33
<212> TYPE: DNA
<213> ORGANISM: Artificial
<220> FEATURE:
<223> OTHER INFORMATION: Engineered antibody sequence

<400> SEQUENCE: 499
tggggcccgg gcaccctcgt caccgtctcg agc                             33

<210> SEQ ID NO 500
<211> LENGTH: 993
<212> TYPE: DNA
<213> ORGANISM: Artificial
<220> FEATURE:
<223> OTHER INFORMATION: Engineered antibody sequence

<400> SEQUENCE: 500
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
```

```
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacgcc    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa tga                                 993
```

<210> SEQ ID NO 501
<211> LENGTH: 219
<212> TYPE: PRT
<213> ORGANISM: Artificial
<220> FEATURE:
<223> OTHER INFORMATION: Engineered antibody sequence

<400> SEQUENCE: 501

```
Ala Ile Val Met Thr Gln Thr Pro Ser Ser Lys Ser Val Pro Val Gly
1               5                   10                  15

Asp Thr Val Thr Ile Asn Cys Gln Ala Ser Glu Ser Leu Tyr Asn Asn
            20                  25                  30

Asn Ala Leu Ala Trp Phe Gln Gln Lys Pro Gly Gln Pro Pro Lys Arg
        35                  40                  45

Leu Ile Tyr Asp Ala Ser Lys Leu Ala Ser Gly Val Pro Ser Arg Phe
    50                  55                  60

Ser Gly Gly Gly Ser Gly Thr Gln Phe Thr Leu Thr Ile Ser Gly Val
65                  70                  75                  80

Gln Cys Asp Asp Ala Ala Thr Tyr Tyr Cys Gly Gly Tyr Arg Ser Asp
                85                  90                  95

Ser Val Asp Gly Val Ala Phe Ala Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 502

<211> LENGTH: 113
<212> TYPE: PRT
<213> ORGANISM: Artificial
<220> FEATURE:
<223> OTHER INFORMATION: Engineered antibody sequence

<400> SEQUENCE: 502

Ala Ile Val Met Thr Gln Thr Pro Ser Ser Lys Ser Val Pro Val Gly
1               5                   10                  15

Asp Thr Val Thr Ile Asn Cys Gln Ala Ser Glu Ser Leu Tyr Asn Asn
            20                  25                  30

Asn Ala Leu Ala Trp Phe Gln Gln Lys Pro Gly Gln Pro Pro Lys Arg
        35                  40                  45

Leu Ile Tyr Asp Ala Ser Lys Leu Ala Ser Gly Val Pro Ser Arg Phe
    50                  55                  60

Ser Gly Gly Gly Ser Gly Thr Gln Phe Thr Leu Thr Ile Ser Gly Val
65                  70                  75                  80

Gln Cys Asp Asp Ala Ala Thr Tyr Tyr Cys Gly Gly Tyr Arg Ser Asp
                85                  90                  95

Ser Val Asp Gly Val Ala Phe Ala Gly Gly Thr Glu Val Val Val Lys
            100                 105                 110

Arg

<210> SEQ ID NO 503
<211> LENGTH: 23
<212> TYPE: PRT
<213> ORGANISM: Artificial
<220> FEATURE:
<223> OTHER INFORMATION: Engineered antibody sequence

<400> SEQUENCE: 503

Ala Ile Val Met Thr Gln Thr Pro Ser Ser Lys Ser Val Pro Val Gly
1               5                   10                  15

Asp Thr Val Thr Ile Asn Cys
            20

<210> SEQ ID NO 504
<211> LENGTH: 13
<212> TYPE: PRT
<213> ORGANISM: Artificial
<220> FEATURE:
<223> OTHER INFORMATION: Engineered antibody sequence

<400> SEQUENCE: 504

Gln Ala Ser Glu Ser Leu Tyr Asn Asn Asn Ala Leu Ala
1               5                   10

<210> SEQ ID NO 505
<211> LENGTH: 15
<212> TYPE: PRT
<213> ORGANISM: Artificial
<220> FEATURE:
<223> OTHER INFORMATION: Engineered antibody sequence

<400> SEQUENCE: 505

Trp Phe Gln Gln Lys Pro Gly Gln Pro Pro Lys Arg Leu Ile Tyr
1               5                   10                  15

<210> SEQ ID NO 506
<211> LENGTH: 7
<212> TYPE: PRT
<213> ORGANISM: Artificial
<220> FEATURE:

<223> OTHER INFORMATION: Engineered antibody sequence

<400> SEQUENCE: 506

Asp Ala Ser Lys Leu Ala Ser
1               5

<210> SEQ ID NO 507
<211> LENGTH: 32
<212> TYPE: PRT
<213> ORGANISM: Artificial
<220> FEATURE:
<223> OTHER INFORMATION: Engineered antibody sequence

<400> SEQUENCE: 507

Gly Val Pro Ser Arg Phe Ser Gly Gly Ser Gly Thr Gln Phe Thr
1               5                   10                  15

Leu Thr Ile Ser Gly Val Gln Cys Asp Asp Ala Ala Thr Tyr Tyr Cys
                20                  25                  30

<210> SEQ ID NO 508
<211> LENGTH: 12
<212> TYPE: PRT
<213> ORGANISM: Artificial
<220> FEATURE:
<223> OTHER INFORMATION: Engineered antibody sequence

<400> SEQUENCE: 508

Gly Gly Tyr Arg Ser Asp Ser Val Asp Gly Val Ala
1               5                   10

<210> SEQ ID NO 509
<211> LENGTH: 11
<212> TYPE: PRT
<213> ORGANISM: Artificial
<220> FEATURE:
<223> OTHER INFORMATION: Engineered antibody sequence

<400> SEQUENCE: 509

Phe Ala Gly Gly Thr Glu Val Val Val Lys Arg
1               5                   10

<210> SEQ ID NO 510
<211> LENGTH: 106
<212> TYPE: PRT
<213> ORGANISM: Artificial
<220> FEATURE:
<223> OTHER INFORMATION: Engineered antibody sequence

<400> SEQUENCE: 510

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105

<210> SEQ ID NO 511
<211> LENGTH: 660
<212> TYPE: DNA
<213> ORGANISM: Artificial
<220> FEATURE:
<223> OTHER INFORMATION: Engineered antibody sequence

<400> SEQUENCE: 511

```
gccatcgtga tgacccagac tccatcttcc aagtctgtcc ctgtgggaga cacagtcacc      60
atcaattgcc aggccagtga gagtctttat aataacaacg ccttggcctg gtttcagcag     120
aaaccagggc agcctcccaa gcgcctgatc tatgatgcat ccaaactggc atctggggtc     180
ccatcgcggt tcagtggcgg tgggtctggg acacagttca ctctcaccat cagtggcgtg     240
cagtgtgacg atgctgccac ttactactgt ggaggctaca gaagtgatag tgttgatggt     300
gttgctttcg ccggagggac cgaggtggtg gtcaaacgta cggtggctgc accatctgtc     360
ttcatcttcc cgccatctga tgagcagttg aaatctggaa ctgcctctgt tgtgtgcctg     420
ctgaataact ctatcccag agaggccaaa gtacagtgga aggtggataa cgccctccaa      480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660
```

<210> SEQ ID NO 512
<211> LENGTH: 339
<212> TYPE: DNA
<213> ORGANISM: Artificial
<220> FEATURE:
<223> OTHER INFORMATION: Engineered antibody sequence

<400> SEQUENCE: 512

```
gccatcgtga tgacccagac tccatcttcc aagtctgtcc ctgtgggaga cacagtcacc      60
atcaattgcc aggccagtga gagtctttat aataacaacg ccttggcctg gtttcagcag     120
aaaccagggc agcctcccaa gcgcctgatc tatgatgcat ccaaactggc atctggggtc     180
ccatcgcggt tcagtggcgg tgggtctggg acacagttca ctctcaccat cagtggcgtg     240
cagtgtgacg atgctgccac ttactactgt ggaggctaca gaagtgatag tgttgatggt     300
gttgctttcg ccggagggac cgaggtggtg gtcaaacgt                           339
```

<210> SEQ ID NO 513
<211> LENGTH: 69
<212> TYPE: DNA
<213> ORGANISM: Artificial
<220> FEATURE:
<223> OTHER INFORMATION: Engineered antibody sequence

<400> SEQUENCE: 513

```
gccatcgtga tgacccagac tccatcttcc aagtctgtcc ctgtgggaga cacagtcacc      60
atcaattgc                                                             69
```

<210> SEQ ID NO 514
<211> LENGTH: 39
<212> TYPE: DNA
<213> ORGANISM: Artificial
<220> FEATURE:
<223> OTHER INFORMATION: Engineered antibody sequence

<400> SEQUENCE: 514
caggccagtg agagtcttta taataacaac gccttggcc        39

<210> SEQ ID NO 515
<211> LENGTH: 45
<212> TYPE: DNA
<213> ORGANISM: Artificial
<220> FEATURE:
<223> OTHER INFORMATION: Engineered antibody sequence

<400> SEQUENCE: 515
tggtttcagc agaaaccagg gcagcctccc aagcgcctga tctat        45

<210> SEQ ID NO 516
<211> LENGTH: 21
<212> TYPE: DNA
<213> ORGANISM: Artificial
<220> FEATURE:
<223> OTHER INFORMATION: Engineered antibody sequence

<400> SEQUENCE: 516
gatgcatcca aactggcatc t        21

<210> SEQ ID NO 517
<211> LENGTH: 96
<212> TYPE: DNA
<213> ORGANISM: Artificial
<220> FEATURE:
<223> OTHER INFORMATION: Engineered antibody sequence

<400> SEQUENCE: 517
ggggtcccat cgcggttcag tggcggtggg tctgggacac agttcactct caccatcagt        60
ggcgtgcagt gtgacgatgc tgccacttac tactgt        96

<210> SEQ ID NO 518
<211> LENGTH: 36
<212> TYPE: DNA
<213> ORGANISM: Artificial
<220> FEATURE:
<223> OTHER INFORMATION: Engineered antibody sequence

<400> SEQUENCE: 518
ggaggctaca gaagtgatag tgttgatggt gttgct        36

<210> SEQ ID NO 519
<211> LENGTH: 33
<212> TYPE: DNA
<213> ORGANISM: Artificial
<220> FEATURE:
<223> OTHER INFORMATION: Engineered antibody sequence

<400> SEQUENCE: 519
ttcgccggag ggaccgaggt ggtggtcaaa cgt        33

<210> SEQ ID NO 520
<211> LENGTH: 321
<212> TYPE: DNA
<213> ORGANISM: Artificial
<220> FEATURE:
<223> OTHER INFORMATION: Engineered antibody sequence

<400> SEQUENCE: 520
acggtggctg caccatctgt cttcatcttc ccgccatctg atgagcagtt gaaatctgga        60
actgcctctg ttgtgtgcct gctgaataac ttctatccca gagaggccaa agtacagtgg        120
aaggtggata acgccctcca atcgggtaac tcccaggaga gtgtcacaga gcaggacagc        180

```
aaggacagca cctacagcct cagcagcacc ctgacgctga gcaaagcaga ctacgagaaa    240
cacaaagtct acgcctgcga agtcacccat cagggcctga gctcgcccgt cacaaagagc    300
ttcaacaggg gagagtgtta g                                              321
```

<210> SEQ ID NO 521
<211> LENGTH: 441
<212> TYPE: PRT
<213> ORGANISM: Artificial
<220> FEATURE:
<223> OTHER INFORMATION: Engineered antibody sequence

<400> SEQUENCE: 521

| Glu | Val | Gln | Leu | Val | Glu | Ser | Gly | Gly | Gly | Leu | Val | Gln | Pro | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Gly | Ser | Leu | Arg | Leu | Ser | Cys | Ala | Val | Ser | Gly | Ile | Gly | Leu | Ser | Ser | Tyr |
|-----|-----|-----|-----|-----|-----|-----|-----|-----|-----|-----|-----|-----|-----|-----|-----|-----|

Glu Val Gln Leu Val Glu Ser Gly Gly Gly Leu Val Gln Pro Gly
1               5                   10                  15

Ser Leu Arg Leu Ser Cys Ala Val Ser Gly Ile Gly Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ser Asp Gly Lys Thr Tyr Tyr Ala Thr Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Thr
                85                  90                  95

Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Ala Arg
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

```
Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 522
<211> LENGTH: 111
<212> TYPE: PRT
<213> ORGANISM: Artificial
<220> FEATURE:
<223> OTHER INFORMATION: Engineered antibody sequence

<400> SEQUENCE: 522

```
Glu Val Gln Leu Val Glu Ser Gly Gly Gly Leu Val Gln Pro Gly Gly
1               5                   10                  15

Ser Leu Arg Leu Ser Cys Ala Val Ser Gly Ile Gly Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ser Asp Gly Lys Thr Tyr Tyr Ala Thr Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Thr
                85                  90                  95

Arg Gly Asp Ile Trp Gly Gln Gly Thr Leu Val Thr Val Ser Ser
            100                 105                 110
```

<210> SEQ ID NO 523
<211> LENGTH: 30
<212> TYPE: PRT
<213> ORGANISM: Artificial
<220> FEATURE:
<223> OTHER INFORMATION: Engineered antibody sequence

<400> SEQUENCE: 523

```
Glu Val Gln Leu Val Glu Ser Gly Gly Gly Leu Val Gln Pro Gly Gly
1               5                   10                  15

Ser Leu Arg Leu Ser Cys Ala Val Ser Gly Ile Gly Leu Ser
            20                  25                  30
```

<210> SEQ ID NO 524
<211> LENGTH: 5
<212> TYPE: PRT
<213> ORGANISM: Artificial
<220> FEATURE:
<223> OTHER INFORMATION: Engineered antibody sequence

<400> SEQUENCE: 524

```
Ser Tyr Tyr Met Gln
1               5

<210> SEQ ID NO 525
<211> LENGTH: 14
<212> TYPE: PRT
<213> ORGANISM: Artificial
<220> FEATURE:
<223> OTHER INFORMATION: Engineered antibody sequence

<400> SEQUENCE: 525

Trp Val Arg Gln Ala Pro Gly Lys Gly Leu Glu Trp Val Gly
1               5                   10

<210> SEQ ID NO 526
<211> LENGTH: 16
<212> TYPE: PRT
<213> ORGANISM: Artificial
<220> FEATURE:
<223> OTHER INFORMATION: Engineered antibody sequence

<400> SEQUENCE: 526

Val Ile Gly Ser Asp Gly Lys Thr Tyr Tyr Ala Thr Trp Ala Lys Gly
1               5                   10                  15

<210> SEQ ID NO 527
<211> LENGTH: 32
<212> TYPE: PRT
<213> ORGANISM: Artificial
<220> FEATURE:
<223> OTHER INFORMATION: Engineered antibody sequence

<400> SEQUENCE: 527

Arg Phe Thr Ile Ser Arg Asp Asn Ser Lys Thr Thr Val Tyr Leu Gln
1               5                   10                  15

Met Asn Ser Leu Arg Ala Glu Asp Thr Ala Val Tyr Phe Cys Thr Arg
            20                  25                  30

<210> SEQ ID NO 528
<211> LENGTH: 3
<212> TYPE: PRT
<213> ORGANISM: Artificial
<220> FEATURE:
<223> OTHER INFORMATION: Engineered antibody sequence

<400> SEQUENCE: 528

Gly Asp Ile
1

<210> SEQ ID NO 529
<211> LENGTH: 11
<212> TYPE: PRT
<213> ORGANISM: Artificial
<220> FEATURE:
<223> OTHER INFORMATION: Engineered antibody sequence

<400> SEQUENCE: 529

Trp Gly Gln Gly Thr Leu Val Thr Val Ser Ser
1               5                   10

<210> SEQ ID NO 530
<211> LENGTH: 330
<212> TYPE: PRT
<213> ORGANISM: Artificial
<220> FEATURE:
<223> OTHER INFORMATION: Engineered antibody sequence
```

```
<400> SEQUENCE: 530

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 531
<211> LENGTH: 1326
<212> TYPE: DNA
<213> ORGANISM: Artificial
<220> FEATURE:
<223> OTHER INFORMATION: Engineered antibody sequence

<400> SEQUENCE: 531
gaggtgcagc ttgtggagtc tgggggaggc ttggtccagc ctggggggtc cctgagactc      60
tcctgtgcag tctctggaat cggcctcagt agctactaca tgcaatgggt ccgtcaggct     120
```

| | |
|---|---|
| ccagggaagg ggctggagtg ggtcggagtc attggtagtg atggtaagac atactacgcg | 180 |
| acctgggcga aaggccgatt caccatctcc agagacaatt ccaagaccac ggtgtatctt | 240 |
| caaatgaaca gcctgagagc tgaggacact gctgtgtatt tctgtaccag aggggacatc | 300 |
| tggggccaag ggaccctcgt caccgtctcg agcgcctcca ccaagggccc atcggtcttc | 360 |
| cccctggcac cctcctccaa gagcacctct gggggcacag cggccctggg ctgcctggtc | 420 |
| aaggactact cccccgaacc ggtgacggtg tcgtggaact caggcgccct gaccagcggc | 480 |
| gtgcacacct tcccggctgt cctacagtcc tcaggactct actccctcag cagcgtggtg | 540 |
| accgtgccct ccagcagctt gggcacccag acctacatct gcaacgtgaa tcacaagccc | 600 |
| agcaacacca aggtggacgc gagagttgag cccaaatctt gtgacaaaac tcacacatgc | 660 |
| ccaccgtgcc cagcacctga actcctgggg ggaccgtcag tcttcctctt ccccccaaaa | 720 |
| cccaaggaca ccctcatgat ctcccggacc cctgaggtca catgcgtggt ggtggacgtg | 780 |
| agccacgaag accctgaggt caagttcaac tggtacgtgg acggcgtgga ggtgcataat | 840 |
| gccaagacaa agccgcggga ggagcagtac gccagcacgt accgtgtggt cagcgtcctc | 900 |
| accgtcctgc accaggactg gctgaatggc aaggagtaca agtgcaaggt ctccaacaaa | 960 |
| gccctcccag cccccatcga gaaaaccatc tccaaagcca agggcagcc cgagaaccca | 1020 |
| caggtgtaca ccctgccccc atcccgggag gagatgacca agaaccaggt cagcctgacc | 1080 |
| tgcctggtca aaggcttcta tcccagcgac atcgccgtgg agtgggagag caatgggcag | 1140 |
| ccggagaaca actacaagac cacgcctccc gtgctggact ccgacggctc cttcttcctc | 1200 |
| tacagcaagc tcaccgtgga caagagcagg tggcagcagg ggaacgtctt ctcatgctcc | 1260 |
| gtgatgcatg aggctctgca caaccactac acgcagaaga gcctctccct gtctccgggt | 1320 |
| aaatga | 1326 |

<210> SEQ ID NO 532
<211> LENGTH: 333
<212> TYPE: DNA
<213> ORGANISM: Artificial
<220> FEATURE:
<223> OTHER INFORMATION: Engineered antibody sequence

<400> SEQUENCE: 532

| | |
|---|---|
| gaggtgcagc ttgtggagtc tggggggaggc ttggtccagc ctgggggggtc cctgagactc | 60 |
| tcctgtgcag tctctggaat cggcctcagt agctactaca tgcaatgggt ccgtcaggct | 120 |
| ccagggaagg ggctggagtg ggtcggagtc attggtagtg atggtaagac atactacgcg | 180 |
| acctgggcga aaggccgatt caccatctcc agagacaatt ccaagaccac ggtgtatctt | 240 |
| caaatgaaca gcctgagagc tgaggacact gctgtgtatt tctgtaccag aggggacatc | 300 |
| tggggccaag ggaccctcgt caccgtctcg agc | 333 |

<210> SEQ ID NO 533
<211> LENGTH: 90
<212> TYPE: DNA
<213> ORGANISM: Artificial
<220> FEATURE:
<223> OTHER INFORMATION: Engineered antibody sequence

<400> SEQUENCE: 533

| | |
|---|---|
| gaggtgcagc ttgtggagtc tggggggaggc ttggtccagc ctgggggggtc cctgagactc | 60 |
| tcctgtgcag tctctggaat cggcctcagt | 90 |

```
<210> SEQ ID NO 534
<211> LENGTH: 15
<212> TYPE: DNA
<213> ORGANISM: Artificial
<220> FEATURE:
<223> OTHER INFORMATION: Engineered antibody sequence

<400> SEQUENCE: 534
agctactaca tgcaa                                                          15

<210> SEQ ID NO 535
<211> LENGTH: 42
<212> TYPE: DNA
<213> ORGANISM: Artificial
<220> FEATURE:
<223> OTHER INFORMATION: Engineered antibody sequence

<400> SEQUENCE: 535
tgggtccgtc aggctccagg gaagggctg gagtgggtcg ga                             42

<210> SEQ ID NO 536
<211> LENGTH: 48
<212> TYPE: DNA
<213> ORGANISM: Artificial
<220> FEATURE:
<223> OTHER INFORMATION: Engineered antibody sequence

<400> SEQUENCE: 536
gtcattggta gtgatggtaa gacatactac gcgacctggg cgaaaggc                      48

<210> SEQ ID NO 537
<211> LENGTH: 96
<212> TYPE: DNA
<213> ORGANISM: Artificial
<220> FEATURE:
<223> OTHER INFORMATION: Engineered antibody sequence

<400> SEQUENCE: 537
cgattcacca tctccagaga caattccaag accacggtgt atcttcaaat gaacagcctg         60
agagctgagg acactgctgt gtatttctgt accaga                                   96

<210> SEQ ID NO 538
<211> LENGTH: 9
<212> TYPE: DNA
<213> ORGANISM: Artificial
<220> FEATURE:
<223> OTHER INFORMATION: Engineered antibody sequence

<400> SEQUENCE: 538 ggggacatc                                                                  9

<210> SEQ ID NO 539
<211> LENGTH: 33
<212> TYPE: DNA
<213> ORGANISM: Artificial
<220> FEATURE:
<223> OTHER INFORMATION: Engineered antibody sequence

<400> SEQUENCE: 539
tggggccaag ggaccctcgt caccgtctcg agc                                      33

<210> SEQ ID NO 540
<211> LENGTH: 993
<212> TYPE: DNA
<213> ORGANISM: Artificial
<220> FEATURE:
```

<223> OTHER INFORMATION: Engineered antibody sequence

<400> SEQUENCE: 540

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacgcgag agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacgcc     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa tga                                  993
```

<210> SEQ ID NO 541
<211> LENGTH: 219
<212> TYPE: PRT
<213> ORGANISM: Artificial
<220> FEATURE:
<223> OTHER INFORMATION: Engineered antibody sequence

<400> SEQUENCE: 541

Gln Val Leu Thr Gln Ser Pro Ser Ser Leu Ser Ala Ser Val Gly Asp
1               5                   10                  15

Arg Val Thr Ile Asn Cys Gln Ala Ser Gln Asn Val Tyr Asn Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Arg Gly Asp Cys Phe Val Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser 165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 542
<211> LENGTH: 113
<212> TYPE: PRT
<213> ORGANISM: Artificial
<220> FEATURE:
<223> OTHER INFORMATION: Engineered antibody sequence

<400> SEQUENCE: 542

Gln Val Leu Thr Gln Ser Pro Ser Ser Leu Ser Ala Ser Val Gly Asp
1               5                   10                  15

Arg Val Thr Ile Asn Cys Gln Ala Ser Gln Asn Val Tyr Asn Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Arg Gly Asp Cys Phe Val Phe Gly Gly Gly Thr Lys Val Glu Ile Lys
            100                 105                 110

Arg

<210> SEQ ID NO 543
<211> LENGTH: 22
<212> TYPE: PRT
<213> ORGANISM: Artificial
<220> FEATURE:
<223> OTHER INFORMATION: Engineered antibody sequence

<400> SEQUENCE: 543

Gln Val Leu Thr Gln Ser Pro Ser Ser Leu Ser Ala Ser Val Gly Asp
1               5                   10                  15

Arg Val Thr Ile Asn Cys
            20

<210> SEQ ID NO 544
<211> LENGTH: 13
<212> TYPE: PRT
<213> ORGANISM: Artificial
<220> FEATURE:
<223> OTHER INFORMATION: Engineered antibody sequence

<400> SEQUENCE: 544

Gln Ala Ser Gln Asn Val Tyr Asn Asn Asn Tyr Leu Ala
1               5                   10

<210> SEQ ID NO 545
<211> LENGTH: 15
<212> TYPE: PRT
<213> ORGANISM: Artificial
<220> FEATURE:

<223> OTHER INFORMATION: Engineered antibody sequence

<400> SEQUENCE: 545

Trp Tyr Gln Gln Lys Pro Gly Lys Val Pro Lys Gln Leu Ile Tyr
1               5                   10                  15

<210> SEQ ID NO 546
<211> LENGTH: 7
<212> TYPE: PRT
<213> ORGANISM: Artificial
<220> FEATURE:
<223> OTHER INFORMATION: Engineered antibody sequence

<400> SEQUENCE: 546

Ser Thr Ser Thr Leu Ala Ser
1               5

<210> SEQ ID NO 547
<211> LENGTH: 32
<212> TYPE: PRT
<213> ORGANISM: Artificial
<220> FEATURE:
<223> OTHER INFORMATION: Engineered antibody sequence

<400> SEQUENCE: 547

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 548
<211> LENGTH: 13
<212> TYPE: PRT
<213> ORGANISM: Artificial
<220> FEATURE:
<223> OTHER INFORMATION: Engineered antibody sequence

<400> SEQUENCE: 548

Leu Gly Ser Tyr Asp Cys Ser Arg Gly Asp Cys Phe Val
1               5                   10

<210> SEQ ID NO 549
<211> LENGTH: 11
<212> TYPE: PRT
<213> ORGANISM: Artificial
<220> FEATURE:
<223> OTHER INFORMATION: Engineered antibody sequence

<400> SEQUENCE: 549

Phe Gly Gly Gly Thr Lys Val Glu Ile Lys Arg
1               5                   10

<210> SEQ ID NO 550
<211> LENGTH: 106
<212> TYPE: PRT
<213> ORGANISM: Artificial
<220> FEATURE:
<223> OTHER INFORMATION: Engineered antibody sequence

<400> SEQUENCE: 550

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser

```
                    35                  40                  45
Gly Asn Ser Gln Glu Ser Val Thr Glu Gln Asp Ser Lys Asp Ser Thr
            50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 551
<211> LENGTH: 660
<212> TYPE: DNA
<213> ORGANISM: Artificial
<220> FEATURE:
<223> OTHER INFORMATION: Engineered antibody sequence

<400> SEQUENCE: 551

```
caagtgctga cccagtctcc atcctccctg tctgcatctg taggagacag agtcaccatc    60
aattgccagg ccagtcagaa tgtttacaat aacaactacc tagcctggta tcagcagaaa   120
ccagggaaag ttcctaagca actgatctat tctacatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtagtcg tggtgattgt   300
tttgttttcg gcggaggaac caaggtggaa atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660
```

<210> SEQ ID NO 552
<211> LENGTH: 339
<212> TYPE: DNA
<213> ORGANISM: Artificial
<220> FEATURE:
<223> OTHER INFORMATION: Engineered antibody sequence

<400> SEQUENCE: 552

```
caagtgctga cccagtctcc atcctccctg tctgcatctg taggagacag agtcaccatc    60
aattgccagg ccagtcagaa tgtttacaat aacaactacc tagcctggta tcagcagaaa   120
ccagggaaag ttcctaagca actgatctat tctacatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtagtcg tggtgattgt   300
tttgttttcg gcggaggaac caaggtggaa atcaaacgt                           339
```

<210> SEQ ID NO 553
<211> LENGTH: 66
<212> TYPE: DNA
<213> ORGANISM: Artificial
<220> FEATURE:
<223> OTHER INFORMATION: Engineered antibody sequence

<400> SEQUENCE: 553

```
caagtgctga cccagtctcc atcctccctg tctgcatctg taggagacag agtcaccatc    60
``` aattgc 66

<210> SEQ ID NO 554
<211> LENGTH: 39
<212> TYPE: DNA
<213> ORGANISM: Artificial
<220> FEATURE:
<223> OTHER INFORMATION: Engineered antibody sequence

<400> SEQUENCE: 554
caggccagtc agaatgttta caataacaac tacctagcc 39

<210> SEQ ID NO 555
<211> LENGTH: 45
<212> TYPE: DNA
<213> ORGANISM: Artificial
<220> FEATURE:
<223> OTHER INFORMATION: Engineered antibody sequence

<400> SEQUENCE: 555
tggtatcagc agaaaccagg gaaagttcct aagcaactga tctat 45

<210> SEQ ID NO 556
<211> LENGTH: 21
<212> TYPE: DNA
<213> ORGANISM: Artificial
<220> FEATURE:
<223> OTHER INFORMATION: Engineered antibody sequence

<400> SEQUENCE: 556
tctacatcca ctctggcatc t 21

<210> SEQ ID NO 557
<211> LENGTH: 96
<212> TYPE: DNA
<213> ORGANISM: Artificial
<220> FEATURE:
<223> OTHER INFORMATION: Engineered antibody sequence

<400> SEQUENCE: 557
ggggtcccat ctcgtttcag tggcagtgga tctgggacag atttcactct caccatcagc 60
agcctgcagc ctgaagatgt tgcaacttat tactgt 96

<210> SEQ ID NO 558
<211> LENGTH: 39
<212> TYPE: DNA
<213> ORGANISM: Artificial
<220> FEATURE:
<223> OTHER INFORMATION: Engineered antibody sequence

<400> SEQUENCE: 558
ctgggcagtt atgattgtag tcgtggtgat tgttttgtt 39

<210> SEQ ID NO 559
<211> LENGTH: 33
<212> TYPE: DNA
<213> ORGANISM: Artificial
<220> FEATURE:
<223> OTHER INFORMATION: Engineered antibody sequence

<400> SEQUENCE: 559
ttcggcggag gaaccaaggt ggaaatcaaa cgt 33

<210> SEQ ID NO 560

```
<211> LENGTH: 321
<212> TYPE: DNA
<213> ORGANISM: Artificial
<220> FEATURE:
<223> OTHER INFORMATION: Engineered antibody sequence

<400> SEQUENCE: 560
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                              321

<210> SEQ ID NO 561
<211> LENGTH: 37
<212> TYPE: PRT
<213> ORGANISM: Homo sapiens
<220> FEATURE:
<223> OTHER INFORMATION: C-term amidated

<400> SEQUENCE: 561

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 562
<211> LENGTH: 37
<212> TYPE: PRT
<213> ORGANISM: Homo sapiens
<220> FEATURE:
<223> OTHER INFORMATION: C-term amidated

<400> SEQUENCE: 562

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35

<210> SEQ ID NO 563
<211> LENGTH: 106
<212> TYPE: PRT
<213> ORGANISM: Homo sapiens

<400> SEQUENCE: 563

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
```

```
                65                  70                  75                  80
His Lys Val Tyr Ala Cys Glu Val Thr His Gln Gly Leu Ser Ser Pro
                    85                  90                  95

Val Thr Lys Ser Phe Asn Arg Gly Glu Cys
            100                 105
```

<210> SEQ ID NO 564
<211> LENGTH: 330
<212> TYPE: PRT
<213> ORGANISM: Artificial
<220> FEATURE:
<223> OTHER INFORMATION: Engineered antibody sequence

<400> SEQUENCE: 564

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
                      325                 330

<210> SEQ ID NO 565
<211> LENGTH: 329
<212> TYPE: PRT
<213> ORGANISM: Artificial
<220> FEATURE:
<223> OTHER INFORMATION: Engineered antibody sequence

<400> SEQUENCE: 565

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 566
<211> LENGTH: 440
<212> TYPE: PRT
```

<213> ORGANISM: Artificial
<220> FEATURE:
<223> OTHER INFORMATION: Engineered antibody sequence

<400> SEQUENCE: 566

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

Tyr Met Asn Trp Val Arg Gln Ala Pro Gly Lys Gly Leu Glu Trp Val
        35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Ala Arg
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu 385                 390                 395                 400
Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly
                435                 440

<210> SEQ ID NO 567
<211> LENGTH: 1323
<212> TYPE: DNA
<213> ORGANISM: Artificial
<220> FEATURE:
<223> OTHER INFORMATION: Engineered antibody sequence

<400> SEQUENCE: 567

```
gaggtgcagc ttgtggagtc tgggggaggc ttggtccagc ctgggggtc cctgagactc      60 tcctgtgcag tctctggaat cgacctcagt ggctactaca tgaactgggt ccgtcaggct    120
ccagggaagg gctgagtg gtcggagtc attggtatta atggtgccac atactacgcg       180
agctgggcga aaggccgatt caccatctcc agagacaatt ccaagaccac ggtgtatctt    240
caaatgaaca gcctgagagc tgaggacact gctgtgtatt tctgtgctag aggggacatc    300
tggggccaag ggaccctcgt caccgtctcg agcgcctcca ccaagggccc atcggtcttc    360
cccctggcac cctcctccaa gagcacctct gggggcacag cggccctggg ctgcctggtc    420
aaggactact tccccgaacc ggtgacggtg tcgtggaact caggcgccct gaccagcggc    480
gtgcacacct tcccggctgt cctacagtcc tcaggactct actccctcag cagcgtggtg    540
accgtgccct ccagcagctt gggcacccag acctacatct gcaacgtgaa tcacaagccc    600
agcaacacca aggtggacgc gagagttgag cccaaatctt gtgacaaaac tcacacatgc    660
ccaccgtgcc cagcacctga actcctgggg ggaccgtcag tcttcctctt ccccccaaaa    720
cccaaggaca cctcatgat ctcccggacc cctgaggtca catgcgtggt ggtgacgtg     780 agccacgaag accctgaggt caagttcaac tggtacgtgg acggcgtgga ggtgcataat    840
gccaagacaa agccgcggga ggagcagtac gccagcacgt accgtgtggt cagcgtcctc    900
accgtcctgc accaggactg gctgaatggc aaggagtaca agtgcaaggt ctccaacaaa    960
gccctcccag cccccatcga gaaaaccatc tccaaagcca agggcagcc ccgagaacca    1020 caggtgtaca ccctgccccc atcccgggag gagatgacca gaaccaggt cagcctgacc    1080 tgcctggtca aaggcttcta tcccagcgac atcgccgtgg agtgggagag caatgggcag    1140
ccggagaaca actacaagac cacgcctccc gtgctggact ccgacggctc cttcttcctc    1200
tacagcaagc tcaccgtgga caagagcagg tggcagcagg ggaacgtctt ctcatgctcc    1260
gtgatgcatg aggctctgca caaccactac acgcagaaga gcctctccct gtctccgggt    1320
tga                                                                  1323
```

ACUTE TREATMENT AND RAPID TREATMENT OF HEADACHE USING ANTI-CGRP ANTIBODIES

RELATED APPLICATIONS

The instant application claims priority to U.S. Provisional Application No. 62/789,828, filed Jan. 8, 2019; U.S. Provisional Application No. 62/872,989, filed Jul. 11, 2019; and U.S. Provisional Application No. 62/842,162, filed May 2, 2019, all of which applications are incorporated by reference in their entireties herein.

SEQUENCE LISTING DISCLOSURE

The instant application contains a Sequence Listing which has been submitted in ASCII format via EFS-Web and is hereby incorporated by reference in its entirety. Said ASCII copy, created on Jan. 7, 2020, is named "11432570008601.txt" and is 357,512 bytes in size.

BACKGROUND

Field

This invention pertains to methods of acute treatment of headache disorders, such as migraine, using antibodies and fragments thereof (including Fab fragments) that specifically bind to human Calcitonin Gene Related Peptide (hereinafter "CGRP"). The invention also pertains to rapid treatment of headache, e.g., chronic migraine, using antibodies and fragments thereof (including Fab fragments) that specifically bind to human Calcitonin Gene Related Peptide (hereinafter "CGRP").

Description of Related Art

Calcitonin Gene Related Peptide (CGRP) is produced as a multifunctional neuropeptide of 37 amino acids in length. Two forms of CGRP, the CGRP-alpha and CGRP-beta forms, exist in humans and have similar activities. CGRP-alpha and CGRP-beta differ by three amino acids in humans, and are derived from different genes. CGRP is released from numerous tissues such as trigeminal nerves, which when activated release neuropeptides within the meninges, mediating neurogenic inflammation that is characterized by vasodilation, vessel leakage, and mast-cell degradation. Durham, P. L., *New Eng. J. Med.*, 350 (11):1073-75 (2004). Biological effects of CGRP are mediated via the CGRP receptor (CGRP-R), which consists of a seven-transmembrane component, in conjunction with receptor-associated membrane protein (RAMP). CGRP-R further requires the activity of the receptor component protein (RCP), which is essential for an efficient coupling to adenylate cyclase through G proteins and the production of cAMP. Doods, H., *Curr. Op. Invest. Drugs*, 2(9):1261-68 (2001).

Migraines are neurovascular disorder affecting approximately 10% of the adult population in the U.S., and are typically accompanied by intense headaches. CGRP is believed to play a prominent role in the development of migraines. In fact several companies, i.e., Amgen, Eli Lilly, Teva and Alder Biopharmaceuticals (recently acquired by Lundbeck A/S) have developed anti-CGRP and anti-CGRP-R antibodies for use in treating or preventing migraine headaches. The present assignee has previously filed patent applications related to anti-CGRP antibodies and uses thereof including published PCT Application WO/2012/162243 filed May 21, 2012 entitled "ANTI-CGRP COMPOSITIONS AND USE THEREOF", published PCT Application WO/2012/162257 filed May 21, 2012, entitled "USE OF ANTI-CGRP ANTIBODIES AND ANTIBODY FRAGMENTS TO PREVENT OR INHIBIT PHOTOPHOBIA OR LIGHT AVERSION IN SUBJECTS IN NEED THEREOF, ESPECIALLY MIGRAINE SUFFERERS" published PCT Application WO/2012/162253, filed May 21, 2012, entitled "USE OF ANTI-CGRP OR ANTI-CGRP-R ANTIBODIES OR ANTIBODY FRAGMENTS TO TREAT OR PREVENT CHRONIC AND ACUTE FORMS OF DIARRHEA" and published PCT Application WO/2015/003122, filed Jul. 3, 2014, entitled "REGULATION OF GLUCOSE METABOLISM USING ANTI-CGRP ANTIBODIES" all of which applications are incorporated by reference in their entirety.

BRIEF SUMMARY

The present disclosure provides methods of acute treatment of headache, comprising administering to a patient in need an effective amount of at least one anti-CGRP antibody or antibody fragment or an anti-CGRP-R antibody or antibody fragment or one or more formulations comprising said antibody or antibody fragment as disclosed herein. Said antibody may be administered while said patient has a headache. Said antibody administration may be initiated within 1-6 hours of the onset of said headache. Said headache may comprise migraine, e.g., episodic migraine or chronic migraine. Said headache may comprise medication overuse headache. Said anti-CGRP antibody or antibody fragment optionally comprises any one of Ab1-Ab14 or a Fab fragment thereof, such as Ab6 or a Fab fragment thereof, e.g., having the light chain CDR 1, 2, and 3 polypeptide sequences of SEQ ID NO: 224; SEQ ID NO: 226; and SEQ ID NO: 228, respectively and the heavy chain CDR 1, 2, and 3 polypeptide sequences of SEQ ID NO: 204; SEQ ID NO: 206; and SEQ ID NO: 208; or having the light chain CDR 1, 2, and 3 polypeptide sequences encoded by SEQ ID NO: 234; SEQ ID NO: 236; and SEQ ID NO: 238, respectively and heavy chain CDR 1, 2, and 3 polypeptide sequences encoded by SEQ ID NO: 214; SEQ ID NO: 216; and SEQ ID NO: 218, respectively. Said anti-CGRP antibody may comprise the variable light chain polypeptide of SEQ ID NO: 222 and the variable heavy chain polypeptide of SEQ ID NO: 202. Said anti-CGRP antibody may comprise the variable light chain polypeptide encoded by SEQ ID NO: 232 and the variable heavy chain polypeptide encoded by SEQ ID NO: 212. Said anti-CGRP antibody may comprise the light chain polypeptide of SEQ ID NO: 221 and the heavy chain polypeptide of SEQ ID NO: 201 or SEQ ID NO: 566. Said anti-CGRP antibody may comprise the light chain polypeptide encoded by SEQ ID NO: 231 and the heavy chain polypeptide encoded by SEQ ID NO: 211 or SEQ ID NO: 567. Said anti-CGRP antibody may comprise the antibody expression product isolated from recombinant cells which express nucleic acid sequences encoding the variable light chain polypeptide of SEQ ID NO: 222 and the variable heavy chain polypeptide of SEQ ID NO: 202, which polypeptides optionally are respectively linked to human light and heavy constant region polypeptides, e.g., human IgG1, IgG2, IgG3 or IgG4 constant regions, which constant regions optionally may be modified to alter glycosylation or proteolysis, wherein said recombinant cells optionally comprise yeast or mammalian cells, e.g., *Pichia pastoris* or CHO cells. Said anti-CGRP antibody may comprise the antibody expression product isolated from recombinant cells which express nucleic acid sequences encoding the light chain of SEQ ID NO: 221 and the heavy chain polypeptide of SEQ ID NO: 201 or SEQ ID NO: 566, wherein said recombinant cells optionally comprise yeast or mammalian cells, e.g., *Pichia pastoris* or CHO cells, wherein the constant regions thereof optionally may be modified to alter glycosylation or proteolysis or other effector functions. Any of the aforementioned anti-CGRP antibodies or antibody fragments, preferably Ab6, may be optionally comprised in a formulation as disclosed herein, e.g., comprising histidine (L-histidine), sorbitol, polysorbate 80, such as, per 1 mL volume, about 100 mg anti-CGRP antibody, about 3.1 mg L-Histidine, about 40.5 mg Sorbitol, and about 0.15 mg Polysorbate 80, having a pH of about 5.8. The administered dosage of said antibody may be between about 100 mg and about 300 mg, such as about 100 mg, about 300 mg, 100 mg, or 300 mg. The dosage may be administered by different means, e.g., intravenously, e.g., in a saline solution such as 0.9% sodium chloride in a suitable volume, such as 100 mL.

Said patient may exhibit less than 25 headache days per month, less than 20 headache days per month, less than 15 headache days per month, or less than 10 headache days per month. For example, said patient may exhibit less than 14 headache days, less than headache 13 days, less than headache 12 days, less than headache 11 days, less than 10 headache days, less than 9 headache days, less than 8 headache days, less than 7 headache days, or less than 6 headache days per month. Said patient may exhibit between 2-15 headache days, e.g., 3-14 headache days, 4-13 headache days, 5-12 headache days, 6-11 headache days, or 7-10 headache days/month.

Said patient may exhibit less than 10 migraines per month, such as between 1-9 migraines per month, such as between 2-8 migraines per month, between 3-7 migraine per month, between 4-6 migraine per month, or about 5 migraines per month. Said patient may exhibit fewer than 1 migraine per month on average, e.g., on average one migraine every 2 months, one every 3 months, one every 4 or 6 months, or intermediate values such as 2 every 3 months, etc. Said migraine may be diagnosed in accord with the ICHD-3 guidelines.

In exemplary embodiments, said headache may comprise medication overuse headache. Said medication overuse headache may be determined based on meeting the following criteria: (a) headache occurring on 15 or more days/month in a patient with a pre-existing headache disorder; and (b) overuse for more than 3 months of one or more drugs that can be taken for acute and/or symptomatic treatment of headache.

Said overuse may comprise use of an ergot alkoid (e.g., ergotamine) on 10 or more days/month, use of a triptan on 10 or more days/month, use of one or more non-opioid analgesics (such as paracetamol (acetaminophen), acetylsalicylic acid (aspirin), another NSAID, or another non-opioid analgesic) on 15 or more days/month, use of one or more combination-analgesics (as further described below) on 10 or more days/month, use of one or more opioids on 10 or more days/month, or use of a combination of two or more drug classes (as further described below) on 10 or more days/month.

In the methods herein, said triptan may include, without limitation thereto, any one of or any combination of triptans such as sumatriptan, zolmitriptan, naratriptan, rizatriptan, eletriptan, almotriptan, and frovatriptan, among others.

Said medication overuse headache may comprise ergotamine-overuse headache, triptan-overuse headache, non-opioid analgesic-overuse headache, opioid-overuse headache, combination-analgesic-overuse headache, medication-overuse headache attributed to multiple drug classes not individually overused, medication-overuse headache attributed to unspecified or unverified overuse of multiple drug classes, or medication-overuse headache attributed to other medication.

Said non-opioid analgesic-overuse headache may comprise paracetamol (acetaminophen)-overuse headache, nonsteroidal anti-inflammatory drug (NSAID)-overuse headache such as acetylsalicylic acid (aspirin)-overuse headache or ibuprofen-overuse headache, or another non-opioid analgesic-overuse headache.

Said ergotamine-overuse headache may comprise headache occurring on 15 or more days/month in a patient with a pre-existing primary headache and developing as a consequence of regular use of an ergot alkaloid such as ergotamine on 10 or more days/month for more than 3 months.

In the methods herein, said ergot alkaloid may comprise ergotamine, nicergoline, methysergide, or dihydroergotamine, or may comprise an ergot derivative.

Said triptan-overuse headache may comprise headache occurring on 15 or more days/month in a patient with a pre-existing primary headache and developing as a consequence of regular use of one or more triptans on 10 or more days/month for more than 3 months.

Said non-opioid analgesic-overuse headache may comprise headache occurring on 15 or more days/month in a patient with a pre-existing primary headache and developing as a consequence of regular use of one or more non-opioid analgesics (such as paracetamol (acetaminophen), acetylsalicylic acid (aspirin), ibuprofen, another NSAID, or another non-opioid analgesic) on 15 or more days/month for more than 3 months.

In the methods herein, said NSAID may comprise any NSAID or combination thereof, including without limitation thereto, ibuprofen, naproxen, or indomethacin.

Said combination-analgesic-overuse headache may comprise headache occurring on 15 or more days/month developing as a consequence of regular use of one or more combination-analgesics on 10 or more days/month for more than 3 months. In the context of medication overuse headache, the term combination-analgesic refers to formulations combining drugs of two or more classes, each with analgesic effects (for example, paracetamol and codeine) or analgesics in combination with agents acting as adjuvants (for example, caffeine). Commonly overused combination-analgesics combine non-opioid analgesics with at least one opioid, barbiturate such as butalbital and/or caffeine. In exemplary embodiments, the combination-analgesic overuse-headache is due to the combination of acetaminophen, aspirin, and caffeine, e.g., EXCEDRIN® or EXCEDRIN MIGRAINE®. Other known combination analgesics comprise an analgesic in combination with at least one non-analgesic, e.g., with a vasoconstrictor drug such as pseudoephedrine for sinus-related preparations, antihistamine drug used to treat allergy sufferers, etc.

Said opioid-overuse headache may comprise headache occurring on 15 or more days/month in a patient with a pre-existing primary headache and developing as a consequence of regular use of one or more opioids 10 or more days/month for more than 3 months.

Said medication-overuse headache attributed to multiple drug classes not individually overused may comprise headache occurring on 15 or more days/month in a patient with a pre-existing primary headache and developing as a result of regular intake of any combination of ergotamine, triptans, non-opioid analgesics and/or opioids on a total of at least 10 days/month for more than 3 months without overuse of any single drug or drug class alone.

In the methods herein, said opioid may be any one or any combination of opioid drugs, including without limitation thereto, oxycodone, tramadol, butorphanol, morphine, codeine, hydrocodone, thebaine, oripavine, mixed opium alkaloids such as papaveretum, diacetylmorphine, nicomorphine, dipropanoylmorphine, diacetyldihydromorphine, acetylpropionylmorphine, desomorphine, methyldesorphine, dibenzoylmorphine, ethylmorphine, heterocodeine, buprenorphine, etorphine, hydromorphone, oxymorphone, fentanyl, alphamethylfentanyl, alfentanil, sufentanil, remifentanil, carfentanyl, ohmefentanyl, pethidine (meperidine), ketobemidone, MPPP, allylprodine, prodine, PEPAP, promedol, diphenylpropylamine, propoxyphene, dextropropoxyphene, dextromoramide, bezitramide, piritramide, among others.

Said medication-overuse headache attributed to unspecified or unverified overuse of multiple drug classes may comprise headache occurring on 15 or more days/month in a patient with a pre-existing primary headache and developing as a result of regular intake of any combination of ergotamine, triptans, non-opioid analgesics and/or opioids on at least 10 days/month for more than 3 months, wherein the identity, quantity and/or pattern of use or overuse of these classes of drug is not reliably established.

Said medication-overuse headache attributed to other medication may comprise headache occurring on 15 or more days/month in a patient with a pre-existing primary headache and developing as a result of regular intake of one or more medications other than those described above, taken for acute or symptomatic treatment of headache, on at least 10 days/month for more than 3 months.

The amount and duration of medication use may be determined utilizing known methods, such as the usage reported by the patient or a relative, a diary, medical records, drug purchase history, prescription fulfillment, biomarkers of medication use, incidence of medication toxicity, incidence of medication overdose, and/or other indicators of a patient's medication use.

The present disclosure provides methods of treating or preventing probable medication overuse headache, comprising administering to a patient in need an effective amount of an anti-CGRP antibody or anti-CGRP antibody fragment or one or more formulations comprising said anti-CGRP antibody or anti-CGRP antibody fragment as disclosed herein. Said anti-CGRP antibody optionally comprises any one of Ab1-Ab14, such as Ab6, e.g., having the light chain CDR 1, 2, and 3 polypeptide sequences of SEQ ID NO: 224; SEQ ID NO: 226; and SEQ ID NO: 228, respectively and the heavy chain CDR 1, 2, and 3 polypeptide sequences of SEQ ID NO: 204; SEQ ID NO: 206; and SEQ ID NO: 208; or having the light chain CDR 1, 2, and 3 polypeptide sequences encoded by SEQ ID NO: 234; SEQ ID NO: 236; and SEQ ID NO: 238, respectively and heavy chain CDR 1, 2, and 3 polypeptide sequences encoded by SEQ ID NO: 214; SEQ ID NO: 216; and SEQ ID NO: 218, respectively. Said anti-CGRP antibody may comprise the variable light chain polypeptide of SEQ ID NO: 222 and the variable heavy chain polypeptide of SEQ ID NO: 202. Said anti-CGRP antibody may comprise the variable light chain polypeptide encoded by SEQ ID NO: 232 and the variable heavy chain polypeptide encoded by SEQ ID NO: 212. Said anti-CGRP antibody may comprise the light chain polypeptide of SEQ ID NO: 221 and the heavy chain polypeptide of SEQ ID NO: 201 or SEQ ID NO: 566. Said anti-CGRP antibody may comprise the light chain polypeptide encoded by SEQ ID NO: 231 and the heavy chain polypeptide encoded by SEQ ID NO: 211 or SEQ ID NO: 567. Said anti-CGRP antibody may comprise the antibody expression product isolated from recombinant cells which express nucleic acid sequences encoding the variable light chain polypeptide of SEQ ID NO: 222 and the variable heavy chain polypeptide of SEQ ID NO: 202, which polypeptides optionally are respectively linked to human light and heavy constant region polypeptides, e.g., human IgG1, IgG2, IgG3 or IgG4 constant regions, which constant regions optionally may be modified to alter glycosylation or proteolysis, wherein said recombinant cells optionally comprise yeast or mammalian cells, e.g., *Pichia pastoris* or CHO cells. Said anti-CGRP antibody may comprise the antibody expression product isolated from recombinant cells which express nucleic acid sequences encoding the light chain of SEQ ID NO: 221 and the heavy chain polypeptide of SEQ ID NO: 201 or SEQ ID NO: 566, wherein said recombinant cells optionally comprise yeast or mammalian cells, e.g., *Pichia pastoris* or CHO cells, wherein the constant regions thereof optionally may be modified to alter glycosylation or proteolysis or other effector functions. Any of the aforementioned anti-CGRP antibodies or antibody fragments, preferably Ab6, may be optionally comprised in a formulation as disclosed herein, e.g., comprising histidine (L-histidine), sorbitol, polysorbate 80, such as, per 1 mL volume, about 100 mg anti-CGRP antibody, about 3.1 mg L-Histidine, about 40.5 mg Sorbitol, and about 0.15 mg Polysorbate 80, having a pH of about 5.8. The administered dosage of said antibody may be between about 100 mg and about 300 mg, such as about 100 mg, about 300 mg, 100 mg, or 300 mg. The dosage may be administered by different means, e.g., intravenously, e.g., in a saline solution such as 0.9% sodium chloride in a suitable volume, such as 100 mL. Probable medication overuse headache refers to criteria (a) and (b) not being entirely fulfilled, e.g., having at least 80% or at least 90% of the specified number of headache days and/or medication use days per month, and/or over a shorter time period such as at least 2 months, optionally in the absence of another ICHD-3 diagnosis.

Said medication-overuse headache (such as ergotamine-overuse headache, triptan-overuse headache, non-opioid analgesic-overuse headache, opioid-overuse headache, combination-analgesic-overuse headache, medication-overuse headache attributed to multiple drug classes not individually overused, medication-overuse headache attributed to unspecified or unverified overuse of multiple drug classes, or medication-overuse headache attributed to other medication) may be diagnosed according to the third edition of the International Classification of Headache Disorders (ICHD-3). See Headache Classification Committee of the International Headache Society (IHS), The International Classification of Headache Disorders, 3rd edition, Cephalalgia. 2018 January; 38(1):1-211, which is hereby incorporated by reference in its entirety.

Herein, the criterion that a headache occurs "as a consequence of" over use of a medication or medications refers to the apparent association between the medication(s) overuse and the headache, e.g., that the medication(s) overuse and headache are present at the above-specified frequency such that causation may be presumed.

The present disclosure also provides methods of treating chronic migraine, comprising intravenously administering to a patient in need thereof a first dosage comprising between about 100 mg and about 300 mg of an anti-CGRP antibody, wherein said anti-CGRP antibody preferably comprises the light chain polypeptide of SEQ ID NO: 221 and the heavy chain polypeptide of SEQ ID NO: 201 or 566, wherein in the first 24 hours after administration of said first dosage the patient exhibits at least a 50% reduction in migraine prevalence.

In another aspect, the disclosure provides methods of treating chronic migraine, comprising intravenously administering to a patient in need thereof a first dosage comprising between about 100 mg and about 300 mg of an anti-CGRP antibody, wherein said anti-CGRP antibody preferably comprises the light chain polypeptide of SEQ ID NO: 221 and the heavy chain polypeptide of SEQ ID NO: 201 or 566, wherein on the first day following the day of administration the patient exhibits at least a 50% reduction in migraine prevalence.

In some exemplary embodiments the dosage, e.g., the first dosage, of said anti-CGRP antibody may be 100 mg.

In other exemplary embodiments the dosage, e.g., the first dosage, of said anti-CGRP antibody may be 300 mg.

The method may further comprise intravenously administering 100 mg of said anti-CGRP antibody every 10-14 weeks, preferably every 11-13 weeks, more preferably every 12 weeks.

The method may further comprise intravenously administering 300 mg of said anti-CGRP antibody every 10-14 weeks, preferably every 11-13 weeks, more preferably every 12 weeks.

The antibody may be provided or administered in a formulation as disclosed herein, e.g., comprising histidine (L-histidine), sorbitol, polysorbate 80, such as, per 1 mL volume, about 100 mg anti-CGRP antibody, about 3.1 mg L-Histidine, about 40.5 mg Sorbitol, and about 0.15 mg Polysorbate 80, having a pH of about 5.8.

Prior to said first dosage, the patient may exhibit between about 10 and about 22 migraine days per month, such as between about 13 and about 19 migraine days per month, such as about 16 migraine days per month.

Prior to said first dosage, the patient may exhibit between about 14 and about 27 headache days per month, such as between about 17 and about 24 headache days per month, such as about 20 or about 21 headache days per month.

Said patient may have been diagnosed with migraine at least 10 years prior to said first dosage, such as at least 15 years prior to said first dosage, such as at least 18 or at least 19 years prior to said first dosage.

Said patient may have been diagnosed with chronic migraine at least 5 years prior to said first dosage, such as at least 8 years prior to said first dosage, such as at least 11 or at least 12 years prior to said first dosage.

The patient may have a headache when administered said first dosage.

The patient may have a migraine, such as a migraine with aura, when administered said first dosage.

Said patient may have a reduction in the number of migraine days by at least 50% in the one month period after being administered said first dose relative to the baseline number of migraine days experienced by that patient prior to said first dose.

Said patient may have a reduction in the number of migraine days by at least 75% in the one month period after being administered said first dose relative to the baseline number of migraine days experienced by that patient prior to said first dose.

Said patient may have a reduction in the number of migraine days by 100% in the one month period after being administered said first dose relative to the baseline number of migraine days experienced by that patient prior to said first dose.

Said patient may have a reduction in the number of migraine days by at least 50% in the 12 week period after being administered said first dose relative to the baseline number of migraine days experienced by that patient prior to said first dose.

Said patient may have a reduction in the number of migraine days by at least 75% in the 12 week period after being administered said first dose relative to the baseline number of migraine days experienced by that patient prior to said first dose.

Said patient may have a reduction in the number of migraine days by 100% in the 12 week period after being administered said first dose relative to the baseline number of migraine days experienced by that patient prior to said first dose.

The method may further comprise administering, e.g., intravenously, a second dose of said anti-CGRP antibody to said patient within about 10-14 weeks, preferably 11-13 weeks, more preferably about 12 weeks or about 3 months, after said first dose.

Said first dose may comprise about 100 mg, about 125 mg, about 150 mg, about 175 mg, about 200 mg, about 225 mg, about 250 mg, about 275 mg, or about 300 mg of said anti-CGRP antibody.

Said patient may be a chronic migraine patient or episodic migraine patient at risk of developing medication overuse headache. Said patient may use acute headache medication on at least 1, 2, 3, 4, 5, 6, 7, 8, 9, or 10 day(s) per month. Said patient may use acute headache medication on at least 10 days per month. Optionally said acute medication use is determined over a baseline period of at least 28 days. Said acute medication use may be reported by the patient, a caregiver, or based on records. Said acute medication may comprise use of ergot alkaloids, triptans, non-opioid analgesics, acetaminophen, aspirin, NSAIDs, non-opioid analgesics, combination-analgesics, or opioids.

Prior to said administration, the patient may exhibit between about 15 and about 30 migraine days per month, such as between about 16 and about 28 migraine days per month, such as between about 17 and about 26 migraine days per month, such as about 16 migraine days per month.

Prior to said administration, the patient may exhibit between about 15 and about 27 headache days per month, such as between about 17 and about 24 headache days per month, such as about 20 or about 21 headache days per month.

Said patient may have been diagnosed with migraine at least 10 years prior to said administration, such as at least 15 years prior to said administration, such as at least 18 or at least 19 years prior to said administration.

Said patient may have been diagnosed with chronic migraine at least 5 years prior to said administration, such as at least 8 years prior to said administration, such as at least 11 or at least 12 years prior to said administration.

Said patient may have a reduction in the number of migraine days by at least 50% in the one month period after being administered said antibody relative to the baseline number of migraine days experienced by that patient prior to said administration.

Said patient may have a reduction in the number of migraine days by at least 75% in the one month period after being administered said antibody relative to the baseline number of migraine days experienced by that patient prior to said administration.

Said patient may have a reduction in the number of migraine days by 100% in the one month period after being administered said antibody relative to the baseline number of migraine days experienced by that patient prior to said administration.

Said patient may have a reduction in the number of migraine days by at least 50% in the 12 week period after being administered said antibody relative to the baseline number of migraine days experienced by that patient prior to said administration.

Said patient may have a reduction in the number of migraine days by at least 75% in the 12 week period after being administered said antibody relative to the baseline number of migraine days experienced by that patient prior to said administration.

Said patient may have a reduction in the number of migraine days by 100% in the 12 week period after being administered said antibody relative to the baseline number of migraine days experienced by that patient prior to said administration.

The method may further comprise administering, e.g., intravenously, a second dose of said anti-CGRP antibody to said patient within about 10-14 weeks, preferably 11-13 weeks, more preferably about 12 weeks or about 3 months, after said administration.

Said administration may comprise about 100 mg, about 125 mg, about 150 mg, about 175 mg, about 200 mg, about 225 mg, about 250 mg, about 275 mg, or about 300 mg of said anti-CGRP antibody.

Said anti-CGRP antibody may be aglycosylated or if glycosylated only may contain only mannose residues.

Said anti-CGRP antibody may consist of the light chain polypeptide of SEQ ID NO: 221 and the heavy chain polypeptide of SEQ ID NO: 201 or SEQ ID NO: 566. Said anti-CGRP antibody may consist of the light chain polypeptide encoded by SEQ ID NO: 231 and the heavy chain polypeptide encoded by SEQ ID NO: 211 or SEQ ID NO: 567.

In some embodiments, said anti-human CGRP antibody or antibody fragment comprises the variable light chain of SEQ ID NO: 222 and/or the variable heavy chain of SEQ ID NO: 202. In some embodiments, said anti-human CGRP antibody or antibody fragment comprises the variable light chain encoded by SEQ ID NO: 232 and/or the variable heavy chain encoded by SEQ ID NO: 212.

In some embodiments, said anti-human CGRP antibody or antibody fragment comprises the light chain of SEQ ID NO: 221 and/or the heavy chain of SEQ ID NO: 201 or SEQ ID NO: 566. In some embodiments, said anti-human CGRP antibody or antibody fragment comprises the light chain encoded by SEQ ID NO: 231 and/or the heavy chain encoded by SEQ ID NO: 211 or SEQ ID NO: 567.

In some embodiments, said anti-CGRP antibody may comprise the antibody expression product isolated from recombinant cells which express nucleic acid sequences encoding the VL polypeptide of SEQ ID NO: 222 and the VH polypeptide of SEQ ID NO: 202, which polypeptides optionally are respectively linked to human light and heavy constant region polypeptides, e.g., human IgG1, IgG2, IgG3 or IgG4 constant regions, which constant regions optionally may be modified to alter glycosylation or proteolysis, wherein said recombinant cells optionally comprise yeast or mammalian cells, e.g., *Pichia pastoris* or CHO cells.

In some embodiments, said anti-CGRP antibody may comprise the antibody expression product isolated from recombinant cells which express nucleic acid sequences encoding the light chain of SEQ ID NO: 221 and the heavy chain polypeptide of SEQ ID NO: 201 or SEQ ID NO: 566, wherein said recombinant cells optionally comprise yeast or mammalian cells, e.g., *Pichia pastoris* or CHO cells, wherein the constant regions thereof optionally may be modified to alter glycosylation or proteolysis or other effector functions.

Inn some embodiments any of the aforementioned anti-CGRP antibodies or antibody fragments may be comprised in a formulation as disclosed herein, e.g., comprising histidine (L-histidine), sorbitol, polysorbate 80, such as, per 1 mL volume, about 100 mg anti-CGRP antibody, about 3.1 mg L-Histidine, about 40.5 mg Sorbitol, and about 0.15 mg Polysorbate 80, having a pH of about 5.8. The antibody or fragment may be administered by different means, e.g., intravenously, e.g., in a saline solution such as 0.9% sodium chloride in a suitable volume, such as 100 mL.

In some embodiments, about 100 mg, about 125 mg, about 150 mg, about 175 mg, about 200 mg, about 225 mg, about 250 mg, about 275 mg, or about 300 mg of said anti-CGRP antibody or antibody fragment is administered, e.g., intravenously.

In other embodiments, about 100 mg of said anti-CGRP antibody or antibody fragment is administered.

In other embodiments, about 300 mg of said anti-CGRP antibody or antibody fragment is administered, e.g., intravenously.

In exemplary embodiments, the anti-human CGRP antibody or antibody fragment is administered, e.g., intravenously at a frequency which is at most every 10-14 weeks, preferably every 11-13 weeks, more preferably every 3 months or every 12 weeks, wherein the antibody dosage is administered in a single formulation or divided into different formulations which are administered at a frequency of approximately every 10-14 weeks, preferably every 11-13 weeks, more preferably every 3 months or every 12 weeks. The phrase "the antibody dosage is administered in a single formulation or divided into different formulations" refers to the administration of the recited amount of antibody within a relatively short period of time, e.g., within a period of several hours, e.g., 1 to 8 hours, about one day, within about two days, or within about one week, which may be by the same or different routes (e.g., i.v., i.m., and/or s.c.), sites of administration. The term "different formulations" in this context refers to antibody dosages that are administered at different times and/or at different sites and/or different routes, irrespective of whether the dosages are the same or different with respect to the chemical composition of the pharmaceutical formulation in with each dosage is administered; for example, the concentration, excipients, carriers, pH, and the like may be the same or different between the different administered dosages.

In other exemplary embodiments, the anti-human CGRP antibody or antibody fragment dosage is administered in a single formulation or divided into different formulations which are administered at a frequency of approximately every 8 weeks or every 2 months.

In other exemplary embodiments, the anti-human CGRP antibody or antibody fragment dosage is administered in a single formulation or divided into different formulations which are administered at a frequency of approximately every 10-14 weeks, preferably every 11-13 weeks, more preferably every 12 weeks or every 3 months.

In other exemplary embodiments, the anti-human CGRP antibody or antibody fragment dosage is administered in a single formulation or divided into different formulations which are administered at a frequency of approximately every 16 weeks or every 4 months.

In other exemplary embodiments, the anti-human CGRP antibody or antibody fragment dosage is administered in a single formulation or divided into different formulations which are administered at a frequency of approximately every 20 weeks or every 5 months.

In other exemplary embodiments, the anti-human CGRP antibody or antibody fragment dosage is administered in a single formulation or divided into different formulations which are administered at a frequency of approximately every 24 weeks or every 6 months.

In other exemplary embodiments, the anti-human CGRP antibody or antibody fragment dosage is administered in a single formulation or divided into different formulations which are administered at a frequency of approximately every 28 weeks or every 7 months.

In other exemplary embodiments, the anti-human CGRP antibody or antibody fragment dosage is administered in a single formulation or divided into different formulations which are administered at a frequency of approximately every 32 weeks or every 8 months.

In other exemplary embodiments, the anti-human CGRP antibody or antibody fragment dosage is administered in a single formulation or divided into different formulations which are administered at a frequency of approximately every 36 weeks or every 9 months.

In other exemplary embodiments, the anti-human CGRP antibody or antibody fragment dosage is administered in a single formulation or divided into different formulations which are administered at a frequency of approximately every 40 weeks or every 8 months.

In other exemplary embodiments, the anti-human CGRP antibody or antibody fragment dosage is administered in a single formulation or divided into different formulations which are administered at a frequency of approximately every 44 weeks or every 9 months.

In other exemplary embodiments, the anti-human CGRP antibody or antibody fragment dosage is administered in a single formulation or divided into different formulations which are administered at a frequency of approximately every 48 weeks or every 10 months.

In other exemplary embodiments, the anti-human CGRP antibody or antibody fragment dosage is administered in a single formulation or divided into different formulations which are administered at a frequency of approximately every 52 weeks or every 11 months.

In other exemplary embodiments, the anti-human CGRP antibody or antibody fragment dosage is administered in a single formulation or divided into different formulations which are administered at a frequency of approximately every 56 weeks or every 12 months.

In other exemplary embodiments, the anti-human CGRP antibody or antibody fragment dosage is administered in a single formulation or divided into different formulations which are administered at a frequency of approximately every 15-18 months.

In other exemplary embodiments, the anti-human CGRP antibody or antibody fragment dosage is administered in a single formulation or divided into different formulations which are administered at a frequency of approximately every 18-21 months.

In other exemplary embodiments, the anti-human CGRP antibody dosage or antibody fragment used in the afore-mentioned methods is administered in a single formulation or divided into different formulations which are administered at a frequency of approximately every 2 years.

In other exemplary embodiments, the anti-human CGRP antibody used in the afore-mentioned methods is administered systemically.

In other exemplary embodiments, the anti-human CGRP antibody or antibody fragment used in the afore-mentioned methods is administered by a mode of administration is selected from intravenous, intramuscular, intravenous, intrathecal, intracranial, topical, intranasal, and oral. In a preferred embodiment, the anti-human CGRP antibody or antibody fragment used in the afore-mentioned methods is administered intravenously.

In other exemplary embodiments, the anti-human CGRP antibody used in the afore-mentioned methods has an in vivo half-life of at least 10 days.

In other exemplary embodiments, the anti-human CGRP antibody has an in vivo half-life of at least 15 days.

In other exemplary embodiments, the anti-human CGRP antibody used in the afore-mentioned methods has an in vivo half-life of at least 20 days.

In other exemplary embodiments, the anti-human CGRP antibody used in the afore-mentioned methods has an in vivo half-life of at least 20-30 days.

In other exemplary embodiments, the anti-human CGRP antibody is administered at a dosage of between about 100 mg and about 300 mg has an in vivo half-life of ±20% of at least about (284±44 hours).

In other exemplary embodiments, the anti-human CGRP antibody used in the afore-mentioned methods binds to human α- and β-CGRP.

In other exemplary embodiments, the administered anti-human CGRP antibody dosage results in the inhibition of vasodilation induced by topically applied capsaicin at least 30 days after antibody administration.

In other exemplary embodiments, the administered anti-human CGRP antibody dosage results in the inhibition of vasodilation induced by topically applied capsaicin at least 60 days after antibody administration.

In other exemplary embodiments, the administered anti-human CGRP antibody dosage results in inhibition of vasodilation induced by topically applied capsaicin at least 90 days after antibody administration.

In other exemplary embodiments, the administered anti-human CGRP antibody dosage results in the inhibition of vasodilation induced by topically applied capsaicin at least 120 days after antibody administration.

In other exemplary embodiments, the administered anti-human CGRP antibody dosage results in the inhibition of vasodilation induced by topically applied capsaicin at least 150 days after antibody administration.

In other exemplary embodiments, the administered anti-human CGRP antibody dosage results in the inhibition of vasodilation induced by topically applied capsaicin at least 180 days after antibody administration.

In other exemplary embodiments, the administered anti-human CGRP antibody dosage results in the inhibition of vasodilation induced by topically applied capsaicin more than 180 days after antibody administration.

In other exemplary embodiments, the administered anti-human CGRP antibody dosage results in sustained pharmacodynamic (PK) activity, within 5% of the maximal response (Imax) (as compared to lower antibody doses).

In other exemplary embodiments, the administered anti-human CGRP antibody dosage results in sustained pharmacodynamic (PK) activity which is maintained for at least 2-3 months after antibody administration, wherein PK analysis of the anti-human CGRP antibody is derived from plasma concentrations.

In other exemplary embodiments, the administered anti-human CGRP antibody dosage is between about 100 mg and about 300 mg or more which is administered no more frequently than every 2 months.

The present invention is additionally directed to the use of specific antibodies and fragments thereof having binding specificity for CGRP, in particular antibodies having desired epitopic specificity, high affinity or avidity and/or functional properties. A preferred embodiment of the invention is directed to usage of chimeric or humanized antibodies and fragments thereof (including Fab fragments) capable of binding to CGRP and/or inhibiting the biological activities mediated by the binding of CGRP to the CGRP receptor ("CGRP-R") e.g., wherein such antibodies optionally are derived from recombinant cells engineered to express same, optionally yeast or mammalian cells, further optionally *Pichia pastoris* and CHO cells.

In another preferred embodiment of the invention, full length antibodies and Fab fragments thereof are contemplated that inhibit the CGRP-alpha-, CGRP-beta-, and rat CGRP-driven production of cAMP. In a further preferred embodiment of the invention, full length and Fab fragments thereof are contemplated that reduce vasodilation in a recipient following administration.

The invention also contemplates usage of conjugates of anti-CGRP antibodies and binding fragments thereof conjugated to one or more functional or detectable moieties. The invention also contemplates usage of chimeric or humanized anti-CGRP or anti-CGRP/CGRP-R complex antibodies and binding fragments thereof. In one embodiment, binding fragments include, but are not limited to, Fab, Fab', F(ab')$_2$, Fv, scFv fragments, SMIPs (small molecule immunopharmaceuticals), camelbodies, nanobodies, and IgNAR.

BRIEF DESCRIPTION OF THE SEVERAL VIEWS OF THE DRAWINGS

FIGS. 1A-1F provide the polypeptide sequences of the full-length heavy chain for antibodies Ab1-Ab14 with their framework regions (FR), complementarity determining regions (CDRs), and constant region sequences delimited.

FIGS. 2A-2D provide the polypeptide sequences of the full-length light chain for antibodies Ab1-Ab14 with their framework regions (FR), complementarity determining regions (CDRs), and constant region sequences delimited.

FIGS. 3A-3P provide exemplary polynucleotide sequences encoding the full-length heavy chain for antibodies Ab1-Ab14 with their framework regions (FR), complementarity determining regions (CDRs), and constant region coding sequences delimited.

FIGS. 4A-4I provide exemplary polynucleotide sequences encoding the full-length light chain for antibodies Ab1-Ab14 with their framework regions (FR), complementarity determining regions (CDRs), and constant region coding sequences delimited.

FIG. 5 provides the polypeptide sequence coordinates within the full-length heavy chain polypeptide sequences of antibodies Ab1-Ab14 of sequence features including the variable region and complementarity determining regions (CDRs), and the SEQ ID NO of each individual feature.

FIG. 6 provides the polypeptide sequence coordinates within the full-length heavy chain polypeptide sequences of antibodies Ab1-Ab14 of sequence features including the framework regions (FRs) and constant region, and the SEQ ID NO of each individual feature.

FIG. 7 provides the polypeptide sequence coordinates within the full-length light chain polypeptide sequences of antibodies Ab1-Ab14 of sequence features including the variable region and complementarity determining regions (CDRs), and the SEQ ID NO of each individual feature.

FIG. 8 provides the polypeptide sequence coordinates within the full-length light chain polypeptide sequences of antibodies Ab1-Ab14 of sequence features including the framework regions (FRs) and constant region, and the SEQ ID NO of each individual feature.

FIG. 9 provides the polynucleotide sequence coordinates within the exemplary polynucleotide sequences encoding the full-length heavy chain polypeptide sequences of antibodies Ab1-Ab14 of sequence features including the variable region and complementarity determining regions (CDRs), and the SEQ ID NO of each individual feature.

FIG. 10 provides the polynucleotide sequence coordinates within the exemplary polynucleotide sequences encoding the full-length heavy chain polypeptide sequences of antibodies Ab1-Ab14 of sequence features including the framework regions (FRs) and constant region, and the SEQ ID NO of each individual feature.

FIG. 11 provides the polynucleotide sequence coordinates within the exemplary polynucleotide sequences encoding the full-length light chain polypeptide sequences of antibodies Ab1-Ab14 of sequence features including the variable region and complementarity determining regions (CDRs), and the SEQ ID NO of each individual feature.

FIG. 12 provides the polynucleotide sequence coordinates within the exemplary polynucleotide sequences encoding the full-length light chain polypeptide sequences of antibodies Ab1-Ab14 of sequence features including the framework regions (FRs) and constant region, and the SEQ ID NO of each individual feature.

FIG. 20 contains the pharmacokinetic (PK) profile for Ab6 administered intravenously at a single dosage of 1000 mg.

FIG. 21 contains plasma-free pharmacokinetic (PK) parameters N (number of patients), mean, and standard deviation (SD) for a single 1000 mg intravenous dosage of Ab6. The parameters shown in the table and the units are $C_{max}$ (μg/mL), $AUC_{0-\infty}$ (mg*hr/mL), half-life (days), $V_z$ (L) and $C_L$ (mL/hr).

FIG. 34 summarizes the change from baseline in measured attributes for the placebo and treatment groups in the study described in Example 2.

FIG. 39 summarizes the characteristics of patients in each treatment group in the clinical trial described in Example 3. * According to the American Academy of Neurology/American Headache Society guidelines for migraine preventative treatment (medications identified by clinical review of coded medical data); SD, standard deviation; BMI, body mass index.

FIG. 45. Summary of Acute Medication Days by Subgroups of Chronic Migraine Patients with Baseline Acute Medication Use.

FIG. 49. Summary of Acute Medication Days by Subgroups of Episodic Migraine Patients with Baseline Acute Medication Use.

DETAILED DESCRIPTION

Figure 13:
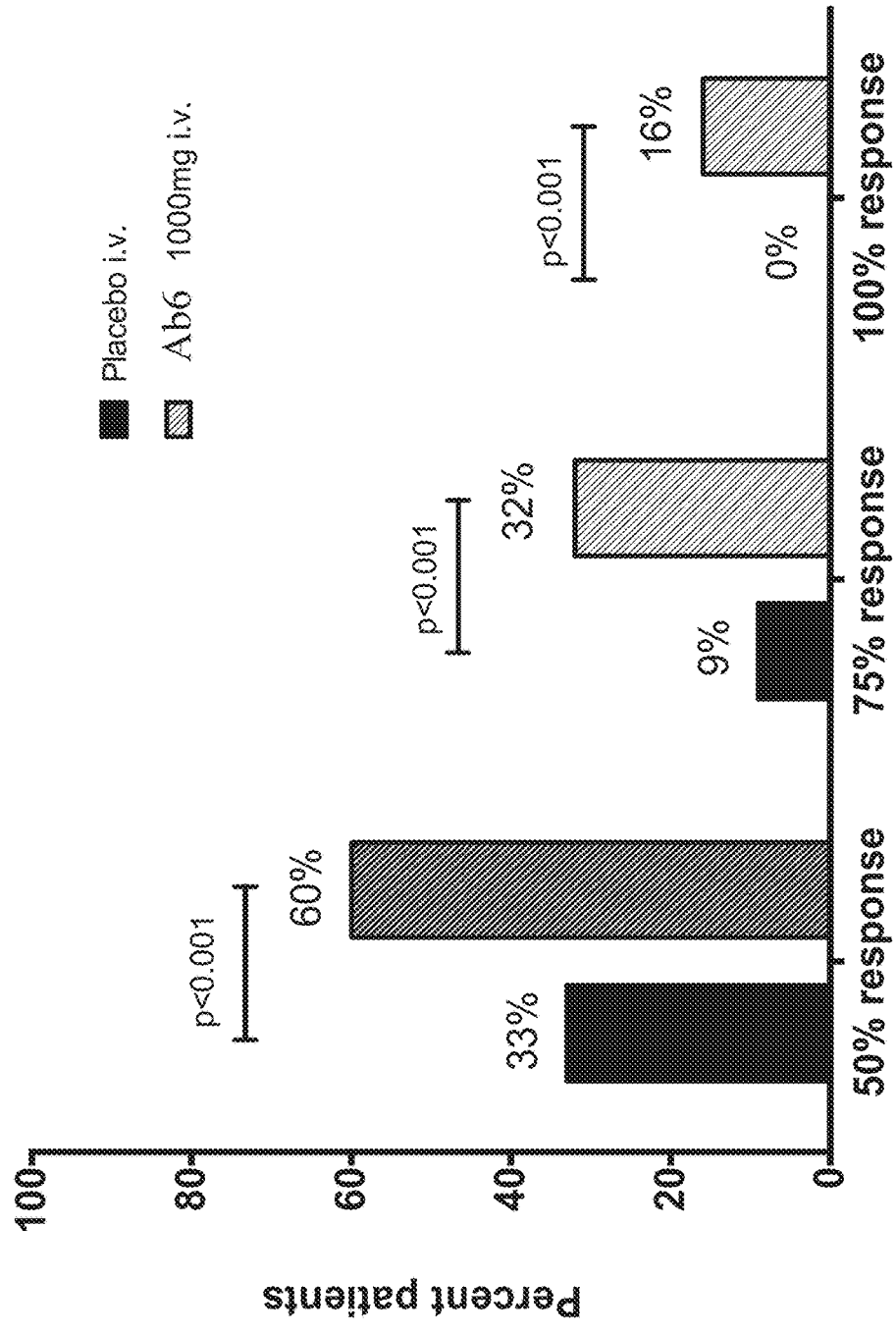
FIG. 13 shows the number of subjects in a human clinical trial described in Example 2 who were either treated with Ab6 (treatment group) or placebo groups who showed a 50, 75 or 100% reduction in migraines at each monitoring point throughout the period. The right bar in each group corresponds to patients receiving 1000 mg Ab6 and the left bar in each group corresponds to matched placebo controls. In each response rate group the patients receiving Ab6 had a significantly greater response rate than placebo-treated controls, with p values of 0.0155, 0.0034, and 0.0006 in each respective group as indicated. The administered antibody was produced in *P. pastoris* and consisted of the light chain polypeptide of SEQ ID NO: 221 and the heavy chain polypeptide of SEQ ID NO: 201.

Use of anti-CGRP antibodies for treatment of medication overuse headache is described herein. Additionally, anti-CGRP antibodies are demonstrated herein to be effective for treatment of chronic migraine. The treatment was shown to have a very rapid onset of efficacy, with relief from migraine observed on the first day following administration.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims. As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

As used herein, the term "medication overuse headache" refers to a headache that meets the criteria for that condition specified in ICHD-3 (Headache Classification Committee of the International Headache Society (IHS), The International Classification of Headache Disorders, 3rd edition, Cephalalgia. 2018 January; 38(1):1-211). The term includes subtypes of medication overuse headache, as defined in the ICHD-3, such as triptan-overuse headache, non-opioid analgesic overuse headache, opioid overuse headache, etc.

As used herein, the term "reduction in migraine prevalence" refers to a reduction (e.g., a stated percentage reduction, such as 50%) in the likelihood of a patient having a migraine in the stated period, such as the 18 hour, 20 hour, 24 hour, 28 hour, or 30 hour period, preferably the 24 hour period, after a first dosage of an antibody, or on the first day following the day of antibody administration (i.e., on the first full day following the day on which the antibody administration is completed). It is to be understood that a given patient may or may not have a migraine during that period, as the reduction in likelihood may be observable over a large number of patients irrespective of the outcome for an individual patient.

As used herein, the term "chronic migraine" refers to a condition wherein a patient exhibits, on average, at least 15 migraine days and/or headache per month. The term "episodic migraine" refers to a condition wherein a patient exhibits, on average, less than 15 headache and/or migraine days per month.

As used herein, the term "diagnosed with chronic migraine" refers to a patient meeting the clinical criteria for chronic migraine, whether or not a formal diagnosis of that patient was performed.

As used herein, the term "intravenously administering" refers to a mode of administration wherein a substance, e.g., an antibody, is introduced directly into the circulation of that patient, most typically into the venous circulation. The substance may be introduced in a carrier fluid, such as an aqueous solution, e.g., normal saline. The substance may be administered in a single formulation or in multiple formulations, as long as the administration is completed over a short period of time (e.g., within 1 day, preferably within 12 hours, more preferably within 6 hours, and most preferably within 1-2 hours).

As used herein, the term "the baseline number of migraine days" refers to the number of migraine days exhibited by a patient in a specified time period, e.g., prior to treatment. For example, the baseline number of migraine days may be determined over a period of one month, or longer, e.g., by recording each day whether or not a migraine occurred.

As used herein, the term "migraine days per month" refers to the number of days per month on which a patient has a migraine, i.e., at any time during that day, the patient has symptoms that meet the clinical definition of migraine. The number of migraine days per month may be determined by recording each day whether or not a migraine occurred.

As used herein, the term "headache days per month" refers to the number of days per month on which a patient has a headache, i.e., at any time during that day, the patient has symptoms that meet the clinical definition of a headache. The number of headache days per month may be determined by recording each day whether or not a headache occurred.

Calcitonin Gene Related Peptide (CGRP):

As used herein, CGRP encompasses not only the following *Homo sapiens* CGRP-alpha and *Homo sapiens* CGRP-beta amino acid sequences available from American Peptides (Sunnyvale Calif.) and Bachem (Torrance, Calif.):

CGRP-alpha:
ACDTATCVTHRLAGLLSRSGGVVKNNFVPTNVG-SKAF-NH$_2$ (SEQ ID NO: 561), wherein the terminal phenylalanine is amidated;

CGRP-beta:
ACNTATCVTHRLAGLLSRSGGMVKSNFVPTNVG-SKAF-NH$_2$ (SEQ ID NO: 562), wherein the terminal phenylalanine is amidated; but also any membrane-bound forms of these CGRP amino acid sequences, as well as mutants (mutiens), splice variants, isoforms, orthologs, homologues and variants of this sequence.

Expression Vector:

These DNA vectors contain elements that facilitate manipulation for the expression of a foreign protein within the target host cell, e.g., a yeast or mammalian cell such as *Pichia pastoris* or CHO cells. Conveniently, manipulation of sequences and production of DNA for transformation is first performed in a bacterial host, e.g. *E. coli*, and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Stearns, T. (2000). Methods in yeast genetics: a Cold Spring Harbor Laboratory course manual. Plainview, N.Y.: Cold Spring Harbor Laboratory Press.

Expression vectors for use in yeast or mammalian cells will generally further include yeast or mammalian specific sequences, including a selectable auxotrophic or drug marker for identifying transformed yeast strains or transformed mammalian cells. A drug marker may further be used to amplify copy number of the vector in the host cell.

The polypeptide coding sequence of interest is operably linked to transcriptional and translational regulatory sequences that provide for expression of the polypeptide in host cells, e.g., *Pichia pastoris* or CHO cells. These vector components may include, but are not limited to, one or more of the following: an enhancer element, a promoter, and a transcription termination sequence. Sequences for the secretion of the polypeptide may also be included, e.g. a signal sequence, and the like. A yeast or mammalian origin of replication is optional, as expression vectors are often integrated into the host cell genome. In one embodiment of the invention, the polypeptide of interest is operably linked, or fused, to sequences providing for optimized secretion of the polypeptide from yeast diploid cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (Gateway® Technology; Invitrogen, Carlsbad Calif.). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The promoter fragment may also serve as the site for homologous recombination and integration of the expression vector into the same site in the host genome; alternatively a selectable marker is used as the site for homologous recombination. Examples of suitable promoters from *Pichia* include the AOX1 and promoter (Cregg et al. (1989) *Mol. Cell. Biol.* 9:1316-1323); ICL1 promoter (Menendez et al. (2003) *Yeast* 20(13):1097-108); glyceraldehyde-3-phosphate dehydrogenase promoter (GAP) (Waterham et al. (1997) *Gene* 186(1):37-44); and FLD1 promoter (Shen et al. (1998) *Gene* 216(1):93-102). The GAP promoter is a strong constitutive promoter and the AOX and FLD1 promoters are inducible.

Other yeast promoters include ADH1, alcohol dehydrogenase II, GAL4, PHO3, PHO5, Pyk, and chimeric promoters derived therefrom. Additionally, non-yeast promoters may be used in the invention such as mammalian, insect, plant, reptile, amphibian, viral, and avian promoters. Most typically the promoter will comprise a mammalian promoter (potentially endogenous to the expressed genes) or will comprise a yeast or viral promoter that provides for efficient transcription in yeast systems.

Examples of mammalian promoters include cytomegalovirus (CMV) derived promoters, chicken 3-actin (CBM) derived promoters, adenomatous polyposis coli (APC) derived promoters, leucine-rich repeat containing G protein-coupled receptor 5 (LGR5) promoters, CAG promoter, Beta actin promoter, elongation factor-1 (EF1) promoter, early growth response 1 (EGR-1) promoter, eukaryotic initiation factor 4A (EIF4A1) promoter, simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter, among others. Combinations of two or more of the foregoing promoters may also be used. Further, inducible promoters may be used. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

The polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell. The *S. cerevisiae* alpha factor pre-pro signal has proven effective in the secretion of a variety of recombinant proteins from *P. pastoris*. Other yeast signal sequences include the alpha mating factor signal sequence, the invertase signal sequence, and signal sequences derived from other secreted yeast polypeptides. Additionally, these signal peptide sequences may be engineered to provide for enhanced secretion in diploid yeast expression systems. Secretion signals for use in mammalian as well as yeast cells include mammalian signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 preprotoxin sequence, PHA-E, FACE, human MCP-1, human serum albumin signal sequences, human Ig heavy chain, human Ig light chain, and the like. For example, see Hashimoto et. al. Protein Eng 11(2) 75 (1998); and Kobayashi et. al. Therapeutic Apheresis 2(4) 257 (1998).

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion and/or sequenced.

As an alternative to restriction and ligation of fragments, recombination methods based on att sites and recombination enzymes may be used to insert DNA sequences into a vector. Such methods are described, for example, by Landy (1989) *Ann. Rev. Biochem.* 58:913-949; and are known to those of skill in the art. Such methods utilize intermolecular DNA recombination that is mediated by a mixture of lambda and *E. coli*-encoded recombination proteins. Recombination occurs between specific attachment (att) sites on the interacting DNA molecules. For a description of att sites see Weisberg and Landy (1983) Site-Specific Recombination in Phage Lambda, in Lambda II, Weisberg, ed. (Cold Spring Harbor, N.Y.:Cold Spring Harbor Press), pp. 211-250. The DNA segments flanking the recombination sites are switched, such that after recombination, the att sites are hybrid sequences comprised of sequences donated by each parental vector. The recombination can occur between DNAs of any topology.

Att sites may be introduced into a sequence of interest by ligating the sequence of interest into an appropriate vector; generating a PCR product containing att B sites through the use of specific primers; generating a cDNA library cloned into an appropriate vector containing att sites; and the like.

Folding, as used herein, refers to the three-dimensional structure of polypeptides and proteins, where interactions between amino acid residues act to stabilize the structure. Proper folding is typically the arrangement of a polypeptide that results in optimal biological activity, and in the case of antibodies can conveniently be monitored by assays for activity, e.g. antigen binding.

The expression host may be further modified by the introduction of sequences encoding one or more enzymes that enhance folding and disulfide bond formation, i.e. foldases, chaperonins, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic PDI is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of BIP (immunoglobulin heavy chain binding protein); cyclophilin; and the like. In one embodiment of the invention, each of the haploid parental strains expresses a distinct folding enzyme, e.g. one strain may express BIP, and the other strain may express PDI or combinations thereof.

The terms "desired protein" or "desired antibody" are used interchangeably and refer generally to a parent antibody specific to a target, i.e., CGRP or a chimeric or humanized antibody or a binding portion thereof derived therefrom as described herein. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Numerous antibody coding sequences have been described; and others may be raised by methods well-known in the art. Examples thereof include chimeric antibodies, human antibodies and other non-human mammalian antibodies, humanized antibodies, single chain antibodies (such as scFvs), camelbodies, nanobodies, IgNAR (single-chain antibodies derived from sharks), small-modular immuno-pharmaceuticals (SMIPs), and antibody fragments such as Fabs, Fab', F(ab')2 and the like. See Streltsov V A, et al., Structure of a shark IgNAR antibody variable domain and modeling of an early-developmental isotype, Protein Sci. 2005 November; 14(11):2901-9. Epub 2005 Sep. 30; Greenberg A S, et al., A new antigen receptor gene family that undergoes rearrangement and extensive somatic diversification in sharks, Nature. 1995 Mar. 9; 374(6518):168-73;

Nuttall S D, et al., Isolation of the new antigen receptor from wobbegong sharks, and use as a scaffold for the display of protein loop libraries, Mol Immunol. 2001 August; 38(4): 313-26; Hamers-Casterman C, et al., Naturally occurring antibodies devoid of light chains, Nature. 1993 Jun. 3; 363(6428):446-8; Gill D S, et al., Biopharmaceutical drug discovery using novel protein scaffolds, Curr Opin Biotechnol. 2006 December; 17(6):653-8. Epub 2006 Oct. 19.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions ($V_L$ and $V_H$), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, and IgG4 constant regions.

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), immunoglobulin fragments comprising the epitope binding site (e.g., Fab', F(ab')$_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, SMIPs (small molecule immunopharmaceuticals), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties and the like, or specific binding moieties, such as streptavidin, avidin, or biotin, and the like may be utilized in the methods and compositions of the present invention. Examples of additional effector molecules are provided infra.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A "coding sequence" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. Promoter sequences typically contain additional sites for binding of regulatory molecules (e.g., transcription factors) which affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

Vectors are used to introduce a foreign substance, such as DNA, RNA or protein, into an organism or host cell. Typical vectors include recombinant viruses (for polynucleotides) and liposomes (for polypeptides). A "DNA vector" is a replicon, such as plasmid, phage or cosmid, to which another polynucleotide segment may be attached so as to bring about the replication of the attached segment. An "expression vector" is a DNA vector which contains regulatory sequences which will direct polypeptide synthesis by an appropriate host cell. This usually means a promoter to bind RNA polymerase and initiate transcription of mRNA, as well as ribosome binding sites and initiation signals to direct translation of the mRNA into a polypeptide(s). Incorporation of a polynucleotide sequence into an expression vector at the proper site and in correct reading frame, followed by transformation of an appropriate host cell by the vector, enables the production of a polypeptide encoded by said polynucleotide sequence.

"Amplification" of polynucleotide sequences is the in vitro production of multiple copies of a particular nucleic acid sequence. The amplified sequence is usually in the form of DNA. A variety of techniques for carrying out such amplification are described in a review article by Van Brunt (1990, Bio/Technol., 8(4):291-294). Polymerase chain reaction or PCR is a prototype of nucleic acid amplification, and use of PCR herein should be considered exemplary of other suitable amplification techniques.

The general structure of antibodies in vertebrates now is well understood (Edelman, G. M., Ann. N.Y. Acad. Sci., 190: 5 (1971)). Antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the $F_c$ region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to γ, α, δ, and ε (gamma, mu, alpha, delta, or epsilon) heavy chain constant regions). The constant region or class determines subsequent effector function of the antibody, including activation of complement (Kabat, E. A., Structural Concepts in Immunology and Immunochemistry, 2nd Ed., p. 413-436, Holt, Rinehart, Winston (1976)), and other cellular responses (Andrews, D. W., et al., Clinical Immunobiology, pp 1-18, W. B. Sanders (1980); Kohl, S., et al., Immunology, 48: 187 (1983)); while the variable region determines the antigen with which it will react. Light chains are classified as either κ (kappa) or λ (lambda). Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The expression "variable region" or "VR" refers to the domains within each pair of light and heavy chains in an antibody that are involved directly in binding the antibody to the antigen. Each heavy chain has at one end a variable domain (VH) followed by a number of constant domains. Each light chain has a variable domain (VL) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions (CDRs) found in the variable regions of light or heavy chains of an antibody (See Kabat, E. A. et al., Sequences of Proteins of Immunological Interest, National Institutes of Health, Bethesda, Md., (1987)). These expressions include the hypervariable regions as defined by Kabat et al. ("Sequences of Proteins of Immunological Interest," Kabat E., et al., US Dept. of Health and Human Services, 1983) or the hypervariable loops in 3-dimensional structures of antibodies (Chothia and Lesk, *J Mol. Biol.* 196 901-917 (1987)). The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction (Kashmiri, S., Methods, 36:25-34 (2005)). In the present invention when specific antibody amino acid or nucleic acid residues are referenced by number this generally refers to its position within a specified amino acid or nucleic acid sequence (i.e., particular sequence identifier) and/or in accordance with Kabat et al numbering.

The expressions "framework region" or "FR" refer to one or more of the framework regions within the variable regions of the light and heavy chains of an antibody (See Kabat, E. A. et al., Sequences of Proteins of Immunological Interest, National Institutes of Health, Bethesda, Md., (1987)). These expressions include those amino acid sequence regions interposed between the CDRs within the variable regions of the light and heavy chains of an antibody.

"Cmax" refers to the maximum (or peak) concentration that an antibody or other compound achieves in tested area (e.g., in the serum or another compartment such as cerebrospinal fluid) after the drug has been administered. For example, serum Cmax may be measured from serum, e.g., prepared by collecting a blood sample, allowing it to clot and separating solid components by centrifugation or other means to yield serum (blood containing neither blood cells nor clotting factors), and then detecting the concentration of the analyte in the serum by ELISA or other means known in the art.

"AUC" refers to the area under the concentration-time curve which is expressed in units of mg/mL*hr (or equivalently mg*hr/ml) unless otherwise specified. "$AUC_{0-t}$" refers to the area under the concentration-time curve from time=0 to last quantifiable concentration. "AUC$_{0-inf}$" refers to the area under the concentration-time curve from time=0 extrapolated to infinity.

"I$_{max}$" refers to the maximal pharmacodynamic response elicited by an anti-CGRP antibody dosage, preferably a dosage of 350 mg or more, more typically at least 750 or 1000 mg, as compared to the response elicited by a lower anti-CGRP antibody doses, e.g., wherein such response may be detected by the inhibition of vasodilation after topical application of capsaicin.

Anti-CGRP Antibodies and Binding Fragments Thereof Having Binding Specificity for CGRP The invention specifically includes the use of specific anti-CGRP antibodies and antibody fragments referred to herein as Ab1-Ab14 which comprise or consist of the CDR, VL, VH, CL, CH polypeptides sequences identified in FIGS. 1A-12. The polypeptides comprised in an especially preferred anti-CGRP antibody, Ab6 is further described below.

Antibody Ab6

In a preferred exemplary embodiment, the invention includes humanized antibodies having binding specificity to CGRP and possessing a variable light chain sequence comprising the sequence set forth below:

(SEQ ID NO: 222)
QVLTQSPSSLSASVGDRVTINCQASQSVYHNTYLAWYQQKPGKVPKQLIY

DASTLASGVPSRFSGSGSGTDFTLTISSLQPEDVATYYCLGSYDCTNGDC

FVFGGGTKVEIKR.

The invention also includes humanized antibodies having binding specificity to CGRP and possessing a light chain sequence comprising the sequence set forth below:

(SEQ ID NO: 221)
QVLTQSPSSLSASVGDRVTINCQASQSVYHNTYLAWYQQKPGKVPKQLIY

DASTLASGVPSRFSGSGSGTDFTLTISSLQPEDVATYYCLGSYDCTNGDC

FVFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

The invention further includes humanized antibodies having binding specificity to CGRP and possessing a variable heavy chain sequence comprising the sequence set forth below: EVQLVESGGGLVQPGGSLRLSCAVSGIDLSGYYMNWVRQAPGKGLEWVGVIGINGATYYASW AKGRFTISRDNSKTTVYLQMNSLRAEDTAVYFCARGDIWGQGTLVTVSS (SEQ ID NO: 202).

The invention also includes humanized antibodies having binding specificity to CGRP and possessing a heavy chain sequence comprising the sequence set forth below:

(SEQ ID NO: 201)
EVQLVESGGGLVQPGGSLRLSCAVSGIDLSGYYMNWVRQAPGKGLEWVGV

IGINGATYYASWAKGRFTISRDNSKTTVYLQMNSLRAEDTAVYFCARGDI

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDARVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPGK.

Alternatively, the heavy chain of Ab6 may lack the C-terminal lysine of SEQ ID NO: 201, i.e., a heavy chain sequence comprising the sequence set forth below:

(SEQ ID NO: 566)
EVQLVESGGGLVQPGGSLRLSCAVSGIDLSGYYMNWVRQAPGKGLEWVGV

IGINGATYYASWAKGRFTISRDNSKTTVYLQMNSLRAEDTAVYFCARGDI

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDARVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPG.

The invention further contemplates antibodies comprising one or more of the polypeptide sequences of SEQ ID NO: 224; SEQ ID NO: 226; and SEQ ID NO: 228 which correspond to the complementarity-determining regions (CDRs, or hypervariable regions) of the variable light chain sequence of SEQ ID NO: 222 or the light chain sequence of SEQ ID NO: 221, and/or one or more of the polypeptide sequences of SEQ ID NO: 204; SEQ ID NO: 206; and SEQ ID NO: 208 which correspond to the complementarity-determining regions (CDRs, or hypervariable regions) of the variable heavy chain sequence of SEQ ID NO: 202 or the heavy chain sequence of SEQ ID NO: 201 or SEQ ID NO: 566, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to CGRP. In one embodiment of the invention, antibody fragments of the invention comprise, or alternatively consist of, the polypeptide sequence of SEQ ID NO: 222 or SEQ ID NO: 221. In another embodiment of the invention, antibody fragments of the invention comprise, or alternatively consist of, the polypeptide sequence of SEQ ID NO: 202 or SEQ ID NO: 201 or SEQ ID NO: 566.

In a further embodiment of the invention, fragments of the antibody having binding specificity to CGRP comprise, or alternatively consist of, one or more of the polypeptide sequences of SEQ ID NO: 224; SEQ ID NO: 226; and SEQ ID NO: 228 which correspond to the complementarity-determining regions (CDRs, or hypervariable regions) of the variable light chain sequence of SEQ ID NO: 222 or the light chain sequence of SEQ ID NO: 221.

In a further embodiment of the invention, fragments of the antibody having binding specificity to CGRP comprise, or alternatively consist of, one or more of the polypeptide sequences of SEQ ID NO: 204; SEQ ID NO: 206; and SEQ ID NO: 208 which correspond to the complementarity-determining regions (CDRs, or hypervariable regions) of the variable heavy chain sequence of SEQ ID NO: 202 or the heavy chain sequence of SEQ ID NO: 201 or SEQ ID NO: 566.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 222; the variable heavy chain region of SEQ ID NO: 202; the complementarity-determining regions (SEQ ID NO: 224; SEQ ID NO: 226; and SEQ ID NO: 228) of the variable light chain region of SEQ ID NO: 222; and the complementarity-determining regions (SEQ ID NO: 204; SEQ ID NO: 206; and SEQ ID NO: 208) of the variable heavy chain region of SEQ ID NO: 202.

In a particularly preferred embodiment of the invention, the humanized anti-CGRP antibody is Ab6, comprising, or alternatively consisting of, SEQ ID NO: 221 and SEQ ID NO: 201 or SEQ ID NO: 566, and having at least one of the biological activities set forth herein.

In a further particularly preferred embodiment of the invention, antibody fragments comprise, or alternatively consist of, Fab (fragment antigen binding) fragments having binding specificity for CGRP. With respect to antibody Ab6, the Fab fragment includes the variable light chain sequence of SEQ ID NO: 222 and the variable heavy chain sequence of SEQ ID NO: 202. This embodiment of the invention further contemplates additions, deletions, and variants of SEQ ID NO: 222 and/or SEQ ID NO: 202 in said Fab while retaining binding specificity for CGRP.

In another particularly preferred embodiment of the invention, said anti-CGRP antibody may comprise the antibody expression product isolated from recombinant cells which express nucleic acid sequences encoding the variable light chain polypeptide of SEQ ID NO: 222 and the variable heavy chain polypeptide of SEQ ID NO: 202, which polypeptides optionally are respectively linked to human light and heavy constant region polypeptides, e.g., human IgG1, IgG2, IgG3 or IgG4 constant regions, which constant regions optionally may be modified to alter glycosylation or proteolysis, wherein said recombinant cells optionally comprise yeast or mammalian cells, e.g., *Pichia pastoris* or CHO cells.

In another particularly preferred embodiment of the invention, said anti-CGRP antibody may comprise the antibody expression product isolated from recombinant cells which express nucleic acid sequences encoding the light chain of SEQ ID NO: 221 and the heavy chain polypeptide of SEQ ID NO: 201 or SEQ ID NO: 566, wherein said recombinant cells optionally comprise yeast or mammalian cells, e.g., *Pichia pastoris* or CHO cells, wherein the constant regions thereof optionally may be modified to alter glycosylation or proteolysis or other effector functions.

In another particularly preferred embodiment of the invention, any of the aforementioned anti-CGRP antibodies or antibody fragments may be optionally comprised in a formulation as disclosed herein, e.g., comprising histidine (L-histidine), sorbitol, polysorbate 80, such as, per 1 mL volume, about 100 mg anti-CGRP antibody, about 3.1 mg L-Histidine, about 40.5 mg Sorbitol, and about 0.15 mg Polysorbate 80, having a pH of about 5.8.

In one embodiment of the invention described herein (infra), Fab fragments may be produced by enzymatic digestion (e.g., papain) of Ab6. In another embodiment of the invention, anti-CGRP antibodies such as Ab6 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

In another embodiment, antibody fragments may be present in one or more of the following non-limiting forms: Fab, Fab', F(ab')₂, Fv and single chain Fv antibody forms. In a preferred embodiment, the anti-CGRP antibodies described herein further comprises the kappa constant light chain sequence comprising the sequence set forth below:

(SEQ ID NO: 563)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.

In another preferred embodiment, the anti-CGRP antibodies described herein further comprises the gamma-1 constant heavy chain polypeptide sequence comprising the sequence set forth below or the same sequence lacking the carboxy terminal lysine residue (SEQ ID NO: 564 and SEQ ID NO: 565, respectively):

(SEQ ID NO: 564)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

(SEQ ID NO: 565)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPG.

For clarity, any antibody disclosed herein is intended to include any variant of the disclosed constant region variant sequences, e.g., Ab6 may comprise the constant region of SEQ ID NO: 564 containing the C-terminal lysine or may comprise the constant region of SEQ ID NO: 565 lacking the C-terminal lysine. Thus, every disclosure herein of the heavy chain of SEQ ID NO: 201 also includes a variant lacking the C-terminal lysine residue thereof, i.e., having the heavy chain variable region sequence of Ab6 (SEQ ID NO: 202) and the constant region sequence of SEQ ID NO: 565. For example, the sequence encoding an antibody comprising a C-terminal lysine in the heavy chain may, when expressed in cell lines such as CHO cells, produce an antibody lacking said C-terminal lysine due to proteolysis, or a mixture of heavy chains containing or lacking said C-terminal lysine.

In another embodiment, the invention contemplates use of an isolated anti-CGRP antibody comprising a VH polypeptide sequence selected from: SEQ ID NO: 2, SEQ ID NO: 42, SEQ ID NO: 82, SEQ ID NO: 122, SEQ ID NO: 162, SEQ ID NO: 202, SEQ ID NO: 242, SEQ ID NO: 282, SEQ ID NO: 322, SEQ ID NO: 362, SEQ ID NO: 402, SEQ ID NO: 442, SEQ ID NO: 482, or SEQ ID NO: 522, or a variant thereof; and further comprising a $V_L$ polypeptide sequence selected from: SEQ ID NO: 22, SEQ ID NO: 62, SEQ ID NO: 102, SEQ ID NO: 142, SEQ ID NO: 182, SEQ ID NO: 222, SEQ ID NO: 262, SEQ ID NO: 302, SEQ ID NO: 342, SEQ ID NO: 382, SEQ ID NO: 422, SEQ ID NO: 462, SEQ ID NO: 502, or SEQ ID NO: 542, or a variant thereof, wherein one or more of the framework residues (FR residues) in said $V_{H\,or}V_L$ polypeptide has been substituted with another amino acid residue resulting in an anti-CGRP antibody that specifically binds CGRP. The invention contemplates humanized and chimeric forms of these antibodies. The chimeric antibodies may include an Fc derived from IgG1, IgG2, IgG3, or IgG4 constant regions.

In one embodiment of the invention, the antibodies or $V_H$ or $V_L$ polypeptides originate or are selected from one or more rabbit B cell populations prior to initiation of the humanization process referenced herein.

In another embodiment of the invention, the anti-CGRP antibodies and fragments thereof do not have binding specificity for CGRP-R. In a further embodiment of the invention, the anti-CGRP antibodies and fragments thereof inhibit the association of CGRP with CGRP-R. In another embodiment of the invention, the anti-CGRP antibodies and fragments thereof inhibit the association of CGRP with CGRP-R and/or additional proteins and/or multimers thereof, and/or antagonizes the biological effects thereof.

As stated herein, antibodies and fragments thereof may be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Antibodies or fragments thereof may also be chemically modified to provide additional advantages such as increased solubility, stability and circulating time (in vivo half-life) of the polypeptide, or decreased immunogenicity (See U.S. Pat. No. 4,179,337). The chemical moieties for derivatization may be selected from water soluble polymers such as polyethylene glycol, ethylene glycol/propylene glycol copolymers, carboxymethylcellulose, dextran, polyvinyl alcohol and the like. The antibodies and fragments thereof may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

There are a number of attachment methods available to those skilled in the art, See e.g., EP 0 401 384, herein incorporated by reference (coupling PEG to G-CSF), See also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to polypeptides via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) or to more than one type of amino acid residue (e.g., lysine, histidine, aspartic acid, glutamic acid, cysteine and combinations thereof).

Alternatively, antibodies or fragments thereof may have increased in vivo half-lives via fusion with albumin (including but not limited to recombinant human serum albumin or fragments or variants thereof (See, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)) or other circulating blood proteins such as transferrin or ferritin. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. Polynucleotides encoding fusion proteins of the invention are also encompassed by the invention.

Regarding detectable moieties, further exemplary enzymes include, but are not limited to, horseradish peroxidase, acetylcholinesterase, alkaline phosphatase, beta-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent moieties include, but are not limited to, luminol. Further exemplary bioluminescent materials include, but are not limited to, luciferin and aequorin. Further exemplary radioactive materials include, but are not limited to, Iodine 125 ($^{125}$I), Carbon 14 ($^{14}$C), Sulfur 35 ($^{35}$S), Tritium ($^{3}$H) and Phosphorus 32 ($^{32}$P).

Regarding functional moieties, exemplary cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the *vinca* alkaloids, vincristine and vinblastine. Other cytotoxic agents include paclitaxel (taxol), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine and bleomycin. Toxic enzymes from plants and bacteria such as ricin, diphtheria toxin and *Pseudomonas* toxin may be conjugated to the humanized or chimeric antibodies, or binding fragments thereof, to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the antibody, or binding fragments thereof, with or without the use of a complex-forming agent. Such radionuclides include beta-emitters such as Phosphorus-32 ($^{32}$P), Scandium-47 ($^{47}$Sc), Copper-67 ($^{67}$Cu), Gallium-67 ($^{67}$Ga), Yttrium-88 ($^{88}$Y), Yttrium-90 ($^{90}$Y), Iodine-125 ($^{125}$I), Iodine-131 ($^{131}$I), Samarium-153 ($^{153}$Sm), Lutetium-177 ($^{177}$Lu), Rhenium-186 ($^{186}$Re) or Rhenium-188 ($^{188}$Re), and alpha-emitters such as Astatine-211 ($^{211}$At), Lead-212 ($^{212}$Pb), Bismuth-212 ($^{212}$Bi) or -213 ($^{213}$Bi) or Actinium-225 ($^{225}$Ac).

Methods are known in the art for conjugating an antibody or binding fragment thereof to a detectable moiety and the like, such as for example those methods described by Hunter et al, Nature 144:945 (1962); David et al, Biochemistry 13:1014 (1974); Pain et al, J. Immunol. Meth. 40:219 (1981); and Nygren, J., Histochem. and Cytochem. 30:407 (1982).

Embodiments described herein further include variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

In another embodiment, the invention contemplates polypeptide sequences having at least 90% or greater sequence homology to any one or more of the polypeptide sequences of antibody fragments, variable regions and CDRs set forth herein. More preferably, the invention contemplates polypeptide sequences having at least 95% or greater sequence homology, even more preferably at least 98% or greater sequence homology, and still more preferably at least 99% or greater sequence homology to any one or more of the polypeptide sequences of antibody fragments, variable regions and CDRs set forth herein. Methods for determining homology between nucleic acid and amino acid sequences are well known to those of ordinary skill in the art.

In another embodiment, the invention further contemplates the above-recited polypeptide homologs of the antibody fragments, variable regions and CDRs set forth herein further having anti-CGRP activity. Non-limiting examples of anti-CGRP activity are set forth herein.

The present invention also contemplates anti-CGRP antibodies comprising any of the polypeptide or polynucleotide sequences described herein substituted for any of the other polynucleotide sequences described herein. For example, without limitation thereto, the present invention contemplates antibodies comprising the combination of any of the variable light chain and variable heavy chain sequences described herein, and further contemplates antibodies resulting from substitution of any of the CDR sequences described herein for any of the other CDR sequences described herein.

Additional Exemplary Embodiments of the Invention

In another embodiment, the invention contemplates treatment methods using one or more anti-human CGRP antibodies or antibody fragments thereof which specifically bind to the same overlapping linear or conformational epitope(s) and/or competes for binding to the same overlapping linear or conformational epitope(s) on an intact human CGRP polypeptide or fragment thereof as an anti-human CGRP antibody selected from Ab1, Ab2, Ab3, Ab4, Ab5, Ab6, Ab7, Ab8, Ab9, Ab10, Ab11, Ab12, Ab13, or Ab14. In a preferred embodiment, the anti-human CGRP antibody or fragment thereof specifically binds to the same overlapping linear or conformational epitope(s) and/or competes for binding to the same overlapping linear or conformational epitope(s) on an intact human CGRP polypeptide or a fragment thereof as Ab3, Ab6, Ab13, or Ab14.

A preferred embodiment of the invention is directed to treatment methods using chimeric or humanized antibodies and fragments thereof (including Fab fragments) having binding specificity for CGRP and inhibiting biological activities mediated by the binding of CGRP to the CGRP receptor. In a particularly preferred embodiment of the invention, the chimeric or humanized anti-CGRP antibodies are selected from Ab3, Ab6, Ab13, or Ab14.

In another embodiment of the invention, the anti-human CGRP antibody used in the described treatment methods is an antibody which specifically binds to the same overlapping linear or conformational epitopes on an intact CGRP polypeptide or fragment thereof that is (are) specifically bound by Ab3, Ab6, Ab13, or Ab14 as ascertained by epitopic mapping using overlapping linear peptide fragments which span the full length of the native human CGRP polypeptide.

The invention is also directed to treatment methods using an anti-CGRP antibody that binds with the same CGRP epitope and/or competes with an anti-CGRP antibody for binding to CGRP as an antibody or antibody fragment disclosed herein, including but not limited to an anti-CGRP antibody selected from Ab1, Ab2, Ab3, Ab4, Ab5, Ab6, Ab7, Ab8, Ab9, Ab10, Ab11, Ab12, Ab13, or Ab14.

In another embodiment, the invention is also directed to treatment methods using an isolated anti-CGRP antibody or antibody fragment comprising one or more of the CDRs contained in the VH polypeptide sequences selected from: 3, 13, 23, 33, 43, 53, 63, 73, 83, 93, 103, 113, 123, or 133, or a variant thereof, and/or one or more of the CDRs contained in the VL polypeptide sequences selected from: 1, 11, 21, 31, 41, 51, 61, 71, 81, 91, 101, 111, 121, or 131, or a variant thereof.

In one embodiment of the invention, the anti-human CGRP antibody discussed in the two prior paragraphs comprises at least 2 complementarity determining regions (CDRs) in each the variable light and the variable heavy regions which are identical to those contained in an anti-human CGRP antibody selected from Ab1, Ab2, Ab3, Ab4, Ab5, Ab6, Ab7, Ab8, Ab9, Ab10, Ab11, Ab12, Ab13, or Ab14.

In a preferred embodiment, the anti-human CGRP antibody used in the described treatment methods comprises at least 2 complementarity determining regions (CDRs) in each the variable light and the variable heavy regions which are identical to those contained in Ab3 or Ab6. In another embodiment, all of the CDRs of the anti-human CGRP antibody discussed above are identical to the CDRs contained in an anti-human CGRP antibody selected from Ab1, Ab2, Ab3, Ab4, Ab5, Ab6, Ab7, Ab8, Ab9, Ab10, Ab11, Ab12, Ab13, or Ab14. In a preferred embodiment of the invention, all of the CDRs of the anti-human CGRP antibody discussed above are identical to the CDRs contained in an anti-human CGRP antibody selected from Ab3 or Ab6.

The invention further contemplates treatment methods wherein the one or more anti-human CGRP antibodies discussed above are aglycosylated or if glycosylated are only mannosylated; that contain an Fc region that has been modified to alter effector function, half-life, proteolysis, and/or glycosylation; are human, humanized, single chain or chimeric; and are a humanized antibody derived from a rabbit (parent) anti-human CGRP antibody. An exemplary mutation which impairs glycosylation comprises the mutation of the Asn residue at position 297 of an IgG heavy chain constant region such as IgG1 to another amino acid, such as Ala as described in U.S. Pat. No. 5,624,821, which is incorporated by reference in its entirety.

The invention further contemplates one or more anti-human CGRP antibodies wherein the framework regions (FRs) in the variable light region and the variable heavy regions of said antibody respectively are human FRs which are unmodified or which have been modified by the substitution of one or more human FR residues in the variable light or heavy chain region with the corresponding FR residues of the parent rabbit antibody, and wherein said human FRs have been derived from human variable heavy and light chain antibody sequences which have been selected from a library of human germline antibody sequences based on their high level of homology to the corresponding rabbit variable heavy or light chain regions relative to other human germline antibody sequences contained in the library.

The invention also contemplates a method of treating or preventing medication overuse headache, e.g., associated with the overuse of anti-migraine drugs and/or associated with triptan and/or ergot and/or analgesic overuse, comprising administering to a patient exhibiting medication overuse headache or at risk of developing medication overuse headache a therapeutically effective amount of at least one anti-human CGRP antibody or fragment described herein. The invention also contemplates that the treatment method may involve the administration of two or more anti-CGRP antibodies or fragments thereof and disclosed herein. If more than one antibody is administered to the patient, the multiple antibodies may be administered simultaneously or concurrently, or may be staggered in their administration. The anti-CGRP activity of the anti-CGRP antibodies of the present invention, and fragments thereof having binding specificity to CGRP, may also be described by their strength of binding or their affinity for CGRP. In one embodiment of the invention, the anti-CGRP antibodies of the present invention, and fragments thereof having binding specificity to CGRP, bind to CGRP with a dissociation constant ($K_D$) of less than or equal to $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, or $10^{-13}$ M. Preferably, the anti-CGRP antibodies and fragments thereof bind CGRP with a dissociation constant of less than or equal to $10^{-11}$ M, $5 \times 10^{-12}$ M, or $10^{-12}$ M. In another embodiment of the invention, the anti-CGRP antibodies of the present invention, and fragments thereof having binding specificity to CGRP, bind to a linear or conformational CGRP epitope.

In another embodiment of the invention, the anti-CGRP activity of the anti-CGRP antibodies of the present invention, and fragments thereof having binding specificity to CGRP, bind to CGRP with an off-rate of less than or equal to $10^{-4}$ $S^{-1}$, $5 \times 10^{-5}$ $S^{-1}$, $10^{-5}$ $S^{-1}$, $5 \times 10^{-6}$ $S^{-1}$, $10^{-6}$ $S^{-1}$, $5 \times 10^{-7}$ $S^{-1}$, or $10^{-7}$ $S^{-1}$.

In a further embodiment of the invention, the anti-CGRP activity of the anti-CGRP antibodies of the present invention, and fragments thereof having binding specificity to CGRP, exhibit anti-CGRP activity by preventing, ameliorating or reducing the symptoms of, or alternatively treating, diseases and disorders associated with CGRP. Non-limiting examples of diseases and disorders associated with CGRP are set forth herein and include headache and migraine disorders.

Polynucleotides Encoding Anti-CGRP Antibody Polypeptides

As aforementioned the invention specifically includes the use of specific anti-CGRP antibodies and antibody fragments referred to herein as Ab1-Ab14 which comprise or consist of the CDR, VL, VH, CL, and CH polypeptides having the sequences identified in FIGS. 1A-12. The nucleic acid sequences encoding the foregoing VL, VH, CL, and CH polypeptides comprised in Ab1-Ab14 are also comprised in FIGS. 1A-12. The nucleic acid sequences which encode the CDR, VL, VH, CL, and CH polypeptides of an especially preferred anti-CGRP antibody, Ab6, are further described below.

Antibody Ab6

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 222:

(SEQ ID NO: 232)
CAAGTGCTGacccagtctccatcctccctgtctgcatctgtaggagacag agtcaccatcAATtgcCAGGCCAGTCAGAGTGTTTATCATAACACCTACC TGGCCtggtatcagcagaaaccagggaaagttcctaagCAActgatctat GATGCATCCACTCTGGCATCTggggtcccatctcgtacagtggcagtgga tctgggacagatttcactctcaccatcagcagcctgcagcctgaagatgt tgcaacttattactgtCTGGGCAGTTATGATTGTACTAATGGTGATTGTT TTGTTttcggcggaggaaccaaggtggaaatcaaacgt.

In one embodiment of the invention, polynucleotides of the invention comprise, or alternatively consist of, the following polynucleotide sequence encoding the light chain polypeptide sequence of SEQ ID NO: 221:

(SEQ ID NO: 231)
CAAGTGCTGacccagtctccatcctccctgtctgcatctgtaggagacag agtcaccatcAATtgcCAGGCCAGTCAGAGTGTTTATCATAACACCTACC TGGCCtggtatcagcagaaaccagggaaagttcctaagCAActgatctat GATGCATCCACTCTGGCATCTggggtcccatctcgtttcagtggcagtgg atctgggacagatttcactctcaccatcagcagcctgcagcctgaagatg ttgcaacttattactgtCTGGGCAGTTATGATTGTACTAATGGTGATTGT TTTGTTttcggcggaggaaccaaggtggaaatcaaacgtACGGTGGCTGC

ACCATCGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGTTAG.

In another embodiment of the invention, polynucleotides of the invention comprise, or alternatively consist of, the following polynucleotide sequence encoding the variable heavy chain polypeptide sequence of SEQ ID NO: 202:

(SEQ ID NO: 212)
gaggtgcagctTgtggagtctgggggaggcttggtccagcctggggggtc cctgagactctcctgtgcaGTCtctggaATCGACCTCagtGGCTACTACA TGAACtgggtccgtcaggctccagggaaggggctggagtgggtcGGAGTC ATTGGTATTAATGGTGCCACATACTACGCGAGCTGGGCGAAAGGCcgatt caccatctccagagacaattccaagACCACGGTGtatcttcaaatgaaca gcctgagagctgaggacactgctgtgtatTTCtgtGCTAGAGGGGACATC tggggccaagggaccctcgtcaccgtcTCGAGC.

In one embodiment of the invention, polynucleotides of the invention comprise, or alternatively consist of, the following polynucleotide sequence encoding the heavy chain polypeptide sequence of SEQ ID NO: 201:

(SEQ ID NO: 211)
gaggtgcagctTgtggagtctgggggaggcttggtccagcctggggggtc cctgagactctcctgtgcaGTCtctggaATCGACCTCagtGGCTACTACA TGAACtgggtccgtcaggctccagggaaggggctggagtgggtcGGAGTC ATTGGTATTAATGGTGCCACATACTACGCGAGCTGGGCGAAAGGCcgatt caccatctccagagacaattccaagACCACGGTGtatcttcaaatgaaca gcctgagagctgaggacactgctgtgtatTTCtgtGCTAGAGGGGACATC tggggccaagggaccctcgtcaccgtcTCGAGCGCCTCCACCAAGGGCCC ATCGGTCTTCCCCCTGGCAccCTCCTCCaAGAGCACCTCTGGGGGCACAG

CGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCT

CCAGCAGCTTGGGCACCCAGACCTACATCTGCAACGTGAATCACAAGCCC

AGCAACACCAAGGTGGACGCGAGAGTTGAGCCCAAATCTTGTGACAAAAC

TCACACATGCCCACCGTGCCCAGCACCTGAACTCCTGGGGGGACCGTCAG

TCTTCCTCTTCCCCCCAAAACCCAAGGACACCCTCATGaTCTCCCgGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACGCCAGCACGTACCGTGTGGTCAGCGTCCTC

ACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAG

GAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTAAATGA.

In one embodiment of the invention, polynucleotides of the invention comprise, or alternatively consist of, the following polynucleotide sequence encoding the heavy chain polypeptide sequence of SEQ ID NO: 566:

(SEQ ID NO: 567)
gaggtgcagctTgtggagtctgggggaggcttggtccagcctggggggtc cctgagactctcctgtgcaGTCtctggaATCGACCTCagtGGCTACTACA TGAACtgggtccgtcaggctccagggaaggggctggagtgggtcGGAGTC ATTGGTATTAATGGTGCCACATACTACGCGAGCTGGGCGAAAGGCcgatt caccatctccagagacaattccaagACCACGGTGtatcttcaaatgaaca gcctgagagctgaggacactgctgtgtatTTCtgtGCTAGAGGGGACATC tggggccaagggaccctcgtcaccgtcTCGAGCGCCTCCACCAAGGGCCC ATCGGTCTTCCCCCTGGCAccCTCCTCCaAGAGCACCTCTGGGGGCACAG

CGGCCCTGGGCTGCCTGGTCAAGGACTACTTCCCCGAACCGGTGACGGTG

```
-continued
TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCT

CCAGCAGCTTGGGCACCCAGACCTACATCTGCAACGTGAATCACAAGCCC

AGCAACACCAAGGTGGACGCGAGAGTTGAGCCCAAATCTTGTGACAAAAC

TCACACATGCCCACCGTGCCCAGCACCTGAACTCCTGGGGGACCGTCAG

TCTTCCTCTTCCCCCCAAAACCCAAGGACACCCTCATGaTCTCCCgGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACGCCAGCACGTACCGTGTGGTCAGCGTCCTC

ACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAG

GAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTTGA.
```

In a further embodiment of the invention, polynucleotides encoding antibody fragments having binding specificity to CGRP comprise, or alternatively consist of, one or more of the polynucleotide sequences of SEQ ID NO: 234; SEQ ID NO: 236; and SEQ ID NO: 238 which correspond to polynucleotides encoding the complementarity-determining regions (CDRs, or hypervariable regions) of the light chain variable sequence of SEQ ID NO: 222 or the light chain sequence of SEQ ID NO: 221.

In a further embodiment of the invention, polynucleotides encoding antibody fragments having binding specificity to CGRP comprise, or alternatively consist of, one or more of the polynucleotide sequences of SEQ ID NO: 214; SEQ ID NO: 216; and SEQ ID NO: 218 which correspond to polynucleotides encoding the complementarity-determining regions (CDRs, or hypervariable regions) of the heavy chain variable sequence of SEQ ID NO: 202 or the heavy chain sequence of SEQ ID NO: 201 or SEQ ID NO: 566.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 232 encoding the light chain variable sequence of SEQ ID NO: 222; the polynucleotide SEQ ID NO: 231 encoding the light chain sequence of SEQ ID NO: 221; the polynucleotide SEQ ID NO: 212 encoding the heavy chain variable sequence of SEQ ID NO: 202; the polynucleotide SEQ ID NO: 211 encoding the heavy chain sequence of SEQ ID NO: 201; the polynucleotide SEQ ID NO: 567 encoding the heavy chain sequence of SEQ ID NO: 566; polynucleotides encoding the complementarity-determining regions (SEQ ID NO: 234; SEQ ID NO: 236; and SEQ ID NO: 238) of the light chain variable sequence of SEQ ID NO: 222 or the light chain sequence of SEQ ID NO: 221; and polynucleotides encoding the complementarity-determining regions (SEQ ID NO: 214; SEQ ID NO: 216; and SEQ ID NO: 218) of the heavy chain variable sequence of SEQ ID NO: 202 or the heavy chain sequence of SEQ ID NO: 201 or SEQ ID NO: 566.

In a preferred embodiment of the invention, polynucleotides of the invention comprise, or alternatively consist of, polynucleotides encoding Fab (fragment antigen binding) fragments having binding specificity for CGRP. With respect to antibody Ab6, the polynucleotides encoding the full length Ab6 antibody comprise, or alternatively consist of, the polynucleotide SEQ ID NO: 231 encoding the light chain sequence of SEQ ID NO: 221 and the polynucleotide SEQ ID NO: 211 encoding the heavy chain sequence of SEQ ID NO: 201 or the polynucleotide SEQ ID NO: 567 encoding the heavy chain sequence of SEQ ID NO: 566.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab6 following expression of the full-length polynucleotides in a suitable host. In another embodiment of the invention, anti-CGRP antibodies such as Ab6 or Fab fragments thereof may be produced via expression of Ab6 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

In one embodiment, the invention is directed to an isolated polynucleotide comprising a polynucleotide encoding an anti-CGRP VH antibody amino acid sequence selected from SEQ ID NO: 2, SEQ ID NO: 42, SEQ ID NO: 82, SEQ ID NO: 122, SEQ ID NO: 162, SEQ ID NO: 202, SEQ ID NO: 242, SEQ ID NO: 282, SEQ ID NO: 322, SEQ ID NO: 362, SEQ ID NO: 402, SEQ ID NO: 442, SEQ ID NO: 482, or SEQ ID NO: 522 or encoding a variant thereof wherein at least one framework residue (FR residue) has been substituted with an amino acid present at the corresponding position in a rabbit anti-CGRP antibody $V_H$ polypeptide or a conservative amino acid substitution.

In another embodiment, the invention is directed to an isolated polynucleotide comprising the polynucleotide sequence encoding an anti-CGRP $V_L$ antibody amino acid sequence of SEQ ID NO: 22, SEQ ID NO: 62, SEQ ID NO: 102, SEQ ID NO: 142, SEQ ID NO: 182, SEQ ID NO: 222, SEQ ID NO: 262, SEQ ID NO: 302, SEQ ID NO: 342, SEQ ID NO: 382, SEQ ID NO: 422, SEQ ID NO: 462, SEQ ID NO: 502, or SEQ ID NO: 542, or encoding a variant thereof wherein at least one framework residue (FR residue) has been substituted with an amino acid present at the corresponding position in a rabbit anti-CGRP antibody VL polypeptide or a conservative amino acid substitution.

In yet another embodiment, the invention is directed to one or more heterologous polynucleotides comprising a sequence encoding the polypeptides contained in SEQ ID NO: 22 and SEQ ID NO: 2; SEQ ID NO: 62 and SEQ ID NO: 42; SEQ ID NO: 102 and SEQ ID NO: 82; SEQ ID NO: 142 and SEQ ID NO: 122; SEQ ID NO: 182 and SEQ ID NO: 162; SEQ ID NO: 222 and SEQ ID NO: 202; SEQ ID NO: 262 and SEQ ID NO: 242; SEQ ID NO: 302 and SEQ ID NO: 282; SEQ ID NO: 342 and SEQ ID NO: 322; SEQ ID NO: 382 and SEQ ID NO: 362; SEQ ID NO: 422 and SEQ ID NO: 402; SEQ ID NO: 462 and SEQ ID NO: 442; SEQ ID NO: 502 and SEQ ID NO: 482; or SEQ ID NO: 542 and SEQ ID NO: 522.

In another embodiment, the invention is directed to an isolated polynucleotide that expresses a polypeptide containing at least one CDR polypeptide derived from an anti-CGRP antibody wherein said expressed polypeptide alone specifically binds CGRP or specifically binds CGRP when expressed in association with another polynucleotide sequence that expresses a polypeptide containing at least one CDR polypeptide derived from an anti-CGRP antibody wherein said at least one CDR is selected from those contained in the VL or VH polypeptides of SEQ ID NO: 22, SEQ ID NO: 2, SEQ ID NO: 62, SEQ ID NO: 42, SEQ ID NO: 102, SEQ ID NO: 82, SEQ ID NO: 142, SEQ ID NO: 122, SEQ ID NO: 182, SEQ ID NO: 162, SEQ ID NO: 222, SEQ ID NO: 202, SEQ ID NO: 262, SEQ ID NO: 242, SEQ ID NO: 302, SEQ ID NO: 282, SEQ ID NO: 342, SEQ ID NO: 322, SEQ ID NO: 382, SEQ ID NO: 362, SEQ ID NO: 422, SEQ ID NO: 402, SEQ ID NO: 462, SEQ ID NO: 442, SEQ ID NO: 502, SEQ ID NO: 482, SEQ ID NO: 542, or SEQ ID NO: 522.

Host cells and vectors comprising said polynucleotides are also contemplated.

The invention further contemplates vectors comprising the polynucleotide sequences encoding the variable heavy and light chain polypeptide sequences, as well as the individual complementarity-determining regions (CDRs, or hypervariable regions), as set forth herein, as well as host cells comprising said vector sequences. In one embodiment of the invention, the host cell is a yeast cell. In another embodiment of the invention, the yeast host cell belongs to the genus *Pichia*.

Methods of Producing Antibodies and Fragments Thereof

In another embodiment, the present invention contemplates methods for producing anti-CGRP antibodies and fragments thereof. Methods for producing antibodies and fragments thereof secreted from polyploidal, preferably diploid or tetraploid strains of mating competent yeast are taught, for example, in U.S. patent application publication no. US 2009/0022659 to Olson et al., and in U.S. Pat. No. 7,935,340 to Garcia-Martinez et al., the disclosures of each of which are herein incorporated by reference in their entireties. Methods for producing antibodies and fragments thereof in mammalian cells, e.g., CHO cells are further well known in the art.

Other methods of producing antibodies are also well known to those of ordinary skill in the art. For example, methods of producing chimeric antibodies are now well known in the art (See, for example, U.S. Pat. No. 4,816,567 to Cabilly et al.; Morrison et al., P.N.A.S. USA, 81:8651-55 (1984); Neuberger, M. S. et al., Nature, 314:268-270 (1985); Boulianne, G. L. et al., Nature, 312:643-46 (1984), the disclosures of each of which are herein incorporated by reference in their entireties).

Likewise, other methods of producing humanized antibodies are now well known in the art (See, for example, U.S. Pat. Nos. 5,530,101, 5,585,089, 5,693,762, and 6,180,370 to Queen et al; U.S. Pat. Nos. 5,225,539 and 6,548,640 to Winter; U.S. Pat. Nos. 6,054,297, 6,407,213 and 6,639,055 to Carter et al; U.S. Pat. No. 6,632,927 to Adair; Jones, P. T. et al, Nature, 321:522-525 (1986); Reichmann, L., et al, Nature, 332:323-327 (1988); Verhoeyen, M, et al, Science, 239:1534-36 (1988), the disclosures of each of which are herein incorporated by reference in their entireties).

The term "opioid analgesic" herein refers to all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans, all of which are within the scope of the term. Exemplary opioid analgesics include codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine or pharmaceutically acceptable salts thereof.

The term "NSAID" refers to a non-steroidal anti-inflammatory compound. NSAIDs are categorized by virtue of their ability to inhibit cyclooxygenase. Cyclooxygenase 1 and cyclooxygenase 2 are two major isoforms of cyclooxygenase and most standard NSAIDs are mixed inhibitors of the two isoforms. Most standard NSAIDs fall within one of the following five structural categories: (1) propionic acid derivatives, such as ibuprofen, naproxen, naprosyn, diclofenac, and ketoprofen; (2) acetic acid derivatives, such as tolmetin and slindac; (3) fenamic acid derivatives, such as mefenamic acid and meclofenamic acid; (4) biphenylcarboxylic acid derivatives, such as diflunisal and flufenisal; and (5) oxicams, such as piroxim, sudoxicam, and isoxicam. Another class of NSAID has been described which selectively inhibit cyclooxygenase 2. Cox-2 inhibitors have been described, e.g., in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain exemplary COX-2 inhibitors include celecoxib (SC-58635), DUP-697, flosulide (CGP-28238), meloxicam, 6-methoxy-2 naphthylacetic acid (6-MNA), rofecoxib, MK-966, nabumetone (prodrug for 6-MNA), nimesulide, NS-398, SC-5766, SC-58215, T-614; or combinations thereof.

In some embodiments, aspirin and/or acetaminophen may be taken in conjunction with the subject CGRP antibody or fragment. Aspirin is another type of non-steroidal anti-inflammatory compound.

The subject to which the pharmaceutical formulation is administered can be, e.g., any human or non-human animal that is in need of such treatment, prevention and/or amelioration, or who would otherwise benefit from the inhibition or attenuation of medication overuse headache. For example, the subject can be an individual that is diagnosed with, or who is deemed to be at risk of being afflicted by medication overuse headache. The present invention further includes the use of any of the pharmaceutical formulations disclosed herein in the manufacture of a medicament for the treatment, prevention and/or amelioration of medication overuse headache.

Administration

In one embodiment of the invention, the anti-CGRP antibodies described herein, or CGRP binding fragments thereof, as well as combinations of said antibodies or antibody fragments, are administered to a subject at a concentration of between about 0.1 and 100.0 mg/kg of body weight of recipient subject. In a preferred embodiment of the invention, the anti-CGRP antibodies described herein, or CGRP binding fragments thereof, as well as combinations of said antibodies or antibody fragments, are administered to a subject at a concentration of about 0.4 mg/kg of body weight of recipient subject and/or at a dosage of 100 or 300 mg. In a preferred embodiment of the invention, the anti-CGRP antibodies described herein, or CGRP binding fragments thereof, as well as combinations of said antibodies or antibody fragments, are administered to a recipient subject with a frequency of once every twenty-six weeks or six months or less, such as once every sixteen weeks or four months or less, once every eight weeks or two months or less, once every four weeks or monthly or less, once every two weeks or bimonthly or less, once every week or less, or once daily or less. In general the administration of sequential doses may vary by plus or minus a few days from the aforementioned schedule, e.g., administration every 3 months or every 12 weeks includes administration of a dose varying from the schedule day by plus or minus 1, 2, 3, 4, 5, 5, or 7 days.

Fab fragments may be administered every two weeks or less, every week or less, once daily or less, multiple times per day, and/or every few hours. In one embodiment of the invention, a patient receives Fab fragments of 0.1 mg/kg to 40 mg/kg per day given in divided doses of 1 to 6 times a day, or in a sustained release form, effective to obtain desired results.

It is to be understood that the concentration of the antibody or Fab administered to a given patient may be greater or lower than the exemplary administration concentrations set forth above.

A person of skill in the art would be able to determine an effective dosage and frequency of administration through routine experimentation, for example guided by the disclosure herein and the teachings in Goodman, L. S., Gilman, A., Brunton, L. L., Lazo, J. S., & Parker, K. L. (2006). Goodman & Gilman's the pharmacological basis of therapeutics. New York: McGraw-Hill; Howland, R. D., Mycek, M. J., Harvey, R. A., Champe, P. C., & Mycek, M. J. (2006). Pharmacology. Lippincott's illustrated reviews. Philadelphia: Lippincott Williams & Wilkins; and Golan, D. E. (2008). Principles of pharmacology: the pathophysiologic basis of drug therapy. Philadelphia, Pa., [etc.]: Lippincott Williams & Wilkins.

In another embodiment of the invention, the anti-CGRP antibodies described herein, or CGRP binding fragments thereof, as well as combinations of said antibodies or antibody fragments, are administered to a subject in a pharmaceutical formulation.

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal, preferably intravenous. In addition, administration can occur by means of injection, powder, liquid, gel, drops, or other means of administration.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations can be found, for example, in Remington's Pharmaceutical Sciences, 19$^{th}$ Ed., Grennaro, A., Ed., 1995 which is incorporated by reference.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The invention contemplates that the pharmaceutical composition is present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition. The proper fluidity can be maintained, for example, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the alkaline polypeptide can be formulated in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

An exemplary composition comprises, consists essentially of, or consists of an anti-CGRP antibody or fragment thereof (e.g., Ab6), an excipient such as histidine, an isotonic agent such as sorbitol, and a surfactant such as polysorbate 80 in an aqueous solution. For example, the composition may comprise, consist essentially of, or consist of histidine (L-histidine), sorbitol, polysorbate 80, such as, per 1 mL volume, about 100 mg anti-CGRP antibody (e.g., Ab6), about 3.1 mg L-Histidine, about 40.5 mg Sorbitol, and about 0.15 mg Polysorbate 80, having a pH of about 5.8, or approximately that constitution, e.g., within 10% of those values, within 5% of those values, within 1% of those values, within 0.5% of those values, or within 0.1% of those values, and water. For example, the pH value may be within 10% of 5.8, i.e., between 5.22 and 6.38. The Ab6 antibody may comprise or consist of the variable light and heavy chain polypeptides of SEQ ID NO: 222 and SEQ ID NO: 202 respectively, or the light and heavy chain polypeptides of SEQ ID NO: 221 and SEQ ID NO: 201 respectively, or the light and heavy chain polypeptides of SEQ ID NO: 221 and SEQ ID NO: 566 respectively. The composition may be in the form of an aqueous solution, or a concentrate (e.g., lyophilized) which when reconstituted, e.g., by addition of water, yields the aforementioned constitution. An exemplary composition consists of, per mL, 100 mg of the light and heavy chain polypeptides of SEQ ID NO: 221 and SEQ ID NO: 201 respectively, about 3.1 mg L-Histidine, about 40.5 mg Sorbitol, and about 0.15 mg Polysorbate 80, and water Q.S, or approximately that constitution, e.g., within 10% of those quantities, within 5% of those quantities, within 1% of those quantities, within 0.5% of those quantities, or within 0.1% of those quantities. Another exemplary composition consists of, per mL, 100 mg of the light and heavy chain polypeptides of SEQ ID NO: 221 and SEQ ID NO: 566 respectively, about 3.1 mg L-Histidine, about 40.5 mg Sorbitol, and about 0.15 mg Polysorbate 80, and water Q.S, or approximately that constitution, e.g., within 10% of those quantities, within 5% of those quantities, within 1% of those quantities, within 0.5% of those quantities, or within 0.1% of those quantities. The composition may be suitable for intravenous or subcutaneous administration, preferably intravenous administration. For example, the composition may be suitable for mixing with an intravenous solution (such as 0.9% sodium chloride) at an amount of between about 100 mg and about 300 mg antibody added to 100 mL of intravenous solution. Preferably the composition may be shelf-stable for at least 1, 3, 6, 12, 18, or 24 months, e.g., showing formation of aggregates of no more than 5% or no more than 10% of the antibody or fragment after storage at room temperature or when refrigerated at 4° C. for the specified duration, or in an accelerated aging test that simulates storage for that duration.

For each of the recited embodiments, the compounds can be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal, preferably intravenous), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain CGRP antibody polynucleotides and polypeptides are disclosed in the sequence listing accompanying this patent application filing, and the disclosure of said sequence listing is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Additional Exemplary Embodiments

Additional exemplary embodiments of the invention are provided as follows:

S1. Use of an anti-CGRP antibody for the manufacturing of a medicament for treating acute migraine, comprising administering to a patient an anti-CGRP antibody while the patient has a headache and within 30 hours of headache onset, preferably within 24 hours of headache onset.

S2. Use of the anti-CGRP antibody of embodiment 1, wherein the medicament is for administration within 18 hours, within 12 hours, within 6 hours, within 5 hours, within 4 hours, within 3 hours, within 2 hours, or within 1 hour of headache onset, such as between 1-6 hours from headache onset.

S3. Use of the anti-CGRP antibody of any one of the foregoing embodiments, wherein said medicament is for intravenous or subcutaneous infusion.

S4. Use of the anti-CGRP antibody of any one of the foregoing embodiments, wherein said medicament is for intravenous infusion.

S5. Use of the anti-CGRP antibody of any one of the foregoing embodiments, wherein said patient is headache free 2 hours post-completion of administration or infusion.

S6. Use of the anti-CGRP antibody of any one of the foregoing embodiments, wherein said patient is free from the most bothersome symptom (MBS) at 2 hours post-completion of administration or infusion.

S7. Use of the anti-CGRP antibody of any one of the foregoing embodiments, wherein the administration of said medicament improves one or more of the following: time to pain relief; time to pain freedom; headache pain freedom at 2 hours with sustained headache pain freedom for 24 and 48 hours post completion of infusion; use of rescue medication by 24 hours and by 48 hours post completion of infusion; absence of photophobia at 2 hours post completion of infusion; absence of phonophobia at 2 hours post completion of infusion; absence of nausea at 2 hours post completion of infusion; change from baseline in Headache Impact Test (HIT-6) at Week 4; or change from baseline in Migraine Treatment Optimization Questionnaire-6 (MTOQ-6) at Week 4.

S8. Use of the anti-CGRP antibody of any one of the foregoing embodiments, wherein said anti-CGRP antibody comprises any one of Ab1-Ab14.

S9. Use of the anti-CGRP antibody of any one of the foregoing embodiments, wherein said anti-CGRP antibody comprises Ab6.

S10. Use of the anti-CGRP antibody of any one of the foregoing embodiments, wherein said anti-CGRP antibody comprises the light chain complementarity-determining region (CDR) 1, 2, and 3 polypeptide sequences of SEQ ID NO: 224; SEQ ID NO: 226; and SEQ ID NO: 228, respectively.

S11. Use of the anti-CGRP antibody of any one of the foregoing embodiments, wherein said anti-CGRP antibody comprises the light chain CDR 1, 2, and 3 polypeptide sequences encoded by SEQ ID NO: 234; SEQ ID NO: 236; and SEQ ID NO: 238, respectively.

S12. Use of the anti-CGRP antibody of any one of the foregoing embodiments, wherein said anti-CGRP antibody comprises the heavy chain CDR 1, 2, and 3 polypeptide sequences of SEQ ID NO: 204; SEQ ID NO: 206; and SEQ ID NO: 208, respectively.

S13. Use of the anti-CGRP antibody of any one of the foregoing embodiments, wherein said anti-CGRP antibody comprises the heavy chain CDR 1, 2, and 3 polypeptide sequences encoded by SEQ ID NO: 214; SEQ ID NO: 216; and SEQ ID NO: 218, respectively.

S14. Use of the anti-CGRP antibody of any one of the foregoing embodiments, wherein said anti-CGRP antibody comprises the light chain CDR 1, 2, and 3 polypeptide sequences of SEQ ID NO: 224; SEQ ID NO: 226; and SEQ ID NO: 228, respectively and heavy chain CDR 1, 2, and 3 polypeptide sequences of SEQ ID NO: 204; SEQ ID NO: 206; and SEQ ID NO: 208, respectively.

S15. Use of the anti-CGRP antibody of any one of the foregoing embodiments, wherein said anti-CGRP antibody comprises the light chain CDR 1, 2, and 3 polypeptide sequences encoded by SEQ ID NO: 234; SEQ ID NO: 236; and SEQ ID NO: 238, respectively and heavy chain CDR 1, 2, and 3 polypeptide sequences encoded by SEQ ID NO: 214; SEQ ID NO: 216; and SEQ ID NO: 218, respectively.

S16. Use of the anti-CGRP antibody of any one of the foregoing embodiments, wherein said anti-CGRP antibody comprises the variable light chain polypeptide of SEQ ID NO: 222.

S17. Use of the anti-CGRP antibody of any one of the foregoing embodiments, wherein said anti-CGRP antibody comprises the variable light chain polypeptide encoded by SEQ ID NO: 232.

S18. Use of the anti-CGRP antibody of any one of the foregoing embodiments, wherein said anti-CGRP antibody comprises the variable heavy chain polypeptide of SEQ ID NO: 202.

S19. Use of the anti-CGRP antibody of any one of the foregoing embodiments, wherein said anti-CGRP antibody comprises the variable heavy chain polypeptide encoded by SEQ ID NO: 212.

S20. Use of the anti-CGRP antibody of any one of the foregoing embodiments, wherein said anti-CGRP antibody comprises the variable light chain polypeptide of SEQ ID NO: 222 and the variable heavy chain polypeptide of SEQ ID NO: 202.

S21. Use of the anti-CGRP antibody of any one of the foregoing embodiments, wherein said anti-CGRP antibody comprises the variable light chain polypeptide encoded by SEQ ID NO: 232 and the variable heavy chain polypeptide encoded by SEQ ID NO: 212.

S22. Use of the anti-CGRP antibody of any one of the foregoing embodiments, wherein said anti-CGRP antibody comprises the light chain polypeptide of SEQ ID NO: 221.

S23. Use of the anti-CGRP antibody of any one of the foregoing embodiments, wherein said anti-CGRP antibody comprises the light chain polypeptide encoded by SEQ ID NO: 231.

S24. Use of the anti-CGRP antibody of any one of the foregoing embodiments, wherein said anti-CGRP antibody comprises the heavy chain polypeptide of SEQ ID NO: 201 or SEQ ID NO: 566.

S25. Use of the anti-CGRP antibody of any one of the foregoing embodiments, wherein said anti-CGRP antibody comprises the heavy chain polypeptide encoded by SEQ ID NO: 211 or SEQ ID NO: 567.

S26. Use of the anti-CGRP antibody of any one of the foregoing embodiments, wherein said anti-CGRP antibody comprises the light chain polypeptide of SEQ ID NO: 221 and the heavy chain polypeptide of SEQ ID NO: 201 or SEQ ID NO: 566.

S27. Use of the anti-CGRP antibody of any one of the foregoing embodiments, wherein said anti-CGRP antibody comprises the light chain polypeptide encoded by SEQ ID NO: 231 and the heavy chain polypeptide encoded by SEQ ID NO: 211 or SEQ ID NO: 567.

S28. Use of the anti-CGRP antibody of any one of the foregoing embodiments, wherein the administered amount of said anti-CGRP antibody is between about 100 mg and about 300 mg, or is about 100 mg, or is about 300 mg.

S29. Use of the anti-CGRP antibody of any one of the foregoing embodiments, wherein the administered amount of said anti-CGRP antibody is 100 mg.

S30. Use of the anti-CGRP antibody of any one of the foregoing embodiments, wherein said medicament is for intravenous administration in a dosage of 100 mg of said anti-CGRP antibody every 10-14 weeks, preferably every 11-13 weeks, more preferably every 12 weeks.

S31. Use of the anti-CGRP antibody of any one of embodiments S1-S29, wherein said medicament is for intravenous administration in a dosage of 300 mg of said anti-CGRP antibody every 10-14 weeks, preferably every 11-13 weeks, more preferably every 12 weeks.

S32. Use of the anti-CGRP antibody of any one of the foregoing embodiments, wherein said patient suffers from medication overuse headache.

S33. Use of the anti-CGRP antibody of any one of the foregoing embodiments wherein, prior to administration of said medicament, the patient exhibits between 1-10 migraine attacks per month in the month or in the 3 months prior to administration.

S34. Use of the anti-CGRP antibody of any one of the foregoing embodiments wherein, prior to administration of said medicament, the patient exhibits between 2-8 migraine attacks per month in the month or in the 3 months prior to administration.

S35. Use of the anti-CGRP antibody of any one of the foregoing embodiments wherein, prior to administration of said medicament, the patient exhibits between 3-7 migraine attacks per month in the month or in the 3 months prior to administration.

S36. Use of the anti-CGRP antibody of any one of the foregoing embodiments wherein, prior to administration of said medicament, the patient exhibits less than 25 headache days per month in the month or in the 3 months prior to administration.

S37. Use of the anti-CGRP antibody of any one of the foregoing embodiments wherein, prior to administration of said medicament, the patient exhibits less than 20 headache days per month in the month or in the 3 months prior to administration.

S38. Use of the anti-CGRP antibody of any one of the foregoing embodiments wherein, prior to administration of said medicament, the patient exhibits less than 15 headache days per month in the month or in the 3 months prior to administration.

S39. Use of the anti-CGRP antibody of any one of the foregoing embodiments wherein, prior to administration of said medicament, the patient exhibits less than 10 headache days per month in the month or in the 3 months prior to administration.

S40. Use of the anti-CGRP antibody of any one of the foregoing embodiments wherein said patient was diagnosed with migraine at least 10 years prior to administration of said medicament.

S41. Use of the anti-CGRP antibody of any one of the foregoing embodiments wherein said patient was diagnosed with migraine at least 15 years prior to administration of said medicament.

S42. Use of the anti-CGRP antibody of any one of the foregoing embodiments wherein said patient was diagnosed with migraine at least 18 or at least 19 years prior to administration of said medicament.

S43. Use of the anti-CGRP antibody of any one of the foregoing embodiments, wherein said patient has a reduction in the number of migraine days by at least 50% in the one month period after being administered said antibody relative to the baseline number of migraine days experienced by that patient prior to administration of said medicament.

S44. Use of the anti-CGRP antibody of any one of the foregoing embodiments, wherein said patient has a reduction in the number of migraine days by at least 75% in the one month period after being administered said antibody relative to the baseline number of migraine days experienced by that patient prior to administration of said medicament.

S45. Use of the anti-CGRP antibody of any one of the foregoing embodiments, wherein said patient has a reduction in the number of migraine days by 100% in the one month period after being administered said antibody relative to the baseline number of migraine days experienced by that patient prior to administration of said medicament.

S46. Use of the anti-CGRP antibody of any one of the foregoing embodiments, wherein said patient has a reduction in the number of migraine days by at least 50% in the 12 week period after being administered said antibody relative to the baseline number of migraine days experienced by that patient prior to administration of said medicament.

S47. Use of the anti-CGRP antibody of any one of the foregoing embodiments, wherein said patient has a reduction in the number of migraine days by at least 75% in the 12 week period after being administered said antibody relative to the baseline number of migraine days experienced by that patient prior to administration of said medicament.

S48. Use of the anti-CGRP antibody of any one of the foregoing embodiments, wherein said patient has a reduction in the number of migraine days by 100% in the 12 week period after being administered said antibody relative to the baseline number of migraine days experienced by that patient prior to administration of said medicament.

S49. Use of the anti-CGRP antibody of any one of the foregoing embodiments, wherein said medicament is further for administration in a second dose of said anti-CGRP antibody about 10-14 weeks, preferably 11-13 weeks, more preferably about 12 weeks or about 3 months after administration of said medicament.

S50. Use of the anti-CGRP antibody of any one of the foregoing embodiments, wherein said medicament comprises about 100 mg, about 125 mg, about 150 mg, about 175 mg, about 200 mg, about 225 mg, about 250 mg, about 275 mg, or about 300 mg of said anti-CGRP antibody.

S51. Use of the anti-CGRP antibody of any one of the foregoing embodiments, wherein said anti-CGRP antibody is aglycosylated or if glycosylated only contains only mannose residues.

S52. Use of the anti-CGRP antibody of any one of the foregoing embodiments, wherein said anti-CGRP antibody consists of the light chain polypeptide of SEQ ID NO: 221 and the heavy chain polypeptide of SEQ ID NO: 201 or SEQ ID NO: 566.

S53. Use of the anti-CGRP antibody of any one of the foregoing embodiments, wherein said anti-CGRP antibody consists of the light chain polypeptide encoded by SEQ ID NO: 231 and the heavy chain polypeptide encoded by SEQ ID NO: 211 or SEQ ID NO: 567.

S54. Use of the anti-CGRP antibody of any one of embodiments S7-S53, wherein said rescue medication comprises one or more of a triptan, non-opioid analgesics (such as paracetamol (acetaminophen), acetylsalicylic acid (aspirin), another NSAID, or another non-opioid analgesic), a combination of two or more drug classes, wherein said triptan use optionally comprises use of one or more of sumatriptan, zolmitriptan, naratriptan, rizatriptan, eletriptan, almotriptan, and frovatriptan, and/or wherein said opioid use optionally comprises use of one or more of oxycodone, tramadol, butorphanol, morphine, codeine, and hydrocodone, and/or wherein said combination of two or more drug class optionally comprises two drugs with analgesic effects (for example, paracetamol and codeine) or acting as adjuvants (for example, caffeine), optionally wherein said combination-analgesics combine non-opioid analgesic includes at least one opioid (such as tramadol, butorphanol, morphine, codeine, hydrocodone, or any combination thereof), barbiturate such as butalbital and/or caffeine.

S55. Use of the anti-CGRP antibody of any one of the foregoing embodiments, wherein said headache or said migraine is diagnosed according to the third edition of the International Classification of Headache Disorders.

S56. Use of the anti-CGRP antibody of any of any one of the foregoing embodiments, wherein said anti-CGRP antibody is expressed in or obtained by expression in *Pichia pastoris*.

S57. Use of the anti-CGRP antibody of any of any one of embodiments S1-S55, wherein said anti-CGRP antibody is expressed in or obtained by expression in CHO cells.

S58. Use of the anti-CGRP antibody of any one of the foregoing embodiments, wherein said anti-CGRP antibody or anti-CGRP antibody fragment is comprised in a formulation comprising or consisting of histidine (L-histidine), sorbitol, polysorbate 80, and water.

S59. Use of the anti-CGRP antibody of embodiment S58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−10% of said values, and having a pH of 5.8 or within +/−10% of said value.

S60. Use of the anti-CGRP antibody of embodiment S58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−5% of said values, and/or having a pH of 5.8 or within +/−5% of said value.

S61. Use of the anti-CGRP antibody of embodiment S58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−1% of said values, and/or having a pH of 5.8 or within +/−1% of said value.

S62. Use of the anti-CGRP antibody of embodiment S58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.5% of said values, and/or having a pH of 5.8 or within +/−0.5% of said value.

S63. Use of the anti-CGRP antibody of embodiment S58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.1% of said values, and/or having a pH of 5.8 or within +/−0.1% of said value.

S64. Use of an anti-CGRP antibody for the manufacture of a medicament for treating chronic migraine, wherein said medicament is for intravenous administration in a first dosage comprising between about 100 mg and about 300 mg of an anti-CGRP antibody, wherein said anti-CGRP antibody comprises the light chain polypeptide of SEQ ID NO: 221 and the heavy chain polypeptide of SEQ ID NO: 201 or SEQ ID NO: 566, wherein in the first 24 hours after administration of said first dosage the patient exhibits at least a 50% reduction in migraine prevalence.

S65. Use of an anti-CGRP antibody for the manufacture of a medicament for treating chronic migraine, wherein said medicament is for intravenous administration in a first dosage comprising between about 100 mg and about 300 mg of an anti-CGRP antibody, wherein said anti-CGRP antibody comprises the light chain polypeptide of SEQ ID NO: 221 and the heavy chain polypeptide of SEQ ID NO: 201 or SEQ ID NO: 566, wherein on the first day following the day of administration the patient exhibits at least a 50% reduction in migraine prevalence.

S66. Use of the anti-CGRP antibody of embodiment S64 or embodiment S65, wherein the first dosage of said anti-CGRP antibody is 100 mg.

S67. Use of the anti-CGRP antibody of embodiment S64 or embodiment S65, wherein the first dosage of said anti-CGRP antibody is 300 mg.

S68. Use of the anti-CGRP antibody of embodiment S64, S65, or S66, wherein said medicament is for intravenous administration in a dosage of 100 mg of said anti-CGRP antibody every 10-14 weeks, preferably 11-13 weeks, more preferably every 12 weeks.

S69. Use of the anti-CGRP antibody of embodiment S64, S65, or S67, wherein said medicament is for intravenous administration in a dosage of 300 mg of said anti-CGRP antibody every 10-14 weeks, preferably 11-13 weeks, more preferably every 12 weeks.

S70. Use of the anti-CGRP antibody of any one of embodiments S64-S69 wherein, prior to said first dosage, the patient exhibits between about 10 and about 22 migraine days per month.

S71. Use of the anti-CGRP antibody of any one of embodiments S64-S70 wherein, prior to said first dosage, the patient exhibits between about 13 and about 19 migraine days per month.

S72. Use of the anti-CGRP antibody of any one of embodiments S64-S71 wherein, prior to said first dosage, the patient exhibits about 16 migraine days per month.

S73. Use of the anti-CGRP antibody of any one of embodiments S64-S72 wherein, prior to said first dosage, the patient exhibits between about 14 and about 27 headache days per month.

S74. Use of the anti-CGRP antibody of any one of embodiments S64-S73 wherein, prior to said first dosage, the patient exhibits between about 17 and about 24 headache days per month.

S75. Use of the anti-CGRP antibody of any one of embodiments S64-S74 wherein, prior to said first dosage, the patient exhibits about 20 or about 21 headache days per month.

S76. Use of the anti-CGRP antibody of any one of embodiments S64-S75 wherein said patient was diagnosed with migraine at least 10 years prior to said first dosage.

S77. Use of the anti-CGRP antibody of any one of embodiments S64-S76 wherein said patient was diagnosed with migraine at least 15 years prior to said first dosage.

S78. Use of the anti-CGRP antibody of any one of embodiments S64-S77 wherein said patient was diagnosed with migraine at least 18 or at least 19 years prior to said first dosage.

S79. Use of the anti-CGRP antibody of any one of embodiments S64-S78 wherein said patient was diagnosed with chronic migraine at least 5 years prior to said first dosage.

S80. Use of the anti-CGRP antibody of any one of embodiments S64-S79 wherein said patient was diagnosed with chronic migraine at least 8 years prior to said first dosage.

S81. Use of the anti-CGRP antibody of any one of embodiments S64-S80 wherein said patient was diagnosed with chronic migraine at least 11 or at least 12 years prior to said first dosage.

S82. Use of the anti-CGRP antibody of any one of embodiments S64-S81 wherein said medicament is for administration of said first dosage when the patient has a headache.

S83. Use of the anti-CGRP antibody of any one of embodiments S64-S82 wherein said medicament is for administration of said first dosage when the patient has a migraine.

S84. Use of the anti-CGRP antibody of any one of embodiments S64-S83 wherein said medicament is for administration of said first dosage when the patient has a migraine with aura.

S85. Use of the anti-CGRP antibody of any one of embodiments S64-S84, wherein said patient has a reduction in the number of migraine days by at least 50% in the one month period after being administered said first dose relative to the baseline number of migraine days experienced by that patient prior to said first dose.

S86. Use of the anti-CGRP antibody of any one of embodiments S64-S85, wherein said patient has a reduction in the number of migraine days by at least 75% in the one month period after being administered said first dose relative to the baseline number of migraine days experienced by that patient prior to said first dose.

S87. Use of the anti-CGRP antibody of any one of embodiments S64-S86, wherein said patient has a reduction in the number of migraine days by 100% in the one month period after being administered said first dose relative to the baseline number of migraine days experienced by that patient prior to said first dose.

S88. Use of the anti-CGRP antibody of any one of embodiments S64-S87, wherein said patient has a reduction in the number of migraine days by at least 50% in the 12 week period after being administered said first dose relative to the baseline number of migraine days experienced by that patient prior to said first dose.

S89. Use of the anti-CGRP antibody of any one of embodiments S64-S88, wherein said patient has a reduction in the number of migraine days by at least 75% in the 12 week period after being administered said first dose relative to the baseline number of migraine days experienced by that patient prior to said first dose.

S90. Use of the anti-CGRP antibody of any one of embodiments S64-S89, wherein said patient has a reduction in the number of migraine days by 100% in the 12 week period after being administered said first dose relative to the baseline number of migraine days experienced by that patient prior to said first dose.

S91. Use of the anti-CGRP antibody of any one of embodiments S64-S90, further comprising administering a second dose of said anti-CGRP antibody to said patient about 12 weeks or about 3 months after said first dose.

S92. Use of the anti-CGRP antibody of any one of embodiments S64-S91, wherein said first dose comprises about 100 mg, about 125 mg, about 150 mg, about 175 mg, about 200 mg, about 225 mg, about 250 mg, about 275 mg, or about 300 mg of said anti-CGRP antibody.

S93. Use of the anti-CGRP antibody of any one of embodiments S64-S92, wherein said anti-CGRP antibody or antibody fragment is aglycosylated or if glycosylated only contains only mannose residues.

S94. Use of the anti-CGRP antibody of any one of embodiments S64-S93, wherein said anti-CGRP antibody consists of the light chain polypeptide of the light chain polypeptide of SEQ ID NO: 221 and the heavy chain polypeptide of SEQ ID NO: 201 or SEQ ID NO: 566.

S95. Use of the anti-CGRP antibody of any of any one of embodiments S64-S94, wherein said anti-CGRP antibody is expressed in or obtained by expression in *Pichia pastoris*.

S96. Use of the anti-CGRP antibody of any of any one of embodiments S64-S94, wherein said anti-CGRP antibody is expressed in or obtained by expression in CHO cells.

S97. Use of the anti-CGRP antibody of any one of embodiments S64-S96, wherein said anti-CGRP antibody or anti-CGRP antibody fragment is comprised in a formulation comprising or consisting of histidine (L-histidine), sorbitol, polysorbate 80, and water.

S98. Use of the anti-CGRP antibody of embodiment S97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−10% of said values, and having a pH of 5.8 or within +/−10% of said value.

S99. Use of the anti-CGRP antibody of embodiment S97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−5% of said values, and/or having a pH of 5.8 or within +/−5% of said value.

S100. Use of the anti-CGRP antibody of embodiment S97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−1% of said values, and/or having a pH of 5.8 or within +/−1% of said value.

S101. Use of the anti-CGRP antibody of embodiment S97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.5% of said values, and/or having a pH of 5.8 or within +/−0.5% of said value.

S102. Use of the anti-CGRP antibody of embodiment S97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.1% of said values, and/or having a pH of 5.8 or within +/−0.1% of said value.

Further Exemplary Embodiments

Further exemplary embodiments of the invention are provided as follows:

E1. An anti-CGRP antibody for use in treating acute migraine while the patient has a headache and within 30 hours of headache onset, preferably within 24 hours of headache onset.

E2. The anti-CGRP antibody for use of embodiment E1, wherein the anti-CGRP antibody is for administration within 18 hours, within 12 hours, within 6 hours, within 5 hours, within 4 hours, within 3 hours, within 2 hours, or within 1 hour of headache onset, such as between 1-6 hours from headache onset.

E3. The anti-CGRP antibody for use of any one of the foregoing embodiments, wherein said anti-CGRP antibody is for intravenous or subcutaneous infusion.

E4. The anti-CGRP antibody for use of any one of the foregoing embodiments, wherein said anti-CGRP antibody is for intravenous infusion.

E5. The anti-CGRP antibody for use of any one of the foregoing embodiments, wherein said patient is headache free 2 hours post-completion of administration or infusion.

E6. The anti-CGRP antibody for use of any one of the foregoing embodiments, wherein said patient is free from the most bothersome symptom (MBS) at 2 hours post-completion of administration or infusion.

E7. The anti-CGRP antibody for use of any one of the foregoing embodiments, wherein the administration of said anti-CGRP antibody improves one or more of the following: time to pain relief; time to pain freedom; headache pain freedom at 2 hours with sustained headache pain freedom for 24 and 48 hours post completion of infusion; use of rescue medication by 24 hours and by 48 hours post completion of infusion; absence of photophobia at 2 hours post completion of infusion; absence of phonophobia at 2 hours post completion of infusion; absence of nausea at 2 hours post completion of infusion; change from baseline in Headache Impact Test (HIT-6) at Week 4; or change from baseline in Migraine Treatment Optimization Questionnaire-6 (MTOQ-6) at Week 4.

E8. The anti-CGRP antibody for use of any one of the foregoing embodiments, wherein said anti-CGRP antibody comprises any one of Ab1-Ab14.

E9. The anti-CGRP antibody for use of any one of the foregoing embodiments, wherein said anti-CGRP antibody comprises Ab6.

E10. The anti-CGRP antibody for use of any one of the foregoing embodiments, wherein said anti-CGRP antibody comprises the light chain complementarity-determining region (CDR) 1, 2, and 3 polypeptide sequences of SEQ ID NO: 224; SEQ ID NO: 226; and SEQ ID NO: 228, respectively.

E11. The anti-CGRP antibody for use of any one of the foregoing embodiments, wherein said anti-CGRP antibody comprises the light chain CDR 1, 2, and 3 polypeptide sequences encoded by SEQ ID NO: 234; SEQ ID NO: 236; and SEQ ID NO: 238, respectively.

E12. The anti-CGRP antibody for use of any one of the foregoing embodiments, wherein said anti-CGRP antibody comprises the heavy chain CDR 1, 2, and 3 polypeptide sequences of SEQ ID NO: 204; SEQ ID NO: 206; and SEQ ID NO: 208, respectively.

E13. The anti-CGRP antibody for use of any one of the foregoing embodiments, wherein said anti-CGRP antibody comprises the heavy chain CDR 1, 2, and 3 polypeptide sequences encoded by SEQ ID NO: 214; SEQ ID NO: 216; and SEQ ID NO: 218, respectively.

E14. The anti-CGRP antibody for use of any one of the foregoing embodiments, wherein said anti-CGRP antibody comprises the light chain CDR 1, 2, and 3 polypeptide sequences of SEQ ID NO: 224; SEQ ID NO: 226; and SEQ ID NO: 228, respectively and heavy chain CDR 1, 2, and 3 polypeptide sequences of SEQ ID NO: 204; SEQ ID NO: 206; and SEQ ID NO: 208, respectively.

E15. The anti-CGRP antibody for use of any one of the foregoing embodiments, wherein said anti-CGRP antibody comprises the light chain CDR 1, 2, and 3 polypeptide sequences encoded by SEQ ID NO: 234; SEQ ID NO: 236; and SEQ ID NO: 238, respectively and heavy chain CDR 1, 2, and 3 polypeptide sequences encoded by SEQ ID NO: 214; SEQ ID NO: 216; and SEQ ID NO: 218, respectively.

E16. The anti-CGRP antibody for use of any one of the foregoing embodiments, wherein said anti-CGRP antibody comprises the variable light chain polypeptide of SEQ ID NO: 222.

E17. The anti-CGRP antibody for use of any one of the foregoing embodiments, wherein said anti-CGRP antibody comprises the variable light chain polypeptide encoded by SEQ ID NO: 232.

E18. The anti-CGRP antibody for use of any one of the foregoing embodiments, wherein said anti-CGRP antibody comprises the variable heavy chain polypeptide of SEQ ID NO: 202.

E19. The anti-CGRP antibody for use of any one of the foregoing embodiments, wherein said anti-CGRP antibody comprises the variable heavy chain polypeptide encoded by SEQ ID NO: 212.

E20. The anti-CGRP antibody for use of any one of the foregoing embodiments, wherein said anti-CGRP antibody comprises the variable light chain polypeptide of SEQ ID NO: 222 and the variable heavy chain polypeptide of SEQ ID NO: 202.

E21. The anti-CGRP antibody for use of any one of the foregoing embodiments, wherein said anti-CGRP antibody comprises the variable light chain polypeptide encoded by SEQ ID NO: 232 and the variable heavy chain polypeptide encoded by SEQ ID NO: 212.

E22. The anti-CGRP antibody for use of any one of the foregoing embodiments, wherein said anti-CGRP antibody comprises the light chain polypeptide of SEQ ID NO: 221.

E23. The anti-CGRP antibody for use of any one of the foregoing embodiments, wherein said anti-CGRP antibody comprises the light chain polypeptide encoded by SEQ ID NO: 231.

E24. The anti-CGRP antibody for use of any one of the foregoing embodiments, wherein said anti-CGRP antibody comprises the heavy chain polypeptide of SEQ ID NO: 201 or SEQ ID NO: 566.

E25. The anti-CGRP antibody for use of any one of the foregoing embodiments, wherein said anti-CGRP antibody comprises the heavy chain polypeptide encoded by SEQ ID NO: 211 or SEQ ID NO: 567.

E26. The anti-CGRP antibody for use of any one of the foregoing embodiments, wherein said anti-CGRP antibody comprises the light chain polypeptide of SEQ ID NO: 221 and the heavy chain polypeptide of SEQ ID NO: 201 or SEQ ID NO: 566.

E27. The anti-CGRP antibody for use of any one of the foregoing embodiments, wherein said anti-CGRP antibody comprises the light chain polypeptide encoded by SEQ ID NO: 231 and the heavy chain polypeptide encoded by SEQ ID NO: 211 or SEQ ID NO: 567.

E28. The anti-CGRP antibody for use of any one of the foregoing embodiments, wherein the administered amount of said anti-CGRP antibody is between about 100 mg and about 300 mg, or is about 100 mg, or is about 300 mg.

E29. The anti-CGRP antibody for use of any one of the foregoing embodiments, wherein the administered amount of said anti-CGRP antibody is 100 mg.

E30. The anti-CGRP antibody for use of any one of the foregoing embodiments, wherein said anti-CGRP antibody is for intravenous administration in a dosage of 100 mg of said anti-CGRP antibody every 10-14 weeks, preferably every 11-13 weeks, more preferably every 12 weeks.

E31. The anti-CGRP antibody for use of any one of embodiments E1-E29, wherein said anti-CGRP antibody is for intravenous administration in a dosage of administering 300 mg of said anti-CGRP antibody every 10-14 weeks, preferably every 11-13 weeks, more preferably every 12 weeks.

E32. The anti-CGRP antibody for use of any one of the foregoing embodiments, wherein said patient suffers from medication overuse headache.

E33. The anti-CGRP antibody for use of any one of the foregoing embodiments wherein, prior to administration of said anti-CGRP antibody, the patient exhibits between 1-10 migraine attacks per month in the month or in the 3 months prior to administration.

E34. The anti-CGRP antibody for use of any one of the foregoing embodiments wherein, prior to administration of said anti-CGRP antibody, the patient exhibits between 2-8 migraine attacks per month in the month or in the 3 months prior to administration.

E35. The anti-CGRP antibody for use of any one of the foregoing embodiments wherein, prior to administration of said anti-CGRP antibody, the patient exhibits between 3-7 migraine attacks per month in the month or in the 3 months prior to administration.

E36. The anti-CGRP antibody for use of any one of the foregoing embodiments wherein, prior to administration of said anti-CGRP antibody, the patient exhibits less than 25 headache days per month in the month or in the 3 months prior to administration.

E37. The anti-CGRP antibody for use of any one of the foregoing embodiments wherein, prior to administration of said anti-CGRP antibody, the patient exhibits less than 20 headache days per month in the month or in the 3 months prior to administration.

E38. The anti-CGRP antibody for use of any one of the foregoing embodiments wherein, prior to administration of said anti-CGRP antibody, the patient exhibits less than 15 headache days per month in the month or in the 3 months prior to administration.

E39. The anti-CGRP antibody for use of any one of the foregoing embodiments wherein, prior to administration of said anti-CGRP antibody, the patient exhibits less than 10 headache days per month in the month or in the 3 months prior to administration.

E40. The anti-CGRP antibody for use of any one of the foregoing embodiments wherein said patient was diagnosed with migraine at least 10 years prior to the administration of said anti-CGRP antibody.

E41. The anti-CGRP antibody for use of any one of the foregoing embodiments wherein said patient was diagnosed with migraine at least 15 years prior to the administration of said anti-CGRP antibody.

E42. The anti-CGRP antibody for use of any one of the foregoing embodiments wherein said patient was diagnosed with migraine at least 18 or at least 19 years prior to the administration of said anti-CGRP antibody.

E43. The anti-CGRP antibody for use of any one of the foregoing embodiments, wherein said patient has a reduction in the number of migraine days by at least 50% in the one month period after being administered said antibody relative to the baseline number of migraine days experienced by that patient prior to the administration of said anti-CGRP antibody.

E44. The anti-CGRP antibody for use of any one of the foregoing embodiments, wherein said patient has a reduction in the number of migraine days by at least 75% in the one month period after being administered said antibody relative to the baseline number of migraine days experienced by that patient prior to the administration of said anti-CGRP antibody.

E45. The anti-CGRP antibody for use of any one of the foregoing embodiments, wherein said patient has a reduction in the number of migraine days by 100% in the one month period after being administered said antibody relative to the baseline number of migraine days experienced by that patient prior to the administration of said anti-CGRP antibody.

E46. The anti-CGRP antibody for use of any one of the foregoing embodiments, wherein said patient has a reduction in the number of migraine days by at least 50% in the 12 week period after being administered said antibody relative to the baseline number of migraine days experienced by that patient prior to the administration of said anti-CGRP antibody.

E47. The anti-CGRP antibody for use of any one of the foregoing embodiments, wherein said patient has a reduction in the number of migraine days by at least 75% in the 12 week period after being administered said antibody relative to the baseline number of migraine days experienced by that patient prior to the administration of said anti-CGRP antibody.

E48. The anti-CGRP antibody for use of any one of the foregoing embodiments, wherein said patient has a reduction in the number of migraine days by 100% in the 12 week period after being administered said antibody relative to the baseline number of migraine days experienced by that patient prior to the administration of said anti-CGRP antibody.

E49. The anti-CGRP antibody for use of any one of the foregoing embodiments, wherein said use comprises administering a second dose of said anti-CGRP antibody to said patient about 10-14 weeks, preferably 11-13 weeks, more preferably about 12 weeks or about 3 months after the administration of said anti-CGRP antibody.

E50. The anti-CGRP antibody for use of any one of the foregoing embodiments, wherein said use comprises administering about 100 mg, about 125 mg, about 150 mg, about 175 mg, about 200 mg, about 225 mg, about 250 mg, about 275 mg, or about 300 mg of said anti-CGRP antibody.

E51. The anti-CGRP antibody for use of any one of the foregoing embodiments, wherein said anti-CGRP antibody is aglycosylated or if glycosylated only contains only mannose residues.

E52. The anti-CGRP antibody for use of any one of the foregoing embodiments, wherein said anti-CGRP antibody consists of the light chain polypeptide of SEQ ID NO: 221 and the heavy chain polypeptide of SEQ ID NO: 201 or SEQ ID NO: 566.

E53. The anti-CGRP antibody for use of any one of the foregoing embodiments, wherein said anti-CGRP antibody consists of the light chain polypeptide encoded by SEQ ID NO: 231 and the heavy chain polypeptide encoded by SEQ ID NO: 211 or SEQ ID NO: 567.

E54. The anti-CGRP antibody for use of any one of embodiments E7-E53, wherein said rescue medication comprises one or more of a triptan, non-opioid analgesics (such as paracetamol (acetaminophen), acetylsalicylic acid (aspirin), another NSAID, or another non-opioid analgesic), a combination of two or more drug classes, wherein said triptan use optionally comprises use of one or more of sumatriptan, zolmitriptan, naratriptan, rizatriptan, eletriptan, almotriptan, and frovatriptan, and/or wherein said opioid use optionally comprises use of one or more of oxycodone, tramadol, butorphanol, morphine, codeine, and hydrocodone, and/or wherein said combination of two or more drug class optionally comprises two drugs with analgesic effects (for example, paracetamol and codeine) or acting as adjuvants (for example, caffeine), optionally wherein said combination-analgesics combine non-opioid analgesic includes at least one opioid (such as tramadol, butorphanol, morphine, codeine, hydrocodone, or any combination thereof), barbiturate such as butalbital and/or caffeine.

E55. The anti-CGRP antibody for use of any one of the foregoing embodiments, wherein said headache or said migraine is diagnosed according to the third edition of the International Classification of Headache Disorders.

E56. The anti-CGRP antibody for use of any of any one of the foregoing embodiments, wherein said anti-CGRP antibody is expressed in or obtained by expression in *Pichia pastoris*.

E57. The anti-CGRP antibody for use of any of any one of embodiments E1-E55, wherein said anti-CGRP antibody is expressed in or obtained by expression in CHO cells.

E58. The anti-CGRP antibody for use of any one of the foregoing embodiments, wherein said anti-CGRP antibody or anti-CGRP antibody fragment is comprised in a formulation comprising or consisting of histidine (L-histidine), sorbitol, polysorbate 80, and water.

E59. The anti-CGRP antibody for use of embodiment E58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−10% of said values, and having a pH of 5.8 or within +/−10% of said value.

E60. The anti-CGRP antibody for use of embodiment E58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−5% of said values, and/or having a pH of 5.8 or within +/−5% of said value.

E61. The anti-CGRP antibody for use of embodiment E58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−1% of said values, and/or having a pH of 5.8 or within +/−1% of said value.

E62. The anti-CGRP antibody for use of embodiment E58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.5% of said values, and/or having a pH of 5.8 or within +/−0.5% of said value.

E63. The anti-CGRP antibody for use of embodiment E58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.1% of said values, and/or having a pH of 5.8 or within +/−0.1% of said value.

E64. An anti-CGRP antibody for use in treating chronic migraine, wherein said antibody is for intravenous administration in a first dosage comprising between about 100 mg and about 300 mg of an anti-CGRP antibody, wherein said anti-CGRP antibody comprises the light chain polypeptide of SEQ ID NO: 221 and the heavy chain polypeptide of SEQ ID NO: 201 or SEQ ID NO: 566, wherein in the first 24 hours after administration of said first dosage the patient exhibits at least a 50% reduction in migraine prevalence.

E65. An anti-CGRP antibody for use in treating chronic migraine, wherein said antibody is for intravenous administration in a first dosage comprising between about 100 mg and about 300 mg of an anti-CGRP antibody, wherein said anti-CGRP antibody comprises the light chain polypeptide of SEQ ID NO: 221 and the heavy chain polypeptide of SEQ ID NO: 201 or SEQ ID NO: 566, wherein on the first day following the day of administration the patient exhibits at least a 50% reduction in migraine prevalence.

E66. The anti-CGRP antibody for use of embodiment E64 or embodiment E65, wherein the first dosage of said anti-CGRP antibody is 100 mg.

E67. The anti-CGRP antibody for use of embodiment E64 or embodiment E65, wherein the first dosage of said anti-CGRP antibody is 300 mg.

E68. The anti-CGRP antibody for use of embodiment E64, E65, or E66, wherein said anti-CGRP antibody is for intravenous administration in a dosage of 100 mg of said anti-CGRP antibody every 10-14 weeks, preferably 11-13 weeks, more preferably every 12 weeks.

E69. The anti-CGRP antibody for use of embodiment E64, E65, or E67, wherein said anti-CGRP antibody is for intravenous administration in a dosage of 300 mg of said anti-CGRP antibody every 10-14 weeks, preferably 11-13 weeks, more preferably every 12 weeks.

E70. The anti-CGRP antibody for use of any one of embodiments E64-E69 wherein, prior to said first dosage, the patient exhibits between about 10 and about 22 migraine days per month.

E71. The anti-CGRP antibody for use of any one of embodiments E64-E70 wherein, prior to said first dosage, the patient exhibits between about 13 and about 19 migraine days per month.

E72. The anti-CGRP antibody for use of any one of embodiments E64-E71 wherein, prior to said first dosage, the patient exhibits about 16 migraine days per month.

E73. The anti-CGRP antibody for use of any one of embodiments E64-E72 wherein, prior to said first dosage, the patient exhibits between about 14 and about 27 headache days per month.

E74. The anti-CGRP antibody for use of any one of embodiments E64-E73 wherein, prior to said first dosage, the patient exhibits between about 17 and about 24 headache days per month.

E75. The anti-CGRP antibody for use of any one of embodiments E64-E74 wherein, prior to said first dosage, the patient exhibits about 20 or about 21 headache days per month.

E76. The anti-CGRP antibody for use of any one of embodiments E64-E75 wherein said patient was diagnosed with migraine at least 10 years prior to said first dosage.

E77. The anti-CGRP antibody for use of any one of embodiments E64-E76 wherein said patient was diagnosed with migraine at least 15 years prior to said first dosage.

E78. The anti-CGRP antibody for use of any one of embodiments E64-E77 wherein said patient was diagnosed with migraine at least 18 or at least 19 years prior to said first dosage.

E79. The anti-CGRP antibody for use of any one of embodiments E64-E78 wherein said patient was diagnosed with chronic migraine at least 5 years prior to said first dosage.

E80. The anti-CGRP antibody for use of any one of embodiments E64-E79 wherein said patient was diagnosed with chronic migraine at least 8 years prior to said first dosage.

E81. The anti-CGRP antibody for use of any one of embodiments E64-E80 wherein said patient was diagnosed with chronic migraine at least 11 or at least 12 years prior to said first dosage.

E82. The anti-CGRP antibody for use of any one of embodiments E64-E81 wherein said anti-CGRP antibody is for administration of said first dosage when the patient has a headache.

E83. The anti-CGRP antibody for use of any one of embodiments E64-E82 wherein said anti-CGRP antibody is for administration of said first dosage when the patient has a migraine.

E84. The anti-CGRP antibody for use of any one of embodiments E64-E83 wherein said anti-CGRP antibody is for administration of said first dosage when the patient has a migraine with aura.

E85. The anti-CGRP antibody for use of any one of embodiments E64-E84, wherein said patient has a reduction in the number of migraine days by at least 50% in the one month period after being administered said first dose relative to the baseline number of migraine days experienced by that patient prior to said first dose.

E86. The anti-CGRP antibody for use of any one of embodiments E64-E85, wherein said patient has a reduction in the number of migraine days by at least 75% in the one month period after being administered said first dose relative to the baseline number of migraine days experienced by that patient prior to said first dose.

E87. The anti-CGRP antibody for use of any one of embodiments E64-E86, wherein said patient has a reduction in the number of migraine days by 100% in the one month period after being administered said first dose relative to the baseline number of migraine days experienced by that patient prior to said first dose.

E88. The anti-CGRP antibody for use of any one of embodiments E64-E87, wherein said patient has a reduction in the number of migraine days by at least 50% in the 12 week period after being administered said first dose relative to the baseline number of migraine days experienced by that patient prior to said first dose.

E89. The anti-CGRP antibody for use of any one of embodiments E64-E88, wherein said patient has a reduction in the number of migraine days by at least 75% in the 12 week period after being administered said first dose relative to the baseline number of migraine days experienced by that patient prior to said first dose.

E90. The anti-CGRP antibody for use of any one of embodiments E64-E89, wherein said patient has a reduction in the number of migraine days by 100% in the 12 week period after being administered said first dose relative to the baseline number of migraine days experienced by that patient prior to said first dose.

E91. The anti-CGRP antibody for use of any one of embodiments E64-E90, further comprising administering a second dose of said anti-CGRP antibody to said patient about 12 weeks or about 3 months after said first dose.

E92. The anti-CGRP antibody for use of any one of embodiments E64-E91, wherein said first dose comprises about 100 mg, about 125 mg, about 150 mg, about 175 mg, about 200 mg, about 225 mg, about 250 mg, about 275 mg, or about 300 mg of said anti-CGRP antibody.

E93. The anti-CGRP antibody for use of any one of embodiments E64-E92, wherein said anti-CGRP antibody or antibody fragment is aglycosylated or if glycosylated only contains only mannose residues.

E94. The anti-CGRP antibody for use of any one of embodiments E64-E93, wherein said anti-CGRP antibody consists of the light chain polypeptide of the light chain polypeptide of SEQ ID NO: 221 and the heavy chain polypeptide of SEQ ID NO: 201 or SEQ ID NO: 566.

E95. The anti-CGRP antibody for use of any of any one of embodiments E64-E94, wherein said anti-CGRP antibody is expressed in or obtained by expression in *Pichia pastoris*.

E96. The anti-CGRP antibody for use of any of any one of embodiments E64-E94, wherein said anti-CGRP antibody is expressed in or obtained by expression in CHO cells.

E97. The anti-CGRP antibody for use of any one of embodiments E64-E96, wherein said anti-CGRP antibody or anti-CGRP antibody fragment is comprised in a formulation comprising or consisting of histidine (L-histidine), sorbitol, polysorbate 80, and water.

E98. The anti-CGRP antibody for use of embodiment E97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +1-10% of said values, and having a pH of 5.8 or within +1-10% of said value.

E99. The anti-CGRP antibody for use of embodiment E97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−5% of said values, and/or having a pH of 5.8 or within +/−5% of said value.

E100. The anti-CGRP antibody for use of embodiment E97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−1% of said values, and/or having a pH of 5.8 or within +/−1% of said value.

E101. The anti-CGRP antibody for use of embodiment E97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.5% of said values, and/or having a pH of 5.8 or within +/−0.5% of said value.

E102. The anti-CGRP antibody for use of embodiment E97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.1% of said values, and/or having a pH of 5.8 or within +/−0.1% of said value.

EXAMPLES

The following examples are provided in order to illustrate the invention, but are not to be construed as limiting the scope of the claims in any way.

Example 1

Preparation of Antibodies that Bind CGRP

The preparation of exemplary anti-CGRP antibodies Ab1-Ab14 having the sequences in FIGS. 1A-12 is disclosed in commonly owned PCT Application WO/2012/162243, published on Nov. 29, 2012, the contents of which are incorporated by reference herein. This application exemplifies synthesis of these antibodies in *Pichia pastoris* cells. The present Applicant further contemplates synthesis of anti-CGRP antibodies Ab1-Ab14, and Ab6 in particular in CHO cells.

Example 2

Human Clinical Study Evaluating the Safety and Efficacy of an Anti-CGRP Antibody According to the Invention Clinical Treatment Protocol The humanized anti-CGRP IgG1 antibody identified herein as Ab6 was assessed in human subjects for its ability to inhibit, alleviate or prevent the number of, duration, and/or the intensity of migraine episodes. The Ab6 antibody contains the VL and light chain polypeptides respectively in SEQ ID NO: 222 and SEQ ID NO: 221, and contains the VH and heavy chain polypeptides respectively in SEQ ID NO: 202 and SEQ ID NO: 201. This antibody comprises an IgG1 constant region that contains a mutation in the heavy chain constant region (replacement of asparagine residue at position 297 with an alanine residue which substantially eliminates glycosylation and lytic activity (see U.S. Pat. No. 5,624,821).

Specifically, the clinical efficacy of the Ab6 antibody was tested in a placebo controlled double-blind, randomized study. The individuals in the study were all selected based on specific criteria. Particularly all were diagnosed as migraine sufferers at <50 years of age (ICHD-II, 2004 Section 1), and further had a history of migraine >12 months with >5 and <14 migraine days in each 28 day period in the 3 months prior to screening.

Further, all of the individuals in the study used acute migraine medications <14 days per 28 day period and, within those days, <10 days of triptan use per 28 day period in the 3 months prior to screening and the 28 day period of completion of eDiary prior to randomization.

Table 1 summarizes the demographic characteristics of the study population.

TABLE 1

Baseline Demographics and Clinical Characteristics

| Characteristic | Placebo iv (n = 82) | Ab6 1000 mg iv (n = 81) |
|---|---|---|
| Mean ± SD Age (years) | 39.0 (9.6) | 38.6 (10.8) |
| Mean ± SD Weight (kg) | 75.4 (14.4) | 75.0 (16.5) |
| Female Gender | 66 (80%) | 67 (83%) |
| Race: | | |
| Caucasian | 66 (80.5%) | 66 (81.5%) |
| African American | 9 (11.0%) | 10 (12.4%) |
| Asian | 3 (3.7%) | 4 (5.0%) |
| Other | 4 (4.8%) | 1 (1.1%) |
| Baseline (per 28 days): | | |
| Mean ± SD Migraine Days | 8.8 (2.7) | 8.4 (2.1) |
| Mean ± SD Migraine Episodes | 6.7 (2.4) | 6.0 (2.2) |
| Mean ± SD Headache Frequency | 9.6 (2.8) | 9.2 (2.6) |
| Mean ± SD Migraine Hours | 72.2 (51.0) | 80.1 (49.1) |
| Mean ± SD HIT-6 Score | 64.5 (4.44) | 63.8 (5.21) |
| Mean ± SD MSQ RFP Score | 49.0 (17.9) | 49.5 (21.2) |
| Mean ± SD MSQ RFR Score | 61.9 (22.7) | 63.9 (24.0) |
| Mean ± SD MSQ EF Score | 59.5 (22.9) | 59.8 (27.0) |

Throughout the study all of the individuals were required to record their migraine status daily using an e-diary. In the e-diary the subjects in the study were required to record the number of migraine days/month, migraine episodes/month, migraine hours/month, migraine severity, and the use of any abortive medicine such as triptans.

In addition, the study participants were required to use the e-diary to record their migraine status in the 28 day period prior to treatment with antibody or placebo in order to establish a migraine day/hour/episode baseline per month. Also, this allowed the subjects in the study to become familiar with the use of the e-diary.

Figure 17:
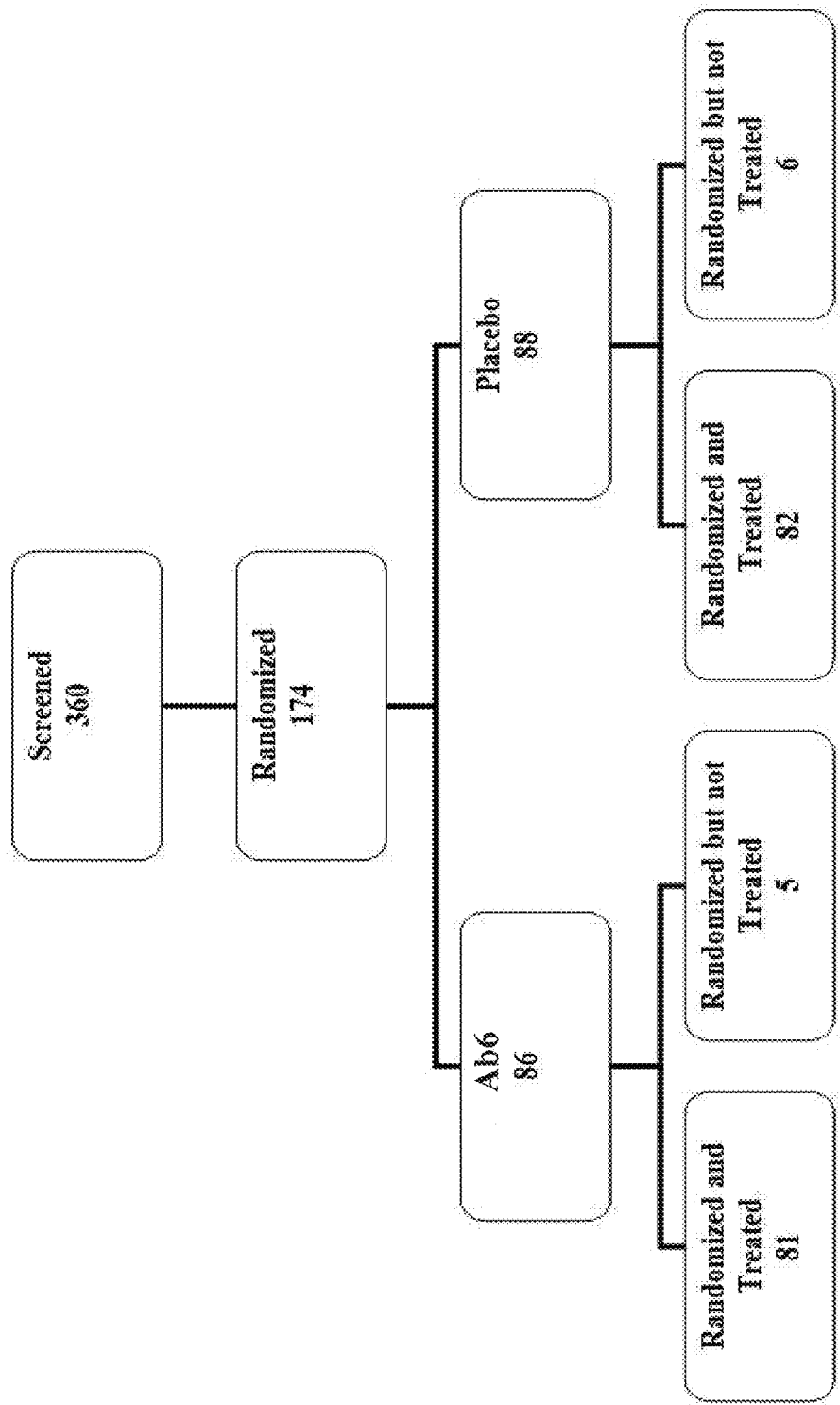
FIG. 17 summarizes the screening of patients, allocation into the treatment and control groups, and loss of patients through follow-up.

After the 28-day run-in the subjects in the study were broken into two groups, each including 80 subjects (FIG. 17). In the first group, i.e., the antibody treatment group, (n=80) each subject in the group was administered intravenously a single 1000 mg dose of Ab6. In the second group (n=80), i.e., the placebo group, each of the subjects was given an intravenous injection containing only the aqueous antibody carrier solution.

The individuals in the treated and placebo groups were assessed in the 24 weeks post-dose administration. Initially, a 12 week interim analysis was conducted. Subsequent to the 12 week interm analysis, a refined analysis was conducted. This refined analysis potentially included, for example, addition or removal of patient data in accord with the study protocol, e.g., updating data that had not been fully loaded from the e-diaries. This refinement resulted in slight changes but did not alter the overall conclusions.

The efficacy of the antibody versus the placebo was assessed in part based on the recorded data in the e-diary entries. For example, this analysis included a comparison of the number of recorded migraine days/month, migraine episodes/month, migraine hours/month in the subjects in the treated versus the placebo group. The percentage of responders in each group (i.e., the subjects with 50%, 75%, and 100% reduction in migraine days) in both groups was also compared.

In addition, the responses of the Ab6- and placebo-treated subjects in both groups to MSQ and HIT-6 questionnaires are to be evaluated and compared. MSQ is a frequently utilized disease-specific tool to assess the impact of migraine on health-related quality of life (HRQL). MSQ comprises a 16-item Migraine-Specific Quality-of-Life Questionnaire (Version 1.0), which was developed by Glaxo Wellcome Inc. MSQ is hypothesized to measure 3 parameters: (i) Role Function-Restrictive; (ii) Role Function-Preventive; and (iii) Emotional Function.

The HIT-6 or functional impact (also called the Headache Impact Test or HIT-6) similarly is a well known tool for assessing migraine intensity. This test uses six questions to capture the impact of headache and its treatment on an individual's functional health and well-being.

Also, the pharmacokinetic (PK) properties of the CGRP antibody and immunogenicity are to be assessed in the Ab6 antibody treated subjects.

Clinical Results and Analysis

The results of this human clinical trial and analysis through week 12 in the treated subjects are summarized in the Table 2 below.

TABLE 2

Responder analysis for migraine days

| Time period | % reduction migraine days | Placebo iv | Ab6 1000 mg iv | P value |
|---|---|---|---|---|
| Week 1-4 | | n = 80 | n = 75 | |
| | 50 | 40 (50.0) | 58 (77.3) | p = 0.0005 |
| | 75 | 19 (23.8) | 39 (52.0) | p = 0.0005 |
| | 100 | 4 (5.0) | 21 (28.0) | p = 0.0001 |
| Week 5-8 | | n = 80 | n = 78 | |
| | 50 | 43 (53.8) | 59 (75.6) | p = 0.0048 |
| | 75 | 28 (35.0) | 35 (44.9) | p = 0.2555 |
| | 100 | 12 (15.0) | 21 (26.9) | p = 0.0791 |
| Week 9-12 | | n = 77 | n = 72 | |
| | 50 | 51 (66.2) | 54 (75.0) | p = 0.2827 |
| | 75 | 24 (31.2) | 38 (52.8) | p = 0.0083 |
| | 100 | 13 (16.9) | 29 (40.3) | p = 0.0019 |

In addition, the results of the clinical study were compared based on the number of responders in the treatment and placebo groups. As shown in FIG. 13 the number of subjects who showed a 50, 75 or 100% reduction in migraine days for each month of the interim period were compared in the treatment and placebo groups. As shown in the figure, 60% of the Ab6-treated group had at least 50% reduction in headache days, 31% of the Ab6-treated group had at least 75% reduction in headache days and 15% of the Ab6 treated group had 100% reduction in headache days.

By contrast, 33% of the placebo-treated group had at least 50% reduction in headache days, 9% of the placebo-treated group had at least 75% reduction in headache days, and 0% (none) of the placebo-treated group had 100% reduction in headache days.

These results clearly show that the reduction in the number of migraine days was much greater in the Ab6-treated group. But for the significant placebo effect, the difference in these numbers would have been more pronounced. (Elevated placebo effect is not surprising as the phenomenon is often very high for migraine and other neurological drugs).

Figure 14:
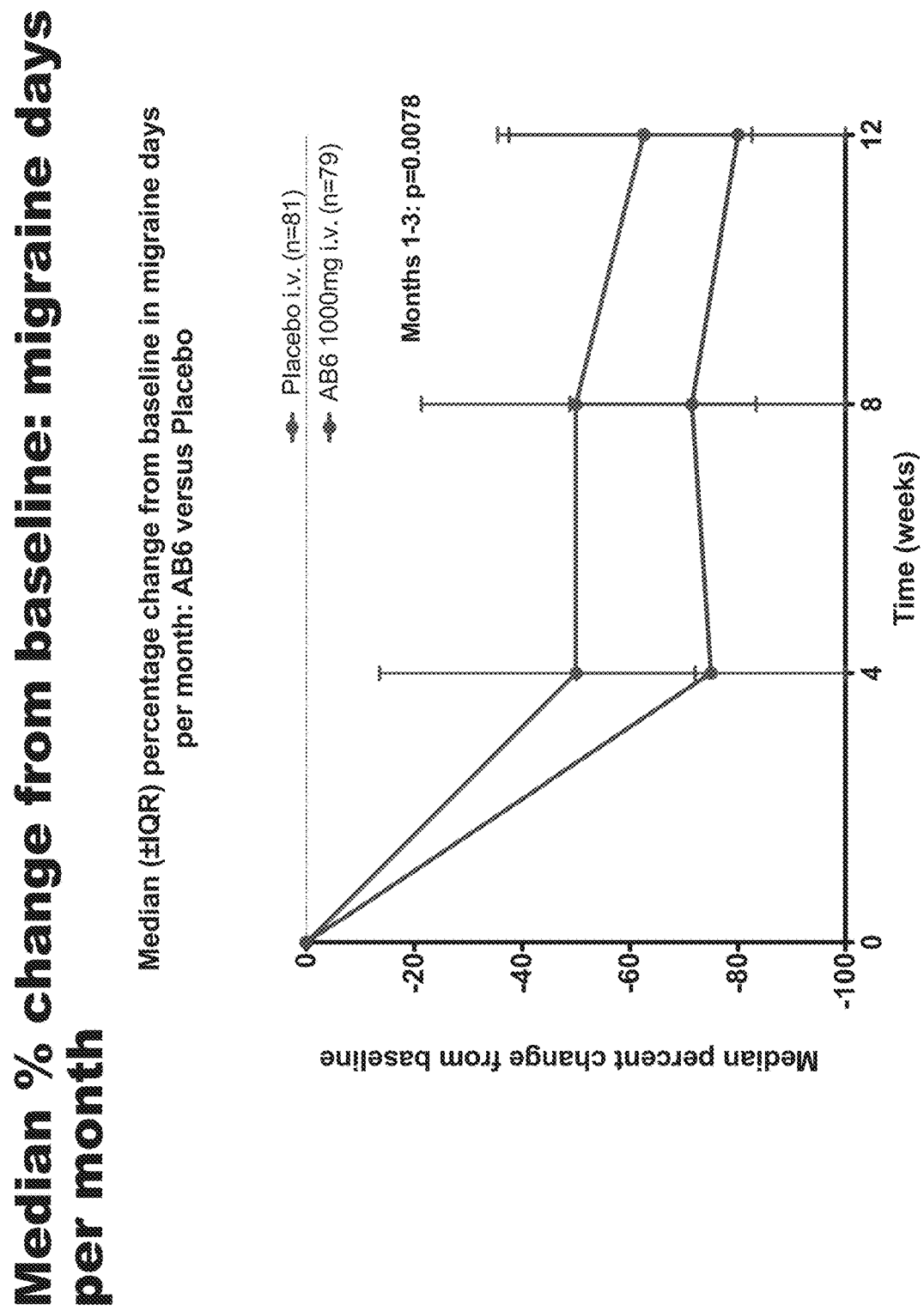
FIG. 14 shows the median (±QR) % change from baseline in the number of migraine days per month in the placebo and Ab6-treated group over the 12 weeks post-treatment. (p=0.0078). The upper (red) line and lower (blue) line show results for placebo-treated controls and patients administered 1000 mg Ab6, respectively.

In addition, the % change from baseline in the number of migraine days per month in the placebo and Ab6-treated group was compared. As shown in FIG. 14, the median (±QR) % change from baseline in the number of migraine days per month in the placebo and Ab6-treated group was compared for the 2 groups during the 12 weeks post-treatment. These results which are statistically significant (p=0.0078) clearly show the Ab6-treated group had a much greater reduction in the number of headache days per month compared to baseline than the placebo-treated group.

Figure 15:
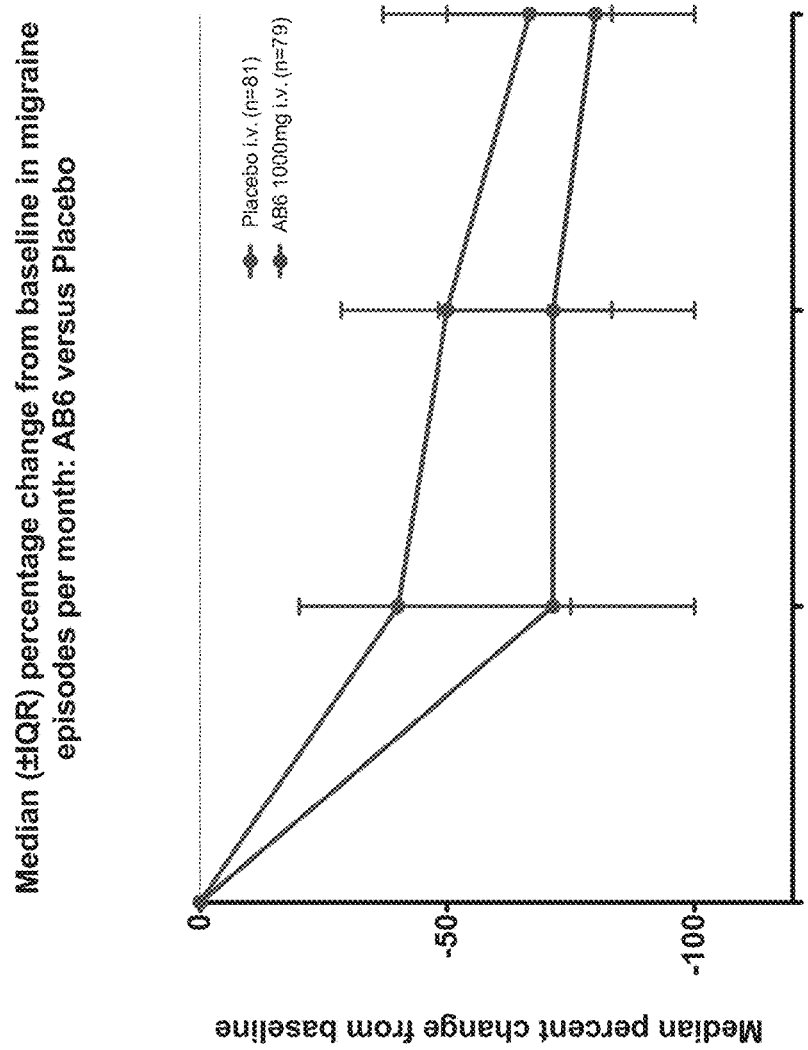
FIG. 15 shows the median (±QR) % change from baseline in the number of migraine episodes per month in the placebo and Ab6-treated group over the 12 weeks post-treatment. The upper (red) line and lower (blue) line show results for placebo-treated controls and patients administered 1000 mg Ab6, respectively.

Also, the % change from baseline in the number of migraine episodes per month in the placebo and Ab6-treated group was compared. As shown in FIG. 15 the median (±QR) % change from baseline in the number of migraine episodes per month in the placebo and Ab6-treated group was compared during the 12 weeks post-treatment. These results indicate that the Ab6-treated group had a significantly greater reduction in the number of migraine episodes per month compared to baseline than the placebo-treated group.

Figure 16:
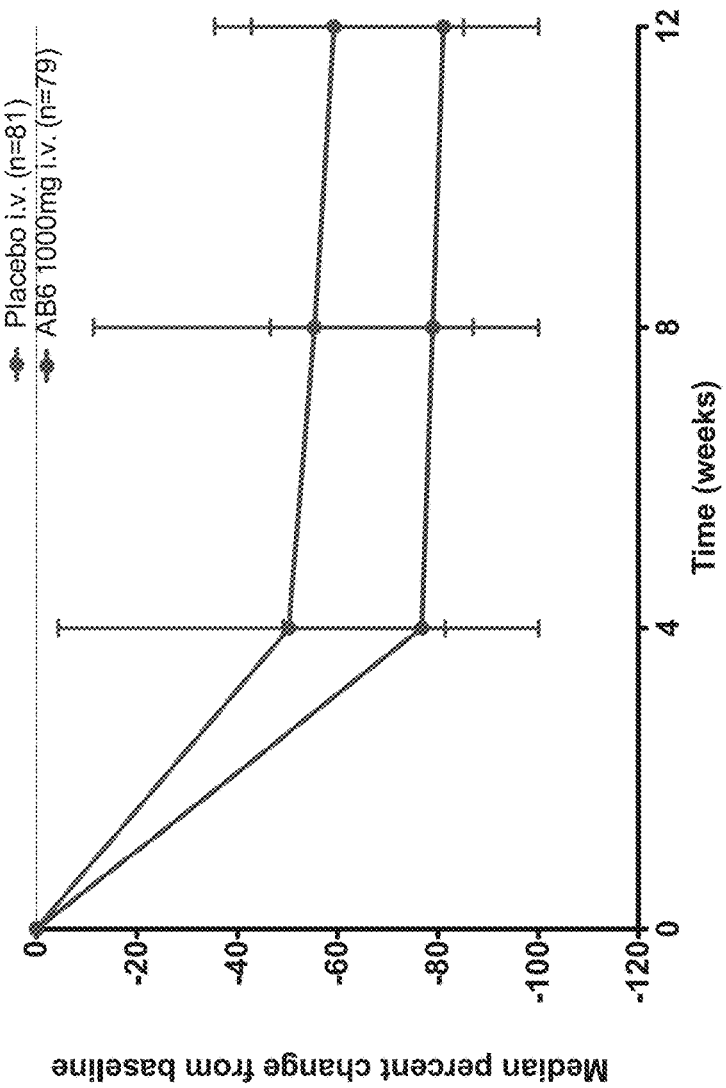
FIG. 16 shows the median (±QR) % change from baseline in the number of migraine hours per month in the placebo and Ab6-treated group over the 12 weeks post-treatment. The upper (red) line and lower (blue) line show results for placebo-treated controls and patients administered 1000 mg Ab6, respectively.

Further, the % change from baseline in the number of migraine hours per month in the placebo and Ab6-treated group was compared. As shown in FIG. 16, the median (±QR) % change from baseline in the number of migraine hours per month in the placebo and Ab6-treated group was compared for the 2 groups during the 12 weeks post-treatment. These results clearly show the Ab6-treated group had a greater reduction in the number of migraine hours per month compared to baseline than the placebo-treated group.

Figure 18:
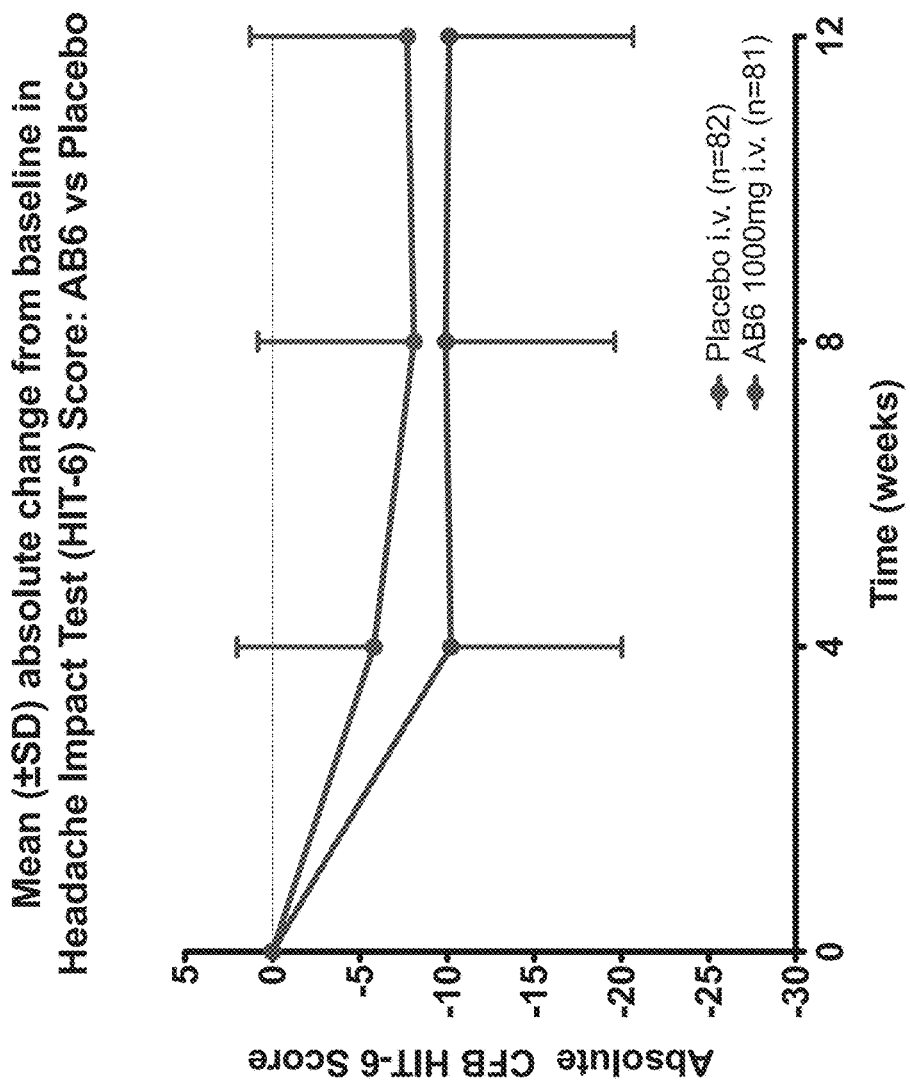
FIG. 18 compares the HIT-6 responder analysis for the Ab6-treated and placebo groups at baseline, week 4 after treatment, week 8 after treatment and week 12 after treatment.
Figure 19:
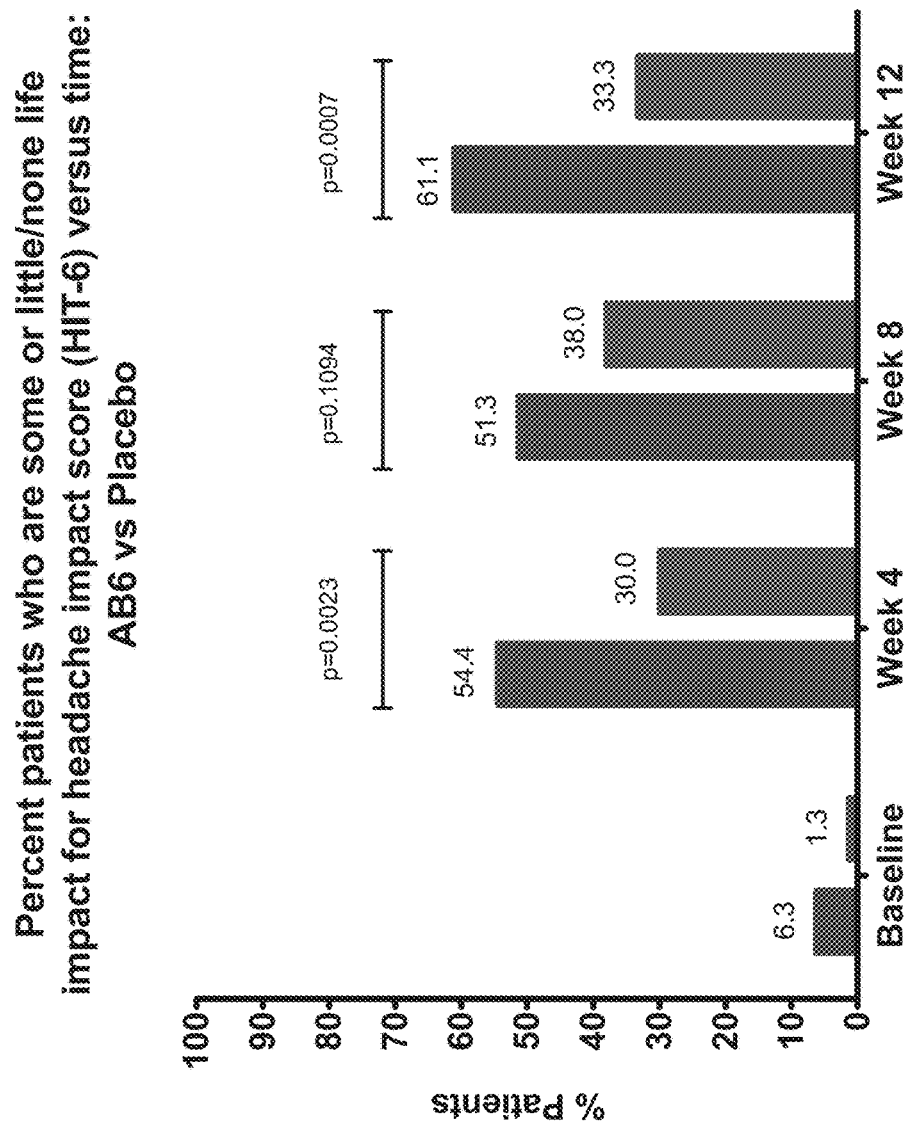
FIG. 19 shows the percentage of patients for whom the HIT-6 analysis indicated that the effect of headaches was only "some" or "little/none" at baseline and after Ab6 administration. At baseline most patients had either "substantial" or "severe" impact from migraines. At each subsequent time point, a significantly greater percentage of patients administered 1000 mg Ab6 had only "some" or "little/none" HIT-6 impact (left bar in each group, colored blue) as compared to placebo controls (right bar in each group, colored red).
Figure 22:
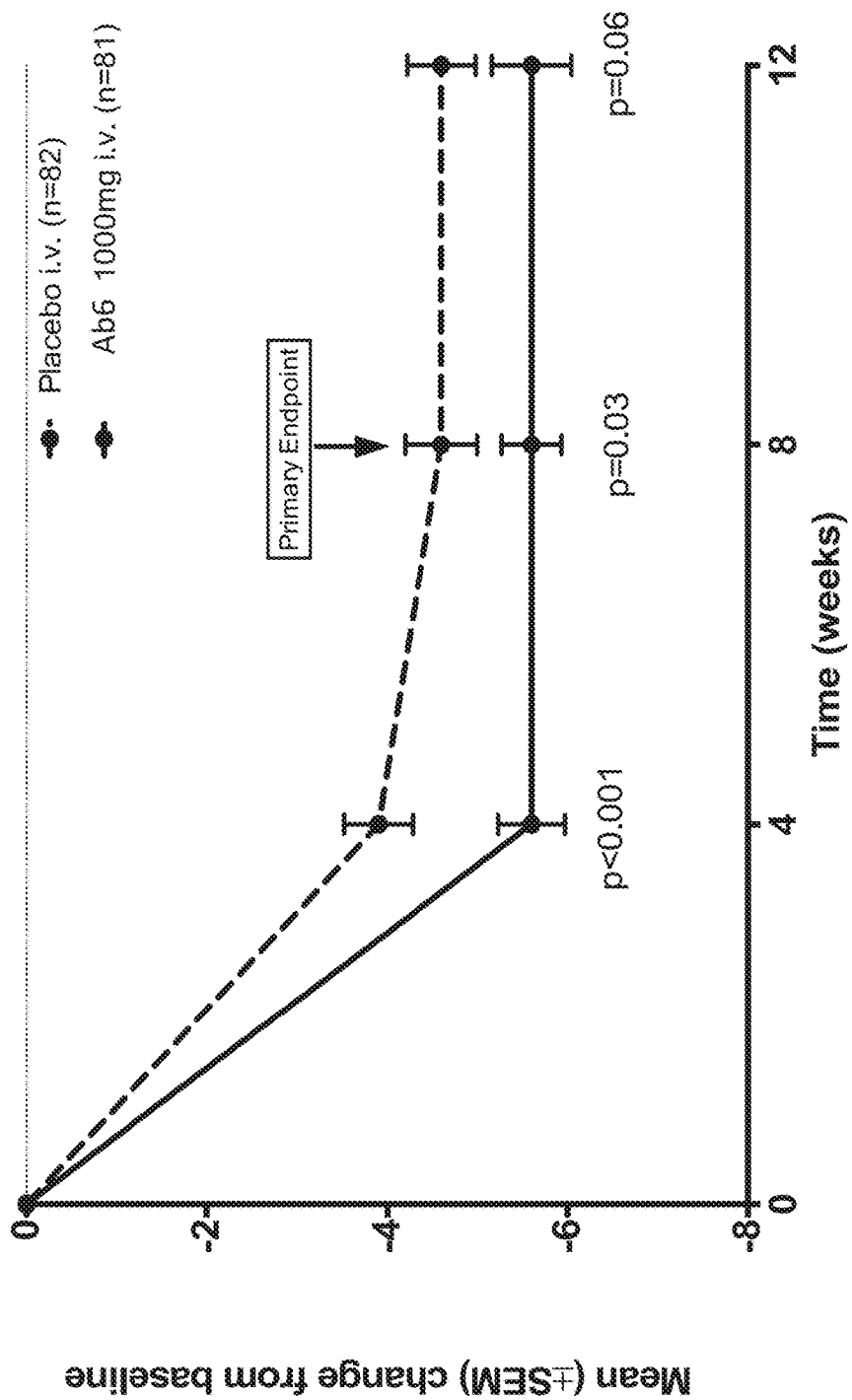
FIG. 22 shows the change (mean+−SEM) change from baseline in migraine days per month for Ab6 (1000 mg i.v.) versus placebo as a single dose for the study described in Example 2.

In addition, the HIT-6 results were compared for both groups. As noted, this questionnaire finds well accepted usage in assessing the migraine status of individuals with frequent/chronic migraine. FIG. 18 compares the HIT-6 responder analysis for the Ab6-treated and placebo groups at baseline, week 4 after treatment, week 8 after treatment, and week 12 after treatment. The results at each time point reveal that the Ab6-treated group had a statistically significant improvement in the HIT-6 scores relative to the placebo group, i.e., 54.4% for the Ab6-treated compared to 30% for the placebo at week 4 (p=0.0023), 51.3% for the Ab6-treated compared to 38.0% for the placebo at week 8 (p=0.1094) and 61.1% for the Ab6-treated compared to 33.3% for the placebo at week 12 (p=0.0007). FIG. 19 shows the percentage of patients having a HIG-6 score of some or little/none over time in the placebo and Ab6 treatment groups (statistical significance a shown).

In addition, FIG. 20 contains the pharmacokinetic (PK) profile for Ab6 administered intravenously at a single dosage of 1000 mg in mg/mL over the 24 week period following Ab6 administration.

FIG. 21 contains plasma-free pharmacokinetic (PK) parameters N (number of patients), mean, and standard deviation (SD) for a single 1000 mg intravenous dosage of Ab6. The parameters shown in the table and the units are $C_{max}$ (μg/mL), $AUC_{0-\infty}$ (mg*hr/mL), half-life (days), $V_z$ (L) and $C_L$ (mL/hr).

Further analysis was conducted for patient data between 12-weeks and 24-weeks. The treatment group continued to exhibit decreased migraine days relative to the control group, however, the magnitude of the difference decreased over time. Additionally, the control group exhibited fewer migraine days per month than at baseline. This was thought to result at least in part from "diary fatigue" wherein patients potentially report no migraine on a day in which a migraine actually occurred, in order to avoid the time and effort of answering further queries about the migraine that would result from giving an affirmative answer to the question of whether they had a migraine on a given day.

Figure 23:
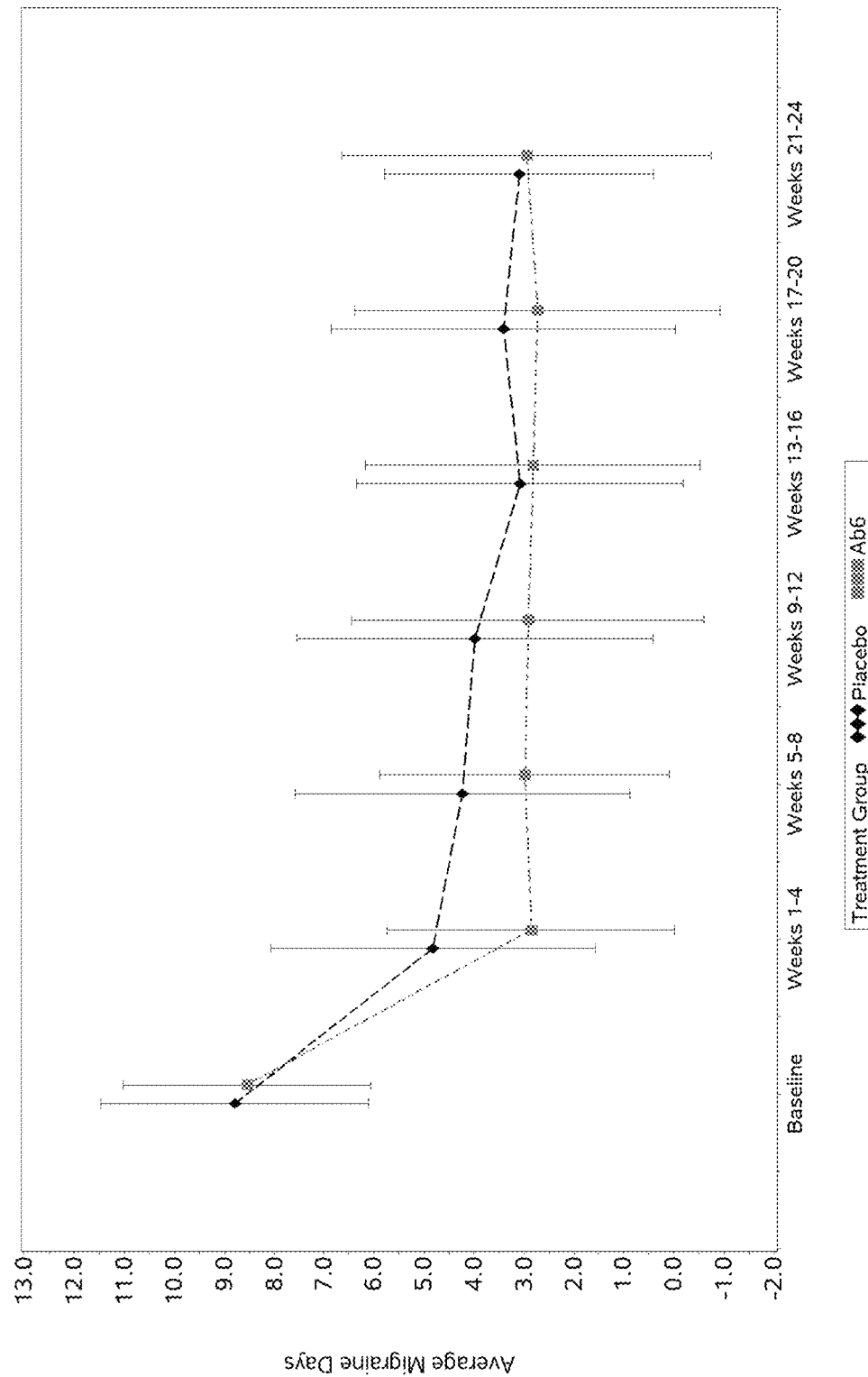
FIG. 23 shows the average migraine days (+/−SD) over time for the full analysis population for the study described in Example 2. Normalization was applied to visit intervals where eDiaries were completed for 21-27 days by multiplying the observed frequency by the inverse of the completion rate.
Figure 24:
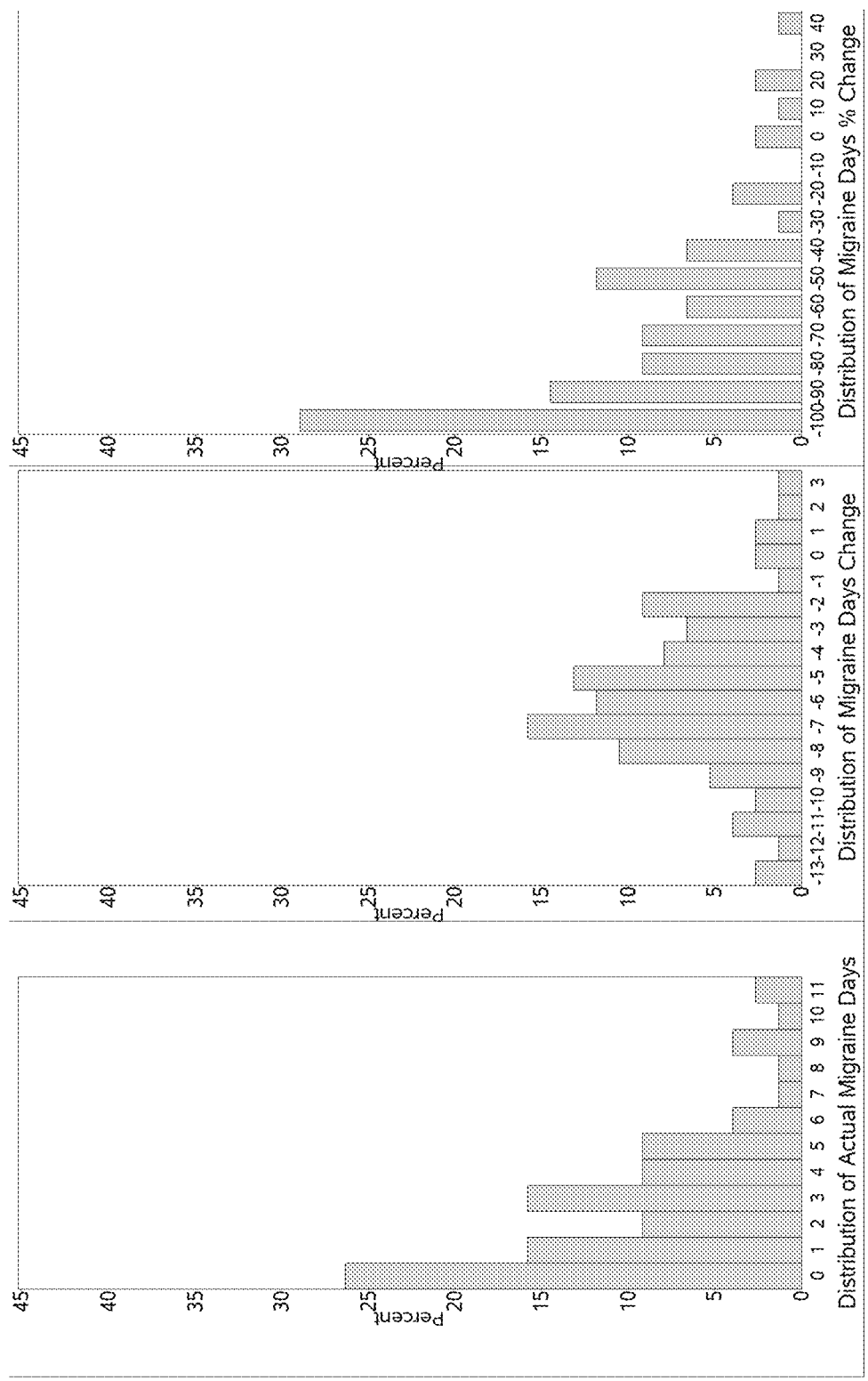
FIG. 24 shows the distribution of migraine days actual and change for the Ab6 treatment group during weeks 1-4 for the study described in Example 2.
Figure 25:
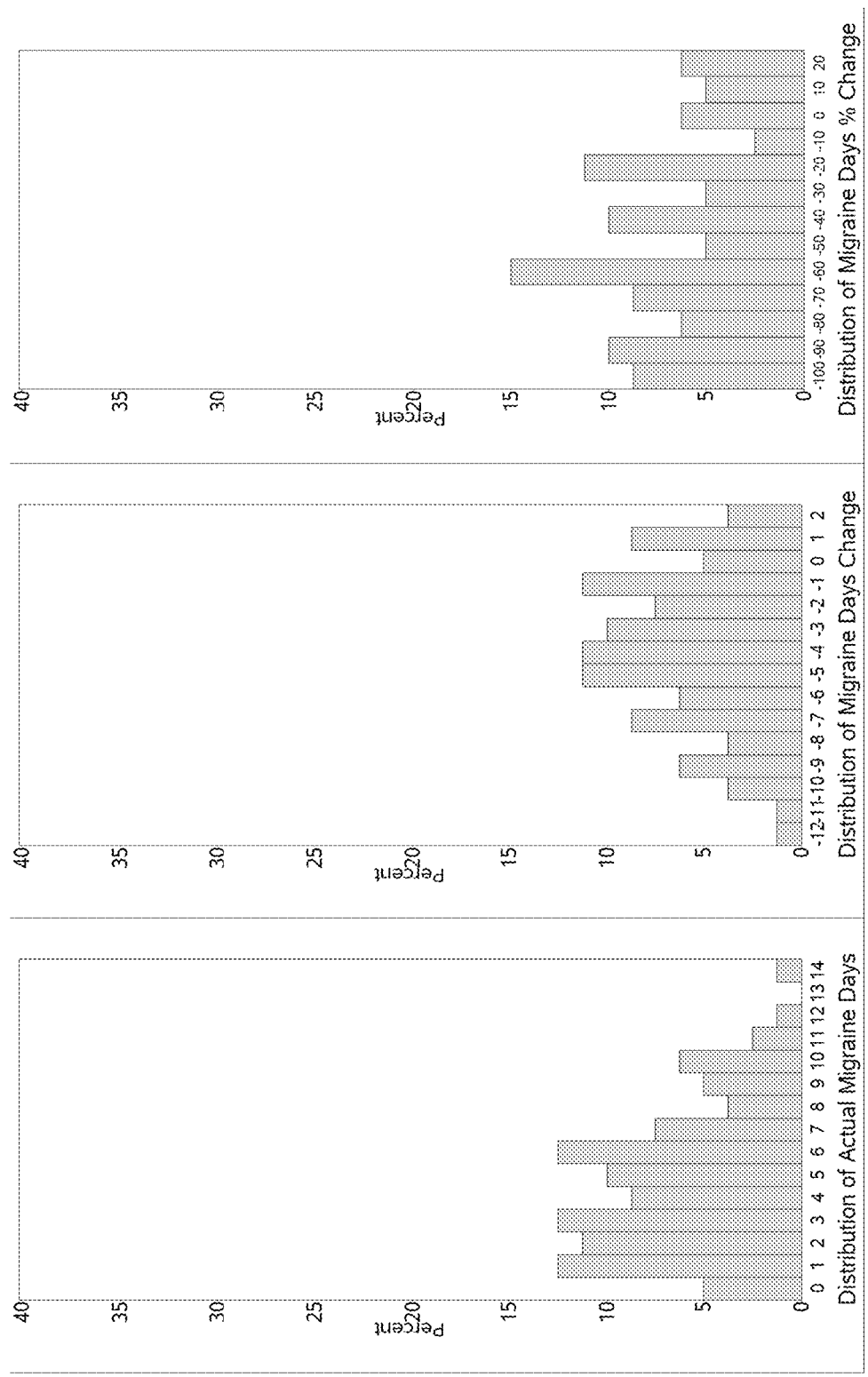
FIG. 25 shows the distribution of migraine days actual and change for the placebo group during weeks 1-4 for the study described in Example 2.
Figure 26:
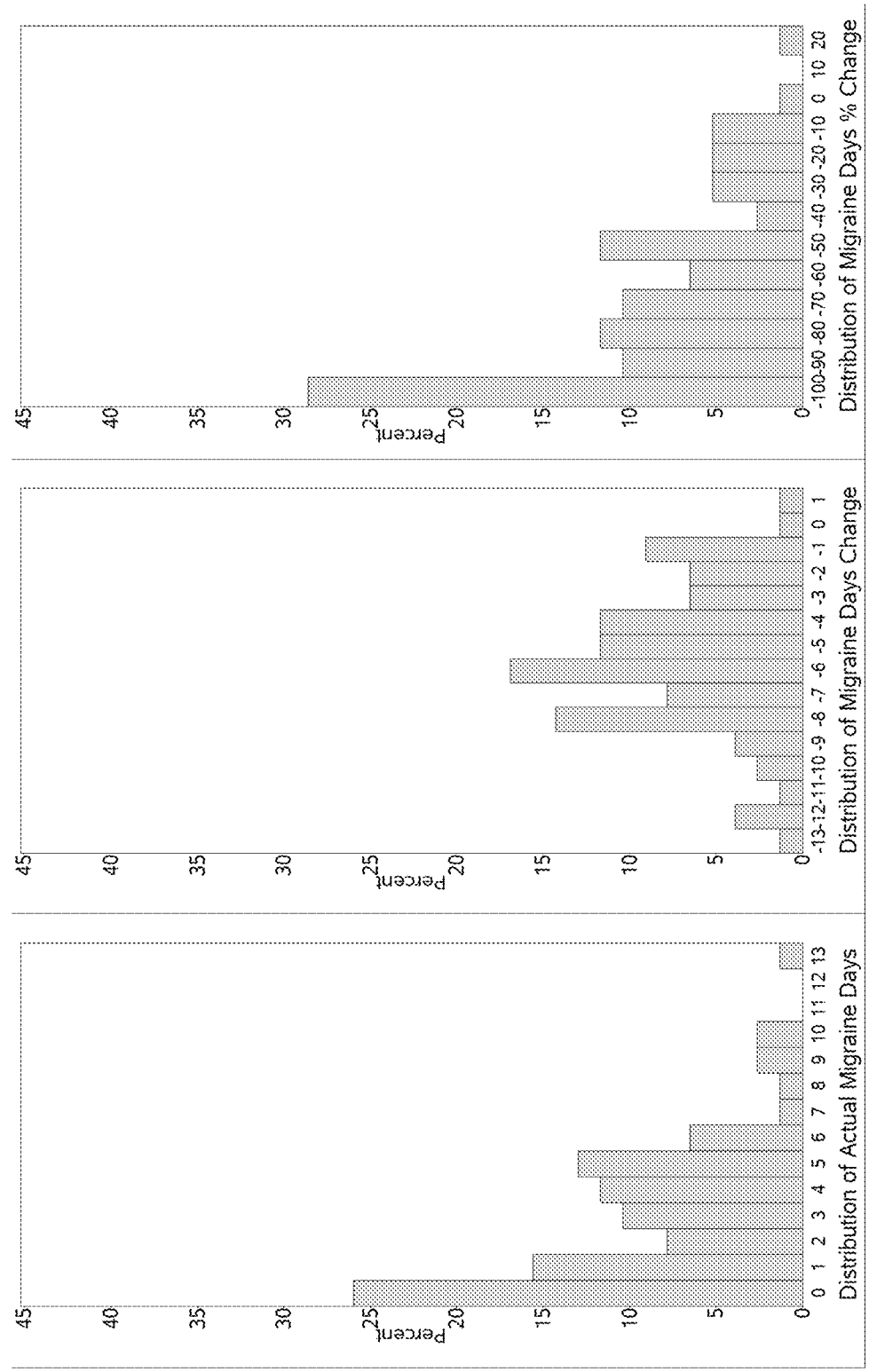
FIG. 26 shows the distribution of migraine days actual and change for the Ab6 treatment group during weeks 5-8 for the study described in Example 2.
Figure 27:
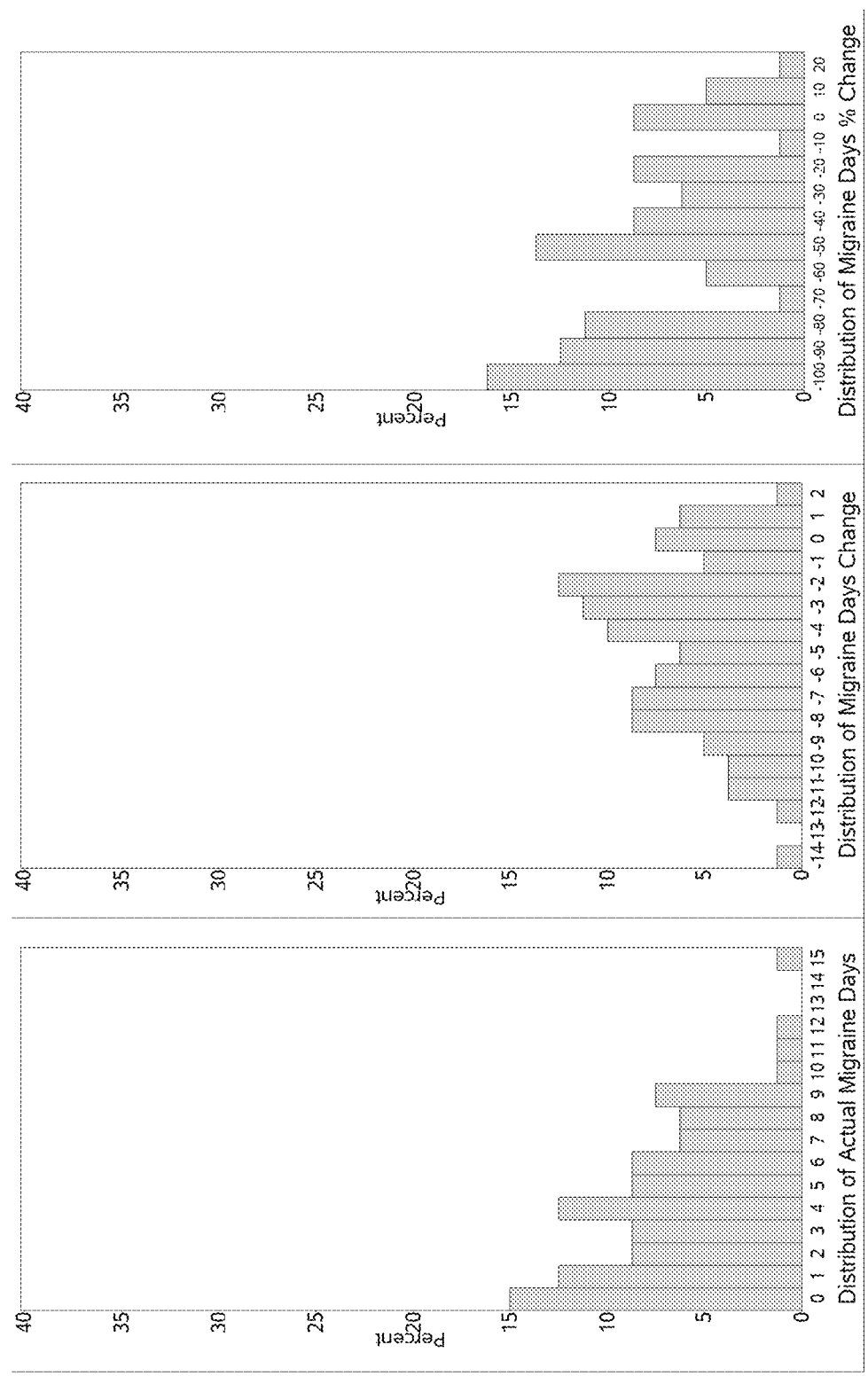
FIG. 27 shows the distribution of migraine days actual and change for the placebo group during weeks 5-8 for the study described in Example 2.
Figure 28:
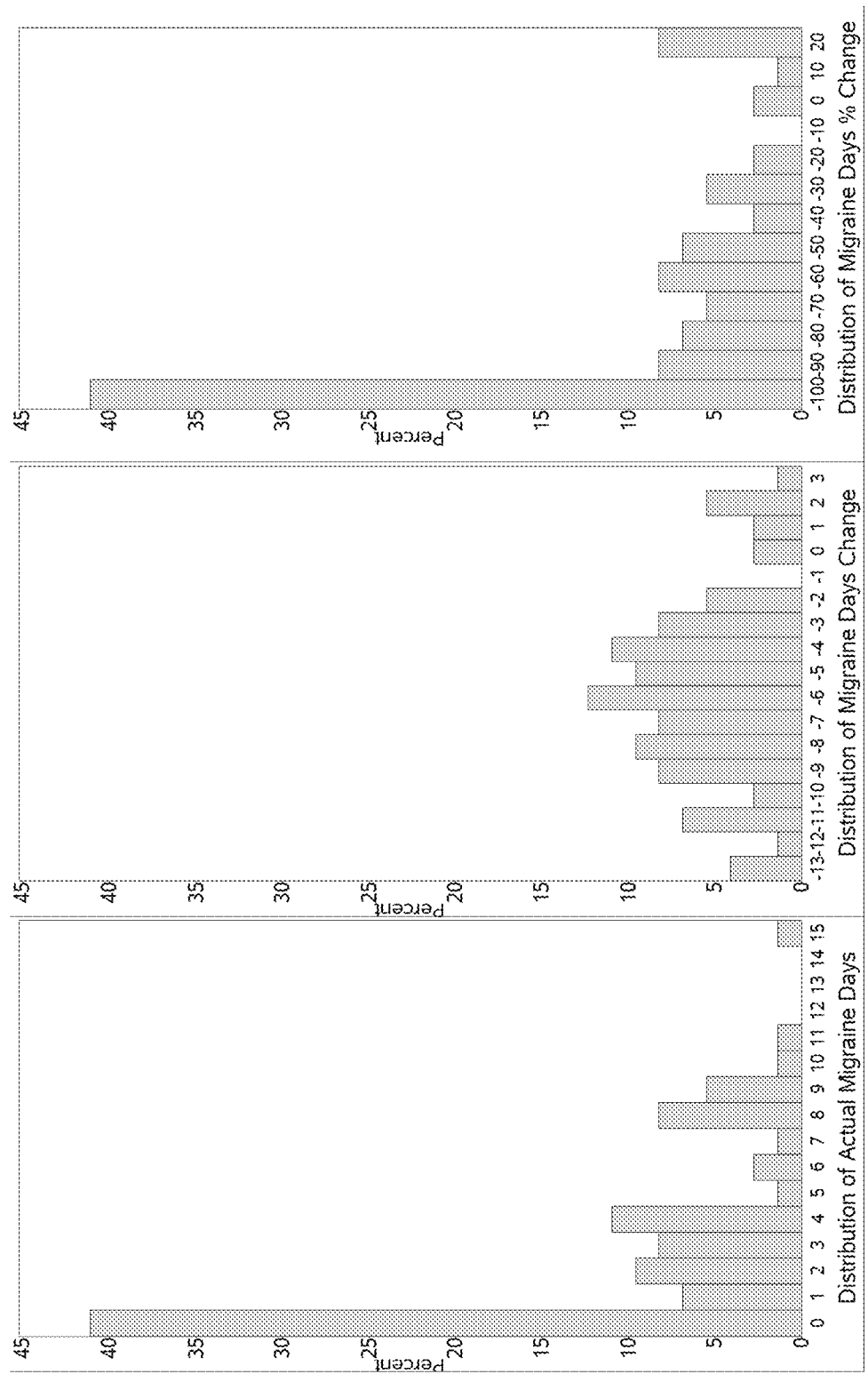
FIG. 28 shows the distribution of migraine days actual and change for the Ab6 treatment group during weeks 9-12 for the study described in Example 2.
Figure 29:
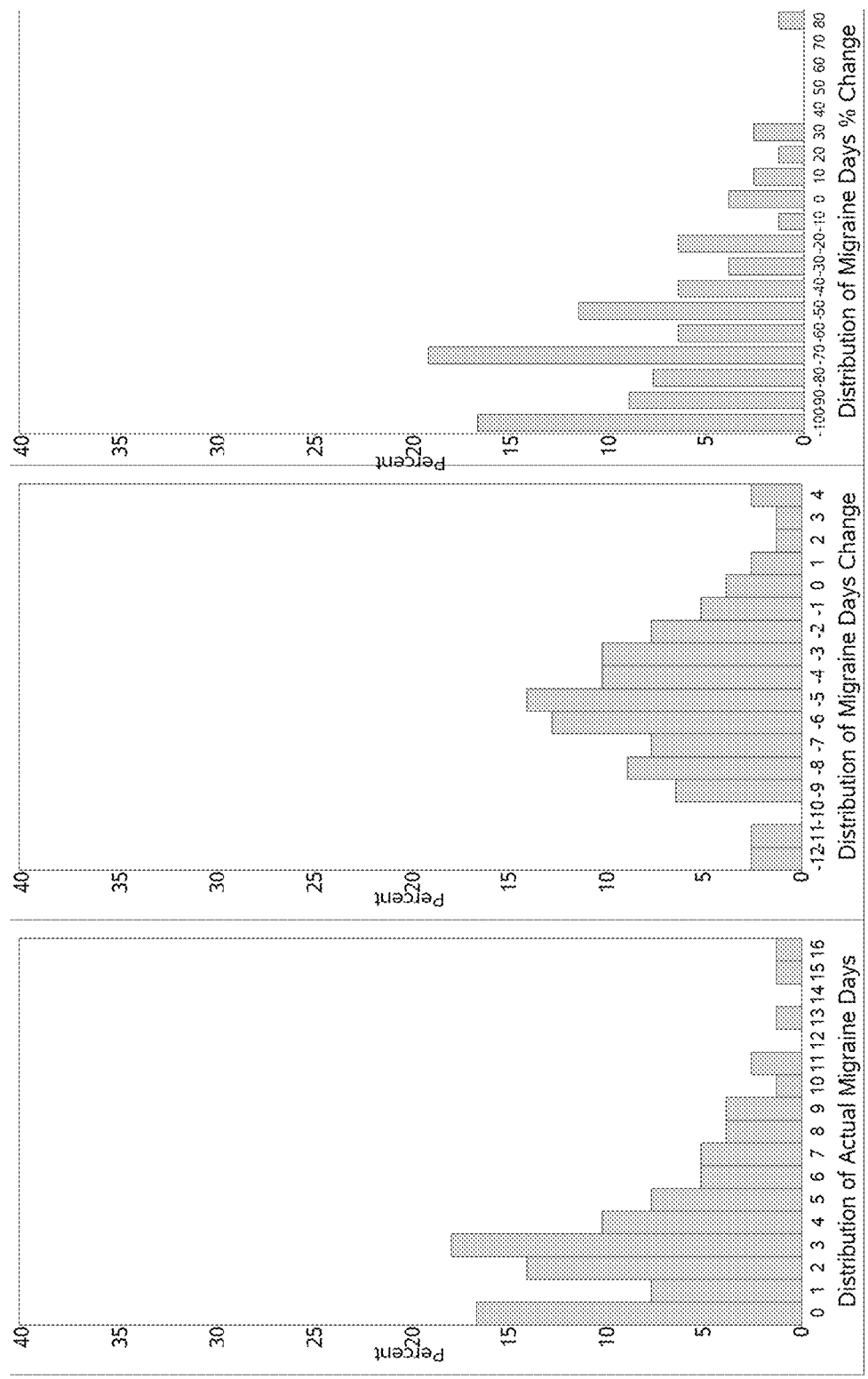
FIG. 29 shows the distribution of migraine days actual and change for the placebo group during weeks 9-12 for the study described in Example 2.

Further analysis of the study results are shown in FIGS. 22-33. These result include analysis of the change (mean+/−SEM) from baseline in migraine days per month for Ab6 (1000 mg i.v.) versus placebo (FIG. 22), change in average migraine days (+/−SD) over time for the full analysis population (FIG. 23). Additionally, shown are the distribution of migraine days actual and change for the Ab6 treatment group during weeks 1-4 (FIG. 24), distribution of migraine days actual and change for the placebo group during weeks 1-4 (FIG. 25), distribution of migraine days actual and change for the Ab6 treatment group during weeks 5-8 (FIG. 26), distribution of migraine days actual and change for the placebo group during weeks 5-8 (FIG. 27), distribution of migraine days actual and change for the Ab6 treatment group during weeks 9-12 (FIG. 28), and distribution of migraine days actual and change for the placebo group during weeks 9-12 (FIG. 29).

Figure 30:
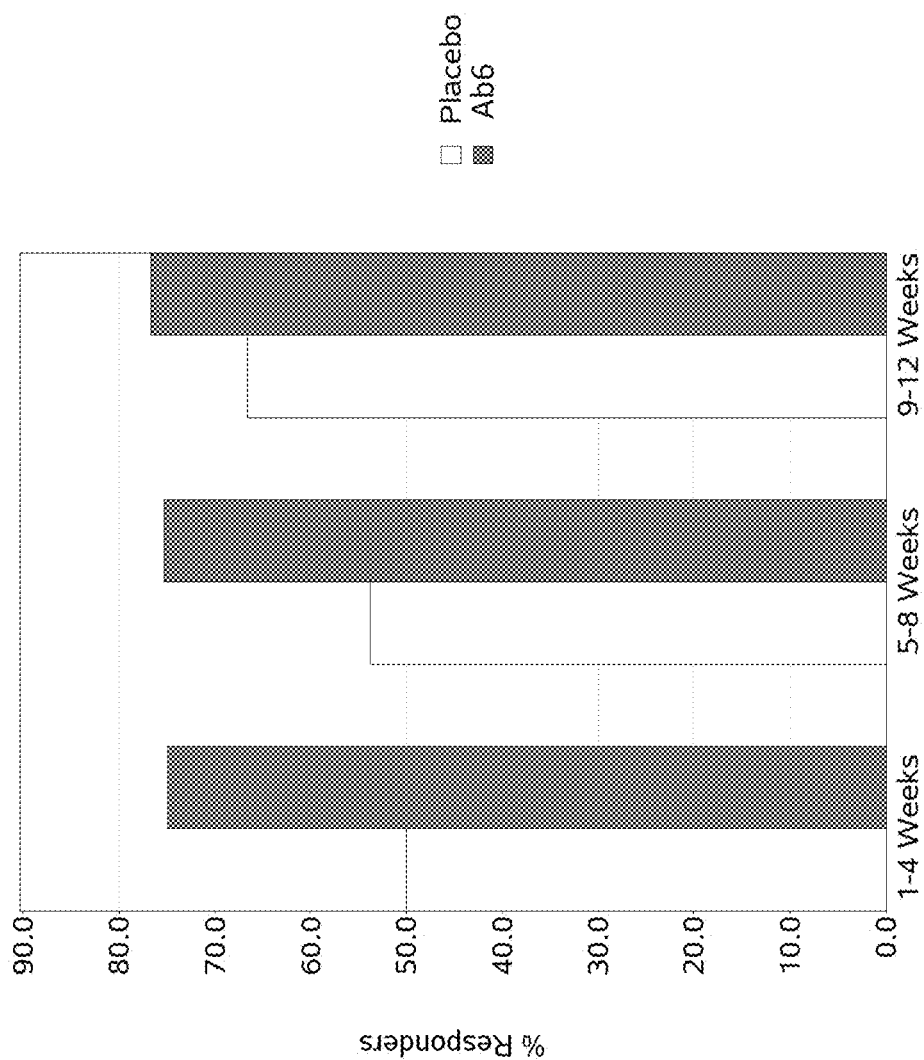
FIG. 30 shows the 50% responder rate for the Ab6 and placebo treatment groups for the study described in Example 2. Subjects with >50% reduction in migraine frequency were considered to be a 50% responder. Normalization was applied to visit intervals where eDiary was completed for 21-27 days by multiplying the observed frequency by the inverse of the completion rate.
Figure 31:
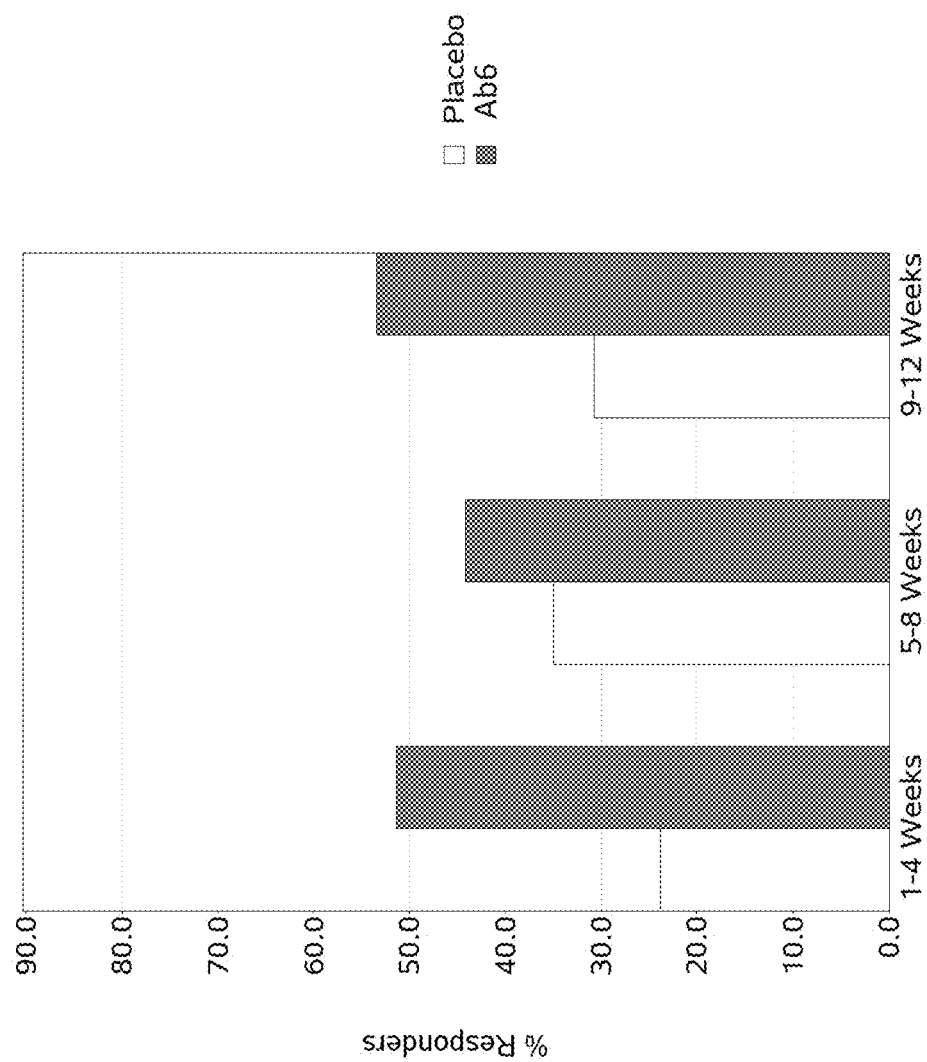
FIG. 31 shows the 75% responder rate for the Ab6 and placebo treatment groups for the study described in Example 2. Subjects with >75% reduction in migraine frequency were considered to be a 75% responder. Normalization was applied as described with FIG. 30.
Figure 32:
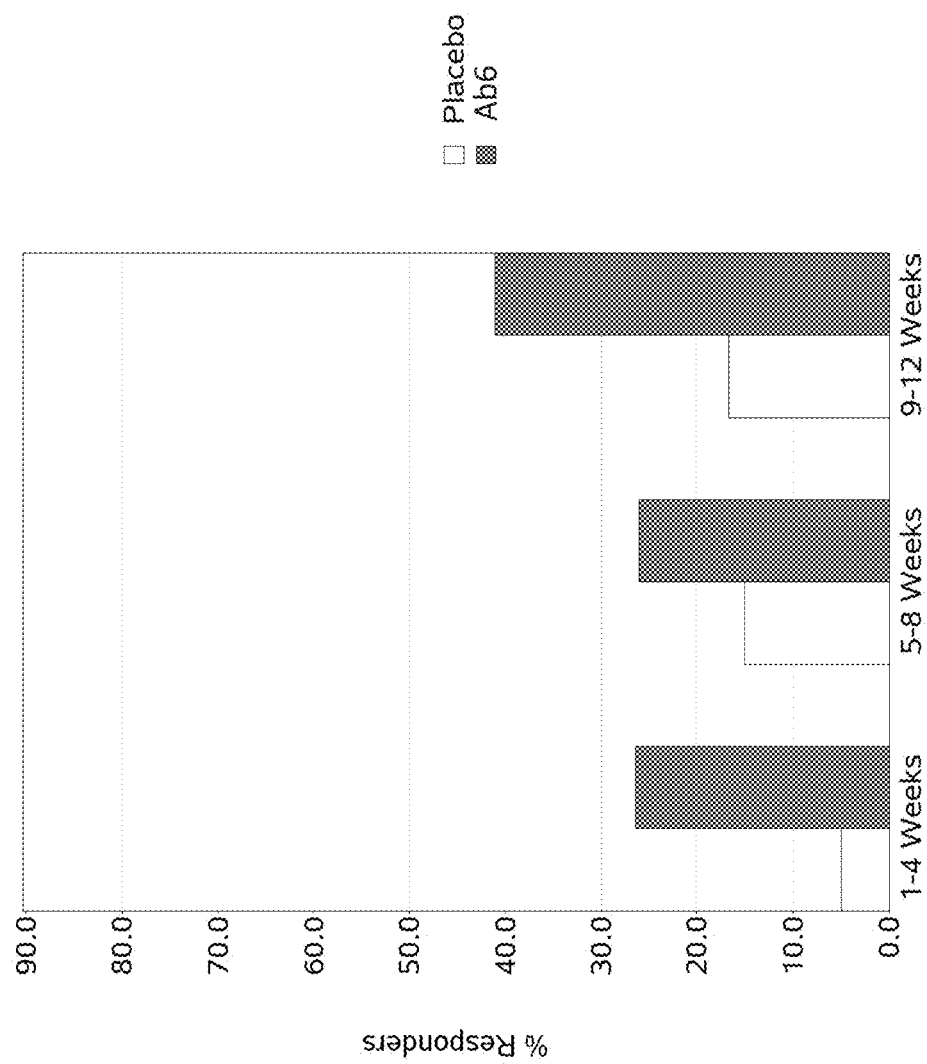
FIG. 32 shows the 100% responder rate for the Ab6 and placebo treatment group for the study described in Example 2. Subjects with 100% reduction in migraine frequency were considered to be a 100% responder. Normalization was applied as described with FIG. 30.

Responder rate analysis was also performed (FIGS. 30-32). These figures respectively show the 50%, 75%, and 100% responder rate for the Ab6 and placebo treatment groups. Subjects with >50% reduction in migraine frequency were considered to be a 50% responder. Subjects with >75% reduction in migraine frequency were considered to be a 75% responder. Likewise, subjects with 100% reduction in migraine frequency were considered to be a 100% responder.

In FIGS. 22 and 30-32, normalization was applied to visit intervals where eDiaries were completed for 21-27 days by multiplying the observed frequency by the inverse of the completion rate.

Figure 33:
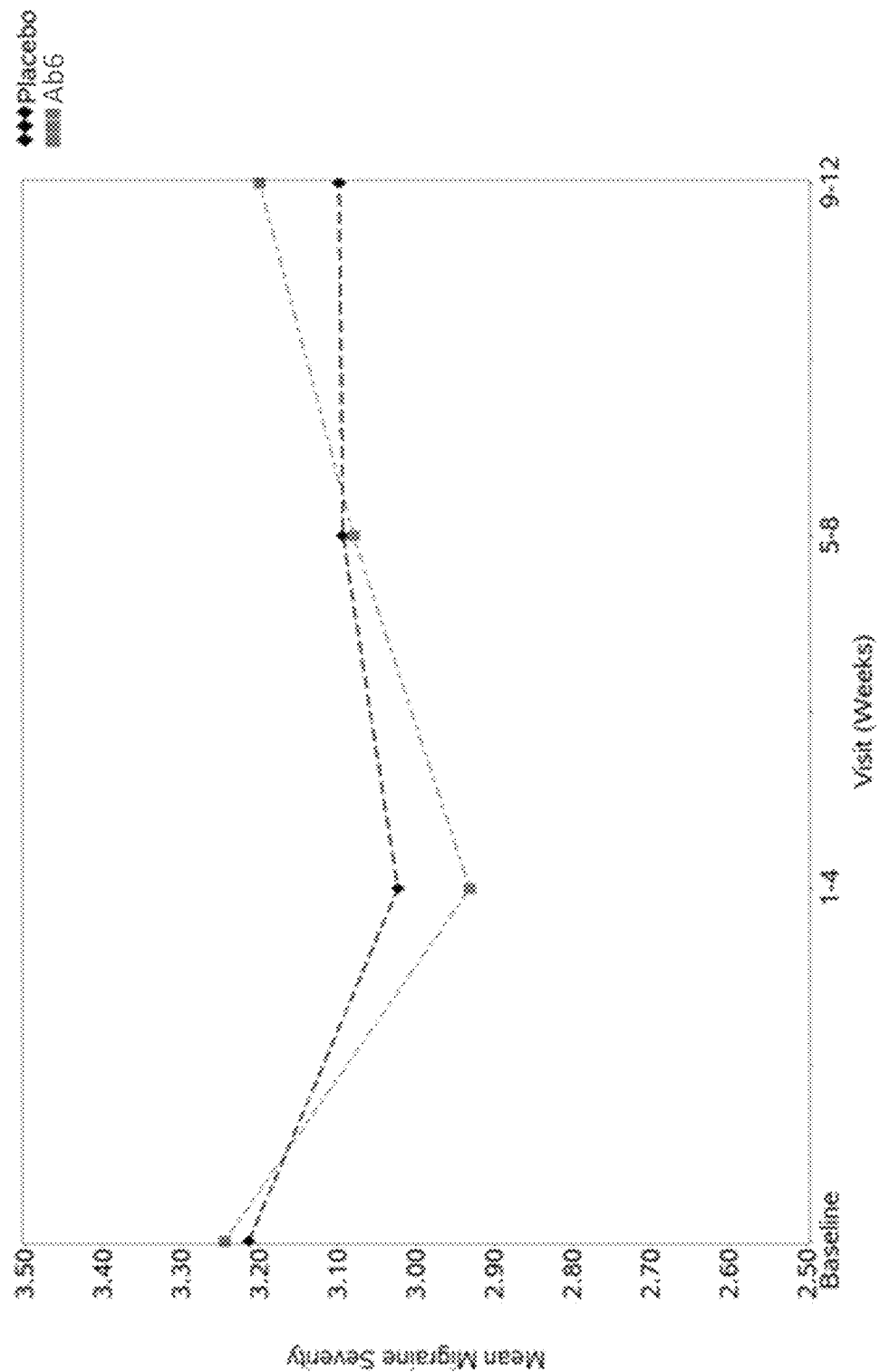
FIG. 33 shows the mean migraine severity over time for the full analysis population for the study described in Example 2. On the scale used, a mean migraine score of 3 represents "moderate pain."

Migraine severity was also analyzed. FIG. 33 shows the mean migraine severity over time for the full analysis population. On the scale used, a mean migraine score of 3 represents "moderate pain."

FIG. 34 summarizes the change from baseline in migraine days, migraine episodes, migraine hours, average migraine severity, headache frequency, and outcome measures including the HIT-6 score, MSQ (Migraine Specific Quality of Life Questionnaire) RFP (Role Function-Preventative), MSQ RFR (Role Function-Restrictive), and MSQ EF (Emotional Function).

Example 3

Human Clinical Study Evaluating the Safety and Efficacy of an Anti-CGRP Antibody in Chronic Migraine Patients This example describes a randomized, double-blind, placebo-controlled clinical trial evaluating the safety and efficacy of Ab6 for chronic migraine prevention. In the study, 1,072 patients were randomized to receive Ab6 (300 mg or 100 mg), or placebo administered by infusion once every 12 weeks. To be eligible for the trial, patients must have experienced at least 15 headache days per month, of which at least eight met criteria for migraine. Patients that participated in the trial had an average of 16.1 migraine days per month at baseline. Study endpoints included the mean change from baseline in monthly migraine days, reduction in migraine prevalence at day 1 and over days 1-28, and reduction of at least 50%, 75%, and 100% from baseline in mean monthly migraine days, change from baseline in mean monthly acute migraine-specific medication days, and reductions from baseline in patient-reported impact scores on the Headache Impact Test (HIT-6). The administered antibody, Ab6, is an anti-CGRP antibody consisting of the light chain polypeptide of SEQ ID NO: 221 and heavy chain polypeptide of SEQ ID NO: 201.

Patient characteristics are summarized in FIG. 39, with separate columns for patients receiving placebo, 100 mg of the antibody, or 300 mg of the antibody. Patients had a mean number of years from migraine diagnosis of between 17.0 and 19.0 years, a mean duration of suffering from chronic migraine of between 11.5 and 12.4 years, and between 44.3% and 45.2% of patients utilized at least one prophylactic medication. At baseline, in both antibody treatment groups the mean number of migraine days per month was 16.1, while for the placebo group, the mean number of migraine days per month was 16.2.

The reduction in a specified percentage (50%, 75%, or 100%) from baseline in mean monthly migraine days refers to the number or percentage of patients in a treatment group that exhibited the given percentage reduction in the number of migraine days per month. For example, a patient exhibiting 16 migraine days per month at baseline would be a 75% responder if the number of migraine days per month was decreased by at least 12 days per month over specified period.

Figure 35:
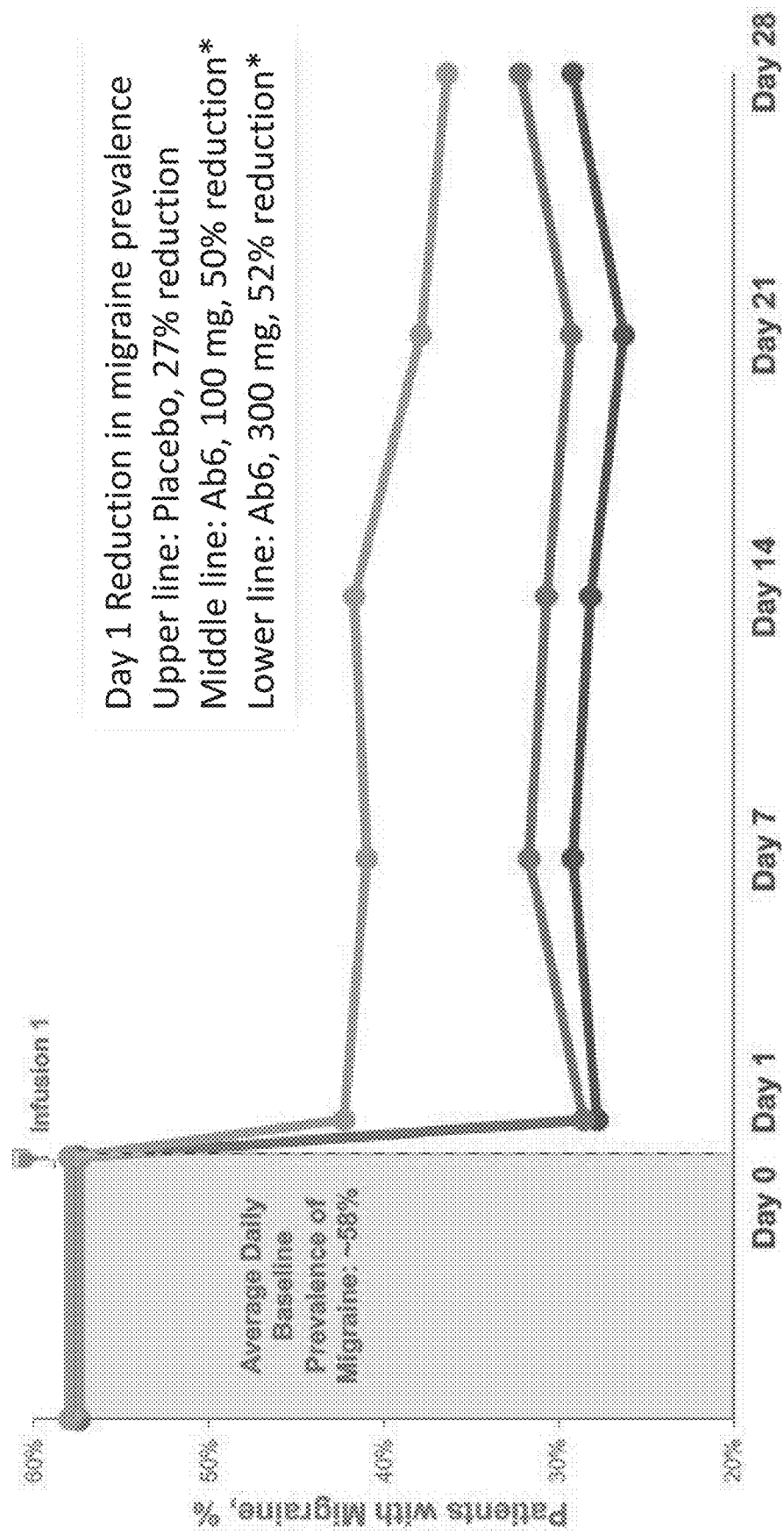
FIG. 35 shows the percentages of patients with migraine in the 300 mg, 100 mg, and placebo treatment groups at days 1, 7, 14, 21, and 28 in the clinical trial described in Example 3. The uppermost line shows results for placebo, the lowest line shows results for the 300 mg dosage, and the middle line shows results for the 100 mg dosage.

The results are shown in FIGS. 35-39. FIG. 35 shows the percentages of patients with migraine in the 300 mg, 100 mg, and placebo treatment groups at days 1, 7, 14, 21, and 28. The uppermost line shows results for placebo, the lowest line shows results for the 300 mg dosage, and the middle line shows results for the 100 mg dosage.

As shown in FIG. 35, at day 1 the percentage reduction in migraine prevalence was 52% for the 300 mg dosage, 50% at the 100 mg dosage, and 27% for placebo. The decrease was statistically significant compared to the placebo group for both the 100 mg and 300 mg treatment groups.

Figure 36:
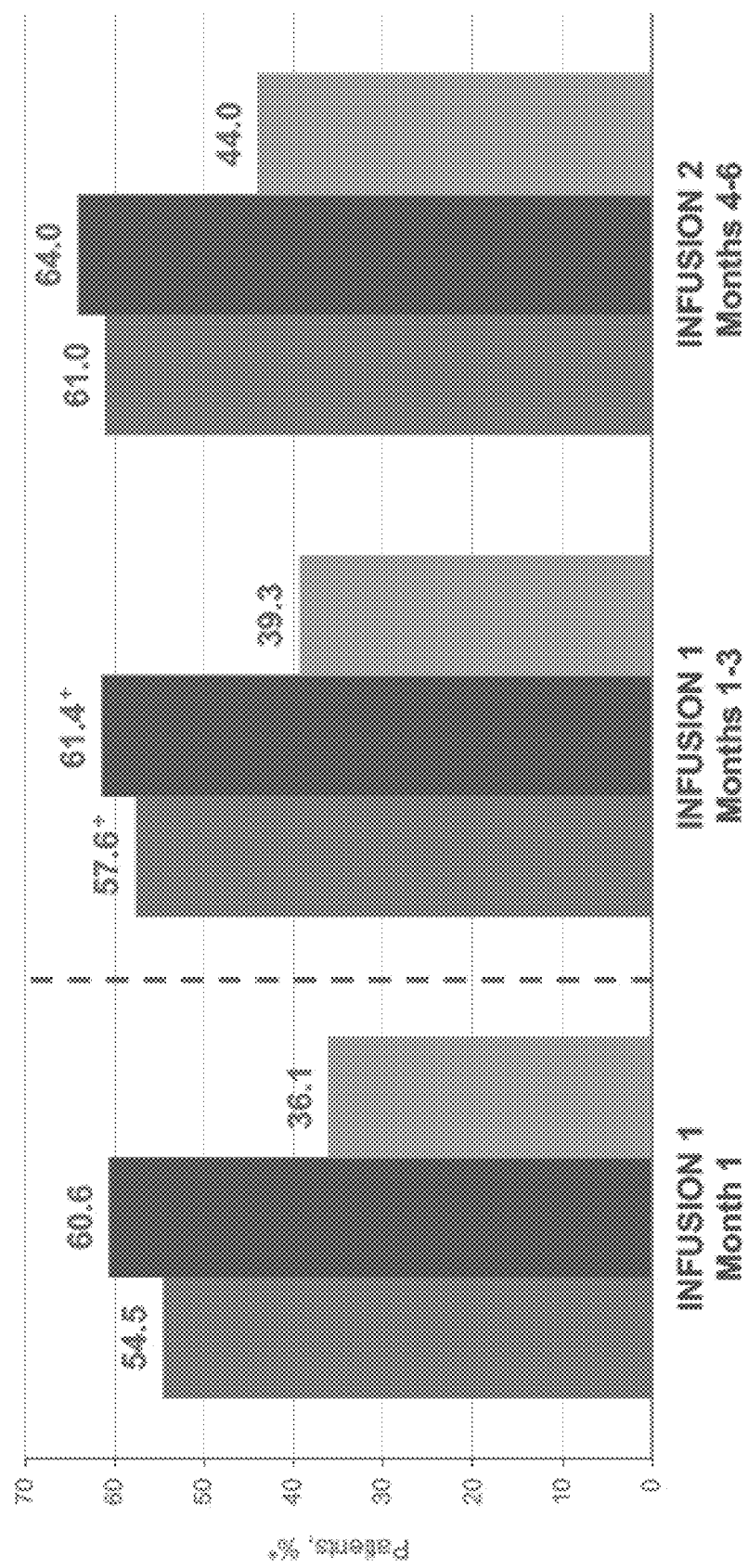
FIG. 36 show the percentage of patients in the 300 mg and 100 mg treatment groups achieving a 50% reduction in migraine days in month 1, over months 1-3 (after the 1st infusion), and over months 4-5 (after the 2nd infusion) in the clinical trial described in Example 3. In each graph, the data bars, from left to right, show results for the 100 mg, 300 mg, and placebo groups. Statistical significance is as shown. ++ indicates a statistically significant difference from placebo; + indicates a statistically significant difference from placebo (unadjusted); and § indicates a statistically significant difference from placebo (post hoc).
Figure 37:
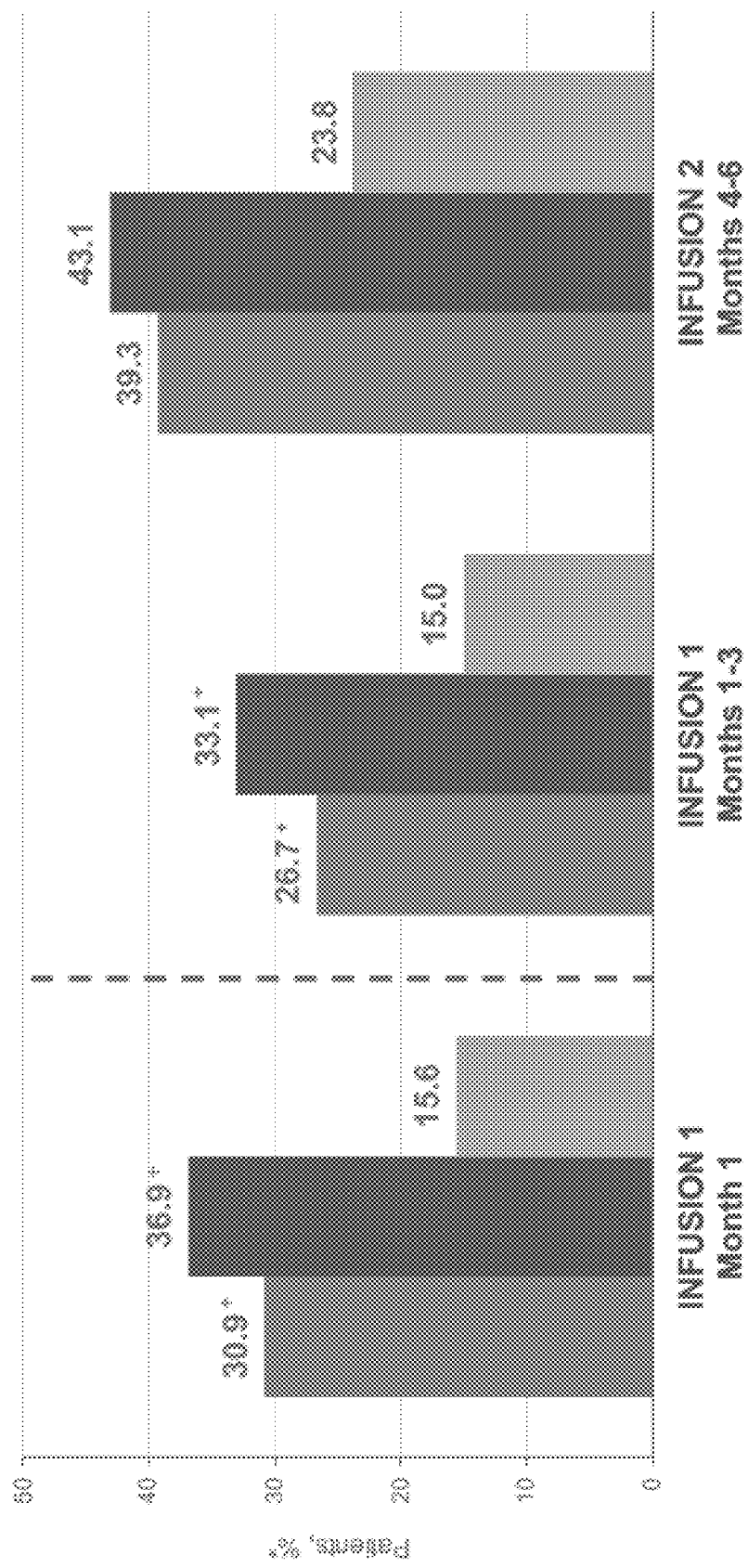
FIG. 37 show the percentage of patients in the 300 mg and 100 mg treatment groups achieving a 75% reduction in migraine days in month 1, over months 1-3 (after the 1st infusion), and over months 4-5 (after the 2nd infusion) in the clinical trial described in Example 3. Data order and statistical significance labels are as indicated with FIG. 36.
Figure 38:
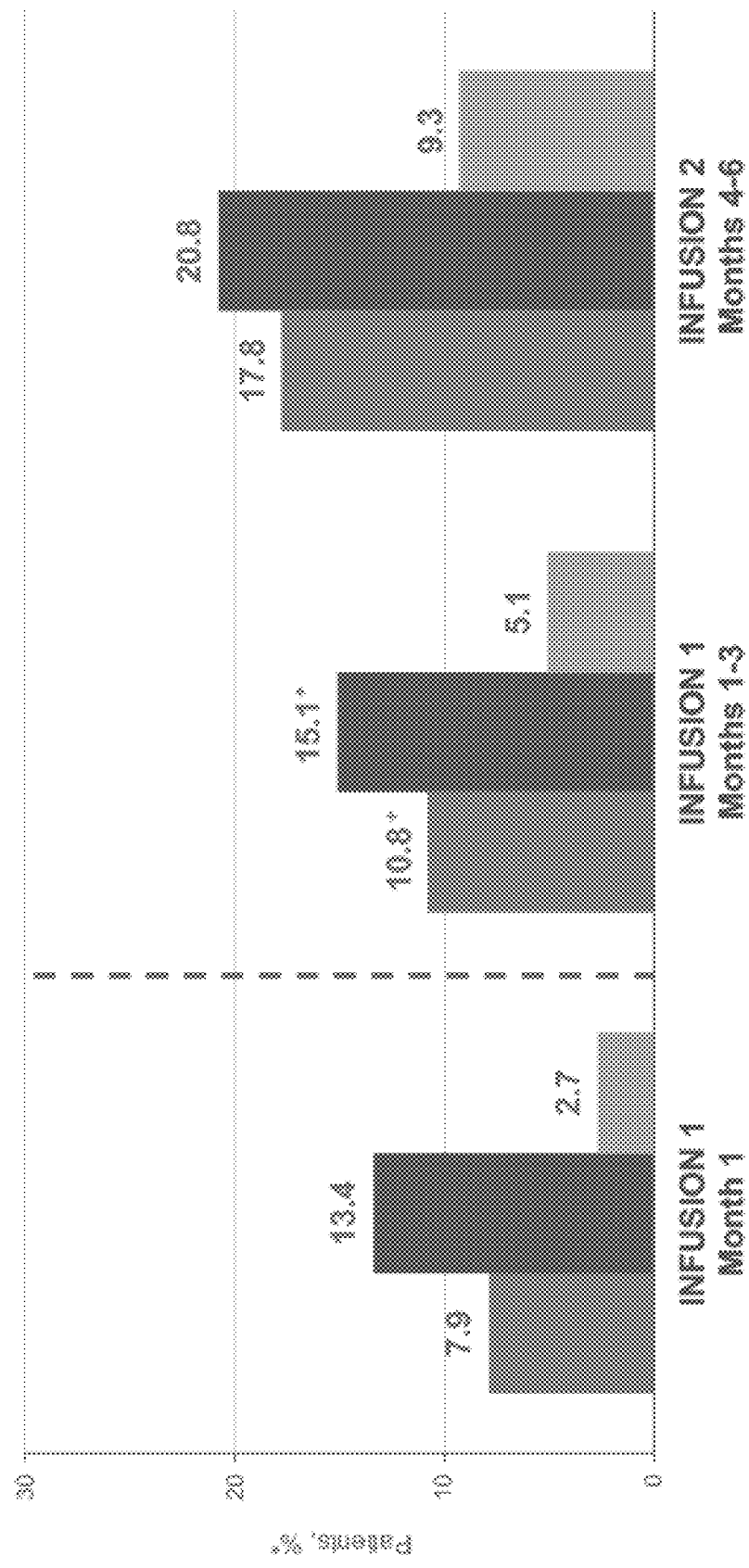
FIG. 38 show the percentage of patients in the 300 mg and 100 mg treatment groups achieving a 100% reduction in migraine days in month 1, over months 1-3 (after the 1st infusion), and over months 4-5 (after the 2nd infusion) in the clinical trial described in Example 3. Data order and statistical significance labels are as indicated with FIG. 36.

FIGS. 36-38 show the percentage of patients in the 300 mg and 100 mg treatment groups achieving, respectively, 50%, 75%, and 100% reduction in migraine days in month 1, over months 1-3 (after the 1st infusion), and over months 4-5 (after the 2nd infusion). In each graph, the data bars, from left to right, show results for the 100 mg, 300 mg, and placebo groups. Statistical significance is as shown. ++ indicates a statistically significant difference from placebo; + indicates a statistically significant difference from placebo (unadjusted); and § indicates a statistically significant difference from placebo (post hoc).

Example 4

Figure 41:
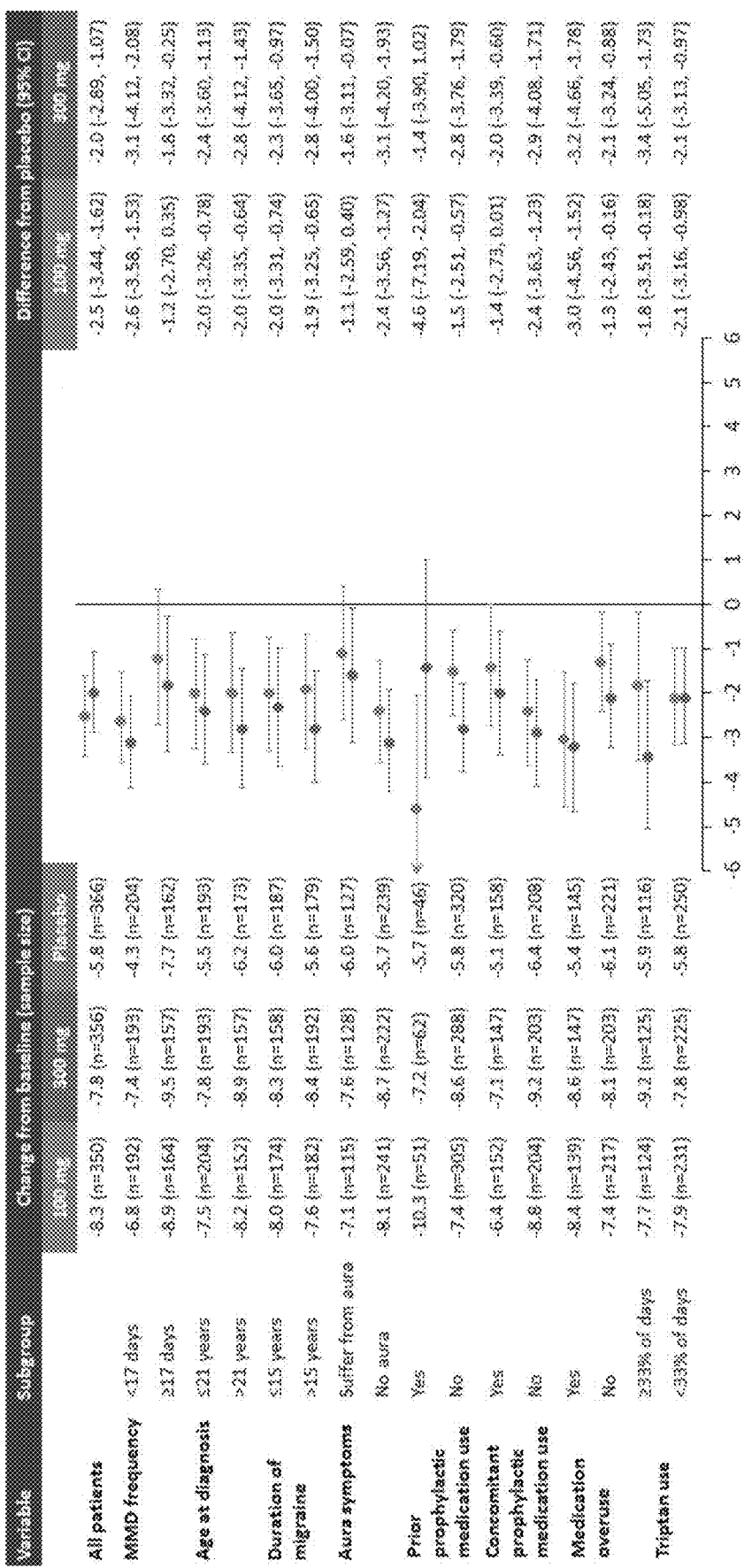
FIG. 41. Difference from placebo in change from baseline in mean migraine days (MMD) over months 1-3 by baseline subgroup for a human clinical trial of episodic migraine patients. The graph is labeled as in FIG. 40.

Baseline Subgroup Analysis for Human Clinical Studies Evaluating the Safety and Efficacy of an Anti-CGRP Antibody in Chronic or Episodic Migraine Patients In the study of Chronic Migraine described in Example 3, at intake, each patient was assessed for potential medication overuse headache (MOH). MOH was present in 39.9% (139 patients) in the 100 mg treatment group, 42.0% (147 patients) in the 300 mg treatment group, and 39.6% (145 patients) in the placebo group. Assessment of the treatment outcomes in this patient subset indicated that treatment with the anti-CGRP antibody was efficacious for MOH (FIG. 41). Specifically, in the 100 mg treatment group, mean migraine days per month changed by −3.0 days (95% CI, −4.56 to −1.52 days) in the patients having MOH at baseline, compared to MOH patients receiving placebo. Similarly, in the 300 mg treatment group, mean migraine days per month changed by −3.2 days (95% CI, −4.66 to −1.78 days) in the patients having MOH at baseline, compared to MOH patients receiving placebo. By contrast, for patients without MOH at baseline, in the 100 mg treatment group, mean migraine days per month changed by −1.3 days (95% CI, −2.43 to −0.16 days), compared to patients without MOH at baseline receiving placebo. Likewise, for patients without MOH at baseline in the 300 mg treatment group, mean migraine days per month changed by −2.1 days (95% CI, −3.24 to −0.88 days), compared to patients without MOH at baseline receiving placebo. Efficacy for other subgroups was shown as well, including efficacy for patients with mean migraine day (MMD) frequency less than 17 days or greater than or equal to 17 days, patients with an age at diagnosis of less than or equal to 21 years or greater than 21 years, patients having a duration of migraine of less than or equal to 15 year or greater than 15 years, patients suffering from migraine with aura or migraine with no aura, patients with prior prophylactic medication use or no prior prophylactic medication use, patients with concomitant prophylactic medication use or no concomitant prophylactic medication use, ant patients with triptan use on greater than or equal to 33% of days, or less than 33% of days. In each case, efficacy for each subgroup was shown (FIG. 41).

Figure 40:
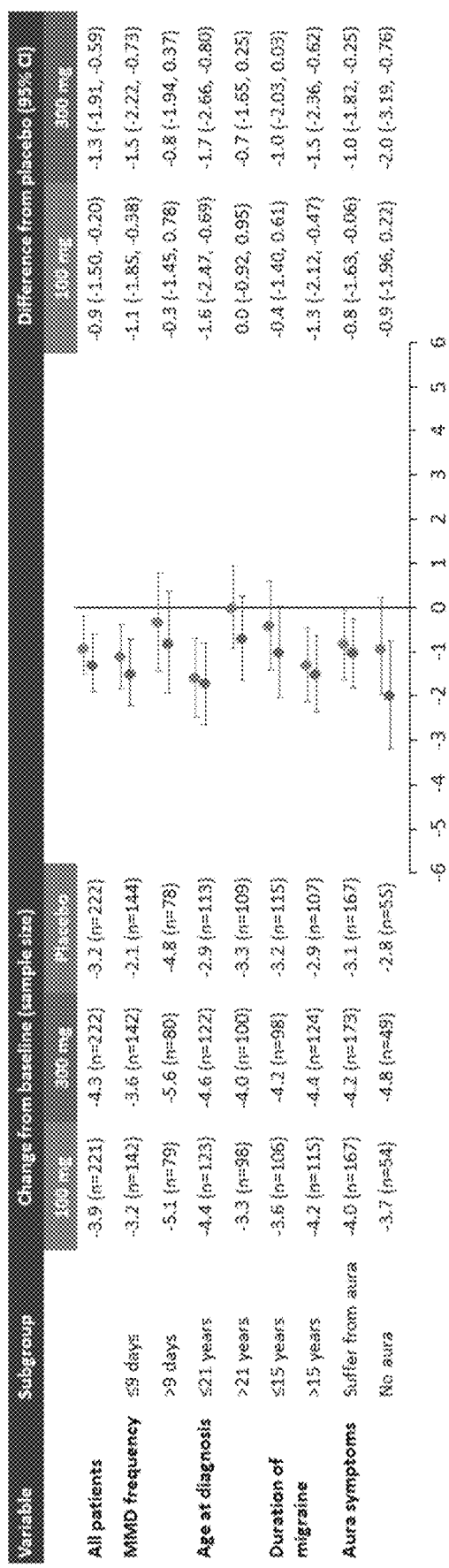
FIG. 40. Difference from placebo in change from baseline in mean migraine days (MMD) over months 1-3 by baseline subgroup for a human clinical trial of chronic migraine patients. In the graph, the data point refers to the mean value and the line shows the 95% confidence interval (CI) of the change from placebo for the 100 mg (upper line) or 300 mg (lower line) treatment group, for each subgroup as labeled at the far left.

In another human clinical trial of patients with episodic migraine, patients were randomized to receive Ab6 100 mg (n=221), 300 mg (n=222), or placebo (n=222) in a double blind, parallel study. After a 28 day screening period, patients were administered the drug or placebo intravenously every 3 months for 4 total infusions (FIG. 40). Efficacy was shown over months 1-3 for both the 100 mg and 300 mg treatment groups, with a mean change in migraine days of −3.9 for the 100 mg treatment group and −4.3 days for the 300 mg treatment group, compared to −3.2 days for the placebo group. Efficacy for subgroups of patients was also shown, including efficacy for patients with mean migraine day (MMD) frequency less than or equal to 9 days or greater than 9 days, patients with an age at diagnosis of less than or equal to 21 years or greater than 21 years, patients having a duration of migraine of less than or equal to 15 year or greater than 15 years, and patients suffering from migraine with aura or migraine with no aura.

Example 5

Effects of Ab6 Treatment on Medication Use in Chronic and Episodic Migraine Patients During the studies of chronic migraine patients described in Example 3 and episodic migraine patients described in Example 4, patients also recorded use of acute medication in a daily eDiary and were allowed to use acute medication at their own discretion. Acute medications for migraine included ergots, triptans, and analgesics (e.g., NSAIDS, opioids, and caffeine-containing combination analgesics).

For further analysis, patients were stratified by the number of days with acute medication use during the 28-day screening period (1-9 or >10 days; "baseline"). Acute medication days were calculated for individual types of acute medications and combined, meaning that if 2 or more types medications were used on the same calendar days, they were counted as separate medication use days. For example, if a patient took an opioid and a triptan on the same day, it counted as 2 days of acute medication use. These analyses included patients with at least 1 acute medication use day during the 28-day baseline screening period.

In both chronic migraine and episodic migraine patients who used acute medication during the 28-day baseline period, Ab6 treatment resulted in greater average reductions in monthly migraine days and acute medication days than placebo as early as Month 1 after dosing, with similar results across 2 dose intervals over 6 months.

Figure 42:
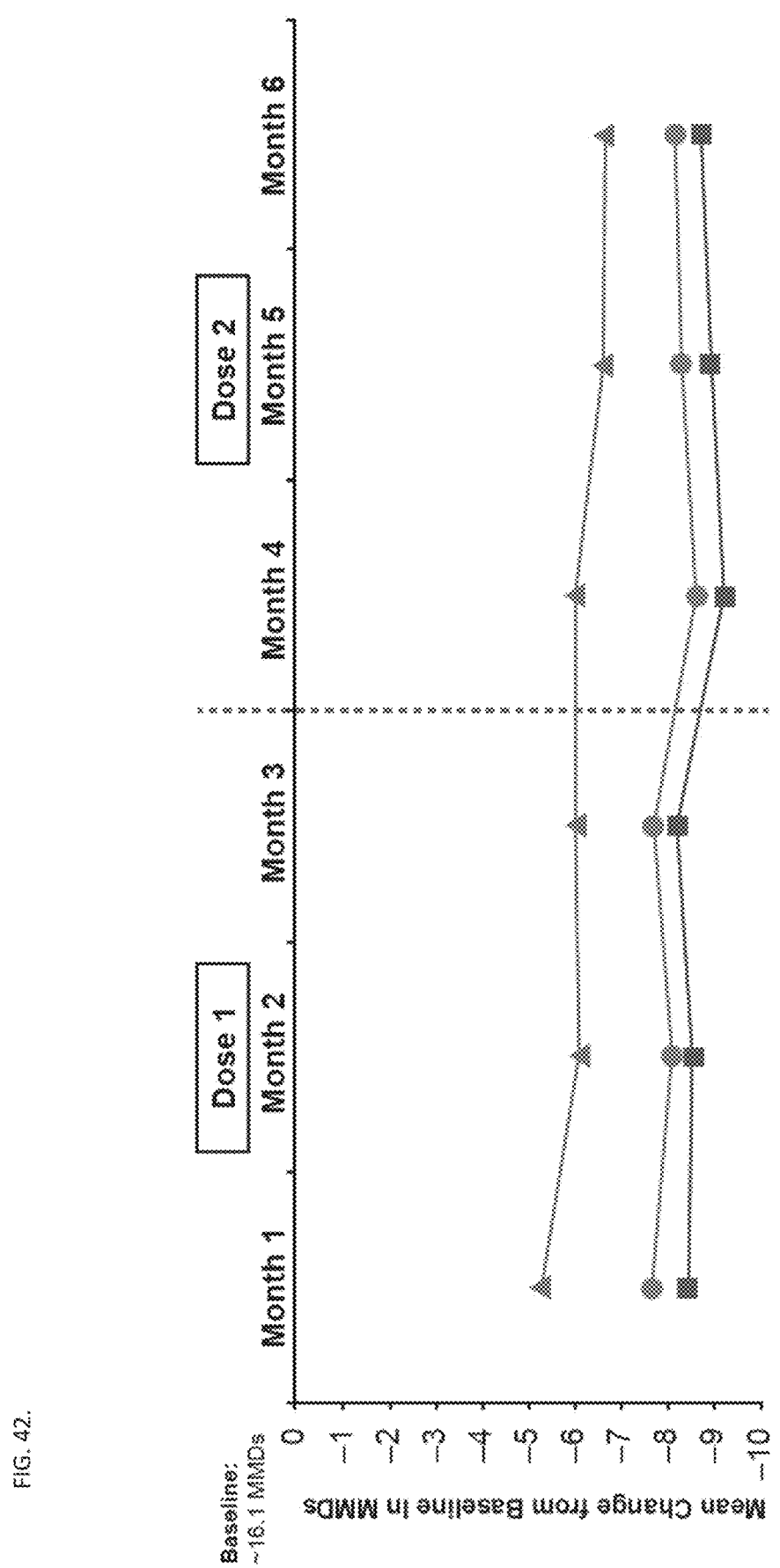
FIG. 42. Change from baseline in mean migraine days (MMDs) across 2 dose intervals in chronic migraine patients with at least 1 day of acute medication use per month at baseline. Triangle: placebo (n=366). Circle: 100 mg Ab6 per dose (n=356). Square: 300 mg Ab6 per dose (n=350).
Figure 43:
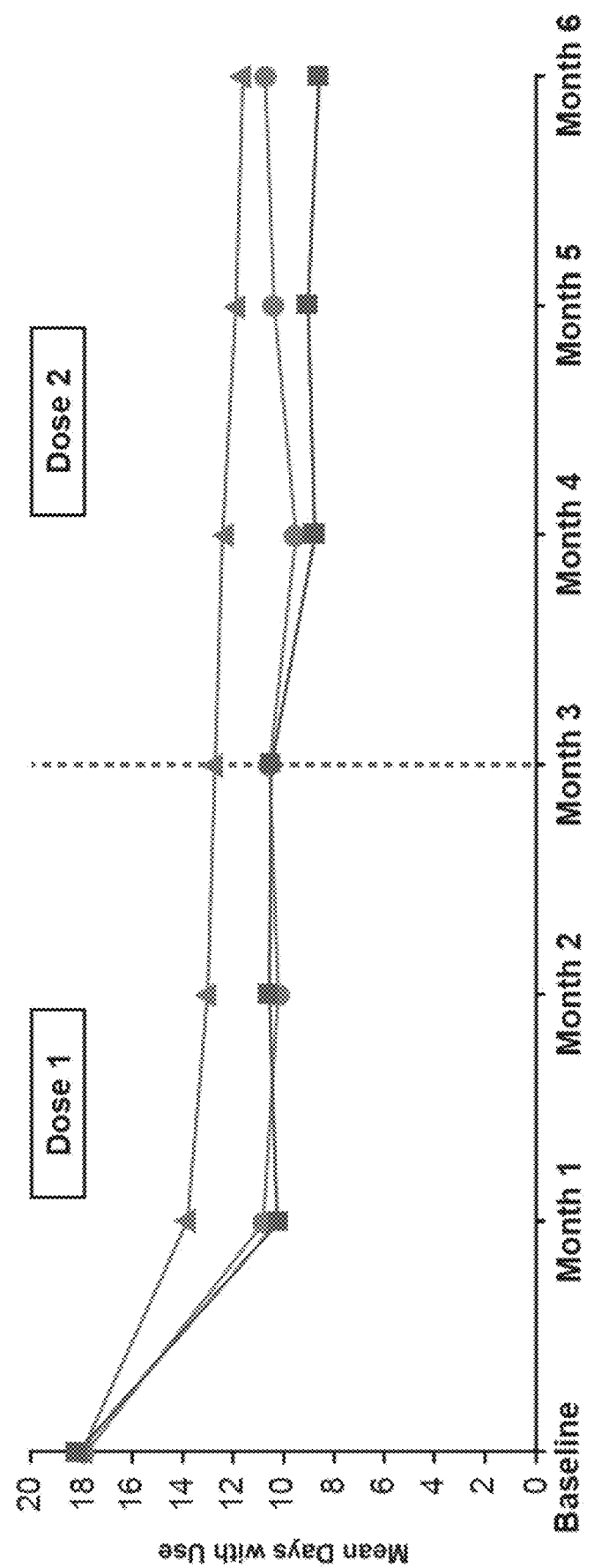
FIG. 43. Mean days with acute medication use in chronic migraine patients with at least one day per month of acute medication use at baseline. Triangle: placebo (n=366). Circle: 100 mg Ab6 per dose (n=356). Square: 300 mg Ab6 per dose (n=350).
Figure 44:
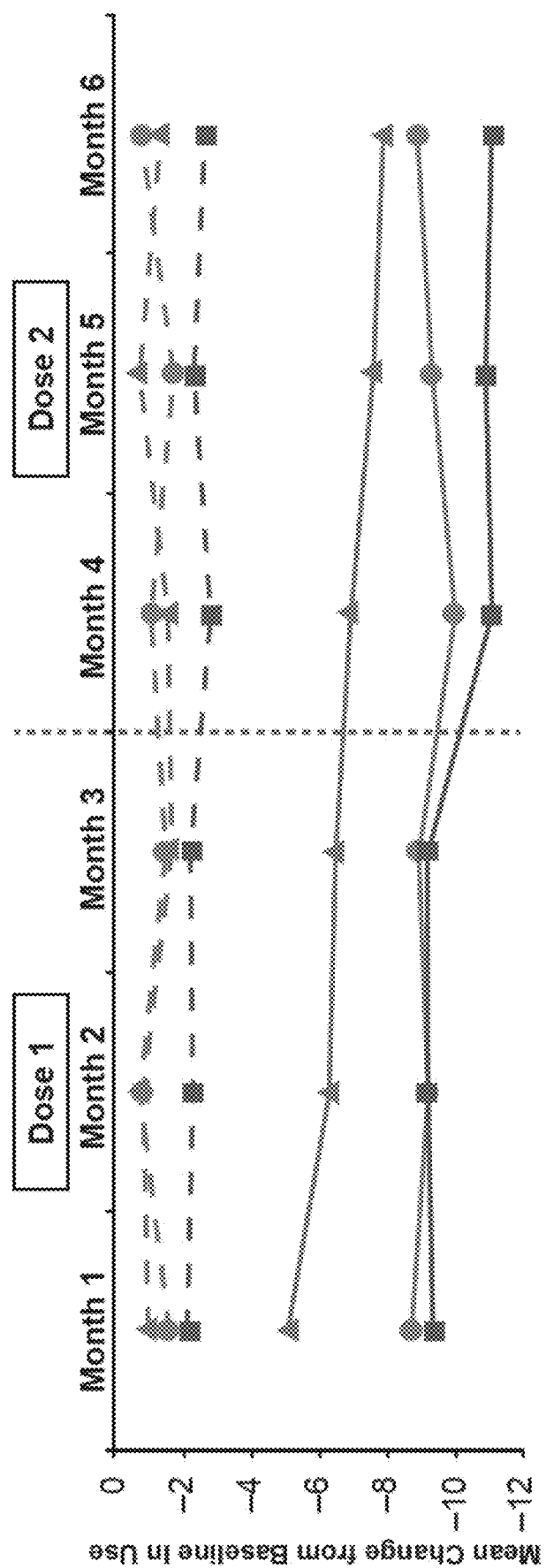
FIG. 44. Change from baseline in acute medication use by subgroups of chronic migraine patients with differing baseline days of acute medication use. Solid lines: patients with 10 or more days of acute medication use per month at baseline. Dashed lines: patients with at least 1 and less than 10 days of acute medication use per month at baseline. Triangle: placebo. Circle: 100 mg Ab6 per dose. Square: 300 mg Ab6 per dose.

Ab6 consistently demonstrated greater reductions in mean monthly migraine days over 6 months of treatment than placebo in chronic migraine patients taking >1 day of acute medication use during baseline (FIG. 42). Chronic migraine patients who had at least one day of acute medication use per month during baseline demonstrated greater decreases in acute medication use than placebo as early as month 1 after treatment and across the entire 6 month treatment period (FIG. 43). In the subgroup of chronic migraine patients who were taking 1-9 days of acute medication during baseline, the change from baseline in days of acute medication use was greater in the 300 mg Ab6 group than placebo across 6 months of treatment (FIG. 44). A clear decrease in medication days per month was observed for patients with at least 10 days of medication use per month at baseline for both Ab6 treatment group compared to placebo over the entire 6 month period. FIG. 45 shows the changes in medication use days at Month 1 and Month 6 in the subgroups of chronic migraine patients with >1, 1-9, and >10 days of acute medication use at baseline. With the exception of Ab6 100 mg at month 6 in patients with 1-9 days/month of use at baseline, Ab6 demonstrated a greater treatment effect in reducing acute medication use than placebo.

Figure 46:
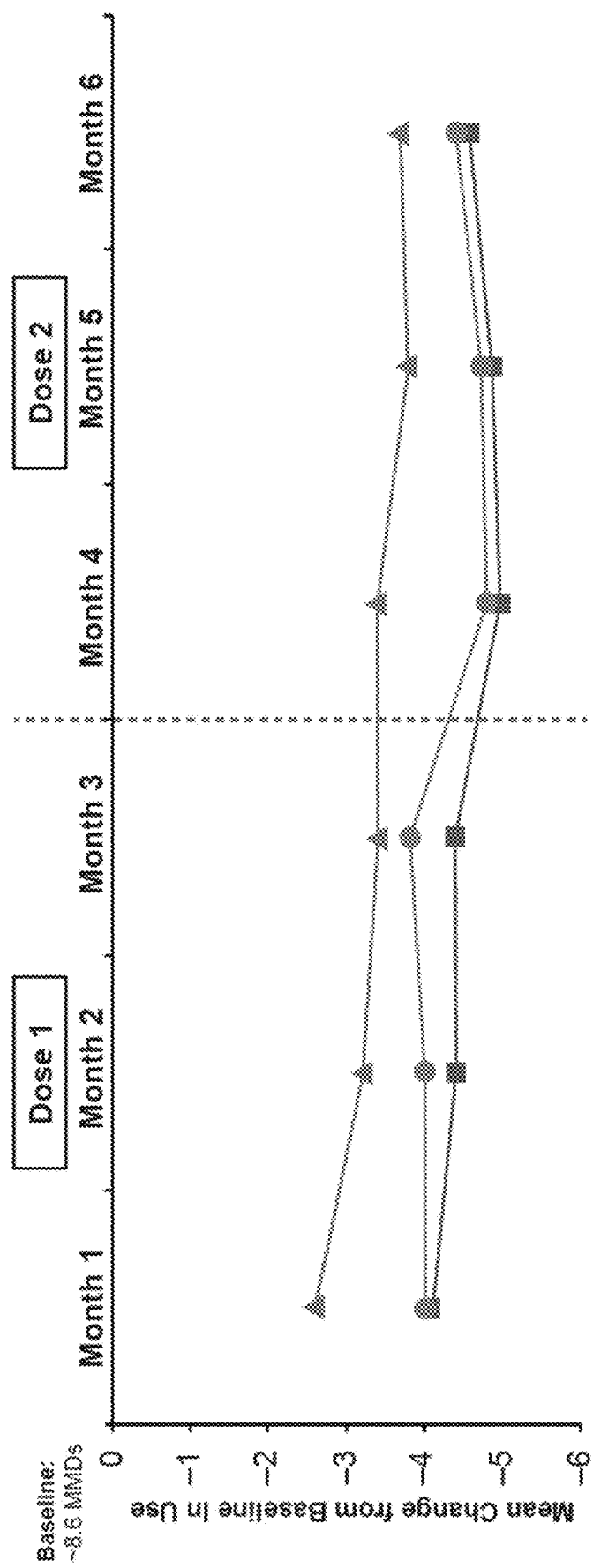
FIG. 46. Change from baseline in mean migraine days (MMDs) across 2 dose intervals in episodic migraine patients with at least 1 day of acute medication use per month at baseline. Triangle: placebo (n=222). Circle: 100 mg Ab6 per dose (n=221). Square: 300 mg Ab6 per dose (n=222).
Figure 47:
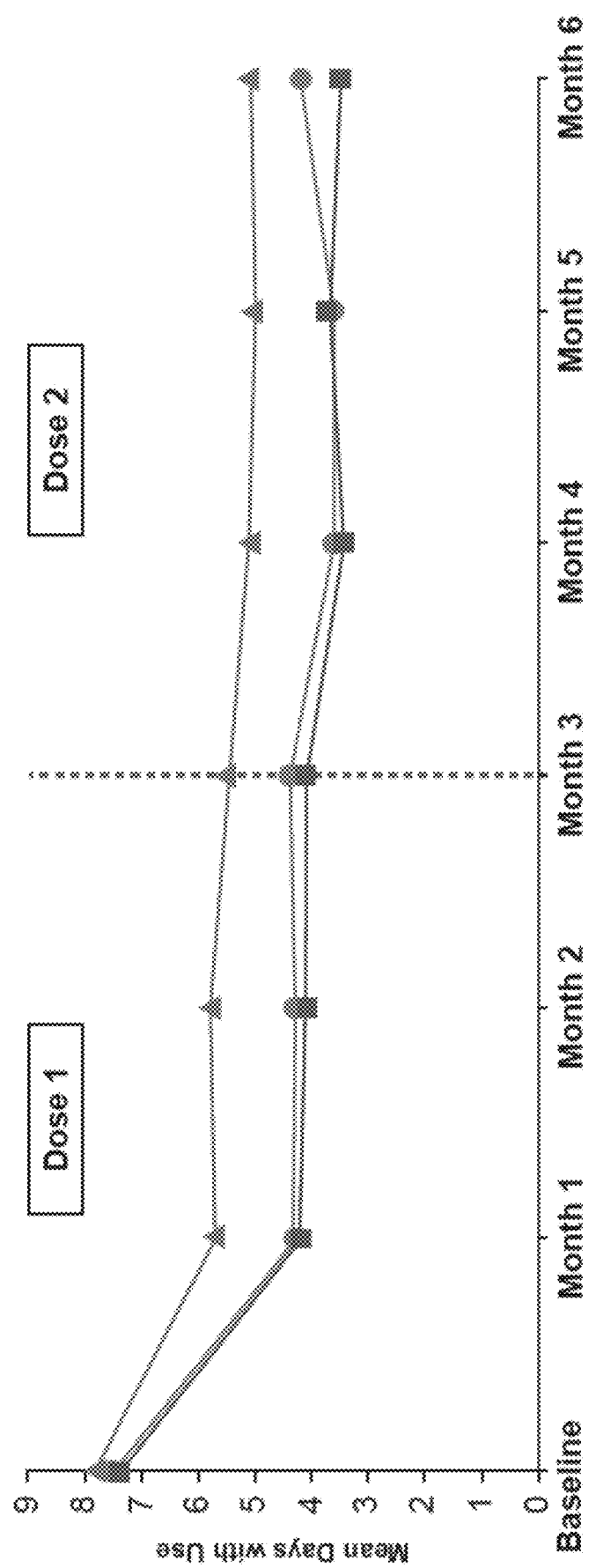
FIG. 47. Mean days with acute medication use in episodic migraine patients with at least one day per month of acute medication use at baseline. Triangle: placebo (n=222). Circle: 100 mg Ab6 per dose (n=221). Square: 300 mg Ab6 per dose (n=222).
Figure 48:
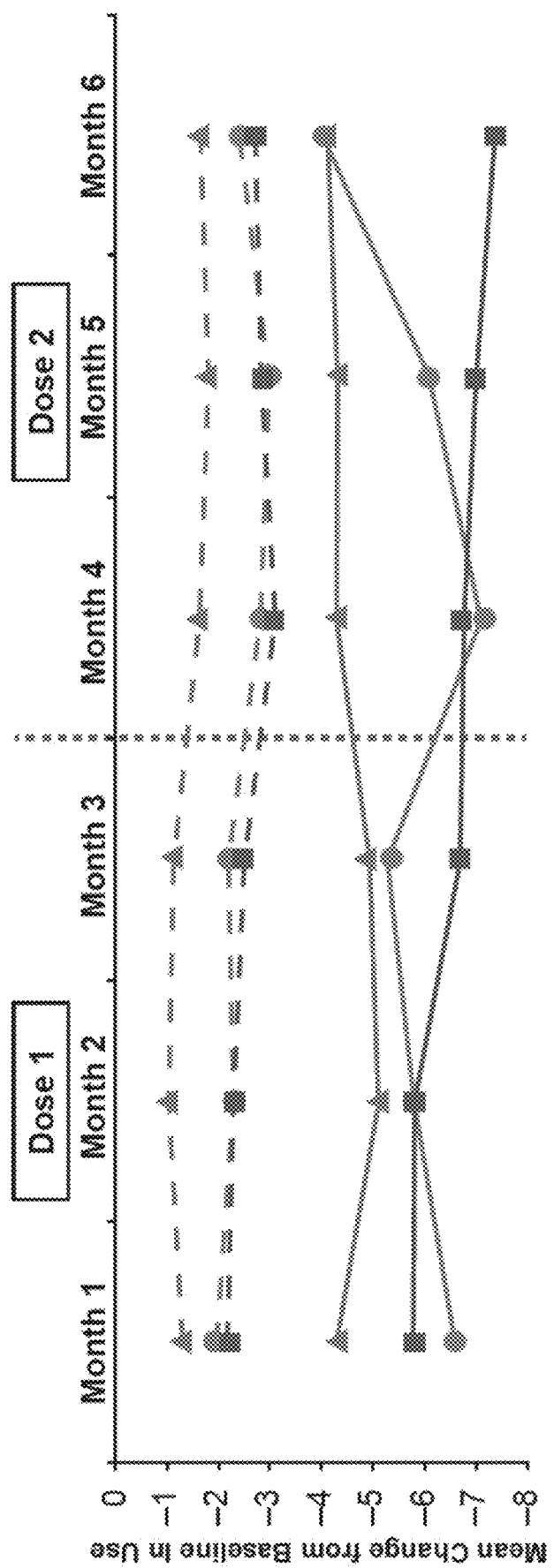
FIG. 48. Change from baseline in acute medication use by subgroups of episodic migraine patients with differing baseline days of acute medication use. Solid lines: patients with 10 or more days of acute medication use per month at baseline. Dashed lines: patients with at least 1 and less than 10 days of acute medication use per month at baseline. Triangle: placebo. Circle: 100 mg Ab6 per dose. Square: 300 mg Ab6 per dose.

Similarly, across 2 dose intervals over 6 months, episodic migraine patients with one or more days of acute medication use during baseline experienced greater reductions in mean monthly migraine days with Ab6 than Placebo (FIG. 46). Episodic migraine patients who had at least one day of acute medication use per month during baseline demonstrated greater decreases in acute medication use than placebo as early as month 1 after treatment and across the entire 6 month treatment period (FIG. 47). In the subgroup of episodic migraine patients who were taking 1-9 days of acute medication during baseline, the change from baseline in days of acute medication use was greater with Ab6 than placebo across 6 months of treatment (FIG. 48). A similar pattern was observed in the subgroup of patients who were taking ≥10 days of acute medication during baseline, though smaller sample sizes may have contributed to the less consistent pattern over time. FIG. 49 shows the changes in medication use days at Month 1 and Month 6 in the subgroups of episodic migraine patients with >1, 1-9, and >10 days of acute medication use at baseline. With the exception of Ab6 100 mg at Month 6 in patients with >10 days/month of use at baseline, the reduction in acute medication use was greater in the Ab6 treatment groups than placebo.

The results show that both episodic migraine and chronic migraine patients who were at risk for medication-overuse headache (>10 days/month of acute medication use) demonstrated the greatest reductions in acute medication use, with Ab6 treatment generally resulting in larger decreases in medication use days than placebo.

The most frequently reported acute headache medications in >10% of subjects included Thomapyrin N (44.5%) (a combination of paracetamol, aspirin, and caffeine), ibuprofen (40.6%), sumatriptan (33.6%), paracetamol (acetaminophen) (20.3%), and naproxen sodium (10.2%). The most frequently reported preventive headache medication in >10% of subjects was topiramate (12.5%).

Example 6

Efficacy of Anti-CGRP Antibodies in Subjects Experiencing an Acute Attack of Migraine This example describes a randomized, double-blind, placebo-controlled clinical trial evaluating the safety and efficacy of Ab6 for the acute treatment of migraine. In the study, approximately 450 patients are randomized 1:1 to receive either 100 mg Ab6 or placebo. During a screening period (approx. 1-8 weeks) patients are assessed for migraine frequency and medication use frequency. Eligible patients have a migraine attack frequency of about 4-15 migraine days per month in the 3 months prior to screening. By history, the subject's typical migraine attack, if untreated, would be associated with headache pain of moderate to severe intensity and a most bothersome symptom of nausea, photophobia, or phonophobia. Subjects must be headache free for at least 24 hours prior to onset of a qualifying migraine in order to participate in the trial. On the day of treatment, the patient will travel to the study site and intravenous infusion of 100 mg Ab6 or placebo will commence between about 1-6 hours from the start of the attack. Patients will not have received any other monoclonal antibody (e.g., any CGRP antagonist antibody) within the 6 month period prior to screening.

Co-Primary Endpoints are time to headache pain freedom and time to absence of most bothersome symptom. Co-Key secondary are headache pain freedom at 2 hours and absence of most bothersome symptom at 2 hours. Secondary endpoints are time to headache pain relief, headache pain freedom at 2 hours with sustained headache pain freedom for 24 and 48 hours, use of rescue medication by 24 hours and by 48 hours, absence of photophobia at 2 hours, absence of phonophobia at 2 hours, absence of nausea at 2 hours, change from Baseline in Headache Impact Test (HIT 6) at Week 4, and change from Baseline in Migraine Treatment Optimization Questionnaire-6 (mTOQ-6) at Week 4. Exploratory Endpoints are absence of headache pain at all timepoints other than 2 hours, absence of photophobia at all timepoints other than 2 hours, absence of phonophobia at all timepoints other than 2 hours, absence of nausea at all timepoints other than 2 hours, pain relapse when the subject was headache pain-free at 2 hours, patient Global Impression of Change (PGIC) at Week 4, and time to next migraine. Headache pain is collected on a 4-point scale with 3 being severe, 2 being moderate, 1 being mild, and 0 being no pain. Pain freedom is no pain (0) with the absence of rescue medication (note that in the trial rescue medication is not to be used for 2 hours post completion of infusion in order to separate the effects of the antibody from the rescue medication, however, in the course of normal use, rescue medication optionally may be used; any use of rescue medication is collected as data).

Statistical analysis is performed to determine significance of the difference in endpoints between patients receiving Ab6 or placebo, including the time to pain freedom and time to absence of most bothersome symptom, and each of the other aforementioned endpoints.

Use of rescue medication refers to any intervention (medical or device) provided to the subject to provide relief of migraine. In the study this should not be provided sooner than 2 hours following completion of the study drug administration in order to separate the effects of the antibody from the effects of said rescue medication, however, rescue medication is not contraindicated. The proportion of subjects requiring rescue medication use is summarized in the study. Acute rescue medication includes any medication to treat migraine or migraine associated symptoms, e.g., triptans, analgesics such as non-opioids or opioids/narcotics, acetaminophen, NSAIDS, combination medications such as EXCEDRIN® or EXCEDRIN MIGRAINE®, antiemetic medications, ergotamines, ergot derivatives, etc.

Absence of Migraine-Associated Symptoms (Photophobia, Phonophobia and Nausea) refers to the absence or presence of each of the aforementioned migraine-associated symptoms, as reported by the subject. The proportion of subjects absent the symptoms, with no administration of rescue medication, is summarized in the study.

Headache Impact Test (HIT-6) is assessed as the change from baseline of the total score, and is summarized and compared between treatment groups in the study.

Migraine Treatment Optimization Questionnaire-6 (mTOQ-6) is assessed as the change from baseline of the total score and is summarized and compared between the treatment groups in the study.

Time to Headache Pain Relief is assessed as the first time point post completion of infusion at which the subject reports relief of pain meaning their headache pain has gone from moderate or severe (2 or 3) to mild or no pain (1 or 0) with no administration of rescue medication.

Pain Relapse is assessed as the occurrence of headache of any severity within 48 hours of drug administration for a patient who has no headache pain (0) at 2 hours. The proportion of subjects with recurrence of headache pain of any severity is summarized in the study.

The study shows that Ab6 is effective and safe for acute migraine treatment.

What is claimed is:

1. A method for providing relief from migraine in a patient experiencing a migraine attack, comprising intravenously administering to the patient an effective amount of an anti-Calcitonin Gene Related Peptide (CGRP) antibody, wherein the intravenous administration of said anti-CGRP antibody begins while said patient is experiencing a migraine attack and within 30 hours after the onset of the attack, and further wherein said anti-CGRP antibody is a full-length IgG antibody which comprises: the light chain complementarity determining region (CDR) 1, 2, and 3 polypeptide sequences of SEQ ID NO: 224, SEQ ID NO: 226, and SEQ ID NO: 228, respectively; and heavy chain CDR 1, 2, and 3 polypeptide sequences of SEQ ID NO: 204, SEQ ID NO: 206, and SEQ ID NO: 208, respectively.

2. The method of claim 1, wherein the intravenously administered amount of said anti-CGRP antibody is between about 100 mg and about 300 mg.

3. The method of claim 1, wherein the intravenously administered amount of said anti-CGRP antibody is about 100 mg.

4. The method of claim 1, wherein the intravenously administered amount of said anti-CGRP antibody is about 300 mg.

5. The method of claim 1, wherein the intravenous anti-CGRP antibody administration begins within 24 hours, within 18 hours, within 12 hours, within 6 hours, within 5 hours, within 4 hours, within 3 hours, within 2 hours, or within 1 hour after the onset of the attack.

6. The method of claim 1, wherein the intravenous anti-CGRP antibody administration begins between 1-6 hours after the onset of the attack.

7. The method of claim 1, wherein the intravenously administered amount of said anti-CGRP antibody is between about 100 mg and about 300 mg and the intravenous anti-CGRP antibody administration begins within 24 hours after the onset of the attack.

8. The method of claim 1, wherein the intravenously administered amount of said anti-CGRP antibody is about 100 mg and the intravenous anti-CGRP antibody administration begins within 18 hours after the onset of the attack.

9. The method of claim 1, wherein said anti-CGRP antibody comprises the variable light chain polypeptide of SEQ ID NO: 222 and the variable heavy chain polypeptide of SEQ ID NO: 202.

10. The method of claim 1, wherein said anti-CGRP antibody comprises the light chain polypeptide of SEQ ID NO: 221 and the heavy chain polypeptide of SEQ ID NO: 201.

11. The method of claim 10, wherein the intravenously administered amount of said anti-CGRP antibody is between about 100 mg and about 300 mg and the intravenous anti-CGRP antibody administration begins within 24 hours after the onset of the attack.

* * * * *